(12) United States Patent
Sanière et al.

(10) Patent No.: US 8,759,334 B2
(45) Date of Patent: Jun. 24, 2014

(54) COMPOUNDS USEFUL FOR THE TREATMENT OF METABOLIC AND INFLAMMATORY DISEASES

(75) Inventors: Laurent Raymond Maurice Sanière, Romainville (FR); Mathieu Rafaël Pizzonero, Romainville (FR); Nicolas Triballeau, Romainville (FR); Nick Ernest René Vandeghinste, Mechelen (BE); Steve Irma Joel De Vos, Mechelen (BE); Reginald Christophe Xavier Brys, Mechelen (BE); Christelle Dominique Bénédicte Pourbaix-L'ebraly, Romainville (FR)

(73) Assignee: Galapagos NV, Mechelen (BE)

( * ) Notice: Subject to any disclaimer, the term of this patent is extended or adjusted under 35 U.S.C. 154(b) by 0 days.

(21) Appl. No.: 13/980,798

(22) PCT Filed: Jan. 10, 2012

(86) PCT No.: PCT/EP2012/050297
§ 371 (c)(1),
(2), (4) Date: Jul. 19, 2013

(87) PCT Pub. No.: WO2012/098033
PCT Pub. Date: Jul. 26, 2012

(65) Prior Publication Data
US 2013/0303515 A1  Nov. 14, 2013

Related U.S. Application Data

(60) Provisional application No. 61/434,077, filed on Jan. 19, 2011.

(51) Int. Cl.
*A61K 31/397* (2006.01)
*C07D 409/12* (2006.01)

(52) U.S. Cl.
USPC ..................... 514/210.19; 548/953

(58) Field of Classification Search
None
See application file for complete search history.

(56) References Cited

FOREIGN PATENT DOCUMENTS

| EP | 0101004 | 2/1984 |
|----|---------|--------|
| WO | WO2008/135525 | 11/2008 |
| WO | WO2009/104155 | 8/2009 |

OTHER PUBLICATIONS

Bjursell, et al., Am. J. Physiol. Endocrinol Metab., "Improved glucose control and reduced body fat mass in free fatty acid receptor 2 (Ffar2) deficient mice fed a high fat diet," 2010.
Brown, et al., The Journal of Biological Chemistry, "The Orphan G Protein-coupled Receptors GPR41 and GPR43 Are Activated by Propionate and Other Short Chain Carboxylic Acids," 2003; 278(13): 11312-11319.
Dass, et al., Neurogastroenterol Motil., "The relationship between the effects of short-chain fatty acids on intestinal motility in vitro and GPR43 receptor activation," 2007; 19: 66-74.
Hatanaka, et al., Cancer Sci., "Identification of transforming activity of free fatty acid receptor 2 by retroviral expression screening," 2012; 101(1): 54-59.
Karaki, et al., Cell Tissue Res., "Short-chain fatty acid receptor, GPR43, is expressed by enteroendocrine cells and mucosal mast cells in rat intestine," 2006; 324: 353-360.
Le Poul, et al., The Journal of Biological Chemistry, "Functional Characterization of Human Receptors for Short Chain Fatty Acids and Their Role in Polymorphonuclear Cell Activation," 2003; 278(28): 25481-25489.
Lee, et al., Tetrahedron, "A new route for the synthesis of furanoflavone and furanochalcone natural products," 1995; 51(17): 4909-4955.
Maslowski, et al., Nature, "Regulation of inflammatory responses by gut microbiota and chemoattractant receptor GPR43," 2009; 46(29): 1282-1286.
Prentki, et al., Endocrine Reviews, "Glycerolipid Metabolism and Signaling in Health and Disease," 2008; 29(6): 647-676.
Rao, et al., Tetrahedron Letters, "Claisen rearragement of aryl propargyl ethers in poly(ethylene glycol)-A remarkable substituent and solvent effect.," 1982; 24(45): 5023-5024.
Sellin, et al., News Physiol. Sci., "SCFAs: The Enigma of Weak Electrolyte Transport in the Colon," 1999; 14: 58-64.
Stoddart, et al., Pharmacological Reviews, "International Union of Pharmacology. LXXI. Free Fatty Acid Receptors FFA1, -2, and -3: Pharmacology and Pathophysiological Functions," 2008; 60(4): 405-417.
Turner, et al., J. Org. Chem., "Regiospecific Electrophilic Substitution of Aminoyridines: Ortho Lithiation of 2-,3-, and 4-(pivaloylamino) pyridines," 1983; 48: 3401-3408.
McGinnity, et al., Drug Metabolism and Disposition, "Evaluation of Fresh and Cryopreserved Hepatocytes as in Vitro Drug Metabolism Tools for the Prediction of Metabolic Clearance," 2004; 31(11): 1247-1253.

(Continued)

*Primary Examiner* — Michael Barker
(74) *Attorney, Agent, or Firm* — Klauber & Jackson LLC

(57) ABSTRACT

Compounds are disclosed that have a formula represented by the following:

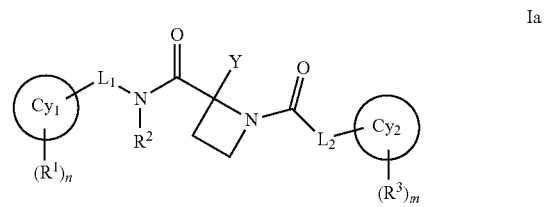

Ia

These compounds may be prepared as a pharmaceutical composition, and may be used for the prevention and treatment of a variety of conditions in mammals including humans, including by way of non-limiting example inflammatory conditions, infectious diseases, autoimmune diseases, diseases involving impairment of immune cell functions, cardiometabolic diseases, and/or proliferative diseases.

17 Claims, No Drawings

(56) References Cited

OTHER PUBLICATIONS

Remington, Remington's Pharmaceutical Sciences, 17th Edition, 1985, Mack Publishing Company, Easton, Pennsylvania (Part 8) Table of Contents attached only.

Sina, et al., J Immunol., "G Protein coupled receptor 43 is essential for neutrophil recruitment during intestinal inflammation," 2009; 183: 7514-7522.

Bundgard H., Design of prodrugs, Amsterdam, Elsevier, 1985. (Table of Contents only).

T. W. Greene and P. G. M. Wuts, Protecting Groups in Organic Synthesis, Second Edition, Wiley, New York, 1991 (Table of Contents only).

COMPOUNDS USEFUL FOR THE TREATMENT OF METABOLIC AND INFLAMMATORY DISEASES

CROSS REFERENCE TO RELATED APPLICATIONS

The present application is a National Stage Application claiming the priority of co-pending PCT Application No. PCT/EP2012/050297 filed Jan. 10, 2012, which in turn, claims priority from U.S. Provisional Application Ser. No. 61/434,077 filed Jan. 19, 2011. Applicants claim the benefits of 35 U.S.C. §120 as to the PCT application and priority under 35 U.S.C. §119 as to the said U.S. provisional application, and the entire disclosures of both applications are incorporated herein by reference in their entireties.

FIELD OF THE INVENTION

The present invention relates to novel compounds that antagonize GPR43 (FFAR2), a G-protein-coupled receptor that is involved in inflammatory conditions, infectious diseases, autoimmune diseases, diseases involving impairment of immune cell functions, cardiometabolic diseases, and/or proliferative diseases.

The present invention also provides methods for the production of these novel compounds, pharmaceutical compositions comprising these compounds, and methods for the prevention and/or treatment of inflammatory conditions, infectious diseases, autoimmune diseases, diseases involving impairment of immune cell functions, cardiometabolic diseases, and/or proliferative diseases, by administering a compound of the invention.

BACKGROUND OF THE INVENTION

Fatty acids (FA) within triglycerides are the major source of energy storage in complex organisms and animals. Besides being an essential component of energy metabolism, FAs are involved in both intracellular and extracellular (autocrine and paracrine) and whole animal (endocrine) signaling processes. It is increasingly becoming evident that disturbances in FA metabolism are strongly associated with the pathogenesis of a large number of chronic conditions including the metabolic syndrome, inflammatory diseases and some cancers (Prentki et al., 2008, Endocrine Review, 29(6), 647-676). Among FAs, the short chain fatty acids (SCFA, carbon length $C_2$-$C_6$) are mainly produced during anaerobic bacterial fermentation of fibers in the gut (Sellin et al., 1999, News. Physiol. Sci, 14, 58-64). It has been found that short chain fatty acids (SCFA) bind to GPR43 (also known as FFAR2) (Le Pouls et al., 2003, The Journal of Biological Chemistry, 278, 28, 25481-25489; Brown et al., 2003, The Journal of Biological Chemistry, 278, 13, 11312-11319). GPR43 expression has been shown in immune cells at least but not limited to polymorphonuclear leukocytes (PMN), purified neutrophils, peripheral blood mononuclear cells (PBMC), purified monocytes, eosinophils, and B lymphocytes ((Le Pouls et al., 2003, The Journal of Biological Chemistry, 278, 28, 25481-25489; Brown et al., 2003, The Journal of Biological Chemistry, 278, 13, 11312-11319; Stoddart et al., 2008, Pharmacological Reviews, 60, 405-417); and also in other tissues that may play a role in the propagation of the inflammatory response (e.g. intestinal cells or endothelial cells, Dass et al., 2007, Neurogastroenterl. Motil., 19:66-74; Karaki et al., 2006, Cell Tissue Res., 324/ 353-360). Recently, short chain fatty acids (SCFAs) have been shown to play a central role in the development of inflammatory conditions such as colitis, arthritis and asthma in a GPR43-dependent manner (K. M. Maslowski et al., 2009, Nature, 461, 1282-1287; C. Sina et al., 2009, The Journal of Immunology, 183:7514-7522). GPR43 knock-out (KO) mice were protected against chronic dextran sodium sulfate (DSS)-induced colitis. In a chronic DSS model, GPR43 KO mice presented less severe colon inflammation than wild-type (WT) mice, with a reduction of infiltrated polymorphonuclear leukocytes (PMN). The activity of granulocyte-specific MPO (myeloperoxidase) was reduced in GPR43 KO colon compared to WT colon, as well as TNFα levels. SCFA have been shown to induce neutrophil migration both in vitro with isolated neutrophilic granulocytes and in vivo in an inflamed air pouch model. GPR43 KO isolated neutrophilic granulocytes lost the ability to migrate in response to SCFAs, suggesting key function of GPR43 is neutrophilic granulocytes (C. Sina et al., 2009, The Journal of Immunology, 183: 7514-7522).

GPR43 KO mice were protected from high fat diet (HFD)-induced obesity and dyslipidemia (Bjursell et al., 2011, Am. J. Physiol. Endocrinol. Metab. 300:(11) E211-E220). GPR43 KO mice presented higher lean body mass and lower body fat mass than compared to WT mice. Plasma adiponectin levels were increased in GPR43 KO mice as compared to littermate controls. The liver of GPR43 KO mice showed reduced triglyceride content. Moreover, insulin sensitivity was improved by GPR43 gene ablation as GPR43 KO mice displayed lower insulin levels, but normal glucose levels, in the oral glucose tolerance test. In addition the reduced macrophage content in GPR43 KO adipose tissue compared to WT mice indicated a protection from HFD induced adipose inflammation. Finally, GPR43 KO mice were also found to be protected from HFD-induced hypercholesterolemia. The improved metabolic profile observed under HFD in GPR43-deficient mice is likely explained, at least in part, by an increase in energy expenditure.

GPR43 was recently implicated in carcinogenesis (Hatanaka et al., 2010, Cancer Sci., 101:54-59). GPR43 expression (both mRNA and protein) was increased in digestive tract cancer tissues compared to normal digestive tract tissues. 3T3 cells infected with recombinant retrovirus encoding GPR43 and treated with acetate shown a pronounced increase in proliferation. 3T3 cells infected with recombinant retrovirus encoding GPR43 were tested for tumorigenicity in athymic nude mice. Tumor formation was apparent with 4 tumors developed for 4 injections, similar to 3T3 cells infected with recombinant retrovirus encoding v-Ras (8/8 tumor/injection), but in opposition to 3T3 cells infected with empty virus (0/8 tumor/injection).

Therefore, the present invention provides novel compounds, processes for their preparation and their use in the preparation of a medicament for the treatment of inflammatory conditions, infectious diseases, autoimmune diseases, diseases involving impairment of immune cell functions, cardiometabolic diseases, and/or proliferative diseases.

SUMMARY OF THE INVENTION

The present invention relates to novel compounds that antagonize GPR43 and that are potentially useful for the treatment of inflammatory conditions, infectious diseases, autoimmune diseases, diseases involving impairment of immune cell functions, cardiometabolic diseases, and/or proliferative diseases. The present invention also provides methods for the production of these compounds, pharmaceutical compositions comprising these compounds and methods for treating inflammatory conditions, infectious diseases, autoimmune diseases, diseases involving impairment of immune cell functions, cardiometabolic diseases, and/or proliferative diseases, by administering a compound of the invention.

In a first aspect of the invention, a compound of the invention is provided having a Formula Ia:

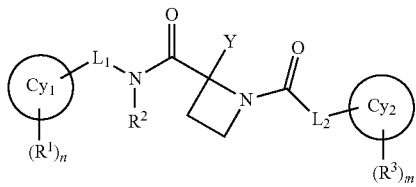

wherein
L$_1$ is a single bond, or CR$^a$R$^b$;
L$_2$ is a single bond, O, NR$^e$ or CR$^c$R$^d$;
each of R$^a$, R$^b$, R$^c$, and R$^d$ is independently selected from H, and C$_{1-4}$ alkyl; or
R$^a$ and R$^b$ together with the carbon to which they are attached may form a C$_{3-7}$ cycloalkyl; or
R$^c$ and R$^d$ together with the carbon to which they are attached may form a C$_{3-7}$ cycloalkyl;
R$^e$ is C$_{1-4}$ alkyl;
Y is
  C$_{1-4}$ alkyl optionally substituted with one or more groups independently selected from fluoro, OH, and phenyl (optionally substituted with one or more groups independently selected from C$_{1-4}$ alkyl (optionally substituted with one or more halo), C$_{1-4}$ alkoxy, halo and cyano), or
  C$_{1-4}$ alkenyl comprising 1 double bond;
each of Cy$_1$ and Cy$_2$ is independently C$_{6-10}$ aryl, or 5-10 membered heteroaryl;
each R$^1$ is independently selected from halo, C$_{1-4}$ alkyl (optionally substituted with one or more halo), and
  C$_{1-4}$ alkoxy (optionally substituted with one or more halo);
R$^2$ is:
  H,
  C$_{1-4}$ alkyl optionally substituted with one or more independently selected R$^{2a}$ groups,
  C$_{3-7}$ cycloalkyl optionally substituted with one or more independently selected R$^{2a}$ groups,
R$^{2a}$ is
  halo,
  C$_{1-6}$ alkoxy,
  OH,
  C(=O)R$^4$,
  S(O)$_2$R$^4$,
  CN,
  NHC(=O)R$^5$,
  NHSO$_2$R$^5$,
  5-7 membered heterocycloalkyl (optionally substituted with one or more groups independently selected from C$_{1-4}$ alkyl, and oxo), or
  5-6 membered heteroaryl (optionally substituted with one or more groups independently selected from halo, OH, C$_{1-4}$ alkoxy and C$_{1-4}$ alkyl);
R$^3$ is selected from halo, C$_{1-6}$ alkyl (optionally substituted with one or more halo), C$_{1-6}$ alkoxy (optionally substituted with one or more groups independently selected from halo or phenyl), C$_{1-6}$ thioalkoxy, phenyl (optionally substituted with one or more groups independently selected from halo, C$_{1-4}$ alkyl (optionally substituted with one or more halo), C$_{1-4}$ alkoxy, C(=O)—C$_{1-4}$ alkoxy and CN);
R$^4$ is
  OH,
  C$_{1-6}$ alkoxy,
  —N-linked 5-7 membered heterocycloalkyl (optionally substituted with one or more groups independently selected from C$_{1-6}$ alkyl, and oxo),
  NR$^{4a}$R$^{4b}$, or
  NHSO$_2$R$^{4c}$;
each of R$^{4a}$ and R$^{4b}$ is independently H, C$_{1-4}$ alkyl (optionally substituted with phenyl (optionally substituted with one or more groups independently selected from halo, CN, C$_{1-6}$ alkyl, and C$_{1-6}$ alkoxy)), or C$_{3-7}$ cycloalkyl;
R$^{4c}$ is phenyl, 5-6 membered heteroaryl, 5-6 membered heterocycloalkyl (optionally substituted with one or more C$_{1-4}$ alkyl) or C$_{1-4}$ alkyl (optionally substituted with one or more halo);
R$^5$ is C$_{1-4}$ alkyl (optionally substituted with one or more halo) or phenyl; and the subscripts n and m are independently selected from 0, 1, and 2.

In a further aspect of the invention, a compound of the invention is provided having a Formula Ib:

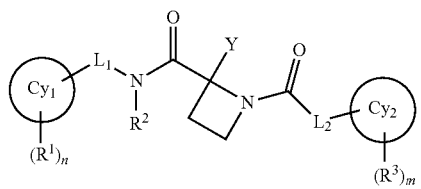

wherein
L$_1$ is a single bond, or CR$^a$R$^b$;
L$_2$ is a single bond, O, NR$^e$ or CR$^c$R$^d$;
each of R$^a$, R$^b$, R$^c$, and R$^d$ is independently selected from H, and C$_{1-4}$ alkyl; or
R$^a$ and R$^b$ together with the carbon to which they are attached may form a C$_{3-7}$ cycloalkyl; or
R$^c$ and R$^d$ together with the carbon to which they are attached may form a C$_{3-7}$ cycloalkyl;
R$^e$ is C$_{1-4}$ alkyl;
Y is C$_{1-4}$ alkyl optionally substituted with one or more groups independently selected from fluoro, OH, and phenyl (optionally substituted with one or more groups independently selected from C$_{1-4}$ alkyl (optionally substituted with one or more halo), C$_{1-4}$ alkoxy, halo and cyano);
each of Cy$_1$ and Cy$_2$ is independently C$_{6-10}$ aryl, or 5-10 membered heteroaryl;
each R$^1$ is independently selected from halo, C$_{1-4}$ alkyl (optionally substituted with one or more halo), and C$_{1-4}$ alkoxy (optionally substituted with one or more halo);
R$^2$ is:
  H,
  C$_{1-4}$ alkyl optionally substituted with one or more independently selected R$^{2a}$ groups,
  C$_{3-7}$ cycloalkyl optionally substituted with one or more independently selected R$^{2a}$ groups;
R$^{2a}$ is
  halo,
  C$_{1-6}$ alkoxy,
  OH,
  C(=O)R$^4$,
  S(O)$_2$R$^4$, CN,
NHC(=O)R$^5$,
NHSO$_2$R$^5$,
5-7 membered heterocycloalkyl (optionally substituted with one or more groups independently selected from C$_{1-4}$ alkyl, and oxo), or
5-6 membered heteroaryl (optionally substituted with one or more groups independently selected from halo, OH, C$_{1-4}$ alkoxy and C$_{1-4}$ alkyl);

R$^3$ is selected from halo, C$_{1-6}$ alkyl (optionally substituted with one or more halo), C$_{1-6}$ alkoxy (optionally substituted with one or more groups independently selected from halo or phenyl), phenyl (optionally substituted with one or more groups independently selected from halo, C$_{1-4}$ alkyl (optionally substituted with one or more halo), C$_{1-4}$ alkoxy, C(=O)—C$_{1-4}$ alkoxy and CN);

R$^4$ is
—OH,
—C$_{1-6}$ alkoxy,
—N-linked 5-7 membered heterocycloalkyl (optionally substituted with one or more groups independently selected from C$_{1-6}$ alkyl, and oxo),
—NR$^{4a}$R$^{4b}$, or
—NHSO$_2$R$^{4c}$;

each of R$^{4a}$ and R$^{4b}$ is independently H, C$_{1-4}$ alkyl (optionally substituted with phenyl (optionally substituted with one or more groups independently selected from halo, CN, C$_{1-6}$ alkyl, and C$_{1-6}$ alkoxy)), or C$_{3-7}$ cycloalkyl;

R$^{4c}$ is phenyl, 5-6 membered heteroaryl, 5-6 membered heterocycloalkyl (optionally substituted with one or more C$_{1-4}$ alkyl) or C$_{1-4}$ alkyl (optionally substituted with one or more halo);

R$^5$ is C$_{1-4}$ alkyl (optionally substituted with one or more halo) or phenyl; and the subscripts n and m are independently selected from 0, 1, and 2.

In a further aspect, the present invention provides pharmaceutical compositions comprising a compound of the invention, and a pharmaceutical carrier, excipient or diluent. Moreover, a compound of the present invention useful in the pharmaceutical compositions and treatment methods disclosed herein is pharmaceutically acceptable as prepared and used. In this aspect of the invention, the pharmaceutical composition may additionally comprise further active ingredients suitable for use in combination with a compound of the invention.

In another aspect of the invention, this invention provides novel compounds of the invention for use in therapy.

In a further aspect of the invention, this invention provides a method of treating a mammal susceptible to or afflicted with a condition from among those listed herein, and particularly, such condition as may be associated with aberrant GPR43 activity and/or aberrant GPR43 expression and/or distribution of GPR43, for example inflammatory conditions, infectious diseases, autoimmune diseases, diseases involving impairment of immune cell functions, cardiometabolic diseases, and/or proliferative diseases, which method comprises administering a therapeutically effective amount of a compound of the invention, or one or more of the pharmaceutical compositions herein described.

In a further aspect, the present invention provides a compound of the invention for use in the treatment or prevention of a condition selected from those listed herein, particularly such conditions as may be associated with aberrant GPR43 activity and/or aberrant GPR43 expression and/or distribution of GPR43 such as inflammatory conditions, infectious diseases, autoimmune diseases, diseases involving impairment of immune cell functions, cardiometabolic diseases, and/or proliferative diseases.

In additional aspects, this invention provides methods for synthesizing a compound of the invention, with representative synthetic protocols and pathways disclosed herein.

Accordingly, it is a principal object of this invention to provide a compound of the invention, which can modify the activity of GPR43 and thus prevent or treat any conditions that may be causally related thereto.

It is further an object of this invention to provide a compound of the invention in order to treat or alleviate conditions or diseases or symptoms of same, such as inflammatory conditions, infectious diseases, autoimmune diseases, diseases involving impairment of immune cell functions, cardiometabolic diseases, and/or proliferative diseases, that may be causally related to the activity and/or expression and/or distribution of GPR43.

A still further object of this invention is to provide pharmaceutical compositions that may be used in the treatment or prevention of a variety of disease states, including the diseases associated with aberrant GPR43 activity and/or aberrant GPR43 expression and/or distribution of GPR43 such as inflammatory conditions, infectious diseases, autoimmune diseases, diseases involving impairment of immune cell functions, cardiometabolic diseases, and/or proliferative diseases.

Other objects and advantages will become apparent to those skilled in the art from a consideration of the ensuing detailed description.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term 'substituted' is to be defined as set out below. It should be further understood that the terms 'groups' and 'radicals' can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Alkyl' means straight or branched aliphatic hydrocarbon having the specified number of carbon atoms. Particular alkyl groups have 1 to 6 carbon atoms or 1 to 4 carbon atoms. Branched means that one or more alkyl groups such as methyl, ethyl or propyl is attached to a linear alkyl chain. Particular alkyl groups are methyl, ethyl, n-propyl, isopropyl, n-butyl, tert-butyl, sec-butyl, n-pentyl, n-hexyl, and 1,2-dimethylbutyl. Particular alkyl groups have between 1 and 4 carbon atoms.

'Alkoxy' refers to the group O-alkyl where the alkyl group has the specified number of carbon atoms. Particularly alkoxy refers to —O—C$_1$-C$_6$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Amino' refers to the radical —NH$_2$.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes the number of ring members specified. Particular aryl groups have from 6 to 10 ring members. Where the aryl group is a monocyclic ring system it preferentially contains 6 carbon atoms. Particularly aryl groups include phenyl, naphthyl, indenyl, and tetrahydronaphthyl.

'Carbamoyl or amido' refers to the radical —C(O)NH$_2$.

'Carboxy' refers to the radical —C(O)OH.

'Cycloalkyl' refers to cyclic non-aromatic hydrocarbyl groups having the number of carbon atoms specified. Particular cycloalkyl groups have from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 5, and particularly from 1 to 3 heteroatoms.

'Heteroaryl' means an aromatic ring structure, mono-cyclic or polycyclic, that includes one or more heteroatoms and the number of ring members specified. Particular heteraryl groups have 5 to 10 ring members, or 5 to 6 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

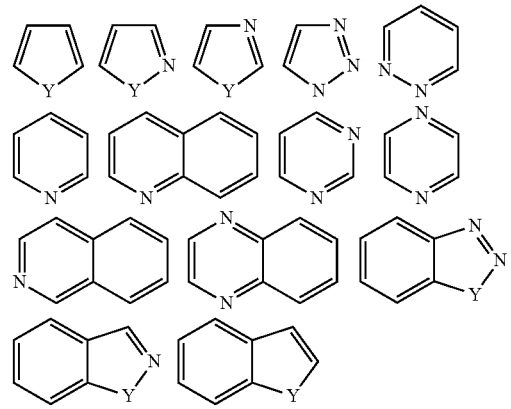

wherein each Y is selected from >C=O, N, O and S.

As used herein, the term 'heterocycloalkyl' refers to a stable heterocyclic non-aromatic ring and/or including rings containing one or more heteroatoms independently selected from N, O and S, fused thereto wherein the group contains the number of ring members specified. Particular heterocycloalkyl groups have 4-10 ring members or 5 to 7 ring members, or 5 to 6 ring members. The heterocycloalkyl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heterocycloalkyl ring will contain up to 4 heteroatoms, more typically up to 3 heteroatoms, more usually up to 2, for example a single heteroatom. In one embodiment, the heterocycloalkyl ring contains at least one ring nitrogen atom. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

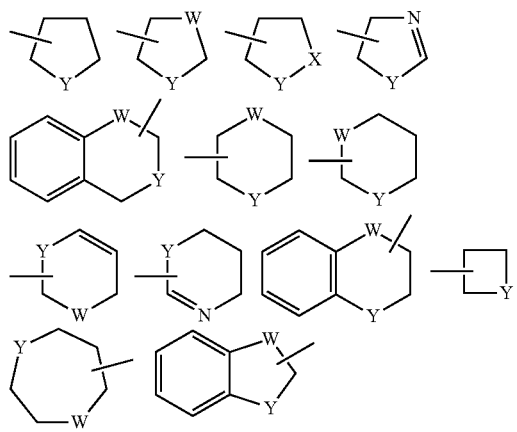

wherein each W is selected from $CH_2$, NH, O and S; and each Y is selected from NH, O, CO, $SO_2$, and S.

'Hydroxy' refers to the radical —OH.

'Nitro' refers to the radical —$NO_2$.

'Substituted' refers to a group in which one or more hydrogen atoms are each independently replaced with the same or different substituent(s).

'Thiol' refers to the group —SH.

'Thioalkoxy' refers to the group —Se where $R^{10}$ is an alkyl group with the number of carbon atoms specified. Particular thioalkoxy groups are where $R^{10}$ is a $C_1$-$C_6$ alkyl. Particular alkoxy groups are thiomethoxy, thioethoxy, n-thiopropoxy, thioisopropoxy, n-thiobutoxy, tert-thiobutoxy, sec-thiobutoxy, n-thiopentoxy, n-thiohexoxy, and 1,2-dimethylthiobutoxy. Particular thioalkoxy groups are lower thioalkoxy, i.e. with between 1 and 6 carbon atoms. Further particular thioalkoxy groups have between 1 and 4 carbon atoms.

As used herein, term 'substituted with one or more' refers to one to four substituents. In one embodiment it refers to one to three substituents. In further embodiments it refers to one or two substituents. In a yet further embodiment it refers to one substituent.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound of the invention that, when administered to a subject for treating a disease, is sufficient to effect such treatment for the disease. The "therapeutically effective amount" can vary depending on the compound, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein the term 'inflammatory condition(s)' refers to the group of conditions including, rheumatoid arthritis, osteoarthritis, juvenile idiopathic arthritis, psoriasis, gout, allergic airway disease (e.g. asthma, rhinitis), inflammatory bowel diseases (e.g. Crohn's disease, ulcerative colitis), endotoxin-driven disease states (e.g. complications after bypass surgery or chronic endotoxin states contributing to e.g. chronic cardiac failure), and related diseases involving cartilage, such as that of the joints. Particularly the term refers to rheumatoid arthritis, osteoarthritis, allergic airway disease (e.g. asthma) and inflammatory bowel diseases.

As used herein, the term 'infectious diseases' refers to bacterial infectious diseases and includes but is not limited to conditions such as sepsis, septicemia, endotoxemia, systemic inflammatory response syndrome (SIRS), gastritis, enteritis, enterocolitis, tuberculosis, and other infections involving *Yersinia, Salmonella, Chlamydia, Shigella*, or enterobacteria species.

As used herein the term 'autoimmune disease(s)' refers to the group of diseases including obstructive airways disease (including conditions such as COPD (Chronic obstructive pulmonary disease)), asthma (e.g intrinsic asthma, extrinsic asthma, dust asthma, infantily asthma) particularly chronic or inveterate asthma (for example late asthma and airway hyperreponsiveness), bronchitis, including bronchial asthma, systemic lupus erythematosus (SLE), multiple sclerosis, type I diabetes mellitus and complications associated therewith, atopic eczema (atopic dermatitis), contact dermatitis and further eczematous dermatitis, inflammatory bowel disease (e.g. Crohn's disease and ulcerative colitis), atherosclerosis and amyotrophic lateral sclerosis. Particularly the term refers to COPD, asthma, psoriasis, systemic lupus erythematosis, type I diabetes mellitus, vasculitis and inflammatory bowel disease.

As used herein, the term 'diseases involving impairment of immune cell functions' includes conditions with symptoms such as recurrent and drawn out viral and bacterial infections, and slow recovery. Other invisible symptoms may be the inability to kill off parasites, yeasts and bad bacteria in the intestines or throughout the body.

As used herein the term 'cardiometabolic disorders' refers to diseases or disorders of the internal body chemistry that triggers the body's metabolism. The term metabolic disorders usually does not include hormonal disorders or endocrine disorders which refer to the interactions between body glands and hormones, and includes but is not limited to conditions such as dyslipidemia, hypercholesterolemia, hypertriglyceridemia, Obesity, metabolic syndrome, atherosclerosis, Type II diabetes, pre-diabetes, insulin resistance, heart disease, stroke, hypertension, perivascular disease.

As used herein the term 'proliferative disease(s)' refers to conditions such as cancer, myeloproliferative disorders (e.g. polycythemia vera, essential thrombocytosis and myelofibrosis), leukemia, multiple myeloma, psoriasis, restenosis, sclerodermitis or fibrosis. In particular the term refers to cancer, leukemia, multiple myeloma and psoriasis.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types, such as but not limited to, melanoma, lymphoma, leukaemia, fibrosarcoma, rhabdomyosarcoma, and mastocytoma and types of tissue carcinoma, such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma.

As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML) and acute lymphoblastic leukemia (ALL).

As used herein the term 'degenerative disorders' refers to is a disease in which the function or structure of the affected tissues or organs will progressively deteriorate over time, whether due to normal bodily wear or lifestyle choices such as exercise or eating habits. Degenerative disorders include for example but without limitation, Amyotrophic lateral sclerosis (ALS), or Lou Gehrig's disease, Alzheimer's disease, Parkinson's disease, multiple system atrophy, Niemann Pick disease, atherosclerosis, progressive supranuclear palsy, cancer, Tay-Sachs disease, diabetes, heart disease, keratoconus, inflammatory bowel disease (IBD), prostatitis, osteoarthritis, osteoporosis, rheumatoid arthritis, Huntington's disease, or chronic traumatic encephalopathy. In particular, herein the term 'degenerative disorders' refers to diabetes inflammatory bowel disease (IBD), osteoarthritis, osteoporosis, or rheumatoid arthritis.

'Compound(s) of the invention', and equivalent expressions, are meant to embrace compounds of the Formula (e) as herein described, which expression includes the pharmaceutically acceptable salts, and the solvates, e.g., hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-6}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_1$ to $C_8$ alkyl, and substituted or unsubstituted $C_{6-10}$ aryl, esters of the compounds of the invention.

As used herein, the term 'isotopic variant' refers to a compound that contains unnatural proportions of isotopes at one or more of the atoms that constitute such compound For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radio-isotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Calm and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

The present invention relates to novel compounds that antagonize GPR43 and that may be potentially useful for the treatment of inflammatory conditions, infectious diseases, autoimmune diseases, diseases involving impairment of immune cell functions, cardiometabolic diseases, and/or proliferative diseases. The present invention also provides methods for the production of the compounds of the invention, pharmaceutical compositions comprising the compounds of the invention and methods for treating diseases involving inflammatory conditions, infectious diseases, autoimmune diseases, diseases involving impairment of immune cell functions, cardiometabolic diseases, and/or proliferative diseases by administering a compound of the invention. A compound of the invention is an inhibitor of GPR43.

In a first aspect of the invention, a compound of the invention is provided having a Formula Ia:

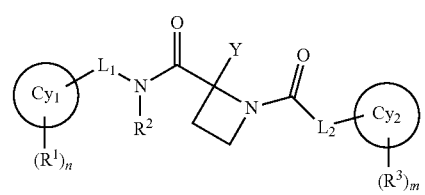

Ia wherein
$L_1$ is a single bond, or $CR^aR^b$;
$L_2$ is a single bond, O, $NR^e$ or $CR^cR^d$;
each of $R^a$, $R^b$, $R^c$, and $R^d$ is independently selected from H, and $C_{1-4}$ alkyl; or
$R^a$ and $R^b$ together with the carbon to which they are attached may form a $C_{3-7}$ cycloalkyl; or
$R^c$ and $R^d$ together with the carbon to which they are attached may form a $C_{3-7}$ cycloalkyl;
$R^e$ is $C_{1-4}$ alkyl;
Y is
  $C_{1-4}$ alkyl optionally substituted with one or more groups independently selected from fluoro, OH, and phenyl (optionally substituted with one or more groups independently selected from $C_{1-4}$ alkyl (optionally substituted with one or more halo), $C_{1-4}$ alkoxy, halo and cyano), or
  $C_{1-4}$ alkenyl comprising 1 double bond;
each of $Cy_1$ and $Cy_2$ is independently $C_{6-10}$ aryl, or 5-10 membered heteroaryl;

each R¹ is independently selected from halo, $C_{1-4}$ alkyl (optionally substituted with one or more halo), and $C_{1-4}$ alkoxy (optionally substituted with one or more halo);

R² is:
H,
$C_{1-4}$ alkyl optionally substituted with one or more independently selected $R^{2a}$ groups,
$C_{3-7}$ cycloalkyl optionally substituted with one or more independently selected $R^{2a}$ groups, $R^{2a}$ is
halo,
$C_{1-6}$ alkoxy,
OH,
$C(=O)R^4$,
$S(O)_2R^4$,
CN,
$NHC(=O)R^5$,
$NHSO_2R^5$,
5-7 membered heterocycloalkyl (optionally substituted with one or more groups independently selected from $C_{1-4}$ alkyl, and oxo), or
5-6 membered heteroaryl (optionally substituted with one or more groups independently selected from halo, OH, $C_{1-4}$ alkoxy and $C_{1-4}$ alkyl);

R³ is selected from halo, $C_{1-6}$ alkyl (optionally substituted with one or more halo), $C_{1-6}$ alkoxy (optionally substituted with one or more groups independently selected from halo or phenyl), $C_{1-6}$ thioalkoxy, phenyl (optionally substituted with one or more groups independently selected from halo, $C_{1-4}$ alkyl (optionally substituted with one or more halo), $C_{1-4}$ alkoxy, $C(=O)$—$C_{1-4}$ alkoxy and CN);

R⁴ is
—OH,
$C_{1-6}$ alkoxy,
—N-linked 5-7 membered heterocycloalkyl (optionally substituted with one or more groups independently selected from $C_{1-6}$ alkyl, and oxo),
$NR^{4a}R^{4b}$, or
—$NHSO_2R^{4c}$;

Each of $R^{4a}$ and $R^{4b}$ is independently H, $C_{1-4}$ alkyl (optionally substituted with phenyl (optionally substituted with one or more groups independently selected from halo, CN, $C_{1-6}$ alkyl, and $C_{1-6}$ alkoxy)), or $C_{3-7}$ cycloalkyl;

$R^{4c}$ is phenyl, 5-6 membered heteroaryl, 5-6 membered heterocycloalkyl (optionally substituted with one or more $C_{1-4}$ alkyl) or $C_{1-4}$ alkyl (optionally substituted with one or more halo);

R⁵ is $C_{1-4}$ alkyl (optionally substituted with one or more halo) or phenyl; and the subscripts n and m are independently selected from 0, 1, and 2.

In a further aspect of the invention, a compound of the invention is disclosed having a Formula Ib:

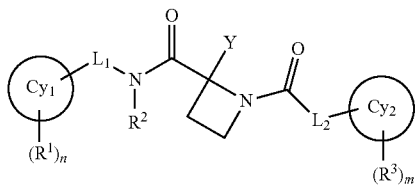

wherein
$L_1$ is a single bond, or $CR^aR^b$;
$L_2$ is a single bond, O, $NR^e$ or $CR^cR^d$;

each of $R^a$, $R^b$, $R^c$, and $R^d$ is independently selected from H, and $C_{1-4}$ alkyl; or
$R^a$ and $R^b$ together with the carbon to which they are attached may form a $C_{3-7}$ cycloalkyl; or
$R^c$ and $R^d$ together with the carbon to which they are attached may form a $C_{3-7}$ cycloalkyl;
$R^e$ is $C_{1-4}$ alkyl;
Y is $C_{1-4}$ alkyl optionally substituted with one or more groups independently selected from fluoro, OH, and phenyl (optionally substituted with one or more groups independently selected from $C_{1-4}$ alkyl (optionally substituted with one or more halo), $C_{1-4}$ alkoxy, halo and cyano);
each of $Cy_1$ and $Cy_2$ is independently $C_{6-10}$ aryl, or 5-10 membered heteroaryl;
each R¹ is independently selected from halo, $C_{1-4}$ alkyl (optionally substituted with one or more halo), and
$C_{1-4}$ alkoxy (optionally substituted with one or more halo);

R² is:
H,
$C_{1-4}$ alkyl optionally substituted with one or more independently selected $R^{2a}$ groups,
$C_{3-7}$ cycloalkyl optionally substituted with one or more independently selected $R^{2a}$ groups, $R^{2a}$ is
halo,
$C_{1-6}$ alkoxy,
OH,
$C(=O)R^4$,
$S(O)_2R^4$,
CN,
$NHC(=O)R^5$,
$NHSO_2R^5$,
5-7 membered heterocycloalkyl (optionally substituted with one or more groups independently selected from $C_{1-4}$ alkyl, and oxo), or
5-6 membered heteroaryl (optionally substituted with one or more groups independently selected from halo, OH, $C_{1-4}$ alkoxy and $C_{1-4}$ alkyl);

R³ is selected from halo, $C_{1-6}$ alkyl (optionally substituted with one or more halo), $C_{1-6}$ alkoxy (optionally substituted with one or more groups independently selected from halo or phenyl), phenyl (optionally substituted with one or more groups independently selected from halo, $C_{1-4}$ alkyl (optionally substituted with one or more halo), $C_{1-4}$ alkoxy, $C(=O)$—$C_{1-4}$ alkoxy and CN);

R⁴ is
—OH,
—$C_{1-6}$ alkoxy,
—N-linked 5-7 membered heterocycloalkyl (optionally substituted with one or more groups independently selected from $C_{1-6}$ alkyl, and oxo),
—$NR^{4a}R^{4b}$ or
—$NHSO_2R^{4c}$;

Each of $R^{4a}$ and $R^{4b}$ is independently H, $C_{1-4}$ alkyl (optionally substituted with phenyl (optionally substituted with one or more groups independently selected from halo, CN, $C_{1-6}$ alkyl, and $C_{1-6}$ alkoxy)), or $C_{3-7}$ cycloalkyl;

$R^{4c}$ is phenyl, 5-6 membered heteroaryl, 5-6 membered heterocycloalkyl (optionally substituted with one or more $C_{1-4}$ alkyl) or $C_{1-4}$ alkyl (optionally substituted with one or more halo);

R⁵ is $C_{1-4}$ alkyl (optionally substituted with one or more halo) or phenyl; and the subscripts n and m are independently selected from 0, 1, and 2.

In one embodiment, a compound of the invention is according to Formula Ia or Ib, wherein $L_2$ is a single bond, $NR^e$ or $CR^cR^d$.

In one embodiment, a compound according to Formula Ia or Ib is according to Formula II:

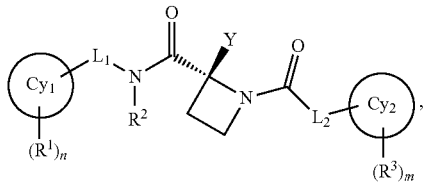

wherein $L_1$, $L_2$, $R^1$, $R^2$, $R^3$, $Cy^1$, $Cy^2$, $R^a$, $R^b$, $R^c$, $R^d$, $R^e$, Y, n, and m are as described above.

In one embodiment, a compound of the invention is according to Formula Ia, Ib, or II, wherein $L_1$ is a single bond.

In another embodiment, a compound of the invention is according to Formula Ia, Ib or II, wherein $L_1$ is $CR^aR^b$, and wherein each $R^a$ and $R^b$ group is independently selected from H and $C_{1-4}$ alkyl. In a particular embodiment, each $R^a$ and $R^b$ group is independently selected from H, Me, Et, Pr, and iPr.

In another embodiment, a compound of the invention is according to Formula Ia, Ib, or II, wherein $L_1$ is $CR^aR^b$, and wherein $R^a$ is H or $C_{1-4}$ alkyl and $R^b$ is H. In a particular embodiment, $R^a$ is H, Me, Et, or Pr, and $R^b$ is H. In more particular embodiment, $R^a$ and $R^b$ are both H.

In one embodiment, a compound of the invention is according to Formula Ia, Ib, or II, wherein Y is $C_{1-4}$ alkyl optionally substituted with one or more groups independently selected from fluoro, OH, and phenyl (optionally substituted with one or more $C_{1-4}$ alkyl (optionally substituted with one ore more halo), $C_{1-4}$ alkoxy, halo or cyano). In a particular embodiment, Y is $C_{1-4}$ alkyl optionally substituted with one group selected from fluoro, OH, and phenyl (optionally substituted with one or more $C_{1-4}$ alkyl (optionally substituted with one or more halo), $C_{1-4}$ alkoxy, halo or cyano).

In another embodiment, compound of the invention is according to Formula Ia, Ib, or II, wherein Y is $C_{1-4}$ alkyl substituted with one or more groups independently selected from fluoro, OH, and phenyl (optionally substituted with one or more $C_{1-4}$ alkyl (optionally substituted with one ore more halo), alkoxy, halo or cyano). In a particular embodiment, Y is $C_{1-4}$ alkyl substituted with one group selected from fluoro, OH, and phenyl (optionally substituted with one or more $C_{1-4}$ alkyl (optionally substituted with one ore more halo), $C_{1-4}$ alkoxy, halo or cyano). In a more particular embodiment, Y is Me, Et, Pr or iPr, substituted with one or more groups selected from fluoro, OH, and phenyl (optionally substituted with one or more $C_{1-4}$ alkyl (optionally substituted with one ore more halo), $C_{1-4}$ alkoxy, halo or cyano). In a further particular embodiment, Y is Me, substituted with OH, or phenyl (optionally substituted with one or more $C_{1-4}$ alkyl (optionally substituted with one ore more halo), $C_{1-4}$ alkoxy, halo or cyano). In a most particular embodiment, Y is —CH$_2$-Ph or —CH$_2$—OH. In a further most particular embodiment, Y is —CH$_2$-Ph.

In one embodiment, a compound of the invention is according to Formula Ia, Ib, or II, wherein Y is $C_{1-4}$ alkyl. In a most particular embodiment, Y is Me, Et, Pr, or iPr. In a further most particular embodiment, Y is Me.

In one embodiment, a compound of the invention is according to Formula Ia, Ib, or II, wherein $Cy_1$ is $C_{6-10}$ aryl. In a particular embodiment, $Cy_1$ is phenyl or naphthyl. In a most particular embodiment, $Cy_1$ is phenyl.

In one embodiment, a compound of the invention is according to Formula Ia, Ib, or II, wherein the subscript n is 1 or 2. In a particular embodiment, the subscript n is 1 or 2, and each $R^1$ group is independently selected from halo, and $C_{1-4}$ alkyl optionally substituted with one or more halo. In a more particular embodiment, the subscript n is 1 or 2, and each $R^1$ group is independently selected from F, Cl, Me, Et, iPr, i-Bu, t-Bu and CF$_3$.

In another embodiment, a compound of the invention is according to Formula Ia, Ib, or II, wherein the subscript n is 1. In a particular embodiment, the subscript n is 1, and each $R^1$ group is independently selected from halo, and $C_{1-4}$ alkyl optionally substituted with one or more halo. In a more particular embodiment, the subscript n is 1, and $R^1$ group is independently selected from F, Cl, Me, Et, iPr, and CF$_3$. In a most particular embodiment, the subscript n is 1, and $R^1$ group is Cl or CF$_3$. In a further most particular embodiment, the subscript n is 1 and $R^1$ group is Cl.

In another embodiment, a compound of the invention is according to Formula Ia, Ib, or II, the subscript n is 1, and $R^1$ group is OCF$_3$.

In one embodiment, a compound of the invention is according to Formula Ia, Ib, or II, wherein $Cy_1$ is 5-10 membered heteroaryl. In a particular embodiment, $Cy_1$ is benzofuranyl, benzothiophenyl, indazolyl, indolyl, or benzothiazolyl.

In one embodiment, a compound of the invention is according to Formula Ia, Ib, or II, wherein $Cy_1$ is $C_{6-10}$ aryl, and the subscript n is 0. In a particular embodiment, $Cy_1$ is phenyl or naphthyl, and the subscript n is 0.

In one embodiment, a compound of the invention is according to Formula Ia, Ib, or II, wherein $Cy_1$ is 5-10 membered heteroaryl, and the subscript n is 0. In a particular embodiment, $Cy_1$ is benzofuranyl, benzothiophenyl, indazolyl, indolyl, or benzothiazolyl, and the subscript n is 0.

In one embodiment, a compound of the invention is according to Formula Ia, Ib or II, wherein the compound is according to Formula IIIa or IIIb:

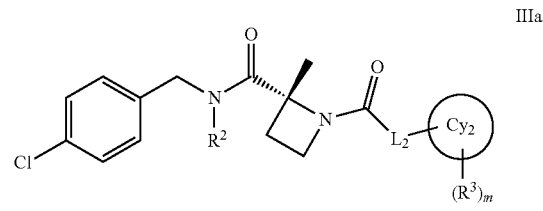

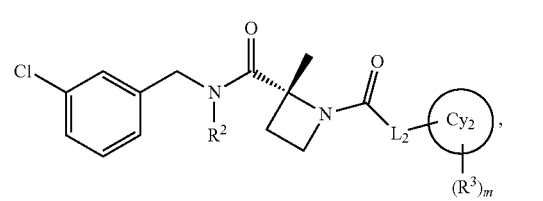

wherein $R^2$, $L_2$, $Cy_2$, $R^3$ and m are as described in any one of the embodiments above.

In one embodiment, a compound of the invention is according to any one of Formulae Ia-IIIb, wherein $R^2$ is H.

In one embodiment, a compound of the invention is according to any one of Formulae Ia-IIIb, wherein $R^2$ is $C_{1-4}$ alkyl optionally substituted with one or more independently selected $R^{2a}$ groups. In a particular embodiment, $R^2$ is $C_{1-4}$ alkyl optionally substituted with one $R^{2a}$ group. In a particular embodiment, $R^2$ is $C_{1-4}$ alkyl. In a more particular embodiment, $R^2$ is Me, Et, Pr, iPr, Bu, or iBu. In an even more particular embodiment, $R^2$ is Me.

In a further embodiment, a compound of the invention is according to any one of Formulae Ia-IIIb, wherein $R^2$ is $C_{1-4}$ alkyl substituted with one or more independently selected $R^{2a}$ groups. In a particular embodiment, $R^2$ is $C_{1-4}$ alkyl substituted with one $R^{2a}$ group. In a more particular embodiment, $R^2$ is Me, Et, Pr, iPr, Bu, or iBu, each of which is substituted with one or more $R^{2a}$ groups. In a most particular embodiment, $R^2$ is Me, Et, Pr, iPr, Bu, or iBu, each of which is substituted with one $R^{2a}$ group.

In an even further embodiment, a compound of the invention is according to any one of Formulae wherein $R^2$ is $C_{1-4}$ alkyl substituted with one or more independently selected $R^{2a}$ groups, wherein $R^{2a}$ is OH, CN, or $C_{1-6}$ alkoxy. In a particular embodiment, $R^2$ is $C_{1-4}$ alkyl substituted with one $R^{2a}$ group, wherein $R^{2a}$ is OH, CN, or $C_{1-6}$ alkoxy. In a more particular embodiment, $R^2$ is Me, Et, Pr, iPr, Bu, or iBu, each of which is substituted with one or more $R^{2a}$ groups, wherein $R^{ea}$ is OH, CN, or $C_{1-6}$ alkoxy. In a most particular embodiment, $R^2$ is Me, Et, Pr, iPr, Bu, or iBu, each of which is substituted with one $R^{2a}$ group, wherein $R^{2a}$ is OH, CN, or $C_{1-6}$ alkoxy. In an even most particular embodiment, $R^2$ is Me, Et, Pr, iPr, Bu, or iBu, each of which is substituted with one $R^{2a}$ group, wherein $R^{ea}$ is OH, CN, or OMe. In a further even most particular embodiment, $R^2$ is —$CH_2$—CN, —$(CH_2)_2$—OH, —$(CH_2)_2$—CN, —$(CH_2)_2$—OMe, —$CH_2$—$CH(CH_3)$—OH, or —$(CH_2)_3$—OH.

In an even further embodiment, a compound of the invention is according to any one of Formulae wherein $R^2$ is $C_{1-4}$ alkyl substituted with one or more independently selected $R^{2a}$ groups, wherein $R^{2a}$ is $COR^4$. In a particular embodiment, $R^2$ is $C_{1-4}$ alkyl substituted with one $R^{2a}$ group, wherein $R^{2a}$ is $C(=O)R^4$. In a more particular embodiment, $R^2$ is Me, Et, Pr, iPr, Bu, or iBu, each of which is substituted with one $R^{2a}$ group, wherein $R^{2a}$ is $C(=O)R^4$. In a most particular embodiment, $R^2$ is Me, Et, Pr, iPr, Bu, or iBu, each of which is substituted with one $R^{2a}$ group, wherein $R^{2a}$ is $C(=O)R^4$.

In one embodiment, a compound of the invention is according to any one of Formulae wherein $R^2$ is $C_{1-4}$ alkyl substituted with one or more independently selected $R^{2a}$ groups, wherein $R^{2a}$ is $C(=O)R^4$, wherein $R^4$ is OH, or $C_{1-6}$ alkoxy. In a particular embodiment, $R^2$ is $C_{1-4}$ alkyl substituted with one $R^{2a}$ group, wherein $R^{2a}$ is $C(=O)R^4$, wherein $R^4$ is OH, or $C_{1-6}$ alkoxy. In a more particular embodiment, $R^2$ is $C_{1-4}$ alkyl substituted with one $R^{2a}$ group, wherein $R^{2a}$ is $C(=O)R^4$, wherein $R^4$ is OH, or OMe, or OEt. In an even more particular embodiment, $R^2$ is $C_{1-4}$ alkyl substituted with one $R^{2a}$ group, wherein $R^{2a}$ is —$C(=O)R^4$, wherein $R^4$ is OH.

In one embodiment, a compound of the invention is according to any one of Formulae wherein $R^2$ is $C_{1-4}$ alkyl substituted with one or more independently selected $R^{2a}$ groups, wherein $R^{2a}$ is $C(=O)R^4$, and $R^4$ is $NR^{4a}R^{4b}$. In a particular embodiment, $R^2$ is $C_{1-4}$ alkyl substituted with one $R^{2a}$ group, wherein $R^{2a}$ is $C(=O)R^4$, and $R^4$ is $NR^{4a}R^{4b}$. In a particular embodiment, each of $R^{4a}$ and $R^{4b}$ is independently selected from H, $C_{3-7}$ cycloalkyl or $C_{1-4}$ alkyl. In a most particular embodiment, each of $R^{4a}$ and $R^{4b}$ is independently selected from H, cyclopropyl, Me, Et, Pr, or iPr.

In one embodiment, a compound of the invention is according to any one of Formulae wherein $R^2$ is $C_{1-4}$ alkyl substituted with one or more independently selected $R^{2a}$ groups, wherein $R^{2a}$ is $C(=O)R^4$, wherein $R^4$ is $NHSO_2R^{4c}$. In a particular embodiment, $R^2$ is $C_{1-4}$ alkyl substituted with one $R^{2a}$ group, wherein $R^{ea}$ is $C(=O)R^4$, and $R^4$ is $NHSO_2R^{4c}$. In a more particular embodiment, $R^{4c}$ is phenyl, 5-6 membered heteroaryl, 5-6 membered heterocycloalkyl (optionally substituted with one or more $C_{1-4}$ alkyl) or $C_{1-4}$ alkyl (optionally substituted with one or more halo). In a most particular embodiment, $R^{4c}$ is Me, phenyl or $CF_3$.

In one embodiment, a compound of the invention is according to any one of Formulae wherein $R^2$ is $C_{1-4}$ alkyl substituted with one or more independently selected $R^{2a}$ groups, wherein $R^{2a}$ is $S(O)_2R^4$. In a particular embodiment, a compound of the invention is according to any one of Formulae I-IIIb, wherein $R^2$ is $C_{1-4}$ alkyl substituted with one $R^{2a}$ group, wherein $R^{2a}$ is $S(O)_2R^4$. In a more particular embodiment, $R^4$ is N-linked 5-7 membered heterocycloalkyl (optionally substituted with one or more groups independently selected from $C_{1-6}$ alkyl, or oxo). In a most particular embodiment, $R^4$ is pyrrolidinyl, piperidinyl, piperazinyl, morpholinyl, or thiomorpholinyl, each of which is optionally substituted with one or more independently selected $C_{1-6}$ alkyl, or oxo.

In one embodiment, a compound of the invention is according to any one of Formulae Ia-IIIb, wherein $R^2$ is $C_{1-4}$ alkyl substituted with one or more independently selected $R^{2a}$ groups, wherein $R^{2a}$ is $S(O)_2R^4$. In a particular embodiment, a compound of the invention is according to any one of Formulae I-IIIb, wherein $R^2$ is $C_{1-4}$ alkyl substituted with one $R^{2a}$ group, wherein $R^{2a}$ is $S(O)_2R^4$. In a more particular embodiment, $R^4$ is $NR^{4a}R^{4b}$, wherein each of $R^{4a}$ and $R^{4b}$ is independently selected from H, or $C_{1-4}$ alkyl. In a most particular embodiment, $R^4$ is —$NH_2$, NHMe, or $NMe_2$.

In one embodiment, a compound of the invention is according to any one of Formulae Ia-IIIb, wherein $R^2$ is $C_{1-4}$ alkyl substituted with one or more 5-6 membered heteroaryl (optionally substituted with one or more groups independently selected from halo, OH, $C_{1-4}$ alkoxy and $C_{1-4}$ alkyl). In a particular embodiment, $R^2$ is $C_{1-4}$ alkyl substituted with one group selected from:

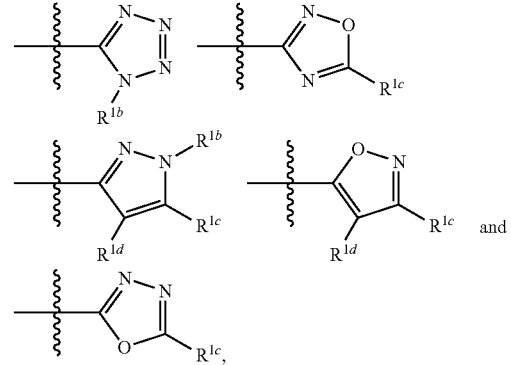

wherein $R^{1b}$ is H, or $C_{1-4}$ alkyl; $R^{1c}$ is OH, or $C_{1-4}$ alkoxy; and $R^{1d}$ is H, F, or $C_{1-4}$ alkyl.

In one embodiment, a compound of the invention is according to any one of Formulae Ia-IIIb, wherein $R^{1b}$ is H, Me, or Et.

In one embodiment, a compound of the invention is according to any one of Formulae Ia-IIIb, wherein $R^{1c}$ is OH, OMe, or OEt.

In one embodiment, a compound of the invention is according to any one of Formulae Ia-IIIb, wherein $R^{1d}$ is H, F, Me, or Et.

In a particular embodiment, a compound of the invention is according to any one of Formulae Ia-IIIb, wherein $R^2$ is —$CH_2$—COOH, —$CH_2$—COOMe, —$CH_2$—COOEt, —$(CH_2)_2$—COOH, —$(CH_2)_2$—COOMe, —$(CH_2)_3$—

COOH, —(CH$_2$)$_3$—SO$_2$NH$_2$, or —(CH$_2$)$_3$—SO$_2$NHMe. In a more particular embodiment, R$^2$ is —(CH$_2$)—COOH, —(CH$_2$)$_3$—COOH, —(CH$_2$)$_3$—SO$_2$NH$_2$, or —(CH$_2$)$_3$—SO$_2$NHMe.

In one embodiment, a compound of the invention is according to Formula Ia-IIIb, wherein R$^2$ is —CH$_2$—CN, —(CH$_2$)$_2$—CN, or —(CH$_2$)$_3$—CN.

In one embodiment, a compound of the invention is according to Formula Ia-IIIb, wherein R$^2$ is —CH$_2$—CONHMe, —(CH$_2$)$_2$—CONHMe, or —(CH$_2$)$_3$—CONHMe.

In one embodiment, a compound of the invention is according to Formula Ia-IIIb, wherein R$^2$ is —CH$_2$—CONMe$_2$, —(CH$_2$)$_2$—CONMe$_2$, or —(CH$_2$)$_3$—CONMe$_2$.

In one embodiment, a compound of the invention is according to Formula Ia-IIIb, wherein R$^2$ is —CH$_2$—OMe, —(CH$_2$)$_2$—OMe, or —(CH$_2$)$_3$—OMe.

In one embodiment, a compound of the invention is according to Formula Ia-IIIb, wherein R$^2$ is —CH$_2$—NHSO$_2$Me, —(CH$_2$)$_2$—NHSO$_2$Me, or —(CH$_2$)$_3$—NHSO$_2$Me.

In one embodiment, a compound of the invention is according to any one of Formulae Ia-IIIb, wherein Cy$_2$ is C$_{6-10}$ aryl. In a particular embodiment, Cy$_2$ is phenyl, or naphthalene. In a more particular embodiment, Cy$_2$ is phenyl.

In one embodiment, a compound of the invention is according to any one of Formulae Ia-IIIb, wherein Cy$_2$ is 5-10 membered heteroaryl. In a particular embodiment, Cy$_2$ is thiophenyl, benzothiophenyl, benzofuranyl, benzoisoxazolyl, benzoxazolyl, or indolyl.

In one embodiment, a compound of the invention is according to any one of Formulae Ia-IIIb, wherein the subscript m is 1 or 2. In a particular embodiment, the subscript m is 1 or 2, and each R$^3$ group is independently selected from halo, C$_{1-6}$ alkyl (optionally substituted with one or more halo), C$_{1-6}$ alkoxy (optionally substituted with one or more halo, or phenyl), phenyl or CN. In a more particular embodiment, the subscript m is 1 or 2, and each R$^3$ group is independently selected from F, Cl, Br, Me, CF$_3$, and OMe.

In one embodiment, a compound of the invention is according to any one of Formulae Ia-IIIb, wherein the subscript m is 1. In a particular embodiment, the subscript m is 1, and R$^3$ group is a phenyl optionally substituted with one or more groups independently selected from halo, C$_{1-4}$ alkyl (optionally substituted with one or more halo), CN, C$_{1-6}$ alkoxy, and C(=O)—C$_{1-4}$ alkoxy. In a more particular embodiment, the subscript m is 1, and R$^3$ is selected from phenyl, 4-F-phenyl, 3-Cl-phenyl, 3-CN-phenyl, 4-CN-phenyl, 4-OMe-phenyl, 2-Me-phenyl, 2-CF$_3$-phenyl, and 3-COOMe-phenyl.

In one embodiment, a compound of the invention is according to any one of Formulae Ia-IIIb, wherein the subscript m is 0.

In one embodiment, a compound of the invention is according to any one of Formulae Ia-IIIb, wherein L$_2$ is a single bond.

In one embodiment, a compound of the invention is according to any one of Formulae Ia-IIIb, wherein L$_2$ is —CR$^c$R$^d$—, wherein each of R$^c$ and R$^d$ are independently selected from H, or C$_{1-4}$ alkyl. In a particular embodiment, L$_2$ is —CR$^c$R$^d$—, and each of R$^c$ and R$^d$ are independently selected from H, Me, and Et. In another particular embodiment, L$_2$ is —CR$^c$R$^d$—, wherein R$^c$ is H, and R$^d$ is selected from H, or C$_{1-4}$ alkyl. In a more particular embodiment, L$_2$ is —CR$^c$R$^d$—, wherein R$^c$ is H, and R$^d$ is selected from H, Me, and Et. In a most particular embodiment, L$_2$ is —CH$_2$—.

In one embodiment, a compound of the invention is according to any one of Formulae Ia-IIIb, wherein L$_2$ is wherein R$^c$ and R$^d$ together with the carbon on which they are attached, form a C$_{3-7}$ cycloalkyl ring. In a particular embodiment, L$_2$ is —CR$^c$R$^d$—, wherein R$^c$ and R$^d$ together with the carbon on which they are attached, form a cyclopropyl ring.

In one embodiment, a compound of the invention is according to Formula Ia-IIIb, wherein L$_2$ is

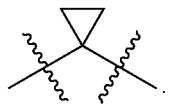

In one embodiment, a compound of the invention is according to any one of Formulae Ia-IIIb, wherein L$_2$ is —O—.

In one embodiment, a compound of the invention is according to any one of Formulae Ia-IIIb, wherein L$_2$ is —NR$^e$, wherein R$^e$ is C$_{1-4}$ alkyl. In a particular embodiment, R$^e$ is Me, Et, Pr, iPr. In a more particular embodiment, R$^e$ is Me.

In one embodiment, a compound of the invention is according to any one of Formulae Ia-IIIb, wherein the compound is according to Formula IVa, IVb, IVc, or IVd:

IVa
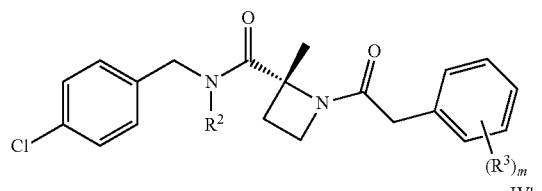

IVb
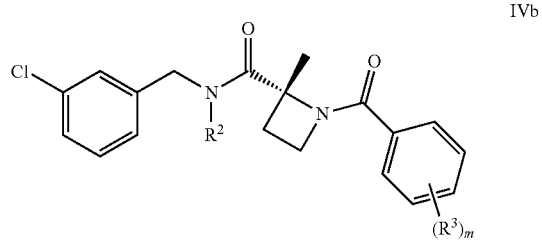

IVc
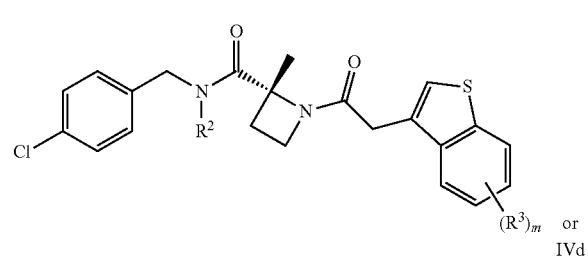

or
IVd
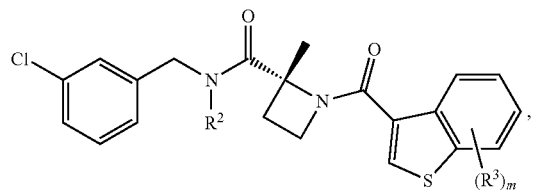

wherein R$^2$, R$^3$, and m are as described in any one of the embodiments above.

In one embodiment, a compound of the invention is according to Formula IVa-IVd, wherein the subscript m is 1 and R$^3$ is Cl.

In one embodiment, a compound of the invention is according to Formula IVa-IVd, wherein the subscript m is 0.

In one embodiment, a compound of the invention is according to any one of Formulae I-IVd, wherein $R^2$ is —$CH_2$—COOH, —$(CH_2)_2$—COOH, or —$(CH_2)_3$—COOH.

In one embodiment, a compound of the invention is selected from the following compounds:

1-[2-(2,4-Dichloro-phenyl)-acetyl]-2-methyl-azetidine-2-carboxylic acid 4-chloro-benzylamide,
2-(4-Chloro-benzylcarbamoyl)-2-methyl-azetidine-1-carboxylic acid 4-chloro-phenyl ester,
1-[2-(3,5-Dimethyl-phenyl)-acetyl]-2-methyl-azetidine-2-carboxylic acid (4-chloro-benzyl)-methyl-amide,
1-[2-(2,4-Dichloro-phenyl)-acetyl]-2-methyl-azetidine-2-carboxylic acid (4-chloro-phenyl)-amide,
1-[2-(3,5-Dimethyl-phenyl)-acetyl]-2-methyl-azetidine-2-carboxylic acid (3-chloro-benzyl)-methyl-amide,
1-[2-(3,5-Dimethyl-phenyl)-acetyl]-2-methyl-azetidine-2-carboxylic acid methyl-(4-methyl-benzyl)-amide,
1-[2-(3,5-Dimethyl-phenyl)-acetyl]-2-methyl-azetidine-2-carboxylic acid methyl-(4-trifluoromethyl-benzyl)-amide,
1-[2-(3-Iodo-phenyl)-acetyl]-2-methyl-azetidine-2-carboxylic acid (4-chloro-benzyl)-methyl-amide,
1-[2-(2-Chloro-phenyl)-acetyl]-2-methyl-azetidine-2-carboxylic acid (4-chloro-benzyl)-methyl-amide,
1-[2-(3-Chloro-phenyl)-acetyl]-2-methyl-azetidine-2-carboxylic acid (4-chloro-benzyl)-methyl-amide,
1-[2-(4-Chloro-phenyl)-acetyl]-2-methyl-azetidine-2-carboxylic acid (4-chloro-benzyl)-methyl-amide,
1-[2-(3,4-Difluoro-phenyl)-acetyl]-2-methyl-azetidine-2-carboxylic acid (4-chloro-benzyl)-methyl-amide,
1-(2-Benzo[b]thiophen-3-yl-acetyl)-2-methyl-azetidine-2-carboxylic acid (4-chloro-benzyl)-methyl-amide,
2-Methyl-1-(2-naphthalen-2-yl-acetyl)-azetidine-2-carboxylic acid (4-chloro-benzyl)-methyl-amide,
1-[2-(4'-Fluoro-biphenyl-4-yl)-acetyl]-2-methyl-azetidine-2-carboxylic acid (4-chloro-benzyl)-methyl-amide,
1-[2-(2-Benzyloxy-phenyl)-acetyl]-2-methyl-azetidine-2-carboxylic acid (4-chloro-benzyl)-methyl-amide,
1-[2-(2-Iodo-phenyl)-acetyl]-2-methyl-azetidine-2-carboxylic acid (4-chloro-benzyl)-methyl-amide,
1-[2-(3,4-Dichloro-phenyl)-acetyl]-2-methyl-azetidine-2-carboxylic acid (4-chloro-benzyl)-methyl-amide,
1-[2-(3,5-Difluoro-phenyl)-acetyl]-2-methyl-azetidine-2-carboxylic acid (4-chloro-benzyl)-methyl-amide,
1-(2-Biphenyl-4-yl-acetyl)-2-methyl-azetidine-2-carboxylic acid (4-chloro-benzyl)-methyl-amide,
1-[2-(3'-Chloro-biphenyl-4-O-acetyl]-2-methyl-azetidine-2-carboxylic acid (4-chloro-benzyl)-methyl-amide,
1-[2-(3'-Cyano-biphenyl-4-yl)-acetyl]-2-methyl-azetidine-2-carboxylic acid (4-chloro-benzyl)-methyl-amide,
1-[2-(4'-Methoxy-biphenyl-4-yl)-acetyl]-2-methyl-azetidine-2-carboxylic acid (4-chloro-benzyl)-methyl-amide,
1-[2-(4'-Cyano-biphenyl-4-yl)-acetyl]-2-methyl-azetidine-2-carboxylic acid (4-chloro-benzyl)-methyl-amide,
2-Methyl-1-[2-(2'-methyl-biphenyl-4-yl)-acetyl]-azetidine-2-carboxylic acid (4-chloro-benzyl)-methyl-amide,
methyl 4'-(2-(2-((4-chlorobenzyl)(methyl)carbamoyl)-2-methylazetidin-1-yl)-2-oxoethyl)biphenyl-3-carboxylate,
1-(2-Biphenyl-3-yl-acetyl)-2-methyl-azetidine-2-carboxylic acid (4-chloro-benzyl)-methyl-amide,
2-Methyl-1-[2-(2'-trifluoromethyl-biphenyl-3-yl)-acetyl]-azetidine-2-carboxylic acid (4-chloro-benzyl)-methyl-amide,
1-[2-(3'-Chloro-biphenyl-3-yl)-acetyl]-2-methyl-azetidine-2-carboxylic acid (4-chloro-benzyl)-methyl-amide,
1-[2-(3,5-Dimethyl-phenyl)-acetyl]-2-methyl-azetidine-2-carboxylic acid (4-bromo-benzyl)-methyl-amide,
1-[2-(3,5-Dimethyl-phenyl)-acetyl]-2-methyl-azetidine-2-carboxylic acid (4-isopropyl-benzyl)-methyl-amide,
1-[2-(3,5-Dimethyl-phenyl)-acetyl]-2-methyl-azetidine-2-carboxylic acid (4-tert-butyl-benzyl)-methyl-amide,
1-[2-(3,5-Dimethyl-phenyl)-acetyl]-2-methyl-azetidine-2-carboxylic acid (2,4-dimethyl-benzyl)-methyl-amide,
1-[2-(3,5-Dimethyl-phenyl)-acetyl]-2-methyl-azetidine-2-carboxylic acid (4-isobutyl-benzyl)-methyl-amide,
1-[2-(3,5-Dimethyl-phenyl)-acetyl]-2-methyl-azetidine-2-carboxylic acid (4-chloro-benzyl)-ethyl-amide,
1-[2-(3,5-Dimethyl-phenyl)-acetyl]-2-methyl-azetidine-2-carboxylic acid (2,4-dichloro-benzyl)-methyl-amide,
1-[2-(3,5-Dimethyl-phenyl)-acetyl]-2-methyl-azetidine-2-carboxylic acid methyl-(4-trifluoromethoxy-benzyl)-amide,
1-[2-(3'-Methoxy-biphenyl-4-yl)-acetyl]-2-methyl-azetidine-2-carboxylic acid (4-chloro-benzyl)-methyl-amide,
1-[2-(3,5-Dimethyl-phenyl)-acetyl]-2-methyl-azetidine-2-carboxylic acid (3-bromo-benzyl)-methyl-amide,
1-[2-(2,5-Dimethyl-phenyl)-acetyl]-2-methyl-azetidine-2-carboxylic acid (4-chloro-benzyl)-methyl-amide,
1-[2-(3,5-Dimethyl-phenyl)-acetyl]-2-methyl-azetidine-2-carboxylic acid (4-chloro-3-fluoro-benzyl)-methyl-amide,
1-[2-(2,4-Dichloro-phenyl)-acetyl]-2-methyl-azetidine-2-carboxylic acid 4-methyl-benzylamide,
1-[2-(2,4-Dichloro-phenyl)-acetyl]-2-methyl-azetidine-2-carboxylic acid 4-trifluoromethyl-benzylamide,
1-[2-(2,4-Dichloro-phenyl)-acetyl]-2-methyl-azetidine-2-carboxylic acid methyl-(4-trifluoromethyl-benzyl)-amide,
1-[2-(3,5-Dimethyl-phenyl)-acetyl]-2-methyl-azetidine-2-carboxylic acid (4-chloro-benzyl)-cyclopropyl-amide,
1-[2-(3,5-Dimethyl-phenyl)-acetyl]-2-methyl-azetidine-2-carboxylic acid (4-chloro-benzyl)-(2-hydroxy-ethyl)-amide,
((4-Chloro-benzyl)-{1-[2-(3,5-dimethyl-phenyl)-acetyl]-2-methyl-azetidine-2-carbonyl}-amino)-acetic acid methyl ester,
((4-Chloro-benzyl)-{1-[2-(3,5-dimethyl-phenyl)-acetyl]-2-methyl-azetidine-2-carbonyl}-amino)-acetic acid,
N-(4-chlorobenzyl)-N,2-dimethyl-1-(3-methylbenzofuran-2-carbonyl)azetidine-2-carboxamide,
1-[2-(2,4-Dichloro-phenyl)-acetyl]-2-methyl-azetidine-2-carboxylic acid 3-methyl-benzylamide,
N-(4-chlorobenzyl)-1-(1-(2,4-dichlorophenyl)cyclopropanecarbonyl)-2-methylazetidine-2-carboxamide,
1-[2-(3,5-Dimethyl-phenyl)-acetyl]-2-methyl-azetidine-2-carboxylic acid (4-chloro-benzyl)-methylcarbamoylmethyl-amide,
1-[2-(3,5-Dimethyl-phenyl)-acetyl]-2-methyl-azetidine-2-carboxylic acid (4-chloro-benzyl)-dimethylcarbamoylmethyl-amide,
(S)-2-((4-Chloro-benzyl)-{1-[2-(3,5-dimethyl-phenyl)-acetyl]-2-methyl-azetidine-2-carbonyl}-amino)-propionic acid methyl ester,
1-[2-(3,5-Dimethyl-phenyl)-acetyl]-2-methyl-azetidine-2-carboxylic acid (4-chloro-benzyl)-(2-methoxy-ethyl)-amide,
1-(2-Benzo[b]thiophen-3-yl-acetyl)-2-methyl-azetidine-2-carboxylic acid 4-chloro-benzylamide,
[[1-(2-Benzo[b]thiophen-3-yl-acetyl)-2-methyl-azetidine-2-carbonyl]-(4-chloro-benzyl)-amino]-acetic acid ethyl ester,
[{1-[2-(3,5-Dimethyl-phenyl)-acetyl]-2-methyl-azetidine-2-carbonyl}-(3-methyl-benzyl)-amino]-acetic acid,
[[1-(2-Benzo[b]thiophen-3-yl-acetyl)-2-methyl-azetidine-2-carbonyl]-(3-chloro-benzyl)-amino]-acetic acid methyl ester,

[[1-(2-Benzo[b]thiophen-3-yl-acetyl)-2-methyl-azetidine-2-carbonyl]-(4-chloro-benzyl)-amino]-acetic acid,
3-((4-Chloro-benzyl)-{1-[2-(3,5-dimethyl-phenyl)-acetyl]-2-methyl-azetidine-2-carbonyl}-amino)-propionic acid methyl ester,
4-((4-Chloro-benzyl)-{1-[2-(3,5-dimethyl-phenyl)-acetyl]-2-methyl-azetidine-2-carbonyl}-amino)-butyric acid methyl ester,
4-((4-Chloro-benzyl)-{1-[2-(3,5-dimethyl-phenyl)-acetyl]-2-methyl-azetidine-2-carbonyl}-amino)-butyric acid,
3-((4-Chloro-benzyl)-{1-[2-(3,5-dimethyl-phenyl)-acetyl]-2-methyl-azetidine-2-carbonyl}-amino)-propionic acid,
[[1-(2-Benzo[b]thiophen-3-yl-acetyl)-2-methyl-azetidine-2-carbonyl]-(3-chloro-benzyl)-amino]-acetic acid,
1-(2-Benzo[b]thiophen-3-yl-acetyl)-2-methyl-azetidine-2-carboxylic acid (4-chloro-benzyl)-(2-hydroxy-ethyl)-amide,
1-[2-(3,5-Dimethyl-phenyl)-acetyl]-2-methyl-azetidine-2-carboxylic acid (4-chloro-benzyl)-cyanomethyl-amide,
[[1-(2-Benzo[b]thiophen-3-yl-acetyl)-2-methyl-azetidine-2-carbonyl]-(3-methyl-benzyl)-amino]-acetic acid,
1-(2-Benzo[b]thiophen-3-yl-acetyl)-2-methyl-azetidine-2-carboxylic acid (4-chloro-benzyl)-(3-hydroxy-propyl)-amide,
1-[2-(3,5-Dimethyl-phenyl)-acetyl]-2-methyl-azetidine-2-carboxylic acid (2-carbamoyl-ethyl)-(4-chloro-benzyl)-amide,
1-[2-(3,5-Dimethyl-phenyl)-acetyl]-2-methyl-azetidine-2-carboxylic acid (4-chloro-benzyl)-(2-hydroxy-propyl)-amide,
(R)-2-((4-Chloro-benzyl)-{1-[2-(3,5-dimethyl-phenyl)-acetyl]-2-methyl-azetidine-2-carbonyl}-amino)-propionic acid methyl ester,
(R)-2-((4-Chloro-benzyl)-{1-[2-(3,5-dimethyl-phenyl)-acetyl]-2-methyl-azetidine-2-carbonyl}-amino)-propionic acid,
1-[2-(3,5-Dimethyl-phenyl)-acetyl]-2-methyl-azetidine-2-carboxylic acid carbamoylmethyl-(4-chloro-benzyl)-amide,
1-[2-(3,5-Dimethyl-phenyl)-acetyl]-2-methyl-azetidine-2-carboxylic acid (4-chloro-benzyl)-(1H-tetrazol-5-ylmethyl)-amide,
1-[2-(3,5-Dimethyl-phenyl)-acetyl]-2-methyl-azetidine-2-carboxylic acid (4-chloro-benzyl)-(2-cyano-ethyl)-amide,
[[1-(2-Benzofuran-3-yl-acetyl)-2-methyl-azetidine-2-carbonyl]-(4-chloro-benzyl)-amino]-acetic acid,
[[1-(2-Benzo[d]isoxazol-3-yl-acetyl)-2-methyl-azetidine-2-carbonyl]-(4-chloro-benzyl)-amino]-acetic acid,
1-[2-(3,5-Dimethyl-phenyl)-acetyl]-2-methyl-azetidine-2-carboxylic acid (4-chloro-benzyl)-(isopropylcarbamoyl-methyl)-amide,
1-[2-(3,5-Dimethyl-phenyl)-acetyl]-2-methyl-azetidine-2-carboxylic acid (4-chloro-benzyl)-cyclopropylcarbamoyl-methyl)-amide,
((4-Chloro-benzyl)-{(S)-1-[2-(3,5-dimethyl-phenyl)-acetyl]-2-methyl-azetidine-2-carbonyl}-amino)-acetic acid,
((4-Chloro-benzyl)-{(R)-1-[2-(3,5-dimethyl-phenyl)-acetyl]-2-methyl-azetidine-2-carbonyl}-amino)-acetic acid,
1-[2-(3,5-Dimethyl-phenyl)-acetyl]-2-methyl-azetidine-2-carboxylic acid (4-chloro-benzyl)-(2-morpholin-4-yl-2-oxo-ethyl)-amide,
1-(2-Benzo[b]thiophen-3-yl-acetyl)-2-methyl-azetidine-2-carboxylic acid (4-chloro-benzyl)-cyanomethyl-amide,
[[1-(2-Benzo[b]thiophen-3-yl-acetyl)-2-hydroxymethyl-azetidine-2-carbonyl]-(4-chloro-benzyl)-amino]-acetic acid,
3-[[1-(2-Benzo[b]thiophen-3-yl-acetyl)-2-methyl-azetidine-2-carbonyl]-(4-chloro-benzyl)-amino]-propionic acid methyl ester,
4-[[1-(2-Benzo[b]thiophen-3-yl-acetyl)-2-methyl-azetidine-2-carbonyl]-(4-chloro-benzyl)-amino]-butyric acid ethyl ester,
3-[[1-(2-Benzo[b]thiophen-3-yl-acetyl)-2-methyl-azetidine-2-carbonyl]-(4-chloro-benzyl)-amino]-propionic acid,
4-[[1-(2-Benzo[b]thiophen-3-yl-acetyl)-2-methyl-azetidine-2-carbonyl]-(4-chloro-benzyl)-amino]-butyric acid,
1-[2-(3,5-Dimethyl-phenyl)-acetyl]-2-methyl-azetidine-2-carboxylic acid (3-carbamoyl-propyl)-(4-chloro-benzyl)-amide,
2-Methyl-1-[2-(1-methyl-1H-indol-3-yl)-acetyl]-azetidine-2-carboxylic acid (4-chloro-benzyl)-methyl-amide,
1-[2-(5-Chloro-benzo[b]thiophen-3-yl)-acetyl]-2-methyl-azetidine-2-carboxylic acid (4-chloro-benzyl)-methyl-amide,
1-[2-(5-Methyl-benzo[b]thiophen-3-yl)-acetyl]-2-methyl-azetidine-2-carboxylic acid (4-chloro-benzyl)-methyl-amide,
1-[2-(3,5-Dimethyl-phenyl)-acetyl]-2-methyl-azetidine-2-carboxylic acid (4-chloro-benzyl)-(2-oxo-2-trifluoromethanesulfonylamino-ethyl)-amide,
1-[2-(3,5-Dimethyl-phenyl)-acetyl]-2-methyl-azetidine-2-carboxylic acid (4-chloro-benzyl)-(2-methanesulfonylamino-2-oxo-ethyl)-amide,
[{1-[2-(3,5-Dimethyl-phenyl)-acetyl]-2-methyl-azetidine-2-carbonyl}-(1H-indol-6-ylmethyl)-amino]-acetic acid,
1-[2-(3,5-Dimethyl-phenyl)-acetyl]-2-methyl-azetidine-2-carboxylic acid (4-chloro-benzyl)-(3-cyano-propyl)-amide,
1-(Benzo[b]thiophene-3-carbonyl)-2-methyl-azetidine-2-carboxylic acid (4-chloro-benzyl)-methyl-amide,
1-(2-Benzo[b]thiophen-3-yl-acetyl)-2-methyl-azetidine-2-carboxylic acid (4-chloro-benzyl)-(3-cyano-propyl)-amide,
1-(2-Benzo[b]thiophen-3-yl-acetyl)-2-methyl-azetidine-2-carboxylic acid (4-chloro-benzyl)-[3-(1-tetrazol-5-O-propyl]-amide,
1-[2-(3,5-Dimethyl-phenyl)-acetyl]-2-methyl-azetidine-2-carboxylic acid (2-acetylamino-ethyl)-(4-chloro-benzyl)-amide,
1-[2-(3,5-Dimethyl-phenyl)-acetyl]-2-methyl-azetidine-2-carboxylic acid (4-chloro-benzyl)-(2-methanesulfonylamino-ethyl)-amide,
4-[[1-(2-Benzofuran-3-yl-acetyl)-2-methyl-azetidine-2-carbonyl]-(4-chloro-benzyl)-amino]-butyric acid,
1-[2-(3,5-Dimethyl-phenyl)-acetyl]-2-methyl-azetidine-2-carboxylic acid (2-benzenesulfonylamino-2-oxo-ethyl)-(4-chloro-benzyl)-amide,
1-(2-Benzo[b]thiophen-4-yl-acetyl)-2-methyl-azetidine-2-carboxylic acid (4-chloro-benzyl)-methyl-amide,
1-[2-(4-Fluoro-naphthalen-1-O-acetyl]-2-methyl-azetidine-2-carboxylic acid (4-chloro-benzyl)-methyl-amide,
1-[2-(3,5-Dimethyl-phenyl)-acetyl]-2-methyl-azetidine-2-carboxylic acid (4-chloro-benzyl)-[2-(5-hydroxy-[1,2,4]oxadiazol-3-yl)-ethyl]-amide,
1-(2-Benzo[b]thiophen-2-yl-acetyl)-2-methyl-azetidine-2-carboxylic acid (4-chloro-benzyl)-methyl-amide,
1-[2-(3,5-Dimethyl-phenyl)-acetyl]-2-methyl-azetidine-2-carboxylic acid (4-chloro-benzyl)-[2-(1H-tetrazol-5-yl)-ethyl]-amide,

[{1-[2-(3,5-Dimethyl-phenyl)-acetyl]-2-methyl-azetidine-2-carbonyl}-(1H-indazol-6-ylmethyl)-amino]-acetic acid,
1-[2-(3,5-Dimethyl-phenyl)-acetyl]-2-methyl-azetidine-2-carboxylic acid (4-chloro-benzyl)-(5-hydroxy-[1,3,4]oxadiazol-2-ylmethyl)-amide,
1-(Benzo[b]thiophene-5-carbonyl)-2-methyl-azetidine-2-carboxylic acid (4-chloro-benzyl)-methyl-amide,
4-[{1-[2-(3,5-Dimethyl-phenyl)-acetyl]-2-methyl-azetidine-2-carbonyl}-(1H-indol-6-ylmethyl)-amino]-butyric acid,
1-[2-(3,5-Dimethyl-phenyl)-acetyl]-2-methyl-azetidine-2-carboxylic acid (4-chloro-benzyl)-(5-hydroxy-[1,2,4]oxadiazol-3-ylmethyl)-amide,
4-[[1-(Benzo[b]thiophene-3-carbonyl)-2-methyl-azetidine-2-carbonyl]-(4-chloro-benzyl)-amino]-butyric acid,
1-[2-(3,5-Dimethyl-phenyl)-acetyl]-2-methyl-azendine-2-carboxylic acid (4-chloro-benzyl)-[2-(5-hydroxy-1-pyrazol-3-yl)-ethyl]-amide,
1-[2-(3,5-Dimethyl-phenyl)-acetyl]-2-methyl-azendine-2-carboxylic acid (4-chloro-benzyl)-[2-(5-hydroxy-1-methyl-1H-pyrazol-3-O-ethyl]-amide,
1-[2-(3,5-Dimethyl-phenyl)-acetyl]-2-methyl-azendine-2-carboxylic acid (4-chloro-benzyl)-[2-(5-ethoxy-1-methyl-1H-pyrazol-3-yl)-ethyl]-amide,
1-[2-(3,5-Dimethyl-phenyl)-acetyl]-2-methyl-azetidine-2-carboxylic acid (4-chloro-benzyl)-[2-(5-hydroxy-[1,3,4]oxadiazol-2-yl)-ethyl]-amide,
1-[2-(3,5-Dimethyl-phenyl)-acetyl]-2-methyl-azetidine-2-carboxylic acid (4-chloro-benzyl)-[2-(5-ethoxy-1-pyrazol-3-O-ethyl]-amide,
1-(benzofuran-5-carbonyl)-N-(4-chlorobenzyl)-N,2-dimethylazetidine-2-carboxamide,
1-[2-(3,5-Dimethyl-phenyl)-acetyl]-2-methyl-azetidine-2-carboxylic acid (4-chloro-benzyl)-(4-morpholin-4-yl-4-oxo-butyl)-amide,
4-[{1-[2-(3,5-Dimethyl-phenyl)-acetyl]-2-methyl-azetidine-2-carbonyl}-(1H-indazol-6-ylmethyl)-amino]-butyric acid,
1-[2-(3,5-Dimethyl-phenyl)-acetyl]-2-methyl-azetidine-2-carboxylic acid (4-chloro-benzyl)-[4-(4-methyl-piperazin-1-yl)-4-oxo-butyl]-amide,
1-[2-(3,5-Dimethyl-phenyl)-acetyl]-2-methyl-azetidine-2-carboxylic acid (4-chloro-benzyl)-(3-dimethylcarbamoyl-propyl)-amide,
1-(2-naphthoyl)-N-(4-chlorobenzyl)-N,2-dimethylazetidine-2-carboxamide,
1-(2-Benzo[b]thiophen-3-yl-acetyl)-2-methyl-azetidine-2-carboxylic acid (3-carbamoyl-propyl)-(4-chloro-benzyl)-amide,
4-[[1-(2-Benzo[b]thiophen-3-yl-acetyl)-2-methyl-azetidine-2-carbonyl]-(1H-indol-6-ylmethyl)-amino]-butyric acid,
1-(2-Benzo[b]thiophen-3-yl-acetyl)-2-methyl-azetidine-2-carboxylic acid (4-chloro-benzyl)-(4-morpholin-4-yl-4-oxo-butyl)-amide,
4-[[1-(2-Benzo[b]thiophen-3-yl-acetyl)-2-methyl-azetidine-2-carbonyl]-(1H-indazol-6-ylmethyl)-amino]-butyric acid,
4-{[1-(2-Benzo[b]thiophen-3-yl-acetyl)-2-methyl-azetidine-2-carbonyl]-benzofuran-6-ylmethyl-amino}-butyric acid,
1-[2-(3,5-Dimethyl-phenyl)-acetyl]-2-methyl-azetidine-2-carboxylic acid (4-chloro-benzyl)-(3-hydroxy-isoxazol-5-ylmethyl)-amide,
1-[2-(3,5-Dimethyl-phenyl)-acetyl]-2-methyl-azetidine-2-carboxylic acid (4-chloro-benzyl)-(5-hydroxy-1-pyrazol-3-ylmethyl)-amide,
4-[[1-(Benzo[b]thiophene-3-carbonyl)-2-methyl-azetidine-2-carbonyl]-(1H-indol-6-ylmethyl)-amino]-butyric acid,
4-[[1-(Benzo[b]thiophene-5-carbonyl)-2-methyl-azetidine-2-carbonyl]-(4-chloro-benzyl)-amino]-butyric acid,
4-[[1-(2-Benzo[b]thiophen-4-yl-acetyl)-2-methyl-azetidine-2-carbonyl]-(4-chloro-benzyl)-amino]-butyric acid,
4-[[1-(2-Benzofuran-3-yl-acetyl)-2-methyl-azetidine-2-carbonyl]-(1H-indol-6-ylmethyl)-amino]-butyric acid,
1-(benzo[b]thiophene-5-carbonyl)-N-(4-chlorobenzyl)-2-methyl-N-(4-morpholino-4-oxobutyl)azetidine-2-carboxamide,
1-(benzo[b]thiophene-3-carbonyl)-N-(4-chlorobenzyl)-2-methyl-N-(4-morpholino-4-oxobutyl)azetidine-2-carboxamide,
1-(2-Benzofuran-3-yl-acetyl)-2-methyl-azetidine-2-carboxylic acid (4-chloro-benzyl)-(4-morpholin-4-yl-4-oxo-butyl)-amide,
ethyl 4-(1-(benzo[b]thiophene-3-carbonyl)-2-methyl-N-(4-(trifluoromethyl)benzyl)azetidine-2-carboxamido)butanoate,
4-[[1-(2-Benzo[b]thiophen-3-yl-acetyl)-2-methyl-azetidine-2-carbonyl]-(4-trifluoromethyl-benzyl)-amino]-butyric acid ethyl ester,
ethyl 4-(1-(benzo[b]thiophene-3-carbonyl)-N-(3-chlorobenzyl)-2-methylazetidine-2-carboxamido)butanoate,
4-[[1-(2-Benzo[b]thiophen-3-yl-acetyl)-2-methyl-azetidine-2-carbonyl]-(4-trifluoromethyl-benzyl)-amino]-butyric acid,
4-[[1-(Benzo[b]thiophene-3-carbonyl)-2-methyl-azetidine-2-carbonyl]-(4-trifluoromethyl-benzyl)-amino]-butyric acid,
4-[[1-(Benzo[b]thiophene-3-carbonyl)-2-methyl-azetidine-2-carbonyl]-(3-chloro-benzyl)-amino]-butyric acid,
4-[[1-(2-Benzo[b]thiophen-3-yl-acetyl)-2-methyl-azetidine-2-carbonyl]-(3-chloro-benzyl)-amino]-butyric acid ethyl ester,
4-[[1-(2-Benzo[b]thiophen-3-yl-acetyl)-2-methyl-azetidine-2-carbonyl]-(3-chloro-benzyl)-amino]-butyric acid,
1-[2-(3,5-Dimethyl-phenyl)-acetyl]-2-methyl-azetidine-2-carboxylic acid (4-chloro-benzyl)-[3-(2-oxo-pyrrolidin-1-yl)-propyl]-amide,
3-[[1-(2-Benzofuran-3-yl-acetyl)-2-methyl-azetidine-2-carbonyl]-(4-chloro-benzyl)-amino]-propionic acid methyl ester,
3-[[1-(Benzo[b]thiophene-3-carbonyl)-2-methyl-azetidine-2-carbonyl]-(4-chloro-benzyl)-amino]-propionic acid methyl ester,
4-[[1-(2-Benzofuran-3-yl-acetyl)-2-methyl-azetidine-2-carbonyl]-(1H-indazol-6-ylmethyl)-amino]-butyric acid ethyl ester,
4-[[1-(Benzo[b]thiophene-3-carbonyl)-2-methyl-azetidine-2-carbonyl]-(1H-indazol-6-ylmethyl)-amino]-butyric acid ethyl ester,
3-[[1-(2-Benzofuran-3-yl-acetyl)-2-methyl-azetidine-2-carbonyl]-(4-chloro-benzyl)-amino]-propionic acid,
3-[[1-(Benzo[b]thiophene-3-carbonyl)-2-methyl-azetidine-2-carbonyl]-(4-chloro-benzyl)-amino]-propionic acid,
4-[[1-(2-Benzofuran-3-yl-acetyl)-2-methyl-azetidine-2-carbonyl]-(1H-indazol-6-ylmethyl)-amino]-butyric acid,
4-[[1-(Benzo[b]thiophene-3-carbonyl)-2-methyl-azetidine-2-carbonyl]-(1H-indazol-6-ylmethyl)-amino]-butyric acid,
1-(Benzo[b]thiophene-3-carbonyl)-2-methyl-azetidine-2-carboxylic acid (3-carbamoyl-propyl)-(4-chloro-benzyl)-amide,
4-[{1-[2-(3,5-Dimethyl-phenyl)-acetyl]-2-methyl-azetidine-2-carbonyl}-(4-trifluoromethyl-benzyl)-amino]-butyric acid, 4-[[1-(2-Benzofuran-3-yl-acetyl)-2-methyl-azetidine-2-carbonyl]-(4-trifluoromethyl-benzyl)-amino]-butyric acid,
4-((3-Chloro-benzyl)-{1-[2-(3,5-dimethyl-phenyl)-acetyl]-2-methyl-azetidine-2-carbonyl}-amino)-butyric acid,
4-(Benzofuran-6-ylmethyl-{1-[2-(3,5-dimethyl-phenyl)-acetyl]-2-methyl-azetidine-2-carbonyl}-amino)-butyric acid,
4-{[1-(Benzo[b]thiophene-3-carbonyl)-2-methyl-azetidine-2-carbonyl]-benzofuran-6-ylmethyl-amino}-butyric acid,
4-{[1-(2-Benzofuran-3-yl-acetyl)-2-methyl-azetidine-2-carbonyl]-benzofuran-6-ylmethyl-amino}-butyric acid,
4-[{1-[2-(3,5-Dimethyl-phenyl)-acetyl]-2-methyl-azetidine-2-carbonyl}-(4-trifluoromethyl-benzyl)-amino]-butyric acid ethyl ester,
1-(2-Benzofuran-3-yl-acetyl)-2-methyl-azetidine-2-carboxylic acid (3-carbamoyl-propyl)-(4-chloro-benzyl)-amide,
4-[[1-(2-Benzofuran-3-yl-acetyl)-2-methyl-azetidine-2-carbonyl]-(4-trifluoromethyl-benzyl)-amino]-butyric acid ethyl ester,
1-[2-(3,5-Dimethyl-phenyl)-acetyl]-2-methyl-azetidine-2-carboxylic acid (4-chloro-benzyl)-[3-(2,4-dimethoxy-benzylsulfamoyl)-propyl]-amide,
3-[[1-(Benzo[b]thiophene-3-carbonyl)-2-methyl-azetidine-2-carbonyl]-(3-chloro-benzyl)-amino]-propionic acid,
3-[[1-(2-Benzo[b]thiophen-3-yl-acetyl)-2-methyl-azetidine-2-carbonyl]-(3-chloro-benzyl)-amino]-propionic acid,
1-[2-(3,5-Dimethyl-phenyl)-acetyl]-2-methyl-azetidine-2-carboxylic acid (4-chloro-benzyl)-(3-sulfamoyl-propyl)-amide,
3-[[1-(Benzo[b]thiophene-3-carbonyl)-2-methyl-azetidine-2-carbonyl]-(3-chloro-benzyl)-amino]-propionic acid methyl ester,
3-[[1-(2-Benzo[b]thiophen-3-yl-acetyl)-2-methyl-azetidine-2-carbonyl]-(3-chloro-benzyl)-amino]-propionic acid methyl ester,
1-[2-(3,5-Dimethyl-phenyl)-acetyl]-2-methyl-azetidine-2-carboxylic acid (4-chloro-benzyl)-(3-methylsulfamoyl-propyl)-amide,
3-[[1-(2-Benzo[b]thiophen-3-yl-acetyl)-2-methyl-azetidine-2-carbonyl]-(1H-indazol-6-ylmethyl)-amino]-propionic acid methyl ester,
3-[[1-(2-Benzo[b]thiophen-3-yl-acetyl)-2-methyl-azetidine-2-carbonyl]-(1H-indazol-6-ylmethyl)-amino]-propionic acid,
4-{[1-(2-Benzo[b]thiophen-3-yl-acetyl)-2-methyl-azetidine-2-carbonyl]-imidazo[1,2-a]pyridin-7-ylmethyl-amino}-butyric acid,
1-(2-Benzo[b]thiophen-3-yl-acetyl)-2-methyl-azetidine-2-carboxylic acid (4-chloro-benzyl)-[3-(2,4-dimethoxy-benzylsulfamoyl)-propyl]-amide,
1-[2-(3,5-Dimethyl-phenyl)-acetyl]-2-methyl-azetidine-2-carboxylic acid (4-chloro-benzyl)-[2-(morpholine-4-sulfonyl)-ethyl]-amide,
1-[2-(3,5-Dimethyl-phenyl)-acetyl]-2-methyl-azetidine-2-carboxylic acid (4-chloro-benzyl)-[3-(4-methyl-piperazine-1-sulfonyl)-propyl]-amide,
1-(2-Benzo[b]thiophen-3-yl-acetyl)-2-methyl-azetidine-2-carboxylic acid (4-chloro-benzyl)-(3-sulfamoyl-propyl)-amide,
1-(Benzo[b]thiophene-3-carbonyl)-2-methyl-azetidine-2-carboxylic acid (4-chloro-benzyl)-(3-sulfamoyl-propyl)-amide,
4-{[1-(2-Benzo[b]thiophen-3-yl-acetyl)-2-methyl-azetidine-2-carbonyl]-benzothiazol-5-ylmethyl-amino}-butyric acid,
4-{[1-(Benzo[b]thiophene-3-carbonyl)-2-methyl-azetidine-2-carbonyl]-benzothiazol-5-ylmethyl-amino}-butyric acid,
4-(Benzothiazol-5-ylmethyl-{1-[2-(3,5-dimethyl-phenyl)-acetyl]-2-methyl-azetidine-2-carbonyl}-amino)-butyric acid,
1-(Benzo[b]thiophene-3-carbonyl)-2-methyl-azetidine-2-carboxylic acid (4-chloro-benzyl)-(3-methylsulfamoyl-propyl)-amide,
1-(Benzo[b]thiophene-3-carbonyl)-2-methyl-azetidine-2-carboxylic acid (3-chloro-benzyl)-(3-sulfamoyl-propyl)-amide,
3-[[1-(Benzo[b]thiophene-3-carbonyl)-2-methyl-azetidine-2-carbonyl]-(1H-indazol-6-ylmethyl)-amino]-propionic acid,
1-(2-Benzo[b]thiophen-3-yl-acetyl)-2-methyl-azetidine-2-carboxylic acid (4-chloro-benzyl)-(3-methylsulfamoyl-propyl)-amide,
1-(Benzo[b]thiophene-3-carbonyl)-2-methyl-azetidine-2-carboxylic acid (3-chloro-benzyl)-(3-methylsulfamoyl-propyl)-amide,
4-[[(R)-1-(Benzo[b]thiophene-3-carbonyl)-2-methyl-azetidine-2-carbonyl]-(3-chloro-benzyl)-amino]-butyric acid,
1-(Benzo[b]thiophene-3-carbonyl)-2-methyl-azetidine-2-carboxylic acid (4-chloro-benzyl)-(2-sulfamoyl-ethyl)-amide,
1-(Benzo[b]thiophene-3-carbonyl)-2-methyl-azetidine-2-carboxylic acid (4-chloro-benzyl)-(2-methylsulfamoyl-ethyl)-amide,
4-[[1-(Benzo[b]thiophene-3-carbonyl)-2-methyl-azetidine-2-carbonyl]-(4-chloro-phenyl)-amino]-butyric acid,
4-[[1-(Benzo[b]thiophene-3-carbonyl)-2-ethyl-azetidine-2-carbonyl]-(3-chloro-benzyl)-amino]-butyric acid,
2-[(3-Carboxy-propyl)-(4-chloro-benzyl)-carbamoyl]-2-methyl-azetidine-1-carboxylic acid 3,5-dimethyl-phenyl ester,
4-{[(R)-1-(Benzo[b]thiophene-3-carbonyl)-2-methyl-azetidine-2-carbonyl]-[(R)-1-(4-chloro-phenyl)-ethyl]-amino}-butyric acid,
4-{[(R)-1-(Benzo[b]thiophene-3-carbonyl)-2-methyl-azetidine-2-carbonyl]-[(S)-1-(4-chloro-phenyl)-ethyl]-amino}-butyric acid,
4-[[1-(Benzo[b]thiophene-3-carbonyl)-2-benzyl-azetidine-2-carbonyl]-(3-chloro-benzyl)-amino]-butyric acid,
4-{(4-Chloro-benzyl)-[1-(3,5-dimethyl-phenylcarbamoyl)-2-methyl-azetidine-2-carbonyl]-amino}-butyric acid,
4-((4-Chloro-benzyl)-{1-[(3,5-dimethyl-phenyl)-methylcarbamoyl]-2-methyl-azetidine-2-carbonyl}-amino)-butyric acid,
2-[(3-Carboxy-propyl)-(4-chloro-benzyl)-carbamoyl]-2-methyl-azetidine-1-carboxylic acid 2-chloro-phenyl ester,
4-[[1-(Benzo[b]thiophene-3-carbonyl)-2-isopropyl-azetidine-2-carbonyl]-(3-chloro-benzyl)-amino]-butyric acid,
4-[[1-(Benzo[b]thiophene-3-carbonyl)-2-propyl-azetidine-2-carbonyl]-(3-chloro-benzyl)-amino]-butyric acid,
2-[(3-Carboxy-propyl)-(4-chloro-benzyl)-carbamoyl]-2-methyl-azetidine-1-carboxylic acid o-tolyl ester; and
1-(Benzo[b]thiophene-3-carbonyl)-2-methyl-azetidine-2-carboxylic acid (4-chloro-phenyl)-(3-sulfamoyl-propyl)-amide.

In another embodiment, a compound of the invention is selected from the following compounds:
(R)-1-(benzo[b]thiophene-3-carbonyl)-N-(3-chlorobenzyl)-2-methyl-N-(4-(methylsulfonamido)-4-oxobutyl)azetidine-2-carboxamide,
1-(benzo[b]thiophene-3-carbonyl)-N-(3-chlorobenzyl)-2-ethyl-N-(3-sulfamoylpropyl)azetidine-2-carboxamide, 1-(benzo[b]thiophene-3-carbonyl)-N-((S)-1-(4-chlorophenyl)ethyl)-2-methyl-N-(3-sulfamoylpropyl)azetidine-2-carboxamide,
4-(N-(4-chlorobenzyl)-1-((2-fluorophenoxy)carbonyl)-2-methylazetidine-2-carboxamido)butanoic acid,
4-(1-((benzo[b]thiophen-3-yloxy)carbonyl)-N-(4-chlorobenzyl)-2-methylazetidine-2-carboxamido)butanoic acid,
4-(N-(4-chlorobenzyl)-1-((2-methoxyphenoxy)carbonyl)-2-methylazetidine-2-carboxamido)butanoic acid,
4-(N-(4-chlorobenzyl)-1-((2,4-dimethylphenoxy)carbonyl)-2-methylazetidine-2-carboxamido)butanoic acid,
4-(N-(4-chlorobenzyl)-2-methyl-1-((2-(trifluoromethyl)phenoxy)carbonyl)azetidine-2-carboxamido)butanoic acid,
4-(1-((2-chloro-5-methoxyphenoxy)carbonyl)-N-(4-chlorobenzyl)-2-methylazetidine-2-carboxamido)butanoic acid,
1-(benzo[b]thiophene-3-carbonyl)-N-(4-chlorobenzyl)-2-ethyl-N-(3-sulfamoylpropyl)azetidine-2-carboxamide,
1-(benzo[b]thiophene-3-carbonyl)-N-(3-chlorobenzyl)-2-isopropyl-N-(3-sulfamoylpropyl)azetidine-2-carboxamide,
4-(N-(4-chlorobenzyl)-1-((3-methoxyphenoxy)carbonyl)-2-methylazetidine-2-carboxamido)butanoic acid,
4-(1-(benzo[b]thiophene-3-carbonyl)-N-(3-chlorobenzyl)-2-(4-fluorobenzyl)azetidine-2-carboxamido)butanoic acid,
4-(1-(benzo[b]thiophene-3-carbonyl)-N-(3-chlorobenzyl)-2-(3-methylbenzyl)azetidine-2-carboxamido)butanoic acid,
4-(1-(benzo[b]thiophene-3-carbonyl)-N-(3-chlorobenzyl)-2-(3-methoxybenzyl)azetidine-2-carboxamido)butanoic acid,
4-(1-(benzo[b]thiophene-3-carbonyl)-N-(3-chlorobenzyl)-2-(3-(trifluoromethyl)benzyl)azetidine-2-carboxamido)butanoic acid,
4-(1-((2-chloro-4-methylphenoxy)carbonyl)-N-(4-chlorobenzyl)-2-methylazetidine-2-carboxamido)butanoic acid,
4-(1-((2-chloro-4-methoxyphenoxy)carbonyl)-N-(4-chlorobenzyl)-2-methylazetidine-2-carboxamido)butanoic acid,
4-(1-(benzo[b]thiophene-3-carbonyl)-N-(3-chlorobenzyl)-2-(4-chlorobenzyl)azetidine-2-carboxamido)butanoic acid,
4-(N-(4-chlorobenzyl)-2-methyl-1-((4-(trifluoromethyl)phenoxy)carbonyl)azetidine-2-carboxamido)butanoic acid,
4-(N-(4-chlorobenzyl)-2-methyl-1-((4-(methylthio)phenoxy)carbonyl)azetidine-2-carboxamido)butanoic acid,
1-(benzo[b]thiophene-3-carbonyl)-N-(3-chlorobenzyl)-2-ethyl-N-(4-(methylsulfonamido)-4-oxobutyl)azetidine-2-carboxamide,
2-allyl-1-(benzo[b]thiophene-3-carbonyl)-N-(3-chlorobenzyl)-N-(4-(methylsulfonamido)-4-oxobutyl)azetidine-2-carboxamide,
1-(benzo[b]thiophene-3-carbonyl)-2-benzyl-N-(3-chlorobenzyl)-N-(4-(methylsulfonamido)-4-oxobutyl)azetidine-2-carboxamide,
(R)-1-(benzo[b]thiophene-3-carbonyl)-N-((S)-1-(3-chlorophenyl)ethyl)-2-methyl-N-(4-(methylsulfonamido)-4-oxobutyl)azetidine-2-carboxamide,
1-(benzo[b]thiophene-3-carbonyl)-N-(3-chlorobenzyl)-N-(4-(methylsulfonamido)-4-oxobutyl)-2-propylazetidine-2-carboxamide,
1-(benzo[b]thiophene-3-carbonyl)-N-(3-chlorobenzyl)-2-isopropyl-N-(4-(methylsulfonamido)-4-oxobutyl)azetidine-2-carboxamide,
1-(benzo[b]thiophene-3-carbonyl)-N-(4-chlorophenyl)-2-methyl-N-(4-(methylsulfonamido)-4-oxobutyl)azetidine-2-carboxamide,
4-(1-((2-bromophenoxy)carbonyl)-N-(4-chlorobenzyl)-2-methylazetidine-2-carboxamido)butanoic acid,
4-(1-((2-chloro-5-(trifluoromethyl)phenoxy)carbonyl)-N-(4-chlorobenzyl)-2-methylazetidine-2-carboxamido)butanoic acid,
4-(N-(4-chlorobenzyl)-1-(1H-indole-1-carbonyl)-2-methylazetidine-2-carboxamido)butanoic acid,
4-(N-(4-chlorobenzyl)-1-((2,4-dichlorophenoxy)carbonyl)-2-methylazetidine-2-carboxamido)butanoic acid,
4-(1-((2-chloro-4-fluorophenoxy)carbonyl)-N-(4-chlorobenzyl)-2-methylazetidine-2-carboxamido)butanoic acid,
1-(benzo[b]thiophene-3-carbonyl)-N-(4-chlorobenzyl)-2-methyl-N-(4-(methylsulfonamido)-4-oxobutyl)azetidine-2-carboxamide,
1-(benzo[b]thiophene-3-carbonyl)-N-(3-chlorobenzyl)-2-(4-fluorobenzyl)-N-(4-(methylsulfonamido)-4-oxobutyl)azetidine-2-carboxamide,
1-(benzo[b]thiophene-3-carbonyl)-N-(3-chlorobenzyl)-2-(3-methoxybenzyl)-N-(4-(methylsulfonamido)-4-oxobutyl)azetidine-2-carboxamide,
1-(benzo[b]thiophene-3-carbonyl)-N-(3-chlorobenzyl)-2-(2-fluorobenzyl)-N-(4-(methylsulfonamido)-4-oxobutyl)azetidine-2-carboxamide,
(R)-1-(benzo[b]thiophene-3-carbonyl)-N—((S)-1-(4-chlorophenyl)ethyl)-2-ethyl-N-(3-sulfamoylpropyl)azetidine-2-carboxamide,
(S)-1-(benzo[b]thiophene-3-carbonyl)-N-((S)-1-(4-chlorophenyl)ethyl)-2-ethyl-N-(3-sulfamoylpropyl)azetidine-2-carboxamide,
1-(benzo[b]thiophene-3-carbonyl)-N-(4-chlorophenyl)-2-ethyl-N-(3-sulfamoylpropyl)azetidine-2-carboxamide,
4-(1-(benzo[b]thiophene-3-carbonyl)-N-(3-chlorobenzyl)-2-(2-methoxybenzyl)azetidine-2-carboxamido)butanoic acid,
4-(1-(benzo[b]thiophene-3-carbonyl)-N-(3-chlorophenyl)-2-methylazetidine-2-carboxamido)butanoic acid,
4-(1-(benzo[b]thiophene-3-carbonyl)-N-(6-chloropyridin-3-yl)-2-methylazetidine-2-carboxamido)butanoic acid,
4-(1-(benzo[b]thiophene-3-carbonyl)-N-(5-chloropyridin-2-yl)-2-methylazetidine-2-carboxamido)butanoic acid,
4-(1-(benzo[b]thiophene-3-carbonyl)-2-methyl-N-(3-(trifluoromethyl)phenyl)azetidine-2-carboxamido)butanoic acid,
4-(1-(benzo[b]thiophene-3-carbonyl)-N-(4-chloropyridin-2-yl)-2-methylazetidine-2-carboxamido)butanoic acid, and,
4-(1-(benzo[b]thiophene-3-carbonyl)-2-methyl-N-(pyridin-2-yl)azetidine-2-carboxamido)butanoic acid.

In one embodiment, a compound of the invention is 4-[[(R)-1-(Benzo[b]thiophene-3-carbonyl)-2-methyl-azetidine-2-carbonyl]-(3-chloro-benzyl)-amino]-butyric acid.

In another embodiment, a compound of the invention is not 4-[[(R)-1-(Benzo[b]thiophene-3-carbonyl)-2-methyl-azetidine-2-carbonyl]-(3-chloro-benzyl)-amino]-butyric acid.

In one embodiment a compound of the invention is not an isotopic variant.

In one aspect a compound of the invention is present as the free base.

In one aspect a compound of the invention is a pharmaceutically acceptable salt.

In one aspect a compound of the invention is present as the free base or a pharmaceutically acceptable salt.

In one aspect a compound of the invention is a solvate.

In one aspect a compound of the invention is a solvate of a pharmaceutically acceptable salt of the compound.

In certain aspects, the present invention provides prodrugs and derivatives of a Compound of the Invention according to the formulae above. Prodrugs are derivatives of a compound of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

Clauses:

Clause 1. A compound of the invention according to Formula Ia:

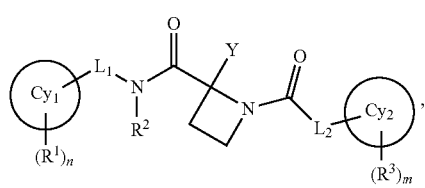

Ia wherein $L_1$ is a single bond, or $CR^aR^b$;

$L_2$ is a single bond, O, $NR^e$ or $CR^cR^d$;

each of $R^a$, $R^b$, $R^c$, and $R^d$ is independently selected from H, and $C_{1-4}$ alkyl; or $R^a$ and $R^b$ together with the carbon to which they are attached may form a $C_{3-7}$ cycloalkyl; or $R^c$ and $R^d$ together with the carbon to which they are attached may form a $C_{3-7}$ cycloalkyl;

$R^e$ is $C_{1-4}$ alkyl;

Y is
- $C_{1-4}$ alkyl optionally substituted with one or more groups independently selected from fluoro, OH, and phenyl (optionally substituted with one or more groups independently selected from $C_{1-4}$ alkyl (optionally substituted with one or more halo), $C_{1-4}$ alkoxy, halo and cyano), or
- $C_{1-4}$ alkenyl comprising 1 double bond;

each of $Cy_1$ and $Cy_2$ is independently $C_{6-10}$ aryl, or 5-10 membered heteroaryl;

each $R^1$ is independently selected from halo, $C_{1-4}$ alkyl (optionally substituted with one or more halo), and $C_{1-4}$ alkoxy (optionally substituted with one or more halo);

$R^2$ is:
- H,
- $C_{1-4}$ alkyl optionally substituted with one or more independently selected $R^{2a}$ groups,
- $C_{3-7}$ cycloalkyl optionally substituted with one or more independently selected $R^{2a}$ groups, $R^{2a}$ is:
- halo,
- $C_{1-6}$ alkoxy,
- OH,
- $C(=O)R^4$,
- $S(O)_2R^4$,
- CN,
- $NHC(=O)R^5$,
- $NHSO_2R^5$,
- 5-7 membered heterocycloalkyl (optionally substituted with one or more groups independently selected from $C_{1-4}$ alkyl, and oxo), or
- 5-6 membered heteroaryl (optionally substituted with one or more groups independently selected from halo, OH, $C_{1-4}$ alkoxy and $C_{1-4}$ alkyl);

$R^3$ is selected from halo, $C_{1-6}$ alkyl (optionally substituted with one or more halo), $C_{1-6}$ alkoxy (optionally substituted with one or more halo, or phenyl), $C_{1-6}$ thioalkoxy, phenyl (optionally substituted with one or more groups independently selected from halo, $C_{1-4}$ alkyl (optionally substituted with one or more halo), $C_{1-4}$ alkoxy, $C(=O)$—$C_{1-4}$ alkoxy and CN);

$R^4$ is
- —OH,
- —$C_{1-6}$ alkoxy,
- —N-linked 5-7 membered heterocycloalkyl (optionally substituted with one or more groups independently selected from $C_{1-6}$ alkyl, and oxo),
- —$NR^{4a}R^{4b}$, or
- —$NHSO_2R^{4c}$;

Each of $R^{4a}$ and $R^{4b}$ is independently H, $C_{1-4}$ alkyl (optionally substituted with phenyl (optionally substituted with one or more groups independently selected from halo, CN, $C_{1-6}$ alkyl, and $C_{1-6}$ alkoxy)), or $C_{3-7}$ cycloalkyl;

$R^{4c}$ is phenyl, 5-6 membered heteroaryl, 5-6 membered heterocycloalkyl (optionally substituted with one or more $C_{1-4}$ alkyl) or $C_{1-4}$ alkyl (optionally substituted with one or more halo);

$R^5$ is $C_{1-4}$ alkyl (optionally substituted with one or more halo) or phenyl; and the subscripts n and m are independently selected from 0, 1, and 2;

or a pharmaceutically acceptable salt, or a solvate, or a solvate of the pharmaceutically acceptable salts.

Clause 2. A compound of the invention according to Formula Ib:

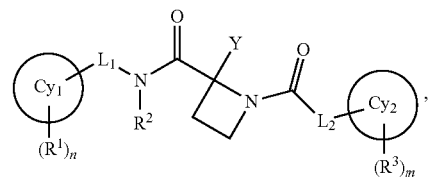

Ib wherein $L_1$ is a single bond, or $CR^aR^b$;

$L_2$ is a single bond, O, $NR^e$ or $CR^cR^d$;

each of $R^a$, $R^b$, $R^c$, and $R^d$ is independently selected from H, and $C_{1-4}$ alkyl; or $R^a$ and $R^b$ together with the carbon to which they are attached may form a $C_{3-7}$ cycloalkyl; or $R^c$ and $R^d$ together with the carbon to which they are attached may form a $C_{3-7}$ cycloalkyl;

$R^e$ is $C_{1-4}$ alkyl;

Y is —$C_{1-4}$ alkyl optionally substituted with one or more groups independently selected from fluoro, OH, and phenyl (optionally substituted with one or more groups independently selected from $C_{1-4}$ alkyl (optionally substituted with one or more halo), $C_{1-4}$ alkoxy, halo and cyano);

each of $Cy_1$ and $Cy_2$ is independently $C_{6-10}$ aryl, or 5-10 membered heteroaryl;

each $R^1$ is independently selected from halo, $C_{1-4}$ alkyl (optionally substituted with one or more halo), and $C_{1-4}$ alkoxy (optionally substituted with one or more halo);

$R^2$ is:

H, $C_{1-4}$ alkyl optionally substituted with one or more independently selected $R^{2a}$ groups, $C_{3-7}$ cycloalkyl optionally substituted with one or more independently selected $R^{2a}$ groups, $R^{2a}$ is halo, $C_{1-6}$ alkoxy,

OH,

C(=O)$R^4$,

S(O)$_2R^4$,

CN,

NHC(=O)$R^5$,

NHSO$_2R^5$, 5-7 membered heterocycloalkyl (optionally substituted with one or more groups independently selected from $C_{1-4}$ alkyl, and oxo), or 5-6 membered heteroaryl (optionally substituted with one or more groups independently selected from halo, OH, $C_{1-4}$ alkoxy and $C_{1-4}$ alkyl);

$R^3$ is selected from halo, $C_{1-6}$ alkyl (optionally substituted with one or more halo), $C_{1-6}$ alkoxy (optionally substituted with one or more halo, or phenyl), phenyl (optionally substituted with one or more groups independently selected from halo, $C_{1-4}$ alkyl (optionally substituted with one or more halo), $C_{1-4}$ alkoxy, C(=O)—$C_{1-4}$ alkoxy and CN);

$R^4$ is

—OH,

—$C_{1-6}$ alkoxy,

—N-linked 5-7 membered heterocycloalkyl (optionally substituted with one or more groups independently selected from $C_{1-6}$ alkyl, and oxo), NR$^{4a}R^{4b}$, or —NHSO$_2R^{4c}$;

Each of $R^{4a}$ and $R^{4b}$ is independently H, $C_{1-4}$ alkyl (optionally substituted with phenyl (optionally substituted with one or more groups independently selected from halo, CN, $C_{1-6}$ alkyl, and $C_{1-6}$ alkoxy)), or $C_{3-7}$ cycloalkyl;

$R^{4c}$ is phenyl, 5-6 membered heteroaryl, 5-6 membered heterocycloalkyl (optionally substituted with one or more $C_{1-4}$ alkyl) or $C_{1-4}$ alkyl (optionally substituted with one or more halo);

$R^5$ is $C_{1-4}$ alkyl (optionally substituted with one or more halo) or phenyl; and the subscripts n and m are independently selected from 0, 1, and 2;

or a pharmaceutically acceptable salt, or a solvate, or a solvate of the pharmaceutically acceptable salts.

Clause 3. A compound of the invention according to clause 1 or 2, wherein the compound is according to Formula II:

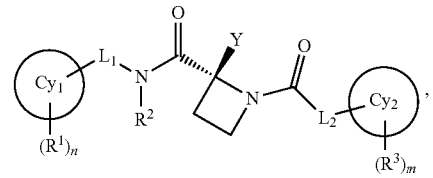

II wherein $L_1$, $L_2$, $R^1$, $R^2$, $R^3$, $Cy^1$, $Cy^2$, $R^a$, $R^b$, $R^c$, $R^d$, $R^e$, Y, n, and m are as described in clause 1 or 2.

Clause 4. A compound of the invention according to clause 1, 2 or 3, wherein $L_1$ is a single bond.

Clause 5. A compound of the invention according to clause 1, 2 or 3, wherein $L_1$ is CR$^aR^b$.

Clause 6. A compound of the invention according to clause 5, wherein $R^a$ is H or $C_{1-4}$ alkyl and $R^b$ is H.

Clause 7. A compound of the invention according to clause 6, wherein $R^a$ and $R^b$ are both H. Clause 8. A compound of the invention according to any one of clauses 1-7, wherein Y is Me, Et, Pr, iPr, or —CH$_2$-Ph.

Clause 9. A compound of the invention according to clause 8, wherein Y is Me.

Clause 10. A compound of the invention according to any one of clauses 1-9, wherein $Cy_1$ is phenyl.

Clause 11. A compound of the invention according to any one of clauses 1-10, wherein n is 1 or 2

Clause 12. A compound of the invention according to clause 11, wherein n is 1.

Clause 13. A compound of the invention according to clause 1-12, wherein each $R^1$ group is independently selected from halo, and $C_{1-4}$ alkyl optionally substituted with one or more halo.

Clause 14. A compound of the invention according to clause 13, wherein each $R^1$ group is independently selected from F, Cl, Me, Et, iPr, and CF$_3$.

Clause 15. A compound of the invention according to any one of clauses 1-9, wherein Cy1 is benzofuranyl, benzothiophenyl, indazolyl, indolyl, or benzothiazolyl.

Clause 16. A compound of the invention according to any one of clauses 1-10 or 15, wherein n is 0.

Clause 17. A compound of the invention according to clause 1, 2 or 3, wherein the compound is according to Formulae Ma or Mb:

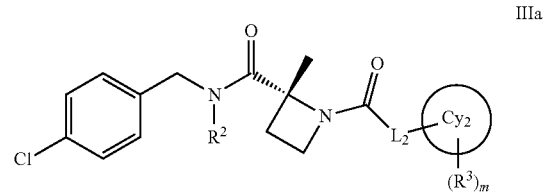

IIIa

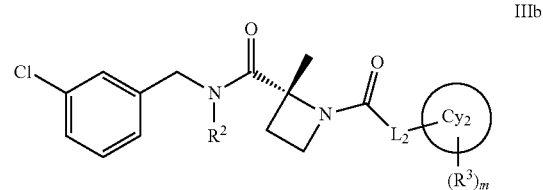

IIIb wherein $R^2$, $L_2$, $Cy_2$, $R^3$ and m are as described in clause 1 or 2.

Clause 18. A compound of the invention according to any one of clauses 1-17, wherein $R^2$ is H Clause 19. A compound of the invention according to any one of clauses 1-17, wherein $R^2$ is $C_{1-4}$ alkyl.

Clause 20. A compound of the invention according to clause 19, wherein $R^2$ is Me, Et, Pr, iPr, Bu, or iBu.

Clause 21. A compound of the invention according to any one of clauses 1-17, wherein $R^2$ is $C_{1-4}$ alkyl substituted with OH, CN, or $C_{1-6}$ alkoxy.

Clause 22. A compound of the invention according to clause 1-17, wherein $R^2$ is $C_{1-4}$ alkyl optionally substituted with one or more C(=O)$R^4$.

Clause 23. A compound of the invention according to clause 22, wherein $R^4$ is OH, or $C_{1-6}$ alkoxy.

Clause 24. A compound of the invention according to clause 22, wherein $R^4$ is $NR^{4a}R^{4b}$, wherein each of $R^{4a}$ and $R^{4b}$ is independently selected from H, $C_{3-7}$ cycloalkyl or $C_{1-4}$ alkyl.

Clause 25. A compound of the invention according to clause 22, wherein $R^4$ is $NHSO_2R^{4c}$, wherein $R^{4c}$ is Me, phenyl or $CF_3$.

Clause 26. A compound of the invention according to clause 1-17, wherein $R^2$ is $C_{1-4}$ alkyl optionally substituted with $S(O)_2R^4$.

Clause 27. A compound of the invention according to clause 26, wherein $R^4$ is N-linked 5-7 membered heterocycloalkyl (optionally substituted with one or more independently selected $C_{h6}$ alkyl, or oxo).

Clause 28. A compound of the invention according to clause 26, wherein $R^4$ is $NR^{4a}R^{4b}$, wherein each of $R^{4a}$ and $R^{4b}$ is independently selected from H, or $C_{1-4}$ alkyl.

Clause 29. A compound of the invention according to clause 1-17, wherein $R^2$ is $C_{1-4}$ alkyl substituted with one:

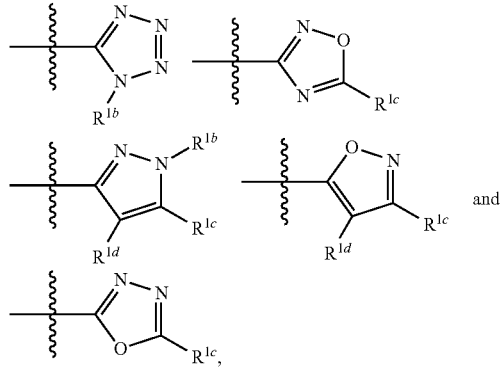

wherein $R^{1b}$ is H, or $C_{1-4}$ alkyl; $R^{1c}$ is OH, or $C_{1-4}$ alkoxy; and $R^{1d}$ is H, F, or $C_{1-4}$ alkyl.

Clause 30. A compound of the invention according to clause 1-17, wherein $R^2$ is $C_{1-4}$ alkyl optionally substituted with NHC(=O)$R^5$, $NHSO_2R^5$.

Clause 31. A compound of the invention according to clause 30, wherein $R^5$ is Me, Et, or $CF_3$.

Clause 32. A compound of the invention according to clauses 1-17, wherein $R^2$ is —(CH$_2$)—COOH, —(CH$_2$)$_3$—COOH, —(CH$_2$)$_3$—SO$_2$NH$_2$, or —(CH$_2$)$_3$—SO$_2$NHMe.

Clause 33. A compound of the invention according to any one of clauses 1-32, wherein $Cy_2$ is phenyl, or naphthalene.

Clause 34. A compound of the invention according to any one of clauses 1-32, wherein $Cy_2$ is 5-10 membered heteroaryl.

Clause 35. A compound of the invention according to clause 34, wherein $Cy_2$ is thiophenyl, benzothiophenyl, benzofuranyl, benzoisoxazolyl, benzoxazolyl or indolyl.

Clause 36. A compound of the invention according to any one of clause 1-35, wherein m is 1 or 2.

Clause 37. A compound of the invention according to clause 35, wherein each $R^3$ group is independently selected from F, Cl, Br, Me, $CF_3$, and OMe.

Clause 38. A compound of the invention according to any one of clause 1-35, wherein m is 0.

Clause 39. A compound of the invention according to any one of clauses 1-38, wherein $L_2$ is a single bond.

Clause 40. A compound of the invention according to any one of clauses 1-38, wherein $L_2$ is —$CR^cR^d$—, and wherein each of $R^c$ and $R^d$ are independently selected from H, Me, and Et.

Clause 41. A compound of the invention according to any one of clauses 1-38, wherein $L_2$ is —$CR^cR^d$—, and wherein $R^c$ is H and $R^d$ is H or $C_{1-4}$ alkyl Clause 42. A compound of the invention according to clause 41, wherein $L_2$ is —$CR^cR^d$—, and wherein $R^c$ is H and $R^d$ is H, Me, or Et.

Clause 43. A compound of the invention according to clause 41, wherein $L_2$ is —$CH_2$—.

Clause 44. A compound of the invention according to any one of clauses 1-38, wherein $L_2$ is Clause 45. A compound of the invention according to any one of clauses 1-38, wherein $L_2$ is —$NR^e$.

Clause 46. A compound of the invention according to clause 45, wherein $R^e$ is Me.

Clause 47. A compound of the invention according to clause 1, wherein the compound is 4-[[(R)-1-(Benzo[b]thiophene-3-carbonyl)-2-methyl-azetidine-2-carbonyl]-(3-chloro-benzyl)-amino]-butyric acid;

or a pharmaceutically acceptable salt, or a solvate, or a solvate of the pharmaceutically acceptable salt.

Clause 48. A pharmaceutical composition comprising a compound of the invention according to any of clauses 1-49, and a pharmaceutically acceptable carrier.

Clause 49. The pharmaceutical composition according to clause 48 comprising a further therapeutic agent.

Clause 50. The use of a compound of the invention according to any of clauses 1-47 in the manufacture of a medicament.

Clause 51. A compound of the invention according to any of clauses 1-47 for use as a medicament.

Clause 52. A method for the treatment or prophylaxis of inflammatory conditions, infectious diseases, autoimmune diseases, diseases involving impairment of immune cell functions, cardiometabolic diseases, and/or proliferative diseases, comprising administering a prophylactically or therapeutically effective amount of a compound of the invention according to any one of clauses 1-47, or a composition of any of clauses 48-49.

Clause 53. A method according to clause 52, wherein the condition or disease involves an inflammatory condition.

Clause 54. A method according to clause 53, wherein the inflammatory condition is rheumatoid arthritis.

Clause 55. A method according to clause 53, wherein the inflammatory condition is inflammatory bowel disorders.

Clause 56. A method according to clause 52, for the treatment or prophylaxis of cardiometabolic diseases.

Clause 57. The method according to clauses 52-56, wherein compound of the invention according to clause 1-48 is administered in combination with a further therapeutic agent.

Clause 58. The compound of the invention according to any one of clauses 1-48, or the pharmaceutical composition according to clauses 49 or 50, for use in the treatment or prophylaxis of inflammatory conditions, infectious diseases, autoimmune diseases, diseases involving impairment of immune cell functions, cardiometabolic diseases, and/or proliferative diseases.

Clause 59. The compound of the invention or the pharmaceutical composition according to clause 58, for use in the treatment of rheumatoid arthritis.

Clause 60. The compound of the invention or the pharmaceutical composition according to clause 58, for use in the treatment of inflammatory bowel disorders.

Clause 61. The compound of the invention or the pharmaceutical composition according to clause 58, for use in the treatment of cardiometabolic diseases.

Clause 62. The compound of the invention or the pharmaceutical composition according to clause 58, for use in the treatment of COPD or vasculitis.

Clause 63. The compound of the invention or the pharmaceutical composition according to clause 58, for use in the treatment of gout.

Clause 64. The compound of the invention or the pharmaceutical composition according to clause 58, for use in the treatment of sepsis, septicemia, endotoxemia, systemic inflammatory response syndrome (SIRS), gastritis, enteritis, enterocolitis, tuberculosis, and other infections involving *Yersinia, Salmonella, Chlamydia, Shigella*, or enterobacteria species.

Clause 65. The compound of the invention according to anyone of clauses 1-64, wherein the compound is present as the free base.

Clause 66. The compound of the invention according to anyone of clauses 1-64, wherein the compound is present as a pharmaceutically acceptable salt.

Clause 67. The compound of the invention according to anyone of clauses 1-64, wherein the compound is present as the free base or a pharmaceutically acceptable salt.

Clause 68. The compound of the invention according to anyone of clauses 1-64, wherein the compound is present as a solvate.

Clause 69. The compound of the invention according to anyone of clauses 1-64, wherein the compound is present as solvate of a pharmaceutically acceptable salt of the compound.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound. Generally, a compound of the invention is administered in a pharmaceutically effective amount. The amount of a compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of the invention can be administered by a variety of routes including oral, rectal, transdermal, subcutaneous, intra-articular, intravenous, intramuscular, and intranasal. Depending on the intended route of delivery, a compound of this invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, a compound of the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1

Tablets

A compound of the invention may be admixed as a dry powder with a dry gelatin binder in an approximate 1:2 weight ratio. A minor amount of magnesium stearate may be added as a lubricant. The mixture may be formed into 240-270 mg tablets (80-90 mg of active amide compound per tablet) in a tablet press.

Formulation 2

Capsules

A compound of the invention may be admixed as a dry powder with a starch diluent in an approximate 1:1 weight ratio. The mixture may be filled into 250 mg capsules (125 mg of active amide compound per capsule).

Formulation 3

Liquid

A compound of the invention (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Sufficient water may be then added to produce a total volume of 5 mL.

Formulation 4

Tablets

A compound of the invention may be admixed as a dry powder with a dry gelatin binder in an approximate 1:2 weight ratio. A minor amount of magnesium stearate may be added as a lubricant. The mixture is formed into 450-900 mg tablets (150-300 mg of active amide compound) in a tablet press.

Formulation 5

Injection

A compound of the invention may be dissolved or suspended in a buffered sterile saline injectable aqueous medium to a concentration of approximately 5 mg/mL.

Formulation 6

Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

A compound of the invention may be used as a therapeutic agent for the treatment of conditions in mammals that are causally related or attributable to aberrant activity of GPR43 and/or aberrant GPR43 expression and/or aberrant GPR43 distribution. Accordingly, a compound of the invention and pharmaceutical compositions of the invention find use as therapeutics for preventing and/or treating inflammatory conditions, infectious diseases, autoimmune diseases, diseases involving impairment of immune cell functions, cardiometabolic diseases, and/or proliferative diseases, in mammals including humans.

In additional method of treatment aspects, this invention provides methods of treating a mammal susceptible to or afflicted with an inflammatory condition. The methods comprise administering an effective condition-treating or condition-preventing amount of one or more of the pharmaceutical compositions or a compound of the invention herein described. In a specific embodiment, the inflammatory condition is selected from rheumatoid arthritis, osteoarthritis, gout, allergic airway disease (e.g. asthma) and inflammatory bowel disease.

In another aspect the present invention provides a compound of the invention for use in the treatment, prevention or prophylaxis of an inflammatory condition. In a specific embodiment, the inflammatory condition is selected from rheumatoid arthritis, osteoarthritis, gout, allergic airway disease (e.g. asthma) and inflammatory bowel disease.

In further method of treatment aspects, this invention provides methods of treating a mammal susceptible to or afflicted with an infectious disease, in particular sepsis, septicemia, endotoxemia, systemic inflammatory response syndrome (SIRS), gastritis, enteritis, enterocolitis, tuberculosis, and other infections involving *Yersinia, Salmonella, Chlamydia, Shigella*, or *enterobacteria* species. In another aspect the present invention provides a compound of the invention for use in the treatment, prevention or prophylaxis of an infectious disease, in particular sepsis, septicemia, endotoxemia, systemic inflammatory response syndrome (SIRS), gastritis, enteritis, enterocolitis, tuberculosis, and other infections involving *Yersinia, Salmonella, Chlamydia, Shigella*, or *enterobacteria* species.

In additional method of treatment aspects, this invention provides methods of treating a mammal susceptible to or afflicted with an autoimmune disease. The methods comprise administering an effective condition-treating or condition-preventing amount of one or more of the pharmaceutical compositions or a compound of the invention herein described. In a specific embodiment, the autoimmune disease is selected from COPD, asthma, psoriasis, systemic lupus erythematosis, type I diabetes mellitus, vasculitis and inflammatory bowel disease.

In another aspect the present invention provides a compound of the invention for use in the treatment, prevention or prophylaxis of an autoimmune disease. In a specific embodiment, the autoimmune disease is selected from COPD, asthma, psoriasis, systemic lupus erythematosis, type I diabetes mellitus, vasculitis and inflammatory bowel disease.

In additional method of treatment aspects, this invention provides methods of treating a mammal susceptible to or afflicted with a metabolic disease. The methods comprise administering an effective condition-treating or condition-preventing amount of one or more of the pharmaceutical compositions or a compound of the invention herein described. In a specific embodiment, the metabolic disease is selected from dyslipidemia, hypercholesterolemia, hypertriglyceridemia, obesity, metabolic syndrome, atherosclerosis, Type II diabetes, pre-diabetes, insulin resistance, heart disease, stroke, hypertension, and perivascular disease.

In another aspect the present invention provides a compound of the invention for use in the treatment, prevention or prophylaxis of a metabolic disease. In a specific embodiment, the metabolic disease is selected from dyslipidemia, hypercholesterolemia, hypertriglyceridemia, obesity, metabolic syndrome, atherosclerosis, Type II diabetes, pre-diabetes, insulin resistance, heart disease, stroke, hypertension, and perivascular disease.

As a further aspect of the invention there is provided a compound of the invention for use as a medicament especially in the treatment or prevention of the aforementioned conditions and diseases. Also provided herein is the use of the compound in the manufacture of a medicament for the treatment or prevention of one of the aforementioned conditions and diseases.

A particular regimen of the present method comprises the administration to a subject in suffering from an inflammatory condition, of an effective amount of a compound of the invention for a period of time sufficient to reduce the level of inflammation in the subject, and preferably terminate, the processes responsible for said inflammation. A special embodiment of the method comprises administering of an effective amount of a compound of the invention to a subject patient suffering from or susceptible to the development of inflammatory condition, for a period of time sufficient to reduce or prevent, respectively, inflammation of said patient, and preferably terminate, the processes responsible for said inflammation.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as degenerative conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of a compound of the invention, with particular doses each providing from about 0.1 to about 10 mg/kg and especially about 1 to about 5 mg/kg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compounds that demonstrate the same or a similar therapeutic activity, and that are determined to be safe and efficacious for such combined administration. In a specific embodiment, co-administration of two (or more) agents allows for significantly lower doses of each to be used, thereby reducing the side effects seen.

In one embodiment, a compound of the invention is co-administered with another therapeutic agent for the treatment and/or prevention of an inflammatory condition; particular agents include, but are not limited to, immunoregulatory agents e.g. azathioprine, corticosteroids (e.g. prednisolone or dexamethasone), cyclophosphamide, cyclosporin A, tacrolimus, Mycophenolate Mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prevention of arthritis (e.g. rheumatoid arthritis); particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, and cyclosporin), and biological DMARDS (for example but without limitation Infliximab, Etanercept, Adalimumab, Rituximab, and Abatacept).

In one embodiment, a compound of the invention is co-administered with another therapeutic agent for the treatment and/or prevention of autoimmune diseases; particular agents include but are not limited to: glucocorticoids, cytostatic agents (e.g. purine analogs), alkylating agents, (e.g nitrogen mustards (cyclophosphamide), nitrosoureas, platinum compounds, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g., anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-$\beta$), TNF binding proteins (e.g. infliximab (Remicade™), etanercept (Enbrel™), or adalimumab (Humira™)), mycophenolate, Fingolimod, and Myriocin.

In one embodiment, a compound of the invention is co-administered with another therapeutic agent for the treatment and/or prevention of infectious diseases; particular agents include but are not limited to antibiotics. In a particular embodiment, a compound of the invention is co-administered with another therapeutic agent for the treatment and/or prevention of infections of any organ of the human body; particular agents include but are not limited to: aminoglycosides, ansamycins, carbacephem, carbapenems, cephalosporins, glycopeptides, lincosamides, macrolides, monobactams, nitrofurans, penicillins, polypeptides, quinolones, sulfonamides, tetracyclins, anti-mycobacterial agents, as well as chloramphenicol, fosfomycin, linezolid, metronidazole, mupirocin, rifamycin, thiamphenicol and tinidazole.

In one embodiment, a compound of the invention is co-administered with another therapeutic agent for the treatment and/or prevention of asthma and/or rhinitis and/or COPD; particular agents include but are not limited to: beta$_2$-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled) Long-acting $\beta_2$-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. ceterizine, cinnarizine, fexofenadine), and vasoconstrictors (e.g. oxymethazoline, xylomethazoline, nafazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine, and intravenous magnesium sulfate.

In one embodiment, a compound of the invention is co-administered with another therapeutic agent for the treatment and/or prevention of inflammatory bowel disease (IBD); particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and ciclosporin) and biological disease modifying, immunomodulatory agents (infliximab, adalimumab, rituximab, and abatacept).

By co-administration is included any means of delivering two or more therapeutic-agents to the patient as part of the same treatment regime, as will be apparent to the skilled person. Whilst the two or more agents may be administered simultaneously in a single formulation this is not essential. The agents may be administered in different formulations and at different times.

General Synthetic Procedures

General

A compound of the invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Wiley-Blackwell; 4th Revised edition (2006), and references cited therein.

The following methods are presented with details as to the preparation of representative bicycloheteroaryls that have been listed hereinabove. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica standard (35-70 μm). Thin layer chromatography was carried out using pre-coated silica gel 60 F-254 plates (thickness 0.25 mm). $^1$H NMR spectra were recorded on a Bruker Advance 400 NMR spectrometer (400 MHz) or a Bruker Advance 300 NMR spectrometer (300 MHz). Chemical shifts (δ) for $^1$H NMR spectra are reported in parts per million (ppm) relative to tetramethylsilane (δ 0.00) or the appropriate residual solvent peak as internal reference. Multiplicities are given as singlet (s), doublet (d), triplet (t), quartet (q), multiplet (m) and broad (br). Electrospray MS spectra were obtained on a Waters platform LC/MS spectrometer. Analytic LCMS: Columns used, Waters Acquity UPLC BEH C18 1.7 μm, 2.1 mm ID×50 mm L or Waters Acquity UPLC BEH C18 1.7 μm, 2.1 mm ID×30 mm L. All the methods are using MeCN/H$_2$O gradients. MeCN and H$_2$O contain either 0.1% Formic Acid or NH$_3$ (10 mM). Preparative LCMS: Column used, Waters XBridge Prep C18 5 μm ODB 30 mm ID×100 mm L. All the methods are using MeOH/H$_2$O gradients. MeOH and H$_2$O contain either 0.1% Formic Acid or 0.1% Diethylamine. Microwave heating was performed with a Biotage Initiator.

The following is a list of abbreviations used in the experimental section:

| | |
|---|---|
| μL | microliter |
| ATP | Adenosine 5'-Triphosphate |
| Boc | tert-Butyloxy-carbonyl |
| Boc$_2$O | Di-tert-butyl dicarbonate |
| br s | broad singlet |
| Cat. | Catalytic amount |
| CDI | 1,1'-Carbonyldiimidazole |
| d | doublet |
| DCC | N,N'-Dicyclohexylcarbodiimide |
| DCE | 1,2-Dichloroethane |
| DCM | Dichloromethane |
| DIPEA | N,N-diisopropylethylamine |
| DMAP | 4-Dimethylaminopyridine |
| DME | Dimethoxyethane |
| DMEM | Dulbecco's Modified Eagle Medium |
| DMF | N,N-dimethylformamide |
| DMSO | Dimethylsulfoxide |
| EDC | N-(3-Dimethylaminopropyl)-N'-ethylcarbodiimide |
| EDTA 4 Na | Ethylenediaminetetraacetic Acid, tetrasodium Salt |
| EGTA | ethylene glycol tetraacetic acid |
| EtOAc | Ethyl acetate |
| FBS | Fetal bovine serum |
| FFAR2 | free fatty acid receptor 2 |
| g | gram |
| GDPDH | Guanosine diphosphate dehydrogenase |
| GTPγS | guanosine 5'-O-[gamma-thio]triphosphate |
| h | hour |
| HEPES | 4-(2-hydroxyethyl)-1-piperazineethanesulfonic acid |
| HOBt | 1-Hydroxybenzotriazole |
| iPr$_2$O | Diisopropyl ether |
| KHMDS | Potassium hexamethyldisilazane |
| LCMS | Liquid Chromatography-Mass Spectrometry |
| LiHMDS | Lithium hexamethyldisilazane |
| m | multiplet |
| MeCN | Acetonitrile |
| mg | milligram |
| min | minute |
| mL | milliliter |
| MW | Molecular weight |

| | |
|---|---|
| NADP | Nicotinamide adenine dinucleotide phosphate |
| NEAA | Non-Essential Amino Acid |
| NMR | Nuclear Magnetic Resonnance |
| PBST | Phosphate buffered saline with Tween 3.2 mM Na$_2$HPO$_4$, 0.5 mM KH$_2$PO$_4$, 1.3 mM KCl, 135 mM NaCl, 0.05% Tween 20, pH 7.4 |
| Pd/C | Palladium on Carbon 10% |
| ppm | part-per-million |
| q | quadruplet |
| rpm | revolutions per minute |
| RPMI medium | Roswell Park Memorial Institute medium |
| Rt | retention time |
| s | singlet |
| SM | Starting Material |
| spA | Scintillation proximity assay |
| t | triplet |
| TBTU | O-Benzotriazol-1-yl-N,N,N',N'-tetramethyluronium tetrafluoroborate |
| TEA | Triethylamine |
| TFA | Trifluoroacetic acid |
| THF | Tetrahydrofuran |

Synthetic Preparation of a Compound of the Invention

The compounds of the invention can be produced according to the following schemes.

General Synthetic Method

Intermediates

Synthesis of Carboxylic Acid

Illustrative Synthesis of Intermediate 1: Benzo[b]thiophen-4-yl-acetic acid

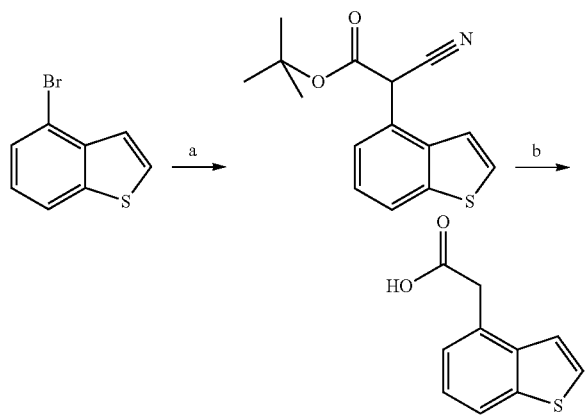

Step a: Benzo[b]thiophen-4-yl-cyano-acetic acid tert-butyl ester

To a solution of 4-bromobenzothiophene (1 eq.) in DME were added tert-butyl cyanoacetate (1.1 eq.) and t-BuOK (2 eq.). The reaction was refluxed for 40 min. Thereto were added dichlorobis(triphenylphosphine)palladium(II) (0.02 eq.) and triphenylphosphine (0.06 eq.). The resulting mixture was refluxed for 1.5 h under argon and then cooled to 20° C. Aqueous HCl (6N) was added dropwise until pH=1 and the reaction mixture was partitioned between water and EtOAc. The organic layer was separated, dried over MgSO$_4$, filtered and concentrated under reduced pressure. The crude was purified by chromatography on silica gel (elution with heptane/DCM: 9/1 to 1/1) to afford benzo[b]thiophen-4-yl-cyano-acetic acid tert-butyl ester.

$^1$H NMR δ (ppm) (CDCl$_3$): 7.92 (1H, d), 7.59 (1H, d), 7.54 (1H, d), 7.49 (1H, d), 7.39 (1H, t), 5.04 (1H, s), 1.42 (9H, s). MW (calcd): 273.4; MW (obsd): 274.0 (M+1).

Step b: Benzo[b]thiophen-4-yl-acetic acid

To a solution of benzo[b]thiophen-4-yl-cyano-acetic acid tert-butyl ester (1 eq.) in ethylene glycol were added an aqueous solution of 38 percent (w/w) potassium hydroxide and water. The reaction was heated at 95° C. for 2 h. The reaction mixture was partitioned between water and toluene, and the organic layer was discarded. The aqueous layer was acidified with aqueous HCl (6N) until pH=2 and extracted three times with EtOAc. The organic layers were combined, dried over MgSO$_4$, filtered and concentrated under reduced pressure. To the resulting residue was added a mixture of Et$_2$O/pentane and the precipitate was collected by filtration to provide benzo[b]thiophen-4-yl-acetic acid.

$^1$H NMR δ (ppm) (CDCl$_3$): 7.82 (1H, d), 7.48 (1H, d), 7.42 (1H, d), 7.31 (1H, t), 7.26 (1H, d), 3.97 (2H, s).

Illustrative Synthesis of Intermediate 2: Benzo[b]thiophen-2-yl-acetic acid

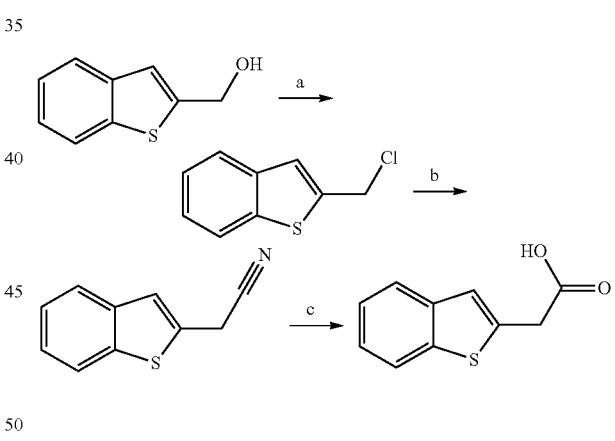

Step a: 2-Chloromethyl-benzo[b]thiophene

A solution of benzo[b]thiophen-2-yl-methanol (1 eq.) in thionyl chloride was stirred at 20° C. for 1 h. The crude was concentrated under reduced pressure then partitioned between a saturated aqueous solution of NaHCO$_3$ and EtOAc. The organic layer was separated, dried over MgSO$_4$, filtered and concentrated under reduced pressure to afford 2-chloromethyl-benzo[b]thiophene, used as such without further purification.

$^1$H NMR δ (ppm) (CDCl$_3$): 7.87-7.82 (1H, m), 7.80-7.75 (1H, m), 7.43-7.37 (2H, m), 7.34 (1H, s), 4.91 (2H, s)

Step b: Benzo[b]thiophen-2-yl-acetonitrile

To a solution of 2-chloromethyl-benzo[b]thiophene (1 eq.) in dioxane/water (2/1) was added KCN (1.5 eq.). The reaction was refluxed for 4 h. The crude was partitioned between water and EtOAc. The organic layer was washed with water, then brine, dried over MgSO$_4$, filtered and concentrated under reduced pressure. The crude was purified by chromatography on silica gel (elution with heptane/EtOAc: 95/5 to 90/10) to afford benzo[b]thiophen-2-yl-acetonitrile.

$^1$H NMR δ (ppm) (CDCl$_3$): 7.86-7.76 (2H, m), 7.45-7.38 (2H, m), 7.37-7.34 (1H, m), 4.04 (2H, s)

Step c: Benzo[b]thiophen-2-yl-acetic acid (Int 1)

To a solution of benzo[b]thiophen-2-yl-acetonitrile (1 eq.) in EtOH/water (1/1) was added NaOH pellets (12 eq.). The reaction was heated at 80° C. for 4 h and then allowed to cooled down to 20° C., at which point concentrated HCl was added carefully until pH=7 was reached. The reaction mixture was partially concentrated under reduced pressure then partitioned between water and EtOAc. The aqueous layer was extracted three times with EtOAc. The organic layers were combined, dried over MgSO$_4$, filtered and concentrated under reduced pressure to afford benzo[b]thiophen-2-yl-acetic acid.

$^1$H NMR δ (ppm) (CDCl$_3$): 7.82 (1H, d), 7.75 (1H, d), 7.42-7.31 (2H, m), 7.24 (1H, s), 4.00 (2H, s).

Synthesis of Chloroformate

Illustrative Synthesis of Intermediate 3: 3,5-dimethyl-phenyl-chloroformate

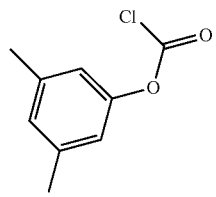

To a solution of triphosgene (0.5 eq.) in THF at 0° C. was added a solution of 3,5-dimethyl-phenol (1 eq.) and DIPEA (1 eq.) in THF. The reaction was stirred for 15 h at 20° C. The crude was partitioned between aqueous HCl (0.1N) and EtOAc. The aqueous layer was extracted three times with EtOAc. The organic layers were combined, dried over MgSO$_4$, filtered and concentrated under reduced pressure to afford 3,5-dimethyl-phenyl-chloroformate, used as such without further purification.

$^1$H NMR δ (ppm) (CDCl$_3$): 6.97 (1H, s), 6.86 (2H, s), 2.36 (6H, s).

Illustrative Synthesis of Intermediate 4: 2-chloro-phenyl-chloroformate

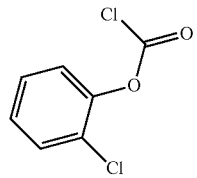 [SMILES: O=C(Cl)Oc1ccccc1Cl]

To a solution of triphosgene (0.5 eq.) in THF at 0° C. was added a solution of 2-chloro-phenol (1 eq.) and DIPEA (1 eq.) in THF. The reaction was stirred for 15 h at 20° C. The crude was partitioned between aqueous HCl (0.1N) and EtOAc. The aqueous layer was extracted three times with EtOAc. The organic layers were combined, dried over MgSO$_4$, filtered and concentrated under reduced pressure to afford 2-chloro-phenyl-chloroformate, used as such without further purification.

Illustrative Synthesis of Intermediate 5: 2-methyl-phenyl-chloroformate

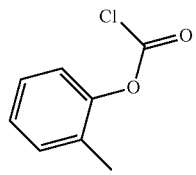

To a solution of 2-methyl-phenol (1 eq.) in DCM at 0° C. were added DMAP (0.1 eq.), TEA (10 eq.) and triphosgene (2 eq.). The reaction was stirred for 30 min at 0° C. The reaction mixture was used as such in the next step without further treatment.

Synthesis of Aldehydes

Illustrative Synthesis of Intermediate 6: 6-Formyl-indole-1-carboxylic acid tert-butyl ester

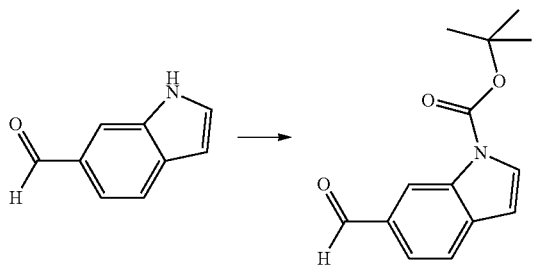 [SMILES: O=Cc1ccc2cc[nH]c2c1 ; CC(C)(C)OC(=O)n1ccc2ccc(C=O)cc21]

To a solution of tBuOK (1 eq.) in THF were added at 0° C. under nitrogen a solution of 1H-Indole-6-carbaldehyde (1 eq.) in THF and a solution of Boc$_2$O (1.2 eq.) in THF. The reaction was stirred at 0° C. for 1 h, then at 20° C. for 15 h. The crude was partitioned between water and EtOAc. The organic layer was dried over MgSO$_4$, filtered and concentrated under reduced pressure. The crude was purified by chromatography on silica gel (elution with heptane/EtOAc: 100/0 to 90/10) to afford 6-formyl-indole-1-carboxylic acid tert-butyl ester $^1$H NMR δ (ppm) (DMSO, d$_6$): 10.08 (1H, s), 8.61 (1H, s), 7.95 (1H, d), 7.80 (2H, q), 6.86 (1H, m), 1.66 (9H, s).

MW (calcd): 245.3; MW (obsd): 189.9 (M-56)

Illustrative Synthesis of Intermediate 7:
6-Formyl-indazole-1-carboxylic acid tert-butyl ester

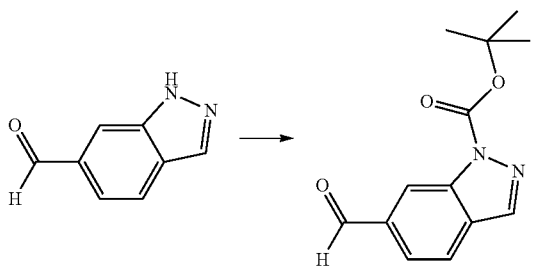 [SMILES: O=Cc1ccc2cn[nH]c2c1 ; CC(C)(C)OC(=O)n1ncc2ccc(C=O)cc21]

6-Formyl-indazole-1-carboxylic acid tert-butyl ester was also prepared following the method described above.

$^1$H NMR δ (ppm) (DMSO, $d_6$): 10.20 (1H, s), 8.64 (1H, s), 8.57 (1H, d), 8.08 (1H, d), 7.87 (1H, dd), 1.68 (9H, s).

MW (calcd): 246.3; MW (obsd): 191.0 (M−56)

Illustrative Synthesis of Intermediate 8:
benzofuran-6-carboxaldehyde

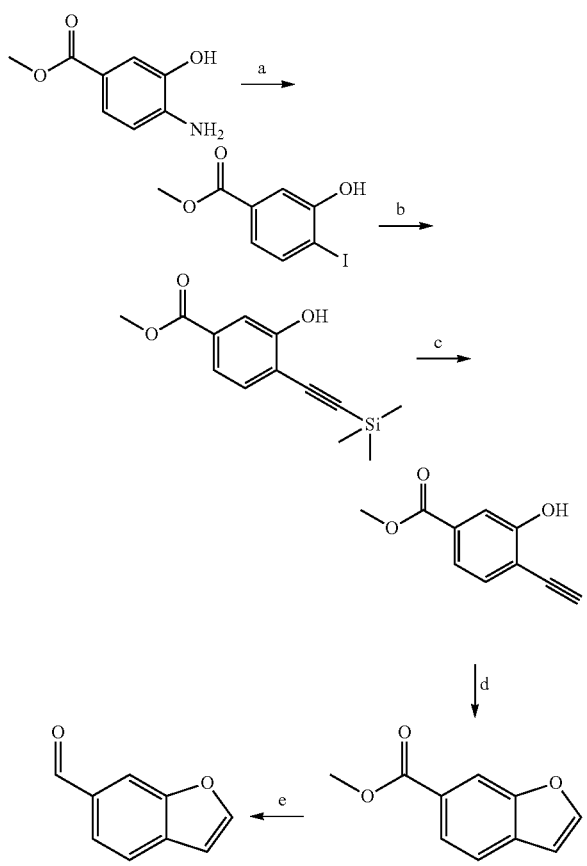

Step a: methyl 3-hydroxy-4-iodobenzoate

A solution of methyl 4-amino-3-hydroxybenzoate (1 eq.) in THF was diluted with aqueous HCl 3N and cooled to 0° C. Sodium nitrite (1.1 eq.) in $H_2O$ was added over 5 min. The reaction mixture was stirred for 25 min at 0° C. and then a solution of potassium iodide (4 eq.) in $H_2O$ was added in one portion, and stirred for 15 min. The reaction mixture was partitioned between water and EtOAc, the organic layer was washed with saturated aqueous NaCl, dried over $MgSO_4$, filtered and concentrated under reduced pressure. The crude was purified by chromatography on silica gel (elution with DCM) to afford methyl 3-hydroxy-4-iodobenzoate.

$^1$H NMR δ (ppm) (CDCl$_3$): 7.67 (1H, d), 7.33 (1H, d), 7.11 (1H, dd), 3.78 (3H, s).

MW (calcd): 278.1; MW (obsd): 276.8 (M−1).

Step b: methyl 3-hydroxy-4-[(trimethylsilyl)ethynyl]benzoate

To a solution of methyl 3-hydroxy-4-iodobenzoate (1 eq.) in dry THF were added trimethylsilylacetylene (5 eq.), tetrakis(triphenylphosphine)palladium (0.03 eq.), copper iodide (0.02 eq.) and diisopropylamine (2.1 eq.) under argon. The reaction mixture was stirred at 60° C. for 15 h, cooled to 20° C. and the solvents removed under reduced pressure. The crude was purified by chromatography on silica gel (elution with heptane/EtOAc: 9/1) to afford methyl 3-hydroxy-4-[(trimethylsilyl)ethynyl]benzoate.

$^1$H NMR δ (ppm) (CDCl$_3$): 7.64 (1H, s), 7.57 (1H, d), 7.43 (1H, d), 5.95 (1H, s), 3.95 (3H, s), 0.33 (9H, s).

MW (calcd): 248.4; MW (obsd): 249.1 (M+1).

Step c: 3-hydroxy-4-ethynylbenzoate

To a solution of methyl 3-hydroxy-4-[(trimethylsilyl)ethynyl]benzoate (1 eq.) in dry THF was added 1M tetrabutylammonium fluoride (1.5 eq.) under argon. The reaction was stirred at 20° C. for 30 min. The reaction mixture was quenched with aqueous HCl (1N), extracted with EtOAc, dried over $MgSO_4$, filtered and concentrated under reduced pressure. The crude was purified by chromatography on silica gel (elution with heptane/EtOAc: 1/1) to afford 3-hydroxy-4-ethynylbenzoate.

$^1$H NMR δ (ppm) (CDCl$_3$): 7.66 (1H, d), 7.60 (1H, dd), 7.48 (1H, d), 5.93 (1H, s), 3.95 (3H, s), 3.63 (9H, s).

MW (calcd): 176.2; MW (obsd): 177.1 (M+1).

Step d: methyl benzofuran-6-carboxylate

To a solution of methyl 3-hydroxy-4-ethynylbenzoate (1 eq.) in dry toluene was added $PtCl_2$ (0.1 eq.) under argon. The reaction mixture was stirred at 80° C. for 1.5 h, warmed to 20° C. and the solvents removed under reduced pressure. The crude was purified by chromatography on silica gel (elution with heptane/EtOAc: 9/1) to afford methyl benzofuran-6-carboxylate.

$^1$H NMR δ (ppm) (CDCl$_3$): 8.21 (1H, s), 7.96 (1H, dd), 7.77 (1H, d), 7.64 (1H, d), 6.85-6.80 (1H, m), 3.95 (3H, s).

MW (calcd): 176.2; MW (obsd): 177.0 (M+1).

Step e: benzofuran-6-carboxaldehyde

To a solution of methyl benzofuran-6-carboxylate (1 eq.) in dry THF was added a solution of $LiAlH_4$ (1M in THF, 1.5 eq.) at 0° C. under argon. The reaction mixture was stirred at 0° C. for 2.5 h. Water, aqueous NaOH (2N) and water were then added and the mixture was stirred at 20° C. for 30 min. The crude was passed through a pad of celite and solvent removed under reduced pressure. To a solution of the residue (1 eq.) in DCM was added $MnO_2$ (10 eq.). The dark suspension was stirred at 20° C. for 15 h, filtered through a pad of celite and the solvent removed under reduced pressure to afford benzofuran-6-carboxaldehyde which was used as such without further purification.

MW (calcd): 146.2; MW (obsd): 147.1 (M+1).

Illustrative Synthesis of Intermediate 9:
Imidazo[1,2-a]pyridine-7-carbaldehyde

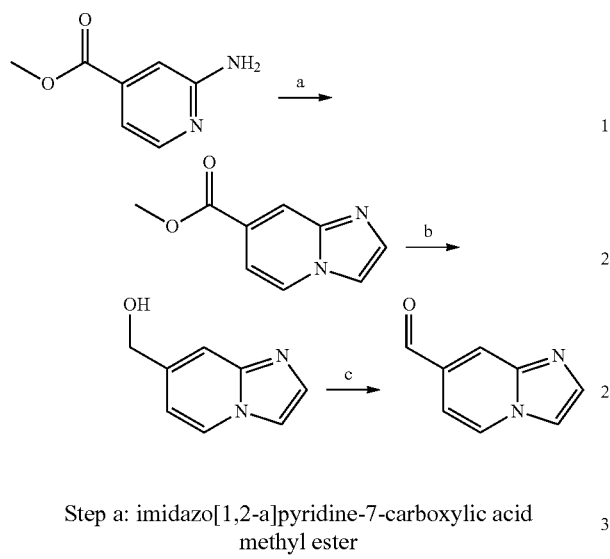

Step a: imidazo[1,2-a]pyridine-7-carboxylic acid methyl ester

To a solution of 2-amino-isonicotinic acid methyl ester (1 eq.) and chloroacetaldehyde (45% w/w in water) (4.5 eq.) in ethanol was added NaHCO$_3$ (1.7 eq.). The reaction mixture was refluxed for 15 h and the solvents removed under reduced pressure. The residue was partitioned between water and EtOAc, the organic layer was washed with a saturated aqueous solution of Na$_2$CO$_3$ and brine, dried over MgSO$_4$, filtered and concentrated under reduced pressure. The crude was purified by chromatography on silica gel (elution with DCM/MeOH: 100/0 to 98/2) to afford imidazo[1,2-a]pyridine-7-carboxylic acid methyl ester.

$^1$H NMR δ (ppm) (CDCl$_3$): 8.36 (1H, s), 8.16 (1H, dd), 7.79 (1H, dd), 7.68 (1H, d), 7.39 (1H, dd), 3.96 (3H, s).

MW (calcd): 178.2; MW (obsd): 177.2 (M−1).

Step b: Imidazo[1,2-a]pyridin-7-yl-methanol

To a −78° C. cooled solution of imidazo[1,2-a]pyridine-7-carboxylic acid methyl ester (1 eq.) in dry THF was slowly added a solution of LiAlH$_4$ in THF (1M in THF, 2 eq.). The reaction mixture was warmed to 0° C. and stirred for 30 min. The reaction mixture was then poured onto a cooled aqueous solution of NaOH 2N, stirred for 5 min and filtered through a pad of celite. The filtrate was partitioned between water and EtOAc, the organic layer was washed with brine, dried over MgSO$_4$, filtered and concentrated under reduced pressure to afford imidazo[1,2-a]pyridin-7-yl-methanol which was used as such without further purification.

$^1$H NMR δ (ppm) (MeOD, d$_4$): 8.41 (1H, d), 7.82 (1H, s), 7.60-7.52 (2H, m), 6.92 (1H, d), 4.70 (2H, d).

Step c: Imidazo[1,2-a]pyridine-7-carbaldehyde

To a solution of imidazo[1,2-a]pyridin-7-yl-methanol (1 eq.) in chloroform was added MnO$_2$ (10 eq.). The dark suspension was heated at 60° C. for 30 min, filtered through a pad of celite and the solvent removed under reduced pressure to afford imidazo[1,2-a]pyridine-7-carbaldehyde which was used as such without further purification.

$^1$H NMR δ (ppm) (CDCl$_3$): 10.03 (1H, s), 8.24 (1H, d), 8.16 (1H, s), 7.89 (1H, d), 7.79 (1H, d), 7.38 (1H, dd).

Illustrative Synthesis of Intermediate 10:
Benzothiazole-5-carbaldehyde

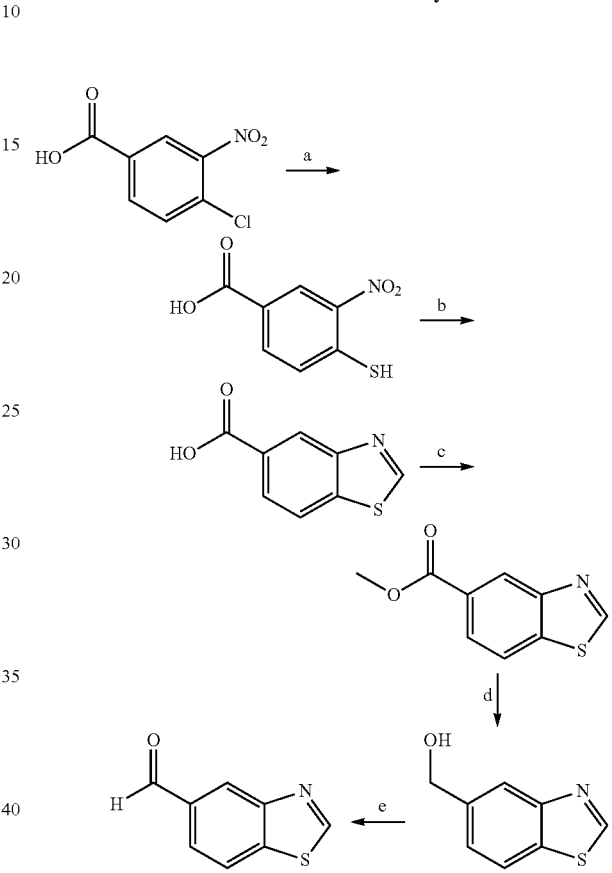

Step a: 4-mercapto-3-nitrobenzoic acid

To a suspension of 4-chloro-3-nitrobenzoic acid (1 eq.) in aqueous NaOH (0.15M) (1 eq.) was added Na$_2$S (4 eq.). The resulting mixture was refluxed for 24 h, cooled to room temperature and aqueous HCl (2N) was added until pH=3. The resultant precipitate was collected by filtration to provide 4-mercapto-3-nitrobenzoic acid which was used as such without further purification.

Step b: benzothiazole-5-carboxylic acid

A mixture of 4-mercapto-3-nitrobenzoic acid (1 eq.) and zinc dust (0.35 eq) in formic acid was refluxed for 6 h. The mixture was allowed to cool to room temperature, filtered and concentrated under reduced pressure. The residue was diluted with water, adjusted to pH=6.5 with aqueous NaOH (2N) and extracted three times with EtOAc. The organic layers were combined, dried over MgSO$_4$, filtered and concentrated under reduced pressure. The crude was purified by chromatography on silica gel (elution with DCM/MeOH: 1/0 to 95/5) to afford benzothiazole-5-carboxylic acid.

¹H NMR δ (ppm) (CDCl₃): 9.51 (1H, s), 8.58 (1H, d), 8.30 (1H, d), 8.03 (1H, dd).
MW (calcd): 179.2; MW (obsd): 180.0 (M+1).

Step c: benzothiazole-5-carboxylic acid methyl ester

To a suspension of benzothiazole-5-carboxylic acid (1 eq.) in MeOH at 0° C. was added dropwise thionyl chloride (2 eq.). The reaction was stirred at 60° C. for 15 h. The solvents were concentrated under reduced pressure to afford benzothiazole-5-carboxylic acid methyl ester.
¹H NMR δ (ppm) (1M in THF): 9.54 (1H, s), 8.60 (1H, d), 8.33 (1H, d), 8.04 (1H, dd), 3.91 (3H, s).
MW (calcd): 193.2; MW (obsd): 194.1 (M+1).

Step d: benzothiazol-5-yl-methanol

To a –78° C. cooled solution of benzothiazole-5-carboxylic acid methyl ester (1 eq.) in dry THF under nitrogen was slowly added a solution of LiAlH₄ (1M in THF, 1.5 eq.). The reaction was stirred at –78° C. for 2 h, then warmed to 20° C. EtOAc was added to the reaction, then aqueous NaOH (2N) and finally water. The reaction mixture was stirred at 20° C. for 30 min, then filtered through a pad of celite. The filtrate was concentrated under reduced pressure. The crude was purified by chromatography on silica gel (elution with heptane/EtOAc: 1/0 to 1/1) to afford benzothiazol-5-yl-methanol.
¹H NMR δ (ppm) (CDCl₃): 9.05 (1H, s), 8.17 (1H, s), 7.97 (1H, d), 7.52 (1H, d), 4.91 (2H, s).
MW (calcd): 165.2; MW (obsd): 166.2 (M+1).

Step e: benzothiazole-5-carbaldehyde

To a solution of benzothiazol-5-yl-methanol (1 eq.) in DCM was added MnO₂ (10 eq.). The dark suspension was stirred at 20° C. for 15 h, filtered through a pad of celite and the solvent removed under reduced pressure to afford benzothiazole-5-carbaldehyde which was used as such without further purification.
¹H NMR δ (ppm) (CDCl₃): 10.2 (1H, s), 9.13 (1H, s), 8.61 (1H, d), 8.12 (1H, d), 8.00 (1H, dd).
MW (calcd): 163.2; MW (obsd): 164.1 (M+1)

General Synthetic Methods

Method A

Azetidine Formation

Illustrative Synthesis of Intermediate 11:
2-Methyl-azetidine-1,2-dicarboxylic acid 1-tert-butyl ester 2-ethyl ester

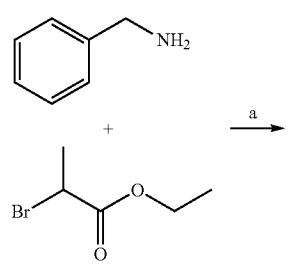

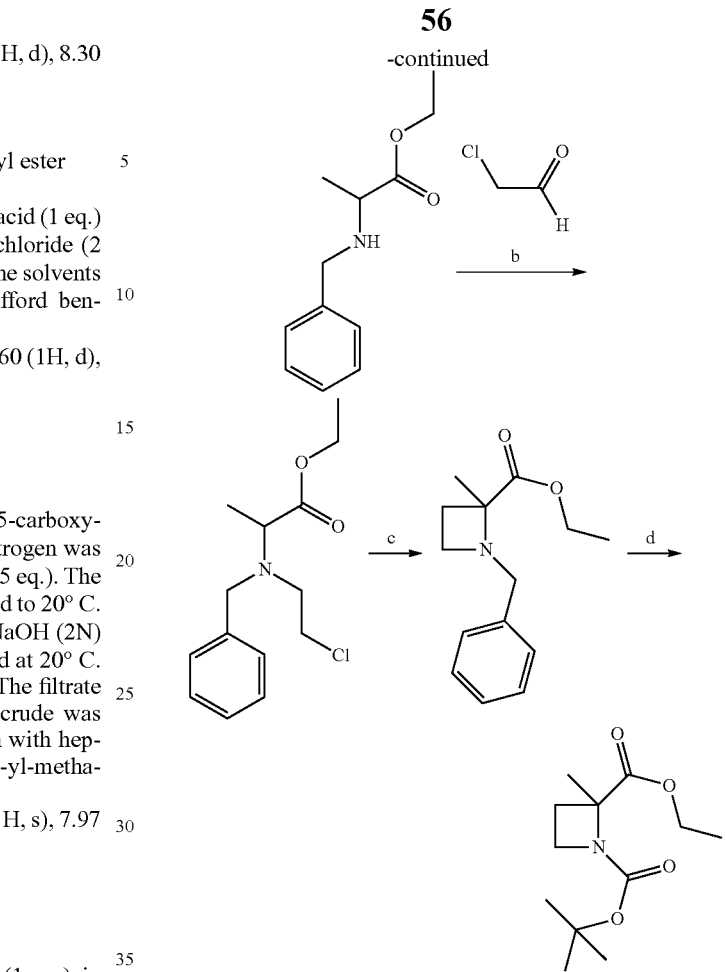

Step a: 2-Benzylamino-propionic acid ethyl ester

To a solution of 2-bromo-propionic acid ethyl ester (1 eq.) in MeCN was added benzylamine (0.9 eq.) and potassium carbonate (1.5 eq.). The reaction was refluxed for 4 h then cooled to 20° C. and diluted with EtOAc. The crude was filtered, the filtrate was concentrated under reduced pressure, then purified by chromatography on silica gel (elution with heptane/EtOAc: 7/3) to afford 2-benzylamino-propionic acid ethyl ester.
¹H NMR δ (ppm) (CDCl₃): 7.37-7.29 (4H, m), 7.28-7.22 (1H, m), 4.20 (2H, q), 3.82 (1H, d), 3.69 (1H, d), 3.38 (1H, q), 1.33 (3H, d), 1.29 (3H, t)
MW (calcd): 207.2; MW (obsd): 208.1 (M+1)

Step b: 2-[Benzyl-(2-chloro-ethyl)-amino]-propionic acid ethyl ester (I) Drying of Chloroacetaldehyde Solution (Solution I):
To a solution of chloroacetaldehyde (45% w/w in water) (3 eq.) in DCM under nitrogen was added MgSO₄ (4 eq.). The mixture was stirred for 15 min at 20° C. under nitrogen. The solid was filtered, washed with dry DCM, and the resulting filtrate (solution I) was rapidly used in the following reaction.
(II) Reaction:
To a solution of 2-benzylamino-propionic acid ethyl ester (1 eq.) in dry DCM was added MgSO₄ (0.75 eq.). The reaction was cooled to 0° C. then the above solution of chloroacetaldehyde in dry DCM (solution I) and acetic acid (1 eq.) were added. Sodium triacetoxyborohydride (1.5 eq.) was added portionwise. The reaction was stirred for 1 h at 0° C. The crude was carefully quenched with a saturated aqueous solution of NaHCO$_3$. Then aqueous NaOH (2N) was added. The aqueous layer was extracted with DCM. The combined organic layers were washed with an aqueous saturated solution of NaHCO$_3$, then dried over MgSO$_4$ and concentrated under reduced pressure. The crude was purified by chromatography on silica gel (elution with heptane/EtOAc 98/2 to 95/5) to afford 2-[benzyl-(2-chloro-ethyl)-amino]-propionic acid ethyl ester.

$^1$H NMR δ (ppm) (CDCl$_3$): 7.40-7.29 (4H, m), 7.29-7.22 (1H, m), 4.24-4.14 (2H, m), 3.90 (1H, d), 3.77 (1H, d), 3.50 (1H, q), 3.43-3.36 (2H, m), 3.13-2.94 (2H, m), 1.34 (3H, d), 1.31 (3H, t)

MW (calcd): 269.8; MW (obsd): 270.1 (M+1, $^{35}$Cl)

Step c: 1-Benzyl-2-methyl-azetidine-2-carboxylic acid ethyl ester

A solution of 2-[benzyl-(2-chloro-ethyl)-amino]-propionic acid ethyl ester (1 eq.) in dry THF was cooled to −78° C. under nitrogen. KHMDS (15% w/w in toluene) (1.25 eq.) was slowly added so that temperature was kept below −65° C. The reaction was stirred for 1 h at −70° C. Then acetic acid (0.3 eq.) was added. The reaction was warmed to 20° C. and stirred for 10 min, then quenched with a saturated aqueous solution of NaHCO$_3$ and partially concentrated under reduced pressure. The crude was extracted twice with DCM. The organic layers were combined, dried over MgSO$_4$, filtered and concentrated under reduced pressure. The crude was purified by chromatography on silica gel (elution with heptane/EtOAc 1/0 then 95/5) to afford 1-benzyl-2-methyl-azetidine-2-carboxylic acid ethyl ester.

$^1$H NMR δ (ppm) (CDCl$_3$): 7.34-7.19 (5H, m), 4.24-4.16 (2H, m), 3.79 (1H, d), 3.58 (1H, d), 3.30-3.22 (1H, m), 3.15-3.05 (1H, m), 2.63-2.54 (1H, m), 1.97-1.88 (1H, m), 1.49 (3H, s), 1.29 (3H, t)

MW (calcd): 233.3; MW (obsd): 234.1 (M+1)

Step d: 2-Methyl-azetidine-1,2-dicarboxylic acid 1-tert-butyl ester 2-ethyl ester To a solution of 1-benzyl-2-methyl-azetidine-2-carboxylic acid ethyl ester (1 eq.) in EtOH was added Boc$_2$O (1.2 eq.) and Pd/C (0.05 eq.). The flask was evacuated and backfilled with argon. Then the reaction was evacuated and backfilled with H$_2$ and stirred for 15 h at 20° C. under atmospheric pressure. The crude was filtered through a pad of celite and washed with EtOH and DCM. The filtrate was concentrated under reduced pressure to afford 2-methyl-azetidine-1,2-dicarboxylic acid 1-tert-butyl ester 2-ethyl ester.

$^1$H NMR δ (ppm) (CDCl$_3$): 4.12-3.92 (2H, m), 3.86-3.71 (1H, m), 3.66-3.54 (1H, m), 2.17-2.00 (1H, m), 1.99-1.83 (1H, m), 1.33 (3H, s), 1.21 (9H, s), 1.11 (3H, t)

MW (calcd): 243.3; MW (obsd): 266$^+$ (M+Na$^+$)

Intermediate 12 and 200, listed in table I were also prepared following the same method.

Method B1

Boc Deprotection

Illustrative Synthesis of Intermediate 13:
2-Methyl-azetidine-2-carboxylic acid ethyl ester hydrochloride

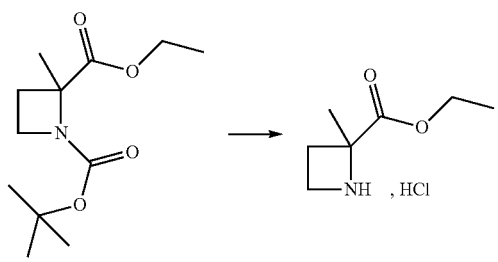

To a solution of Intermediate 11 (1 eq.) in dioxane under Argon was added a solution of HCl (4N in dioxane, 10 eq.). The reaction was stirred for 16 h at 20° C., then concentrated under reduced pressure. The crude was triturated with a mixture of DCM/iPr$_2$O, and the resulting solid was filtered and dried to afford 2-methyl-azetidine-2-carboxylic acid ethyl ester hydrochloride.

$^1$H NMR δ (ppm) (CDCl$_3$): 9.48 (1H, br s), 4.35 (2H, q), 4.16-4.00 (2H, m), 2.82-2.70 (1H, m), 2.60-2.45 (1H, m), 1.95 (3H, s), 1.36 (3H, t)

Method B2

Boc Deprotection

Illustrative Synthesis of Intermediate 28:
2-Methyl-azetidine-2-carboxylic acid
4-chloro-benzylamide, trifluoroacetic acid

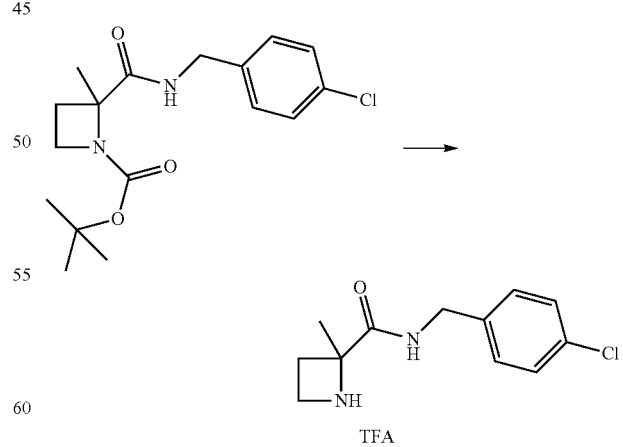

2-(4-Chloro-benzylcarbamoyl)-2-methyl-azetidine-1-carboxylic acid tert-butyl ester, Intermediate 138 was dissolved in a solution of TFA (20% in DCM) and the reaction was stirred for 15 h at 20° C. The solvents were removed under reduced pressure to afford the desired product which was used as such without further purification.

¹H NMR δ (ppm) (DMSO-d₆): 9.25 (1H, br s), 9.00 (1H, t), 7.41 (2H, d), 7.30 (2H, d), 4.35 (2H, d), 4.00-3.86 (1H, m), 3.70-3.59 (1H, m), 2.68-2.55 (1H, m), 2.46-2.35 (1H, m), 1.75 (3H, s)

Method C

Saponification

Illustrative Synthesis of Intermediate 31: 2-Methyl-azetidine-1,2-dicarboxylic acid 1-tert-butyl ester

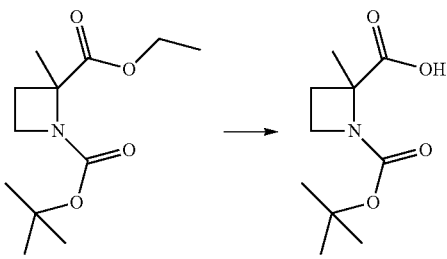 [SMILES: CCOC(=O)C1(C)CCN1C(=O)OC(C)(C)C ; CC(C)(C)OC(=O)N1CCC1(C)C(=O)O]

To a solution of 2-methyl-azetidine-1,2-dicarboxylic acid 1-tert-butyl ester 2-ethyl ester, Intermediate 11 (1 eq.) in EtOH was added an aqueous solution of 2N NaOH (2 eq.). The reaction was stirred at 20° C. for 15 h. The solvent was removed under reduced pressure and the crude was partitioned between water and EtOAc. The organic layer was discarded and the aqueous layer was acidified by addition of a solution of citric acid 10% in water until pH=3 and thoroughly extracted by EtOAc. The organic layers were combined, dried over MgSO₄, filtered and concentrated under reduced pressure to afford 2-methyl-azetidine-1,2-dicarboxylic acid 1-tert-butyl ester.

¹H NMR δ (ppm) (CDCl₃): 3.93-3.81 (1H, m), 3.81-3.68 (1H, m), 2.85-2.71 (1H, m), 2.12-2.00 (1H, m), 1.72 (3H, s), 1.48 (9H, s)

Method D

Chiral Separation

Illustrative Synthesis of Intermediate 33: (R)-2-Methyl-azetidine-1,2-dicarboxylic acid 1-tert-butyl ester

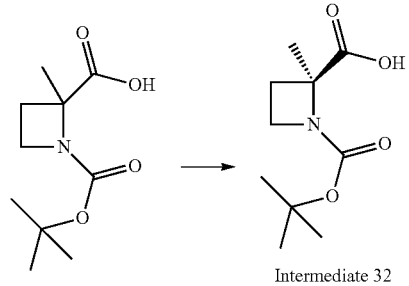

Intermediate 31

Intermediate 32
Configuration (S)
Rt = 6.42

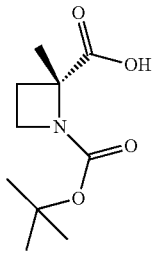

Intermediate 33
Configuration (R)
Rt = 9.00

The chiral separation of racemic Intermediate 31 was performed by preparative chiral chromatography using the following conditions:
  column: Chiralpak AD-H, (20×250 mm), 5 µm,
  mobile phase: Hexane:Ethanol:Formic acid (95:5:0.05), flow rate of 9.5 mL/min, at 20° C.
thus affording Intermediates 32 and 33 in their enantiopure forms.

Determination of the Absolute Configuration of Intermediate 33:

The absolute configuration of Intermediate 33 was determined by converting it to Intermediate 34 (R)-1-benzyl-2-methyl-azetidine-2-carboxylic acid methyl ester for which [α]_D and absolute configuration are described in the literature (J. Org. Chem. 2009, 6077).

Synthesis of Intermediate 34
(R)-1-Benzyl-2-methyl-azetidine-2-carboxylic acid methyl ester

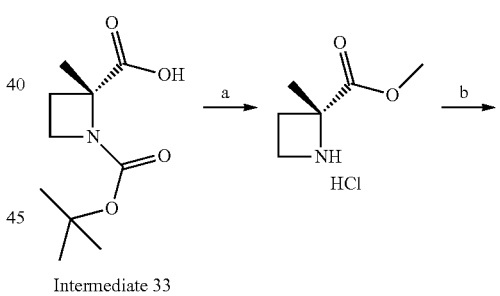

Intermediate 33

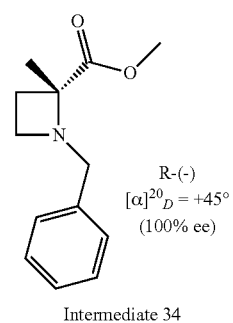

R-(-)
[α]²⁰_D = +45°
(100% ee)

Intermediate 34

Step a: (R)-2-Methyl-azetidine-2-carboxylic acid methyl ester hydrochloride

After a chiral separation of the Intermediate 33 (1 eq.) (100% ee) in solution in MeOH was cooled at 0° C. under nitrogen. Thionyl chloride (2.5 eq) was added dropwise, the reaction was stirred at 20° C. for 15 h. The solvents were concentrated under reduced pressure to afford (R)-2-methyl-azetidine-2-carboxylic acid methyl ester hydrochloride.

Step b:
(R)-1-Benzyl-2-methyl-azetidine-2-carboxylic acid methyl ester

To a solution of (R)-2-methyl-azetidine-2-carboxylic acid methyl ester (1 eq.) in THF were added TEA (2 eq.) and benzyl bromide (1 eq.). The reaction was heated at 50° C. for 15 h. The solvent was concentrated under reduced pressure, the crude was purified by chromatography on silica gel (elution with heptane/EtOAc 1/0 to 1/1) to afford (R)-1-benzyl-2-methyl-azetidine-2-carboxylic acid methyl ester.

$^1$H NMR δ (ppm) (CDCl$_3$): 7.42-7.21 (5H, m), 3.86-3.74 (4H, m), 3.66-3.54 (1H, m), 3.34-3.07 (2H, m), 2.68-2.55 (1H, m), 2.02-1.91 (1H, m), 1.53 (3H, s)

$[α]^{20}_D$=+45 (c=1.55, CHCl$_3$)

Reported value for (R) enantiomer: $[α]^{25}_D$=+36° (c=0.5, CHCl$_3$, 91% ee), described in the literature (*J. Org. Chem.* 2009, 6077)

Intermediate 34 corresponds to isomer (R). Therefore Intermediate 33 is undoubtedly (R)-2-methyl-azetidine-1,2-dicarboxylic acid 1-tert-butyl ester.

Intermediate 33 was also converted in Intermediate 35 (R)-1-(4-Bromo-benzoyl)-2-methyl-azetidine-2-carboxylic acid in order to determine the X-Ray structure.

Synthesis of Intermediate 35. (R)-1-(4-Bromo-benzoyl)-2-methyl-azetidine-2-carboxylic acid Step a: (R)-2-Methyl-azetidine-2-carboxylic acid hydrochloride After a chiral separation, Intermediate 33 (1 eq.) (100% ee) was solubilised in dioxane. A solution of HCl (4N) in dioxane was added and the reaction was stirred at 20° C. for 15 h. The solvent was removed under reduced pressure and the crude was crystallised in a mixture of DCM/iPr$_2$O/pentane to afford (R)-2-methyl-azetidine-2-carboxylic acid hydrochloride.

Step b: (R)-1-(4-Bromo-benzoyl)-2-methyl-azetidine-2-carboxylic acid

To a solution of (R)-2-methyl-azetidine-2-carboxylic acid methyl ester (1 eq.) in water were added aqueous NaOH (1M) (3 eq.) then 4-bromo-benzoyl-chloride (1 eq.) dropwise. The reaction was stirred for 4 h at 20° C. The reaction was neutralised with acetic acid. The solvent was partially removed under reduced pressure and the crude was extracted with EtOAc. The organic layer was dried over MgSO$_4$, filtered and concentrated under reduced pressure. The crude was purified by chromatography on silica gel (elution with DCM/MeOH/AcOEt/AcOH/iPr2O: 95/5/98/2/300) to afford (R)-1-(4-bromo-benzoyl)-2-methyl-azetidine-2-carboxylic acid.

$^1$H NMR δ (ppm) (CDCl$_3$): 7.65 (2H, d), 7.59 (2H, d), 4.48-4.39 (1H, m), 4.28-4.19 (1H, m), 3.07-2.97 (1H, m), 2.34-2.24 (1H, m), 1.95 (3H, s)

The X-Ray structure of Intermediate 35 confirms (R) absolute configuration and consequently Intermediate 33 corresponds to isomer (R).

Method E

Synthesis of Secondary Amines

Method E1

Illustrative Synthesis of Intermediate 36: (4-Chloro-benzylamino)-acetic acid methyl ester

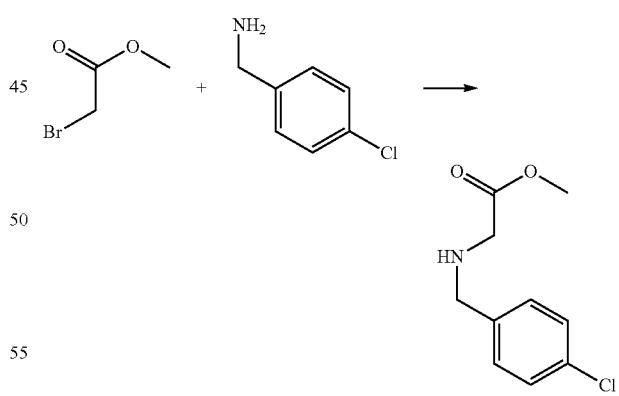

To a solution of 4-chloro-benzylamine (1 eq.) in MeCN was added bromo-acetic acid methyl ester (1 eq.), K$_2$CO$_3$ (1.5 eq.) and KI (0.1 eq.). The reaction was stirred for 15 h at 20° C. The crude was concentrated under reduced pressure then partitioned between water and EtOAc. The organic layer was dried over MgSO$_4$, filtered and concentrated under reduced pressure. The crude was purified by chromatography on silica gel (elution with heptane/EtOAc: 1/0 to 8/2) to afford (4-chloro-benzylamino)-acetic acid methyl ester.

$^1$H NMR δ (ppm) (CDCl$_3$): 7.35-7.28 (4H, m), 3.81 (2H, s), 3.77 (3H, s), 3.44 (2H, s), 2.00 (1H, s)

Method E2

Illustrative Synthesis of Intermediate 44: 4-[(R)-1-(4-Chloro-phenyl)-ethylamino]-butyric acid methyl ester

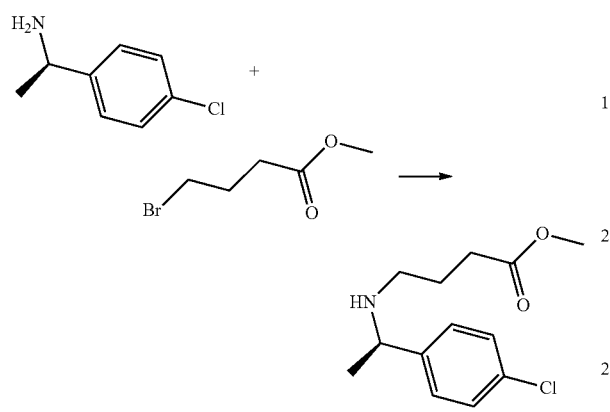

To a suspension of K$_2$CO$_3$ (1.5 eq.) and (R)-1-(4-chlorophenyl)-ethylamine (0.9 eq.) in MeCN was added 4-bromobutyric acid methyl ester (1 eq.) and KI (0.1 eq.). The reaction was stirred for 15 h at 20° C., then heated to reflux until completion. The crude was partitioned between water and EtOAc. The organic layer was washed with brine, dried over MgSO$_4$, filtered and concentrated under reduced pressure. The crude was purified by chromatography on silica gel (elution with DCM/MeOH: 99/1 to 90/10) to afford 4-[(R)-1-(4-chloro-phenyl)-ethylamino]-butyric acid methyl ester.

$^1$H NMR δ (ppm) (CDCl$_3$): 7.35-7.24 (4H, m), 3.81-3.70 (1H, m), 3.68 (3H, s), 2.62-2.51 (1H, m), 2.47-2.31 (3H, m), 1.85-1.72 (2H, m), 1.39 (1H, br s), 1.33 (3H, d)

MW (calcd): 255.7; MW (obsd): 256.3 (M+1, $^{35}$Cl)

Method E3

Illustrative Synthesis of Intermediate 50: (4-Chloro-benzyl)-ethyl-amine

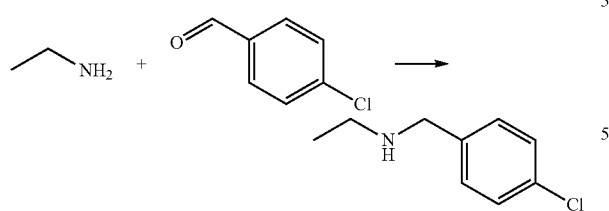

To a solution of 4-chlorobenzaldehyde (1 eq.) in MeOH was added ethylamine 70% in water (10 eq.). The reaction was stirred for 15 h at 20° C. under argon then NaBH$_4$ (2 eq.) was added. The reaction was stirred at 20° C. for 5 h. The reaction was quenched with water then acidified with aqueous HCl (2M). The aqueous layer was washed with EtOAc. The organic layer was discarded. Aqueous NaOH (2M) was then added to the aqueous layer until pH=10 and the crude was extracted twice with EtOAc. The organic layers were combined, dried over MgSO$_4$, filtered and concentrated under reduced pressure to afford (4-chloro-benzyl)-ethyl-amine.

$^1$H NMR δ (ppm) (CDCl$_3$): 7.27-7.12 (4H, m), 3.69 (2H, s), 2.60 (2H, q), 1.64 (1H, br s), 1.06 (3H, t)

Method E4

Illustrative Synthesis of Intermediate 56: (4-Chloro-benzylamino)-acetic acid ethyl ester

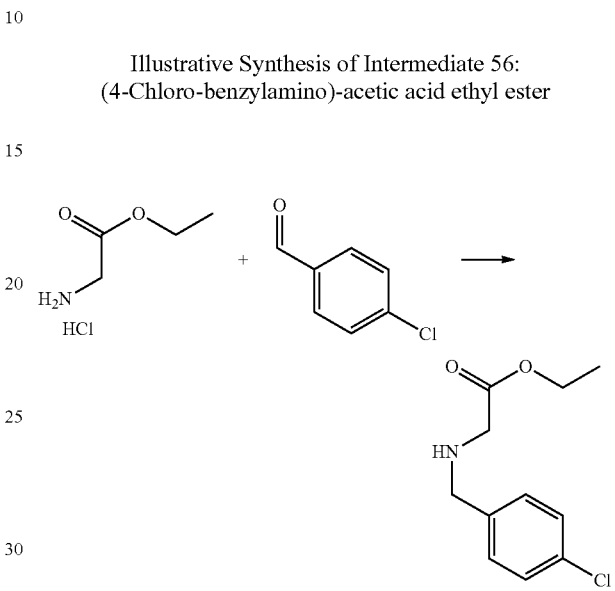

To a suspension of glycine ethyl ester hydrochloride (1.2 eq.) in DCE was added TEA (2 eq.) The reaction was stirred for 10 min at 20° C. then 4-chlorobenzaldehyde (1 eq.), acetic acid (4 eq.) and sodium triacetoxyborohydride (2 eq.) were added. The reaction was stirred for 15 h at 20° C. The crude was partitioned between DCM and a saturated aqueous solution of NaHCO$_3$. The aqueous layer was then extracted twice with DCM. The organic layers were combined, washed with brine, dried on MgSO$_4$, filtered and concentrated under reduced pressure to afford (4-chloro-benzylamino)-acetic acid ethyl ester.

$^1$H NMR δ (ppm) (CDCl$_3$): 7.25-7.16 (4H, m), 4.12 (2H, q), 3.71 (2H, s), 3.32 (2H, s), 1.79 (1H, br s), 1.20 (3H, t)

MW (calcd): 227.7; MW (obsd): 228.3 (M+1, $^{35}$Cl)

Method E5

Illustrative Synthesis of Intermediate 61: 3-(4-Chloro-benzylamino)-propionic acid methyl ester

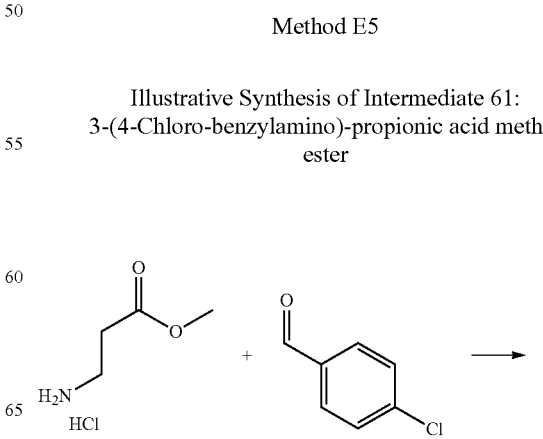

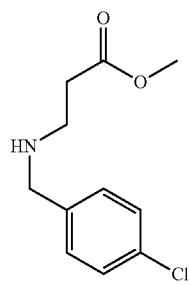

To a solution of 4-chlorobenzaldehyde (1 eq.) in MeOH were added NaHCO$_3$ (1.3 eq.) and (β-alanine methyl ester hydrochloride (1.2 eq.). The reaction was stirred for 15 h at 20° C. under nitrogen, then cooled to 0° C. Sodium triacetoxyborohydride (1.5 eq.) was added portionwise. The reaction was then warmed to 20° C. and stirred for 8 h. The crude was concentrated under reduced pressure then partitioned between EtOAc and a saturated aqueous solution of NaHCO$_3$. The aqueous layer was extracted twice with EtOAc. The organic layers were combined, dried over MgSO$_4$, filtered and concentrated under reduced pressure. The crude was purified by chromatography on silica gel (elution with heptane/DCM/MeOH: 50/50/0, then 0/100/0, then 0/99/1) to afford 3-(4-chloro-benzylamino)-propionic acid methyl ester.

$^1$H NMR δ (ppm) (CDCl$_3$): 7.34-7.23 (4H, m), 3.77 (2H, s), 3.68 (3H, s), 2.87 (2H, t), 2.54 (2H, t), 1.90 (1H, br s).

Method E6

Illustrative Synthesis of Intermediate 67: 2-(4-Chloro-benzylamino)-ethanol

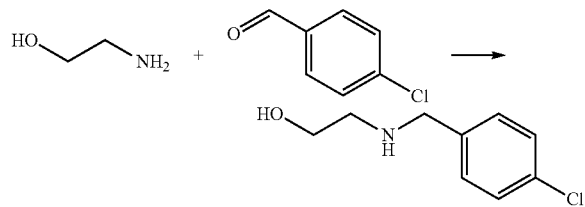

To a solution of ethanolamine (1.2 eq.) in either MeOH or THF were added NaHCO$_3$ (1.5 eq.) and 4-chlorobenzaldehyde (1 eq.). The reaction was refluxed for 4 h, then cooled to 0° C. NaBH$_4$ (1.2 eq.) was added portionwise. The reaction was stirred for 1 h at 0° C., then 15 h at 20° C. The crude was concentrated under reduced pressure then partitioned between water and DCM. The aqueous layer was then extracted twice with DCM. The organic layers were combined, dried over MgSO$_4$, filtered and concentrated under reduced pressure. The crude was purified by chromatography on silica gel (elution with DCM/MeOH: 1/0 to 95/5) to afford 2-(4-chloro-benzylamino)-ethanol.

$^1$H NMR δ (ppm) (CDCl$_3$): 7.37-7.26 (4H, m), 3.82 (2H, s), 3.70 (2H, t), 2.83 (2H, t), 2.19 (2H, br s)

Method E7

Illustrative Synthesis of Intermediate 71: 6-[(3-Ethoxycarbonyl-propylamino)-methyl]-indole-1-carboxylic acid tert-butyl ester

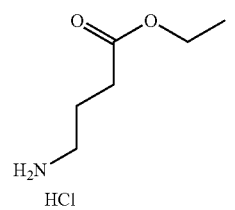

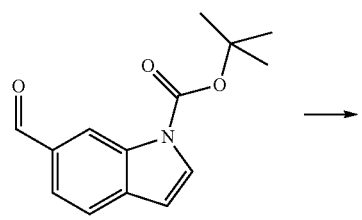

To a solution of 4-amino-butyric acid ethyl ester hydrochloride (1 eq.) in either MeOH or EtOH were added TEA (2.5 eq.), 6-formyl-indole-1-carboxylic acid tert-butyl ester (0.95 eq.) and MgSO$_4$ (1.5 eq.). The reaction was stirred at 20° C. for 15 h, then cooled to −15° C. NaBH$_4$ (2 to 6 eq.) was added portionwise. The reaction was stirred for 1 h at −15° C., then 1 h at 0° C. The reaction was quenched with the addition of cold water at 0° C. The crude was extracted three times with DCM. The organic layers were combined, dried over MgSO$_4$, filtered and concentrated under reduced pressure at 20° C. The crude was purified by chromatography on silica gel (elution with DCM/MeOH: 1/0 to 99/1) to afford 6-[(3-ethoxycarbonyl-propylamino)-methyl]-indole-1-carboxylic acid tert-butyl ester.

$^1$H NMR δ (ppm) (DMSO-d$_6$): 8.06 (1H, s), 7.60 (1H, d), 7.52 (1H, d), 7.22-7.16 (1H, m), 6.68-6.64 (1H, m), 4.02 (2H, q), 3.77 (2H, s), 2.54-2.46 (2H, m), 2.37-2.30 (2H, t), 2.15 (1H, br s), 1.73-1.64 (2H, m), 1.63 (9H, s), 1.14 (3H, t).

MW (calcd): 360.5; MW (obsd): 361.1 (M+1)

Method E8

Illustrative Synthesis of Intermediate 82: 4-[(Benzofuran-6-ylmethyl)-amino]-butyric acid ethyl ester

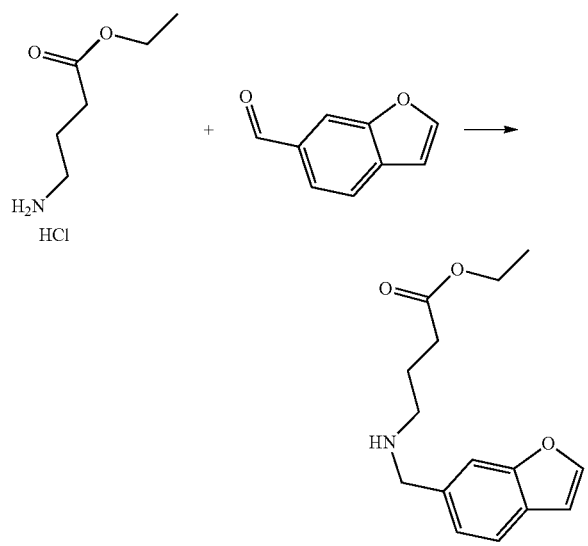

To a solution of 4-amino-butyric acid ethyl ester hydrochloride (1 eq.) in THF was added TEA (2.5 eq.). The mixture was stirred 5 min at 20° C., then benzofuran-6-carbaldehyde (0.95 eq.) and MgSO$_4$ (3 eq.) were added. The reaction was refluxed for 2 h, then cooled to 20° C. and filtered. The filtrate was added to a suspension of NaBH$_4$ (2 to 6 eq.) in MeOH at −15° C. The reaction was stirred for 2 h at −15° C. The reaction was quenched with the addition of aqueous HCl 2N until pH=2. The aqueous layer was washed twice with EtOAc. The organic layers were discarded. Solid KOH was added to the aqueous layer. The crude was extracted three times with EtOAc. The organic layers were combined, dried over MgSO$_4$, filtered and concentrated under reduced pressure at 20° C. The crude was purified by chromatography on silica gel (elution with DCM/MeOH: 95/5) to afford 4-[(benzofuran-6-ylmethyl)-amino]-butyric acid ethyl ester.

$^1$H NMR δ (ppm) (CDCl$_3$): 7.65-7.63 (1H, m), 7.60-7.56 (1H, m), 7.54-7.51 (1H, m), 7.27-7.23 (1H, m), 6.79-6.76 (1H, m), 4.15 (2H, q), 3.95 (2H, s), 2.74 (2H, t), 2.42 (2H, t), 1.95-1.76 (3H, m), 1.27 (3H, t).

MW (calcd): 261.3; MW (obsd): 262.3 (M+1)

Method E9

Illustrative Synthesis of Intermediate 84: N-[2-(4-Chloro-benzylamino)-ethyl]-acetamide

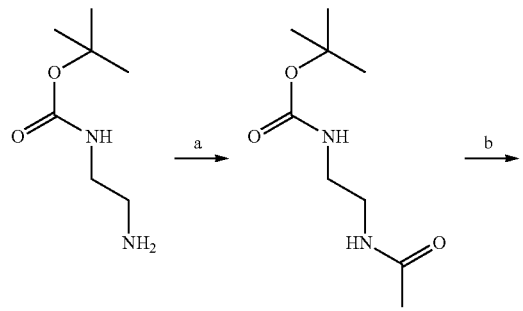

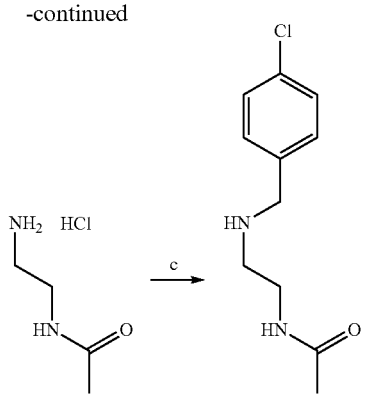

Step a: (2-Acetylamino-ethyl)-carbamic acid tert-butyl ester

To a solution of (2-amino-ethyl)-carbamic acid tert-butyl ester (1 eq.) in DCM was added TEA (3 eq.). The reaction was cooled to 0° C. Acetyl chloride (1 eq.) was filtered through a pad of alumina then added dropwise in solution in DCM to the reaction at 0° C. The reaction was stirred at 20° C. for 4 h. The crude was diluted with DCM, washed twice with water, then twice with a saturated aqueous solution of NaHCO$_3$. The organic layer was dried over MgSO$_4$, filtered and concentrated under reduced pressure to afford (2-acetylamino-ethyl)-carbamic acid tert-butyl ester. The compound was used as such without further purification.

$^1$H NMR δ (ppm) (CDCl$_3$): 6.32-6.03 (1H, m), 5.06-4.74 (1H, m), 3.35 (2H, t), 3.32-3.22 (2H, m), 1.99 (3H, s), 1.45 (9H, s)

Step b: N-(2-Amino-ethyl)-acetamide

To a solution of (2-acetylamino-ethyl)-carbamic acid tert-butyl ester (1 eq.) in DCM was added dropwise TFA (30 eq.) at 0° C. The reaction was stirred at 20° C. for 15 h, then concentrated under reduced pressure. A solution of HCl 2N in Et$_2$O was added. The crude was triturated with DCM. The resulting solid was filtered and dry to afford N-(2-amino-ethyl)-acetamide. The compound was used as such without further purification.

$^1$H NMR δ (ppm) (MeOD-d$_4$): 3.44 (2H, t), 3.05 (2H, t), 1.99 (3H, s)

Step c: N-[2-(4-Chloro-benzylamino)-ethyl]-acetamide

To a solution of N-(2-amino-ethyl)-acetamide (1.2 eq.) in MeOH were added NaHCO$_3$ (1.5 eq.) and 4-chlorobenzaldehyde (1 eq.). The reaction was refluxed for 4 h, then cooled to 0° C. NaBH$_4$ (1.2 eq.) was added portionwise. The reaction was stirred for 1 h at 0° C., then 15 h at 20° C. The crude was concentrated under reduced pressure then partitioned between water and DCM. The aqueous layer was then extracted twice with DCM. The organic layers were combined, dried over MgSO$_4$, filtered and concentrated under reduced pressure. The crude was purified by chromatography on silica gel (elution with heptane/EtOAc: 1/0 to 0/1) to afford N-[2-(4-chloro-benzylamino)-ethyl]-acetamide.

¹H NMR δ (ppm) (CDCl₃): 7.33-7.23 (4H, m), 6.10-6.00 (1H, m), 3.78 (2H, s), 3.39-3.33 (2H, m), 2.77 (2H, t), 1.99 (3H, s)

Method E10

Illustrative Synthesis of Intermediate 86:
3-(4-Chloro-benzylamino)-propane-1-sulfonic acid 2,4-dimethoxy-benzylamide

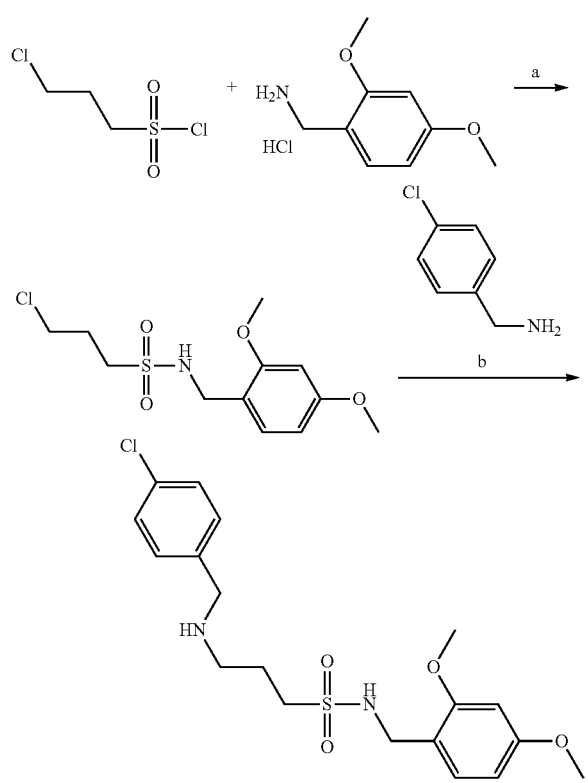

Step a: 3-Chloro-propane-1-sulfonic acid 2,4-dimethoxy-benzylamide

To a solution of 2,4-dimethoxy-benzylamine hydrochloride (1 eq.) and TEA (2 eq.) in DCM was added dropwise at 0° C. a solution of 3-chloro-propane-1-sulfonyl chloride (1 eq.) in DCM. The reaction was stirred at 20° C. for 20 h. The crude was diluted with DCM, washed twice with water, twice with aqueous HCl (0.1N) and twice with a saturated aqueous solution of NaHCO₃. The organic layer was dried over MgSO₄, filtered and concentrated under reduced pressure. The crude was purified by chromatography on silica gel (elution with heptane/EtOAc: 100/0 to 20/80) to afford 3-chloro-propane-1-sulfonic acid 2,4-dimethoxy-benzylamide.

¹H NMR δ (ppm) (CDCl₃): 7.16 (1H, d), 6.47-6.42 (2H, m), 4.87 (1H, t), 4.23 (2H, d), 3.85 (3H, s), 3.81 (3H, s), 3.52 (2H, t), 3.03-2.97 (2H, m), 2.19-2.10 (2H, m).

Step b:
3-(4-Chloro-benzylamino)-propane-1-sulfonic acid 2,4-dimethoxy-benzylamide To a solution of the Intermediate obtained in step a (1 eq.) in THF were added a catalytic amount of sodium iodide and 4-chloro-benzylamine (5 eq.). The reaction was heated at 160° C. under microwave irradiation for 2 h. The solvent was concentrated under reduced pressure and the crude was partitioned between water and EtOAc. The organic layer was dried over MgSO₄, filtered and concentrated under reduced pressure. The crude was purified by chromatography on silica gel (elution with heptane/EtOAc/DCM/MeOH: 90/10/0/0 to 50/50/90/10) to afford 3-(4-chloro-benzylamino)-propane-1-sulfonic acid 2,4-dimethoxy-benzylamide.

¹H NMR δ (ppm) (CDCl₃): 7.30-7.26 (2H, m), 7.22-7.17 (2H, m), 7.16 (1H, d), 6.46-6.38 (2H, m), 4.21 (2H, s), 3.81 (3H, s), 3.78 (3H, s), 3.66 (2H, s), 2.99-2.94 (2H, m), 2.58 (2H, t), 191-1.82 (2H, m).

MW (calcd): 412.9; MW (obsd): 413.4 (M+1, ³⁵Cl)

Method E11

Illustrative Synthesis of Intermediate 244:
4-(3-Trifluoromethyl-phenylamino)-butyric acid ethyl ester

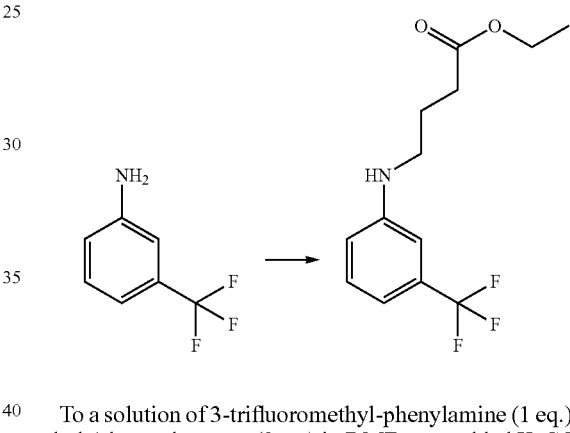

To a solution of 3-trifluoromethyl-phenylamine (1 eq.) and ethyl 4-bromobutyrate (2 eq.) in DMF were added K₂CO₃ (3 eq.) and KI (cat.). The mixture was heated at 100° C. for 16 h, water and EtOAc were added, the organic layer was washed with water, brine, dried over MgSO₄, filtered and concentrated under reduced pressure. The crude was purified by chromatography on silica gel (elution with heptane/EtOAc: 90/10 to 70/30) to afford 4-(3-trifluoromethyl-phenylamino)-butyric acid ethyl ester as a yellow oil.

Method F

Amide Formation

Illustrative Synthesis of Intermediate 94: 1-[2-(3,5-Dimethyl-phenyl)-acetyl]-2-methyl-azetidine-2-carboxylic acid ethyl ester

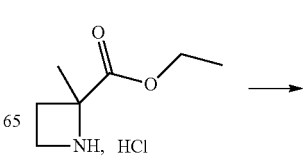

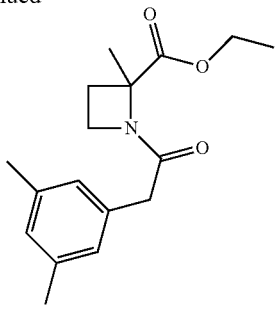

To a solution of (3,5-dimethyl-phenyl)-acetic acid (1 eq.) in either DCM or THF was added HOBt (1.1 eq.), EDC.HCl (1.5 eq.). Then, 2-methyl-azetidine-2-carboxylic acid ethyl ester hydrochloride, Intermediate 13 (1 eq.) and TEA (4 eq.) were added. The reaction was stirred at 20° C. for 15 h. The crude was concentrated under reduced pressure and partitioned between a saturated aqueous solution of NaHCO₃ and EtOAc. The aqueous layer was extracted three times with EtOAc. The organic layers were combined, washed with water then with brine, dried over MgSO₄, filtered and concentrated under reduced pressure to afford 1-[2-(3,5-dimethyl-phenyl)-acetyl]-2-methyl-azetidine-2-carboxylic acid ethyl ester.

$^1$H NMR δ (ppm) (CDCl₃): 6.93-6.84 (3H, m), 4.29-4.09 (3H, m), 4.07-3.88 (1H, m), 3.38 (2H, s), 2.53-2.25 (7H, m), 2.17-2.07 (1H, m), 1.80-1.66 (3H, m), 1.31-1.18 (3H, m)

MW (calcd): 289.4; MW (obsd): 290.0 (M+1)

Method G

Saponification

Illustrative Synthesis of Intermediate 119: 1-[2-(3,5-Dimethyl-phenyl)-acetyl]-2-methyl-azetidine-2-carboxylic acid

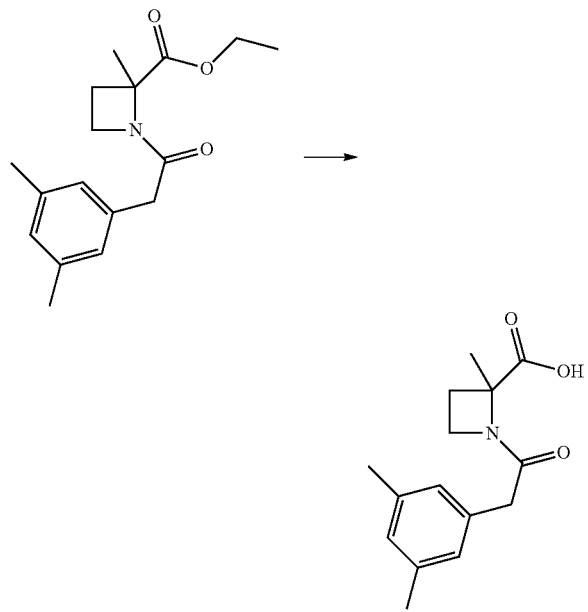

To a solution of 1-[2-(3,5-dimethyl-phenyl)-acetyl]-2-methyl-azetidine-2-carboxylic acid ethyl ester, Intermediate 94 (1 eq.) in either EtOH or MeOH was added aqueous NaOH (2N) (2 eq.). The reaction was stirred at 20° C. for 6 h. The solvent was removed under reduced pressure and the crude was partitioned between water and EtOAc. The organic layer was discarded and the aqueous layer was neutralized by addition of aqueous HCl (2N) and thoroughly extracted with EtOAc. The organic layers were combined, dried over MgSO₄, filtered and concentrated under reduced pressure to afford 1-[2-(3,5-dimethyl-phenyl)-acetyl]-2-methyl-azetidine-2-carboxylic acid.

$^1$H NMR δ (ppm) (CDCl₃): 6.94 (1H, s), 6.85 (2H, s), 4.10-3.89 (2H, m), 3.44 (2H, s), 2.95-2.84 (1H, m), 2.31 (6H, s), 2.17-2.06 (1H, m), 1.78 (3H, s)

MW (calcd): 261.3; MW (obsd): 262.0 (M+1)

Method H

Carbamate Formation

Illustrative Synthesis of Compound 2: 2-(4-Chloro-benzylcarbamoyl)-2-methyl-azetidine-1-carboxylic acid 4-chloro-phenyl ester

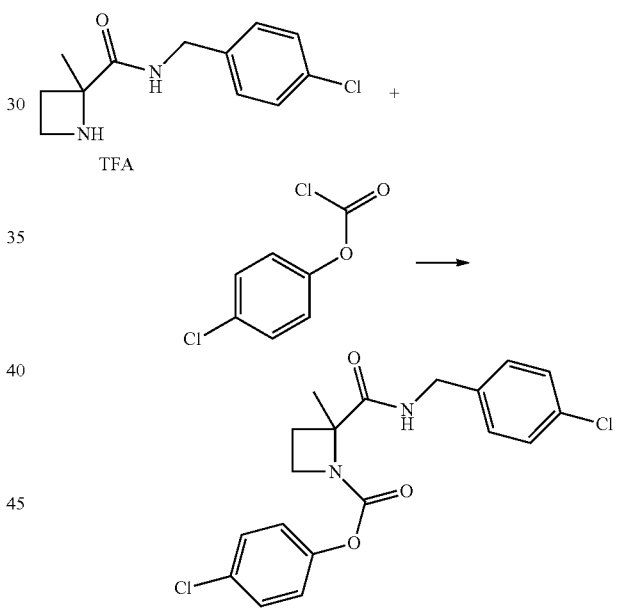

To a solution of 2-methyl-azetidine-2-carboxylic acid 4-chloro-benzylamide, trifluoroacetic acid salt, Intermediate 28 (1 eq.) in THF were added TEA (2 eq.) and 4-chlorophenyl-chloroformate (2 eq.). The reaction was stirred at 20° C. for 15 h. The crude was concentrated under reduced pressure and partitioned between a saturated aqueous solution of NaHCO₃ and EtOAc. The aqueous layer was extracted three times with EtOAc. The organic layers were combined, washed with water then with brine, dried over MgSO₄, filtered and concentrated under reduced pressure. The crude was purified by chromatography on silica gel (elution with DCM/Et₂O: 98/2) to afford 2-(4-chloro-benzylcarbamoyl)-2-methyl-azetidine-1-carboxylic acid 4-chloro-phenyl ester.

$^1$H NMR δ (ppm) (MeOD, d₄): 7.44-7.15 (7H, m), 7.02-6.94 (1H, m), 4.37-4.33 (2H, m), 4.29-3.94 (2H, m), 2.61-2.23 (2H, m), 1.88-1.75 (3H, m).

MW (calcd): 393; MW (obsd): 393.3 (M+1, $^{35}$Cl).

Method I

Amide Formation

Method I1

Illustrative Synthesis of Compound 6: 1-[2-(3,5-Dimethyl-phenyl)-acetyl]-2-methyl-azetidine-2-carboxylic acid methyl-(4-methyl-benzyl)-amide

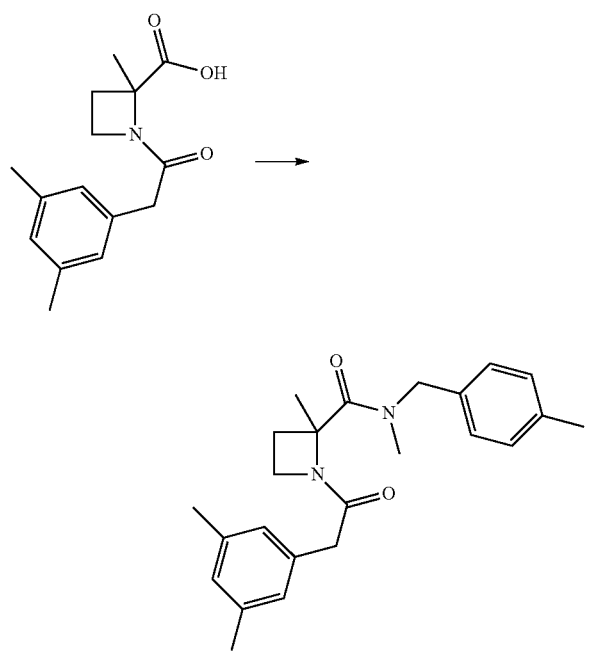

To a solution of Intermediate 119 1-[2-(3,5-dimethyl-phenyl)-acetyl]-2-methyl-azetidine-2-carboxylic acid (1 eq.) in either DCM, THF or DMF was added HOBt (1.1 eq.), EDC.HCl (1.5 eq.), TEA (3 eq.) and methyl-(4-methyl benzyl)-amine (1.5 eq.). The reaction was stirred at 20° C. for 15 h, then the crude was concentrated under reduced pressure and partitioned between a saturated aqueous solution of NaHCO₃ and EtOAc. The aqueous layer was extracted three times with EtOAc. The organic layers were combined, washed with water then with brine, dried over MgSO₄, filtered and concentrated under reduced pressure. The crude was purified by chromatography on silica gel (elution with DCM/MeOH: 100/0 to 99/1) to afford 1-[2-(3,5-dimethyl-phenyl)-acetyl]-2-methyl-azetidine-2-carboxylic acid methyl-(4-methyl-benzyl)-amide.

$^1$H NMR δ (ppm) (CDCl₃): 7.23-7.04 (4H, m), 6.99-6.82 (3H, m), 4.81-4.21 (2H, m), 4.08-3.82 (2H, m), 3.81-3.15 (2H, m), 2.98-2.74 (3H, m), 2.64-2.44 (1H, m), 2.42-2.15 (10H, m), 1.96-1.74 (3H, m).

MW (calcd): 378.5; MW (obsd): 379.2 (M+1)

Method I2

Illustrative Synthesis of Compound 43: 1-[2-(2,4-Dichloro-phenyl)-acetyl]-2-methyl-azetidine-2-carboxylic acid 4-methyl-benzylamide

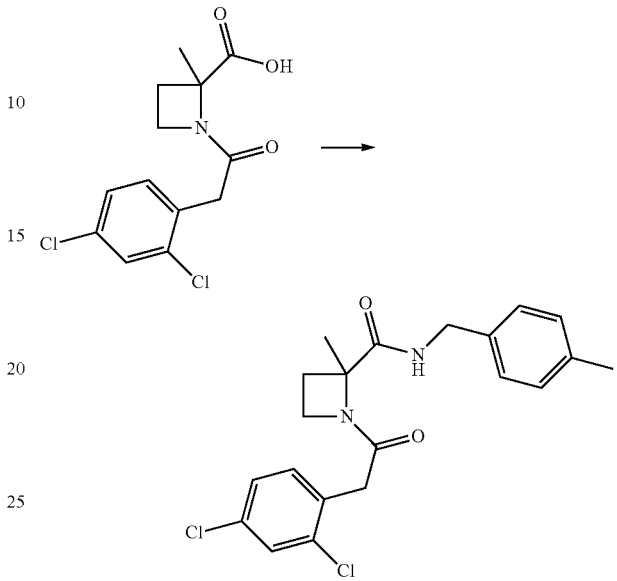

To a solution of 1-[2-(2,4-dichloro-phenyl)-acetyl]-2-methyl-azetidine-2-carboxylic acid, Intermediate 120 (1 eq.) in either THF or DMF was added TEA (4 eq.) and TBTU (2 eq.). The reaction was stirred at 20° C. for 30 min, then 4-methyl-benzylamine (1.5 eq.) was added. The reaction was stirred at 20° C. for 72 h. The crude was concentrated under reduced pressure then partitioned between water and EtOAc. The organic layer was washed twice with water, dried over MgSO₄, filtered and concentrated under reduced pressure. The crude was purified by preparative LCMS to afford 1-[2-(2,4-dichloro-phenyl)-acetyl]-2-methyl-azetidine-2-carboxylic acid 4-methyl-benzylamide.

$^1$H NMR δ (ppm) (CDCl₃): 8.59-8.50 (1H, m), 7.42 (1H, s), 7.22 (2H, s), 7.18-7.09 (4H, m), 4.44-4.39 (2H, m), 4.18-4.00 (2H, m), 3.56-3.50 (2H, m), 3.01-2.91 (1H, m), 2.36 (3H, s), 2.19-2.10 (1H, m), 1.81 (3H, s).

MW (calcd): 405.3; MW (obsd): 405.1 (M+1, $^{35}$Cl)

Method I3

Illustrative Synthesis of Compound 48: ((4-Chloro-benzyl)-{1-[2-(3,5-dimethyl-phenyl)-acetyl]-2-methyl-azetidine-2-carbonyl}-amino)-acetic acid methyl ester

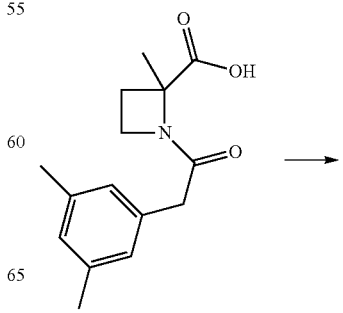

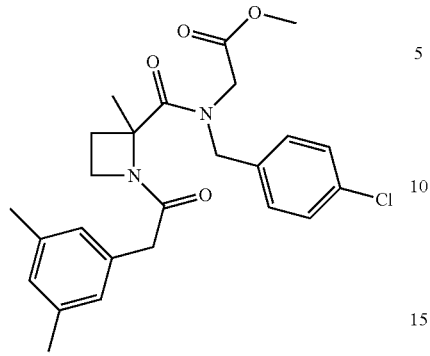

To a solution of 1-[2-(3,5-dimethyl-phenyl)-acetyl]-2-methyl-azetidine-2-carboxylic acid, Intermediate 119 (1 eq.) in DCM under nitrogen, was added DMF (0.01 eq.) then oxalyl chloride (2 eq.). The solution was stirred at 20° C. for 30 min, then cooled to 0° C. A solution of (4-Chloro-benzylamino)-acetic acid methyl ester (1.5 eq.) and either TEA or DIPEA (2 to 7 eq.) in DCM was then added to the previous mixture. The solution was stirred at 0° C. for 1 h then at 20° C. until completion (1 h). The reaction was quenched with a saturated aqueous solution of NaHCO₃ and extracted three times with DCM. The organic layers were combined, dried over MgSO₄, filtered and concentrated under reduced pressure. The crude was purified by chromatography on silica gel (elution with heptane/EtOAc: 1/0 to 1/1) to afford ((4-chloro-benzyl)-{1-[2-(3,5-dimethyl-phenyl)-acetyl]-2-methyl-azetidine-2-carbonyl}-amino)-acetic acid methyl ester.

¹H NMR δ (ppm) (CDCl₃): 7.42-7.23 (2H, m), 7.21-7.09 (2H, m), 6.99-6.72 (3H, m), 5.09-4.33 (2H, m), 4.26-3.81 (3H, m), 3.79-3.60 (4H, m), 3.48-3.15 (m, 2H), 2.75-2.60 (1H, m), 2.35-2.18 (7H, m), 1.91-1.76 (3H, m).

MW (calcd): 457.0; MW (obsd): 457.2 (M+1, ³⁵Cl)

To a solution of 1-chloro-N,N,2-trimethylpropenylamine (2 eq.) in DCM under nitrogen was added 1-(2-benzo[b]thiophen-3-yl-acetyl)-2-methyl-azetidine-2-carboxylic acid, Intermediate 121 (1 eq.). The solution was stirred at 20° C. for 1 h, then added to a solution of 4-[(Benzofuran-6-ylmethyl)-amino]-butyric acid ethyl ester, Intermediate 82 (1.2 eq.) in DCM at 0° C. TEA (2 eq.) was then added and the mixture was stirred at 0° C. for 3 h. The crude was diluted with DCM, washed twice with a saturated aqueous solution of NaHCO₃, twice with aqueous HCl (0.5N), twice with water, dried over MgSO₄, filtered, concentrated under reduced pressure and purified by chromatography on silica gel (elution with heptane/EtOAc 25/75 to 10/90) to afford 4-{[1-(2-benzo[b]thiophen-3-yl-acetyl)-2-methyl-azetidine-2-carbonyl]-benzofuran-6-ylmethyl-amino}-butyric acid ethyl ester.

¹H NMR δ (ppm) (CDCl₃): 8.02 (1H, s), 7.94-7.28 (7H, m), 7.18-6.96 (1H, m), 6.75 (1H, bs), 5.03-4.36 (2H, m), 4.15-4.01 (2H, m), 4.00-3.79 (2H, m), 3.78-2.96 (4H, m), 2.66-2.44 (1H, m), 2.40-2.12 (3H, m), 2.03-1.74 (5H, m), 1.28-1.16 (3H, m).

MW (calcd): 532.7; MW (obsd): 533.4 (M+1l)

Method J

Saponification

Illustrative Synthesis of Compound 49: ((4-Chlorobenzyl)-{1-[2-(3,5-dimethyl-phenyl)-acetyl]-2-methyl-azetidine-2-carbonyl}-amino)-acetic acid Method I4

Illustrative Synthesis of Intermediate 164: 4-{[1-(2-Benzo[b]thiophen-3-yl-acetyl)-2-methyl-azetidine-2-carbonyl]-benzofuran-6-ylmethyl-amino}-butyric acid ethyl ester

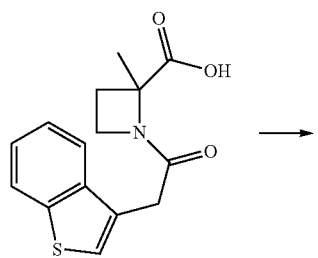

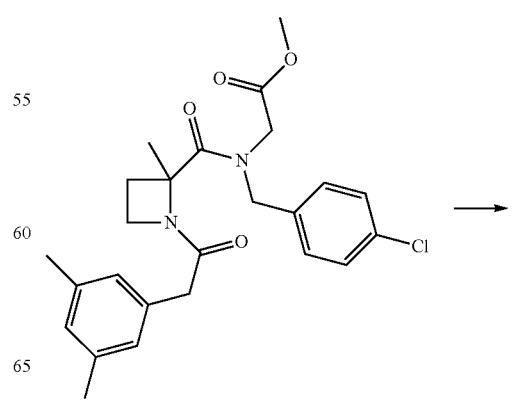

77

-continued

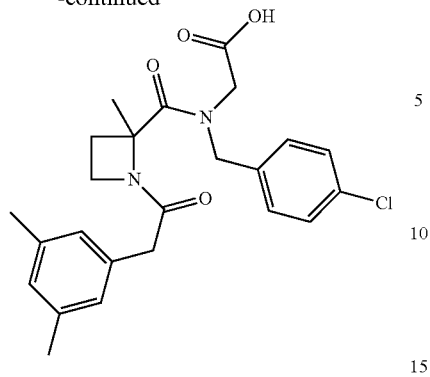

To a solution of ((4-chloro-benzyl)-{1-[2-(3,5-dimethyl-phenyl)-acetyl]-2-methyl-azetidine-2-carbonyl}-amino)-acetic acid methyl ester, compound 48 (1 eq.) in either EtOH or MeOH was added aqueous NaOH (2N) (2 eq.). The reaction was stirred at 20° C. for 2 h. The solvent was removed under reduced pressure and the crude was partitioned between water and EtOAc. The organic layer was discarded and the aqueous layer was acidified by addition of aqueous HCl (2N) and thoroughly extracted with EtOAc. The organic layers were combined, dried over MgSO$_4$, filtered and concentrated to afford ((4-chloro-benzyl)-{1-[2-(3,5-dimethyl-phenyl)-acetyl]-2-methyl-azetidine-2-carbonyl}-amino)-acetic acid.

$^1$H NMR δ (ppm) (CDCl$_3$): 7.41-7.25 (2H, m), 7.21-7.10 (2H, m), 6.94-6.75 (3H, m), 5.16-4.60 (1H, m), 4.59-4.26 (1H, m), 4.25-3.64 (4H, m), 3.49-3.21 (2H, m), 2.70-2.59 (1H, m), 2.36-2.16 (7H, m), 1.91-1.76 (3H, m).

MW (calcd): 442.9; MW (obsd): 443.2 (M+1, $^{35}$Cl)

Method K

Amide Formation

Illustrative Synthesis of Compound 53: 1-[2-(3,5-Dimethyl-phenyl)-acetyl]-2-methyl-azetidine-2-carboxylic acid (4-chloro-benzyl)-methylcarbamoylmethyl-amide

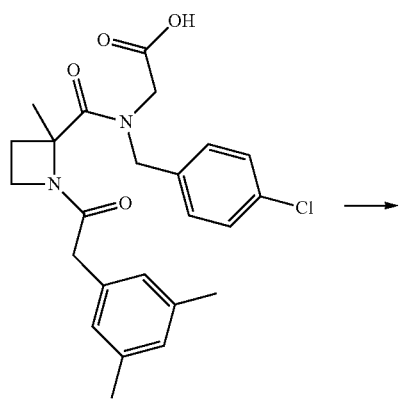

78

-continued

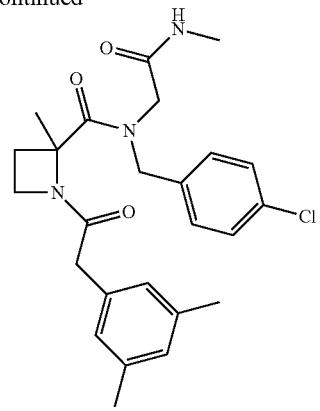

To a solution of ((4-chloro-benzyl)-{1-[2-(3,5-dimethyl-phenyl)-acetyl]-2-methyl-azetidine-2-carbonyl}-amino)-acetic acid, compound 49 (1 eq.) in DMF were added methylamine (33% w/w in EtOH) (1 eq.), TEA (1 eq.) and TBTU (1 eq.). The reaction was stirred at 20° C. for 15 h. The reaction was carried on with addition of methylamine (33% w/w in EtOH), TEA (1 eq.) and TBTU (1 eq.), then stirring at 20° C. for 15 h. The crude was concentrated under reduced pressure then partitioned between water and EtOAc. The organic layer was washed twice with water, dried over MgSO$_4$, filtered and concentrated under reduced pressure. The crude was purified by preparative LCMS to afford 1-[2-(3,5-dimethyl-phenyl)-acetyl]-2-methyl-azetidine-2-carboxylic acid (4-chloro-benzyl)-methylcarbamoylmethyl-amide.

$^1$H NMR δ (ppm) (MeOD-d$_4$): 7.50-7.21 (4H, m), 7.01-6.85 (3H, m), 4.84-4.74 (1H, m), 4.68-4.44 (1H, m), 4.24-4.00 (2H, m), 3.95-3.71 (2H, m), 3.65-3.50 (1H, m), 3.42-3.34 (3H, m), 2.85-2.74 (3H, m), 2.32 (6H, s), 2.01-1.86 (3H, m).

MW (calcd): 456.0; MW (obsd): 456.4 (M+1, $^{35}$Cl)

Method L

Illustrative Synthesis of Compound 76: 1-[2-(3,5-Dimethyl-phenyl)-acetyl]-2-methyl-azetidine-2-carboxylic acid (4-chloro-benzyl)-(1H-tetrazol-5-ylmethyl)-amide

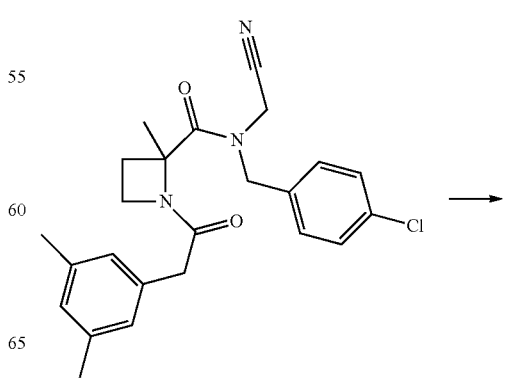

79
-continued

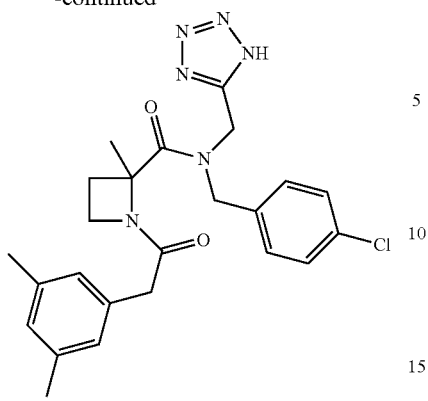

To a solution of 1-[2-(3,5-dimethyl-phenyl)-acetyl]-2-methyl-azetidine-2-carboxylic acid (4-chloro-benzyl)-cyanomethyl-amide, Compound 68 (1 eq.) in toluene was added $Bu_3SnN_3$ (10 eq.). The reaction was refluxed for 6 h and cooled to 20° C. then HCl 2N in $Et_2O$ was added. After 15 h of stirring, the solid was filtered, dissolved in DCM and precipitated with $iPr_2O$. The solid was purified by chromatography on silica gel (elution with DCM/MeOH: 1/0 to 95/5) to afford 1-[2-(3,5-dimethyl-phenyl)-acetyl]-2-methyl-azetidine-2-carboxylic acid (4-chloro-benzyl)-(1H-tetrazol-5-yl-methyl)-amide.

$^1$H NMR δ (ppm) (CDCl$_3$): 7.35 (2H, d), 7.04 (2H, d), 6.78 (3H, d), 5.08 (1H, d), 4.61 (1H, d), 4.28 (1H, d), 4.21-3.91 (3H, m), 3.40-3.26 (2H, m), 2.74-2.55 (1H, m), 2.31-2.19 (1H, m), 2.15 (6H, s), 1.88 (3H, s).

MW (calcd): 467.0; MW (obsd): 467.3 (M+1, $^{35}$Cl)

Method M

Illustrative Synthesis of Compound 90: 1-[2-(3,5-Dimethyl-phenyl)-acetyl]-2-methyl-azetidine-2-carboxylic acid (3-carbamoyl-propyl)-(4-chloro-benzyl)-amide

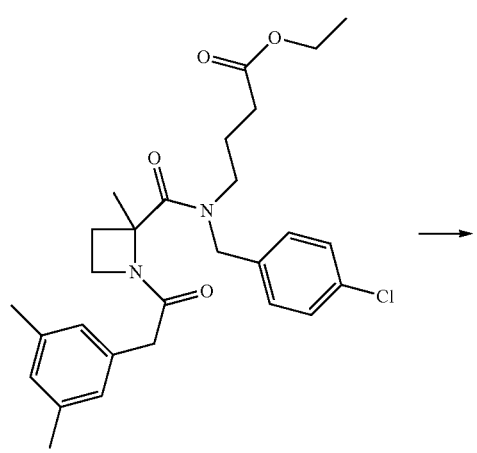

80
-continued

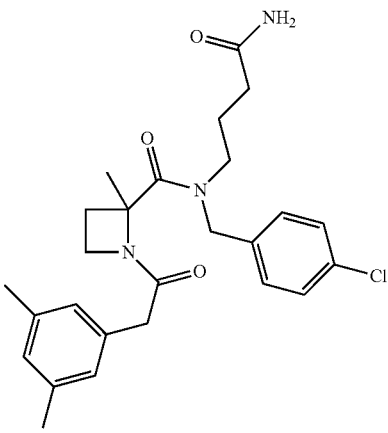

To a solution of 4-((4-chloro-benzyl)-{1-[2-(3,5-dimethyl-phenyl)-acetyl]-2-methyl-azetidine-2-carbonyl}-amino)-butyric acid ethyl ester, Intermediate 146 (1 eq.) in MeOH was added an aqueous solution of $NH_3$ (20% in water). The reaction was stirred at 60° C. for 15 h then cooled to 20° C. The solvents were evaporated under reduced pressure and the crude was purified by preparative LCMS to afford 1-[2-(3,5-dimethyl-phenyl)-acetyl]-2-methyl-azetidine-2-carboxylic acid (3-carbamoyl-propyl)-(4-chloro-benzyl)-amide.

$^1$H NMR δ (ppm) (CDCl$_3$): 7.47-7.27 (2H, m), 7.24-6.98 (2H, m), 6.97-6.56 (3H, m), 5.61-5.20 (1H, m), 4.97-4.52 (1H, m), 4.49-4.06 (1H, m), 4.04-3.52 (3H, m), 3.43-2.97 (2H, m), 2.62-2.43 (1H, m), 2.40-2.10 (7H, m), 2.09-1.73 (5H, m), 1.72-1.51 (2H, m).

MW (calcd): 470.0; MW (obsd): 470.1 (M+1, $^{35}$Cl)

Method N

Illustrative synthesis of compound 94: 1-[2-(3,5-Dimethyl-phenyl)-acetyl]-2-methyl-azetidine-2-carboxylic acid (4-chloro-benzyl)-(2-oxo-2-trifluoromethanesulfonylamino-ethyl)-amide

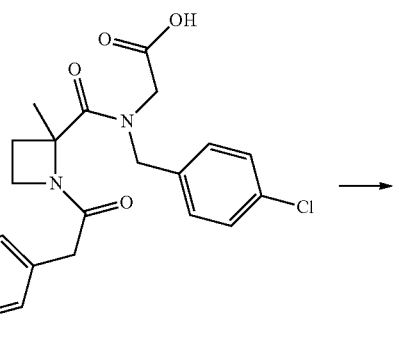

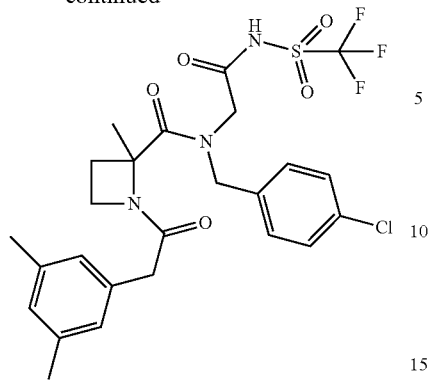

To a solution of compound 49 ((4-chloro-benzyl)-{1-[2-(3,5-dimethyl-phenyl)-acetyl]-2-methyl-azetidine-2-carbonyl}-amino)-acetic acid (1 eq.) in DMF was added EDC.HCl (1.3 eq.), DMAP (1.3 eq.) and trifluoromethanesulfonamide (1.3 eq.). The reaction was stirred for 15 h at 20° C. The crude was concentrated under reduced pressure then partitioned between water and EtOAc. The layers were separated and the organic layer was dried over MgSO$_4$, filtered and concentrated under reduced pressure. The crude was purified by preparative LCMS to afford 1-[2-(3,5-dimethyl-phenyl)-acetyl]-2-methyl-azetidine-2-carboxylic acid (4-chloro-benzyl)-(2-oxo-2-trifluoromethanesulfonylamino-ethyl)-amide.

$^1$H NMR δ (ppm) (CDCl$_3$): 7.32 (2H, d), 7.24-7.10 (3H, m), 6.91-6.89 (1H, m), 6.87-6.85 (2H, m), 4.50-4.22 (3H, m), 4.19-4.02 (2H, m), 3.47-3.25 (3H, m), 2.59-2.47 (1H, m), 2.37-2.21 (7H, m), 1.99 (3H, s)

MW (calcd): 574.0; MW (obsd): 573.7 (M+1, $^{35}$Cl)

Method O

Illustrative Synthesis of Compound 107: 1-[2-(3,5-Dimethyl-phenyl)-acetyl]-2-methyl-azetidine-2-carboxylic acid (4-chloro-benzyl)-[2-(5-hydroxy-[1,2,4]oxadiazol-3-yl)-ethyl]-amide

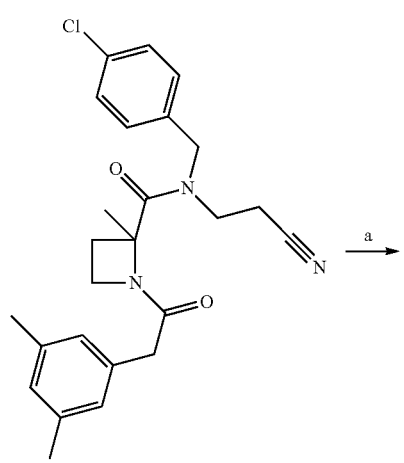

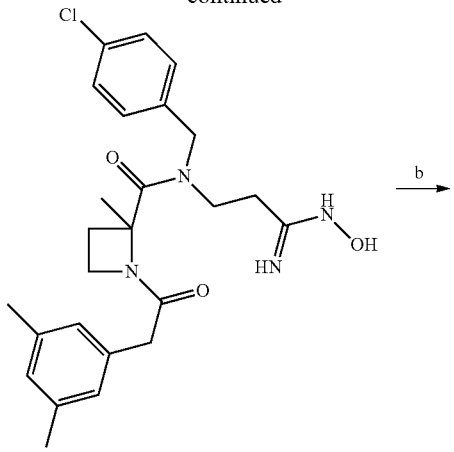

Step a

To a solution of Compound 77 (1 eq.) in EtOH was added a solution of hydroxylamine 50% in water (2 eq.). The reaction was refluxed for 15 h. The crude was concentrated under reduced pressure and used as such without further purification.

MW (calcd): 471.0; MW (obsd): 471.0 (M+1, $^{35}$Cl)

Step b

To a solution of 1-[2-(3,5-dimethyl-phenyl)-acetyl]-2-methyl-azetidine-2-carboxylic acid (4-chloro-benzyl)-[2-(N-hydroxycarbamimidoyl)-ethyl]-amide (1 eq.) in dioxane was added triphosgene (1.7 eq.) under nitrogen. The reaction was stirred at 20° C. for 15 h. The crude was concentrated under reduced pressure then partitioned between water and EtOAc. The layers were separated, the organic layer was dried over MgSO$_4$, filtered and concentrated under reduced pressure. The crude was purified by chromatography on silica gel (elution with heptane/EtOAc/DCM/MeOH: 50/50/0/0 to 50/50/90/10) to afford 1-[2-(3,5-dimethyl-phenyl)-acetyl]-2-methyl-azetidine-2-carboxylic acid (4-chloro-benzyl)-[2-(5-hydroxy-[1,2,4]oxadiazol-3-yl)-ethyl]-amide.

$^1$H NMR δ (ppm) (CDCl$_3$): 7.35 (2H, d), 7.21-6.98-(2H, m), 6.97-6.80 (3H, m), 4.72-4.51 (1H, m), 4.37-3.90 (4H, m), 3.36 (2H, bs), 3.07-2.86 (1H, m), 2.74-2.40 (3H, m), 2.35-2.10 (7H, m), 1.82 (3H, bs)

MW (calcd): 497.0; MW (obsd): 497.1 (M+1, $^{35}$Cl)

Method P

Illustrative Synthesis of Compound 111: 1-[2-(3,5-Dimethyl-phenyl)-acetyl]-2-methyl-azetidine-2-carboxylic acid (4-chloro-benzyl)-(5-hydroxy-[1,3,4]oxadiazol-2-ylmethyl)-amide

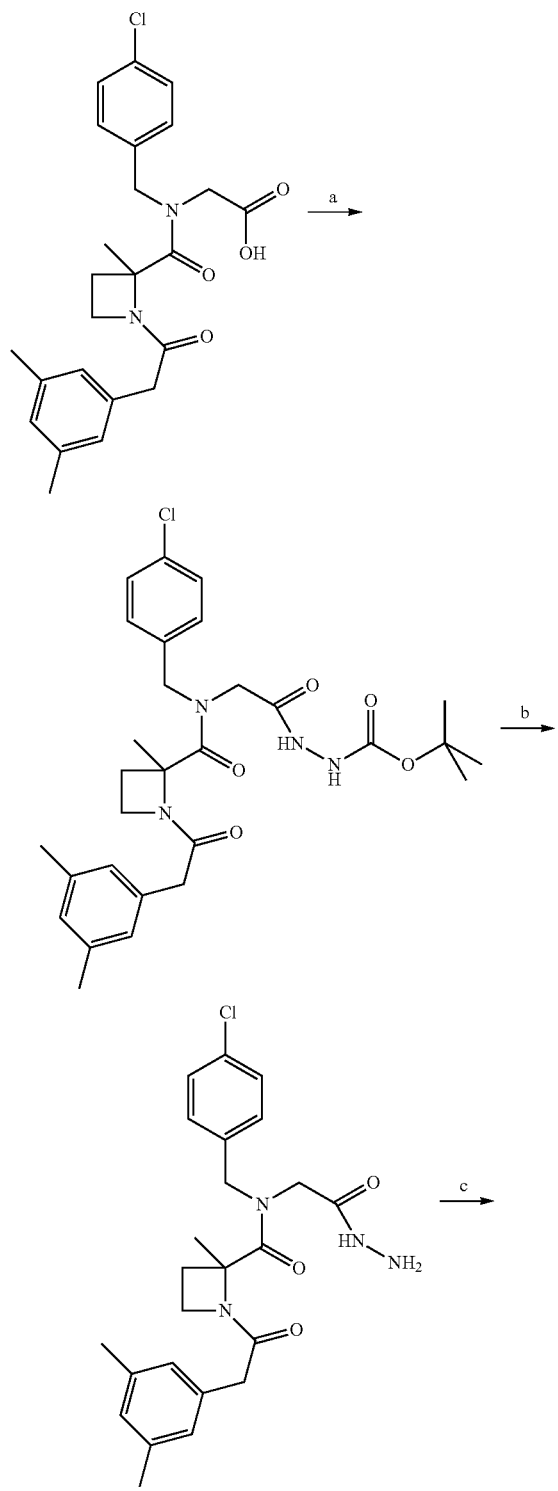

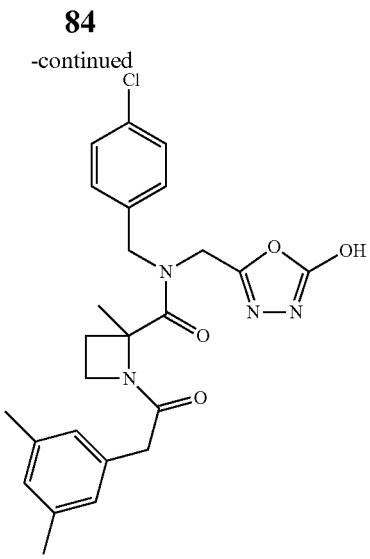

Step a: N'-[2-((4-Chloro-benzyl)-{1-[2-(3,5-dimethyl-phenyl)-acetyl]-2-methyl-azetidine-2-carbonyl}-amino)-acetyl]-hydrazinecarboxylic acid tert-butyl ester N'-[2-((4-chloro-benzyl)-{1-[2-(3,5-dimethyl-phenyl)-acetyl]-2-methyl-azetidine-2-carbonyl}-amino)-acetyl]-hydrazinecarboxylic acid tert-butyl ester was prepared via method I1, using Compound 49 and Boc-hydrazine.

$^1$H NMR δ (ppm) (CDCl$_3$): 7.41-7.27 (2H, m), 7.22-7.05 (2H, m), 6.97-6.80 (3H, m), 4.92-4.33 (2H, m), 4.22-3.81 (2H, m), 3.78-3.21 (3H, m), 3.01-2.83 (1H, m), 2.83-2.53 (1H, m), 2.38-2.22 (6H, m), 2.22-2.07 (1H, m), 1.96-1.79 (3H, m), 1.55-1.32 (9H, m).

MW (calcd): 557.1; MW (obsd): 557.1 (M+1, $^{35}$Cl)

Step b: 1-[2-(3,5-Dimethyl-phenyl)-acetyl]-2-methyl-azetidine-2-carboxylic acid (4-chloro-benzyl)-hydrazinocarbonylmethyl-amide 1-[2-(3,5-dimethyl-phenyl)-acetyl]-2-methyl-azetidine-2-carboxylic acid (4-chloro-benzyl)-hydrazinocarbonylmethyl-amide was prepared via method B2. The crude was concentrated under reduced pressure then partitioned between EtOAc and a saturated aqueous solution of NaHCO$_3$. The layers were separated, the organic layer was dried over MgSO$_4$, filtered and concentrated under reduced pressure. The crude was purified by chromatography on silica gel (elution with heptane/EtOAc/DCM/MeOH: 50/50/95/5 to 0/0/98/2).

$^1$H NMR δ (ppm) (CDCl$_3$): 8.40-8.11 (1H, m), 7.48-7.27 (3H, m), 7.24-7.12 (1H, m), 7.10-6.95 (2H, m), 6.95-6.80 (3H, m), 4.77 (1H, d), 4.36 (1H, d), 4.24 (1H, d), 4.12-3.83 (2H, m), 3.73 (1H, d), 3.53-3.25 (2H, m), 2.68-2.46 (1H, m), 2.36-2.22 (6H, m), 2.22-2.10 (1H, m), 1.91-1.79 (3H, m)

MW (calcd): 457.0; MW (obsd): 457.1 (M+1, $^{35}$Cl)

Step c: 1-[2-(3,5-Dimethyl-phenyl)-acetyl]-2-methyl-azetidine-2-carboxylic acid (4-chloro-benzyl)-(5-hydroxy-[1,3,4]oxadiazol-2-ylmethyl)-amide To a solution of the Intermediate obtained in step b above (1 eq.) in dioxane was added triphosgene (1.5 eq.) under nitrogen. The reaction was stirred at 20° C. for 15 h. The crude was concentrated under reduced pressure then partitioned between water and EtOAc. The layers were separated, the organic layer was dried over MgSO₄, filtered and concentrated under reduced pressure. The crude was purified by chromatography on silica gel (elution with Hept/EtOAc/DCM/MeOH: 50/50/0/0 to 50/50/95/5) to afford 1-[2-(3,5-dimethyl-phenyl)-acetyl]-2-methyl-azetidine-2-carboxylic acid (4-chloro-benzyl)-(5-hydroxy-[1,3,4]oxadiazol-2-ylmethyl)-amide.

$^1$H NMR δ (ppm) (CDCl₃): 9.51-9.32 (1H, m), 7.44-7.29 (2H, m), 7.23-7.11 (2H, m), 6.97-6.75 (3H, m), 4.87 (1H, d), 4.65-4.32 (2H, m), 4.21-3.69 (3H, m), 3.45-3.21 (2H, m), 2.75-2.56 (1H, m), 2.36-2.21 (7H, m), 1.89 (3H, bs)

MW (calcd): 483.0; MW (obsd): 483.1 (M+1, $^{35}$Cl)

Method Q

Illustrative Synthesis of Compound 116: 1-[2-(3,5-Dimethyl-phenyl)-acetyl]-2-methyl-azetidine-2-carboxylic acid (4-chloro-benzyl)-[2-(5-hydroxy-1H-pyrazol-3-yl)-ethyl]-amide and compound 120: 1-[2-(3,5-Dimethyl-phenyl)-acetyl]-2-methyl-azetidine-2-carboxylic acid (4-chloro-benzyl)-[2-(5-ethoxy-1H-pyrazol-3-yl)-ethyl]-amide

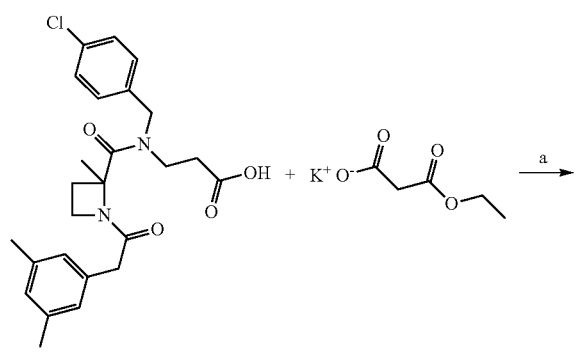

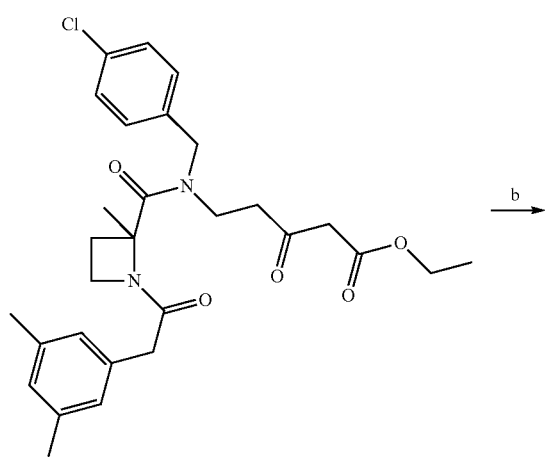

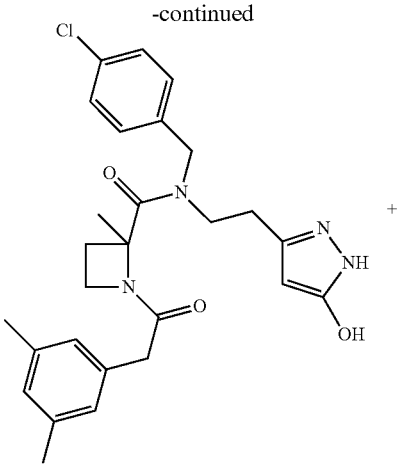

Compound 116

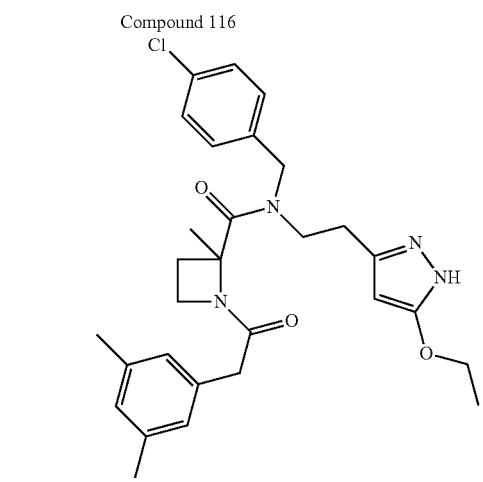

Compound 120

Step a: 5-((4-Chloro-benzyl)-{1-[2-(3,5-dimethyl-phenyl)-acetyl]-2-methyl-azetidine-2-carbonyl}-amino)-3-oxo-pentanoic acid ethyl ester To a solution of CDI (4 eq) in THF was added 3-((4-chloro-benzyl)-{1-[2-(3,5-dimethyl-phenyl)-acetyl]-2-methyl-azetidine-2-carbonyl}-amino)-propionic acid, compound 65 (1 eq.), the mixture was stirred for 4 h at 20° C., then MgCl₂ (4 eq.) and ethyl potassium malonate (5 eq.) were added. The reaction was stirred for 15 h at 20° C. The crude was concentrated under reduced pressure then partitioned between water and EtOAc. The layers were separated and the organic layer was dried over MgSO₄, filtered and concentrated under reduced pressure. The crude was purified by chromatography on silica gel (elution with Hept/EtOAc/DCM/MeOH: 50/50/95/5 then 50/50/90/10) to afford 5-((4-chloro-benzyl)-{1-[2-(3,5-dimethyl-phenyl)-acetyl]-2-methyl-azetidine-2-carbonyl}-amino)-3-oxo-pentanoic acid ethyl ester.

$^1$H NMR δ (ppm) (CDCl₃): 7.46-7.30 (2H, m), 7.25-7.05 (2H, m), 7.04-6.75 (3H, m), 5.09-4.36 (2H, m), 4.21 (2H, q), 4.07-3.85 (2H, m), 3.85-3.16 (6H, m), 3.05-2.73 (2H, m), 2.62-2.49 (1H, m), 2.37-2.18 (7H, m), 1.84 (3H, d), 1.30 (3H, t)

MW (calcd): 527.1; MW (obsd): 527.1 (M+1, $^{35}$Cl)

Step b: Compound 116 and 120

To a solution of the Intermediate obtained in step a above (1 eq.) in EtOH were added few drops of concentrated. HCl and hydrazine hydrate (4 eq.). The reaction was stirred at 20° C. for 2 h. The crude was concentrated under reduced pressure then partitioned between water and EtOAc. The layers were separated, the organic layer was dried over $MgSO_4$, filtered and concentrated under reduced pressure. The crude was purified by chromatography on silica gel (elution with Hept/ EtOAc/DCM/MeOH: 50/50/95/5 then 50/50/90/10, then DCM/MeOH: 98/2) to afford two compounds: Compound 116 and Compound 120.

Compound 116: 1-[2-(3,5-dimethyl-phenyl)-acetyl]-2-methyl-azetidine-2-carboxylic acid (4-chloro-benzyl)-(5-hydroxy-1H-pyrazol-3-ylmethyl)-amide.

$^1$H NMR δ (ppm) (CDCl$_3$): 7.40-7.07 (2H, m), 7.03-6.91 (2H, m), 6.92-6.80 (3H, m), 5.49-5.33 (1H, m), 4.72-4.56 (1H, m), 4.11-3.72 (4H, m), 3.41-3.09 (3H, m), 3.02-2.74 (2H, m), 2.47-2.35 (1H, m), 2.28 (6H, s), 2.17-2.05 (1H, m), 1.83 (3H, s)

MW (calcd): 494.2; MW (obsd): 495.1 (M+1, $^{35}$Cl)

Compound 120: 14-[2-(3,5-Dimethyl-phenyl)-acetyl]-2-methyl-azetidine-2-carboxylic acid (4-chloro-benzyl)-(5-ethoxy-1H-pyrazol-3-ylmethyl)-amide.

$^1$H NMR δ (ppm) (CDCl$_3$): 7.44-7.11 (3H, m), 7.03-6.85 (4H, m), 5.60-5.40 (1H, m), 4.74 (1H, m), 4.28-3.75 (6H, m), 3.58-2.77 (6H, m), 2.35-2.09 (7H, m), 1.91-1.74 (3H, m), 1.41 (3H, t)

MW (calcd): 522.2; MW (obsd): 523.4 (M+1, $^{35}$Cl)

Method R

Illustrative Synthesis of Compound 171: 1-[2-(3,5-Dimethyl-phenyl)-acetyl]-2-methyl-azetidine-2-carboxylic acid (4-chloro-benzyl)-(3-sulfamoyl-propyl)-amide

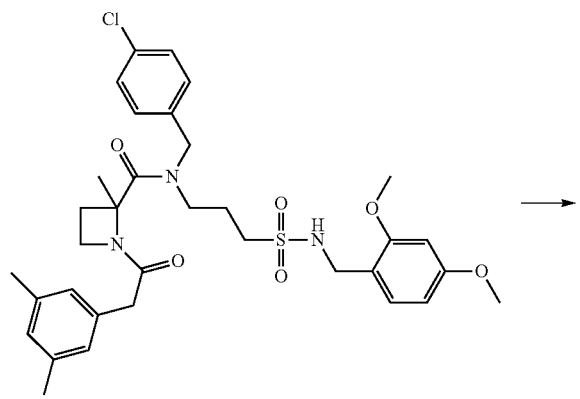

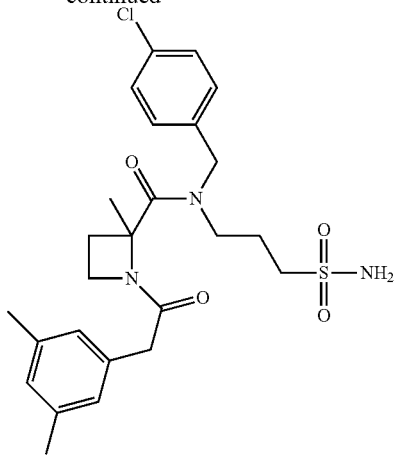

1-[2-(3,5-Dimethyl-phenyl)-acetyl]-2-methyl-azetidine-2-carboxylic acid (4-chloro-benzyl)-[3-(2,4-dimethoxy-benzylsulfamoyl)-propyl]-amide, compound 168 was dissolved in TFA and stirred at 20° C. for 15 h. The crude was concentrated under reduced pressure then partitioned between water and EtOAc. The organic layer was washed twice with water, then dried over $MgSO_4$, filtered and concentrated under reduced pressure. The crude was purified by chromatography on silica gel (elution with heptane/EtOAc/DCM/MeOH: 1/0/0/0 then 0/1/0/0 then 50/50/95/5 then 50/50/90/10) to afford 1-[2-(3,5-dimethyl-phenyl)-acetyl]-2-methyl-azetidine-2-carboxylic acid (4-chloro-benzyl)-(3-sulfamoyl-propyl)-amide.

$^1$H NMR δ (ppm) (CDCl$_3$): 7.43-7.29 (2H, m), 7.22-6.99 (2H, m), 6.96-6.79 (3H, m), 5.30-5.01 (2H, m), 4.75 (1H, d), 4.59-4.14 (1H, m), 4.06-3.80 (2H, m), 3.79-3.58 (1H, m), 3.34-3.01 (5H, m), 2.61-2.43 (1H, m), 2.33-2.24 (6H, m), 2.24-2.12 (1H, m), 2.13-2.03 (2H, m), 1.84 (3H, bs)

MW (calcd): 506.1; MW (obsd): 506.5 (M+1, $^{35}$Cl)

Method S

Illustrative Synthesis of Intermediate 188: 2-Benzyl-azetidine-1,2-dicarboxylic acid 1-tert-butyl ester 2-methyl ester

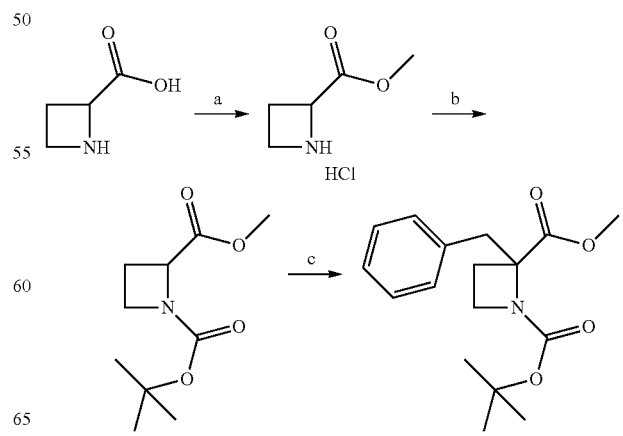

Step a: Azetidine-2-carboxylic acid methyl ester hydrochloride

To a solution of azetidine-2-carboxylic acid (1 eq.) in MeOH at 0° C. was added dropwise thionyl chloride (2.5 eq.). The reaction was stirred at 20° C. for 15 h. The crude was concentrated under reduced pressure and used as such without further purification.

$^1$H NMR δ (ppm) (CDCl$_3$): 5.18 (1H, br s), 4.53-4.05 (2H, m), 3.92 (3H, br s), 3.09-2.56 (2H, m), 2.39-2.05 (1H, m)

Step b: Azetidine-1,2-dicarboxylic acid 1-tert-butyl ester 2-methyl ester

To a solution of azetidine-2-carboxylic acid methyl ester hydrochloride (1 eq.) in MeOH were added TEA (2.5 eq.) and Boc$_2$O (1.1 eq.). The reaction was stirred at 20° C. for 15 h. The solvent was concentrated under reduced pressure. The crude was partitioned between water and EtOAc. The organic layer was washed with water and brine, dried over MgSO$_4$, filtered and concentrated under reduced pressure. The crude was used as such without further purification.

$^1$H NMR δ (ppm) (CDCl$_3$): 4.71-4.60 (1H, m), 4.14-3.86 (2H, m), 3.81 (3H, s), 2.62-2.46 (1H, m), 2.29-2.13 (1H, m), 1.46 (9H, s)

Step c: 2-Benzyl-azetidine-1,2-dicarboxylic acid 1-tert-butyl ester 2-methyl ester To a solution of azetidine-1,2-dicarboxylic acid 1-tert-butyl ester 2-methyl ester (1 eq.) in dry THF under Argon at −78° C. was added a solution of LiHMDS 1M in hexane (1.3 eq.). The mixture was stirred at −78° C. for 1 h, then benzyl bromide (1.3 eq.) was added. The reaction was stirred at −78° C. for 30 min, then at 0° C. for 2 h, then at 20° C. for 1 h. The crude was diluted with EtOAc, carefully hydrolyzed with a saturated aqueous solution of NH$_4$Cl. The organic layer was washed with water and brine, dried over MgSO$_4$, filtered and concentrated under reduced pressure. The crude was purified by chromatography on silica gel (elution with heptane/EtOAc: 98/2 to 80/20) to afford 2-benzyl-azetidine-1,2-dicarboxylic acid 1-tert-butyl ester 2-methyl ester.

$^1$H NMR δ (ppm) (CDCl$_3$): 7.40-7.23 (5H, m), 3.85 (3H, s), 3.84-3.51 (1H, m), 3.42-3.33 (1H, m), 3.14-3.04 (1H, m), 2.18-2.09 (2H, m), 1.59 (2H, s), 1.50 (9H, s)

MW (calcd): 305.4; MW (obsd): 328.3 (M+23)

Intermediate 189, listed in table I was also prepared following the same method, using Chloromethoxymethyl-benzene as the electrophile.

Method T

Illustrative Synthesis of Intermediate 191: [[1-(2-Benzo[b]thiophen-3-yl-acetyl)-2-hydroxymethyl-azetidine-2-carbonyl]-(4-chloro-benzyl)-amino]-acetic acid ethyl ester

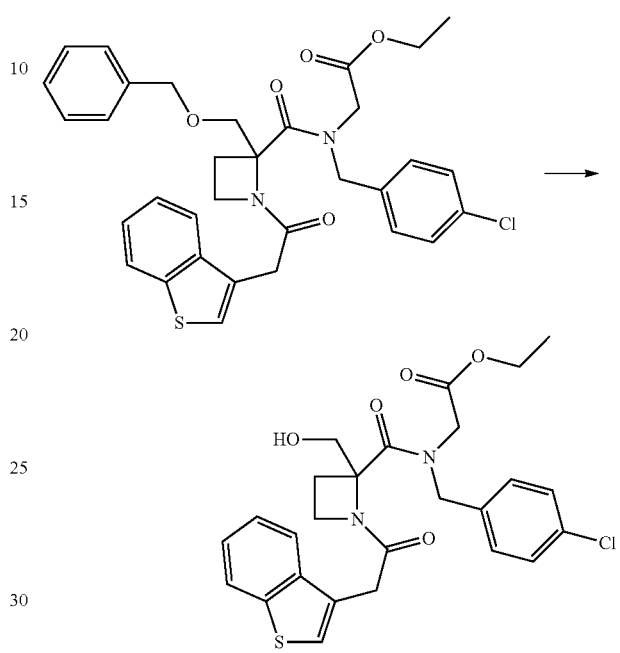

To a solution of [[1-(2-benzo[b]thiophen-3-yl-acetyl)-2-benzyloxymethyl-azetidine-2-carbonyl]-(4-chloro-benzyl)-amino]-acetic acid ethyl ester, Intermediate 163 (1 eq.) in DCM at 0° C. was added BBr$_3$. The reaction was stirred at 0° C. for 2 h. The crude was diluted with DCM and poured into a saturated aqueous solution of NaHCO$_3$. The layers were separated, the organic layer was dried over MgSO$_4$, filtered and concentrated under reduced pressure. The crude was purified by chromatography on silica gel (elution with DCM/MeOH: 100/0 to 95/5) to afford [[1-(2-benzo[b]thiophen-3-yl-acetyl)-2-hydroxymethyl-azetidine-2-carbonyl]-(4-chloro-benzyl)-amino]-acetic acid ethyl ester.

MW (calcd): 515.0; MW (obsd): 514.8 (M+1, $^{35}$Cl)

Method U

Illustrative Synthesis of Compound 27: 1-(2-Biphenyl-3-yl-acetyl)-2-methyl-azetidine-2-carboxylic acid (4-chloro-benzyl)-methyl-amide

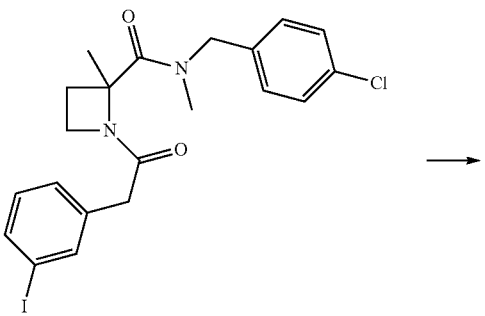

-continued

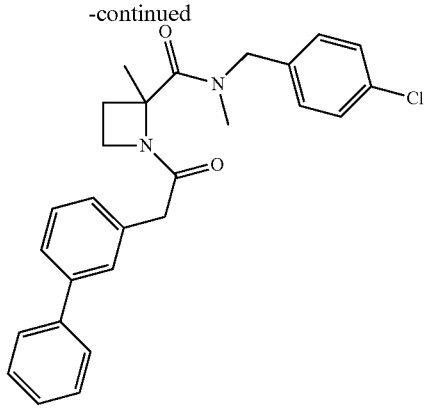

To a solution of phenyl boronic acid (1.5 eq.) in Dioxane/H₂O (9/1) were added Na₂CO₃ (4 eq.) and 1-[2-(3-iodo-phenyl)-acetyl]-2-methyl-azetidine-2-carboxylic acid (4-chloro-benzyl)-methyl-amide, compound 8 (1 eq.). The flask was evacuated and backfilled with argon. Then Pd(PPh₃)₄ was added and the reaction was heated at 90° C. until completion. The crude was partitioned between water and EtOAc. The organic layer was washed with water and brine, dried over MgSO₄, filtered and concentrated under reduced pressure. The crude was purified by chromatography on silica gel (elution with Heptane/EtOAc: 100/0 to 20/80) to afford 1-(2-biphenyl-3-yl-acetyl)-2-methyl-azetidine-2-carboxylic acid (4-chloro-benzyl)-methyl-amide.

$^1$H NMR δ (ppm) (MeOD-d₄): 7.85-7.73 (3H, m), 7.72-7.36 (10H, m), 4.80-4.60 (2H, m), 4.40-4.20 (1H, m), 4.13-3.62 (3H, m), 3.14-2.99 (3H, m), 2.84-2.49 (2H, m), 2.17-2.00 (3H, m)

MW (calcd): 447.0; MW (obsd): 447.2 (M+1, $^{35}$Cl)

Method V

Illustrative Synthesis of Intermediate 192: 1-(Benzo[b]thiophene-3-carbonyl)-2-propyl-azetidine-2-carboxylic acid methyl ester

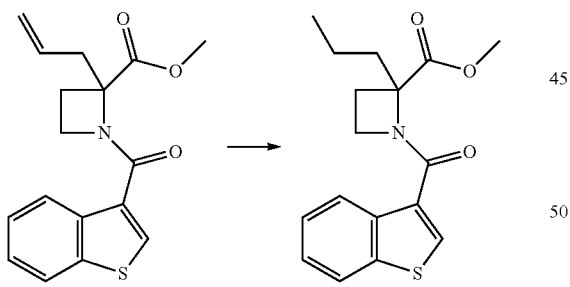

To a solution of 2-allyl-1-(benzo[b]thiophene-3-carbonyl)-azetidine-2-carboxylic acid methyl ester Intermediate 197 (1 eq.) in MeOH was added Pd/C (0.2 eq.), the flask was evacuated and backfilled with H₂. The reaction was stirred for 15 h at 20° C. under atmospheric pressure. The crude was filtered through a pad of celite and washed with EtOH and EtOAc. The filtrate was concentrated under reduced pressure to afford 1-(benzo[b]thiophene-3-carbonyl)-2-propyl-azetidine-2-carboxylic acid methyl ester.

$^1$H NMR δ (ppm) (CDCl₃): 8.37-8.24 (1H, m), 7.89 (1H, d), 7.73 (1H, s), 7.53-7.37 (2H, m), 4.35-4.08 (2H, m), 3.87 (3H, s), 2.48-2.29 (3H, m), 2.16-1.97 (1H, m), 1.75-1.50 (2H, m), 1.15-0.98 (3H, m)

MW (calcd): 317.4; MW (obsd): 318.0 (M+1)

Method W

Illustrative Synthesis of Compound 201: 4-((4-Chloro-benzyl)-{1-[(3,5-dimethyl-phenyl)-methyl-carbamoyl]-2-methyl-azetidine-2-carbonyl}-amino)-butyric acid

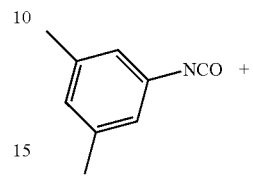

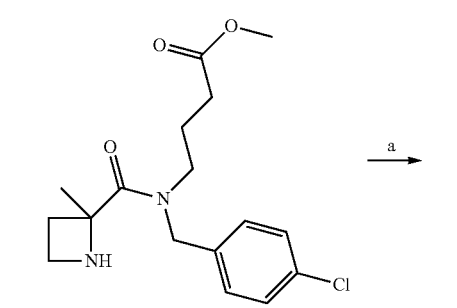

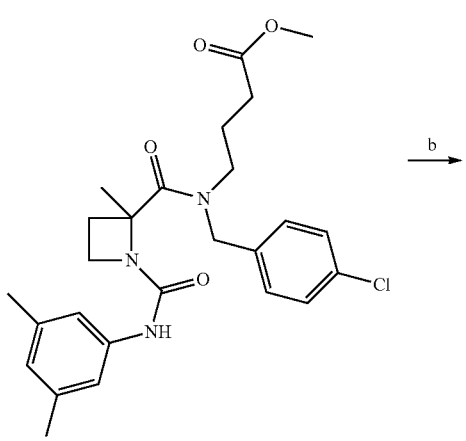

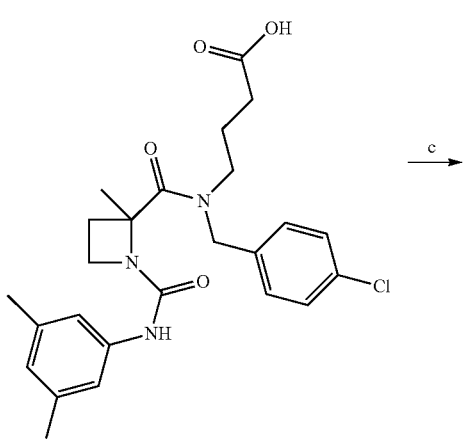

-continued

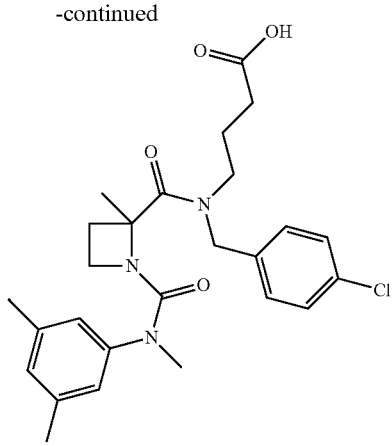

Step a: 4-{(4-Chloro-benzyl)-[1-(3,5-dimethyl-phenylcarbamoyl)-2-methyl-azetidine-2-carbonyl]amino}-butyric acid methyl ester To a solution of 4-[(4-chloro-benzyl)-(2-methyl-azetidine-2-carbonyl)-amino]-butyric acid methyl ester hydrochloride, Intermediate 23 (1 eq.) and TEA (5 eq.) in THF under nitrogen was added 3,5-dimethyl-phenyl-isocyanate (1.5 eq.). The reaction was stirred for 15 h at 20° C. The crude was partitioned between a saturated aqueous solution of NaHCO$_3$ and EtOAc. The organic layer was washed with water and brine, dried over MgSO$_4$, filtered and concentrated under reduced pressure. The crude was purified by chromatography on silica gel (elution with heptane/EtOAc: 75/25 to 40/60) to afford 4-{(4-chloro-benzyl)-[1-(3,5-dimethyl-phenylcarbamoyl)-2-methyl-azetidine-2-carbonyl]-amino}-butyric acid methyl ester.

MW (calcd): 486.0; MW (obsd): 486.4 (M+1, $^{35}$Cl)

Step b: Compound 200, 4-{(4-Chloro-benzyl)-[1-(3,5-dimethyl-phenylcarbamoyl)-2-methyl-azendine-2-carbonyl]-amino}-butyric acid Compound 200, 4-{(4-chloro-benzyl)-[1-(3,5-dimethyl-phenylcarbamoyl)-2-methyl-azetidine-2-carbonyl]-amino}-butyric acid was prepared via method J.

$^1$H NMR δ (ppm) (CDCl$_3$): 9.82-9.74 (1H, m), 7.44-7.40 (1H, m), 7.39-7.34 (1H, m), 7.26-7.21 (1H, m), 7.20-7.15 (2H, m), 7.13-7.11 (1H, m), 6.68 (1H, s), 4.79-4.62 (1H, m), 4.51-4.36 (1H, m), 4.19-3.97 (1H, m), 3.72-3.47 (2H, m), 3.36-3.10 (2H, m), 2.80-2.65 (1H, m), 2.48-2.35 (2H, m), 2.32 (3H, s), -2.30 (3H, s), 1.99-1.91 (2H, m), 1.82-1.71 (3H, m)

MW (calcd): 472.0; MW (obsd): 472.4 (M+1, $^{35}$Cl)

Step c: Compound 201, 4-((4-Chloro-benzyl)-{1-[(3,5-dimethyl-phenyl)-methyl-carbamoyl]-2-methyl-azetidine-2-carbonyl}-amino)-butyric acid To a solution of 4-{(4-chloro-benzyl)-[1-(3,5-dimethyl-phenylcarbamoyl)-2-methyl-azetidine-2-carbonyl]-amino}-butyric acid, compound 200 (1 eq.) in DMF was added NaH (3 eq.). The reaction was stirred for 1 h at 20° C., then MeI (2.5 eq.) was added. The reaction was stirred for 15 h at 20° C. The crude was partitioned between aqueous HCl (0.1N) and EtOAc. The organic layer was washed with water, dried over MgSO$_4$, filtered and concentrated under reduced pressure. The crude was purified by preparative LCMS to afford 4-((4-chloro-benzyl)-{1-[(3,5-dimethyl-phenyl)-methyl-carbamoyl]-2-methyl-azetidine-2-carbonyl}-amino)-butyric acid.

$^1$H NMR δ (ppm) (MeOD, d$_4$): 7.52-7.31 (4H, m), 7.07-6.91 (2H, m), 6.72-6.63 (1H, m), 4.87-4.61 (2H, m), 3.50-3.41 (1H, m), 3.23-3.10 (3H, m), 3.01-2.74 (2H, m), 2.44-2.23 (9H, m), 1.99-1.82 (5H, m), 1.39-1.10 (2H, m)

MW (calcd): 486.0; MW (obsd): 486.4 (M+1, $^{35}$Cl)

Method X

Illustrative Synthesis of Compound 228: 1-(benzo[b]thiophene-3-carbonyl)-N-(3-chlorobenzyl)-2-ethyl-N-(4-(methylsulfonamido)-4-oxobutyl)azetidine-2-carboxamide

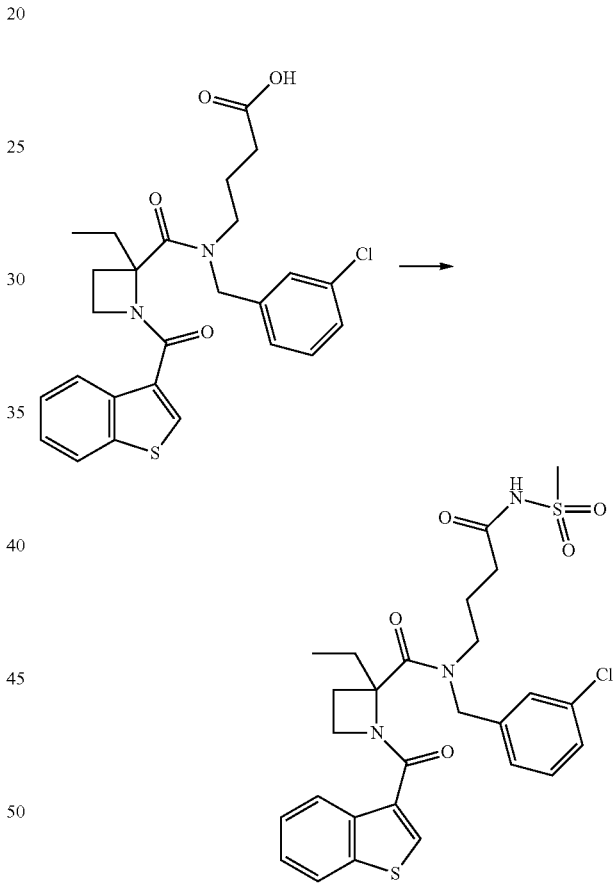

To a solution of compound 195 in THF is added CDI (2 eq.), The mixture is heated at 40° C. for 2.5 h, 1,8-Diazabicyclo[5.4.0]undec-7-ene (2 eq.) and methanesulfonamide (2 eq.) are added and the mixture is stirred at 20° C. for 1 h30. The mixture is hydrolysed by addition of aqueous HCl 0.1N and diluted in DCM. The organic layer was washed with water and brine, dried over MgSO$_4$, filtered and concentrated under reduced pressure. The residue was coevaporated with Et$_2$O to afford 1-(benzo[b]thiophene-3-carbonyl)-N-(3-chlorobenzyl)-2-ethyl-N-(4-(methylsulfonamido)-4-oxobutyl)azetidine-2-carboxamide as a white solid.

MW (calcd): 576.2; MW (obsd): 576.1 (M+1, $^{35}$Cl)

Method Y

Illustrative Synthesis of Compound 249: 4-(1-(benzo[b]thiophene-3-carbonyl)-N-(6-chloropyridin-3-yl)-2-methylazetidine-2-carboxamido)butanoic acid

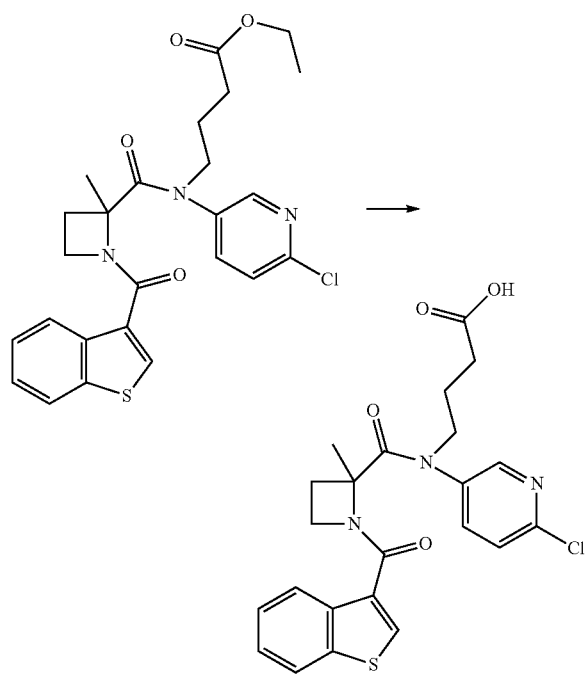

To a solution of Intermediate 239 in THF/water (1/1) is added LiOH monohydrate (1 eq.), The mixture is stirred at 20° C. for 16 h. The pH is adjusted to pH=7-8 by addition of aqueous HCl 0.1N and the mixture is concentrated. The crude is purified by preparative LCMS to afford 4-(1-(benzo[b]thiophene-3-carbonyl)-N-(6-chloropyridin-3-yl)-2-methylazetidine-2-carboxamido)butanoic acid.

MW (calcd): 472.0; MW (obsd): 472.0 (M+1, $^{35}$Cl)

Method Z

Illustrative Synthesis of Intermediate 251: 2-[(4-Chloro-benzyl)-(3-methoxycarbonyl-propyl)-carbamoyl]-2-methyl-azetidine-1-carboxylic acid 4-trifluoromethyl-phenyl ester

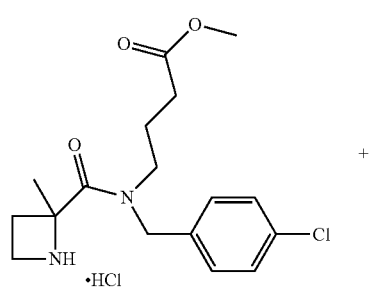

+

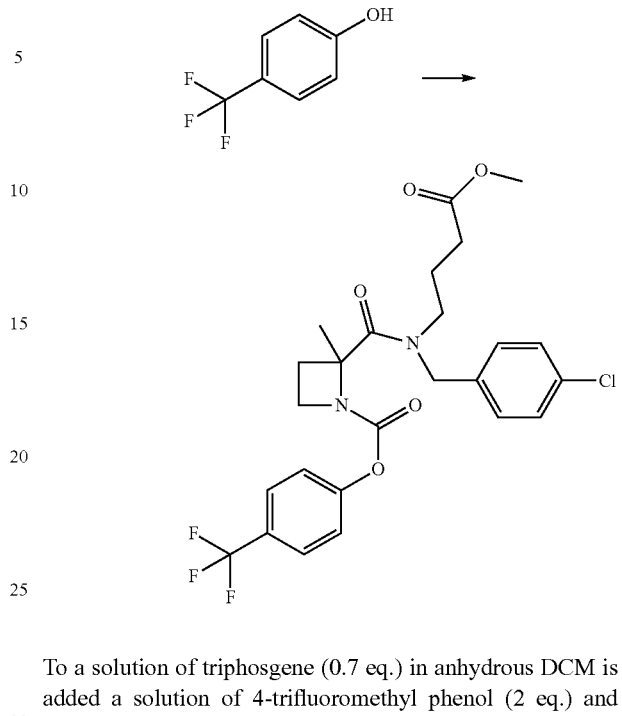

To a solution of triphosgene (0.7 eq.) in anhydrous DCM is added a solution of 4-trifluoromethyl phenol (2 eq.) and DIPEA (2 eq.) in DCM. After stirring for 1 h at 20° C., Intermediate 23 and DIPEA (2 eq.) are added. The mixture is stirred at 20° C. for 16 h, diluted with DCM, washed with aqueous HCl (0.1N), a saturated aqueous solution of NaHCO$_3$ and brine. The organic layer is dried over MgSO$_4$, filtered and concentrated under reduced pressure. The crude is purified by chromatography on silica gel (elution with heptane/EtOAc: 90/10 to 60/40) to afford 2-[(4-Chloro-benzyl)-(3-methoxycarbonyl-propyl)-carbamoyl]-2-methyl-azetidine-1-carboxylic acid 4-trifluoromethyl-phenyl ester.

MW (calcd): 526.9; MW (obsd): 527.1 (M+1, $^{35}$Cl)

Method AA

Illustrative Synthesis of Intermediate 275: 4-{(4-Chloro-benzyl)-[1-(indole-1-carbonyl)-2-methyl-azetidine-2-carbonyl]-amino}-butyric acid methyl ester

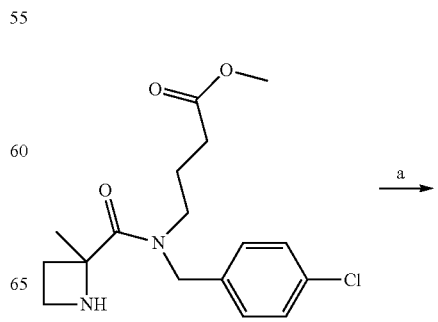

-continued

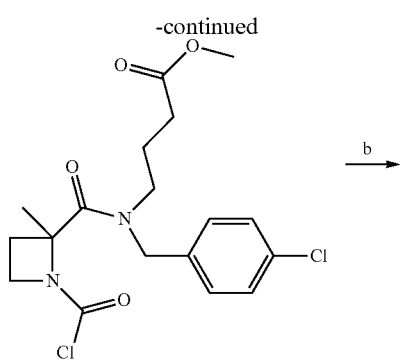

Step a: 4-[(4-Chloro-benzyl)-(1-chlorocarbonyl-2-methyl-azetidine-2-carbonyl)-amino]-butyric acid methyl ester A solution of Intermediate 23 and DIPEA (3 eq.) in DCM is added at 0° C. to a solution of triphosgene (1 eq.) in DCM and the mixture is stirred at 0° C. for 1 h, diluted with DCM, washed with aqueous HCl (0.1N) dried over $Na_2SO_4$ and concentrated to afford 4-[(4-Chloro-benzyl)-(1-chlorocarbonyl-2-methyl-azetidine-2-carbonyl)-amino]-butyric acid methyl ester.

Step b: 4-{(4-Chloro-benzyl)-[1-(indole-1-carbonyl)-2-methyl-azetidine-2-carbonyl]-amino}-butyric acid methyl ester To a solution of indole (1 eq.) in THF is added NaH (1.5 eq., 60% in oil) and the mixture is stirred at 20° C. for 1 h. A solution of 4-[(4-Chloro-benzyl)-(1-chlorocarbonyl-2-methyl-azetidine-2-carbonyl)-amino]-butyric acid methyl ester in THF in added dropwise and the mixture is stirred at 20° C. for 16 h. The mixture was concentrated and the residue dissolved in EtOAc, washed with aqueous HCl (0.1N), a saturated aqueous solution of $NaHCO_3$ and brine. The organic layer is dried over $Na_2SO_4$, filtered and concentrated under reduced pressure. The crude residue is used as such in next step.

TABLE Ia

Synthesis of intermediates for the preparation of the compounds of the invention

| Int | Structure | SM | Mtd | MW | MS Mes'd |
|---|---|---|---|---|---|
| 1 | 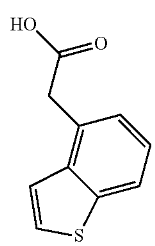 [SMILES: O=C(O)Cc1cccc2sccc12] | — | Acid | 192.2 | NMR |
| 2 | 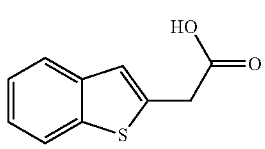 [SMILES: O=C(O)Cc1cc2ccccc2s1] | — | Acid | | NMR |
| 3 | 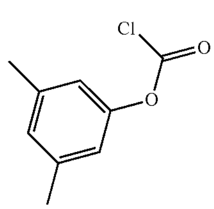 | — | Chloroformate | 184.6 | NMR |

TABLE Ia-continued

Synthesis of intermediates for the preparation of the compounds of the invention

| Int | Structure | SM | Mtd | MW | MS Mes'd |
|---|---|---|---|---|---|
| 4 | (2-chlorophenyl chloroformate) | — | Chloroformate | 191.0 | N/A |
| 5 | (2-methylphenyl chloroformate) | — | Chloroformate | 170.6 | N/A |
| 6 | (tert-butyl 6-formyl-1H-indole-1-carboxylate) | 1H-Indole-6-carbaldehyde | Ald | 245.3 | 246.1 (M + 1) |
| 7 | (tert-butyl 6-formyl-1H-indazole-1-carboxylate) | 1H-Indazole-6-carbaldehyde | Ald | 246.3 | 191.0 (M − 55) |
| 8 | (benzofuran-6-carbaldehyde) | Benzofuran-6-carboxylic acid methyl ester | Ald | 146.1 | 147.1 (M + 1) |
| 9 | (imidazo[1,2-a]pyridine-7-carbaldehyde) | — | Ald | 146.1 | NMR |
| 10 | (benzothiazole-5-carbaldehyde) | — | Ald | 163.2 | 164.1 (M + 1) |

TABLE Ia-continued

Synthesis of intermediates for the preparation of the compounds of the invention

| Int | Structure | SM | Mtd | MW | MS Mes'd |
|---|---|---|---|---|---|
| 11 | 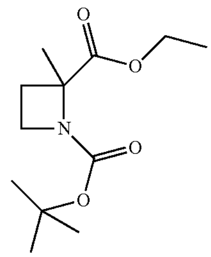 [SMILES: CCOC(=O)C1(C)CCN1C(=O)OC(C)(C)C] | Benzylamine, 2-bromo-propionic acid ethyl ester, chloroacetaldehyde and Boc₂O | A | 243.3 | 266.2 (M + 23) |
| 12 | 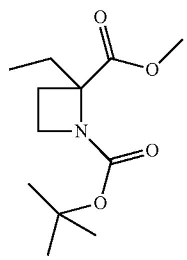 [SMILES: CCC1(C(=O)OC)CCN1C(=O)OC(C)(C)C] | Benzylamine, 2-bromo-propionic acid methyl ester, chloroacetaldehyde and Boc₂O | A | 243.3 | NMR |
| 13 | 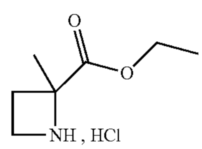 | Int 11 | B1 | 143.2 | NMR |
| 14 | 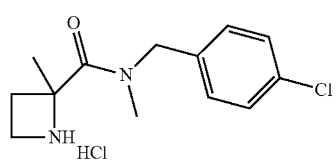 | Int 139 | B1 | 252.7 | NMR |
| 15 | 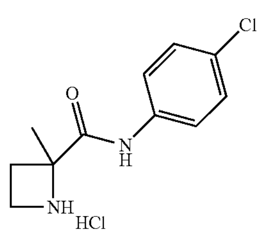 | Int 140 | B1 | 224.7 | NMR |
| 16 | Chiral | Int 142 | B1 | 129.2 | N/A |
| 17 | Chiral | Int 143 | B1 | 129.2 | NMR |

TABLE Ia-continued
Synthesis of intermediates for the preparation of the compounds of the invention
| Int | Structure | SM | Mtd | MW | MS Mes'd |
|---|---|---|---|---|---|
| 18 | 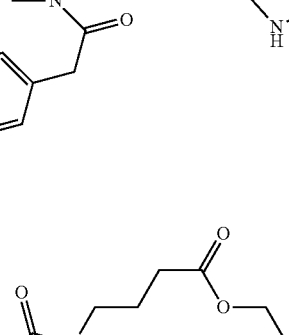 | Int 147 | B1 | 475.6 | 476.1 (M + 1) |
| 19 | 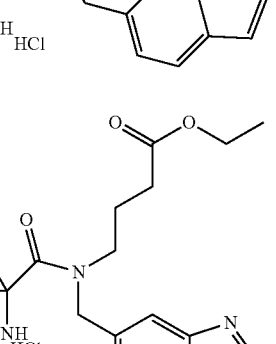 | Int 165 | B1 | 358.4 | 359.4 (M + 1) |
| 20 | 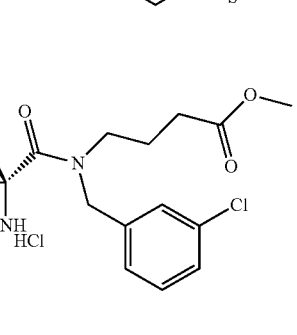 | Int 169 | B1 | 375.5 | 376.4 (M + 1) |
| 21 | Chiral 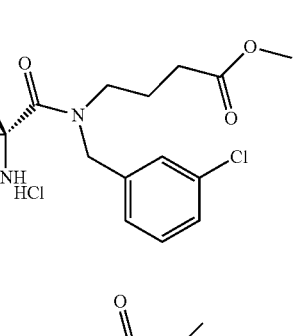 | Int 175 | B1 | 338.89 | 339.3 (M + 1, $^{35}$Cl) |
| 22 | 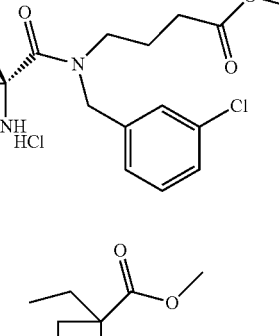 | Int 12 | B1 | 143.2 | NMR |

TABLE Ia-continued

Synthesis of intermediates for the preparation of the compounds of the invention

| Int | Structure | SM | Mtd | MW | MS Mes'd |
|---|---|---|---|---|---|
| 23 | [structure: methyl 4-[N-(4-chlorobenzyl)-(2-methylazetidine-2-carboxamido)]butanoate · HCl] | Int 181 | B1 | 338.8 | N/A |
| 24 | Chiral [structure: methyl 4-[N-((R or S)-1-(4-chlorophenyl)ethyl)-(2-methylazetidine-2-carboxamido)]butanoate · HCl] | Int 182 | B1 | 352.9 | 353.3 (M + 1, $^{35}$Cl) |
| 25 | Chiral [structure: methyl 4-[N-((S or R)-1-(4-chlorophenyl)ethyl)-(2-methylazetidine-2-carboxamido)]butanoate · HCl] | Int 183 | B1 | 352.9 | 353.3 (M + 1, $^{35}$Cl) |
| 26 | [structure: methyl 2-benzylazetidine-2-carboxylate · HCl] | Int 188 | B1 | 205.3 | 206.2 (M + 1) |
| 27 | [structure: methyl 2-((benzyloxy)methyl)azetidine-2-carboxylate · HCl] | Int 189 | B1 | 235.3 | NMR |
| 28 | [structure: N-(4-chlorobenzyl)-2-methylazetidine-2-carboxamide · TFA] | Int 138 | B2 | 238.7 | NMR |

TABLE Ia-continued

Synthesis of intermediates for the preparation of the compounds of the invention

| Int | Structure | SM | Mtd | MW | MS Mes'd |
|---|---|---|---|---|---|
| 29 | 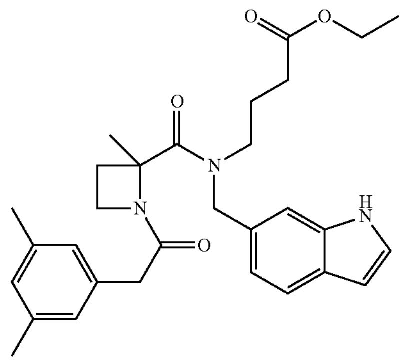 [SMILES: CCOC(=O)CCCN(Cc1ccc2cc[nH]c2c1)C(=O)C1(C)CCN1C(=O)Cc1cc(C)cc(C)c1] | Int 149 | B2 | 503.6 | 504.2 (M + 1) |
| 30 | 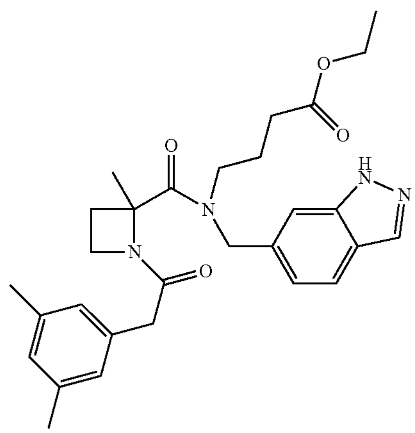 [SMILES: CCOC(=O)CCCN(Cc1ccc2cn[nH]c2c1)C(=O)C1(C)CCN1C(=O)Cc1cc(C)cc(C)c1] | Int 151 | B2 | 504.6 | 505.1 (M + 1) |
| 31 | 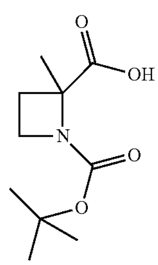 | Int 11 | C | 215.2 | N/A |
| 32 | Chiral | Int 31 | D | 215.2 | N/A |

TABLE Ia-continued

Synthesis of intermediates for the preparation of the compounds of the invention

| Int | Structure | SM | Mtd | MW | MS Mes'd |
|---|---|---|---|---|---|
| 33 | Chiral | Int 31 | D | 215.2 | N/A |
| 34 | 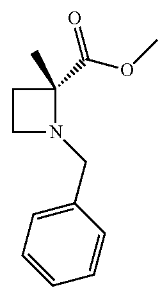 [SMILES: COC(=O)[C@@]1(C)CCN1Cc1ccccc1] | Int 33 | D | 219.3 | NMR |
| 35 | 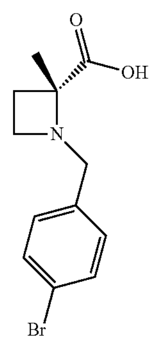 [SMILES: C[C@]1(C(=O)O)CCN1Cc1ccc(Br)cc1] | Int 33 | D | 298.1 | NMR |
| 36 | 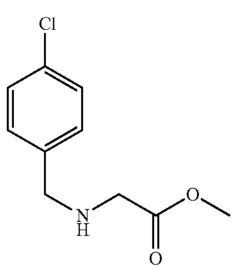 | 4-chlorobenzylamine and bromo-acetic acid methyl ester | E1 | 213.7 | NMR |
| 37 | 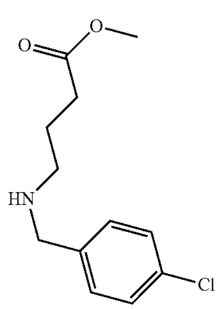 [SMILES: COC(=O)CCCNCc1ccc(Cl)cc1] | 4-Bromo-butyric acid methyl ester and 4-chlorobenzylamine | E1 | 241.7 | 242.3 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 38 | 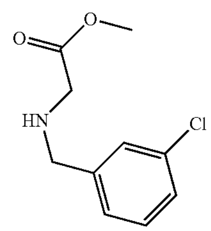 | Bromo-acetic acid methyl ester and 3-chlorobenzylamine | E1 | 213.6 | NMR |
| 39 | 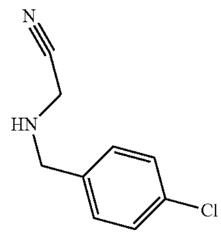 [SMILES: N#CCNCc1ccc(Cl)cc1] | Bromo-acetonitrile and 4-chloro-benzylamine | E1 | 180.6 | NMR |
| 40 | 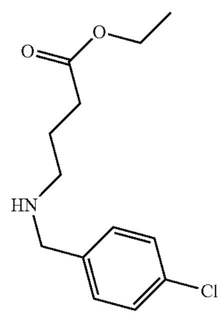 [SMILES: CCOC(=O)CCCNCc1ccc(Cl)cc1] | 4-Bromo-butyric acid ethyl ester and 4-chloro-benzylamine | E1 | 255.7 | NMR |
| 41 | 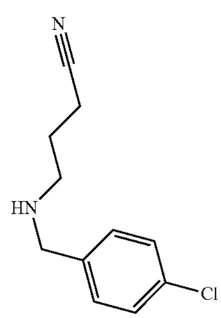 [SMILES: N#CCCCNCc1ccc(Cl)cc1] | 4-Bromo-butyronitrile and 4-chloro-benzylamine | E1 | 208.7 | 209.0 (M + 1, $^{35}$Cl) |
| 42 | 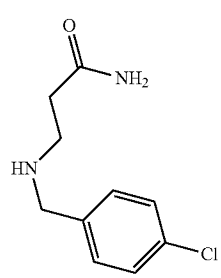 [SMILES: NC(=O)CCNCc1ccc(Cl)cc1] | 3-Bromo-propionamide and 4-chloro-bnzylamine | E1 | 212.7 | 213.1 (M + 1, $^{35}$Cl) |

TABLE Ia-continued

Synthesis of intermediates for the preparation of the compounds of the invention

| Int | Structure | SM | Mtd | MW | MS Mes'd |
|-----|-----------|-----|-----|-----|---------|
| 43 | 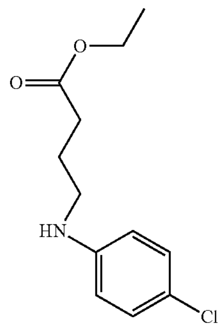 [SMILES: CCOC(=O)CCCNc1ccc(Cl)cc1] | 4-Bromo-butyric acid ethyl ester (4 eq.), K₂CO₃ (3 eq.) and 4-chloro-aniline | E2 | 241.7 | 242.3 (M + 1, $^{35}$Cl) |
| 44 | Chiral | (R)-1-(4-Chloro-phenyl)-ethylamine and 4-bromo-butyric acid methyl ester | E2 | 255.7 | 256.3 (M + 1, $^{35}$Cl) |
| 45 | Chiral | (S)-1-(4-Chloro-phenyl)-ethylamine and 4-bromo-butyric acid methyl ester | E2 | 255.7 | 256.3 (M + 1, $^{35}$Cl) |
| 46 | 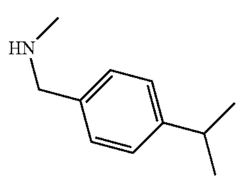 | Methylamine and 4-Isopropyl-benzaldehyde | E3 | | N/A |
| 47 | 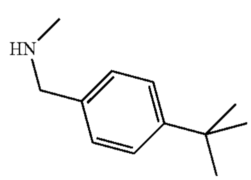 | Methylamine and 4-tert-butyl-benzaldehyde | E3 | | N/A |
| 48 | 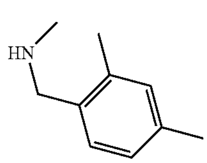 | Methylamine and 2,4-dimethyl-benzaldehyde | E3 | | N/A |

TABLE Ia-continued

Synthesis of intermediates for the preparation of the compounds of the invention

| Int | Structure | SM | Mtd | MW | MS Mes'd |
|---|---|---|---|---|---|
| 49 | 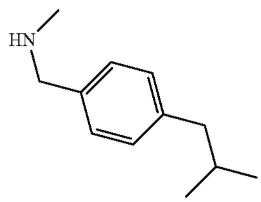 | Methylamine and 4-iso-butyl-benzaldehyde | E3 | | N/A |
| 50 | 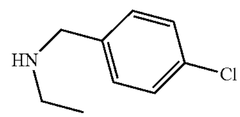 | Ethylamine (70% in $H_2O$) and 4-chloro-benzaldehyde | E3 | | NMR |
| 51 | 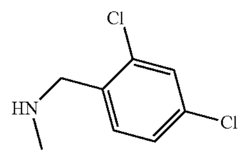 | Methylamine and 2,4-dichloro-benzaldehyde | E3 | | N/A |
| 52 | 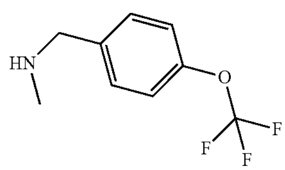 | Methylamine and 4-trifluoromethoxy-benzaldehyde | E3 | | N/A |
| 54 | 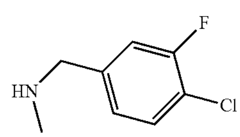 | Methylamine and 4-chloro-3-fluoro-benzaldehyde | E3 | | N/A |
| 55 | 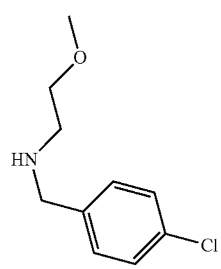 | 2-methoxyethylamine and 4-chlorobenzaldehyde | E4 | 199.9 | NMR |
| 56 | 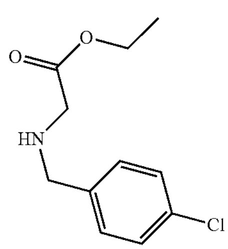 | Glycine ethyl ester hydrochloride and 4-chlorobenzaldehyde | E4 | 227.7 | 228.3 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 57 | 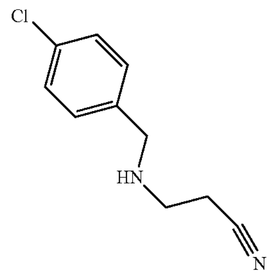 [SMILES: N#CCCNCc1ccc(Cl)cc1] | 3-Amino-propionitrile and 4-chloro-benzaldehyde | E4 | 194.7 | 195.1 (M + 1, $^{35}$Cl) |
| 58 | 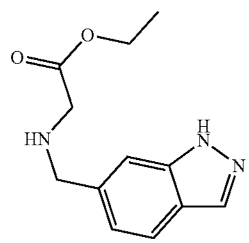 [SMILES: CCOC(=O)CNCc1ccc2cn[nH]c2c1] | Glycine ethyl ester hydrohloride and 1H-Indazole-6-carbaldehyde | E4 | 233.3 | 234.1 (M + 1) |
| 59 | 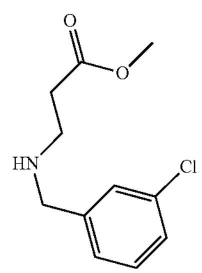 | □-alanine methyl ester hydrochloride and 3-chlorobenzaldehyde | E4 | 227.7 | NMR |
| 60 | 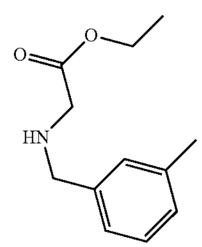 | Glycine ethyl ester hydrochloride and 3-methylbenzaldehyde | E4 | 207.3 | 208.5 (M + 1) |
| 61 | 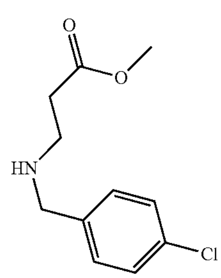 | □-aniline methyl ester hydrochloride and 4-chlorobenzaldehyde | E5 | 227.7 | NMR |
| 62 | 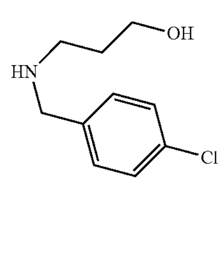 [SMILES: OCCCNCc1ccc(Cl)cc1] | 3-aminopropan-1-ol and 4-chloro-benzaldehyde | E5 | 199.7 | N/A |

TABLE Ia-continued

Synthesis of intermediates for the preparation of the compounds of the invention

| Int | Structure | SM | Mtd | MW | MS Mes'd |
|---|---|---|---|---|---|
| 63 | 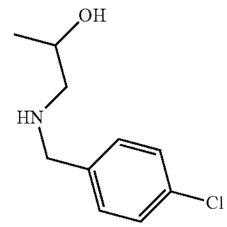 | 1-Amino-propan-2-ol and 4-chloro-benzaldehyde | E5 | 199.7 | 200.1 (M + 1, $^{35}$Cl) |
| 64 | Chiral | D-alanine methyl ester hydrochloride and 4-chloro-benzaldehyde | E5 | 227.7 | NMR |
| 65 | 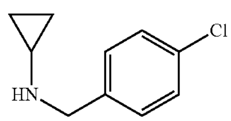 [SMILES: Clc1ccc(CNC2CC2)cc1] | Cyclopropylamine and 4-chlorobenzaldehyde | E6 | 181.7 | N/A |
| 66 | Chiral | L-alanine methyl ester hydrochloride and 4-chloro-benzaldehyde | E5 | 227.7 | N/A |
| 67 | 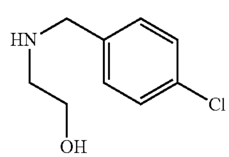 [SMILES: OCCNCc1ccc(Cl)cc1] | Ethanolamine and 4-chlorobenzaldehyde | E6 | 185.7 | NMR |
| 68 | 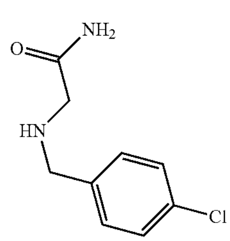 [SMILES: NC(=O)CNCc1ccc(Cl)cc1] | 2-Amino-acetamide and 4-chloro-benzaldehyde | E6 | 198.6 | 199.1 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 69 | 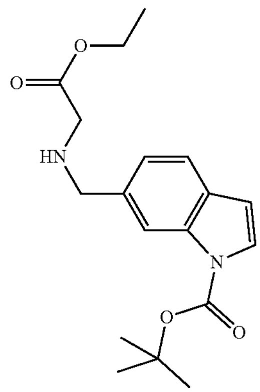 [SMILES: CCOC(=O)CNCc1ccc2ccn(C(=O)OC(C)(C)C)c2c1] | Int 6 and glycine ethyl ester hydrochloride | E6 | 332.4 | NMR |
| 70 | 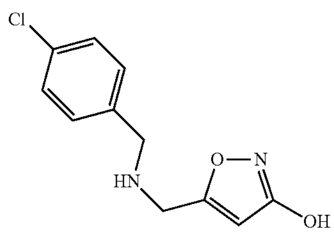 [SMILES: Oc1cc(CNCc2ccc(Cl)cc2)on1] | Muscimol and 4-chloro-benzaldehyde | E6 | 238.7 | 239.0 (M + 1, $^{35}$Cl) |
| 71 | 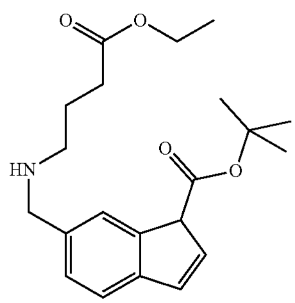 [SMILES: CCOC(=O)CCCNCc1ccc2c(c1)C(C(=O)OC(C)(C)C)C=C2] | Int 6 and 4-amino-butyric acid ethyl ester hydrochloride | E7 | 360.5 | 361.1 (M + 1) |
| 72 | 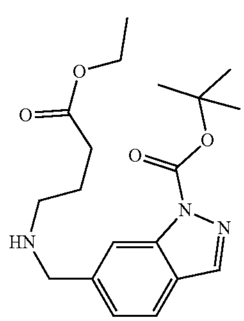 [SMILES: CCOC(=O)CCCNCc1ccc2cnn(C(=O)OC(C)(C)C)c2c1] | Int 7 and 4-amino-butyric acid ethyl ester hydrochloride | E7 | 361.4 | 362.1 (M + 1) |
| 73 | 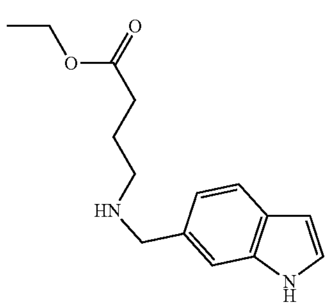 [SMILES: CCOC(=O)CCCNCc1ccc2cc[nH]c2c1] | 4-amino-butyric acid ethyl ester hydrochloride and 1H-Indole-6-carbaldehyde | E7 | 260.3 | 261.3 (M + 1) |

TABLE Ia-continued

Synthesis of intermediates for the preparation of the compounds of the invention

| Int | Structure | SM | Mtd | MW | MS Mes'd |
|---|---|---|---|---|---|
| 74 | 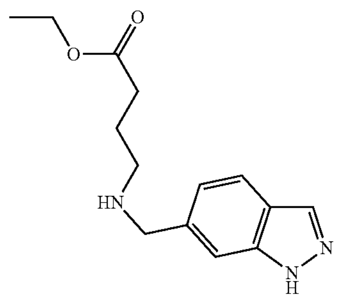 [SMILES: CCOC(=O)CCCNCc1ccc2cn[nH]c2c1] | 4-amino-butyric acid ethyl ester hydrochloride and 1H-Indaole-6-carbaldehyde | E7 | 261.3 | 262.3 (M + 1) |
| 75 | 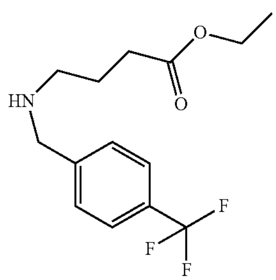 [SMILES: CCOC(=O)CCCNCc1ccc(C(F)(F)F)cc1] | 4-amino-butyric acid ethyl ester hydrochloride and 4-trifluoromethyl-benzaldehyde | E7 | 289.3 | 290.3 (M + 1) |
| 76 | 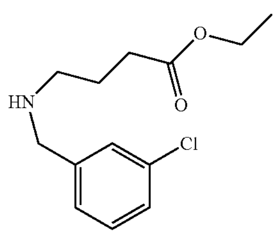 [SMILES: CCOC(=O)CCCNCc1cccc(Cl)c1] | 4-amino-butyric acid ethyl ester hydrochloride and 3-chloro-benzaldehyde | E7 | 255.7 | 256.2 (M + 1, $^{35}$Cl) |
| 77 | 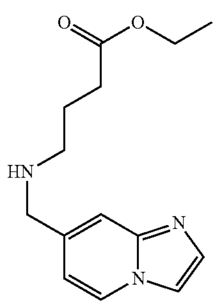 [SMILES: CCOC(=O)CCCNCc1ccn2ccnc2c1] | 4-amino-butyric acid ethyl ester hydrochloride and int 9 | E7 | 261.3 | 262.4 (M + 1) |
| 78 | 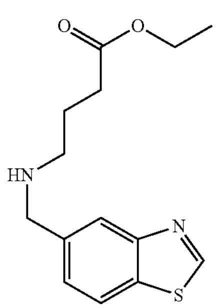 [SMILES: CCOC(=O)CCCNCc1ccc2scnc2c1] | Int 10 and 4-amino-butyric acid ethyl ester hydrochloride | E7 | 278.4 | 279.3 (M + 1) |

TABLE Ia-continued

Synthesis of intermediates for the preparation of the compounds of the invention

| Int | Structure | SM | Mtd | MW | MS Mes'd |
|---|---|---|---|---|---|
| 79 | (methyl 3-{[(1H-indazol-6-yl)methyl]amino}propanoate) | β-alanine methyl ester hydrochloride and 1H-Indazole-6-carbaldehyde | E7 | 233.3 | 234.3 (M + 1) |
| 80 | (methyl 4-{[(3-chlorobenzyl)amino]}butanoate) | 4-amino-butyric acid ethyl ester hydrochloride and 3-chloro-benzaldehyde | E7 | 241.7 | 242.2 (M + 1, $^{35}$Cl) |
| 82 | (ethyl 4-{[(1-benzofuran-6-yl)methyl]amino}butanoate) | 4-amino-butyric acid ethyl ester hydrochloride and int 8 | E8 | 261.3 | 262.3 (M + 1) |
| 83 | (1-(3-{[(4-chlorobenzyl)amino]propyl})pyrrolidin-2-one) | 1-(3-Amino-propyl)-pyrrolidin-2-one and 4-chloro-benzaldehyde | E8 | 266.8 | 267.3 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 84 | 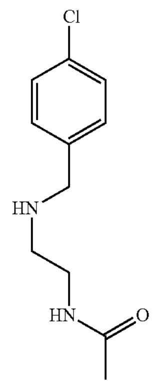 | (2-amino-ethyl)-carbamic acid tert-butyl ester, acetyl chloride and 4-chloro-benzaldehyde | E9 | 226.7 | NMR |
| 85 | 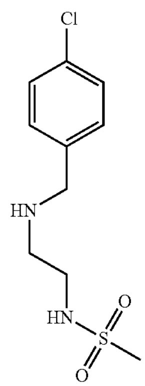 [SMILES: CS(=O)(=O)NCCNCc1ccc(Cl)cc1] | (2-amino-ethyl)-carbamic acid tert-butyl ester, methane sulfonyl chloride and 4-chloro-benzaldehyde | E9 | 262.8 | 263.0 (M + 1, $^{35}$Cl) |
| 86 | 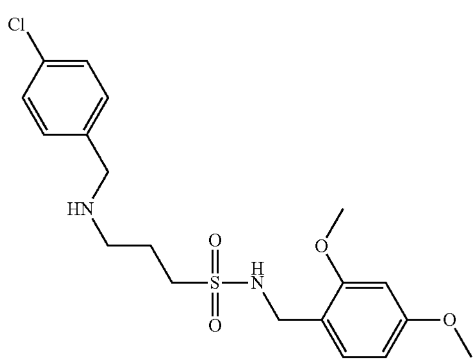 [SMILES: COc1ccc(CNS(=O)(=O)CCCNCc2ccc(Cl)cc2)c(OC)c1] | 3-Chloro-propanesulfonyl chloride, 2,4-Dimethoxy-benzylamine and 4-chlorobenzylamine | E10 | 412.9 | 413.4 (M + 1, $^{35}$Cl) |
| 87 | 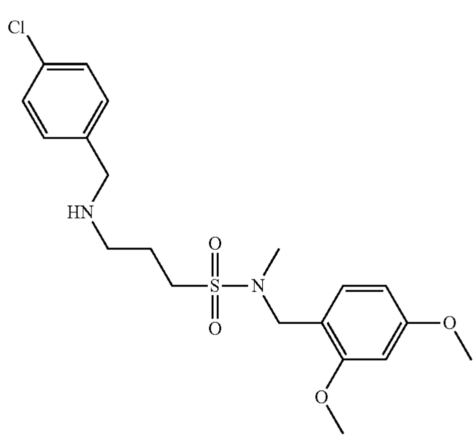 [SMILES: COc1ccc(CN(C)S(=O)(=O)CCCNCc2ccc(Cl)cc2)c(OC)c1] | 3-Chloro-propanesulfonyl chloride, (2,4-Dimethoxy-benzyl)-methyl-amine, and 4-chlorobenzylamine | E10 | 427.0 | 427.4 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 88 | 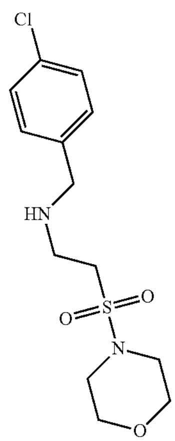 [SMILES: O=S(=O)(CCNCc1ccc(Cl)cc1)N1CCOCC1] | 2-Chloro-ethanesulfonyl chloride, morpholine and 4-chlorobenzylamine | E10 | 318.8 | 319.3 (M + 1, $^{35}$Cl) |
| 89 | 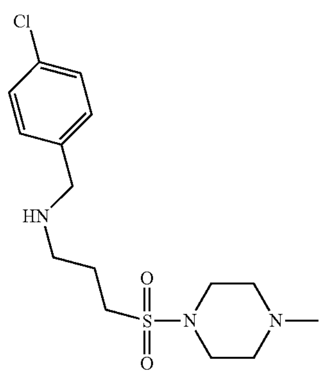 [SMILES: CN1CCN(S(=O)(=O)CCCNCc2ccc(Cl)cc2)CC1] | 3-Chloro-propanesulfonyl chloride, 1-methyl-piperaine and 4-chlorobenzylamine | E10 | 345.9 | 346.4 (M + 1, $^{35}$Cl) |
| 90 | 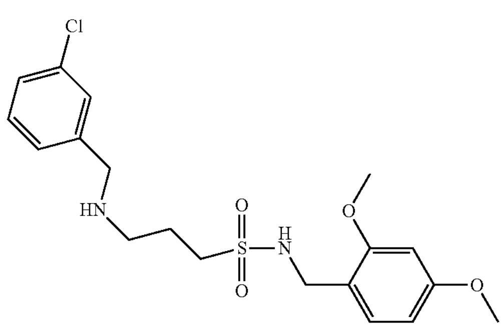 [SMILES: COc1ccc(CNS(=O)(=O)CCCNCc2cccc(Cl)c2)c(OC)c1] | 3-Chloro-propanesulfonyl chloride, 2,4-Dimethoxy-benzylamine and 3-chlorobenzylamine | E10 | 412.9 | 413.4 (M + 1, $^{35}$Cl) |
| 91 | 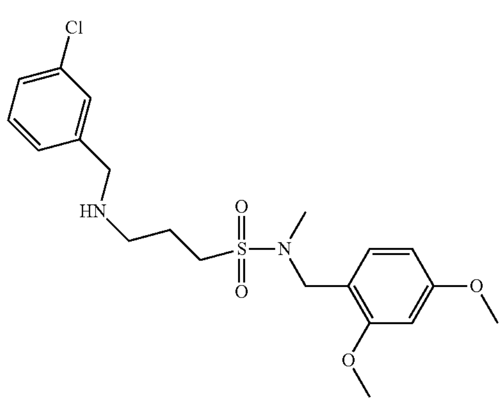 [SMILES: COc1ccc(CN(C)S(=O)(=O)CCCNCc2cccc(Cl)c2)c(OC)c1] | 3-Chloro-propanesulfonyl chloride, (2,4-Dimethoxy-benzyl)-methyl-amine and 3-chlorobenzylamine | E10 | 427.0 | 427.4 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 92 | 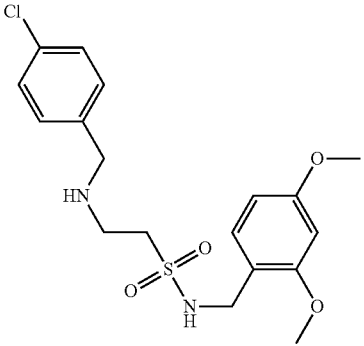 [SMILES: COc1ccc(CNS(=O)(=O)CCNCc2ccc(Cl)cc2)c(OC)c1] | 2-Chloro-ethanesulfonyl chloride, 2,4-Dimethoxy-bnzylamine and 4-chlorobenzylamine | E10 | 398.9 | 399.3 (M + 1, $^{35}$Cl) |
| 93 | 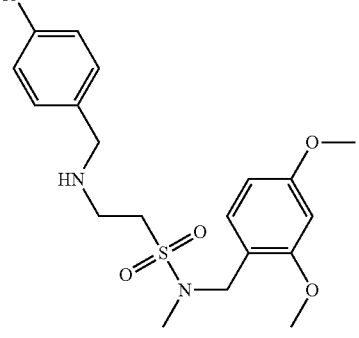 | 2-Chloro-ethanesulfonyl chloride, (2,4-Dimethoxy-benzyl)-methyl-amine and 4-chlorobenzylamine | E10 | 412.9 | 413.4 (M + 1, $^{35}$Cl) |
| 94 | 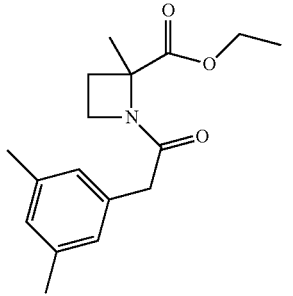 [SMILES: CCOC(=O)C1(C)CCN1C(=O)Cc1cc(C)cc(C)c1] | Int 13 and (3,5-Dimethyl-phenyl)-acetic acid | F | 289.4 | 290.0 (M + 1) |
| 95 | 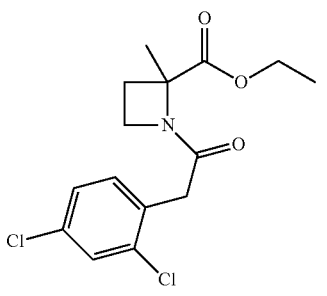 [SMILES: CCOC(=O)C1(C)CCN1C(=O)Cc1ccc(Cl)cc1Cl] | Int 13 and (2,4-dichloro-phenyl)-acetic acid | F | 330.2 | 330.0 (M + 1, $^{35}$Cl) |

TABLE Ia-continued
Synthesis of intermediates for the preparation of the compounds of the invention
| Int | Structure | | SM | Mtd | MW | MS Mes'd |
|---|---|---|---|---|---|---|
| 96 | 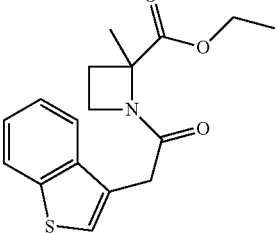 | | Int 13 and Benzo[b]thiophen-3-yl-acetic acid | F | 317.4 | 318.0 (M + 1) |
| 97 | 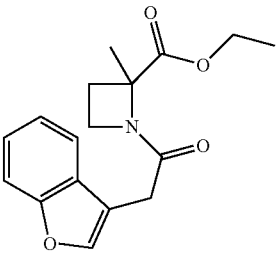 [SMILES: CCOC(=O)C1(C)CCN1C(=O)Cc1coc2ccccc12] | | Int 13 and Benzofuran-3-yl-acetic acid | F | 301.3 | 302.0 (M + 1) |
| 98 | 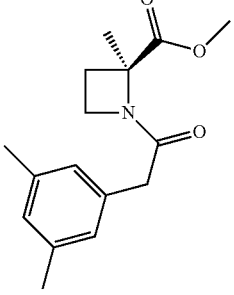 | Chiral | Int 16 and (3,5-Dimethyl-phenyl)-acetic acid | F | 275.3 | 276.0 (M + 1) |
| 99 | 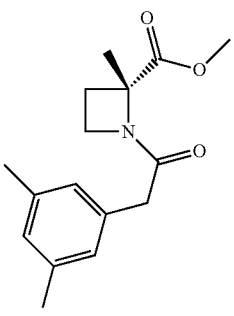 | Chiral | Int 17 and (3,5-Dimethyl-phenyl)-acetic acid | F | 275.3 | 276.1 (M + 1) |
| 100 | 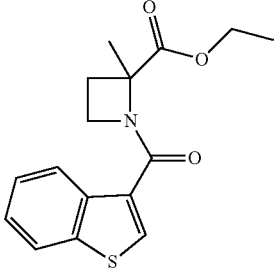 [SMILES: CCOC(=O)C1(C)CCN1C(=O)c1csc2ccccc12] | | Int 13 and Bromo[b]thiophene-3-carboxylic acid | F | 303.4 | 304.0 (M + 1) |

TABLE Ia-continued

Synthesis of intermediates for the preparation of the compounds of the invention

| Int | Structure | SM | Mtd | MW | MS Mes'd |
|---|---|---|---|---|---|
| 101 | 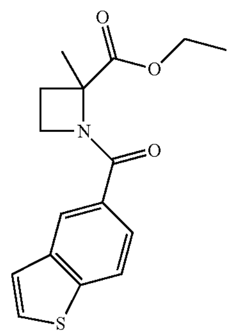 [SMILES: CCOC(=O)C1(C)CCN1C(=O)c1ccc2sccc2c1] | Int 13 and Bromo[b]thiophene-5-carboxylic acid | F | 303.4 | 304.2 (M + 1) |
| 102 | 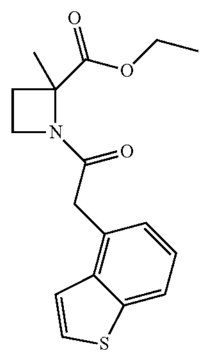 [SMILES: CCOC(=O)C1(C)CCN1C(=O)Cc1cccc2sccc12] | Int 13 and int 1 | F | 317.4 | 318.2 (M + 1) |
| 103 | 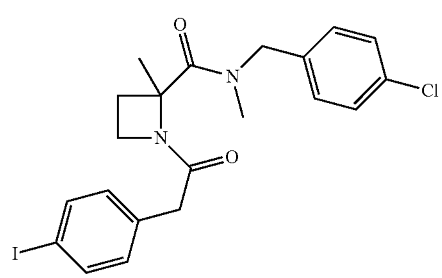 [SMILES: CN(Cc1ccc(Cl)cc1)C(=O)C1(C)CCN1C(=O)Cc1ccc(I)cc1] | Int 14 and (4-iodo-phenyl)-acetic acid | F | 496.8 | 497.3 (M + 1) |
| 104 | 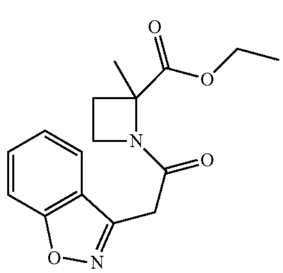 [SMILES: CCOC(=O)C1(C)CCN1C(=O)Cc1noc2ccccc12] | Int 13 and Benzo[d]isoxazol-3-yl-acetic acid | F | 302.3 | 303.5 (M + 1) |
| 105 | 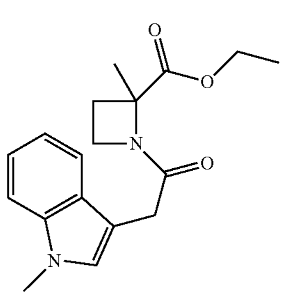 [SMILES: CCOC(=O)C1(C)CCN1C(=O)Cc1cn(C)c2ccccc12] | Int 13 and (1-Methyl-1H-indol-3-yl)-acetic acid | F | 314.4 | 314.9 (M + 1) |

TABLE Ia-continued

Synthesis of intermediates for the preparation of the compounds of the invention

| Int | Structure | SM | Mtd | MW | MS Mes'd |
|---|---|---|---|---|---|
| 106 | 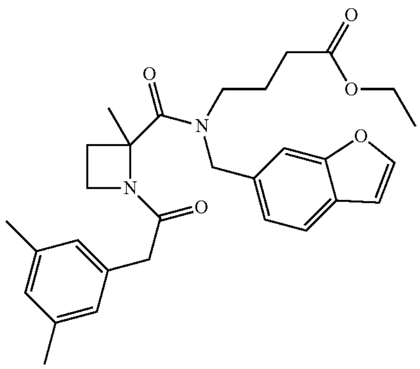 [SMILES: CCOC(=O)CCCN(Cc1ccc2ccoc2c1)C(=O)C1(C)CCN1C(=O)Cc1cc(C)cc(C)c1] | Int 19 and (3,5-Dimethyl-phenyl)-acetic acid | F | 504.6 | 505.5 (M + 1) |
| 107 | 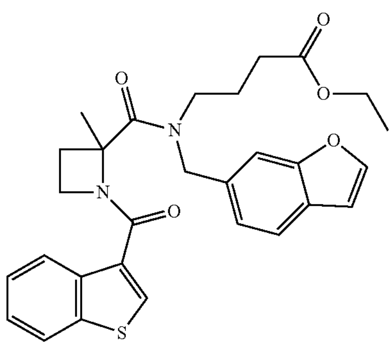 [SMILES: CCOC(=O)CCCN(Cc1ccc2ccoc2c1)C(=O)C1(C)CCN1C(=O)c1csc2ccccc12] | Int 19 and Benzo[b]thiophene-3-carboxylic acid | F | 518.6 | 519.4 (M + 1) |
| 108 | 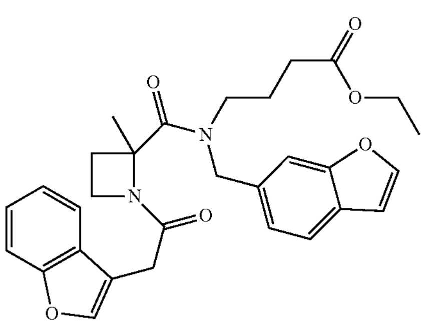 [SMILES: CCOC(=O)CCCN(Cc1ccc2ccoc2c1)C(=O)C1(C)CCN1C(=O)Cc1coc2ccccc12] | Int 19 and Benzofuran-3-acetic acid | F | 516.6 | 517.5 (M + 1) |
| 109 | 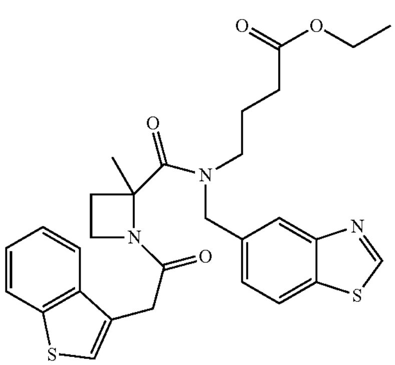 [SMILES: CCOC(=O)CCCN(Cc1ccc2scnc2c1)C(=O)C1(C)CCN1C(=O)Cc1csc2ccccc12] | Int 20 and Benzo[b]thiophene-3-acetic acid | F | 549.7 | 550.4 (M + 1) |

TABLE Ia-continued

Synthesis of intermediates for the preparation of the compounds of the invention

| Int | Structure | SM | Mtd | MW | MS Mes'd |
|---|---|---|---|---|---|
| 110 | 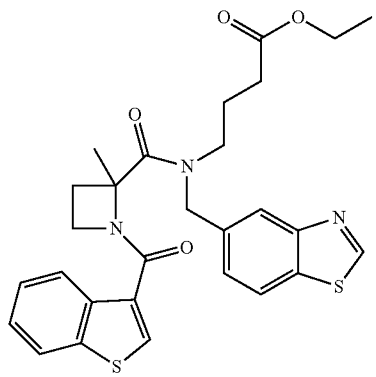 [SMILES: CCOC(=O)CCCN(Cc1ccc2scnc2c1)C(=O)C1(C)CCN1C(=O)c1csc2ccccc12] | Int 20 and Benzo[b]thiophene-3-carboxylic acid | F | 535.7 | 536.5 (M + 1) |
| 111 | 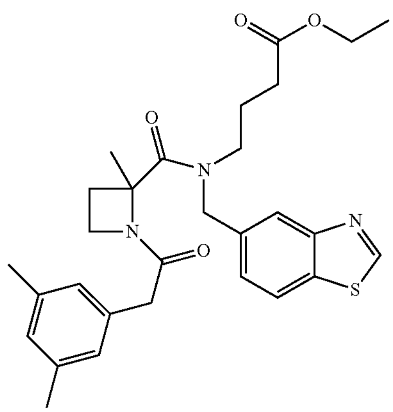 [SMILES: CCOC(=O)CCCN(Cc1ccc2scnc2c1)C(=O)C1(C)CCN1C(=O)Cc1cc(C)cc(C)c1] | Int 20 and (3,5-Dimethyl-phenyl)-acetic acid | F | 521.7 | 522.5 (M + 1) |
| 112 | Chiral | Int 21 and Benzo[b]thiophene-3-carboxylic acid | F | 499.0 | 499.3 (M + 1, $^{35}$Cl) |
| 113 | 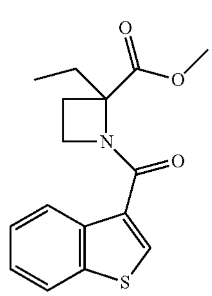 [SMILES: CCC1(C(=O)OC)CCN1C(=O)c1csc2ccccc12] | Int 22 and Benzo[b]thiophene-3-carboxylic acid | F | 303.4 | 304.3 (M + 1) |

TABLE Ia-continued

Synthesis of intermediates for the preparation of the compounds of the invention

| Int | Structure | SM | Mtd | MW | MS Mes'd |
|---|---|---|---|---|---|
| 114 | Chiral | Int 24 and Benzo[b]thiophene-3-carboxylic acid | F | 513.1 | 513.4 (M + 1, $^{35}$Cl) |
| 115 | Chiral | Int 25 and Benzo[b]thiophene-3-carboxylic acid | F | 513.1 | NMR |
| 116 | 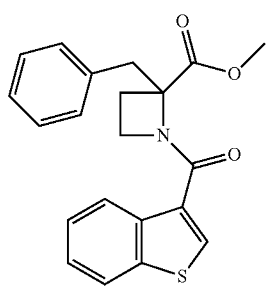 [SMILES: COC(=O)C1(Cc2ccccc2)CCN1C(=O)c1csc2ccccc12] | Int 26 and Benzo[b]thiophene-3-carboxylic acid | F | 365.4 | 366.2 (M + 1) |
| 117 | 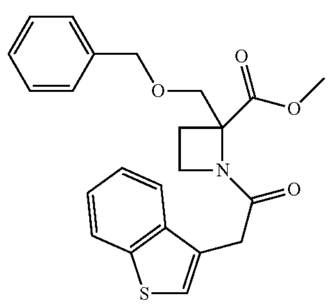 [SMILES: COC(=O)C1(COCc2ccccc2)CCN1C(=O)Cc1csc2ccccc12] | Int 27 and Benzo[b]thiophene-3-acetic acid | F | 409.5 | 410.4 (M + 1) |
| 118 | 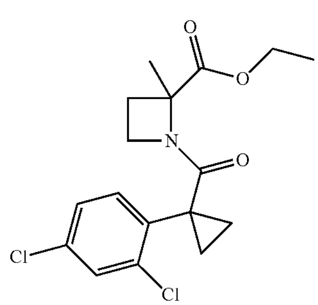 [SMILES: CCOC(=O)C1(C)CCN1C(=O)C1(c2ccc(Cl)cc2Cl)CC1] | Int 13 and 1-(2,4-Dichloro-phenyl)cyclopropane carboxlic acid | F | 356.2 | 356.0 (M + 1, $^{35}$Cl) |

TABLE Ia-continued
Synthesis of intermediates for the preparation of the compounds of the invention
| Int | Structure | SM | Mtd | MW | MS Mes'd |
|---|---|---|---|---|---|
| 119 | 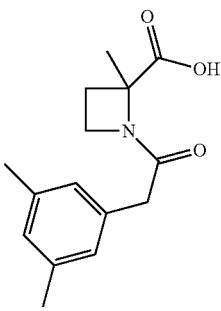 [SMILES: Cc1cc(C)cc(CC(=O)N2CCC2(C)C(=O)O)c1] | Int 94 | G | 261.3 | 262.0 (M + 1) |
| 120 | 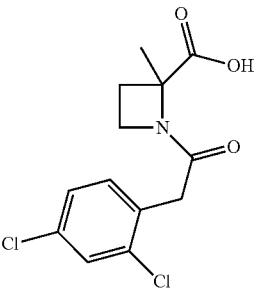 [SMILES: CC1(C(=O)O)CCN1C(=O)Cc1ccc(Cl)cc1Cl] | Int 95 | G | 302.2 | 302.0 (M + 1, $^{35}$Cl) |
| 121 | 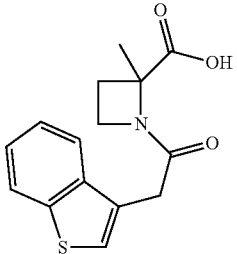 [SMILES: CC1(C(=O)O)CCN1C(=O)Cc1csc2ccccc12] | Int 96 | G | 289.3 | NMR |
| 122 | 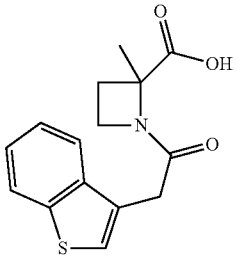 | Int 97 | G | 273.3 | 274.1 (M + 1) |
| 123 | Chiral 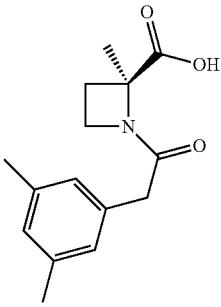 | Int 98 | G | 261.3 | 262.0 |

TABLE Ia-continued

Synthesis of intermediates for the preparation of the compounds of the invention

| Int | Structure | SM | Mtd | MW | MS Mes'd |
|---|---|---|---|---|---|
| 124 | Chiral | Int 99 | G | 261.3 | N/A |
| 125 | 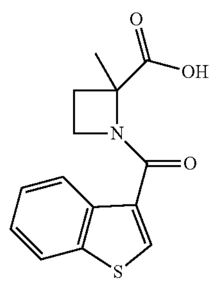 [SMILES: CC1(C(=O)O)CCN1C(=O)c1csc2ccccc12] | Int 100 | G | 275.3 | NMR |
| 126 | 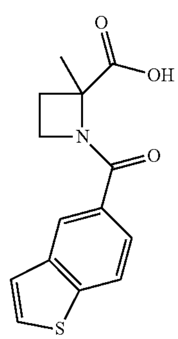 [SMILES: CC1(C(=O)O)CCN1C(=O)c1ccc2sccc2c1] | Int 101 | G | 275.3 | 276.2 (M + 1) |
| 127 | 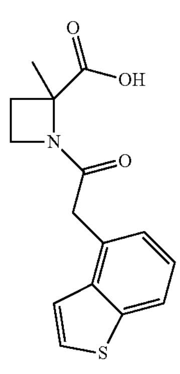 [SMILES: CC1(C(=O)O)CCN1C(=O)Cc1cccc2sccc12] | Int 102 | G | 289.4 | 290.2 (M + 1) |

TABLE Ia-continued
Synthesis of intermediates for the preparation of the compounds of the invention
| Int | Structure | SM | Mtd | MW | MS Mes'd |
|---|---|---|---|---|---|
| 128 | 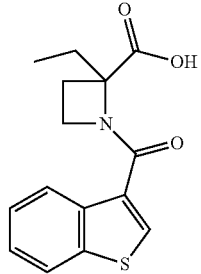 [SMILES: CCC1(C(=O)O)CCN1C(=O)c1csc2ccccc12] | Int 113 | G | 289.4 | 290.3 (M + 1) |
| 129 | 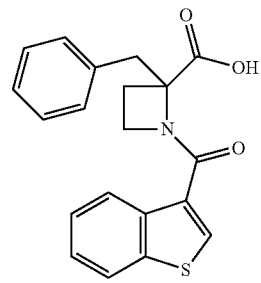 [SMILES: O=C(c1csc2ccccc12)N1CCC1(Cc1ccccc1)C(=O)O] | Int 116 | G | 351.4 | 352.2 (M + 1) |
| 130 | 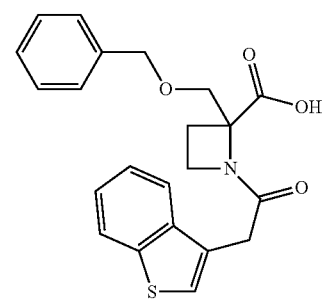 [SMILES: O=C(Cc1csc2ccccc12)N1CCC1(COCc1ccccc1)C(=O)O] | Int 117 | G | 395.5 | 396.2 (M + 1) |
| 131 | 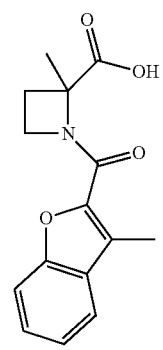 [SMILES: Cc1c(C(=O)N2CCC2(C)C(=O)O)oc2ccccc12] | Int 159 | G | 273.3 | 296.1 (M + 23) |
| 132 | 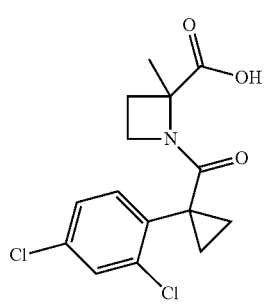 [SMILES: CC1(C(=O)O)CCN1C(=O)C1(c2ccc(Cl)cc2Cl)CC1] | Int 118 | G | 328.2 | 327.9 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 133 | 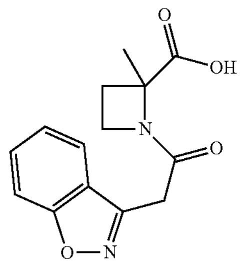 [SMILES: CC1(C(=O)O)CCN1C(=O)Cc1noc2ccccc12] | Int 104 | G | 274.3 | 275.1 (M + 1) |
| 134 | 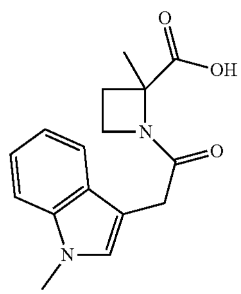 [SMILES: Cn1cc(CC(=O)N2CCC2(C)C(=O)O)c2ccccc21] | Int 105 | G | 286.3 | 287.1 (M + 1) |
| 135 | 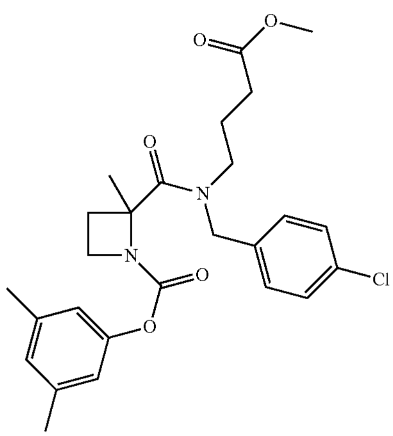 [SMILES: COC(=O)CCCN(Cc1ccc(Cl)cc1)C(=O)C1(C)CCN1C(=O)Oc1cc(C)cc(C)c1] | Int 3 and int 23 | H | 487.0 | 487.7 (M + 1, $^{35}$Cl) |
| 136 | 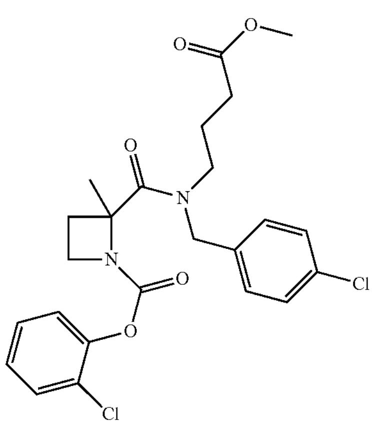 | Int 4 and int 23 | H | 507.4 | 507.3 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 137 | 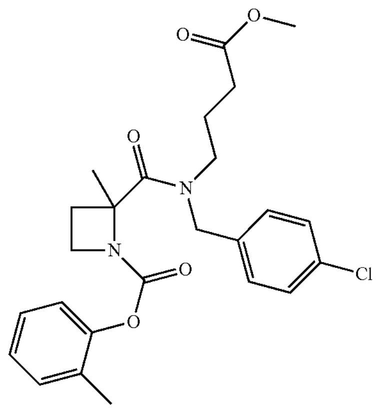 [SMILES: COC(=O)CCCN(Cc1ccc(Cl)cc1)C(=O)C1(C)CCN1C(=O)Oc1ccccc1C] | Int 5 and int 23 | H | 473.0 | 473.1 (M + 1, $^{35}$Cl) |
| 138 | 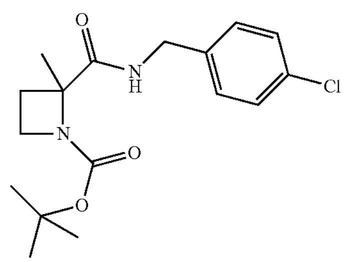 [SMILES: CC(C)(C)OC(=O)N1CCC1(C)C(=O)NCc1ccc(Cl)cc1] | Int 31 and 4-chloro-benzylamine | I1 | 338.8 | NMR |
| 139 | 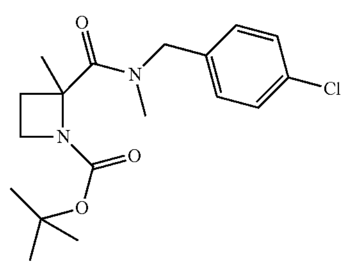 [SMILES: CN(Cc1ccc(Cl)cc1)C(=O)C1(C)CCN1C(=O)OC(C)(C)C] | Int 31 and (4-Chloro-benzyl)-methyl-amine | I1 | 352.8 | NMR |
| 140 | 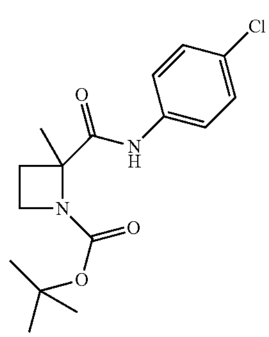 [SMILES: CC(C)(C)OC(=O)N1CCC1(C)C(=O)Nc1ccc(Cl)cc1] | Int 31 and 4-chloro-aniline | I1 | 324.8 | N/A |

TABLE Ia-continued
Synthesis of intermediates for the preparation of the compounds of the invention
| Int | Structure | SM | Mtd | MW | MS Mes'd |
|---|---|---|---|---|---|
| 141 | 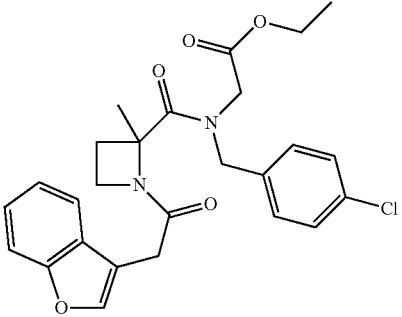 [SMILES: CCOC(=O)CN(Cc1ccc(Cl)cc1)C(=O)C1(C)CCN1C(=O)Cc1coc2ccccc12] | Int 56 and int 122 | I3 | 483.0 | 483.0 (M + 1, $^{35}$Cl) |
| 142 | Chiral 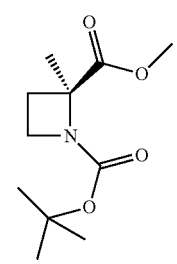 | Int 32 and MeOH | I3 | 229.3 | N/A |
| 143 | Chiral 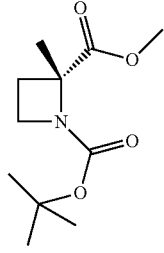 | Int 33 and MeOH | I3 | 229.3 | NMR |
| 144 | Chiral 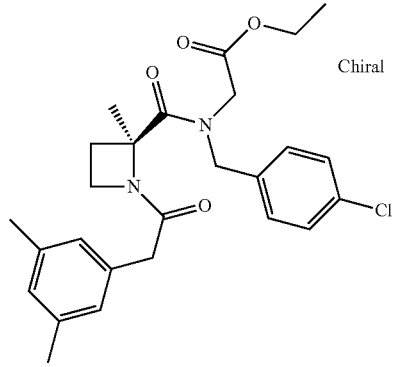 [SMILES: CCOC(=O)CN(Cc1ccc(Cl)cc1)C(=O)[C@]1(C)CCN1C(=O)Cc1cc(C)cc(C)c1] | Int 56 and 123 | I3 | 471.0 | 470.9 (M + 1, $^{35}$Cl) |

TABLE Ia-continued
Synthesis of intermediates for the preparation of the compounds of the invention
| Int | Structure | SM | Mtd | MW | MS Mes'd |
|---|---|---|---|---|---|
| 145 | 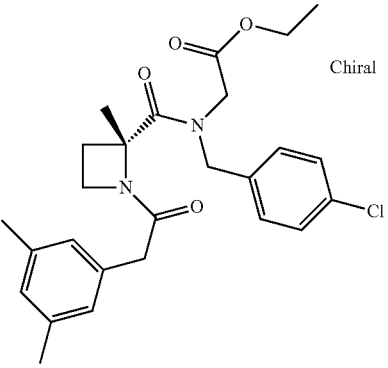 [SMILES: CCOC(=O)CN(Cc1ccc(Cl)cc1)C(=O)[C@@]1(C)CCN1C(=O)Cc1cc(C)cc(C)c1] | Int 56 and int 124 | I3 | 471.0 | 470.9 (M + 1, $^{35}$Cl) |
| 146 | 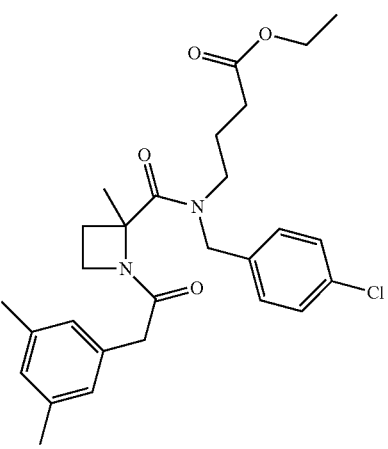 [SMILES: CCOC(=O)CCCN(Cc1ccc(Cl)cc1)C(=O)C1(C)CCN1C(=O)Cc1cc(C)cc(C)c1] | Int 40 and int 119 | I3 | 499.1 | 498.6 (M + 1, $^{35}$Cl) |
| 147 | 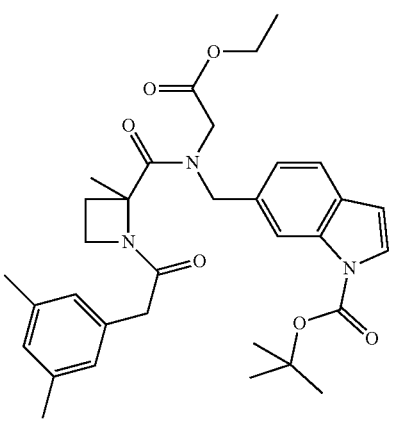 [SMILES: CCOC(=O)CN(Cc1ccc2ccn(C(=O)OC(C)(C)C)c2c1)C(=O)C1(C)CCN1C(=O)Cc1cc(C)cc(C)c1] | Int 69 and Int 119 | I3 | 575.5 | 576.2 (M + 1) |

TABLE Ia-continued

Synthesis of intermediates for the preparation of the compounds of the invention

| Int | Structure | SM | Mtd | MW | MS Mes'd |
|---|---|---|---|---|---|
| 148 | 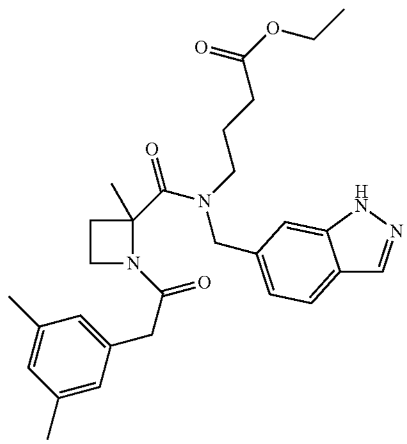 | Int 58 and Int 119 | I3 | 476.6 | 477.1 (M + 1) |
| 149 | 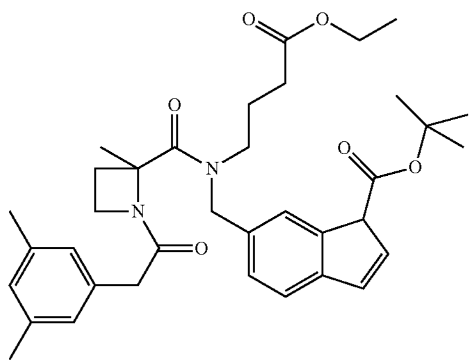 [SMILES: CCOC(=O)CCCN(Cc1ccc2c(c1)C(C(=O)OC(C)(C)C)C=C2)C(=O)C1(C)CCN1C(=O)Cc1cc(C)cc(C)c1] | Int 71 and int 119 | I3 | 603.8 | 604.2 (M + 1) |
| 150 | 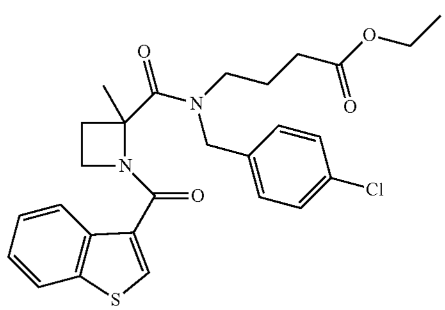 [SMILES: CCOC(=O)CCCN(Cc1ccc(Cl)cc1)C(=O)C1(C)CCN1C(=O)c1csc2ccccc12] | Int 40 and int 125 | I3 | 513.1 | 513.0 (M + 1, $^{35}$Cl) |
| 151 | 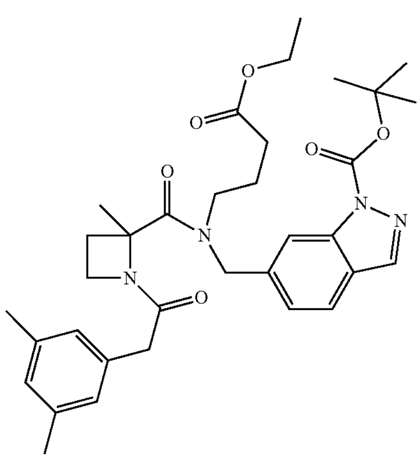 [SMILES: CCOC(=O)CCCN(Cc1ccc2cnn(C(=O)OC(C)(C)C)c2c1)C(=O)C1(C)CCN1C(=O)Cc1cc(C)cc(C)c1] | Int 72 and int 119 | I3 | 604.7 | 605.1 (M + 1) |

TABLE Ia-continued

Synthesis of intermediates for the preparation of the compounds of the invention

| Int | Structure | SM | Mtd | MW | MS Mes'd |
|---|---|---|---|---|---|
| 152 | 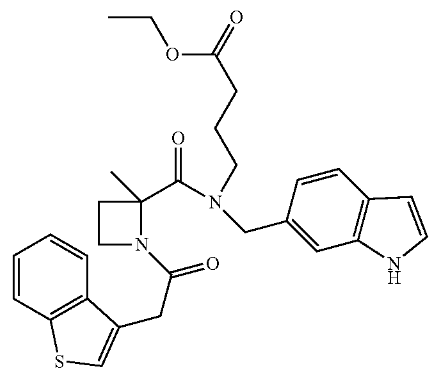 [SMILES: CCOC(=O)CCCN(Cc1ccc2cc[nH]c2c1)C(=O)C1(C)CCN1C(=O)Cc1csc2ccccc12] | Int 73 and int 121 | I3 | 531.7 | 532.4 (M + 1) |
| 153 | 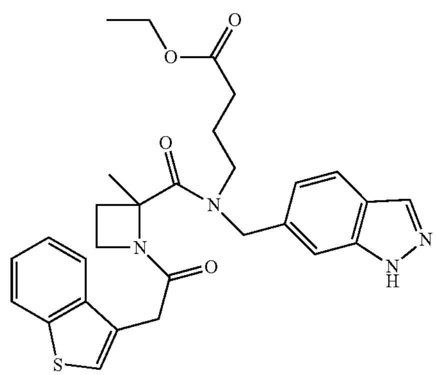 [SMILES: CCOC(=O)CCCN(Cc1ccc2cn[nH]c2c1)C(=O)C1(C)CCN1C(=O)Cc1csc2ccccc12] | Int 74 and int 121 | I3 | 532.7 | 533.4 (M + 1) |
| 154 | 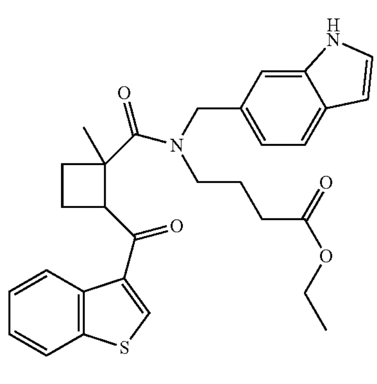 [SMILES: CCOC(=O)CCCN(Cc1ccc2cc[nH]c2c1)C(=O)C1(C)CCC1C(=O)c1csc2ccccc12] | Int 73 and int 125 | I3 | 517.6 | 518.4 (M + 1) |

TABLE Ia-continued

Synthesis of intermediates for the preparation of the compounds of the invention

| Int | Structure | SM | Mtd | MW | MS Mes'd |
|---|---|---|---|---|---|
| 155 | 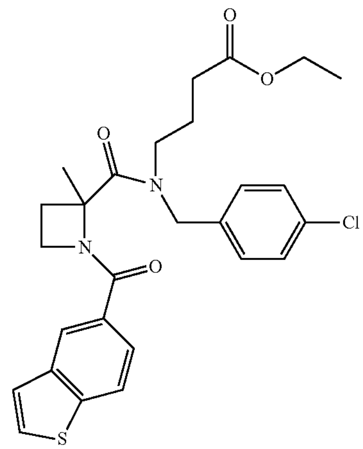 [SMILES: CCOC(=O)CCCN(Cc1ccc(Cl)cc1)C(=O)C1(C)CCN1C(=O)c1ccc2sccc2c1] | Int 40 and int 126 | I3 | 513.1 | 513.3 (M + 1, $^{35}$Cl) |
| 156 | 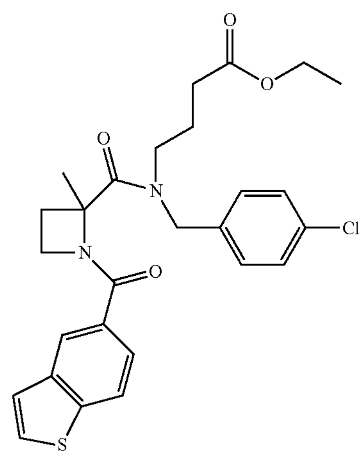 | Int 40 and int 127 | I3 | 527.1 | 527.3 (M + 1, $^{35}$Cl) |
| 157 | 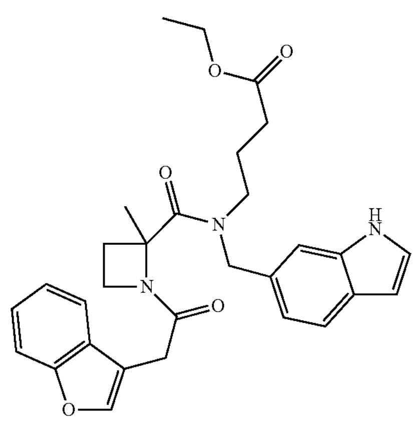 [SMILES: CCOC(=O)CCCN(Cc1ccc2cc[nH]c2c1)C(=O)C1(C)CCN1C(=O)Cc1coc2ccccc12] | Int 73 and int 122 | I3 | 515.6 | 516.5 (M + 1) |

TABLE Ia-continued

Synthesis of intermediates for the preparation of the compounds of the invention

| Int | Structure | SM | Mtd | MW | MS Mes'd |
|---|---|---|---|---|---|
| 158 | 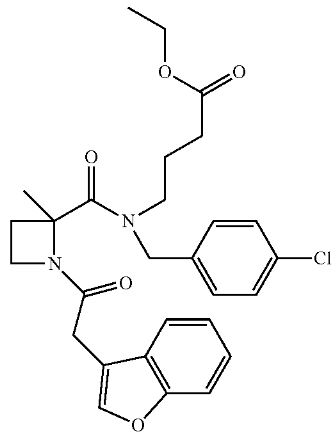 [SMILES: CCOC(=O)CCCN(Cc1ccc(Cl)cc1)C(=O)C1(C)CCN1C(=O)Cc1coc2ccccc12] | Int 40 and int 122 | F | 511.0 | 511.1 (M + 1, $^{35}$Cl) |
| 159 | 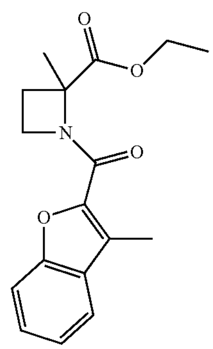 [SMILES: CCOC(=O)C1(C)CCN1C(=O)c1oc2ccccc2c1C] | Int 13 and 3-Methylbenzofuran-2-carboxylic acid | I3 | 301.3 | 324.1 (M + 23) |
| 160 | 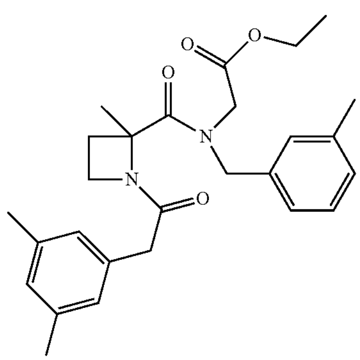 | Int 60 and int 119 | I3 | 450.6 | 451.1 (M + 1) |
| 161 | 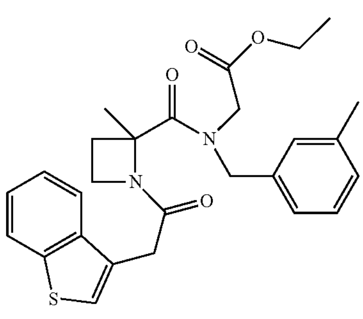 [SMILES: CCOC(=O)CN(Cc1cccc(C)c1)C(=O)C1(C)CCN1C(=O)Cc1csc2ccccc12] | Int 60 and int 121 | I3 | 478.6 | 479.3 (M + 1) |

TABLE Ia-continued

Synthesis of intermediates for the preparation of the compounds of the invention

| Int | Structure | SM | Mtd | MW | MS Mes'd |
|---|---|---|---|---|---|
| 162 | 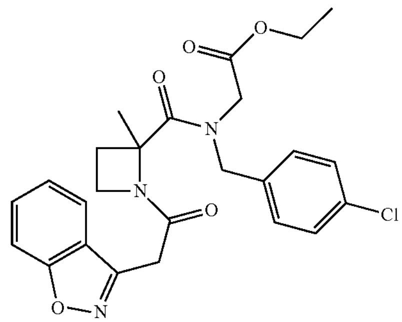 [SMILES: CCOC(=O)CN(Cc1ccc(Cl)cc1)C(=O)C1(C)CCN1C(=O)Cc1noc2ccccc12] | Int 133 and int 56 | I3 | 484.0 | 483.9 (M + 1, $^{35}$Cl) |
| 163 | 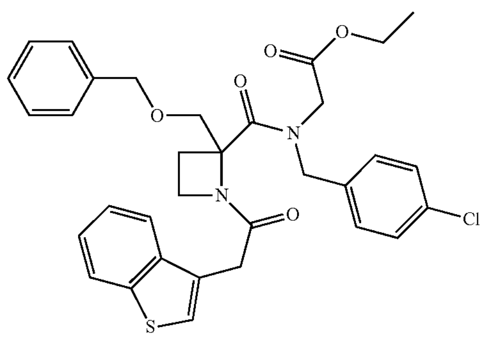 [SMILES: CCOC(=O)CN(Cc1ccc(Cl)cc1)C(=O)C1(COCc2ccccc2)CCN1C(=O)Cc1csc2ccccc12] | Int 56 and int 130 | I3 | 605.2 | 605.3 (M + 1, $^{35}$Cl) |
| 164 | 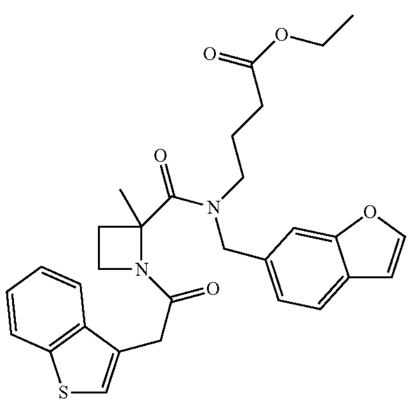 [SMILES: CCOC(=O)CCCN(Cc1ccc2ccoc2c1)C(=O)C1(C)CCN1C(=O)Cc1csc2ccccc12] | Int 82 and int 121 | I4 | 532.7 | 533.4 (M + 1) |
| 165 | 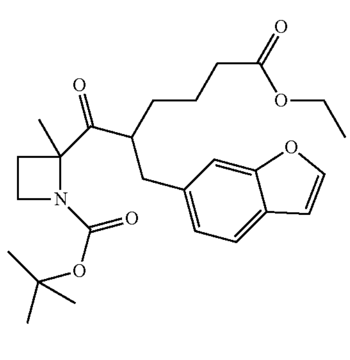 [SMILES: CCOC(=O)CCCC(Cc1ccc2ccoc2c1)C(=O)C1(C)CCN1C(=O)OC(C)(C)C] | Int 31 and int 82 | I4 | 458.6 | 459.4 (M + 1) |

TABLE Ia-continued

Synthesis of intermediates for the preparation of the compounds of the invention

| Int | Structure | SM | Mtd | MW | MS Mes'd |
|---|---|---|---|---|---|
| 166 | 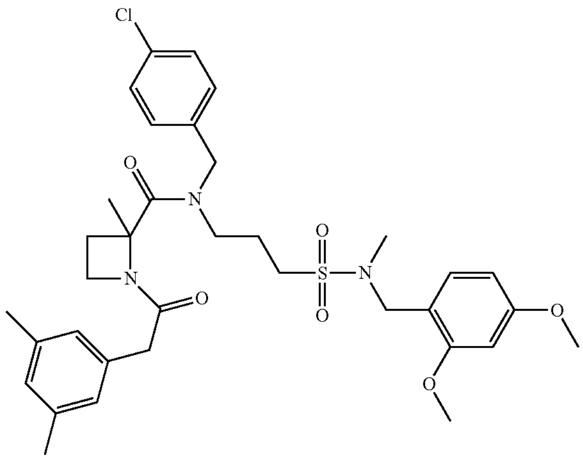 | Int 87 and int 119 | I4 | 670.3 | 670.6 (M + 1, $^{35}$Cl) |
| 167 | 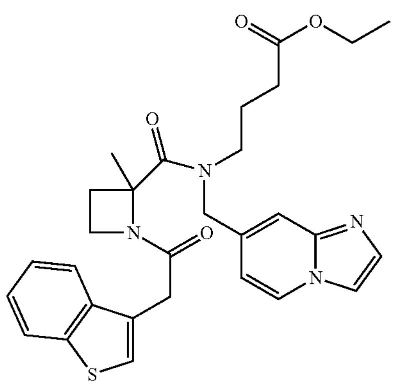 [SMILES: CCOC(=O)CCCN(Cc1ccn2ccnc2c1)C(=O)C1(C)CCN1C(=O)Cc1csc2ccccc12] | Int 77 and int 121 | I4 | 532.7 | 533.5 (M + 1) |
| 168 | 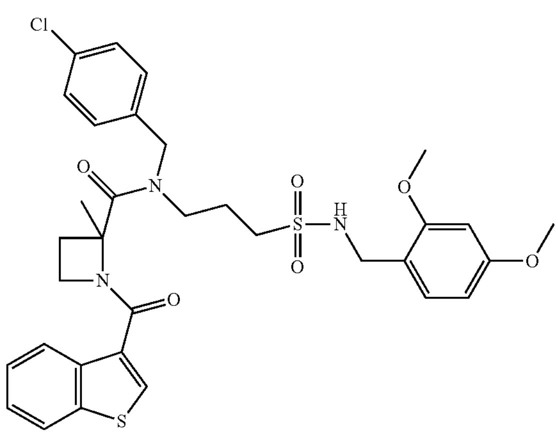 [SMILES: COc1ccc(CNS(=O)(=O)CCCN(Cc2ccc(Cl)cc2)C(=O)C2(C)CCN2C(=O)c2csc3ccccc23)c(OC)c1] | Int 86 and int 125 | I4 | 670.2 | 670.5 (M + 1, $^{35}$Cl) |

TABLE Ia-continued
Synthesis of intermediates for the preparation of the compounds of the invention
| Int | Structure | SM | Mtd | MW | MS Mes'd |
|---|---|---|---|---|---|
| 169 | 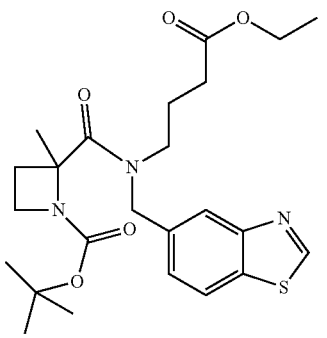 [SMILES: CCOC(=O)CCCN(Cc1ccc2scnc2c1)C(=O)C1(C)CCN1C(=O)OC(C)(C)C] | Int 31 and int 78 | I4 | 475.6 | 476.5 (M + 1) |
| 170 | 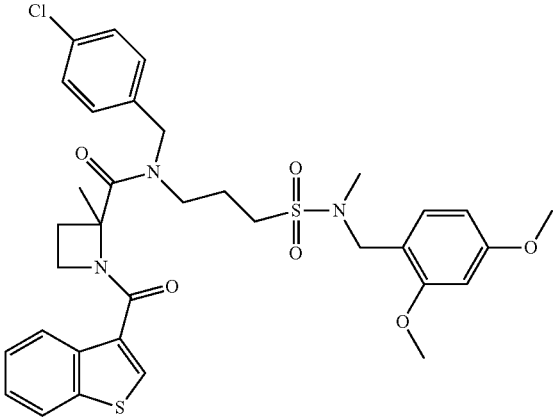 [SMILES: COc1ccc(CN(C)S(=O)(=O)CCCN(Cc2ccc(Cl)cc2)C(=O)C2(C)CCN2C(=O)c2csc3ccccc23)c(OC)c1] | Int 87 and in 125 | I4 | 684.3 | 684.5 (M + 1, $^{35}$Cl) |
| 171 | 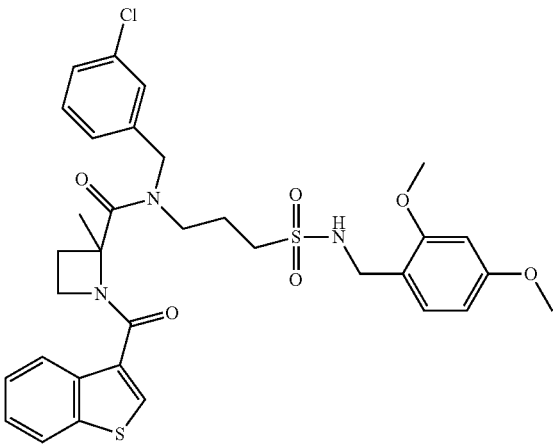 [SMILES: COc1ccc(CNS(=O)(=O)CCCN(Cc2cccc(Cl)c2)C(=O)C2(C)CCN2C(=O)c2csc3ccccc23)c(OC)c1] | Int 90 and int 125 | I4 | 670.2 | 670.5 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 172 | 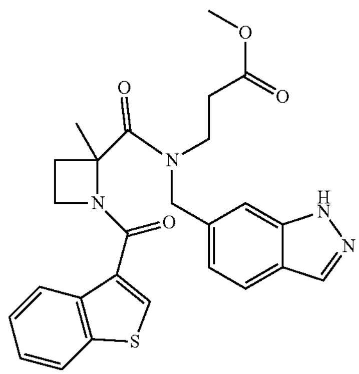 [SMILES: COC(=O)CCN(Cc1ccc2cn[nH]c2c1)C(=O)C1(C)CCN1C(=O)c1csc2ccccc12] | Int 79 and int 125 | I4 | 490.6 | 491.5 (M + 1) |
| 173 | 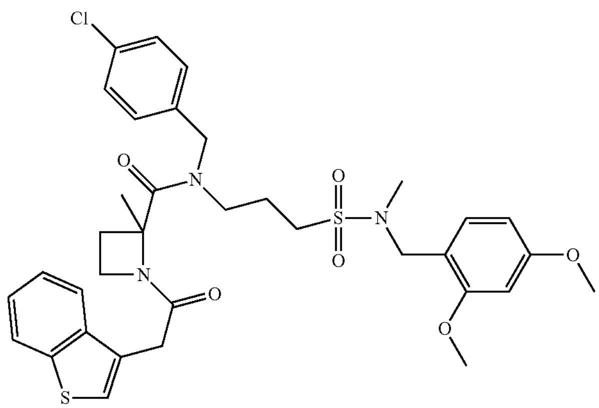 [SMILES: COc1ccc(CN(C)S(=O)(=O)CCCN(Cc2ccc(Cl)cc2)C(=O)C2(C)CCN2C(=O)Cc2csc3ccccc23)c(OC)c1] | Int 87 and int 121 | I4 | 698.3 | 698.6 (M + 1, $^{35}$Cl) |
| 174 | 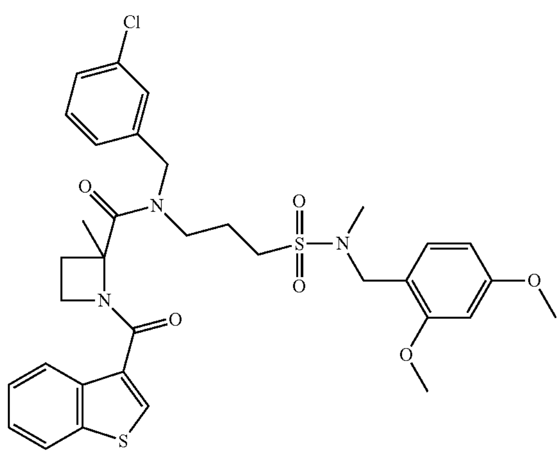 [SMILES: COc1ccc(CN(C)S(=O)(=O)CCCN(Cc2cccc(Cl)c2)C(=O)C2(C)CCN2C(=O)c2csc3ccccc23)c(OC)c1] | Int 91 and int 125 | I4 | 683.3 | 684.6 (M + 1, $^{35}$Cl) |
| 175 | Chiral | Int 33 and int 80 | I4 | 439.0 | 439.4 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 176 | 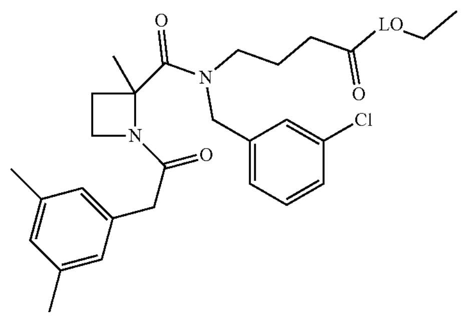 | Int 76 and int 119 | I4 | 499.0 | 499.5 (M + 1, $^{35}$Cl) |
| 177 | 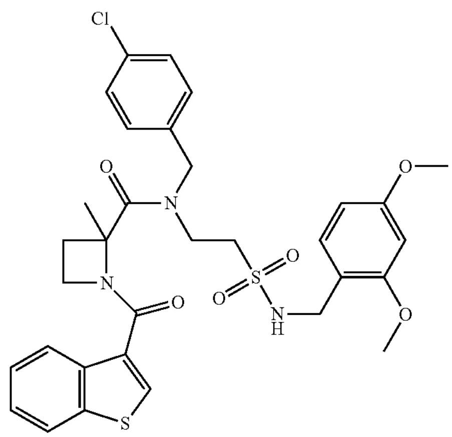 [SMILES: COc1ccc(CNS(=O)(=O)CCN(Cc2ccc(Cl)cc2)C(=O)C2(C)CCN2C(=O)c2csc3ccccc23)c(OC)c1] | Int 92 and int 125 | I4 | 656.3 | 656.5 (M + 1, $^{35}$Cl) |
| 178 | 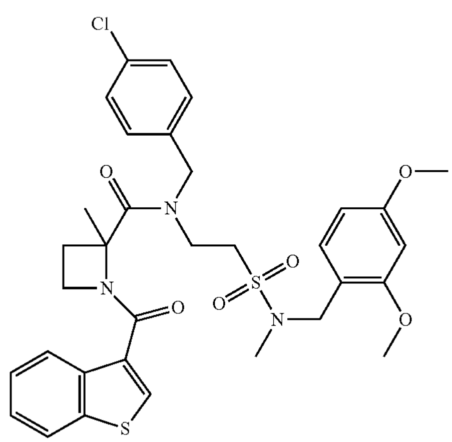 [SMILES: COc1ccc(CN(C)S(=O)(=O)CCN(Cc2ccc(Cl)cc2)C(=O)C2(C)CCN2C(=O)c2csc3ccccc23)c(OC)c1] | Int 93 and int 125 | I4 | 670.2 | 670.4 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 179 | 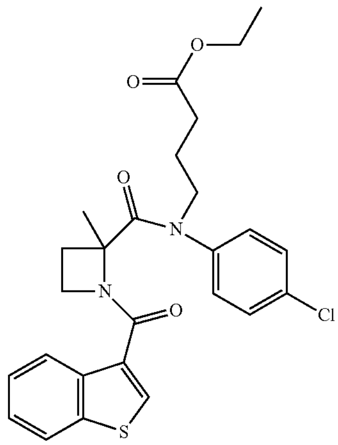 [SMILES: CCOC(=O)CCCN(C(=O)C1(C)CCN1C(=O)c1csc2ccccc12)c1ccc(Cl)cc1] | Int 43 and int 125 | I4 | 499.0 | 499.3 (M + 1, $^{35}$Cl) |
| 180 | 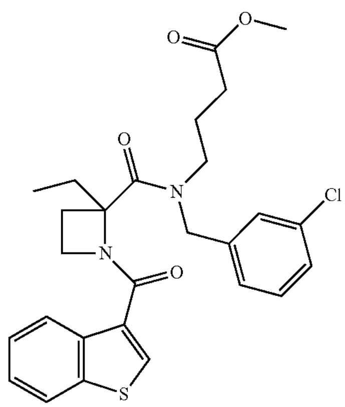 [SMILES: CCC1(C(=O)N(CCCC(=O)OC)Cc2cccc(Cl)c2)CCN1C(=O)c1csc2ccccc12] | Int 80 and int 128 | I4 | 513.1 | 513.4 (M + 1, $^{35}$Cl) |
| 181 | 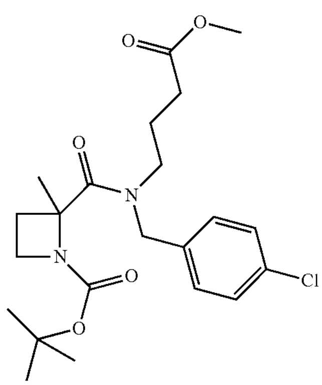 [SMILES: COC(=O)CCCN(Cc1ccc(Cl)cc1)C(=O)C1(C)CCN1C(=O)OC(C)(C)C] | Int 31 and int 137 | I4 | 439.0 | 439.4 (M + 1, $^{35}$Cl) |
| 182 | Chiral | Int 33 and int 44 | I4 | 453.0 | 453.5 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 183 | Chiral | Int 33 and int 45 | I4 | 453.0 | 453.5 (M + 1, $^{35}$Cl) |
| 184 | 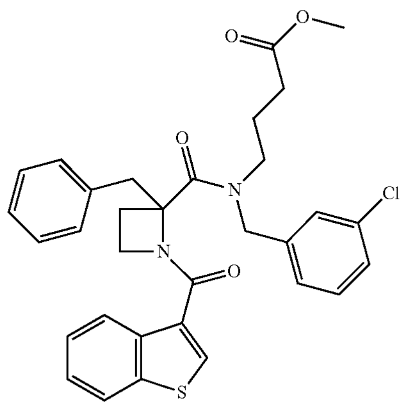 [SMILES: COC(=O)CCCN(Cc1cccc(Cl)c1)C(=O)C1(Cc2ccccc2)CCN1C(=O)c1csc2ccccc12] | Int 80 and int 129 | I4 | 575.1 | 575.4 (M + 1, $^{35}$Cl) |
| 185 | 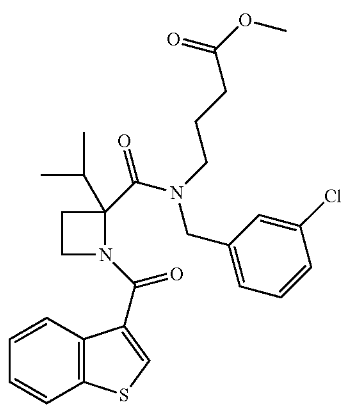 [SMILES: COC(=O)CCCN(Cc1cccc(Cl)c1)C(=O)C1(C(C)C)CCN1C(=O)c1csc2ccccc12] | Int 80 and int 193 | I4 | 527.1 | 527.4 (M + 1, $^{35}$Cl) |
| 186 | 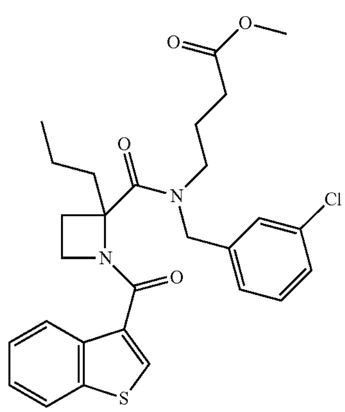 [SMILES: CCCC1(C(=O)N(CCCC(=O)OC)Cc2cccc(Cl)c2)CCN1C(=O)c1csc2ccccc12] | Int 80 and int 194 | I4 | 527.1 | 527.4 (M + 1, $^{35}$Cl) |

TABLE Ia-continued
Synthesis of intermediates for the preparation of the compounds of the invention
| Int | Structure | SM | Mtd | MW | MS Mes'd |
|---|---|---|---|---|---|
| 187 | 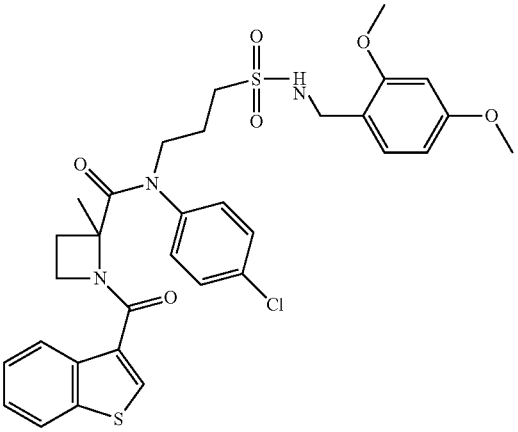 [SMILES: COc1ccc(CNS(=O)(=O)CCCN(C(=O)C2(C)CCN2C(=O)c2csc3ccccc23)c2ccc(Cl)cc2)c(OC)c1] | Int 195 and int 125 | I4 | 656.2 | 656.1 (M + 1, $^{35}$Cl) |
| 188 | 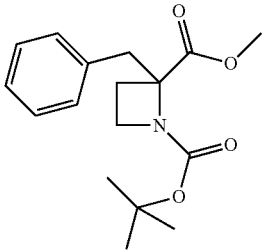 [SMILES: COC(=O)C1(Cc2ccccc2)CCN1C(=O)OC(C)(C)C] | Benzyl bromide | S | 305.4 | 328.3 (M + 23) |
| 189 | 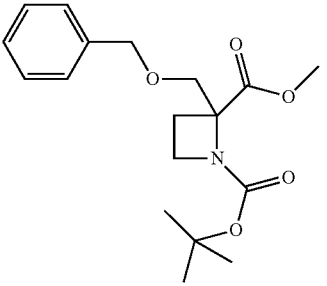 [SMILES: COC(=O)C1(COCc2ccccc2)CCN1C(=O)OC(C)(C)C] | Chloromethoxymethyl-benzene | S | 335.4 | 358.2 (M + 23) |
| 190 | 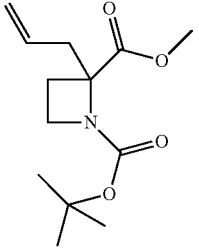 [SMILES: C=CCC1(C(=O)OC)CCN1C(=O)OC(C)(C)C] | Allyl bromide | S | 255.3 | 278.3 (M + 23) |

TABLE Ia-continued

Synthesis of intermediates for the preparation of the compounds of the invention

| Int | Structure | SM | Mtd | MW | MS Mes'd |
|---|---|---|---|---|---|
| 191 | 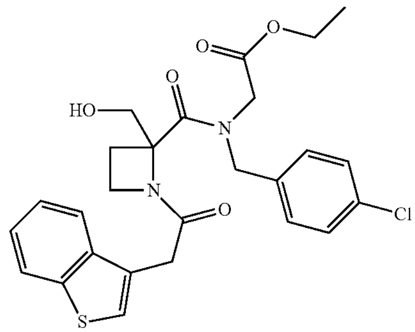 [SMILES: CCOC(=O)CN(Cc1ccc(Cl)cc1)C(=O)C1(CO)CCN1C(=O)Cc1csc2ccccc12] | Int 163 | T | 515.0 | 514.8 (M + 1, $^{35}$Cl) |
| 192 | 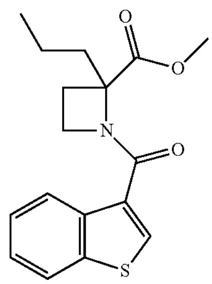 [SMILES: CCCC1(C(=O)OC)CCN1C(=O)c1csc2ccccc12] | Int 197 | V | 317.4 | 318.0 (M + 1) |
| 193 | 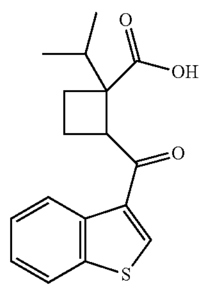 [SMILES: CC(C)C1(C(=O)O)CCC1C(=O)c1csc2ccccc12] | Int 196 | G | 303.4 | 304.3 (M + 1) |
| 194 | 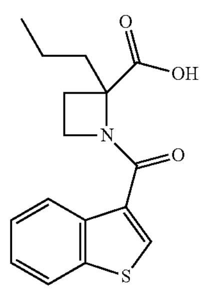 [SMILES: CCCC1(C(=O)O)CCN1C(=O)c1csc2ccccc12] | Int 192 | G | 303.4 | 304.0 (M + 1) |
| 195 | 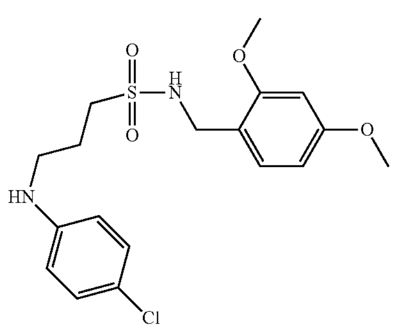 [SMILES: COc1ccc(CNS(=O)(=O)CCCNc2ccc(Cl)cc2)c(OC)c1] | 3-Chloro-propanesulfonyl chloride, 2,4-Dimethoxy-benzylamine and 4-chloroaniline | E10 | 398.9 | 399.2 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 196 | 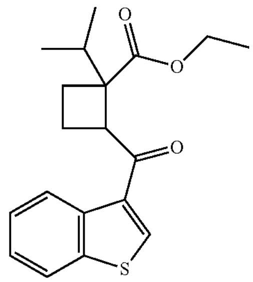 [SMILES: CCOC(=O)C1(C(C)C)CCC1C(=O)c1csc2ccccc12] | Int 198 and Benzo[b]thiophene-3-carboxylic acid | F | 331.4 | 332.3 (M + 1) |
| 197 | 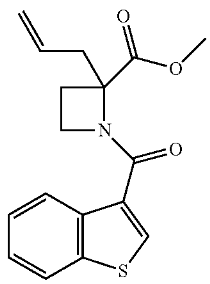 [SMILES: C=CCC1(C(=O)OC)CCN1C(=O)c1csc2ccccc12] | Int 199 and Benzo[b]thiophene-3-carboxlyic acid | F | 315.4 | 316.2 (M + 1) |
| 198 | 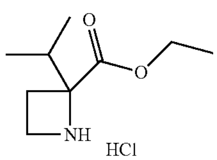 | Int 200 | B1 | 171.2 | N/A |
| 199 | 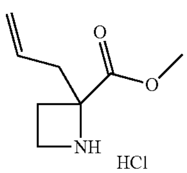 | Int 190 | B1 | 155.2 | N/A |
| 200 | 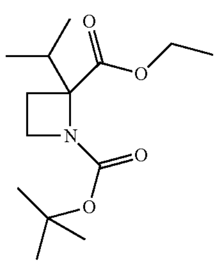 [SMILES: CCOC(=O)C1(C(C)C)CCN1C(=O)OC(C)(C)C] | Benzylamine, 2-Bromo-3-methyl-butyric acid ethyl ester, chloroacetaldehyde and Boc$_2$O | A | 271.6 | N/A |
| 201 | 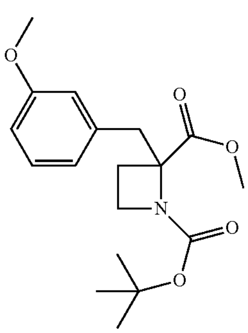 [SMILES: COC(=O)C1(Cc2cccc(OC)c2)CCN1C(=O)OC(C)(C)C] | 3-Methoxy benzyl bromide | S | 335.4 | NMR |

TABLE Ia-continued

Synthesis of intermediates for the preparation of the compounds of the invention

| Int | Structure | SM | Mtd | MW | MS Mes'd |
|---|---|---|---|---|---|
| 202 | 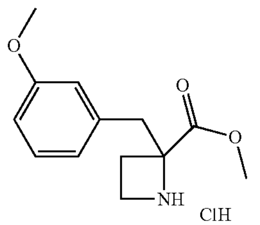 | Int 201 | B1 | 235.3 | N/A |
| 203 | 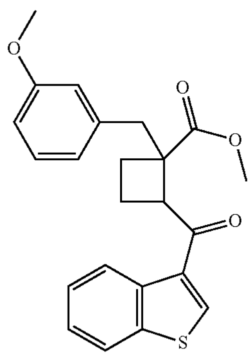 [SMILES: COC(=O)C1(Cc2cccc(OC)c2)CCC1C(=O)c1csc2ccccc12] | Int 202 and 3-thiophene carboxylic acid | I1 | 396.5 | 396.1 (M + 1) |
| 204 | 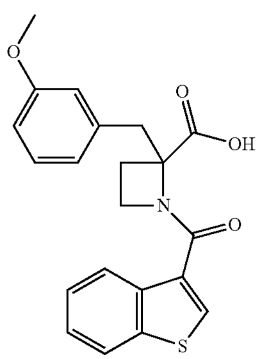 [SMILES: COc1cccc(CC2(C(=O)O)CCN2C(=O)c2csc3ccccc23)c1] | Int 203 | J | 381.5 | 382.1 (M + 1) |
| 205 | 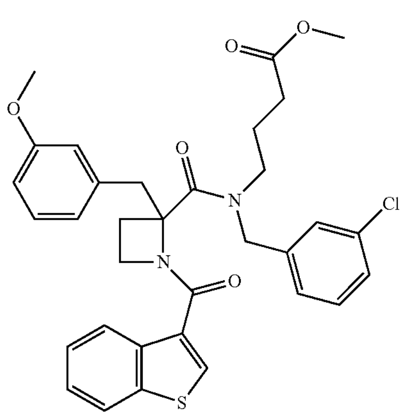 [SMILES: COC(=O)CCCN(Cc1cccc(Cl)c1)C(=O)C1(Cc2cccc(OC)c2)CCN1C(=O)c1csc2ccccc12] | Int 204 and Int 80 | I4 | 605.2 | N/A |

TABLE Ia-continued
Synthesis of intermediates for the preparation of the compounds of the invention
| Int | Structure | SM | Mtd | MW | MS Mes'd |
|---|---|---|---|---|---|
| 206 | 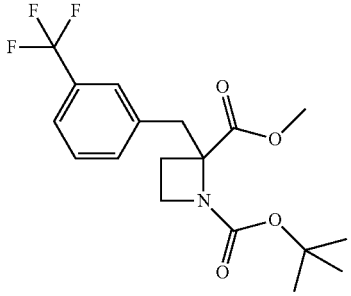 [SMILES: COC(=O)C1(Cc2cccc(C(F)(F)F)c2)CCN1C(=O)OC(C)(C)C] | 3-Trifluoromethyl benzyl bromide | S | 373.4 | NMR |
| 207 | 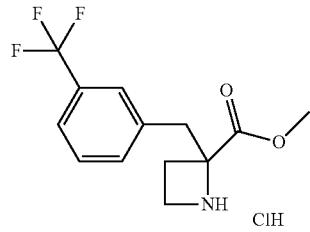 | Int 206 | B1 | 273.3 | N/A |
| 208 | 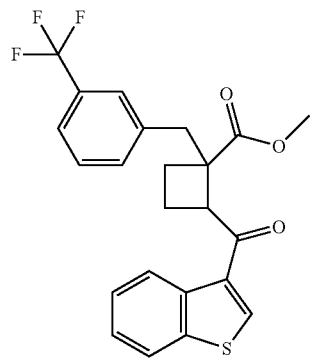 [SMILES: COC(=O)C1(Cc2cccc(C(F)(F)F)c2)CCC1C(=O)c1csc2ccccc12] | Int 207 and 3-thiophene carboxylic acid | I1 | 433.5 | 434.1 (M + 1) |
| 209 | 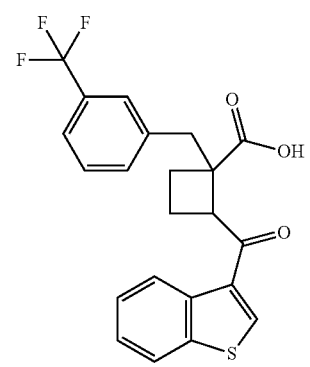 [SMILES: O=C(c1csc2ccccc12)C1CCC1(Cc1cccc(C(F)(F)F)c1)C(=O)O] | Int 208 | J | 419.4 | 420.1 (M + 1) |

TABLE Ia-continued

Synthesis of intermediates for the preparation of the compounds of the invention

| Int | Structure | SM | Mtd | MW | MS Mes'd |
|---|---|---|---|---|---|
| 210 | 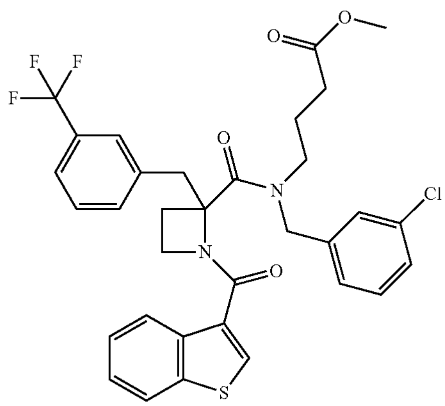 [SMILES: COC(=O)CCCN(Cc1cccc(Cl)c1)C(=O)C1(Cc2cccc(C(F)(F)F)c2)CCN1C(=O)c1csc2ccccc12] | Int 209 and Int 80 | I4 | 643.1 | N/A |
| 211 | 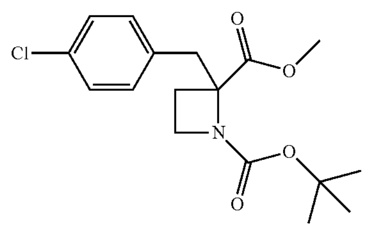 [SMILES: COC(=O)C1(Cc2ccc(Cl)cc2)CCN1C(=O)OC(C)(C)C] | 4-Chlorobenzyl bromide | S | 339.8 | NMR |
| 212 | 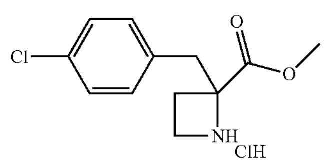 | Int 211 | B1 | 239.7 | N/A |
| 213 | 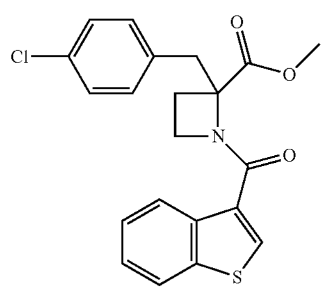 [SMILES: COC(=O)C1(Cc2ccc(Cl)cc2)CCN1C(=O)c1csc2ccccc12] | Int 212 and 3-thiophene carboxylic acid | F | 399.9 | 400.0 (M + 1, $^{35}$Cl) |
| 214 | 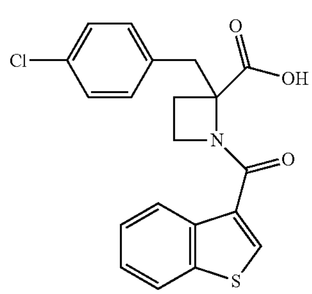 [SMILES: O=C(c1csc2ccccc12)N1CCC1(Cc1ccc(Cl)cc1)C(=O)O] | Int 213 | G | 385.9 | 386.0 (M + 1, $^{35}$Cl) |

TABLE Ia-continued
Synthesis of intermediates for the preparation of the compounds of the invention
| Int | Structure | SM | Mtd | MW | MS Mes'd |
|---|---|---|---|---|---|
| 215 | 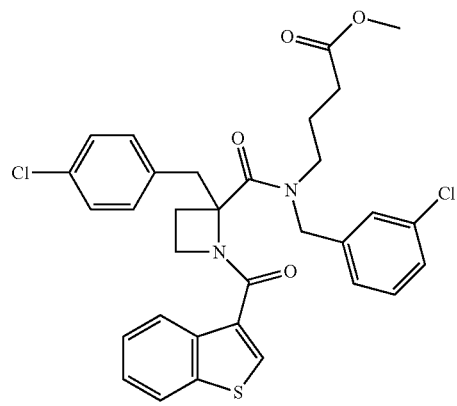 | Int 214 and Int 80 | I4 | 609.6 | 609.0 (M + 1, $^{35}$Cl) |
| 216 | 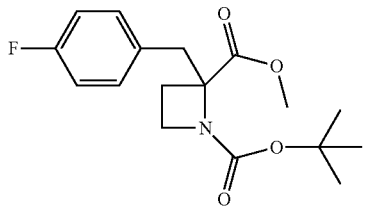 [SMILES: COC(=O)C1(Cc2ccc(F)cc2)CCN1C(=O)OC(C)(C)C] | 4-Fluorobenzyl bromide | S | 323.4 | NMR |
| 217 | 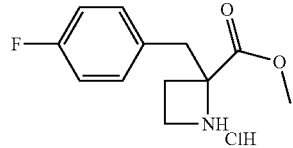 | Int 216 | B1 | 223.3 | N/A |
| 218 | 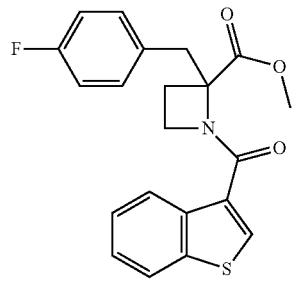 [SMILES: COC(=O)C1(Cc2ccc(F)cc2)CCN1C(=O)c1csc2ccccc12] | Int 217 and 3-thiophene carboxylic acid | F | 383.4 | 384.0 (M + 1) |
| 219 | 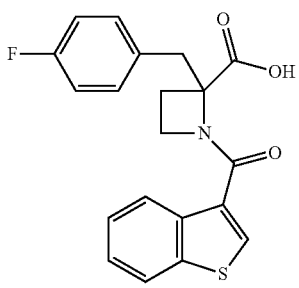 [SMILES: O=C(c1csc2ccccc12)N1CCC1(Cc1ccc(F)cc1)C(=O)O] | Int 218 | G | 369.4 | 370.0 (M + 1) |

TABLE Ia-continued

Synthesis of intermediates for the preparation of the compounds of the invention

| Int | Structure | SM | Mtd | MW | MS Mes'd |
|---|---|---|---|---|---|
| 220 | 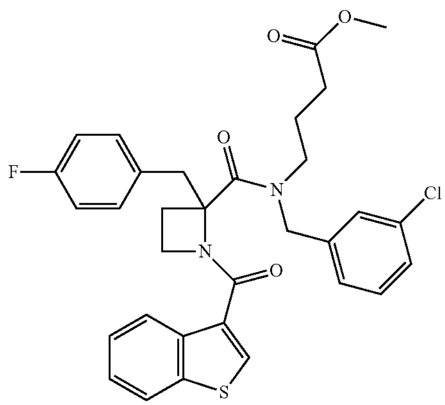 [SMILES: COC(=O)CCCN(Cc1cccc(Cl)c1)C(=O)C1(Cc2ccc(F)cc2)CCN1C(=O)c1csc2ccccc12] | Int 219 and Int 80 | I4 | 593.1 | N/A |
| 221 | 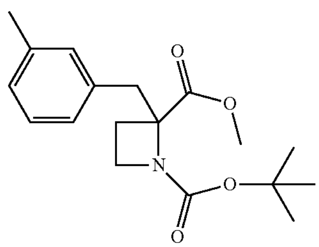 [SMILES: COC(=O)C1(Cc2cccc(C)c2)CCN1C(=O)OC(C)(C)C] | 3-Methylbenzyl bromide | S | 319.4 | NMR |
| 222 | 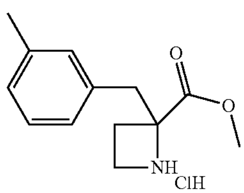 | Int 220 | B1 | 219.3 | N/A |
| 223 | 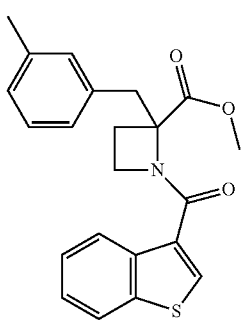 [SMILES: COC(=O)C1(Cc2cccc(C)c2)CCN1C(=O)c1csc2ccccc12] | Int 221 and 3-thiophene carboxylic acid | F | 379.5 | 380.5 (M + 1) |
| 224 | 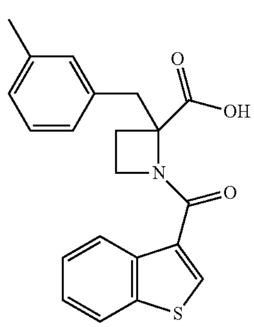 [SMILES: Cc1cccc(CC2(C(=O)O)CCN2C(=O)c2csc3ccccc23)c1] | Int 223 | G | 365.5 | 366.1 (M + 1) |

TABLE Ia-continued

Synthesis of intermediates for the preparation of the compounds of the invention

| Int | Structure | SM | Mtd | MW | MS Mes'd |
|---|---|---|---|---|---|
| 225 | 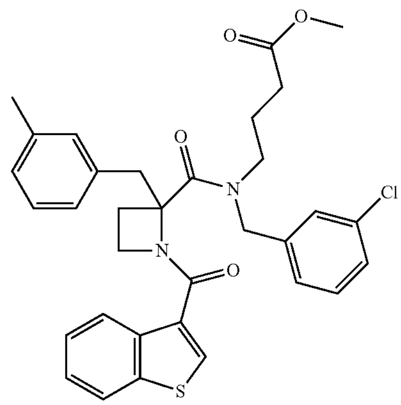 [SMILES: COC(=O)CCCN(Cc1cccc(Cl)c1)C(=O)C1(Cc2cccc(C)c2)CCN1C(=O)c1csc2ccccc12] | Int 224 and Int 80 | I4 | 589.2 | N/A |
| 226 | 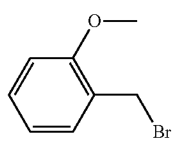 | 2-Methoxybenzyl alcohol | Patent Schering corp. U.S. Pat. No. 5,892,039 (1999) | 201.1 | NMR |
| 227 | 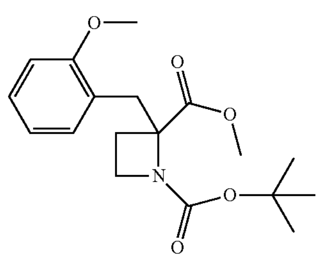 [SMILES: COC(=O)C1(Cc2ccccc2OC)CCN1C(=O)OC(C)(C)C] | Int 226 | S | 335.4 | NMR |
| 228 | 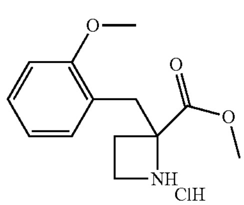 | Int 227 | B1 | 239.7 | N/A |
| 229 | 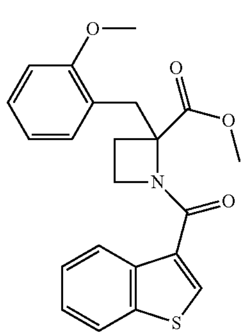 [SMILES: COC(=O)C1(Cc2ccccc2OC)CCN1C(=O)c1csc2ccccc12] | Int 228 and 3-thiophene carboxylic acid | F | 395.5 | 396.1 (M + 1) |

TABLE Ia-continued

Synthesis of intermediates for the preparation of the compounds of the invention

| Int | Structure | SM | Mtd | MW | MS Mes'd |
|---|---|---|---|---|---|
| 230 | 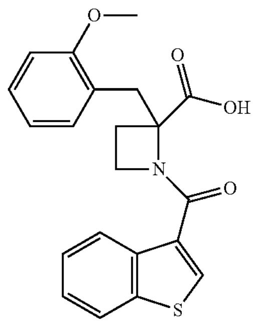 [SMILES: COc1ccccc1CC1(C(=O)O)CCN1C(=O)c1csc2ccccc12] | Int 229 | G | 381.5 | 382.1 (M + 1) |
| 231 | 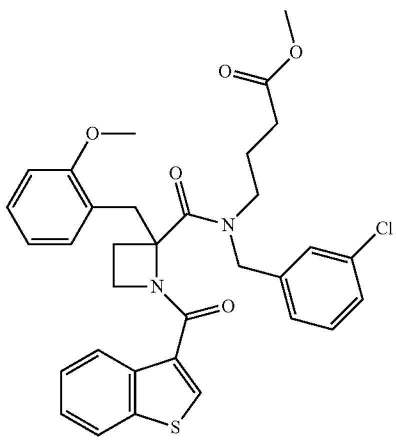 [SMILES: COC(=O)CCCN(Cc1cccc(Cl)c1)C(=O)C1(Cc2ccccc2OC)CCN1C(=O)c1csc2ccccc12] | Int 230 | I4 | 605.2 | 605.1 (M + 1, $^{35}$Cl) |
| 232 | 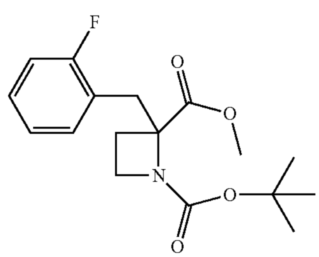 [SMILES: COC(=O)C1(Cc2ccccc2F)CCN1C(=O)OC(C)(C)C] | 2-Fluorobenzyl bromide | S | 323.4 | NMR |
| 233 | 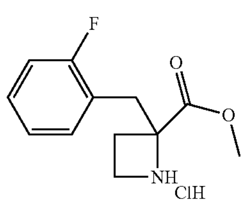 | Int 232 | B1 | 223.3 | N/A |
| 234 | 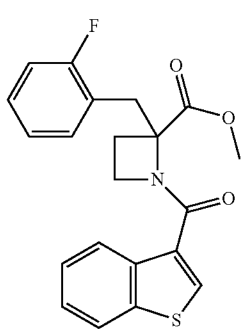 [SMILES: COC(=O)C1(Cc2ccccc2F)CCN1C(=O)c1csc2ccccc12] | Int 233 and 3-thiophene carboxylic acid | F | 383.4 | 384.1 (M + 1) |

TABLE Ia-continued

Synthesis of intermediates for the preparation of the compounds of the invention

| Int | Structure | SM | Mtd | MW | MS Mes'd |
|-----|-----------|-----|-----|-----|----------|
| 235 | 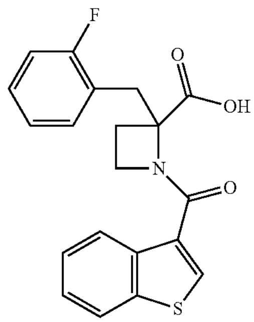 [SMILES: O=C(c1csc2ccccc12)N1CCC1(Cc1ccccc1F)C(=O)O] | Int 234 | G | 369.4 | N/A |
| 236 | 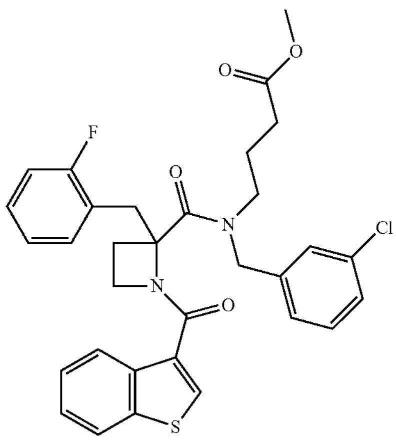 [SMILES: COC(=O)CCCN(Cc1cccc(Cl)c1)C(=O)C1(Cc2ccccc2F)CCN1C(=O)c1csc2ccccc12] | Int 235 | I4 | 593.1 | N/A |
| 237 | 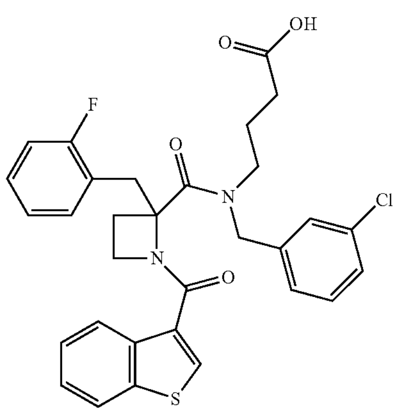 [SMILES: O=C(O)CCCN(Cc1cccc(Cl)c1)C(=O)C1(Cc2ccccc2F)CCN1C(=O)c1csc2ccccc12] | Int 236 | J | 579.1 | 579.1 (M + 1, $^{35}$Cl) |
| 238 | 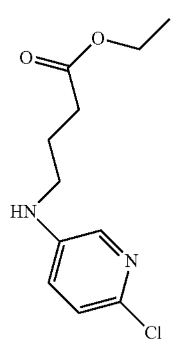 [SMILES: CCOC(=O)CCCNc1ccc(Cl)nc1] | 5-amino-2-chloropyridine and ethyl 4-bromobutyrate | E11 | 242.7 | N/A |

TABLE Ia-continued

Synthesis of intermediates for the preparation of the compounds of the invention

| Int | Structure | SM | Mtd | MW | MS Mes'd |
|---|---|---|---|---|---|
| 239 | 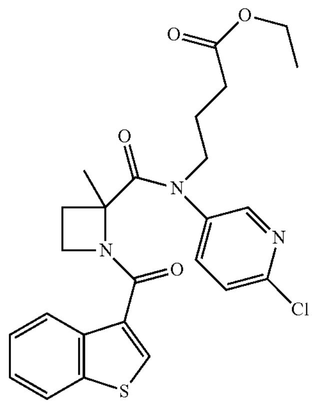 [SMILES: CCOC(=O)CCCN(C(=O)C1(C)CCN1C(=O)c1csc2ccccc12)c1ccc(Cl)nc1] | Int 238 and Int 125 | I4 | 500.0 | 500.1 (M + 1, $^{35}$Cl) |
| 240 | 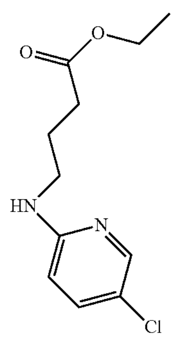 [SMILES: CCOC(=O)CCCNc1ccc(Cl)cn1] | 2-amino-5-chloropyridine and ethyl 4-bromobutyrate | E11 | 242.7 | N/A |
| 241 | 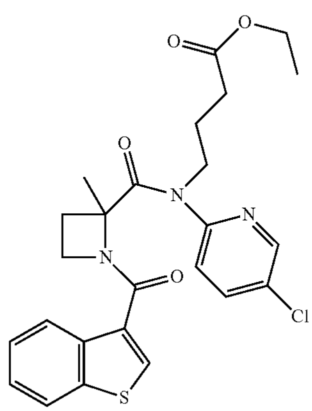 [SMILES: CCOC(=O)CCCN(C(=O)C1(C)CCN1C(=O)c1csc2ccccc12)c1ccc(Cl)cn1] | Int 240 and Int 125 | I4 | 500.0 | 500.1 (M + 1, $^{35}$Cl) |
| 242 | 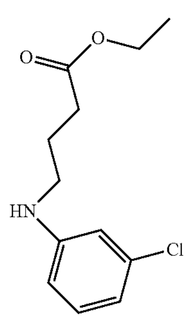 [SMILES: CCOC(=O)CCCNc1cccc(Cl)c1] | 3-chloroaniline and ethyl 4-bromobutyrate | E2 | 241.7 | 242.0 (M + 1, $^{35}$Cl) |

TABLE Ia-continued
Synthesis of intermediates for the preparation of the compounds of the invention
| Int | Structure | SM | Mtd | MW | MS Mes'd |
|---|---|---|---|---|---|
| 243 | 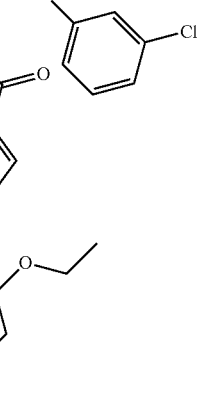 | Int 242 and Int 125 | I4 | 499.0 | 499.1 (M + 1, $^{35}$Cl) |
| 244 | 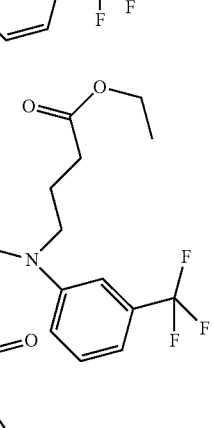 | 3-trifluoromethylaniline and ethyl 4-bromobutyrate | E11 | 275.3 | N/A |
| 245 | 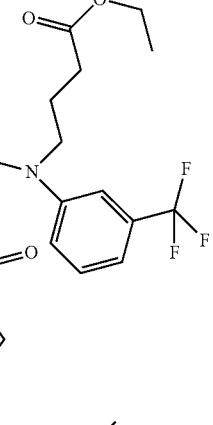 | Int 244 and Int 125 | I4 | 532.6 | N/A |
| 246 | 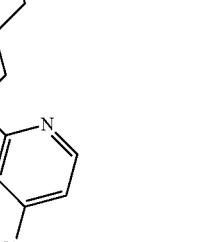 | 4-chloro-2-aminopyridine and ethyl 4-bromobutyrate | E11 (µW heating) | 242.7 | NMR |

TABLE Ia-continued

Synthesis of intermediates for the preparation of the compounds of the invention

| Int | Structure | SM | Mtd | MW | MS Mes'd |
|---|---|---|---|---|---|
| 247 | 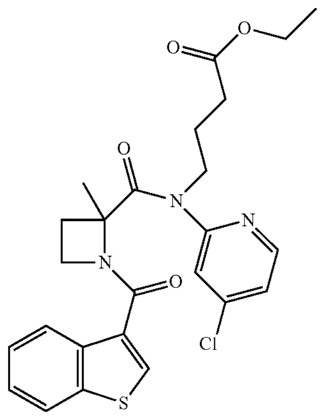 [SMILES: CCOC(=O)CCCN(C(=O)C1(C)CCN1C(=O)c1csc2ccccc12)c1cc(Cl)ccn1] | Int 246 and Int 125 | I4 | 500.0 | 500.4 (M + 1, $^{35}$Cl) |
| 248 | 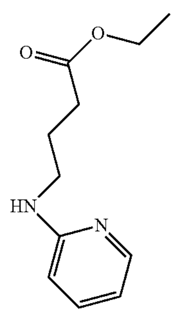 | 4-aminopyridine and ethyl 4-bromobutyrate | E11 | 208.3 | 209.4 (M + 1) |
| 249 | 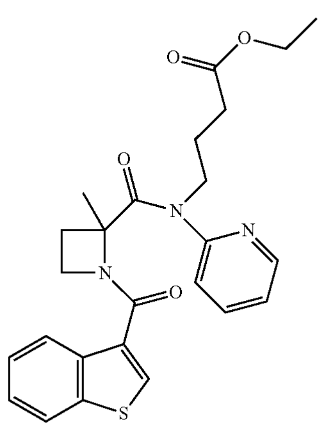 [SMILES: CCOC(=O)CCCN(C(=O)C1(C)CCN1C(=O)c1csc2ccccc12)c1ccccn1] | Int 248 and Int 125 | I4 | 465.6 | 466.1 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 250 | 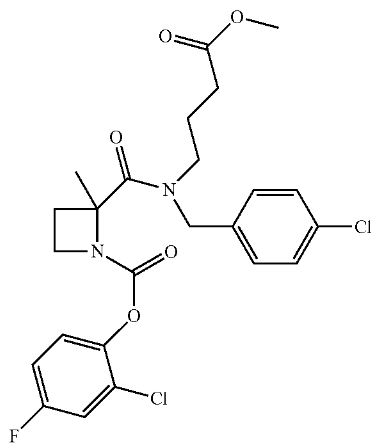 [SMILES: COC(=O)CCCN(Cc1ccc(Cl)cc1)C(=O)C1(C)CCN1C(=O)Oc1ccc(F)cc1Cl] | Int 123 and 2-chloro-4-fluoro-phenol | Z | 511.4 | 511.1 (M + 1, $^{35}$Cl) |
| 251 | 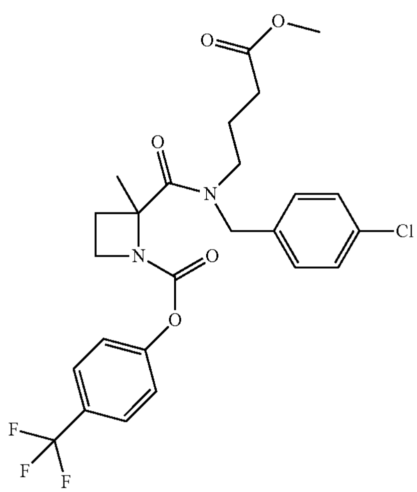 [SMILES: COC(=O)CCCN(Cc1ccc(Cl)cc1)C(=O)C1(C)CCN1C(=O)Oc1ccc(C(F)(F)F)cc1] | Int 23 and 4-trifluoromethyl-phenol | Z | 526.9 | 527.1 (M + 1, $^{35}$Cl) |
| 252 | 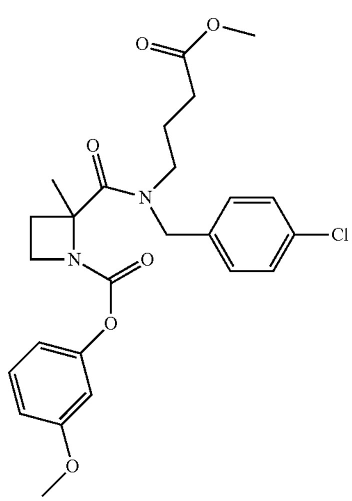 [SMILES: COC(=O)CCCN(Cc1ccc(Cl)cc1)C(=O)C1(C)CCN1C(=O)Oc1cccc(OC)c1] | Int 23 and 3-methoxy-phenol | Z | 489.0 | 489.2 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 253 | 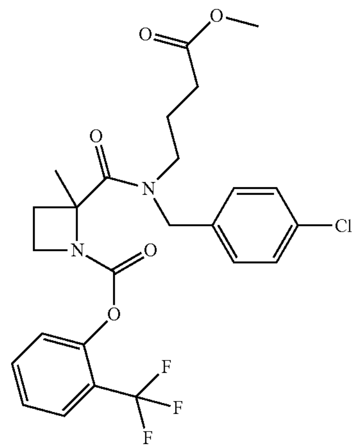 [SMILES: COC(=O)CCCN(Cc1ccc(Cl)cc1)C(=O)C1(C)CCN1C(=O)Oc1ccccc1C(F)(F)F] | Int 23 and 2-trifluoromethyl-phenol | Z (with DMAP and TEA instead of DIPEA) | 526.9 | 527.1 (M + 1, $^{35}$Cl) |
| 254 | 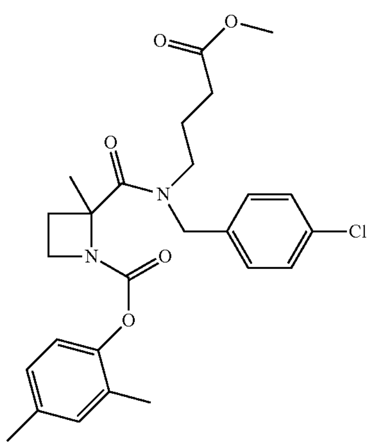 [SMILES: COC(=O)CCCN(Cc1ccc(Cl)cc1)C(=O)C1(C)CCN1C(=O)Oc1ccc(C)cc1C] | Int 23 and 2,4-dimethyl-phenol | Z (with DMAP and TEA instead of DIPEA) | 487.0 | 487.2 (M + 1, $^{35}$Cl) |
| 255 | 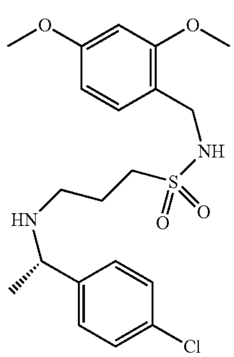 | 3-Chloro-propanesulfonyl chloride, 2,4-Dimethoxy-benzylamine and (S)-1-(4-chloro-phenyl)-ethylamine | E10 | 427.0 | NMR |

TABLE Ia-continued

Synthesis of intermediates for the preparation of the compounds of the invention

| Int | Structure | SM | Mtd | MW | MS Mes'd |
|---|---|---|---|---|---|
| 256 | 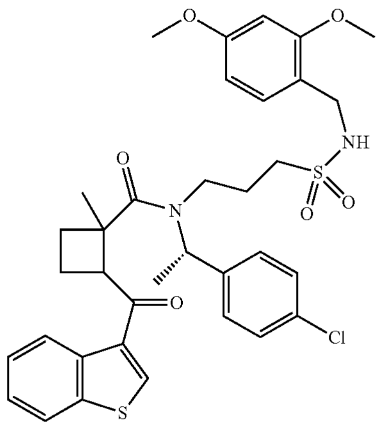 [SMILES: COc1ccc(CNS(=O)(=O)CCCN(C(=O)C2(C)CCC2C(=O)c2csc3ccccc23)[C@@H](C)c2ccc(Cl)cc2)c(OC)c1] | Int 125 and Int 255 | I4 | 684.3 | 684.2 (M + 1, $^{35}$Cl) |
| 257 | 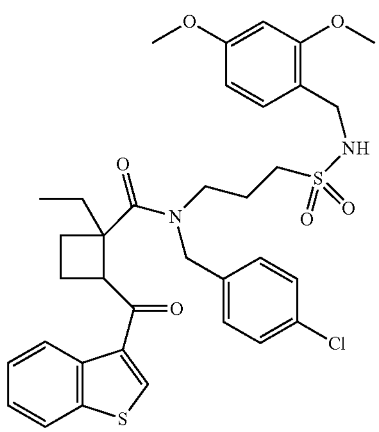 [SMILES: CCC1(C(=O)N(CCCS(=O)(=O)NCc2ccc(OC)cc2OC)Cc2ccc(Cl)cc2)CCC1C(=O)c1csc2ccccc12] | Int 128 and Int 86 | I4 | 684.3 | 684.2 (M + 1, $^{35}$Cl) |
| 258 | 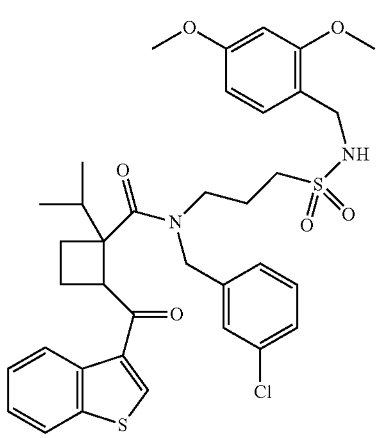 [SMILES: COc1ccc(CNS(=O)(=O)CCCN(Cc2cccc(Cl)c2)C(=O)C2(C(C)C)CCC2C(=O)c2csc3ccccc23)c(OC)c1] | Int 193 and Int 90 | I4 | 698.3 | 698.2 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 259 | 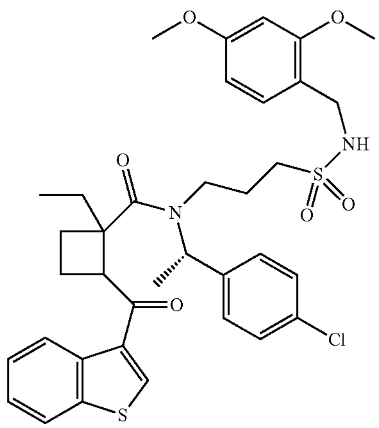 [SMILES: CCC1(C(=O)N(CCCS(=O)(=O)NCc2ccc(OC)cc2OC)[C@@H](C)c2ccc(Cl)cc2)CCC1C(=O)c1csc2ccccc12] | Int 128 and Int 255 | I4 | 698.3 | 698.2 (M + 1, ³⁵Cl) |
| 260 | 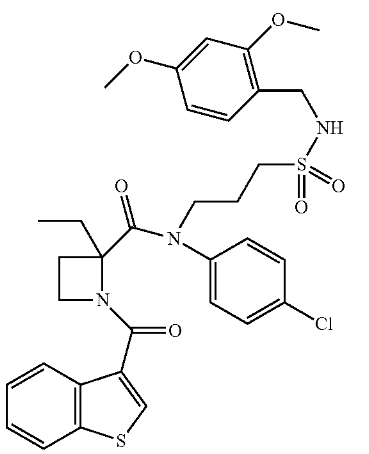 [SMILES: CCC1(C(=O)N(CCCS(=O)(=O)NCc2ccc(OC)cc2OC)c2ccc(Cl)cc2)CCN1C(=O)c1csc2ccccc12] | Int 128 and Int 195 | I4 | 670.2 | 670.2 (M + 1, ³⁵Cl) |
| 261 | 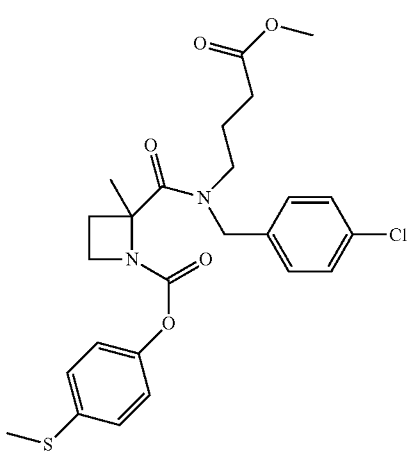 [SMILES: COC(=O)CCCN(Cc1ccc(Cl)cc1)C(=O)C1(C)CCN1C(=O)Oc1ccc(SC)cc1] | Int 23 and 4-methylsulfanyl-phenol | Z | 505.0 | 505.1 (M + 1, ³⁵Cl) |

TABLE Ia-continued

Synthesis of intermediates for the preparation of the compounds of the invention

| Int | Structure | SM | Mtd | MW | MS Mes'd |
|---|---|---|---|---|---|
| 262 | 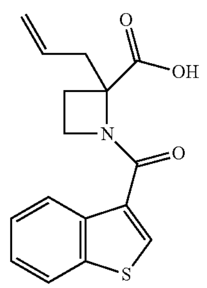 [SMILES: C=CCC1(C(=O)O)CCN1C(=O)c1csc2ccccc12] | Int 197 | G | 301.4 | 302.0 (M + 1) |
| 263 | 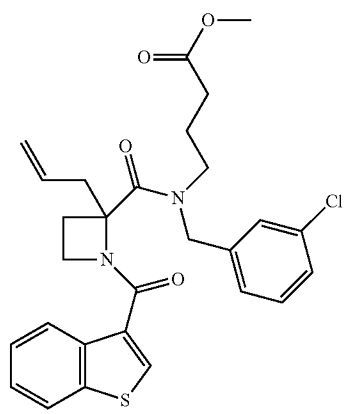 [SMILES: C=CCC1(C(=O)N(CCCC(=O)OC)Cc2cccc(Cl)c2)CCN1C(=O)c1csc2ccccc12] | Int 262 and Int 80 | I4 | 525.1 | 525.1 (M + 1, $^{35}$Cl) |
| 264 | 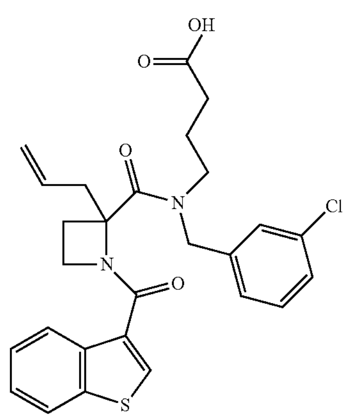 [SMILES: C=CCC1(C(=O)N(CCCC(=O)O)Cc2cccc(Cl)c2)CCN1C(=O)c1csc2ccccc12] | Int 263 | J | 511.0 | 511.1 (M + 1, $^{35}$Cl) |
| 265 | 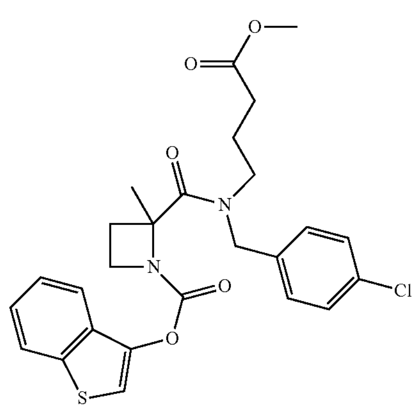 [SMILES: COC(=O)CCCN(Cc1ccc(Cl)cc1)C(=O)C1(C)CCN1C(=O)Oc1csc2ccccc12] | Int 23 and benzo[b]thiophen-3-ol | Z | 515.0 | 515.1 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 266 | 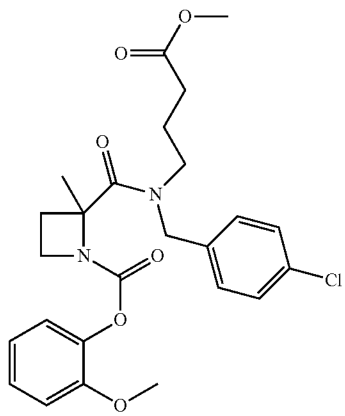 [SMILES: COC(=O)CCCN(Cc1ccc(Cl)cc1)C(=O)C1(C)CCN1C(=O)Oc1ccccc1OC] | Int 23 and 2-methoxy-phenol | Z | 489.0 | 489.1 (M + 1, $^{35}$Cl) |
| 267 | 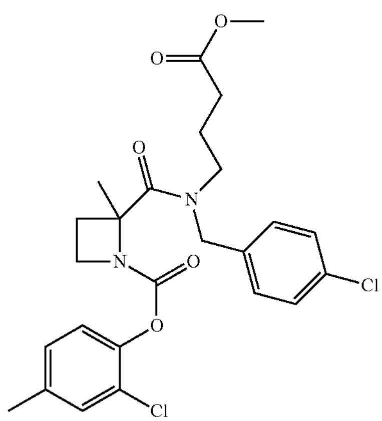 [SMILES: COC(=O)CCCN(Cc1ccc(Cl)cc1)C(=O)C1(C)CCN1C(=O)Oc1ccc(C)cc1Cl] | Int 23 and 2-chloro-4-methyl-phenol | Z | 507.4 | 507.1 (M + 1, $^{35}$Cl) |
| 268 | 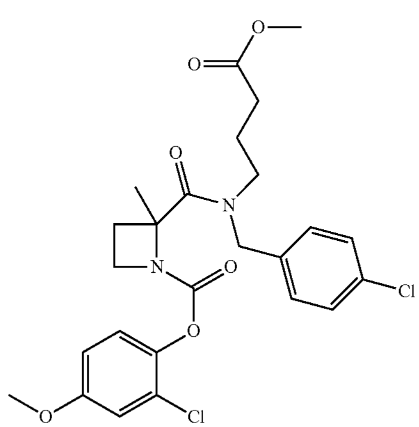 [SMILES: COC(=O)CCCN(Cc1ccc(Cl)cc1)C(=O)C1(C)CCN1C(=O)Oc1ccc(OC)cc1Cl] | Int 23 and 2-chloro-4-methoxy-phenol | Z | 523.4 | 523.1 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 269 | 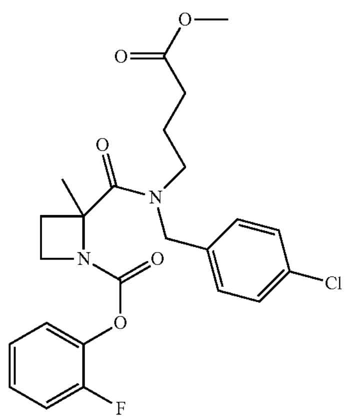 [SMILES: COC(=O)CCCN(Cc1ccc(Cl)cc1)C(=O)C1(C)CCN1C(=O)Oc1ccccc1F] | Int 23 and 2-fluoro-phenol | Z | 476.9 | 477.1 (M + 1, $^{35}$Cl) |
| 270 | 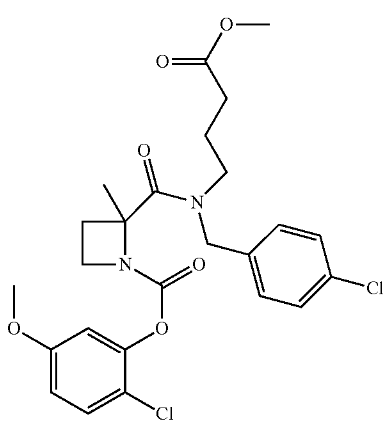 [SMILES: COC(=O)CCCN(Cc1ccc(Cl)cc1)C(=O)C1(C)CCN1C(=O)Oc1cc(OC)ccc1Cl] | Int 23 and 2-chloro-5-methoxy-phenol | Z | 523.4 | 523.1 (M + 1, $^{35}$Cl) |
| 271 | 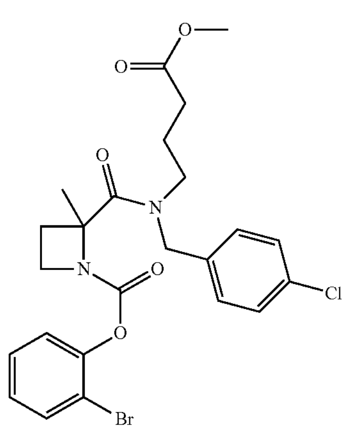 [SMILES: COC(=O)CCCN(Cc1ccc(Cl)cc1)C(=O)C1(C)CCN1C(=O)Oc1ccccc1Br] | Int 23 and 2-bromo-phenol | Z | 537.8 | 539.0 (M + 1) |

TABLE Ia-continued

Synthesis of intermediates for the preparation of the compounds of the invention

| Int | Structure | SM | Mtd | MW | MS Mes'd |
|---|---|---|---|---|---|
| 272 | 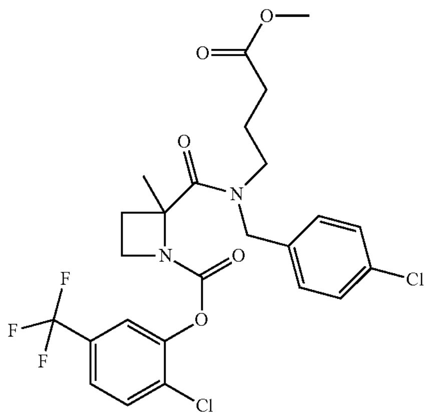 [SMILES: COC(=O)CCCN(Cc1ccc(Cl)cc1)C(=O)C1(C)CCN1C(=O)Oc1cc(C(F)(F)F)ccc1Cl] | Int 23 and 2-chloro-5-trifluoromethyl-phenol | Z | 561.4 | 561.1 (M + 1, $^{35}$Cl) |
| 273 | 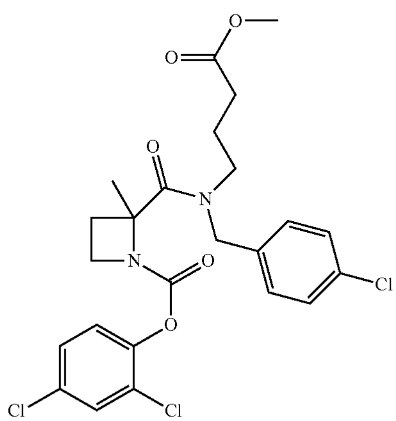 [SMILES: COC(=O)CCCN(Cc1ccc(Cl)cc1)C(=O)C1(C)CCN1C(=O)Oc1ccc(Cl)cc1Cl] | Int 23 and 2,4-dichloro-phenol | Z | 527.8 | 529.0 (M + 1) |
| 274 | 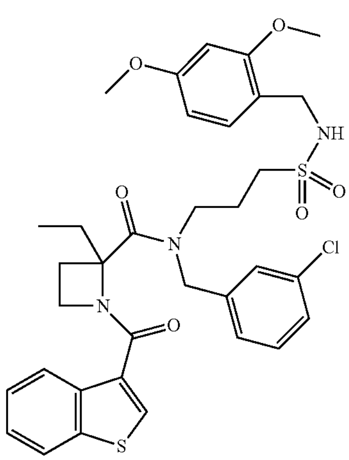 [SMILES: CCC1(C(=O)N(CCCS(=O)(=O)NCc2ccc(OC)cc2OC)Cc2cccc(Cl)c2)CCN1C(=O)c1csc2ccccc12] | Int 128 and Int 90 | I4 | 684.3 | 684.4 (M + 1, $^{35}$Cl) |

TABLE Ia-continued

Synthesis of intermediates for the preparation of the compounds of the invention

| Int | Structure | SM | Mtd | MW | MS Mes'd |
|---|---|---|---|---|---|
| 275 | 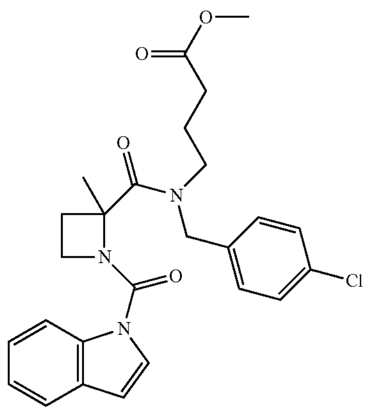 [SMILES: COC(=O)CCCN(Cc1ccc(Cl)cc1)C(=O)C1(C)CCN1C(=O)n1ccc2ccccc21] | Int 23 and indole | AA | 482.0 | NA |

SM = Starting Material
Mtd = Method
MS Mes'd = Measured mass

TABLE Ib

NMR Data of the Intermediates of the Invention

| Int | NMR data |
|---|---|
| 1 | $^1$H NMR δ (ppm) (CDCl$_3$): 7.82 (1H, d), 7.48 (1H, d), 7.42 (1H, d), 7.31 (1H, t), 7.26 (1H, d), 3.97 (2H, s) |
| 2 | $^1$H NMR δ (ppm) (CDCl$_3$): 7.82 (1H, d), 7.75 (1H, d), 7.42-7.31 (2H, m), 7.24 (1H, s), 4.00 (2H, s) |
| 3 | $^1$H NMR δ (ppm) (CDCl$_3$): 6.97 (1H, s), 6.86 (2H, s) |
| 9 | $^1$H NMR δ (ppm) (CDCl$_3$): 10.03 (1H, s), 8.24 (1H, d), 8.16 (1H, s), 7.89 (1H, d), 7.79 (1H, d), 7.38 (1H, dd) |
| 12 | $^1$H NMR δ (ppm) (CDCl$_3$): 4.05-3.94 (1H, m), 3.80 (3H, s), 3.79-3.71 (1H, m), 2.31-2.14 (2H, m), 2.10-1.88 (2H, m), 1.52-1.37 (9H, m), 1.06 (3H, t) |
| 13 | $^1$H NMR δ (ppm) (CDCl$_3$): 9.48 (1H, br s), 4.35 (2H, q), 4.16-4.00 (2H, m), 2.82-2.70 (1H, m), 2.60-2.45 (1H, m), 1.95 (3H, s), 1.36 (3H, t) |
| 14 | $^1$H NMR δ (ppm) (MeOD, d$_4$): 7.46-7.40 (2H, m), 7.38-7.32 (2H, m), 4.78-4.58 (2H, m), 4.21-4.07 (1H, m), 3.87-3.77 (1H, m), 3.11-2.98 (1H, m), 2.93 (3H, s), 2.76-2.65 (1H, m), 1.97 (3H, s) |
| 15 | $^1$H NMR δ (ppm) (MeOD, d$_4$): 7.74 (2H, d), 7.40 (2H, d), 4.21-4.10 (1H, m), 4.00-3.90 (1H, m), 3.00-2.90 (1H, m), 2.82-2.72 (1H, m), 2.03 (3H, s) |
| 17 | $^1$H NMR δ (ppm) (CDCl$_3$): 9.53 (1H, br s), 4.20-4.03 (2H, m), 3.94 (3H, s), 2.90-2.79 (1H, m), 2.63-2.50 (1H, m), 2.00 (3H, s) |
| 22 | $^1$H NMR δ (ppm) (CDCl$_3$): 9.60 (1H, br s), 4.18-4.00 (2H, m), 3.94 (3H, s), 2.84-2.70 (1H, m), 2.63-2.40 (2H, m), 2.32-2.17 (1H, m), 1.14-0.99 (3H, m) |
| 27 | $^1$H NMR δ (ppm) (CDCl$_3$): 9.79 (1H, br s), 7.48-7.30 (5H, m), 4.75 (2H, s), 4.18 (1H, d), 4.15-4.04 (2H, m), 4.00 (1H, d), 3.90 (3H, s), 2.72-2.56 (1H, m) |
| 28 | $^1$H NMR δ (ppm) (DMSO, d$_6$): 9.25 (1H, br s), 9.00 (1H, t), 7.41 (2H, d), 7.30 (2H, d), 4.35 (2H, d), 4.00-3.86 (1H, m), 3.70-3.59 (1H, m), 2.68-2.55 (1H, m), 2.46-2.35 (1H, m), 1.75 (3H, s) |
| 31 | $^1$H NMR δ (ppm) (CDCl$_3$): 3.93-3.81 (1H, m), 3.81-3.68 (1H, m), 2.85-2.71 (1H, m), 2.12-2.00 (1H, m), 1.72 (3H, s), 1.48 (9H, s) |
| 34 | $^1$H NMR δ (ppm) (CDCl$_3$): 7.42-7.21 (5H, m), 3.86-3.74 (4H, m), 3.66-3.54 (1H, m), 3.34-3.07 (2H, m), 2.68-2.55 (1H, m), 2.02-1.91 (1H, m), 1.53 (3H, s) |
| 35 | $^1$H NMR δ (ppm) (CDCl$_3$): 7.65 (2H, d), 7.59 (2H, d), 4.48-4.39 (1H, m), 4.28-4.19 (1H, m), 3.07-2.97 (1H, m), 2.34-2.24 (1H, m), 1.95 (3H, s) |
| 36 | $^1$H NMR δ (ppm) (CDCl$_3$): 7.35-7.28 (4H, m), 3.81 (2H, s), 3.77 (3H, s), 3.44 (2H, s), 2.00 (1H, s) |
| 38 | $^1$H NMR δ (ppm) (CDCl$_3$): 7.40-7.35 (1H, m), 7.32-7.21 (3H, m), 3.82 (2H, s), 3.77 (3H, s), 3.45 (2H, s), 2.02 (1H, s) |
| 39 | $^1$H NMR δ (ppm) (CDCl$_3$): 7.41-7.31 (4H, m), 3.94 (2H, s), 3.59 (2H, s), 1.68 (1H, s) |
| 40 | $^1$H NMR δ (ppm) (CDCl$_3$): 7.37-7.26 (4H, m), 4.15 (2H, q), 3.79 (2H, s), 2.68 (2H, t), 2.40 (2H, t), 1.86 (2H, tt), 1.78 (1H, br s), 1.27 (3H, t) |
| 50 | $^1$H NMR δ (ppm) (CDCl$_3$): 7.27-7.12 (4H, m), 3.69 (2H, s), 2.60 (2H, q), 1.64 (1H, br s), 1.06 (3H, t) |
| 55 | $^1$H NMR δ (ppm) (CDCl$_3$): 7.36-7.27 (4H, m), 3.82 (2H, s), 3.54 (2H, t), 3.39 (3H, s), 2.84 (2H, t), 1.94 (1H, br s) |

TABLE Ib-continued

NMR Data of the Intermediates of the Invention

| | Int | NMR data |
|---|---|---|
| | 59 | $^1$H NMR δ (ppm) (CDCl$_3$): 7.37-7.35 (1H, m), 7.29-7.21 (3H, m), 3.82 (2H, s), 3.72 (3H, s), 2.92 (2H, t), 2.58 (2H, t), 2.30 (1H, s) |
| | 61 | $^1$H NMR δ (ppm) (CDCl$_3$): 7.34-7.23 (4H, m), 3.77 (2H, s), 3.68 (3H, s), 2.87 (2H, t), 2.54 (2H, t), 1.90 (1H, br s) |
| | 62 | $^1$H NMR δ (ppm) (CDCl$_3$): 7.28-7.13 (4H, m), 3.73 (2H, t), 3.70 (2H, s), 3.04 (2H, br s), 2.81 (2H, t), 1.66 (2H, tt) |
| | 64 | $^1$H NMR δ (ppm) (CDCl$_3$): 7.34-7.27 (4H, m), 3.82 (1H, d), 3.77 (3H, s), 3.67 (1H, d), 3.41 (1H, q), 2.25 (1H, br s), 1.26 (3H, d) |
| | 67 | $^1$H NMR δ (ppm) (CDCl$_3$): 7.37-7.26 (4H, m), 3.82 (2H, s), 3.70 (2H, t), 2.83 (2H, t), 2.19 (2H, br s) |
| | 69 | $^1$H NMR δ (ppm) (MeOD, d$_4$): 8.28 (1H, s), 7.71 (1H, d), 7.62 (1H, d), 7.40-7.35 (1H, m), 6.68 (1H, d), 4.27-4.20 (1H, m), 4.17-4.08 (2H, m), 4.00-3.92 (1H, m), 3.57-3.42 (2H, m), 1.75 (9H, s), 1.23 (3H, t) |
| | 84 | $^1$H NMR δ (ppm) (CDCl$_3$): 7.33-7.23 (4H, m), 6.10-6.00 (1H, m), 3.78 (2H, s), 3.39-3.33 (2H, m), 2.77 (2H, t), 1.99 (3H, s) |
| | 115 | $^1$H NMR δ (ppm) (CDCl$_3$): 8.31-8.21 (1H, m), 7.89 (1H, d), 7.72 (1H, br s), 7.51-7.39 (2H, m), 7.39-7.33 (2H, m), 7.29-7.18 (2H, m), 4.28-4.17 (1H, m), 4.09-3.94 (1H, m), 3.67 (3H, s), 3.59-3.44 (1H, m), 2.86-2.70 (1H, m), 2.44-2.04 (5H, m), 2.03-1.74 (2H, m), 1.70 (3H, d), 1.69 (3H, s) |
| | 121 | $^1$H NMR δ (ppm) (CDCl$_3$): 87.92 (1H, d), 7.78 (1H, d), 7.50-7.40 (2H, m), 7.35 (1H, s), 4.05-3.93 (2H, m), 3.79 (2H, s), 2.96-2.76 (1H, m), 2.19-2.08 (1H, m), 1.80 (3H, s) |
| | 125 | $^1$H NMR δ (ppm) (CDCl$_3$): 8.41 (1H, d), 7.92 (1H, d), 7.87 (1H, s), 7.57-7.44 (2H, m), 4.49-4.39 (1H, m), 4.31-4.21 (1H, m), 3.10-3.00 (1H, m), 2.36-2.25 (1H, m), 2.01 (3H, s) |
| | 138 | $^1$H NMR δ (ppm) (CDCl$_3$): 8.33 (1H, br s), 7.37-7.20 (4H, m), |
| | 139 | $^1$H NMR δ (ppm) (CDCl$_3$): 7.39-7.31 (2H, m), 7.26-7.15 (2H, m), 4.77-4.44 (2H, m), 3.94-3.74 (2H, m), 2.94 (3H, s), 2.55-2.39 (1H, m), 2.31-2.18 (1H, m), 1.82 (3H, s), 1.48 (9H, s) |
| | 201 | $^1$H NMR δ (ppm) (CDCl$_3$): 7.22 (1 H, d), 6.91-6.67 (3 H, m), 3.87-3.75 (7 H, m), 3.49 (0.3 H, d), 3.32 (0.7 H, d), 3.26-3.11 (1 H, m), 3.04 (1 H, d), 2.18-2.05 (2 H, m), 1.47 (9 H, s) |
| | 206 | $^1$H NMR δ (ppm) (CDCl$_3$): 7.58-7.49 (2 H, m), 7.44 (2 H, d), 3.91-3.75 (4 H, m), 3.58 (0.4 H, d), 3.39 (0.6 H, d), 3.25-3.04 (2 H, m), 2.20-2.05 (2 H, m), 1.45 (9 H, s) |
| GG136-004-A01 | 211 | $^1$H NMR δ (ppm) (CDCl$_3$): 7.33 (2 H, d), 7.16-7.26 (2 H, m), 3.94-3.84 (3.7 H, m), 3.83-3.75 (0.3 H, m), 3.52 (0.3 H, d), 3.33 (0.7 H, d), 3.27-3.18 (0.7 H, m), 3.17-3.12 (0.3 H, m), 3.08 (1 H, d), 2.18-2.06 (2 H, m), 1.52-1.47 (9 H, m) |
| | 216 | $^1$H NMR δ (ppm) (CDCl$_3$): 7.25-7.14 (2 H, m), 7.02 (2 H, t), 3.90-3.65 (4 H, m), 3.30 (1 H, d), 3.24-3.10 (1 H, m), 3.10-2.96 (1 H, m), 2.16-1.95 (2 H, m), 1.52-1.39 (9 H, m) |
| | 221 | $^1$H NMR δ (ppm) (CDCl$_3$): 7.20 (1 H, t), 7.11-7.00 (3 H, m), 3.87-3.68 (4 H, m), 3.49 (0.3 H, d), 3.31 (0.7 H, d), 3.22-3.06 (1 H, m), 3.02 (1 H, d), 2.34 (3 H, s), 2.19-2.01 (2 H, m), 1.47 (9 H, s) |
| GG136-045-A01 | 226 | $^1$H NMR δ (ppm) (CDCl$_3$): 7.36-7.26 (2 H, m), 6.95-6.85 (2 H, m), 4.57 (2 H, s), 3.90 (3 H, s) |
| GG136-046-A01 | 227 | $^1$H NMR δ (ppm) (CDCl$_3$): 7.31-7.11 (2 H, m), 6.96-6.80 (2 H, m), 3.87-3.70 (7 H, m), 3.60-3.45 (1 H, d), 3.27-2.96 (2 H, m), 2.08 (2 H, t), 1.47 (9 H, s) |
| | 232 | $^1$H NMR δ (ppm) (CDCl$_3$): 7.33-7.17 (2 H, m), 7.17-6.98 (2 H, m), 3.94-3.69 (4 H, m), 3.53-3.28 (1 H, m), 3.28-3.08 (2 H, m), 2.25-2.06 (2 H, m), 1.46 (9 H, s) |
| | 246 | $^1$H NMR δ (ppm) (CDCl$_3$): 7.98 (1 H, d), 6.59 (1 H, dd), 6.41 (1 H, d), 4.84 (1 H, br. s.), 4.17 (2 H, q), 3.41-3.29 (2 H, m), 2.45 (2 H, t), 1.98 (2 H, quin), 1.29 (3 H, t) |
| | 255 | $^1$H NMR δ (ppm) (CDCl$_3$): 7.36-7.27 (3 H, m), 7.27-7.14 (3 H, m), 6.50 (1 H, d), 6.46 (1 H, dd), 5.13 (1 H, br. s.), 4.24 (2 H, d), 3.83 (3 H, s), 3.87 (3 H, s), 3.68 (1 H, q), 3.07-2.92 (1 H, m), 2.92-2.77 (1 H, m), 2.52 (1 H, dt), 2.34 (1 H, dt), 1.78 (2 H, quin), 1.30 (3 H, d) |

Synthesis of Representative Compounds of the Invention
Compound 191: 4-[[(R)-1-(Benzo[b]thiophene-3-carbonyl)-2-methyl-azetidine-2-carbonyl](3-chlorobenzyl)-amino]-butyric acid
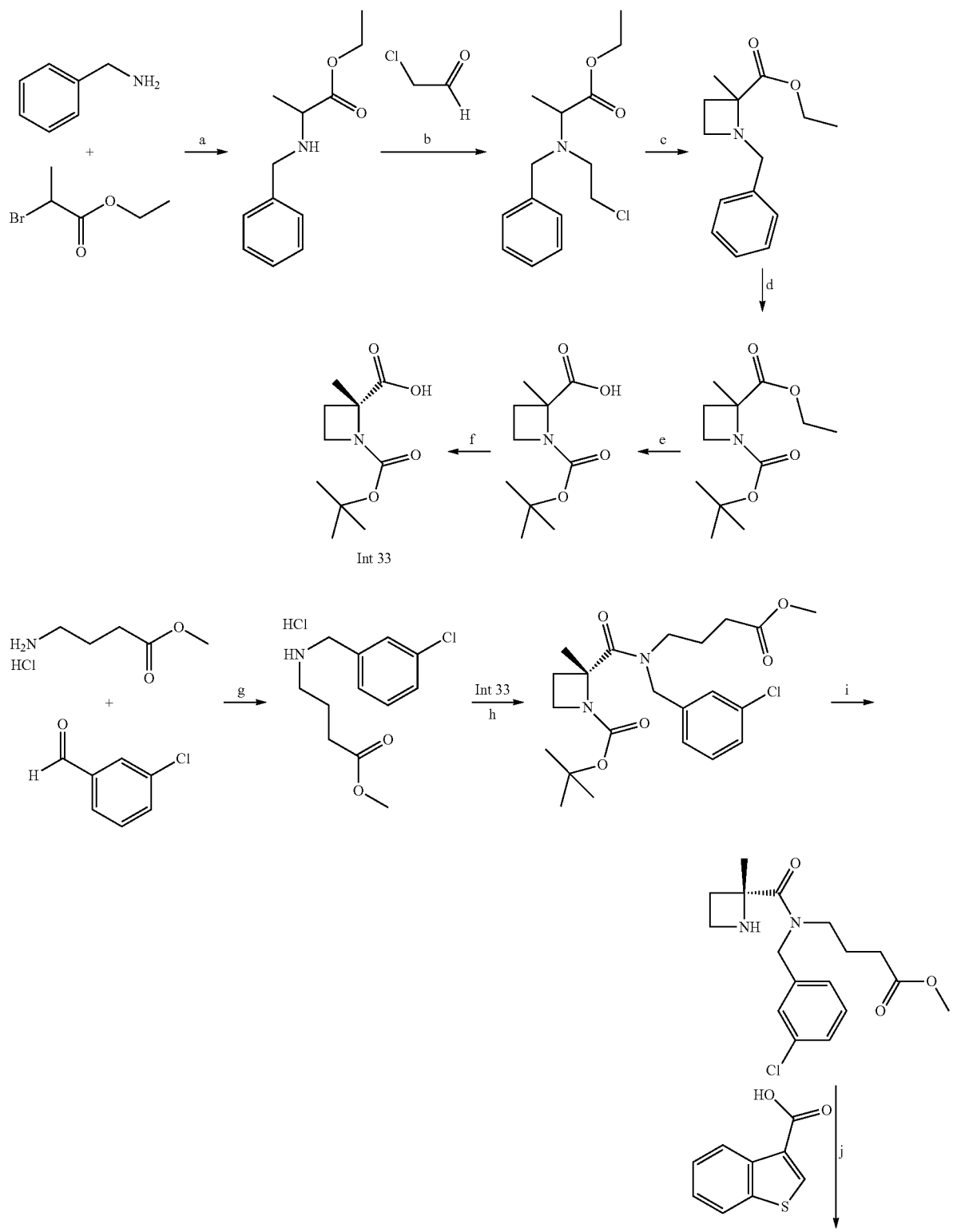

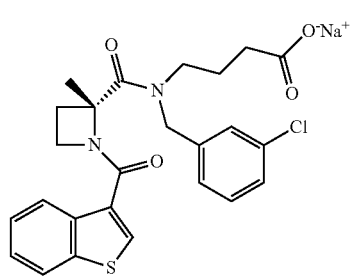
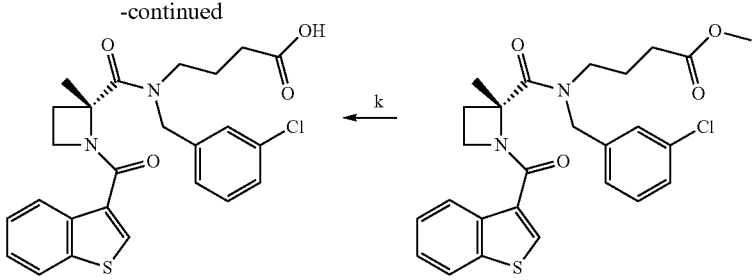

Step a: 2-Benzylamino-propionic acid ethyl ester

To a solution of 2-bromo-propionic acid ethyl ester (17.90 mL, 1 eq.) in 250 mL of MeCN were added benzylamine (13.45 mL, 0.9 eq.) and potassium carbonate (28.60 g, 1.5 eq.). The reaction was refluxed for 2 h then cooled to 20° C. The crude was filtered, washed with EtOAc. The filtrate was concentrated under reduced pressure, then purified by chromatography on silica gel (elution with heptane/EtOAc: 9/1 to 7/3) to afford 2-benzylamino-propionic acid ethyl ester (24.74 g, yield=97%).

$^1$H NMR δ (ppm) (CDCl$_3$): 7.37-7.29 (4H, m), 7.28-7.22 (1H, m), 4.20 (2H, q), 3.82 (1H, d), 3.69 (1H, d), 3.38 (1H, q), 1.33 (3H, d), 1.29 (3H, t)

MW (calcd): 207.2; MW (obsd): 208.1 (M+1)

Step b: 2-[Benzyl-(2-chloro-ethyl)-amino]propionic acid ethyl ester (I) Drying of Chloroacetaldehyde Solution (Solution I):

To a solution of chloroacetaldehyde (45% w/w in water, 56 mL, 3 eq.) in 75 mL of dry DCM under nitrogen was added MgSO$_4$ (55 g, 3.8 eq.). The mixture was stirred for 1 h at 20° C. The solid was filtered, washed twice with 110 mL of dry DCM, and the resulting filtrate (solution I) was rapidly used in the following reaction.

(II) Reaction:

To a solution of 2-benzylamino-propionic acid ethyl ester (24.72 g, 1 eq.) in 114 mL of dry DCM under nitrogen was added MgSO$_4$ (10.80 g, 0.75 eq.). The reaction was cooled to 0° C. then acetic acid (6.82 mL, 1 eq) and the above solution of chloroacetaldehyde in dry DCM (solution I) were added. Sodium triacetoxyborohydride (38 g, 1.5 eq.) was added portionwise. The reaction was stirred for 2 h at 0° C. The crude was carefully quenched with 160 mL of a saturated aqueous solution of NaHCO$_3$. Then 75 mL of an aqueous solution of NaOH (2N) was added. The aqueous layer was extracted twice with 120 mL of DCM. The combined organic layers were washed twice with 120 mL of a saturated aqueous solution of NaHCO$_3$, then dried over MgSO$_4$, filtered and concentrated under reduced pressure. The crude was purified by chromatography on silica gel (elution with heptane/EtOAc: 100/0 to 93/7) to afford 2-[benzyl-(2-chloro-ethyl)-amino]-propionic acid ethyl ester (27.40 g, yield=85%).

$^1$H NMR δ (ppm) (CDCl$_3$): 7.40-7.29 (4H, m), 7.29-7.22 (1H, m), 4.24-4.14 (2H, m), 3.90 (1H, d), 3.77 (1H, d), 3.50 (1H, q), 3.43-3.36 (2H, m), 3.13-2.94 (2H, m), 1.34 (3H, d), 1.31 (3H, t)

MW (calcd): 269.8; MW (obsd): 270.1 (M+1, $^{35}$Cl)

Step c: 1-Benzyl-2-methyl-azetidine-2-carboxylic acid ethyl ester

A solution of 2-[benzyl-(2-chloro-ethyl)-amino]-propionic acid ethyl ester (27.4 g, 1 eq.) in 253 mL of dry THF was cooled to −78° C. under argon. KHMDS (15% w/w in toluene, 170.40 g, 1.25 eq.) was slowly added so that temperature was kept below −76° C. The reaction was stirred for 1 h at −76° C., then warmed to 20° C. and stirred for 1 h. Acetic acid (1.74 mL, 0.3 eq.) was added and the reaction was stirred at 20° C. for 10 min. The reaction was quenched with 50 mL of a saturated aqueous solution of NaHCO$_3$ and partially concentrated under reduced pressure. The crude was extracted three times with DCM. The organic layers were dried over MgSO$_4$, filtered and concentrated under reduced pressure. The crude was purified by chromatography on silica gel (elution with heptane/EtOAc 100/0 to 90/10) to afford 1-benzyl-2-methyl-azetidine-2-carboxylic acid ethyl ester (18.75 g, yield=79%).

$^1$H NMR δ (ppm) (CDCl$_3$): 7.34-7.19 (5H, m), 4.24-4.16 (2H, m), 3.79 (1H, d), 3.58 (1H, d), 3.30-3.22 (1H, m), 3.15-3.05 (1H, m), 2.63-2.54 (1H, m), 1.97-1.88 (1H, m), 1.49 (3H, s), 1.29 (3H, t)

MW (calcd): 233.3; MW (obsd): 234.1 (M+1)

Step d: Intermediate 11
2-Methyl-azetidine-1,2-dicarboxylic acid 1-tert-butyl ester 2-ethyl ester To a solution of 1-benzyl-2-methyl-azetidine-2-carboxylic acid ethyl ester (69.27 g, 1 eq.) in 1500 mL of EtOH were added Boc$_2$O (74.93 g, 1.15 eq.) and Pd/C (7.29 g, 0.02 eq.). The flask was evacuated and backfilled with argon. Then the reaction was backfilled with H$_2$ and stirred for 24 h at 20° C. under atmospheric pressure. The crude was filtered through a pad of celite and washed with EtOH. The filtrate was concentrated under reduced pressure and purified by chromatography on silica gel (elution with heptane/EtOAc 100/0 to 80/20) to afford 2-methyl-azetidine-1,2-dicarboxylic acid 1-tert-butyl ester 2-ethyl ester (57 g, yield=79%).

$^1$H NMR δ (ppm) (CDCl$_3$): 4.12-3.92 (2H, m), 3.86-3.71 (1H, m), 3.66-3.54 (1H, m), 2.17-2.00 (1H, m), 1.99-1.83 (1H, m), 1.33 (3H, s), 1.21 (9H, s), 1.11 (3H, t)

MW (calcd): 243.3; MW (obsd): 266 (M+Na$^+$)

Step e: Intermediate 31
2-Methyl-azetidine-1,2-dicarboxylic acid 1-tert-butyl ester To a solution of 2-methyl-azetidine-1,2-dicarboxylic acid 1-tert-butyl ester 2-ethyl ester (63 g, 1 eq.) in 260 mL of EtOH was added 260 mL of an aqueous solution of NaOH 2N (2 eq.). The reaction was stirred at 20° C. for 15 h. The solvent was removed under reduced pressure and the crude was partitioned between water and EtOAc. The organic layer was discarded and the aqueous layer was acidified by addition of a solution of citric acid 10% in water until pH=5 and thoroughly extracted with EtOAc. The organic layers were combined, dried over MgSO$_4$, filtered and concentrated under reduced pressure to afford 2-methyl-azetidine-1,2-dicarboxylic acid 1-tert-butyl ester (50 g, yield=89%).

¹H NMR δ (ppm) (CDCl₃): 3.93-3.81 (1H, m), 3.81-3.68 (1H, m), 2.85-2.71 (1H, m), 2.12-2.00 (1H, m), 1.72 (3H, s), 1.48 (9H, s)

Step f: Intermediate 33 (R)-2-Methyl-azetidine-1,2-dicarboxylic acid 1-tert-butyl ester The chiral separation of racemic Intermediate 31, 2-methyl-azetidine-1,2-dicarboxylic acid 1-tert-butyl ester was performed by preparative chiral chromatography using a column Chiralpak AD-H, (20×250 mm), 5μ, a mobile phase: hexane:ethanol:Formic acid (95:5:0.05), a flow rate of 9.5 mL/min, at 20° C. Retention time of isomer (R): 9.00 min. ee=100%

Step g: Intermediate 80 4-(3-Chloro-benzylamino)-butyric acid methyl ester hydrochloride To a solution of 4-amino-butyric acid methyl ester hydrochloride (30 g, 1 eq.) in 360 mL of THF were added TEA (67.7 mL, 2.5 eq.), then 3-chlorobenzaldehyde (19 mL, 0.9 eq.) and MgSO₄ (35 g, 1.5 eq.). The reaction was stirred at 20° C. for 15 h under nitrogen. 360 mL of MeOH was added then the reaction was cooled to −20° C. NaBH₄ (14.75 g, 2 eq.) was added portionwise. The reaction was stirred for 1 h at 0° C. The crude was partially concentrated under reduced pressure at 20° C., filtered and washed with DCM. The filtrate was washed with water and brine. The organic layer was dried over MgSO₄, filtered and concentrated under reduced pressure at 20° C. The residue, in solution in 1600 mL of Et₂O, was treated with 87 mL of HCl 2N in Et₂O. A solid was formed, filtrated, washed with Et₂O, then pentane and dried to afford 4-(3-chloro-benzylamino)-butyric acid methyl ester hydrochloride (32 g, yield=65%).

¹H NMR δ (ppm) (CDCl₃): 7.66-7.58 (2H, m), 7.43-7.36 (2H, m), 4.16-4.09 (2H, m), 3.67 (3H, s), 3.00-2.90 (2H, m), 2.54-2.46 (2H, m), 2.27-2.16 (2H, m)

MW (calcd): 241.7; MW (obsd): 242.3 (M+1, ³⁵Cl)

Step h: Intermediate 175 (R)-2-[(3-Chloro-benzyl)-(3-methoxycarbonyl-propyl)-carbamoyl]-2-methyl-azetidine-1-carboxylic acid tert-butyl ester To a solution of (R)-2-methyl-azetidine-1,2-dicarboxylic acid 1-tert-butyl ester, Intermediate 33 (13 g, 1 eq.) in 300 mL of dry DCM under nitrogen was added dropwise a solution of 1-chloro-N,N,2-trimethylpropenylamine (16 mL, 2 eq.) in 50 mL of DCM. The solution was stirred at 20° C. for 30 min, then cooled to −5° C. A solution of 4-(3-chloro-benzylamino)-butyric acid methyl ester hydrochloride, Intermediate 80 (18.5 g, 1.1 eq.) and TEA (25 mL, 3 eq.) in 200 mL of DCM was added slowly to the previous mixture. The reaction was stirred at 20° C. for 2.5 h. The mixture was added to 500 mL of a saturated aqueous solution of NaHCO₃. The crude was extracted three times with DCM. The organic layers were combined, washed with brine, dried over MgSO₄, filtered, concentrated under reduced pressure. The crude was purified by chromatography on silica gel (elution with heptane/EtOAc: 90/10 to 50/50) to afford (R)-2-[(3-chloro-benzyl)-(3-methoxycarbonyl-propyl)-carbamoyl]-2-methyl-azetidine-1-carboxylic acid tert-butyl ester (27 g, yield=quantitative).

¹H NMR δ (ppm) (CDCl₃): 7.35-7.04 (4H, m), 5.13-4.29 (2H, m), 3.96-3.74 (1H, m), 3.68 (3H, s), 3.13-2.90 (4H, m), 2.65-2.40 (1H, m), 2.39-2.15 (2H, m), 2.00-1.65 (5H, m), 1.58-1.30 (9H, m)

MW (calcd): 439.0; MW (obsd): 439.4 (M+1, ³⁵Cl)

Step i: Intermediate 21 4-[(3-Chloro-benzyl)-((R)-2-methyl-azetidine-2-carbonyl)-amino]-butyric acid methyl ester hydrochloride To a solution of (R)-2-[(3-chloro-benzyl)-(3-methoxycarbonyl-propyl)-carbamoyl]-2-methyl-azetidine-1-carboxylic acid tert-butyl ester, Intermediate 175 (17.6 g, 1 eq.) in 200 mL of dioxane under nitrogen was added a solution of HCl (4N) in dioxane (50 mL, 5 eq.). The reaction was stirred for 16 h at 20° C., then concentrated under reduced pressure. The crude was solubilised in DCM, poured into Et₂O and the resulting solid was filtered, washed with Et₂O and pentane and dried to afford 4-[(3-chloro-benzyl)-((R)-2-methyl-azetidine-2-carbonyl)-amino]-butyric acid methyl ester hydrochloride (12.5 g, yield=81%).

¹H NMR δ (ppm) (CDCl₃): 8.82 (1H, br s), 7.41-7.26 (2H, m), 7.25-7.11 (2H, m), 4.83-4.53 (1H, m), 4.47-4.31 (1H, m), 4.31-3.95 (2H, m), 3.72-3.64 (3H, m), 3.51-3.26 (1H, m), 3.17-3.07 (1H, m), 3.02-2.86 (1H, m), 2.78-2.52 (1H, m), 2.40-2.30 (2H, m), 2.16-2.01 (3H, m), 1.97-1.83 (2H, m)

MW (calcd): 338.8; MW (obsd): 339.3 (M+1, ³⁵Cl)

Step j: Intermediate 112 4-[[(R)-1-(Benzo[b]thiophene-3-carbonyl)-2-methyl-azetidine-2-carbonyl]-(3-chloro-benzyl)-amino]-butyric acid methyl ester To a suspension of benzo[b]thiophene-3-carboxylic acid (7.12 g, 1.2 eq.) in 210 mL of DCM and 210 mL of THF were added HOBt (5.4 g, 1.2 eq.) EDC.HCl (9.6 g, 1.5 eq.) and TEA (18.5 mL, 4 eq.). The reaction was stirred at 20° C. for 15 h, then a solution of 4-[(3-chloro-benzyl)-((R)-2-methyl-azetidine-2-carbonyl)-amino]-butyric acid methyl ester hydrochloride obtained in step i above (12.5 g, 1 eq.) in 105 mL of DCM and 105 mL of THF was added. The reaction was stirred at 20° C. for 4.5 h. The crude was diluted with DCM. A saturated aqueous solution of NaHCO₃ was added. The aqueous layer was extracted three times with DCM. The organic layers were combined, dried over MgSO₄, filtered and concentrated under reduced pressure. The crude was purified by chromatography on silica gel (elution with heptane/EtOAc: 90/10 to 50/50) to afford 4-[[(R)-1-(benzo[b]thiophene-3-carbonyl)-2-methyl-azetidine-2-carbonyl]-(3-chloro-benzyl)-amino]-butyric acid methyl ester (14.53 g, yield=87%).

¹H NMR δ (ppm) (CDCl₃): 8.37-8.07 (1H, m), 7.92-7.77 (1H, m), 7.51-7.36 (2H, m), 7.34-6.67 (5H, m), 5.49-4.72 (1H, m), 4.57-4.33 (1H, m), 4.05-3.76 (2H, m), 3.69 (3H, s), 3.29-2.66 (2H, m), 2.50-2.19 (3H, m), 2.15-1.83 (5H, m), 1.74-1.57 (1H, m)

MW (calcd): 499.0; MW (obsd): 499.3 (M+1, ³⁵Cl)

Step k: Compound 191 4-[[(R)-1-(Benzo[b]thiophene-3-carbonyl)-2-methyl-azetidine-2-carbonyl]-(3-chloro-benzyl)-amino]-butyric acid To a solution of 4-[[(R)-1-(benzo[b]thiophene-3-carbonyl)-2-methyl-azetidine-2-carbonyl]-(3-chloro-benzyl)-amino]-butyric acid methyl ester, Intermediate 112 (25 g, 1 eq.) in 750 mL of MeOH was added aqueous NaOH (2N) (75 mL, 3 eq.). The reaction was stirred at 20° C. for 15 h. The solvent was removed under reduced pressure and the crude was partitioned between water and EtOAc. The organic layer was discarded. The aqueous layer was acidified by addition of HCl (2N) until pH=2 and thoroughly extracted three times with EtOAc. The organic layers were combined, dried over MgSO$_4$, filtered and concentrated under reduced pressure to afford 4-[[(R)-1-(benzo[b]thiophene-3-carbonyl)-2-methyl-azetidine-2-carbonyl]-(3-chloro-benzyl)-amino]-butyric acid (23.7 g, yield=97%).

[α]$^{20}$$_D$=+176 (c=1.01, CHCl$_3$); ee>99.0%

$^1$H NMR δ (ppm) (DMSO, d$_6$) at 80° C.: 8.14-8.08 (1H, m), 7.99-7.93 (1H, m), 7.90 (1H, s), 7.44-7.31 (3H, m), 7.30-7.25 (2H, m), 7.22-7.16 (1H, m), 4.73-4.54 (2H, m), 4.11-3.98 (2H, m), 3.44-3.34 (1H, m), 3.26-3.15 (1H, m), 2.58-2.51 (1H, m), 2.41-2.32 (1H, m), 2.18 (2H, t), 1.85-1.76 (5H, m)

MW (calcd): 485.0; MW (obsd): 485.4 (M+1, $^{35}$Cl)

Step 1: 4-[[(R)-1-(Benzo[b]thiophene-3-carbonyl)-2-methyl-azetidine-2-carbonyl]-(3-chloro-benzyl)-amino]-butyric acid, sodium salt To a solution of 4-[[(R)-1-(benzo[b]thiophene-3-carbonyl)-2-methyl-azetidine-2-carbonyl]-(3-chloro-benzyl)-amino]-butyric acid (51.00 g, 1 eq.) in 1000 mL of EtOH was added aqueous NaOH (1N) (105.15 mL, 1 eq.). The reaction was stirred at 20° C. for 15 min under nitrogen. The solvent was removed under reduced pressure. The crude was solubilised in 200 mL of DCM, poured dropwise into 4000 mL of Et$_2$O. The resulting solid was filtered, washed with pentane and dried to afford 4-[[(R)-1-(benzo[b]thiophene-3-carbonyl)-2-methyl-azetidine-2-carbonyl]-(3-chloro-benzyl)-amino]-butyric acid, sodium salt (49.3 g, yield=92%).

$^1$H NMR δ (ppm) (CDCl$_3$): 8.14-8.06 (1H, m), 7.82-7.72 (1H, m), 7.40-7.27 (3H, m), 7.23-7.08 (3H, m), 7.05-6.96 (1H, m), 4.82-4.64 (1H, m), 4.33-4.22 (1H, m), 4.06-3.94 (1H, m), 3.80-3.25 (3H, m), 3.10-2.53 (2H, m), 2.21-1.47 (7H, m)

MW (calcd): 485.0; MW (obsd): 485.4 (M+1, $^{35}$Cl)

Alternative route to 4-[[(R)-1-(Benzo[b]thiophene-3-carbonyl)-2-methyl-azetidine-2-carbonyl]-(3-chloro-benzyl)-amino]-butyric acid

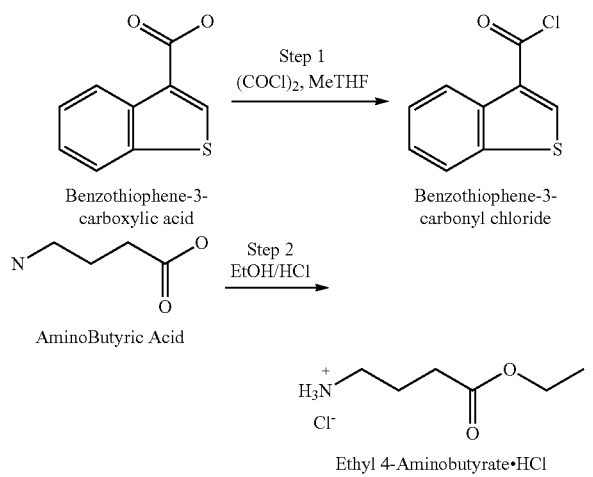

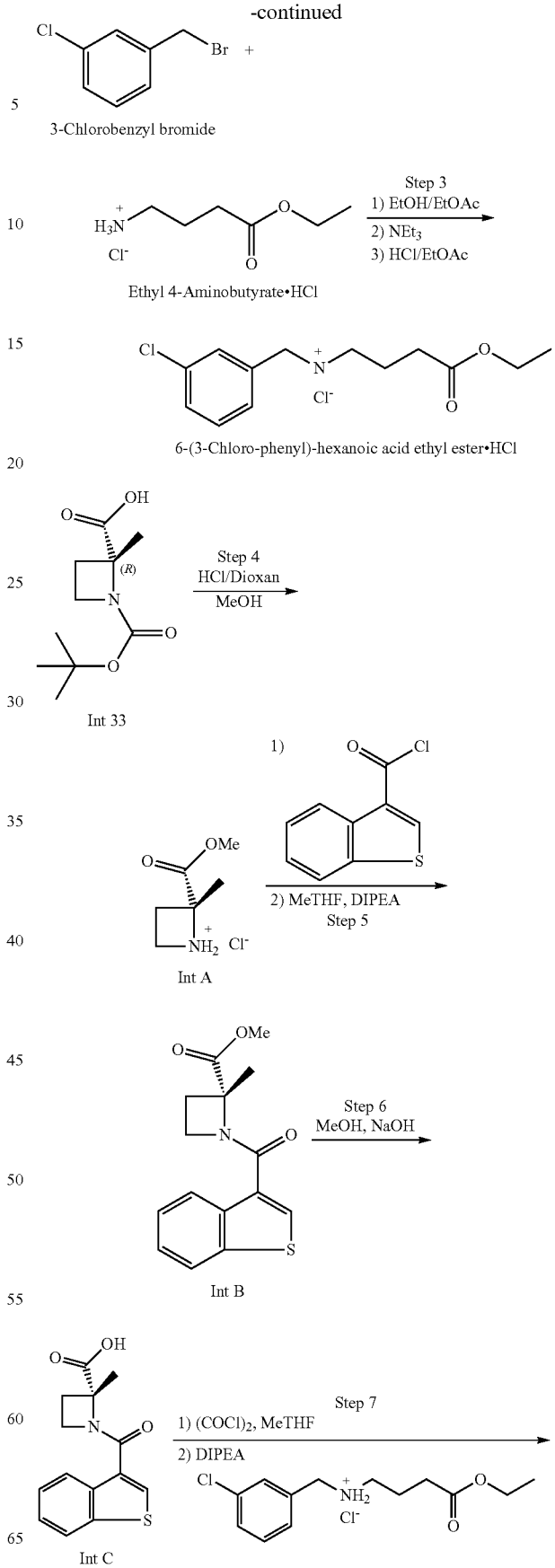

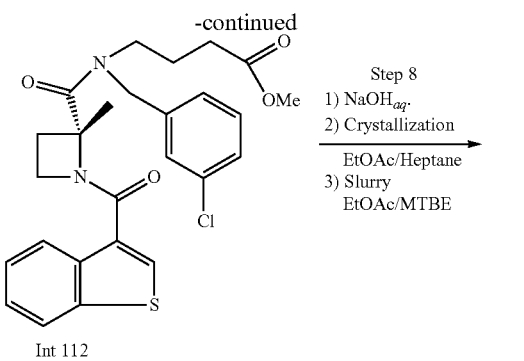

Int 112

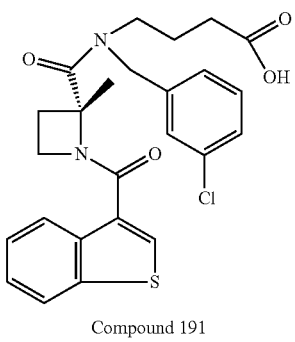

Compound 191

Step 1: Synthesis of the benzo[b]thiophene-3-carbonyl chloride

To benzothiophene carboxylic acid (7 g) in MeTHF (6.5 Vols, 45.5 mL) is added a catalytic amount of DMF (0.01 eq.). Then, oxalyl chloride (1.1 eq.) is charged slowly to control the gaz release. After 16 h of stirring at 20° C., the end of the reaction is controlled by HPLC. MeTHF (6.5 Vols) is next added and the reaction mixture is concentrated to 5 volumes to remove the excess of oxalyl chloride. The resulting benzo[b]thiophene-3-carbonyl chloride is stored in a MeTHF solution.

Step 2: Synthesis of the Ethyl 4-amino butyrate hydrochloride

Aminobutyric acid (103.6 g, 5.5 eq.) is dissolved in ethanol (1.5 Vols, 156 mL) at 15° C. A solution of hydrochloric acid in ethanol 2.5N (2.2 eq., 890 mL) is slowly added over 30 min. After 16 h, the reaction is complete (TLC), and the ethyl 4-aminobutyrate solution in ethanol is concentrated to 2 residual volumes.

Step 3: Synthesis of ethyl 4-(3-chlorobenzylamino) butyrate hydrochloride

To the solution of ethyl 4-aminobutyrate in ethanol obtained in step 2 above, is added ethyl acetate (12 Vols, 450 mL), then the reaction mixture is cooled to 0-5° C. The triethylamine (5.7 eq.) is charged, followed by the addition of the 3-chlorobenzyl bromide (1 eq., 37.6 g) over 30 min. The reaction is ended after 5 h (HPLC monitoring), and quenched by the addition of water (3 Vols). The organic phase is separated, and the aqueous phase is extracted twice with ethyl acetate (3 Vols). The organic phases are combined and washed several times by water (7 Vols) to eliminate the triethylamine, and finally washed with a brine solution (7 Vols). A solution of HCl in EtOAc at 1.1N is added (1.2 eq.) to precipitate ethyl 4-(3-chlorobenzylamino) butyrate hydrochloride. After 1 h stirring at 5° C., the resulting white powder is filtered, rinsed twice with ethyl acetate (2 Vols), and dried at 40° C. under reduced pressure for 16 h.

Step 4: Synthesis of Int A: (R)-Methyl-2-methyl-azetidine-2-carboxylate hydrochloride salt Int 33 (7 g) is dissolved in methanol (4 Vols, 28 mL) and a solution of HCl/dioxan at 4N (5 eq., 40.6 mL) is added. The reaction mixture is stirred for 16 h at 30° C. Once the reaction is complete, a solvent exchange from methanol to MeTHF-dioxan is performed to finally store the suspension of Int A in 5 volumes of MeTHF-dioxan.

Step 5: Synthesis of Int B: (R)-methyl 1-(benzo[b]thiophene-2-carbonyl)-2-methyl azetidine-2-carboxylate To Int A (5.4 g) in MeTHF/dioxan suspension is added DIPEA (5 eq.). After 1 h stirring at 20° C., the pH is adjusted at 10 (pH≥9 targeted), and the reaction is cooled down to 5° C. Then, the solution of benzothiophene 3-carbonyl chloride (Step 1) in MeTHF (1.05 eq.) is charged over 30 min. The reaction mixture is next warmed up to 20° C. and left stirring 16 h to complete the reaction. After a quench with water (7 Vols), washed twice with 7 HCl 1N (7 Vols), and water (7 Vols) to obtain Int B in MeTHF.

Step 6: Synthesis of Int C: (R)-methyl 1-(benzo[b]thiophene-2-carbonyl)-2-methyl azetidine-2-carboxylic acid A solvent exchange from the MeTHF to methanol (7 Vols, 49 mL) is performed on the Int B solution obtained in Step 5 above. Then, an aqueous solution of NaOH 2N (2.5 eq.) is added. After 1 h stirring at 20° C., the completion of the reaction is obtained. The methanol is then removed by distillation (0.2% w/w), dichloromethane (3 Vols, 21 mL) is added followed by the acidification of the aqueous layer with an aqueous solution of HCl at 2N (to pH=1). Int 4 is then extracted with dichloromethane (7 Vols, 49 mL). Finally, the organic solution is concentrated to 1.5 volumes (10 mL).

The precipitated residual benzothiophene carboxylic acid is separated by filtration, rinsed with dichloromethane (0.5 Vols). Int C is obtained in solution in 2 volumes of dichloromethane.

Diisopropylether (7 Vols, 49 mL) is then added, the resulting mixture is heated to 40° C. for 2 h and cooled down to 20° C. in 1 h. The reaction mixture is maintained for 16 h at 20° C., then heptane (5 Vols, 35 mL) is added, cooled down to 5° C. After 2 h at that temperature, Int C has precipitated, is filtered, rinsed twice with diisopropylether (2 Vols, 14 mL) and dried for 16 h at 40° C. under reduced pressure.

Step 7: Synthesis of Int 112: Ethyl 4-[[(R)-1-(benzo[b]thiophene-3-carbonyl)-2-methyl-azetidine-2-carbonyl]-(3-chloro-benzyl)-amino]-butyrate Int C (31 g) is dissolved in MeTHF (25 Vols, 775 mL) and a catalytic amount of DMF (0.01 eq.) is charged. The resulting mixture is cooled down to 10° C. and oxalyl chloride (1.1 eq.) is added slowly. After 30 min, DIPEA (9 eq.) is added to reach a pH≥9 (10). Int 5 (1.3 eq.) is added over 30 min. After 16 h of stirring at 20° C., the reaction mixture is quenched with water (7 Vols, 217 mL), washed twice with HCl 2N (7

Vols, 217 mL) and water (7 Vols, 217 mL). The resulting Int 112 is stored in MeTHF (10 Vols, 310 mL).

Step 8: Synthesis of Compound 191: Ethyl 4-[[(R)-1-(benzo[b]thiophene-3-carbonyl)-2-methyl-azetidine-2-carbonyl]-(3-chloro-benzyl)-amino]-butyric acid A solvent exchange from MeTHF to ethanol (7 Vols, 217 mL) of Int 112 solution (31 g) obtained in Step 7 above is performed. Then, an aqueous solution of NaOH 1N (2.5 eq.) is added. After 15 h stirring at 20° C., a full conversion is obtained. The reaction mixture is then acidified with HCl 2N (10 Vols) to pH=1 and is extracted with dichloromethane (15 Vols).

A solvent exchange from dichloromethane to ethyl acetate (7 Vols) is performed. The resulting ethyl acetate solution is heated to 50° C., and heptane (4.5 Vols) is slowly added. A temperature drop ramp to 10° C. is performed over 1 h, and heptane (5 Vols) is added. The resulting suspension is then re-heated to 70° C. for 5 h. Finally, the suspension is cooled down to 10° C. over 2 h and maintained for 16 h at this temperature before filtration. The wet cake is washed twice by MTBE (2 Vols).

The wet cake is charged in the reactor and slurried at 50° C. for 5 h in a mixture EtOAc/MTBE (4 Vols). The slurry is then cooled down to 0° C. over 2 h, and maintained at 0° C. for 16 h before filtration. The wet cake is rinsed twice by MTBE (2 Vols) and dried at 40° C. for 16 h under reduced pressure to obtain 4-[[(R)-1-(Benzo[b]thiophene-3-carbonyl)-2-methyl-azetidine-2-carbonyl]-(3-chloro-benzyl)-amino]-butyric acid (Compound 191) at 99.7% purity by HPLC.

Compounds of the Invention that have been or can be prepared according to the synthetic method described herein are listed in Table IIa below. The NMR spectral data of said compounds of the invention are given in Table IIb.

TABLE IIa

Mass spectral data of the Compounds of the Invention

| Cpd # | Structures | Name | Mtd | SM | Exact mass | MS Ms'd |
|---|---|---|---|---|---|---|
| 1 | 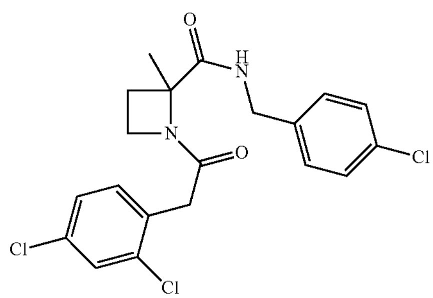 [SMILES: CC1(C(=O)NCc2ccc(Cl)cc2)CCN1C(=O)Cc1ccc(Cl)cc1Cl] | 1-[2-(2,4-Dichloro-phenyl)-acetyl]-2-methyl-azetidine-2-carboxylic acid 4-chloro-benzylamide | F | Int 28 and (2,4-Dichloro-phenyl)-acetic acid | 424.1 | 425.3 (M + 1, $^{35}$Cl) |
| 2 | 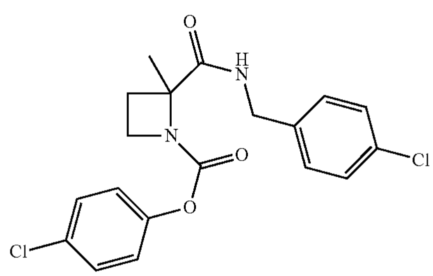 [SMILES: CC1(C(=O)NCc2ccc(Cl)cc2)CCN1C(=O)Oc1ccc(Cl)cc1] | 2-(4-Chloro-benzylcarbamoyl)-2-methyl-azetidine-1-carboxylic acid acid 4-chloro-phenyl ester | H | Int 28 and 4-chlorophen-yl-chloro-formate | 392.1 | 393.3 (M + 1, $^{35}$Cl) |
| 3 | 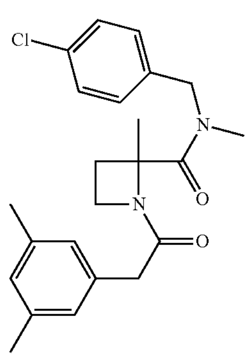 [SMILES: Cc1cc(C)cc(CC(=O)N2CCC2(C)C(=O)N(C)Cc2ccc(Cl)cc2)c1] | 1-[2-(3,5-Dimethyl-phenyl)-acetyl]-2-methyl-azetidine-2-carboxylic acid (4-chloro-benzyl)-methyl-amide | F | Int 14 and (3,5-Dimethyl-phenyl)-acetic acid | 398.2 | 399.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 4 | 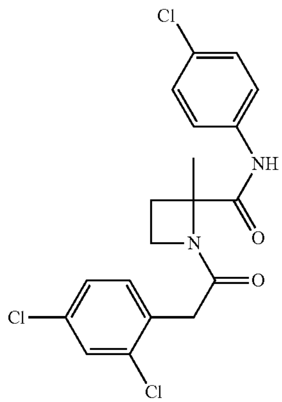 [SMILES: CC1(C(=O)Nc2ccc(Cl)cc2)CCN1C(=O)Cc1ccc(Cl)cc1Cl] | 1-[2-(2,4-Dichloro-phenyl)-acetyl]-2-methyl-azetidine-2-carboxylic acid (4-chloro-phenyl)-amide | F | Int 15 and (2,4-Dichloro-phenyl)-acetic acid | 410.0 | 411.2 (M + 1, $^{35}$Cl) |
| 5 | 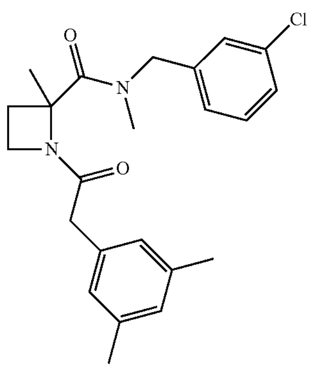 [SMILES: Cc1cc(C)cc(CC(=O)N2CCC2(C)C(=O)N(C)Cc2cccc(Cl)c2)c1] | 1-[2-(3,5-Dimethyl-phenyl)-acetyl]-2-methyl-azetidine-2-carboxylic acid (3-chloro-benzyl)-methyl-amide | I1 | Int 119 and Methyl-(3-chlorobenz-yl)-amine | 398.2 | 399.2 (M + 1, $^{35}$Cl) |
| 6 | 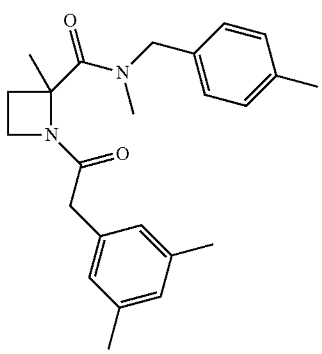 [SMILES: Cc1ccc(CN(C)C(=O)C2(C)CCN2C(=O)Cc2cc(C)cc(C)c2)cc1] | 1-[2-(3,5-Dimethyl-phenyl)-acetyl]-2-methyl-azetidine-2-carboxylic acid methyl-(4-methyl-benzyl)-amide | I1 | Int 119 and Methyl-(4-methyl-benzyl)-amine | 378.2 | 379.4 (M + 1) |
| 7 | 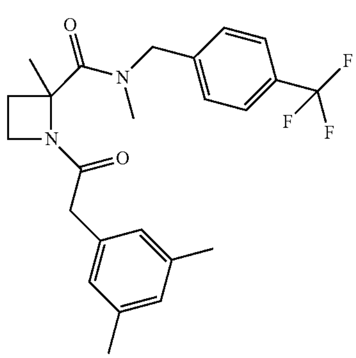 [SMILES: Cc1cc(C)cc(CC(=O)N2CCC2(C)C(=O)N(C)Cc2ccc(C(F)(F)F)cc2)c1] | 1-[2-(3,5-Dimethyl-phenyl)-acetyl]-2-methyl-azetidine-2-carboxylic acid methyl-(4-trifluoromethyl-benzyl)-amide | I1 | Int 119 and Methyl-(4-methyl-benzyl)-amine | 432.2 | 433.4 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 8 | 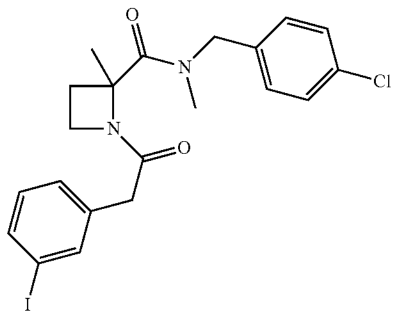 [SMILES: CN(Cc1ccc(Cl)cc1)C(=O)C1(C)CCN1C(=O)Cc1cccc(I)c1] | 1-[2-(3-Iodo-phenyl)-acetyl]-2-methyl-azetidine-2-carboxylic acid (4-chloro-benzyl)-methyl-amide | F | Int 14 and (3-Iodo-phenyl)-acetic acid | 496.0 | 497.2 (M + 1, $^{35}$Cl) |
| 9 | 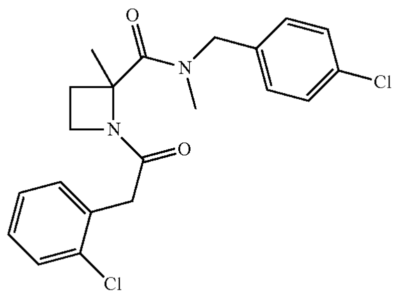 [SMILES: CN(Cc1ccc(Cl)cc1)C(=O)C1(C)CCN1C(=O)Cc1ccccc1Cl] | 1-[2-(2-Chloro-phenyl)-acetyl]-2-methyl-azetidine-2-carboxylic acid (4-chloro-benzyl)-methyl-amide | F | Int 14 and (2-Chloro-phenyl)-acetic acid | 404.1 | 405.3 (M + 1, $^{35}$Cl) |
| 10 | 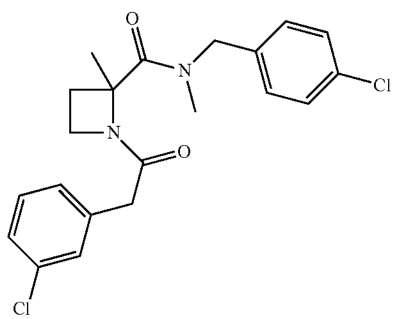 [SMILES: CN(Cc1ccc(Cl)cc1)C(=O)C1(C)CCN1C(=O)Cc1cccc(Cl)c1] | 1-[2-(3-Chloro-phenyl)-acetyl]-2-methyl-azetidine-2-carboxylic acid (4-chloro-benzyl)-methyl-amide | F | Int 14 and (3-Chloro-phenyl)-acetic acid | 404.1 | 405.3 (M + 1, $^{35}$Cl) |
| 11 | 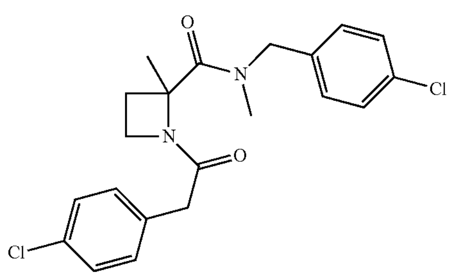 [SMILES: CN(Cc1ccc(Cl)cc1)C(=O)C1(C)CCN1C(=O)Cc1ccc(Cl)cc1] | 1-[2-4-Chloro-phenyl)-acetyl]-2-methyl-azetidine-2-carboxylic acid (4-chloro-benzyl)-methyl-amide | F | Int 14 and (4-Chloro-phenyl)-acetic acid | 404.1 | 405.4 (M + 1, $^{35}$Cl) |
| 12 | 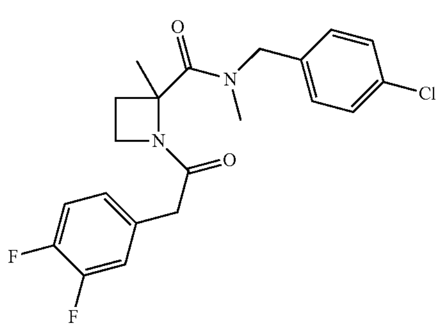 [SMILES: CN(Cc1ccc(Cl)cc1)C(=O)C1(C)CCN1C(=O)Cc1ccc(F)c(F)c1] | 1-[2-(3,4-Difluoro-phenyl)-acetyl]-2-methyl-azetidine-2-carboxylic acid (4-chloro-benzyl)-methyl-amide | F | Int 14 and (3,4-Difluoro-phenyl)-acetic acid | 406.1 | 407.3 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 13 | 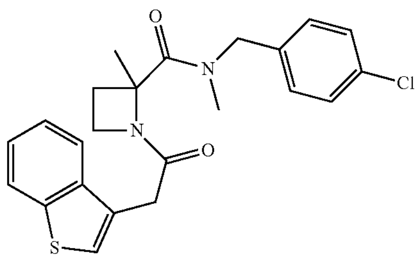 [SMILES: CN(Cc1ccc(Cl)cc1)C(=O)C1(C)CCN1C(=O)Cc1csc2ccccc12] | 1-(2-Benzo[b]thiophen-3-yl-acetyl)-2-methyl-azetidine-2-carboxylic acid (4-chloro-benzyl)-methyl-amide | F | Int 14 and Benzo[b]thiophen-3-yl-acetic acid | 426.1 | 427.3 (M + 1, $^{35}$Cl) |
| 14 | 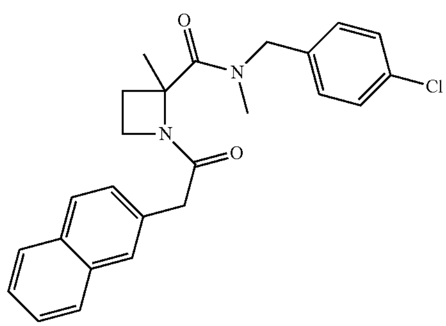 [SMILES: CN(Cc1ccc(Cl)cc1)C(=O)C1(C)CCN1C(=O)Cc1ccc2ccccc2c1] | 2-Methyl-1-(2-naphthalen-2-yl-acetyl)-azetidine-2-carboxylic acid (4-chloro-benzyl)-methyl-amide | F | Int 14 and Naphthalen-2-yl-acetic acid | 420.2 | 421.3 (M + 1, $^{35}$Cl) |
| 15 | 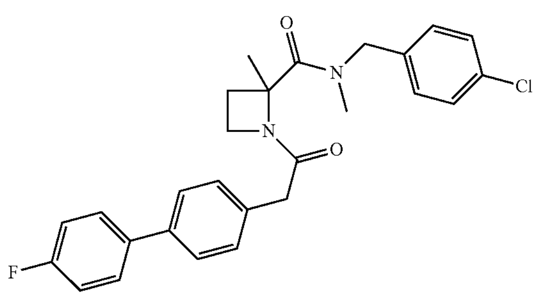 [SMILES: CN(Cc1ccc(Cl)cc1)C(=O)C1(C)CCN1C(=O)Cc1ccc(-c2ccc(F)cc2)cc1] | 1-[2-(4'-Fluoro-biphenyl-4-yl)-acetyl]-2-methyl-azetidine-2-carboxylic acid (4-chloro-benzyl)-methyl-amide | F | Int 14 and (4'-Fluoro-biphenyl-4-yl)-acetic acid | 464.2 | 465.4 (M + 1, $^{35}$Cl) |
| 16 | 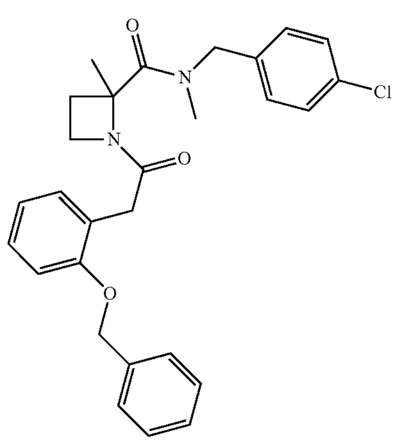 [SMILES: CN(Cc1ccc(Cl)cc1)C(=O)C1(C)CCN1C(=O)Cc1ccccc1OCc1ccccc1] | 1-[2-(2-Benzyloxy-phenyl)-acetyl]-2-methyl-azetidine-2-carboxylic acid (4-chloro-benzyl)-methyl-amide | F | Int 14 and (2-Benzyloxy-phenyl)-acetic acid | 476.2 | 477.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 17 | 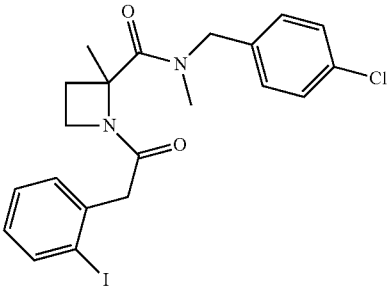 [SMILES: CN(Cc1ccc(Cl)cc1)C(=O)C1(C)CCN1C(=O)Cc1ccccc1I] | 1-[2-(2-Iodo-phenyl)-acetyl]-2-methyl-azetidine-2-carboxylic acid (4-chloro-benzyl)-methyl-amide | F | Int 14 and (2-Iodo-phenyl)-acetic acid | 496.0 | 497.3 (M + 1, $^{35}$Cl) |
| 18 | 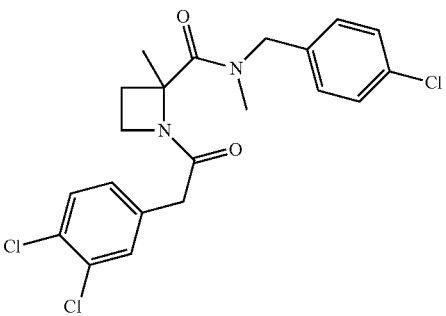 [SMILES: CN(Cc1ccc(Cl)cc1)C(=O)C1(C)CCN1C(=O)Cc1ccc(Cl)c(Cl)c1] | 1-[2-(3,4-Dichloro-phenyl)-acetyl]-2-methyl-azetidine-2-carboxylic acid (4-chloro-benzyl)-methyl-amide | F | Int 14 and (3,4-Dichloro-phenyl)-acetic acid | 438.1 | 439.3 (M + 1, $^{35}$Cl) |
| 19 | 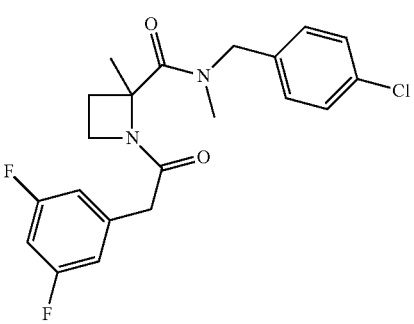 [SMILES: CN(Cc1ccc(Cl)cc1)C(=O)C1(C)CCN1C(=O)Cc1cc(F)cc(F)c1] | 1-[2-(3,5-Difluoro-phenyl)-acetyl]-2-methyl-azetidine-2-carboxylic acid (4-chloro-benzyl)-methyl-amide | F | Int 14 and (3,5-Difluoro-phenyl)-acetic acid | 406.1 | 407.3 (M + 1, $^{35}$Cl) |
| 20 | 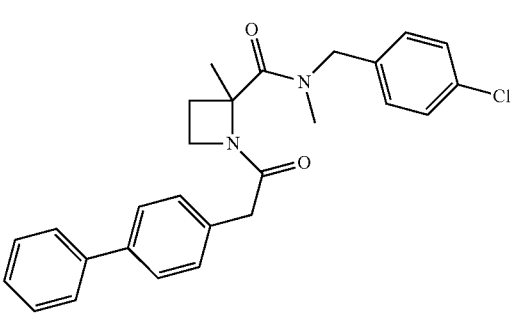 [SMILES: CN(Cc1ccc(Cl)cc1)C(=O)C1(C)CCN1C(=O)Cc1ccc(-c2ccccc2)cc1] | 1-(2-Biphenyl-4-yl-acetyl)-2-methyl-azetidine-2-carboxylic acid (4-chloro-benzyl)-methyl-amide | U | Int 103 and phenyl boronic acid | 446.2 | 447.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 21 | 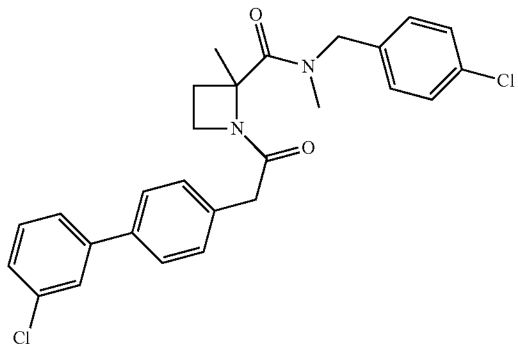 [SMILES: CN(Cc1ccc(Cl)cc1)C(=O)C1(C)CCN1C(=O)Cc1ccc(-c2cccc(Cl)c2)cc1] | 1-[2-(3'-Chloro-biphenyl-4-yl)-acetyl]-2-methyl-azetidine-2-carboxylic acid (4-chloro-benzyl)-methyl-amide | U | Int 103 and 3-chloro-phenyl boronic acid | 480.1 | 481.2 (M + 1, $^{35}$Cl) |
| 22 | 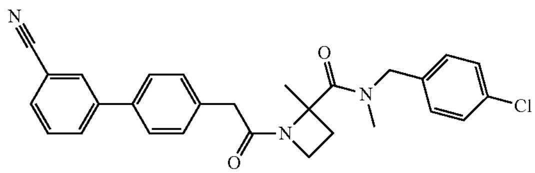 [SMILES: CN(Cc1ccc(Cl)cc1)C(=O)C1(C)CCN1C(=O)Cc1ccc(-c2cccc(C#N)c2)cc1] | 1-[2-(3'-Cyano-biphenyl-4-yl)-acetyl]-2-methyl-azetidine-2-carboxylic acid (4-chloro-benzyl)-methyl-amide | U | Int 103 and 3-cyano-phenyl boronic acid | 471.2 | 472.2 (M + 1, $^{35}$Cl) |
| 23 | 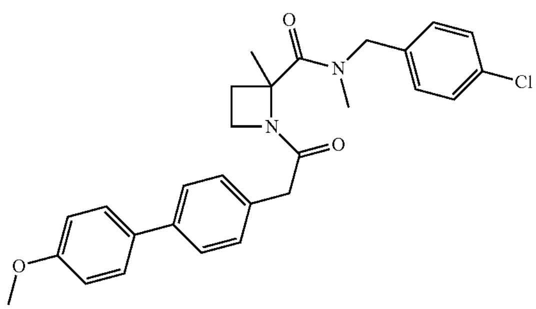 [SMILES: COc1ccc(-c2ccc(CC(=O)N3CCC3(C)C(=O)N(C)Cc3ccc(Cl)cc3)cc2)cc1] | 1-[2-(4'-Methoxy-biphenyl-4-yl)-acetyl]-2-methyl-azetidine-2-carboxylic acid (4-chloro-benzyl)-methyl-amide | U | Int 103 and 4-methoxy-phenyl boronic acid | 476.2 | 477.2 (M + 1, $^{35}$Cl) |
| 24 | 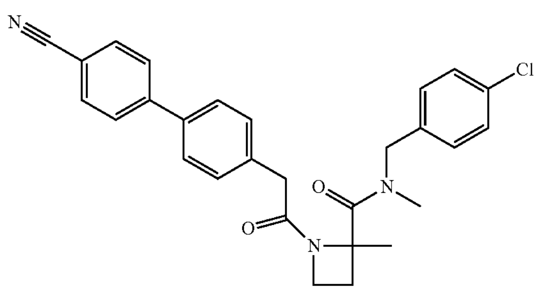 [SMILES: CN(Cc1ccc(Cl)cc1)C(=O)C1(C)CCN1C(=O)Cc1ccc(-c2ccc(C#N)cc2)cc1] | 1-[2-(4'-Cyano-biphenyl-4-yl)-acetyl]-2-methyl-azetidine-2-carboxylic acid (4-chloro-benzyl)-methyl-amide | U | Int 103 and 4-cyano-phenyl boronic acid | 471.2 | 472.2 (M + 1, $^{35}$Cl) |
| 25 | 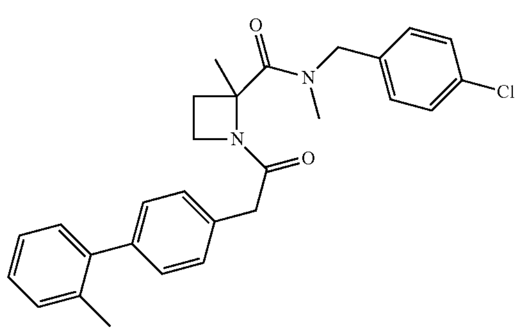 [SMILES: Cc1ccccc1-c1ccc(CC(=O)N2CCC2(C)C(=O)N(C)Cc2ccc(Cl)cc2)cc1] | 2-Methyl-1-[2-(2'-methyl-biphenyl-4-yl)-acetyl]-azetidine-2-carboxylic acid (4-chloro-benzyl)-methyl-amide | U | Int 103 and 2-methyl-phenyl boronic acid | 460.2 | 461.3 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 26 | 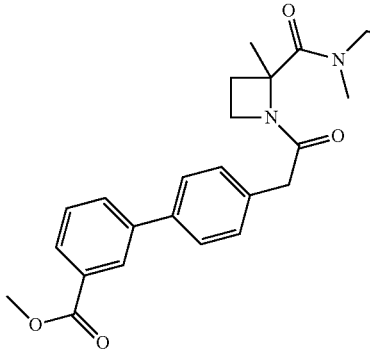 | methyl 4'-(2-(2-((4-chlorobenzyl)(methyl)carbamoyl)-2-methylazetidin-1-yl)-2-oxoethyl)biphenyl-3-carboxylate | U | Int 103 and 3-methoxy-carbonyl-phenyl boronic acid | 504.2 | 505.2 (M + 1, $^{35}$Cl) |
| 27 | 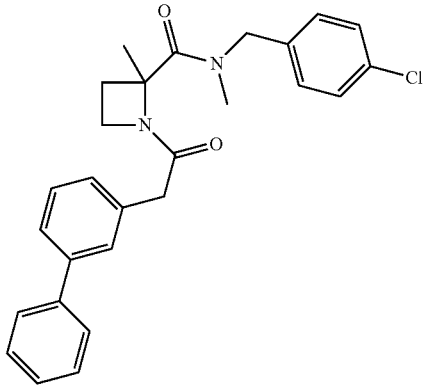 [SMILES: CN(Cc1ccc(Cl)cc1)C(=O)C1(C)CCN1C(=O)Cc1cccc(-c2ccccc2)c1] | 1-(2-Biphenyl-3-yl-acetyl)-2-methyl-azetidine-2-carboxylic acid (4-chloro-benzyl)-methyl-amide | U | Cpd 8 and phenyl boronic acid | 446.2 | 447.2 (M + 1, $^{35}$Cl) |
| 28 | 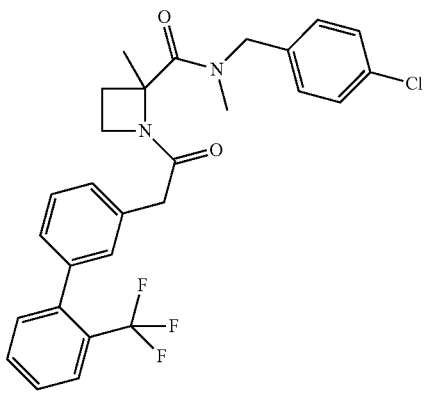 [SMILES: CN(Cc1ccc(Cl)cc1)C(=O)C1(C)CCN1C(=O)Cc1cccc(-c2ccccc2C(F)(F)F)c1] | 2-Methyl-1-[2-(2'-trifluoromethyl-biphenyl-3-yl)-acetyl]-azetidine-2-carboxylic acid (4-chloro-benzyl)-methyl-amide | U | Cpd 8 and 2-trifluoro-methyl-phenyl boronic acid | 514.2 | 515.1 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 29 | 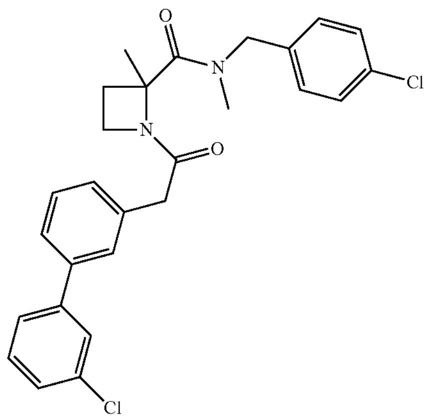 [SMILES: CN(Cc1ccc(Cl)cc1)C(=O)C1(C)CCN1C(=O)Cc1cccc(-c2cccc(Cl)c2)c1] | 1-[2-(3'-Chloro-biphenyl-3-yl)-acetyl]-2-methyl-azetidine-2-carboxylic acid (4-chloro-benzyl)-methyl-amide | U | Cpd 8 and 3-chloro-phenyl boronic acid | 480.1 | 481 (M + 1, $^{35}$Cl) |
| 30 | 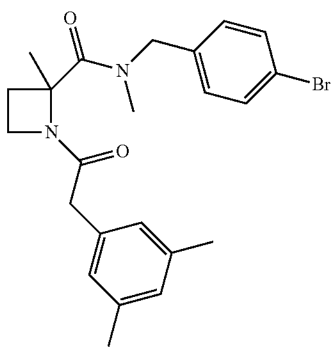 [SMILES: Cc1cc(C)cc(CC(=O)N2CCC2(C)C(=O)N(C)Cc2ccc(Br)cc2)c1] | 1-[2-(3,5-Dimethyl-phenyl)-acetyl]-2-methyl-azetidine-2-carboxylic acid (4-bromo-benzyl)-methyl-amide | I1 | Int 119 and Methyl-(4-bromo-benzyl)-amine | 442.1 | 443.3 (M + 1, $^{79}$Br) |
| 31 | 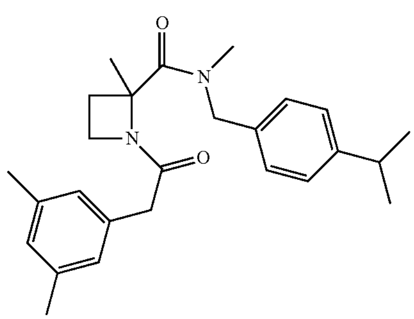 [SMILES: Cc1cc(C)cc(CC(=O)N2CCC2(C)C(=O)N(C)Cc2ccc(C(C)C)cc2)c1] | 1-[2-(3,5-Dimethyl-phenyl)-acetyl]-2-methyl-azetidine-2-carboxylic acid (4-isopropyl-benzyl)-methyl-amide | I1 | Int 46 and int 119 | 406.3 | 407.5 (M + 1) |
| 32 | 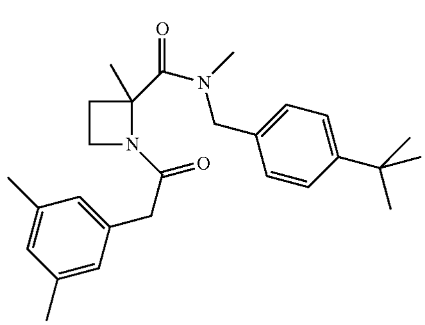 [SMILES: Cc1cc(C)cc(CC(=O)N2CCC2(C)C(=O)N(C)Cc2ccc(C(C)(C)C)cc2)c1] | 1-[2-(3,5-Dimethyl-phenyl)-acetyl]-2-methyl-azetidine-2-carboxylic acid (4-tert-butyl-benzyl)-methyl-amide | I1 | Int 47 and int 119 | 420.3 | 421.5 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 33 | 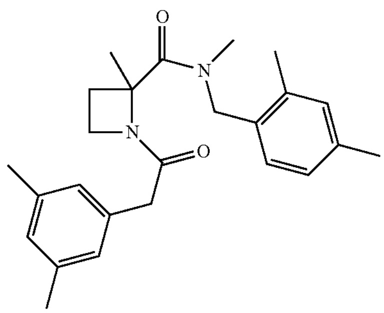 | 1-[2-(3,5-Dimethyl-phenyl)-acetyl]-2-methyl-azetidine-2-carboxylic acid (2,4-dimethyl-benzyl)-methyl-amide | I1 | Int 48 and int 119 | 392.2 | 393.5 (M + 1) |
| 34 | 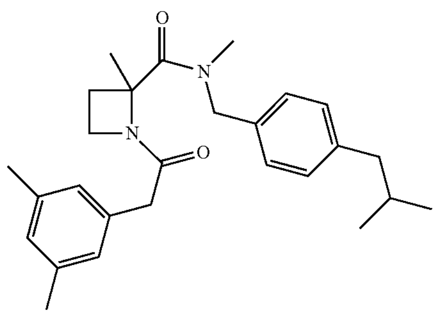 [SMILES: Cc1cc(C)cc(CC(=O)N2CCC2(C)C(=O)N(C)Cc2ccc(CC(C)C)cc2)c1] | 1-[2-(3,5-Dimethyl-phenyl)-acetyl]-2-methyl-azetidine-2-carboxylic acid (4-isobutyl-benzyl)-methyl-amide | I1 | Int 49 and int 119 | 420.3 | 421.4 (M + 1) |
| 35 | 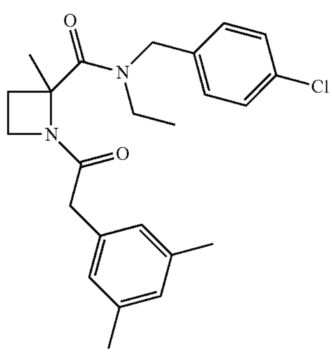 [SMILES: CCN(Cc1ccc(Cl)cc1)C(=O)C1(C)CCN1C(=O)Cc1cc(C)cc(C)c1] | 1-[2-(3,5-Dimethyl-phenyl)-acetyl]-2-methyl-azetidine-2-carboxylic acid (4-chloro-benzyl)-ethyl-amide | I1 | Int 50 and int 119 | 412.2 | 413.4 (M + 1, $^{35}$Cl) |
| 36 | 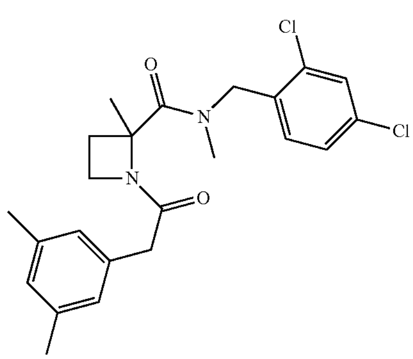 [SMILES: Cc1cc(C)cc(CC(=O)N2CCC2(C)C(=O)N(C)Cc2ccc(Cl)cc2Cl)c1] | 1-[2-(3,5-Dimethyl-phenyl)-acetyl]-2-methyl-azetidine-2-carboxylic acid (2,4-dichloro-benzyl)-methyl-amide | I1 | Int 51 and int 119 | 432.1 | 433.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 37 | 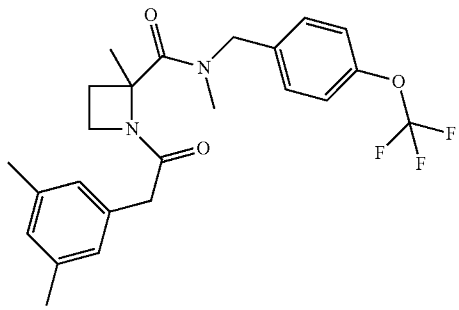 [SMILES: Cc1cc(C)cc(CC(=O)N2CCC2(C)C(=O)N(C)Cc2ccc(OC(F)(F)F)cc2)c1] | 1-[2-(3,5-Dimethyl-phenyl)-acetyl]-2-methyl-azetidine-2-carboxylic acid methyl-(4-trifluoromethoxy-benzyl)-amide | I1 | Int 52 and int 119 | 448.2 | 449.4 (M + 1) |
| 38 | 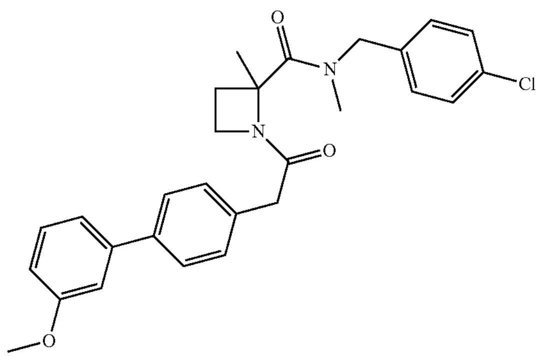 [SMILES: COc1cccc(-c2ccc(CC(=O)N3CCC3(C)C(=O)N(C)Cc3ccc(Cl)cc3)cc2)c1] | 1-[2-(3'-Methoxy-biphenyl-4-yl)-acetyl]-2-methyl-azetidine-2-carboxylic acid (4-chloro-benzyl)-methyl-amide | U | Int 103 and 3-methoxy-phenyl boronic acid | 477.0 | 477.2 (M + 1, $^{35}$Cl) |
| 39 | 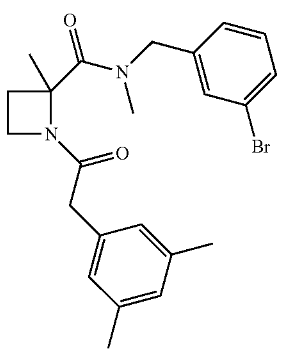 [SMILES: Cc1cc(C)cc(CC(=O)N2CCC2(C)C(=O)N(C)Cc2cccc(Br)c2)c1] | 1-[2-(3,5-Dimethyl-phenyl)-acetyl]-2-methyl-azetidine-2-carboxylic acid (3-bromo-benzyl)-methyl-amide | I1 | Int 119 and Methyl-(3-bromo-benzyl)-amine | 442.1 | 443.3 (M + 1, $^{79}$Br) |
| 41 | 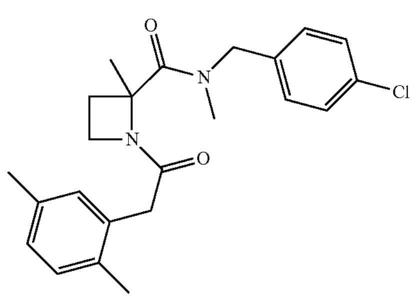 [SMILES: Cc1ccc(C)c(CC(=O)N2CCC2(C)C(=O)N(C)Cc2ccc(Cl)cc2)c1] | 1-[2-(2,5-Dimethyl-phenyl)-acetyl]-2-methyl-azetidine-2-carboxylic acid (4-chloro-benzyl)-methyl-amide | F | Int 14 and (2,5-Dimethyl-phenyl)-acetic acid | 398.2 | 399.3 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 42 | 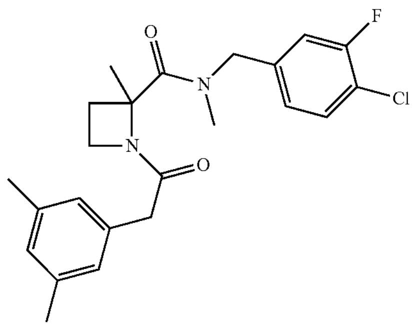 [SMILES: Cc1cc(C)cc(CC(=O)N2CCC2(C)C(=O)N(C)Cc2ccc(Cl)c(F)c2)c1] | 1-[2-(3,5-Dimethyl-phenyl)-acetyl]-2-methyl-azetidine-2-carboxylic acid (4-chloro-3-fluoro-benzyl)-methyl-amide | I1 | Int 54 and int 119 | 416.2 | 417.3 (M + 1, $^{35}$Cl) |
| 43 | 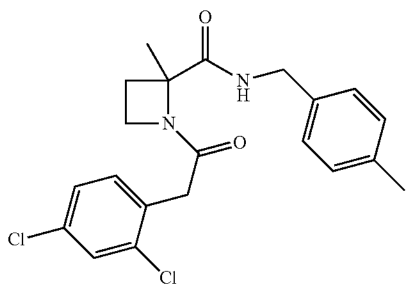 [SMILES: Cc1ccc(CNC(=O)C2(C)CCN2C(=O)Cc2ccc(Cl)cc2Cl)cc1] | 1-[2-(2,4-Dichloro-phenyl)-acetyl]-2-methyl-azetidine-2-carboxylic acid 4-methyl-benzylamide | I2 | Int 120 and 4-methyl-benzylamine | 404.1 | 405.3 (M + 1, $^{35}$Cl) |
| 44 | 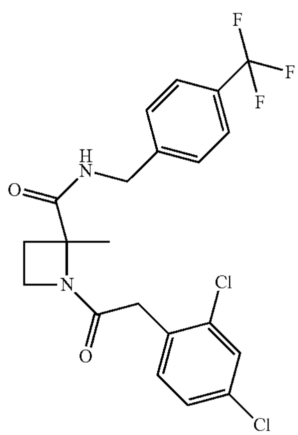 [SMILES: CC1(C(=O)NCc2ccc(C(F)(F)F)cc2)CCN1C(=O)Cc1ccc(Cl)cc1Cl] | 1-[2-(2,4-Dichloro-phenyl)-acetyl]-2-methyl-azetidine-2-carboxylic acid 4-trifluoromethyl-benzylamide | I1 | Int 120 and 4-trifluoro-methyl-benzylamine | 458.1 | 459.1 (M + 1, $^{35}$Cl) |
| 45 | 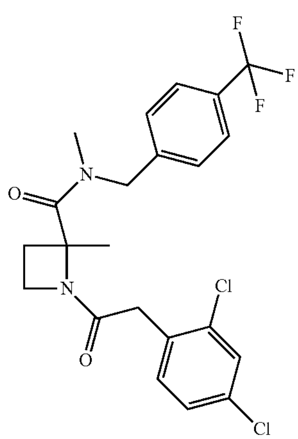 [SMILES: CN(Cc1ccc(C(F)(F)F)cc1)C(=O)C1(C)CCN1C(=O)Cc1ccc(Cl)cc1Cl] | 1-[2-(2,4-Dichloro-phenyl)-acetyl]-2-methyl-azetidine-2-carboxylic acid methyl-(4-trifluoromethyl-benzyl)-amide | I1 | Int 120 and Methyl-(4-trifluoro-methyl-benzyl)-amine | 472.1 | 473.1 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 46 | 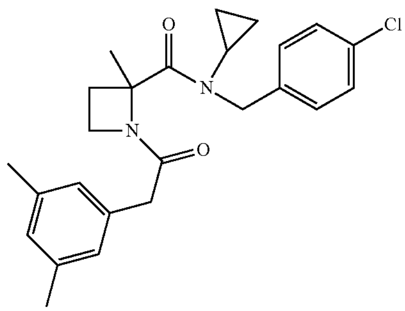 [SMILES: Cc1cc(C)cc(CC(=O)N2CCC2(C)C(=O)N(Cc2ccc(Cl)cc2)C2CC2)c1] | 1-[2-(3,5-Dimethyl-phenyl)-acetyl]-2-methyl-azetidine-2-carboxylic acid (4-chloro-benzyl)-cyclopropyl-amide | I3 | Int 65 and int 119 | 424.2 | 425.2 (M + 1, $^{35}$Cl) |
| 47 | 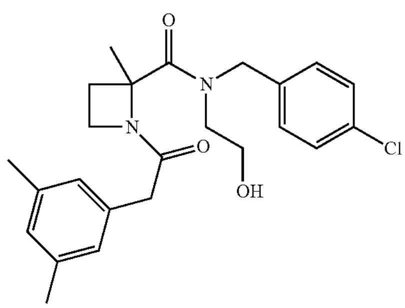 [SMILES: Cc1cc(C)cc(CC(=O)N2CCC2(C)C(=O)N(CCO)Cc2ccc(Cl)cc2)c1] | 1-[2-(3,5-Dimethyl-phenyl)-acetyl]-2-methyl-azetidine-2-carboxylic acid (4-chloro-benzyl)-(2-hydroxy-ethyl)-amide | I3 | Int 67 and int 119 | 428.2 | 429.4 (M + 1, $^{35}$Cl) |
| 48 | 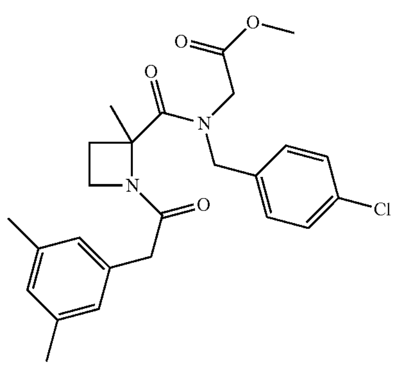 [SMILES: COC(=O)CN(Cc1ccc(Cl)cc1)C(=O)C1(C)CCN1C(=O)Cc1cc(C)cc(C)c1] | ((4-Chloro-benzyl)-{1-[2-(3,5-dimethyl-phenyl)-acetyl]-2-methyl-azetidine-2-carbonyl}-amino)-acetic acid methyl ester | I3 | Int 36 and int 119 | 456.2 | 457.4 (M + 1, $^{35}$Cl) |
| 49 | 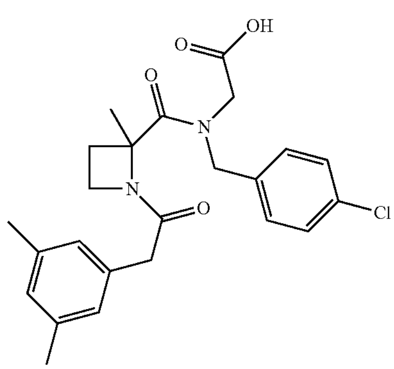 | ((4-Chloro-benzyl)-{1-[2-(3,5-dimethyl-phenyl)-acetyl]-2-methyl-azetidine-2-carbonyl}-amino)-acetic acid | J | Cpd 48 | 442.2 | 443.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 50 | 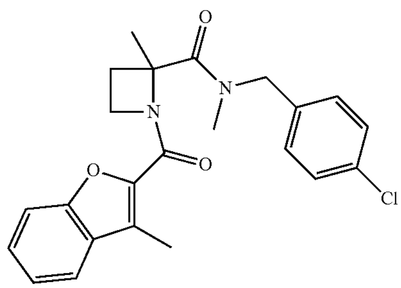 [SMILES: Cc1c(C(=O)N2CCC2(C)C(=O)N(C)Cc2ccc(Cl)cc2)oc2ccccc12] | N-(4-chlorobenzyl)-N,2-dimethyl-1-(3-methylbenzofuran-2-carbonyl)azetidine-2-carboxamide | I3 | Int 131 and Methyl-(4-chloro-benzyl)-amine | 410.1 | 411.1 (M + 1, $^{35}$Cl) |
| 51 | 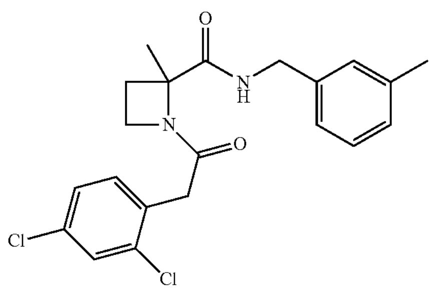 [SMILES: Cc1cccc(CNC(=O)C2(C)CCN2C(=O)Cc2ccc(Cl)cc2Cl)c1] | 1-[2-(2,4-Dichloro-phenyl)-acetyl]-2-methyl-azetidine-2-carboxylic acid 3-methyl-benzylamide | I1 | Int 120 and 3-methyl-benzylamine | 404.1 | 405.3 (M + 1, $^{35}$Cl) |
| 52 | 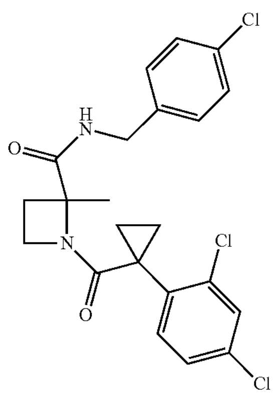 [SMILES: CC1(C(=O)NCc2ccc(Cl)cc2)CCN1C(=O)C1(c2ccc(Cl)cc2Cl)CC1] | N-(4-chlorobenzyl)-1-(1-(2,4-dichlorophenyl)cyclopropanecarbonyl)-2-methylazetidine-2-carboxamide | I1 | Int 132 and 4-chloro-benzylamine | 450.1 | 450.8 (M + 1, $^{35}$Cl) |
| 53 | 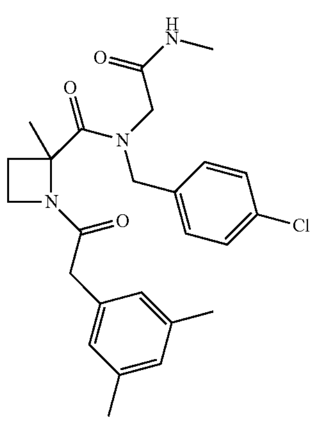 [SMILES: CNC(=O)CN(Cc1ccc(Cl)cc1)C(=O)C1(C)CCN1C(=O)Cc1cc(C)cc(C)c1] | 1-[2-(3,5-Dimethyl-phenyl)-acetyl]-2-methyl-azetidine-2-carboxylic acid (4-chloro-benzyl)-methylcarbamoylmethyl-amide | K | Cpd 49 and methylamine | 455.2 | 456.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 54 | 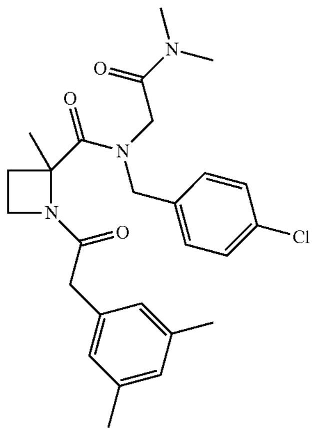 [SMILES: Cc1cc(C)cc(CC(=O)N2CCC2(C)C(=O)N(CC(=O)N(C)C)Cc2ccc(Cl)cc2)c1] | 1-[2-(3,5-Dimethyl-phenyl)-acetyl]-2-methyl-azetidine-2-carboxylic acid (4-chloro-benzyl)-dimethylcarbamoylmethyl-amide | K | Cpd 49 and dimethyl-amine | 469.2 | 470.4 (M + 1, $^{35}$Cl) |
| 55 | 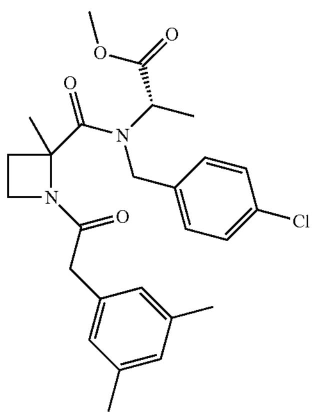 [SMILES: COC(=O)[C@H](C)N(Cc1ccc(Cl)cc1)C(=O)C1(C)CCN1C(=O)Cc1cc(C)cc(C)c1] | (S)-2-((4-Chloro-benzyl)-{1-[2-(3,5-dimethyl-phenyl)-acetyl]-2-methyl-azetidine-2-carbonyl}-amino)-propionic acid methyl ester | I3 | Int 66 and int 119 | 470.2 | 471.5 (M + 1, $^{35}$Cl) |
| 56 | 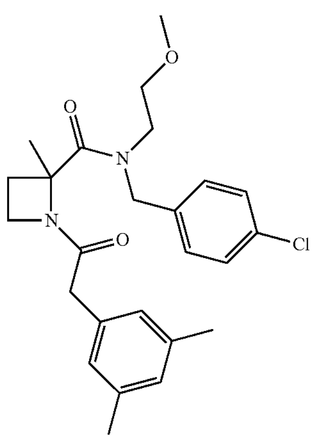 [SMILES: COCCN(Cc1ccc(Cl)cc1)C(=O)C1(C)CCN1C(=O)Cc1cc(C)cc(C)c1] | 1-[2-(3,5-Dimethyl-phenyl)-acetyl]-2-methyl-azetidine-2-carboxylic acid (4-chloro-benzyl)-(2-methoxy-ethyl)-amide | I3, 15h | Int 55 and int 119 | 442.2 | 443.4 (M + 1, $^{35}$Cl) |
| 57 | 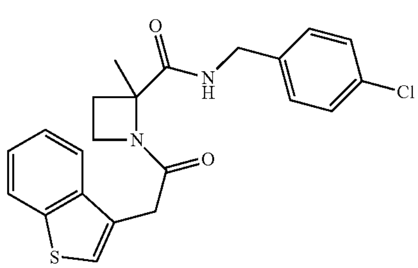 [SMILES: CC1(C(=O)NCc2ccc(Cl)cc2)CCN1C(=O)Cc1csc2ccccc12] | 1-(2-Benzo[b]thiophen-3-yl-acetyl)-2-methyl-azetidine-2-carboxylic acid 4-chloro-benzylamide | I3, 15h | Int 121 and 4-chloro-benzylamine | 412.1 | 413.3 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 58 | 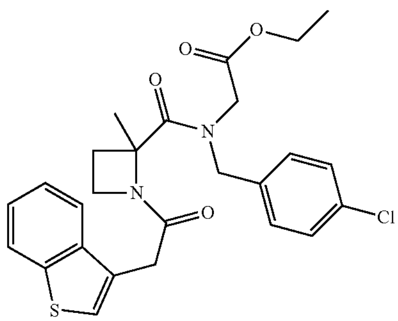 [SMILES: CCOC(=O)CN(Cc1ccc(Cl)cc1)C(=O)C1(C)CCN1C(=O)Cc1csc2ccccc12] | [[1-(2-Benzo[b]thiophen-3-yl-acetyl)-2-methyl-azetidine-2-carbonyl]-(4-chloro-benzyl)-amino]-acetic acid ethyl ester | I3, 15h | Int 56 and int 121 | 498.1 | 499.4 (M + 1, $^{35}$Cl) |
| 59 | 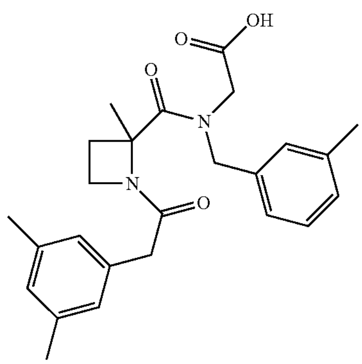 | [{1-[2-(3,5-Dimethyl-phenyl)-acetyl]-2-methyl-azetidine-2-carbonyl}-(3-methyl-benzyl)-amino]-acetic acid | J | Int 160 | 422.2 | 423.3 (M + 1) |
| 60 | 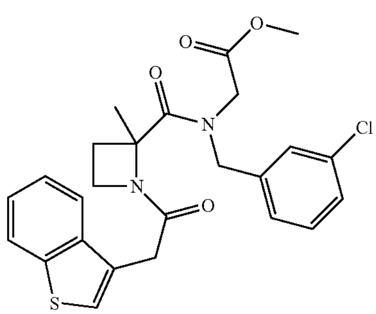 [SMILES: COC(=O)CN(Cc1cccc(Cl)c1)C(=O)C1(C)CCN1C(=O)Cc1csc2ccccc12] | [[1-(2-Benzo[b]thiophen-3-yl-acetyl)-2-methyl-azetidine-2-carbonyl]-(3-chloro-benzyl)-amino]acetic acid methyl ester | I3 | Int 38 and int 121 | 484.1 | 485.3 (M + 1, $^{35}$Cl) |
| 61 | 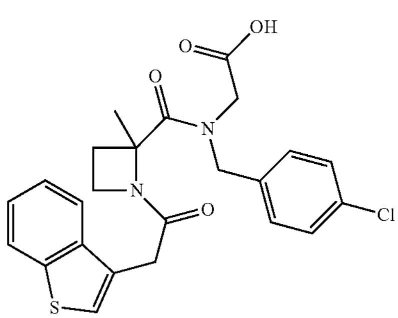 | [[1-(2-Benzo[b]thiophen-3-yl-acetyl)-2-methyl-azetidine-2-carbonyl]-(4-chloro-benzyl)-amino]-acetic acid | J | Cpd 58 | 470.1 | 471.3 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 62 | 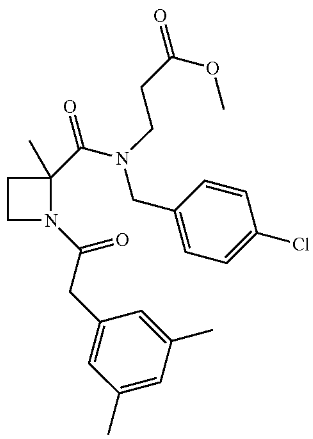 [SMILES: COC(=O)CCN(Cc1ccc(Cl)cc1)C(=O)C1(C)CCN1C(=O)Cc1cc(C)cc(C)c1] | 3-((4-Chloro-benzyl)-{1-[2-(3,5-dimethyl-phenyl)-acetyl]-2-methyl-azetidine-2-carbonyl}-amino)-propionic acid methyl ester | I3, 15h | Int 61 and int 119 | #N/A | 471.4 (M + 1, $^{35}$Cl) |
| 63 | 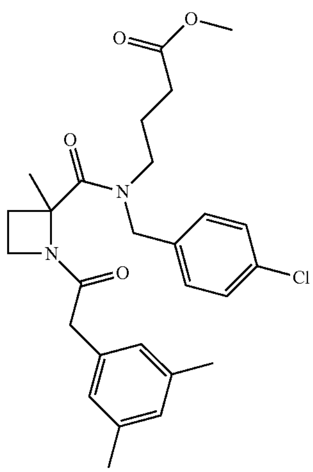 [SMILES: COC(=O)CCCN(Cc1ccc(Cl)cc1)C(=O)C1(C)CCN1C(=O)Cc1cc(C)cc(C)c1] | 4-((4-Chloro-benzyl)-{1-[2-(3,5-dimethyl-phenyl)-acetyl]-2-methyl-azetidine-2-carbonyl}-amino)-butyric acid methyl ester | I3, 15h | Int 37 and int 119 | 484.2 | 485.5 (M + 1, $^{35}$Cl) |
| 64 | 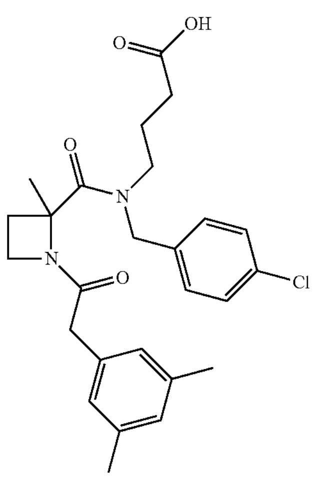 [SMILES: Cc1cc(C)cc(CC(=O)N2CCC2(C)C(=O)N(CCCC(=O)O)Cc2ccc(Cl)cc2)c1] | 4-((4-Chloro-benzyl)-{1-[2-(3,5-dimethyl-phenyl)-acetyl]-2-methyl-azetidine-2-carbonyl}-amino)-butyric acid | J | Cpd 63 | 470.2 | 471.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 65 | 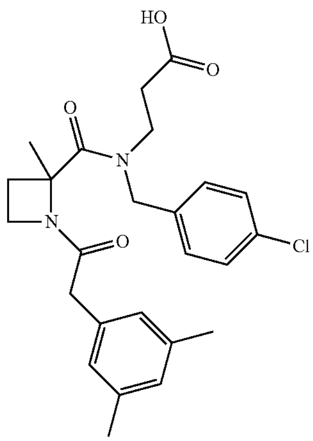 [SMILES: Cc1cc(C)cc(CC(=O)N2CCC2(C)C(=O)N(CCC(=O)O)Cc2ccc(Cl)cc2)c1] | 3-((4-Chloro-benzyl)-{1-[2-(3,5-dimethyl-phenyl)-acetyl]-2-methyl-azetidine-2-carbonyl}-amino)-propionic acid | J | Cpd 62 | 456.2 | 457.3 (M + 1, $^{35}$Cl) |
| 66 | 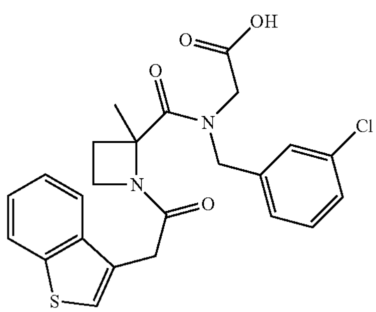 [SMILES: CC1(C(=O)N(CC(=O)O)Cc2cccc(Cl)c2)CCN1C(=O)Cc1csc2ccccc12] | [[1-(2-Benzo[b]thiophen-3-yl-acetyl)-2-methyl-azetidine-2-carbonyl]-(3-chloro-benzyl)-amino]-acetic acid | J | Cpd 60 | 470.1 | 471.3 (M + 1, $^{35}$Cl) |
| 67 | 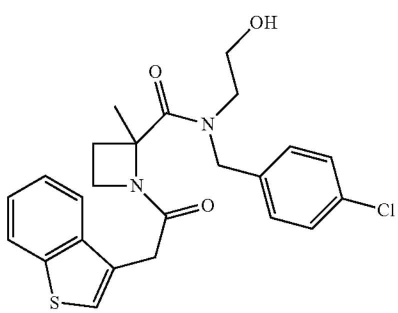 [SMILES: CC1(C(=O)N(CCO)Cc2ccc(Cl)cc2)CCN1C(=O)Cc1csc2ccccc12] | 1-(2-Benzo[b]thiophen-3-yl-acetyl)-2-methyl-azetidine-2-carboxylic acid (4-chloro-benzyl)-(2-hydroxy-ethyl)-amide | I3, 15h | Int 67 and int 121 | 456.1 | 457.3 (M + 1, $^{35}$Cl) |
| 68 | 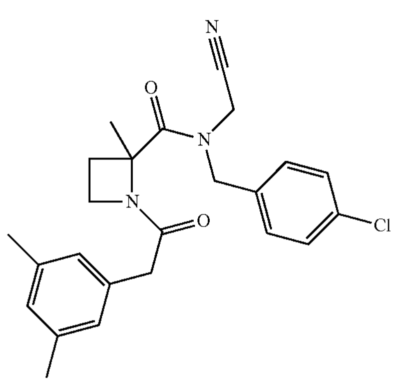 [SMILES: Cc1cc(C)cc(CC(=O)N2CCC2(C)C(=O)N(CC#N)Cc2ccc(Cl)cc2)c1] | 1-[2-(3,5-Dimethyl-phenyl)-acetyl]-2-methyl-azetidine-2-carboxylic acid (4-chloro-benzyl)-cyanomethyl-amide | I3 | Int 39 and int 119 | 423.2 | 424.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 69 | 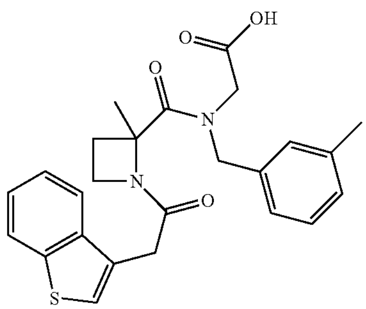 [SMILES: Cc1cccc(CN(CC(=O)O)C(=O)C2(C)CCN2C(=O)Cc2csc3ccccc23)c1] | [[1-(2-Benzo[b]thiophen-3-yl-acetyl)-2-methyl-azetidine-2-carbonyl]-(3-methyl-benzyl)-amino]-acetic acid | J | Int 161 | 450.2 | 451.2 (M + 1) |
| 70 | 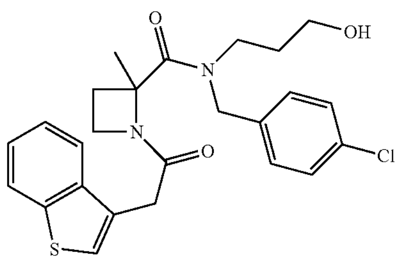 [SMILES: CC1(C(=O)N(CCCO)Cc2ccc(Cl)cc2)CCN1C(=O)Cc1csc2ccccc12] | 1-(2-Benzo[b]thiophen-3-yl-acetyl)-2-methyl-azetidine-2-carboxylic acid (4-chloro-benzyl)-(3-hydroxy-propyl)-amide | I3, 15h | Int 62 and int 121 | 470.1 | 471.3 (M + 1, $^{35}$Cl) |
| 71 | 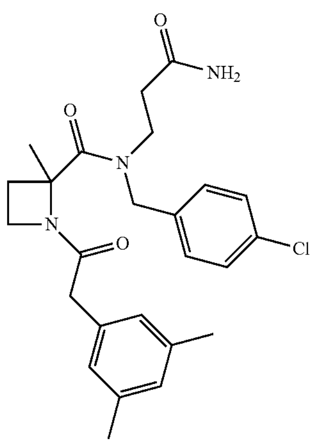 [SMILES: Cc1cc(C)cc(CC(=O)N2CCC2(C)C(=O)N(CCC(N)=O)Cc2ccc(Cl)cc2)c1] | 1-[2-(3,5-Dimethyl-phenyl)-acetyl]-2-methyl-azetidine-2-carboxylic acid (2-carbamoyl-ethyl)-(4-chloro-benzyl)-amide | I3 | Int 42 and int 119 | 455.2 | 456.3 (M + 1, $^{35}$Cl) |
| 72 | 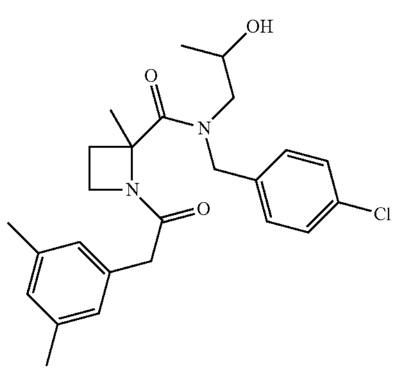 [SMILES: Cc1cc(C)cc(CC(=O)N2CCC2(C)C(=O)N(Cc2ccc(Cl)cc2)CC(C)O)c1] | 1-[2-(3,5-Dimethyl-phenyl)-acetyl]-2-methyl-azetidine-2-carboxylic acid (4-chloro-benzyl)-(2-hydroxy-propyl)-amide | I3, 15h | Int 63 and int 119 | 442.2 | 465.3 (M + 23, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 73 | Chiral | (R)-2-((4-Chloro-benzyl)-{1-[2-(3,5-dimethyl-phenyl)-acetyl]-2-methyl-azetidine-2-carbonyl}-amino)-propionic acid methyl ester | I3, 15h | Int 64 and int 119 | 470.2 | 471.3 (M + 1, $^{35}$Cl) |
| 74 | Abs | (R)-2-((4-Chloro-benzyl)-{1-[2-(3,5-dimethyl-phenyl)-acetyl]-2-methyl-azetidine-2-carbonyl}-amino)-propionic acid | J | Cpd 73 | 456.2 | 457.3 (M + 1, $^{35}$Cl) |
| 75 | 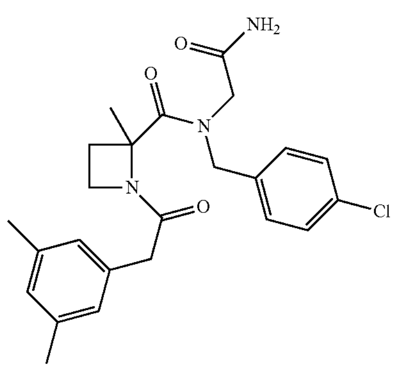 [SMILES: Cc1cc(C)cc(CC(=O)N2CCC2(C)C(=O)N(CC(N)=O)Cc2ccc(Cl)cc2)c1] | 1-[2-(3,5-Dimethyl-phenyl)-acetyl]-2-methyl-azetidine-2-carboxylic acid carbamoylmethyl-(4-chloro-benzyl)-amide | I3, 2.5h | Int 68 and int 119 | 441.2 | 442.3 (M + 1, $^{35}$Cl) |
| 76 | 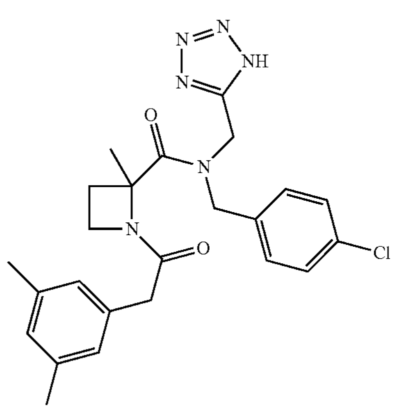 [SMILES: Cc1cc(C)cc(CC(=O)N2CCC2(C)C(=O)N(Cc2ccc(Cl)cc2)Cc2nnn[nH]2)c1] | 1-[2-(3,5-Dimethyl-phenyl)-acetyl]-2-methyl-azetidine-2-carboxylic acid (4-chloro-benzyl)-(1H-tetrazol-5-ylmethyl)-amide | L | Cpd 68 | 466.2 | 467.3 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 77 | 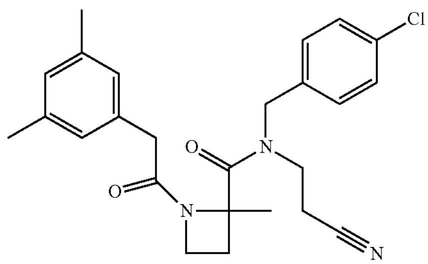 [SMILES: Cc1cc(C)cc(CC(=O)N2CCC2(C)C(=O)N(CCC#N)Cc2ccc(Cl)cc2)c1] | 1-[2-(3,5-Dimethyl-phenyl)-acetyl]-2-methyl-azetidine-2-carboxylic acid (4-chloro-benzyl)-(2-cyano-ethyl)-amide | I3 | Int 57 and int 119 | 437.2 | 438.1 (M + 1, $^{35}$Cl) |
| 78 | 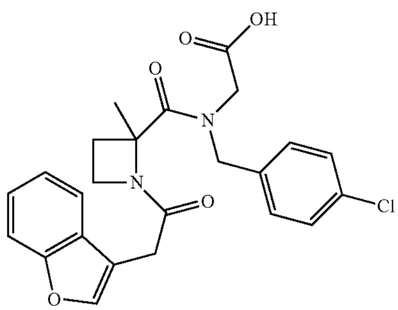 [SMILES: CC1(C(=O)N(CC(=O)O)Cc2ccc(Cl)cc2)CCN1C(=O)Cc1coc2ccccc12] | [[1-(2-Benzofuran-3-yl-acetyl)-2-methyl-azetidine-2-carbonyl]-(4-chloro-benzyl)-amino]-acetic acid | J | Int 141 | 454.1 | 454.9 (M + 1, $^{35}$Cl) |
| 79 | 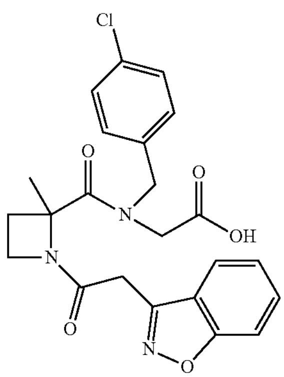 [SMILES: CC1(C(=O)N(CC(=O)O)Cc2ccc(Cl)cc2)CCN1C(=O)Cc1noc2ccccc12] | [[1-(2-Benzo[d]isoxazol-3-yl-acetyl)-2-methyl-azetidine-2-carbonyl]-(4-chloro-benzyl)-amino]-acetic acid | J | Int 162 | 455.1 | 455.9 (M + 1, $^{35}$Cl) |
| 80 | 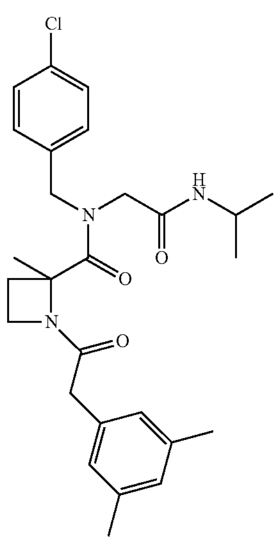 [SMILES: Cc1cc(C)cc(CC(=O)N2CCC2(C)C(=O)N(CC(=O)NC(C)C)Cc2ccc(Cl)cc2)c1] | 1-[2-(3,5-Dimethyl-phenyl)-acetyl]-2-methyl-azetidine-2-carboxylic acid (4-chloro-benzyl)-(isopropylcarbamoyl-methyl)-amide | K | Cpd 49 and isopropyl-amine | 483.2 | 484.0 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 81 | 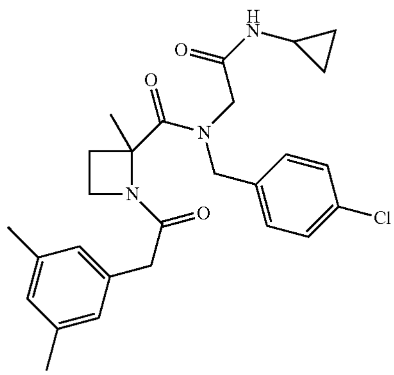 [SMILES: Cc1cc(C)cc(CC(=O)N2CCC2(C)C(=O)N(CC(=O)NC2CC2)Cc2ccc(Cl)cc2)c1] | 1-[2-(3,5-Dimethyl-phenyl)-acetyl]-2-methyl-azetidine-2-carboxylic acid (4-chloro-benzyl)-cyclopropylcarbamoyl-methyl-amide | K | Cpd 49 and cyclopropyl-amine | 481.2 | 482.0 (M + 1, $^{35}$Cl) |
| 81a | Chiral | ((4-Chloro-benzyl)-{(S)-1-[2-(3,5-dimethyl-phenyl)-acetyl]-2-methyl-azetidine-2-carbonyl}-amino)-acetic acid | J | Int 144 | 442.2 | 443.0 (M + 1, $^{35}$Cl) |
| 82 | Chiral | ((4-Chloro-benzyl)-{(R)-1-[2-(3,5-dimethyl-phenyl)-acetyl]-2-methyl-azetidine-2-carbonyl}-amino)-acetic acid | J | Int 145 | 442.2 | 442.9 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 83 | 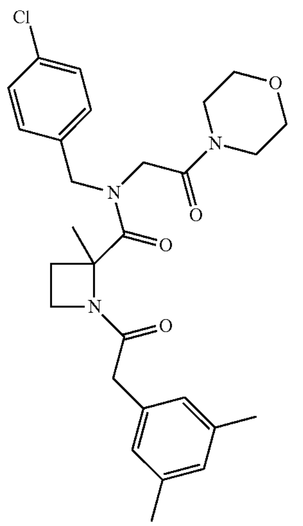 [SMILES: Cc1cc(C)cc(CC(=O)N2CCC2(C)C(=O)N(CC(=O)N2CCOCC2)Cc2ccc(Cl)cc2)c1] | 1-[2-(3,5-Dimethyl-phenyl)-acetyl]-2-methyl-azetidine-2-carboxylic acid (4-chloro-benzyl)-(2-morpholin-4-yl-2-oxo-ethyl)-amide | K | Cpd 49 and morpholine | 511.2 | 512.0 (M + 1, $^{35}$Cl) |
| 84 | 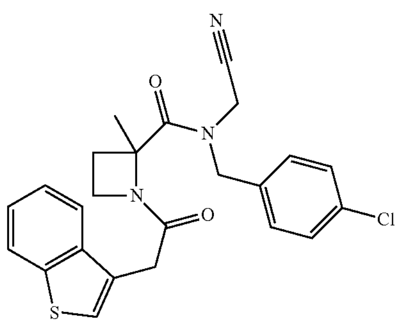 [SMILES: CC1(C(=O)N(CC#N)Cc2ccc(Cl)cc2)CCN1C(=O)Cc1csc2ccccc12] | 1-(2-Benzo[b]thiophen-3-yl-acetyl)-2-methyl-azetidine-2-carboxylic acid (4-chloro-benzyl)-cyanomethyl-amide | I3, 15h | Int 39 and int 121 | 451.1 | 451.9 (M + 1, $^{35}$Cl) |
| 85 | 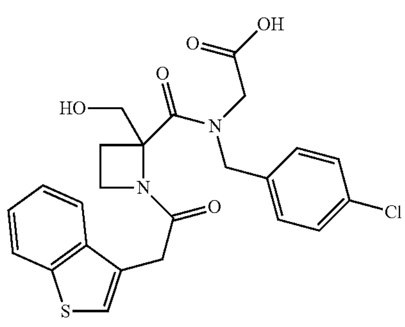 [SMILES: O=C(O)CN(Cc1ccc(Cl)cc1)C(=O)C1(CO)CCN1C(=O)Cc1csc2ccccc12] | [[1-(2-Benzo[b]thiophen-3-yl-acetyl)-2-hydroxymethyl-azetidine-2-carbonyl]-(4-chloro-benzyl)-amino]-acetic acid | J | Int 191 | 486.1 | 486.7 (M + 1, $^{35}$Cl) |
| 86 | 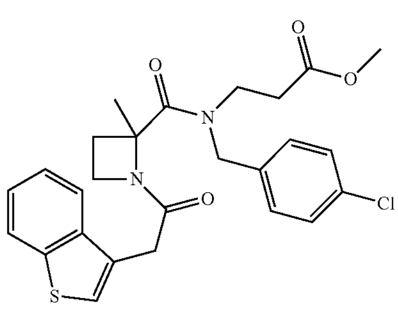 [SMILES: COC(=O)CCN(Cc1ccc(Cl)cc1)C(=O)C1(C)CCN1C(=O)Cc1csc2ccccc12] | 3-[[1-(2-Benzo[b]thiophen-3-yl-acetyl)-2-methyl-azetidine-2-carbonyl]-(4-chloro-benzyl)-amino]-propionic acid methyl ester | I3 | Int 61 and int 121 | 498.1 | 498.7 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 87 | 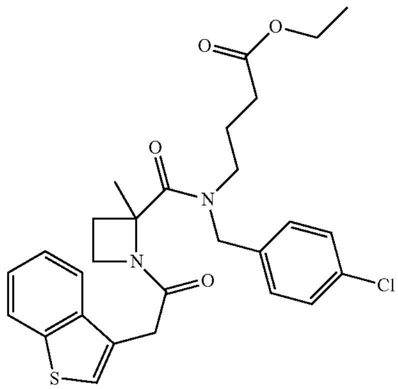 [SMILES: CCOC(=O)CCCN(Cc1ccc(Cl)cc1)C(=O)C1(C)CCN1C(=O)Cc1csc2ccccc12] | 4-[[1-(2-Benzo[b]thiophen-3-yl-acetyl)-2-methyl-azetidine-2-carbonyl]-(4-chloro-benzyl)-amino]-butyric acid ethyl ester | I3, 15h | Int 40 and int 121 | 526.2 | 526.7 (M + 1, $^{35}$Cl) |
| 88 | 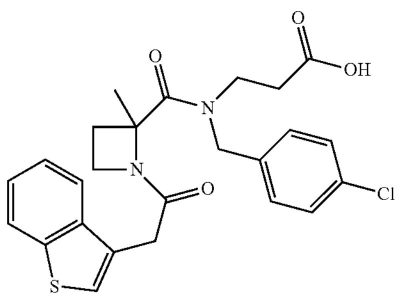 [SMILES: CC1(C(=O)N(CCC(=O)O)Cc2ccc(Cl)cc2)CCN1C(=O)Cc1csc2ccccc12] | 3-[[1-(2-Benzo[b]thiophen-3-yl-acetyl)-2-methyl-azetidine-2-carbonyl]-(4-chloro-benzyl)-amino]-propionic acid | J | Cpd 86 | 484.1 | 484.7 (M + 1, $^{35}$Cl) |
| 89 | 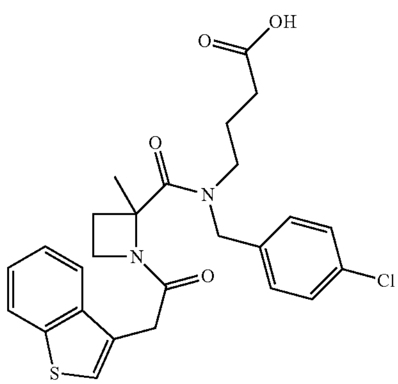 [SMILES: CC1(C(=O)N(CCCC(=O)O)Cc2ccc(Cl)cc2)CCN1C(=O)Cc1csc2ccccc12] | 4-[[1-(2-Benzo[b]thiophen-3-yl-acetyl)-2-methyl-azetidine-2-carbonyl]-(4-chloro-benzyl)-amino]-butyric acid | J | Cpd 87 | 498.1 | 498.7 (M + 1, $^{35}$Cl) |
| 90 | 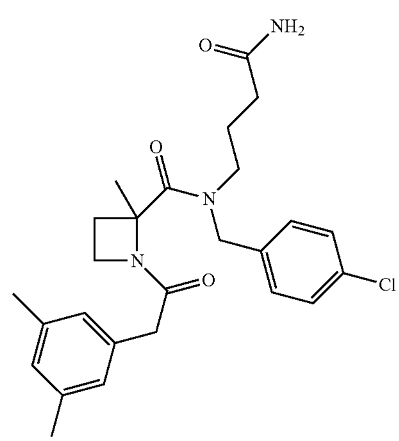 [SMILES: Cc1cc(C)cc(CC(=O)N2CCC2(C)C(=O)N(CCCC(N)=O)Cc2ccc(Cl)cc2)c1] | 1-[2-(3,5-Dimethyl-phenyl)-acetyl]-2-methyl-azetidine-2-carboxylic acid (3-carbamoyl-propyl)-(4-chloro-benzyl)-amide | M | Int 146 | 469.2 | 470.1 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 91 | 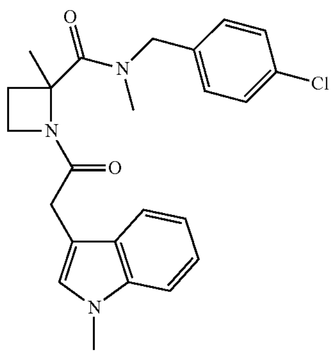 [SMILES: CN(Cc1ccc(Cl)cc1)C(=O)C1(C)CCN1C(=O)Cc1cn(C)c2ccccc12] | 2-Methyl-1-[2-(1-methyl-1H-indol-3-yl)-acetyl]-azetidine-2-carboxylic acid (4-chloro-benzyl)-methyl-amide | I1 | Int 134 and Methyl-(4-chloro-benzyl)-amine | 423.2 | 424.1 (M + 1, $^{35}$Cl) |
| 92 | 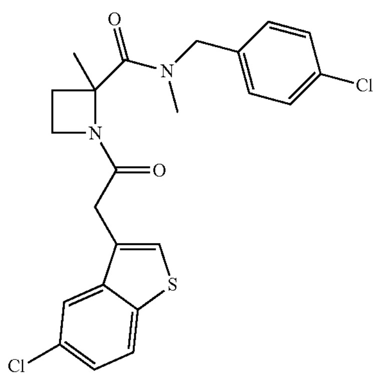 [SMILES: CN(Cc1ccc(Cl)cc1)C(=O)C1(C)CCN1C(=O)Cc1csc2ccc(Cl)cc12] | 1-[2-(5-Chloro-benzo[b]thiophen-3-yl)-acetyl]-2-methyl-azetidine-2-carboxylic acid (4-chloro-benzyl)-methyl-amide | F | Int 14 and (5-Chloro-benzo[b]thiophen-3-yl)-acetic acid | 460.1 | NMR |
| 93 | 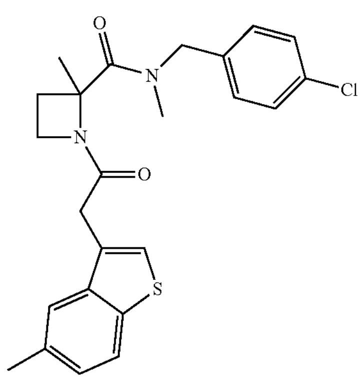 [SMILES: Cc1ccc2scc(CC(=O)N3CCC3(C)C(=O)N(C)Cc3ccc(Cl)cc3)c2c1] | 1-[2-(5-Methyl-benzo[b]thiophen-3-yl)-acetyl]-2-methyl-azetidine-2-carboxylic acid (4-chloro-benzyl)-methyl-amide | F | Int 14 and (5-Methyl-benzo[b]thiophen-3-yl)-acetic acid | 440.1 | NMR |
| 94 | 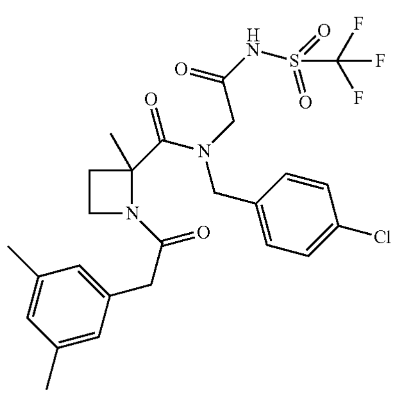 [SMILES: Cc1cc(C)cc(CC(=O)N2CCC2(C)C(=O)N(CC(=O)NS(=O)(=O)C(F)(F)F)Cc2ccc(Cl)cc2)c1] | 1-[2-(3,5-Dimethyl-phenyl)-acetyl]-2-methyl-azetidine-2-carboxylic acid (4-chloro-benzyl)-(2-oxo-2-trifluoromethanesulfonyl-amino-ethyl)-amide | N | Cpd 49 and Trifluoro-methane-sulfonamide | 573.1 | 573.7 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 95 | 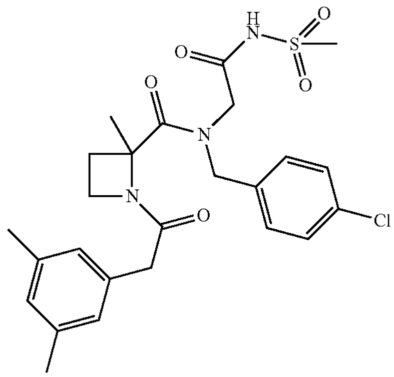 [SMILES: Cc1cc(C)cc(CC(=O)N2CCC2(C)C(=O)N(CC(=O)NS(C)(=O)=O)Cc2ccc(Cl)cc2)c1] | 1-[2-(3,5-Dimethyl-phenyl)-acetyl]-2-methyl-azetidine-2-carboxylic acid (4-chloro-benzyl)-(2-methanesulfonylamino-2-oxo-ethyl)-amide | N | Cpd 49 and methane-sulfonamide | 519.2 | 520.1 (M + 1, $^{35}$Cl) |
| 96 | 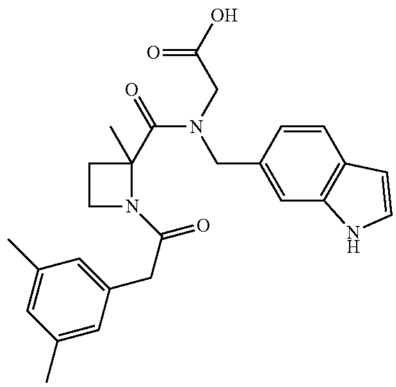 [SMILES: Cc1cc(C)cc(CC(=O)N2CCC2(C)C(=O)N(CC(=O)O)Cc2ccc3cc[nH]c3c2)c1] | [{1-[2-(3,5-Dimethyl-phenyl)-acetyl]-2-methyl-azetidine-2-carbonyl}-(1H-indol-6-ylmethyl)-amino]-acetic acid | J | Int 18 | 447.2 | 448.2 (M + 1, $^{35}$Cl) |
| 97 | 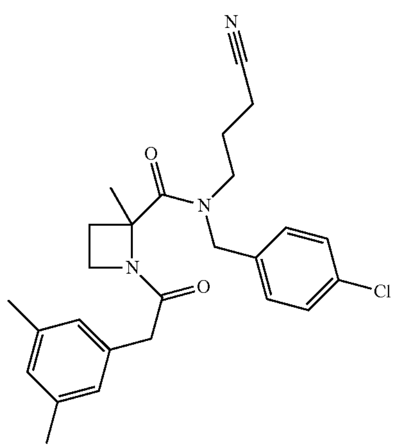 [SMILES: Cc1cc(C)cc(CC(=O)N2CCC2(C)C(=O)N(CCCC#N)Cc2ccc(Cl)cc2)c1] | 1-[2-(3,5-Dimethyl-phenyl)-acetyl]-2-methyl-azetidine-2-carboxylic acid (4-chloro-benzyl)-(3-cyano-propyl)-amide | I3 | Int 41 and int 119 | 451.2 | 452.1 (M + 1, $^{35}$Cl) |
| 98 | 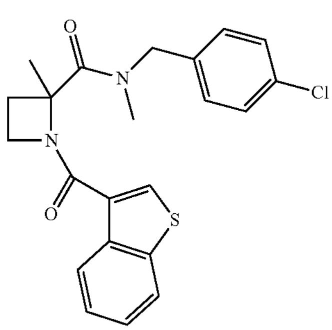 [SMILES: CN(Cc1ccc(Cl)cc1)C(=O)C1(C)CCN1C(=O)c1csc2ccccc12] | 1-(Benzo[b]thiophene-3-carbonyl)-2-methyl-azetidine-2-carboxylic acid (4-chloro-benzyl)-methyl-amide | F | Int 14 and Benzo[b]thiophene-3-carboxylic acid | 412.1 | 413.0 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 99 | 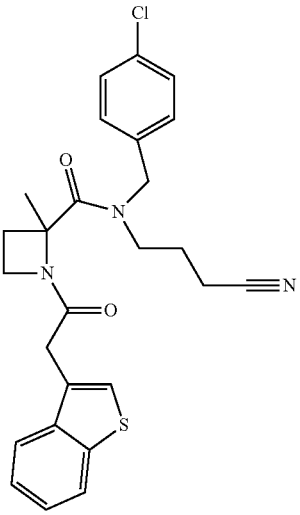 [SMILES: CC1(C(=O)N(CCCC#N)Cc2ccc(Cl)cc2)CCN1C(=O)Cc1csc2ccccc12] | 1-(2-Benzo[b]thiophen-3-yl-acetyl)-2-methyl-azetidine-2-carboxylic acid (4-chloro-benzyl)-(3-cyano-propyl)-amide | I3 | Int 41 and int 121 | 479.1 | 480.0 (M + 1, $^{35}$Cl) |
| 100 | 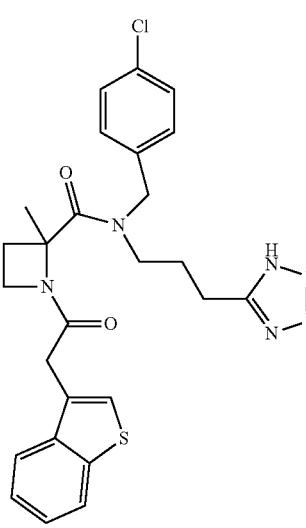 | 1-(2-Benzo[b]thiophen-3-yl-acetyl)-2-methyl-azetidine-2-carboxylic acid (4-chloro-benzyl)-[3-(1H-tetrazol-5-yl)-propyl]-amide | L | Cpd 99 | 522.2 | 523.1 (M + 1, $^{35}$Cl) |
| 101 | 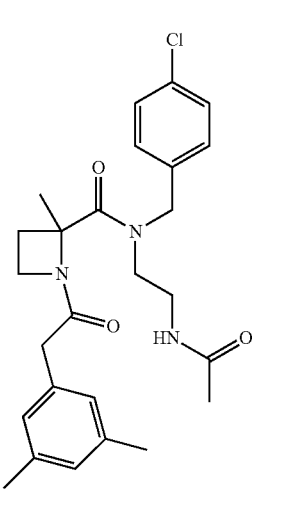 [SMILES: CC(=O)NCCN(Cc1ccc(Cl)cc1)C(=O)C1(C)CCN1C(=O)Cc1cc(C)cc(C)c1] | 1-[2-(3,5-Dimethyl-phenyl)-acetyl]-2-methyl-azetidine-2-carboxylic acid (2-acetylamino-ethyl)-(4-chloro-benzyl)-amide | I4 | Int 84 and int 119 | 469.2 | 470.1 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 102 | 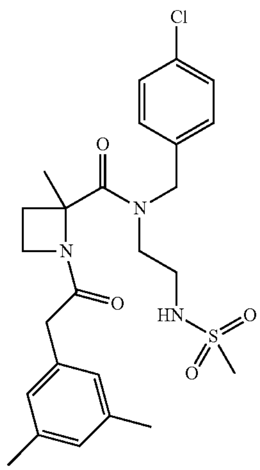 [SMILES: Cc1cc(C)cc(CC(=O)N2CCC2(C)C(=O)N(CCNS(C)(=O)=O)Cc2ccc(Cl)cc2)c1] | 1-[2-(3,5-Dimethyl-phenyl)-acetyl]-2-methyl-azetidine-2-carboxylic acid (4-chloro-benzyl)-(2-methanesulfonylamino-ethyl)-amide | I4 | Int 85 and int 119 | 505.2 | 506.1 (M + 1, $^{35}$Cl) |
| 103 | 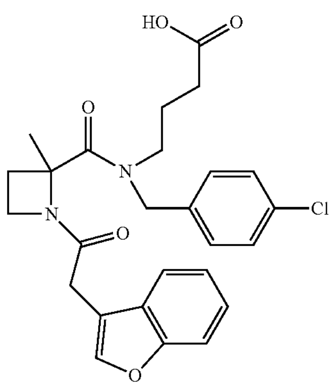 [SMILES: CC1(C(=O)N(CCCC(=O)O)Cc2ccc(Cl)cc2)CCN1C(=O)Cc1coc2ccccc12] | 4-[[1-(2-Benzofuran-3-yl-acetyl)-2-methyl-azetidine-2-carbonyl]-(4-chloro-benzyl)-amino]-butyric acid | J | Int 158 | 482.2 | 483.0 (M + 1, $^{35}$Cl) |
| 104 | 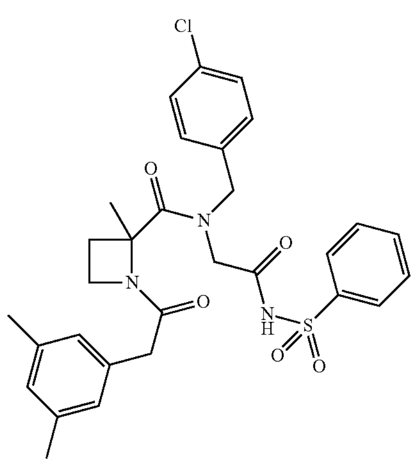 [SMILES: Cc1cc(C)cc(CC(=O)N2CCC2(C)C(=O)N(CC(=O)NS(=O)(=O)c2ccccc2)Cc2ccc(Cl)cc2)c1] | 1-[2-(3,5-Dimethyl-phenyl)-acetyl]-2-methyl-azetidine-2-carboxylic acid (2-benzenesulfonylamino-2-oxo-ethyl)-(4-chloro-benzyl)-amide | N | Cpd 49 and phenyl-sulfon-amide | 581.2 | 582.0 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 105 | 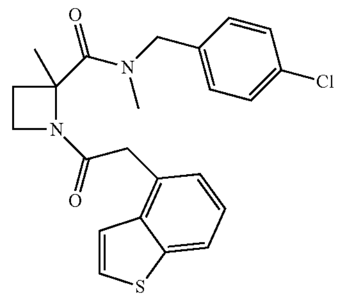 [SMILES: CN(Cc1ccc(Cl)cc1)C(=O)C1(C)CCN1C(=O)Cc1cccc2sccc12] | 1-(2-Benzo[b]thiophen-4-yl-acetyl)-2-methyl-azetidine-2-carboxylic acid (4-chloro-benzyl)-methyl-amide | F | Int 1 and int 14 | 426.1 | 427.0 (M + 1, $^{35}$Cl) |
| 106 | 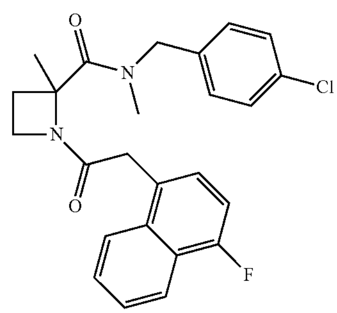 [SMILES: CN(Cc1ccc(Cl)cc1)C(=O)C1(C)CCN1C(=O)Cc1ccc(F)c2ccccc12] | 1-[2-(4-Fluoro-naphthalen-1-yl)-acetyl]-2-methyl-azetidine-2-carboxylic acid (4-chloro-benzyl)-methyl-amide | F | Int 14 and (4-Fluoro-naphtalen-1-yl)-acetic acid | 438.2 | 439.0 (M + 1, $^{35}$Cl) |
| 107 | 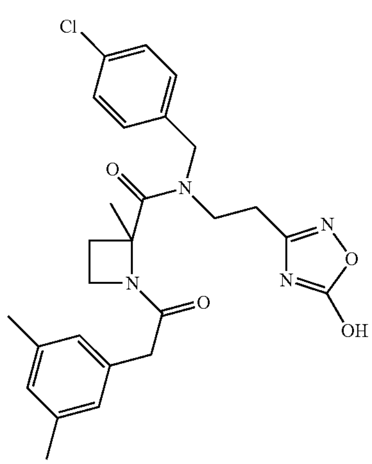 [SMILES: Cc1cc(C)cc(CC(=O)N2CCC2(C)C(=O)N(CCc2noc(O)n2)Cc2ccc(Cl)cc2)c1] | 1-[2-(3,5-Dimethyl-phenyl)-acetyl]-2-methyl-azetidine-2-carboxylic acid (4-chloro-benzyl)-[2-(5-hydroxy-[1,2,4]oxadiazol-3-yl)-ethyl]-amide | O | Cpd 77 | 496.2 | 497.1 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 108 | 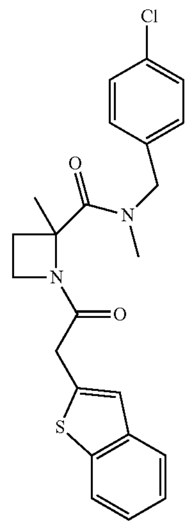 [SMILES: CN(Cc1ccc(Cl)cc1)C(=O)C1(C)CCN1C(=O)Cc1cc2ccccc2s1] | 1-(2-Benzo[b]thiophen-2-yl-acetyl)-2-methyl-azetidine-2-carboxylic acid (4-chloro-benzyl)-methyl-amide | F | Int 2 and int 14 | 426.1 | 427.0 (M + 1, $^{35}$Cl) |
| 109 | 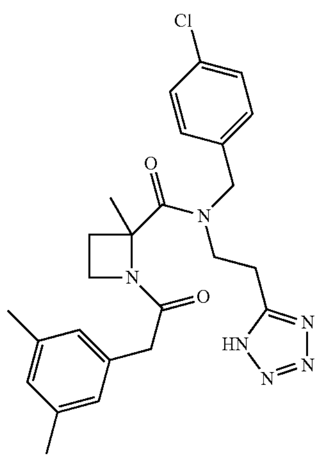 [SMILES: Cc1cc(C)cc(CC(=O)N2CCC2(C)C(=O)N(CCc2nnn[nH]2)Cc2ccc(Cl)cc2)c1] | 1-[2-(3,5-Dimethyl-phenyl)-acetyl]-2-methyl-azetidine-2-carboxylic acid (4-chloro-benzyl)-[2-(1H-tetrazol-5-yl)-ethyl]-amide | L | Cpd 77 | 480.2 | 481.0 (M + 1, $^{35}$Cl) |
| 110 | 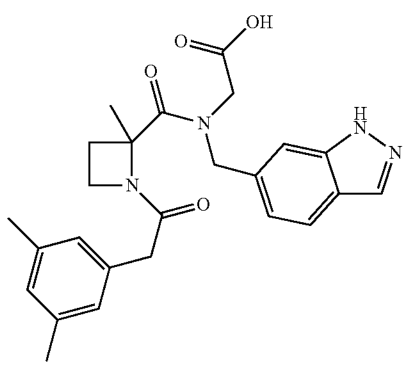 [SMILES: Cc1cc(C)cc(CC(=O)N2CCC2(C)C(=O)N(CC(=O)O)Cc2ccc3cn[nH]c3c2)c1] | [{1-[2-(3,5-Dimethyl-phenyl)-acetyl]-2-methyl-azetidine-2-carbonyl}-(1H-indazol-6-ylmethyl)-amino]-acetic acid | J | Int 148 | 448.2 | 449.1 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 111 | 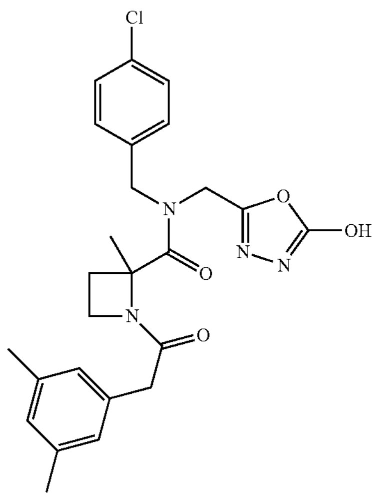 [SMILES: Cc1cc(C)cc(CC(=O)N2CCC2(C)C(=O)N(Cc2ccc(Cl)cc2)Cc2nnc(O)o2)c1] | 1-[2-(3,5-Dimethyl-phenyl)-acetyl]-2-methyl-azetidine-2-carboxylic acid (4-chloro-benzyl)-(5-hydroxy-[1,3,4]oxadiazol-2-ylmethyl)-amide | P | Cpd 49 | 482.2 | 483.1 (M + 1, $^{35}$Cl) |
| 112 | 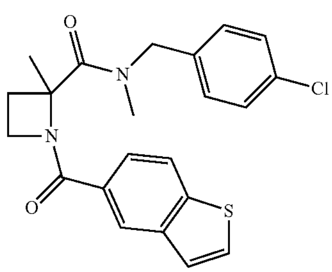 [SMILES: CN(Cc1ccc(Cl)cc1)C(=O)C1(C)CCN1C(=O)c1ccc2sccc2c1] | 1-(Benzo[b]thiophene-5-carbonyl)-2-methyl-azetidine-2-carboxylic acid (4-chloro-benzyl) methyl-amide | F | Int 14 and Benzo[b]thiophene-5-carboxylic acid | 412.1 | 413.0 (M + 1, $^{35}$Cl) |
| 113 | 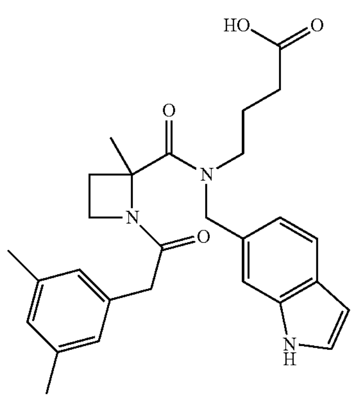 [SMILES: Cc1cc(C)cc(CC(=O)N2CCC2(C)C(=O)N(CCCC(=O)O)Cc2ccc3cc[nH]c3c2)c1] | 4-[{1-[2-(3,5-Dimethyl-phenyl)-acetyl]-2-methyl-azetidine-2-carbonyl}-(1H-indol-6-ylmethyl)-amino]-butyric acid | J | Int 29 | 475.2 | 477.2 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 114 | 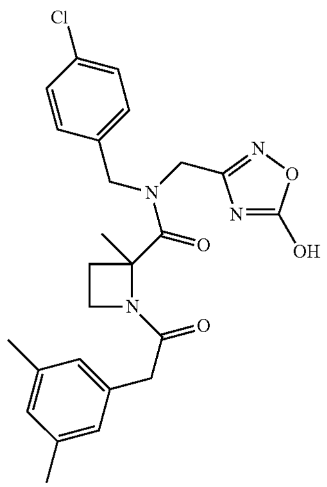 [SMILES: Cc1cc(C)cc(CC(=O)N2CCC2(C)C(=O)N(Cc2ccc(Cl)cc2)Cc2noc(O)n2)c1] | 1-[2-(3,5-Dimethyl-phenyl)-acetyl]-2-methyl-azetidine-2-carboxylic acid (4-chloro-benzyl)-(5-hydroxy-[1,2,4]oxadiazol-3-ylmethyl)-amide | O | Cpd 68 | 482.2 | 483.1 (M + 1, $^{35}$Cl) |
| 115 | 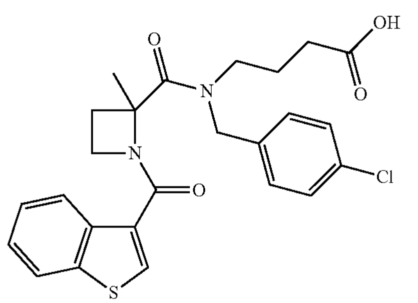 [SMILES: CC1(C(=O)N(CCCC(=O)O)Cc2ccc(Cl)cc2)CCN1C(=O)c1csc2ccccc12] | 4-[[1-(Benzo[b]thiophene-3-carbonyl)-2-methyl-azetidine-2-carbonyl]-(4-chloro-benzyl)-amino]-butyric acid | J | Int 150 | 484.1 | 485.0 (M + 1, $^{35}$Cl) |
| 116 | 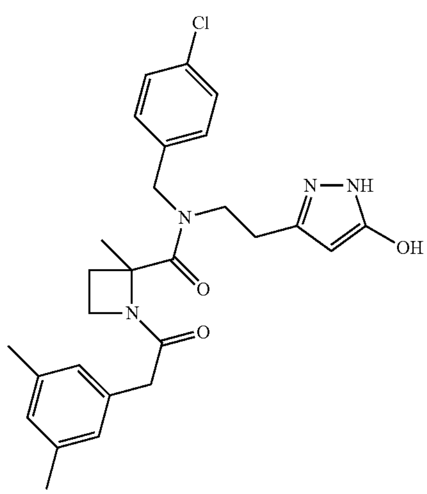 [SMILES: Cc1cc(C)cc(CC(=O)N2CCC2(C)C(=O)N(CCc2cc(O)[nH]n2)Cc2ccc(Cl)cc2)c1] | 1-[2-(3,5-Dimethyl-phenyl)-acetyl]-2-methyl-azetidine-2-carboxylic acid (4-chloro-benzyl)-[2-(5-hydroxy-1H-pyrazol-3-yl)-ethyl]-amide | Q | Cpd 65 with hydrazine | 494.2 | 495.1 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 117 | 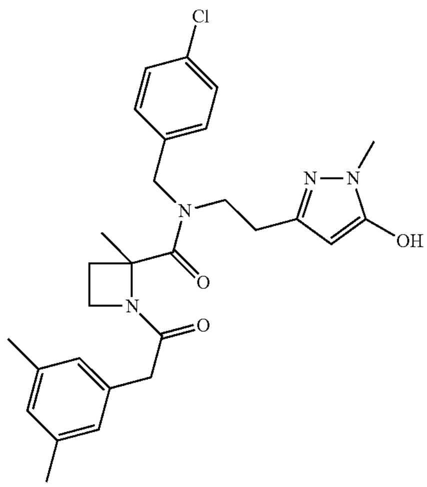 [SMILES: Cc1cc(C)cc(CC(=O)N2CCC2(C)C(=O)N(CCc2cc(O)n(C)n2)Cc2ccc(Cl)cc2)c1] | 1-[2-(3,5-Dimethyl-phenyl)-acetyl]-2-methyl-azetidine-2-carboxylic acid (4-chloro-benzyl)-[2-(5-hydroxy-1-methyl-1H-pyrazol-3-yl)-ethyl]-amide | Q | Cpd 65 with methyl-hydrazine | 508.2 | 509.0 (M + 1, $^{35}$Cl) |
| 118 | 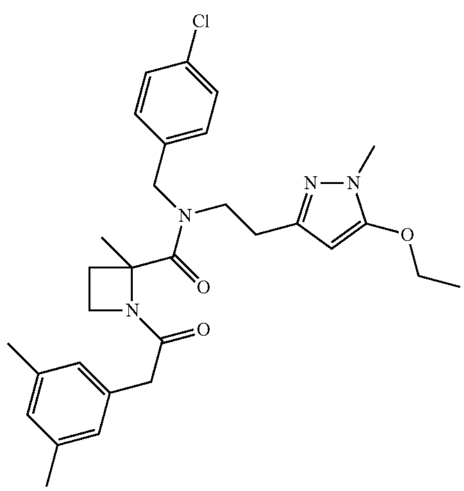 [SMILES: CCOc1cc(CCN(Cc2ccc(Cl)cc2)C(=O)C2(C)CCN2C(=O)Cc2cc(C)cc(C)c2)nn1C] | 1-[2-(3,5-Dimethyl-phenyl)-acetyl]-2-methyl-azetidine-2-carboxylic acid (4-chloro-benzyl)-[2-(5-ethoxy-1-methyl-1H-pyrazol-3-yl)-ethyl]-amide | Q | Cpd 65 with methyl-hydrazine | 536.3 | 537.1 (M + 1, $^{35}$Cl) |
| 119 | 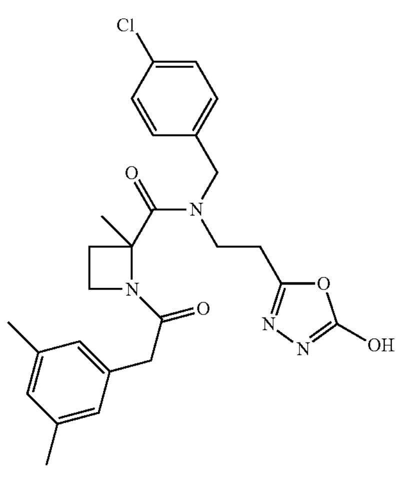 [SMILES: Cc1cc(C)cc(CC(=O)N2CCC2(C)C(=O)N(CCc2nnc(O)o2)Cc2ccc(Cl)cc2)c1] | 1-[2-(3,5-Dimethyl-phenyl)-acetyl]-2-methyl-azetidine-2-carboxylic acid (4-chloro-benzyl)-[2-(5-hydroxy-[1,3,4]oxadiazol-2-yl)-ethyl]-amide | P | Cpd 65 | 496.2 | 497.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 120 | 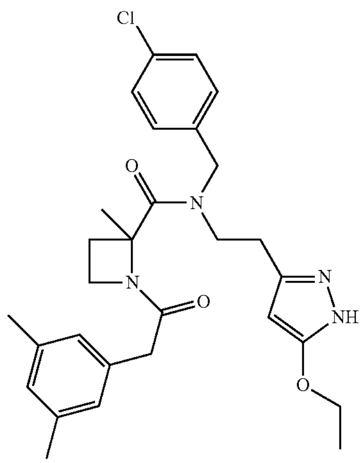 [SMILES: CCOc1cc(CCN(Cc2ccc(Cl)cc2)C(=O)C2(C)CCN2C(=O)Cc2cc(C)cc(C)c2)n[nH]1] | 1-[2-(3,5-Dimethyl-phenyl)-acetyl]-2-methyl-azetidine-2-carboxylic acid (4-chloro-benzyl)-[2-(5-ethoxy-1H-pyrazol-3-yl)-ethyl]-amide | Q | Cpd 65 with hydrazine | 522.2 | 523.4 (M + 1, $^{35}$Cl) |
| 121 | 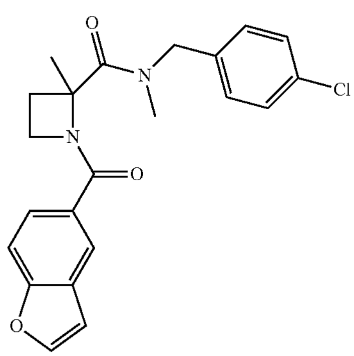 [SMILES: CN(Cc1ccc(Cl)cc1)C(=O)C1(C)CCN1C(=O)c1ccc2occc2c1] | 1-(benzofuran-5-carbonyl)-N-(4-chlorobenzyl)-N,2-dimethylazetidine-2-carboxamide | F | Int 14 and benzofuran-5-carboxylic acid | 396.1 | 397.4 (M + 1, $^{35}$Cl) |
| 122 | 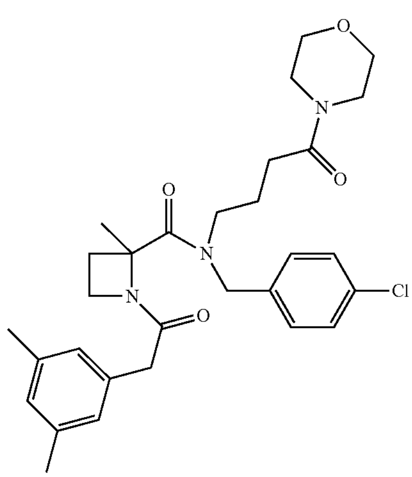 [SMILES: Cc1cc(C)cc(CC(=O)N2CCC2(C)C(=O)N(CCCC(=O)N2CCOCC2)Cc2ccc(Cl)cc2)c1] | 1-[2-(3,5-Dimethyl-phenyl)-acetyl]-2-methyl-azetidine-2-carboxylic acid (4-chloro-benzyl)-(4-morpholin-4-yl-4-oxo-butyl)-amide | I1 | Cpd 64 and morpholine | 539.3 | 540.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 123 | 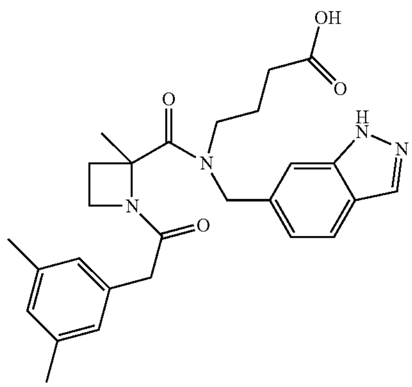 [SMILES: Cc1cc(C)cc(CC(=O)N2CCC2(C)C(=O)N(CCCC(=O)O)Cc2ccc3cn[nH]c3c2)c1] | 4-[{1-[2-(3,5-Dimethyl-phenyl)-acetyl]-2-methyl-azetidine-2-carbonyl}-(1H-indazol-6-ylmethyl)-amino]-butyric acid | J | Int 30 | 476.2 | 477.1 (M + 1) |
| 124 | 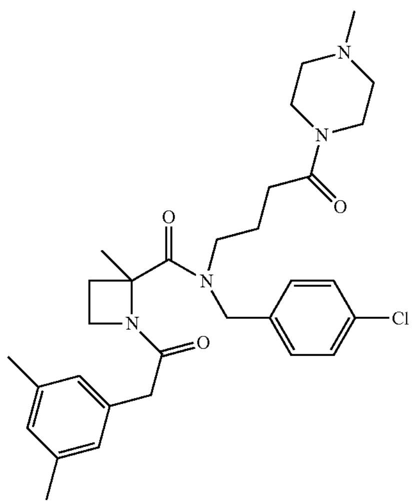 [SMILES: Cc1cc(C)cc(CC(=O)N2CCC2(C)C(=O)N(CCCC(=O)N2CCN(C)CC2)Cc2ccc(Cl)cc2)c1] | 1-[2-(3,5-Dimethyl-phenyl)-acetyl]-2-methyl-azetidine-2-carboxylic acid (4-chloro-benzyl)-[4-(4-methyl-piperazin-1-yl)-4-oxo-butyl]-amide | I1 | Cpd 64 and 1-methyl-piperazine | 552.3 | 553.4 (M + 1, $^{35}$Cl) |
| 125 | 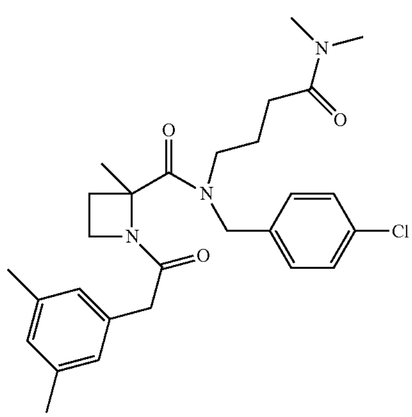 [SMILES: Cc1cc(C)cc(CC(=O)N2CCC2(C)C(=O)N(CCCC(=O)N(C)C)Cc2ccc(Cl)cc2)c1] | 1-[2-(3,5-Dimethyl-phenyl)-acetyl]-2-methyl-azetidine-2-carboxylic acid (4-chloro-benzyl)-(3-dimethylcarbamoyl-propyl)-amide | I1 | Cpd 64 and 9 eq of dimethyl-amine (1N in THF) | 497.2 | 498.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 126 | 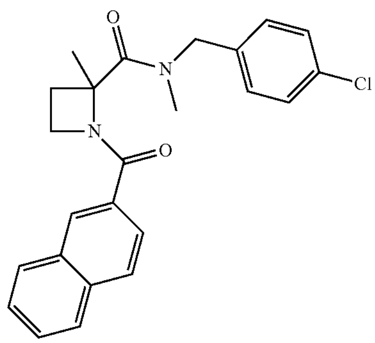 [SMILES: CN(Cc1ccc(Cl)cc1)C(=O)C1(C)CCN1C(=O)c1ccc2ccccc2c1] | 1-(2-naphthoyl)-N-(4-chlorobenzyl)-N,2-dimethylazetidine-2-carboxamide | F | Int 14 and naphthalene-2-carboxylic acid | 406.1 | 407.3 (M + 1, $^{35}$Cl) |
| 127 | 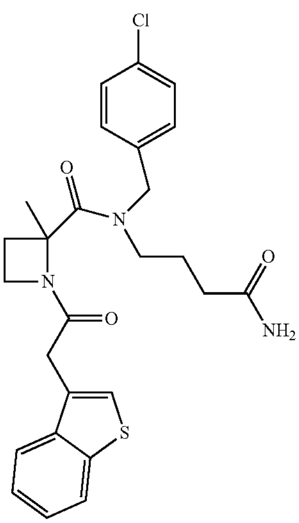 [SMILES: CC1(C(=O)N(CCCC(N)=O)Cc2ccc(Cl)cc2)CCN1C(=O)Cc1csc2ccccc12] | 1-(2-Benzo[b]thiophen-3-yl-acetyl)-2-methyl-azetidine-2-carboxylic acid (3-carbamoyl-propyl)-(4-chloro-benzyl)-amide | M | Cpd 87 | 497.2 | 498.3 (M + 1, $^{35}$Cl) |
| 128 | 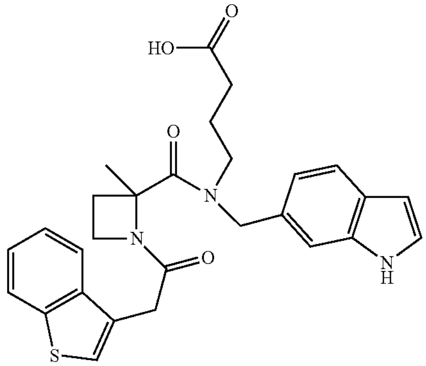 [SMILES: CC1(C(=O)N(CCCC(=O)O)Cc2ccc3cc[nH]c3c2)CCN1C(=O)Cc1csc2ccccc12] | 4-[[1-(2-Benzo[b]thiophen-3-yl-acetyl)-2-methyl-azetidine-2-carbonyl]-(1H-indol-6-ylmethyl)-amino]-butyric acid | J | Int 152 | 503.2 | 504.3 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 129 | 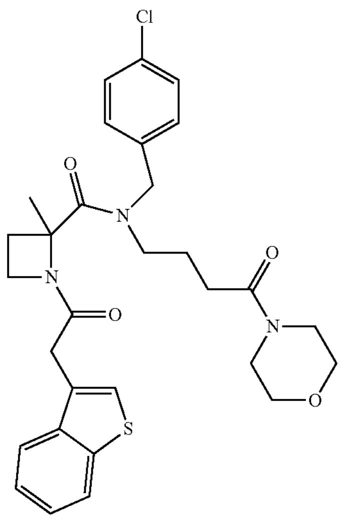 [SMILES: CC1(C(=O)N(CCCC(=O)N2CCOCC2)Cc2ccc(Cl)cc2)CCN1C(=O)Cc1csc2ccccc12] | 1-(2-Benzo[b]thiophen-3-yl-acetyl)-2-methyl-azetidine-2-carboxylic acid (4-chloro-benzyl)-(4-morpholin-4-yl-4-oxo-butyl)-amide | I1 | Cpd 89 and morpholine | 567.2 | 568.4 (M + 1, $^{35}$Cl) |
| 130 | 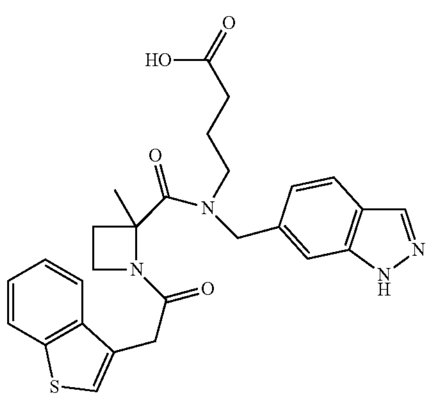 [SMILES: CC1(C(=O)N(CCCC(=O)O)Cc2ccc3cn[nH]c3c2)CCN1C(=O)Cc1csc2ccccc12] | 4-[[1-(2-Benzo[b]thiophen-3-yl-acetyl)-2-methyl-azetidine-2-carbonyl]-(1H-indazol-6-ylmethyl)-amino]-butyric acid | J | Int 153 | 504.2 | 505.4 (M + 1) |
| 131 | 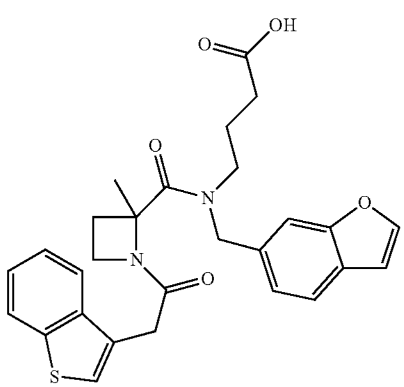 [SMILES: CC1(C(=O)N(CCCC(=O)O)Cc2ccc3ccoc3c2)CCN1C(=O)Cc1csc2ccccc12] | 4-{[1-(2-Benzo[b]thiophen-3-yl-acetyl)-2-methyl-azetidine-2-carbonyl]-benzofuran-6-ylmethyl-amino}-butyric acid | J | Int 164 | 504.2 | 505.3 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 132 | 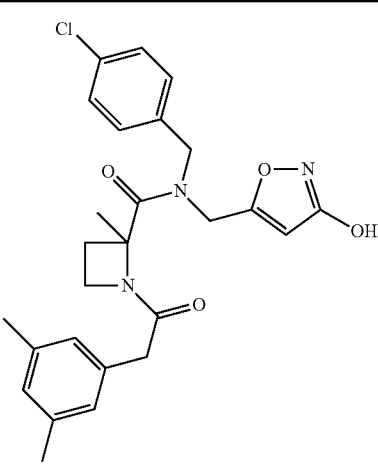 | 1-[2-(3,5-Dimethyl-phenyl)-acetyl]-2-methyl-azetidine-2-carboxylic acid (4-chloro-benzyl)-(3-hydroxy-isoxazol-5-ylmethyl)-amide | I4 | Int 70 and int 119 | 481.2 | 482.3 (M + 1, $^{35}$Cl) |
| 133 | 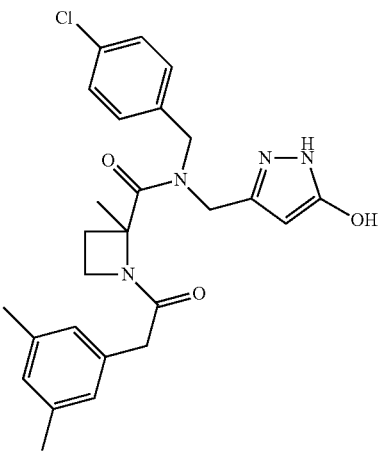 [SMILES: Cc1cc(C)cc(CC(=O)N2CCC2(C)C(=O)N(Cc2ccc(Cl)cc2)Cc2cc(O)[nH]n2)c1] | 1-[2-(3,5-Dimethyl-phenyl)-acetyl]-2-methyl-azetidine-2-carboxylic acid (4-chloro-benzyl)-(5-hydroxy-1H-pyrazol-3-ylmethyl)-amide | Q | Cpd 49 with hydrazine | 480.2 | 481.3 (M + 1, $^{35}$Cl) |
| 134 | 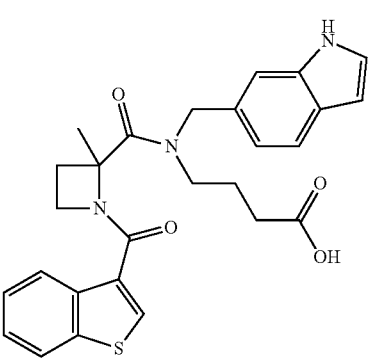 [SMILES: CC1(C(=O)N(CCCC(=O)O)Cc2ccc3cc[nH]c3c2)CCN1C(=O)c1csc2ccccc12] | 4-[[1-(Benzo[b]thiophene-3-carbonyl)-2-methyl-azetidine-2-carbonyl]-(1H-indol-6-ylmethyl)-amino]-butyric acid | J | Int 154 | 489.2 | 490.3 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 135 | 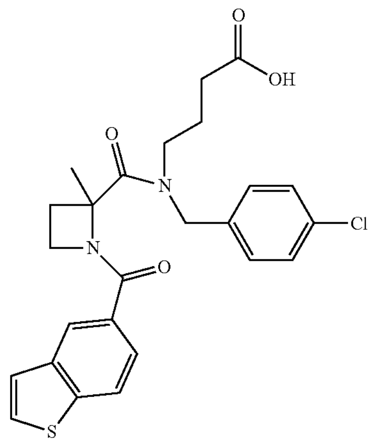 [SMILES: CC1(C(=O)N(CCCC(=O)O)Cc2ccc(Cl)cc2)CCN1C(=O)c1ccc2sccc2c1] | 4-[[1-(Benzo[b]thiophene-5-carbonyl)-2-methyl-azetidine-2-carbonyl]-(4-chloro-benzyl)-amino]-butyric acid | J | Int 155 | 484.1 | 485.3 (M + 1, $^{35}$Cl) |
| 136 | 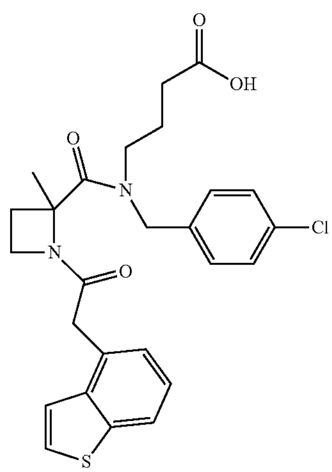 [SMILES: CC1(C(=O)N(CCCC(=O)O)Cc2ccc(Cl)cc2)CCN1C(=O)Cc1cccc2sccc12] | 4-[[1-(2-Benzo[b]thiophen-4-yl-acetyl)-2-methyl azetidine-2-carbonyl]-(4-chloro-benzyl)-amino]-butyric acid | J | Int 156 | 498.1 | 499.3 (M + 1, $^{35}$Cl) |
| 137 | 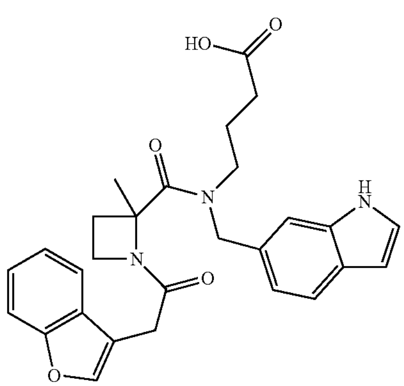 [SMILES: CC1(C(=O)N(CCCC(=O)O)Cc2ccc3cc[nH]c3c2)CCN1C(=O)Cc1coc2ccccc12] | 4-[[1-(2-Benzofuran-3-yl-acetyl)-2-methyl-azetidine-2-carbonyl]-(1H-indol-6-ylmethyl)-amino]-butyric acid | J | Int 157 | 487.2 | 488.4 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 138 | 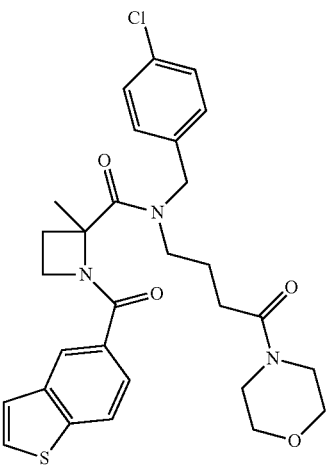 [SMILES: CC1(C(=O)N(CCCC(=O)N2CCOCC2)Cc2ccc(Cl)cc2)CCN1C(=O)c1ccc2sccc2c1] | 1-(benzo[b]thiophene-5-carbonyl)-N-(4-chlorobenzyl)-2-methyl-N-(4-morpholino-4-oxobutyl)azetidine-2-carboxamide | I4 | Cpd 135 and morpholine | 553.2 | 554.4 (M + 1, $^{35}$Cl) |
| 139 | 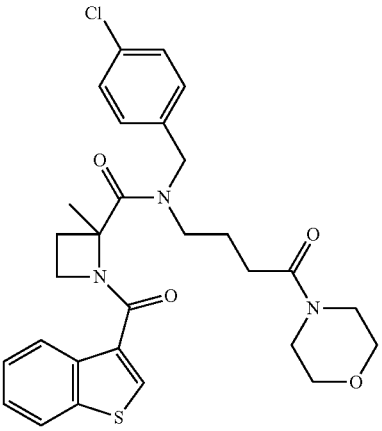 [SMILES: CC1(C(=O)N(CCCC(=O)N2CCOCC2)Cc2ccc(Cl)cc2)CCN1C(=O)c1csc2ccccc12] | 1-(benzo[b]thiophene-3-carbonyl)-N-(4-chlorobenzyl)-2-methyl-N-(4-morpholino-4-oxobutyl)azetidine-2-carboxamide | I4 | Cpd 115 and morpholine | 553.2 | 554.3 (M + 1, $^{35}$Cl) |
| 140 | 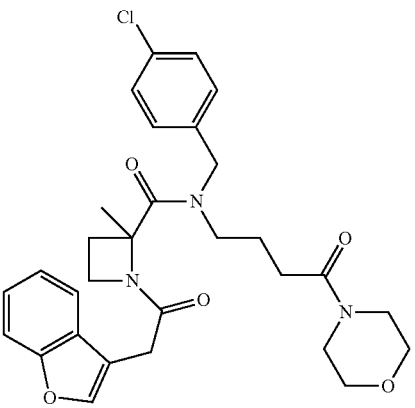 [SMILES: CC1(C(=O)N(CCCC(=O)N2CCOCC2)Cc2ccc(Cl)cc2)CCN1C(=O)Cc1coc2ccccc12] | 1-(2-Benzofuran-3-yl-acetyl)-2-methyl-azetidine-2-carboxylic acid (4-chloro-benzyl)-(4-morpholin-4-yl-4-oxo-butyl)-amide | I4 | Cpd 103 and morpholine | 551.2 | 552.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 141 | 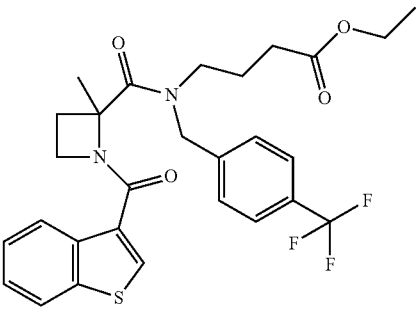 [SMILES: CCOC(=O)CCCN(Cc1ccc(C(F)(F)F)cc1)C(=O)C1(C)CCN1C(=O)c1csc2ccccc12] | ethyl 4-(1-(benzo[b]thiophene-3-carbonyl)-2-methyl-N-(4-(trifluoromethyl)benzyl)azetidine-2-carboxamido)butanoate | I4 | Int 75 and int 125 | 546.2 | 547.4 (M + 1) |
| 142 | 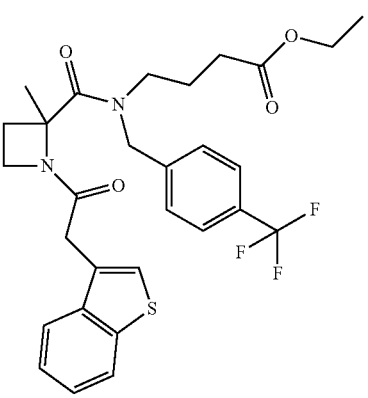 [SMILES: CCOC(=O)CCCN(Cc1ccc(C(F)(F)F)cc1)C(=O)C1(C)CCN1C(=O)Cc1csc2ccccc12] | 4-[[1-(2-Benzo[b]thiophen-3-yl-acetyl)-2-methyl-azetidine-2-carbonyl]-(4-trifluoromethyl-benzyl)-amino]-butyric acid ethyl ester | I4 | Int 75 and int 121 | 560.2 | 561.4 (M + 1) |
| 143 | 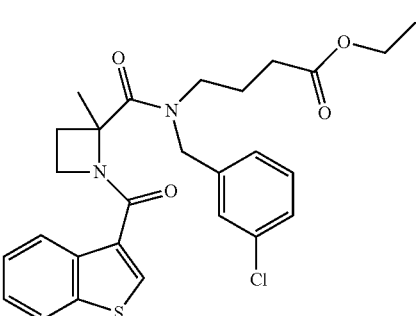 | ethyl 4-(1-(benzo[b]thiophene-3-carbonyl)-N-(3-chlorobenzyl)-2-methylazetidine-2-carboxamido)butanoate | I4 | Int 76 and int 125 | 512.2 | 513.3 (M + 1, $^{35}$Cl) |
| 144 | 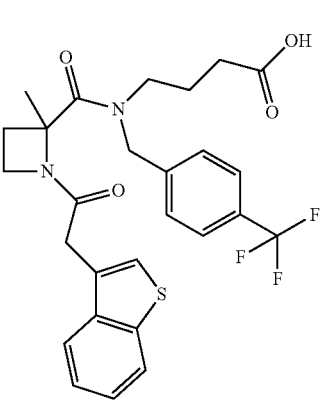 [SMILES: CC1(C(=O)N(CCCC(=O)O)Cc2ccc(C(F)(F)F)cc2)CCN1C(=O)Cc1csc2ccccc12] | 4-[[1-(2-Benzo[b]thiophen-3-yl-acetyl)-2-methyl-azetidine-2-carbonyl]-(4-trifluoromethyl-benzyl)-amino]-butyric acid | J | Cpd 142 | 532.2 | 533.3 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 145 | 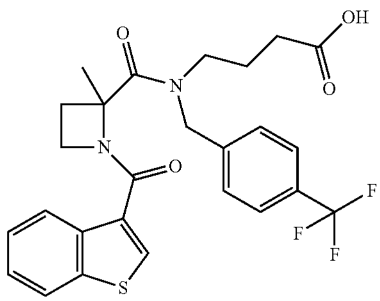 [SMILES: CC1(C(=O)N(CCCC(=O)O)Cc2ccc(C(F)(F)F)cc2)CCN1C(=O)c1csc2ccccc12] | 4-[[1-(Benzo[b]thiophene-3-carbonyl)-2-methyl-azetidine-2-carbonyl]-(4-trifluoromethyl-benzyl)-amino]-butyric acid | J | Cpd 141 | 518.1 | 519.3 (M + 1) |
| 146 | 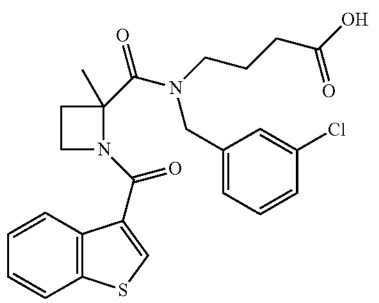 [SMILES: CC1(C(=O)N(CCCC(=O)O)Cc2cccc(Cl)c2)CCN1C(=O)c1csc2ccccc12] | 4-[[1-(Benzo[b]thiophene-3-carbonyl)-2-methyl-azetidine-2-carbonyl]-(3-chloro-benzyl)-amino]-butyric acid | J | Cpd 143 | 484.1 | 485.3 (M + 1) |
| 147 | 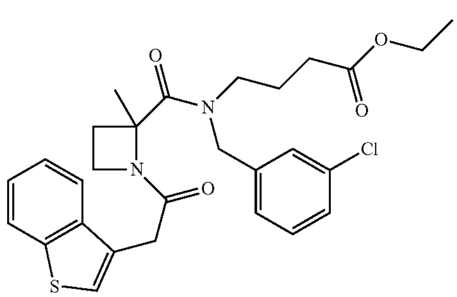 [SMILES: CCOC(=O)CCCN(Cc1cccc(Cl)c1)C(=O)C1(C)CCN1C(=O)Cc1csc2ccccc12] | 4-[[1-(2-Benzo[b]thiophen-3-yl-acetyl)-2-methyl-azetidine-2-carbonyl]-(3-chloro-benzyl)-amino]-butyric acid ethyl ester | I4 | Int 76 and int 121 | 526.2 | 527.3 (M + 1, $^{35}$Cl) |
| 148 | 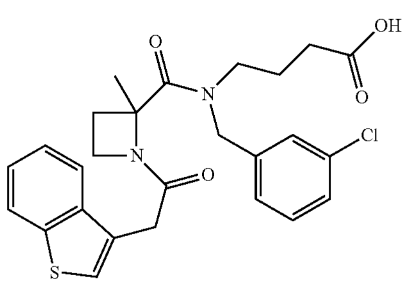 [SMILES: CC1(C(=O)N(CCCC(=O)O)Cc2cccc(Cl)c2)CCN1C(=O)Cc1csc2ccccc12] | 4-[[1-(2-Benzo[b]thiophen-3-yl-acetyl)-2-methyl-azetidine-2-carbonyl]-(3-chloro-benzyl)-amino]-butyric acid | J | Cpd 147 | 498.1 | 499.3 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 149 | 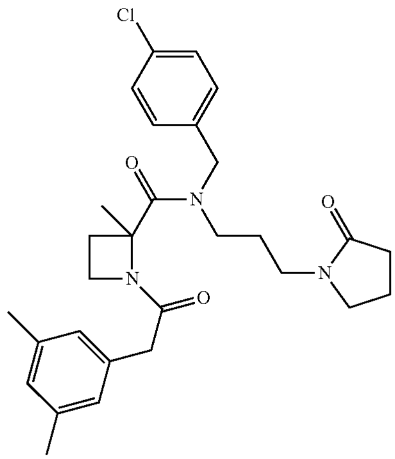 [SMILES: Cc1cc(C)cc(CC(=O)N2CCC2(C)C(=O)N(CCCN2CCCC2=O)Cc2ccc(Cl)cc2)c1] | 1-[2-(3,5-Dimethyl-phenyl)-acetyl]-2-methyl-azetidine-2-carboxylic acid (4-chloro-benzyl)-[3-(2-oxo-pyrrolidin-1-yl)-propyl]-amide | I4 | Int 83 and int 119 | 509.2 | 510.4 (M + 1, $^{35}$Cl) |
| 150 | 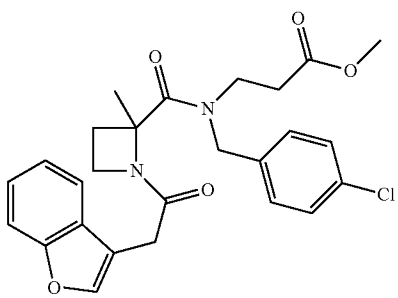 [SMILES: COC(=O)CCN(Cc1ccc(Cl)cc1)C(=O)C1(C)CCN1C(=O)Cc1coc2ccccc12] | 3-[[1-(2-Benzofuran-3-yl-acetyl)-2-methyl-azetidine-2-carbonyl]-(4-chloro-benzyl)-amino]-propionic acid methyl ester | I4 | Int 61 and int 122 | 482.2 | 483.3 (M + 1, $^{35}$Cl) |
| 151 | 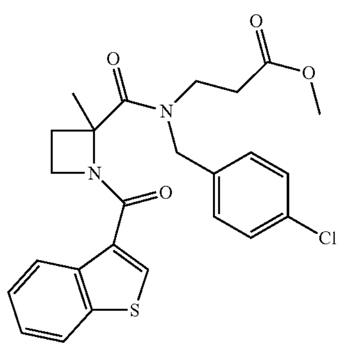 [SMILES: COC(=O)CCN(Cc1ccc(Cl)cc1)C(=O)C1(C)CCN1C(=O)c1csc2ccccc12] | 3-[[1-(Benzo[b]thiophene-3-carbonyl)-2-methyl-azetidine-2-carbonyl]-(4-chloro-benzyl)-amino]-propionic acid methyl ester | I4 | Int 61 and int 125 | 484.1 | 485.3 (M + 1, $^{35}$Cl) |
| 152 | 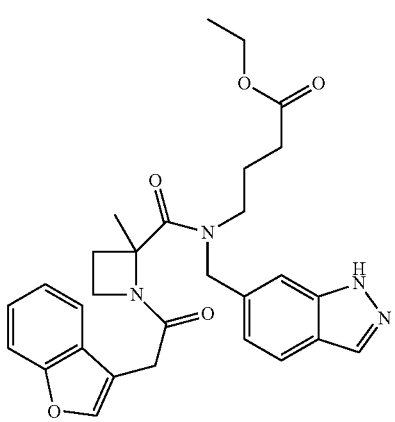 [SMILES: CCOC(=O)CCCN(Cc1ccc2cn[nH]c2c1)C(=O)C1(C)CCN1C(=O)Cc1coc2ccccc12] | 4-[[1-(2-Benzofuran-3-yl-acetyl)-2-methyl-azetidine-2-carbonyl]-(1H-indazol-6-ylmethyl)-amino]-butyric acid ethyl ester | I4 | Int 74 and int 122 | 516.2 | 517.4 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 153 | 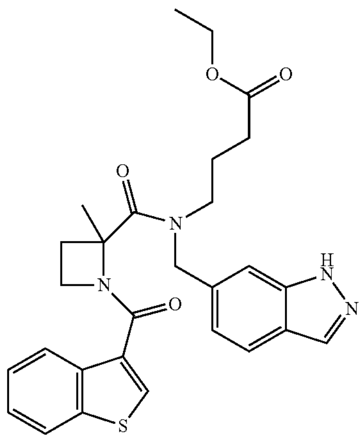 [SMILES: CCOC(=O)CCCN(Cc1ccc2cn[nH]c2c1)C(=O)C1(C)CCN1C(=O)c1csc2ccccc12] | 4-[[1-(Benzo[b]thiophene-3-carbonyl)-2-methyl-azetidine-2-carbonyl]-(1H-indazol-6-ylmethyl)-amino]-butyric acid ethyl ester | I4 | Int 74 and int 125 | 518.2 | 519.4 (M + 1) |
| 154 | 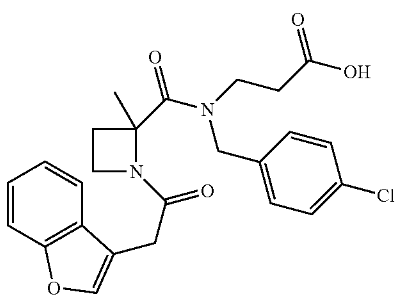 | 3-[[1-(2-Benzofuran-3-yl-acetyl)-2-methyl-azetidine-2-carbonyl]-(4-chloro-benzyl)-amino]-propionic acid | J | Cpd 150 | 468.1 | 469.3 (M + 1, ³⁵Cl) |
| 155 | 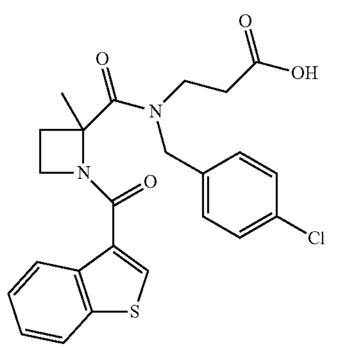 [SMILES: CC1(C(=O)N(CCC(=O)O)Cc2ccc(Cl)cc2)CCN1C(=O)c1csc2ccccc12] | 3-[[1-(Benzo[b]thiophene-3-carbonyl)-2-methyl-azetidine-2-carbonyl]-(4-chloro-benzyl)-amino]-propionic acid | J | Cpd 151 | 470.1 | 471.3 (M + 1, ³⁵Cl) |
| 156 | 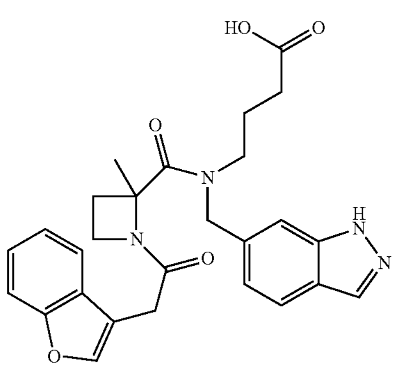 [SMILES: CC1(C(=O)N(CCCC(=O)O)Cc2ccc3cn[nH]c3c2)CCN1C(=O)Cc1coc2ccccc12] | 4-[[1-(2-Benzofuran-3-yl-acetyl)-2-methyl-azetidine-2-carbonyl]-(1H-indazol-6-ylmethyl)-amino]-butyric acid | J | Cpd 152 | 488.2 | 489.4 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 157 | 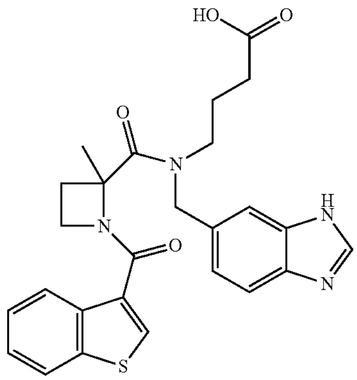 [SMILES: CC1(C(=O)N(CCCC(=O)O)Cc2ccc3nc[nH]c3c2)CCN1C(=O)c1csc2ccccc12] | 4-[[1-(Benzo[b]thiophene-3-carbonyl)-2-methyl-azetidine-2-carbonyl]-(1H-indazol-6-ylmethyl)-amino]-butyric acid | J | Cpd 153 | 490.2 | 491.4 (M + 1) |
| 158 | 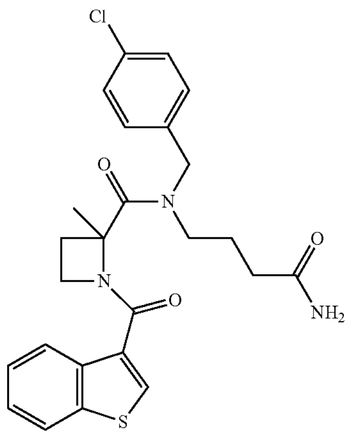 [SMILES: CC1(C(=O)N(CCCC(N)=O)Cc2ccc(Cl)cc2)CCN1C(=O)c1csc2ccccc12] | 1-(Benzo[b]thiophene-3-carbonyl)-2-methyl-azetidine-2-carboxylic acid (3-carbamoyl-propyl)-(4-chloro-benzyl)-amide | M | Int 150 | 483.1 | 484.4 (M + 1, $^{35}$Cl) |
| 159 | 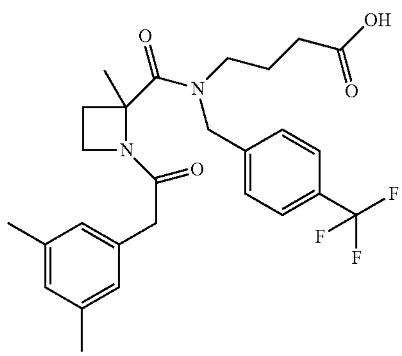 [SMILES: Cc1cc(C)cc(CC(=O)N2CCC2(C)C(=O)N(CCCC(=O)O)Cc2ccc(C(F)(F)F)cc2)c1] | 4-[{1-[2-(3,5-Dimethyl-phenyl)-acetyl]-2-methyl-azetidine-2-carbonyl}-(4-trifluoromethyl-benzyl)-amino]-butyric acid | J | Cpd 165 | 504.2 | 505.5 (M + 1) |
| 160 | 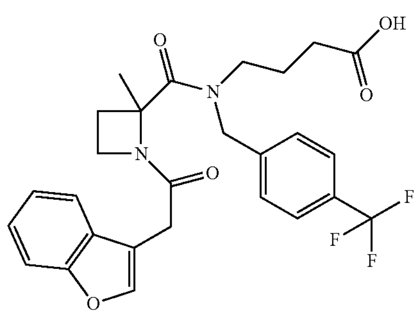 [SMILES: CC1(C(=O)N(CCCC(=O)O)Cc2ccc(C(F)(F)F)cc2)CCN1C(=O)Cc1coc2ccccc12] | 4-[[1-(2-Benzofuran-3-yl-acetyl)-2-methyl-azetidine-2-carbonyl]-(4-trifluoromethyl-benzyl)-amino]-butyric acid | J | Cpd 167 | 516.2 | 517.4 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 161 | 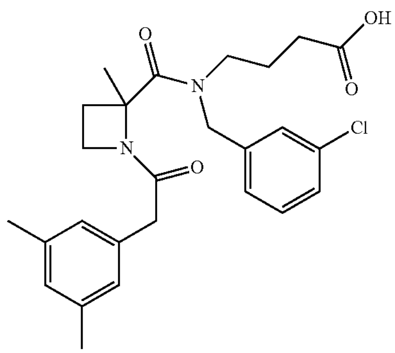 [SMILES: Cc1cc(C)cc(CC(=O)N2CCC2(C)C(=O)N(CCCC(=O)O)Cc2cccc(Cl)c2)c1] | 4-((3-Chloro-benzyl)-{1-[2-(3,5-dimethyl-phenyl)-acetyl]-2-methyl-azetidine-2-carbonyl}-amino)-butyric acid | J | Int 176 | 470.2 | |
| 162 | 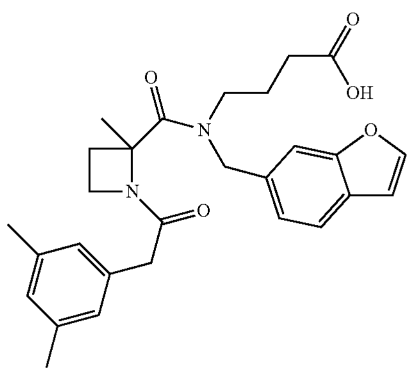 [SMILES: Cc1cc(C)cc(CC(=O)N2CCC2(C)C(=O)N(CCCC(=O)O)Cc2ccc3ccoc3c2)c1] | 4-(Benzofuran-6-ylmethyl-{1-[2-(3,5-dimethyl-phenyl)-acetyl]-2-methyl-azetidine-2-carbonyl}-amino)-butyric acid | J | Int 106 | 476.2 | 477.5 (M + 1) |
| 163 | 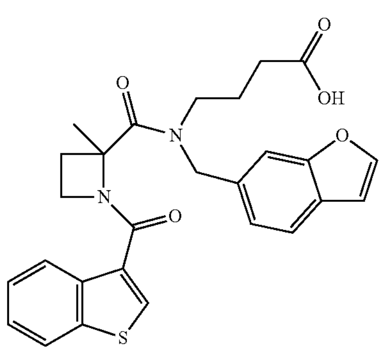 [SMILES: CC1(C(=O)N(CCCC(=O)O)Cc2ccc3ccoc3c2)CCN1C(=O)c1csc2ccccc12] | 4-{[1-(Benzo[b]thiophene-3-carbonyl)-2-methyl-azetidine-2-carbonyl]-benzofuran-6-ylmethyl-amino}-butyric acid | J | Int 107 | 490.2 | 491.4 (M + 1) |
| 164 | 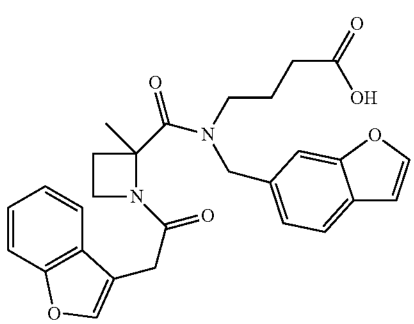 [SMILES: CC1(C(=O)N(CCCC(=O)O)Cc2ccc3ccoc3c2)CCN1C(=O)Cc1coc2ccccc12] | 4-{[1-(2-Benzofuran-3-yl-acetyl)-2-methyl-azetidine-2-carbonyl]-benzofuran-6-ylmethyl-amino}-butyric acid | J | Int 108 | 488.2 | 489.4 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 165 | 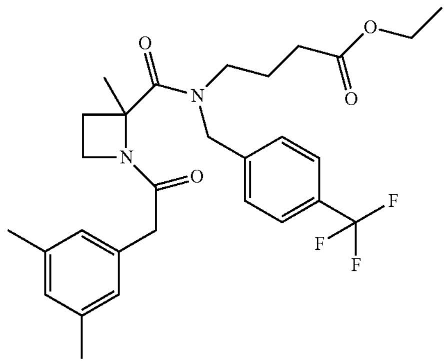 [SMILES: CCOC(=O)CCCN(Cc1ccc(C(F)(F)F)cc1)C(=O)C1(C)CCN1C(=O)Cc1cc(C)cc(C)c1] | 4-[{1-[2-(3,5-Dimethyl-phenyl)-acetyl]-2-methyl-azetidine-2-carbonyl}-(4-trifluoromethyl-benzyl)-amino]-butyric acid ethyl ester | I4 | Int 75 and int 119 | 532.3 | 533.5 (M + 1) |
| 166 | 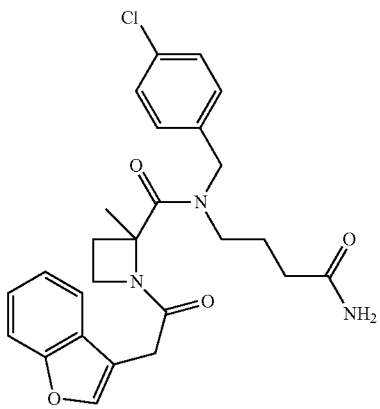 [SMILES: CC1(C(=O)N(CCCC(N)=O)Cc2ccc(Cl)cc2)CCN1C(=O)Cc1coc2ccccc12] | 1-(2-Benzofuran-3-yl-acetyl)-2-methyl-azetidine-2-carboxylic acid (3-carbamoyl-propyl)-(4-chloro-benzyl)-amide | M | Int 158 | 481.2 | 482.4 (M + 1, $^{35}$Cl) |
| 167 | 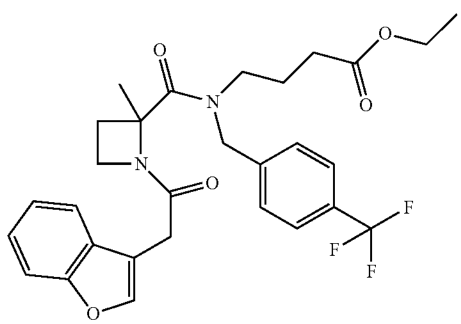 [SMILES: CCOC(=O)CCCN(Cc1ccc(C(F)(F)F)cc1)C(=O)C1(C)CCN1C(=O)Cc1coc2ccccc12] | 4-[[1-(2-Benzofuran-3-yl-acetyl)-2-methyl-azetidine-2-carbonyl]-(4-trifluoromethyl-benzyl)-amino]-butyric acid ethyl ester | I4 | Int 75 and int 122 | 544.2 | 545.5 (M + 1) |
| 168 | 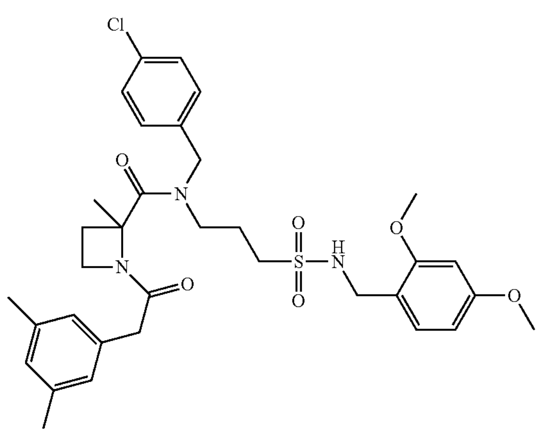 | 1-[2-(3,5-Dimethyl-phenyl)-acetyl]-2-methyl-azetidine-2-carboxylic acid (4-chloro-benzyl)-[3-(2,4-dimethoxy-benzylsulfamoyl)-propyl]-amide | I4 | Int 86 and int 119 | 655.2 | 565.6 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 169 | 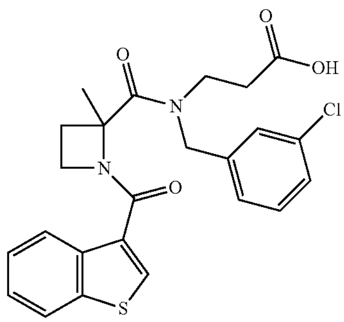 [SMILES: CC1(C(=O)N(CCC(=O)O)Cc2cccc(Cl)c2)CCN1C(=O)c1csc2ccccc12] | 3-[[1-(Benzo[b]thiophene-3-carbonyl)-2-methyl-azetidine-2-carbonyl]-(3-chloro-benzyl)-amino]-propionic acid | J | Cpd 172 | 470.1 | 471.4 (M + 1, $^{35}$Cl) |
| 170 | 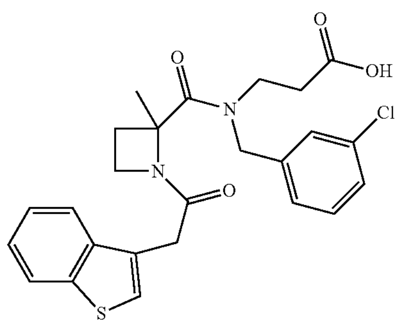 [SMILES: CC1(C(=O)N(CCC(=O)O)Cc2cccc(Cl)c2)CCN1C(=O)Cc1csc2ccccc12] | 3-[[1-(2-Benzo[b]thiophen-3-yl-acetyl)-2-methyl-azetidine-2-carbonyl]-(3-chloro-benzyl)-amino]-propionic acid | J | Cpd 173 | 484.1 | 485.4 (M + 1, $^{35}$Cl) |
| 171 | 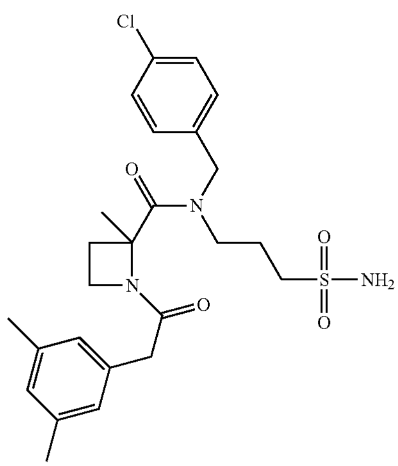 [SMILES: Cc1cc(C)cc(CC(=O)N2CCC2(C)C(=O)N(CCCS(N)(=O)=O)Cc2ccc(Cl)cc2)c1] | 1-[2-(3,5-Dimethyl-phenyl)-acetyl]-2-methyl-azetidine-2-carboxylic acid (4-chloro-benzyl)-(3-sulfamoyl-propyl)-amide | R | Cpd 168 | 505.2 | 506.5 (M + 1, $^{35}$Cl) |
| 172 | 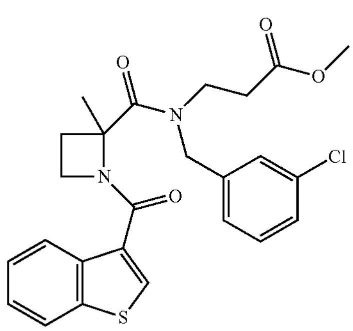 [SMILES: COC(=O)CCN(Cc1cccc(Cl)c1)C(=O)C1(C)CCN1C(=O)c1csc2ccccc12] | 3-[[1-(Benzo[b]thiophene-3-carbonyl)-2-methyl-azetidine-2-carbonyl]-(3-chloro-benzyl)-amino]-propionic acid methyl ester | I4 | Int 59 and int 125 | 484.1 | 485.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 173 | 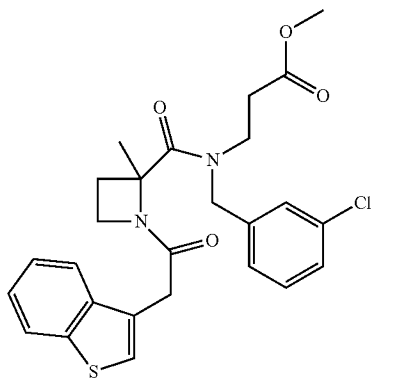 [SMILES: COC(=O)CCN(Cc1cccc(Cl)c1)C(=O)C1(C)CCN1C(=O)Cc1csc2ccccc12] | 3-[[1-(2-Benzo[b]thiophen-3-yl-acetyl)-2-methyl-azetidine-2-carbonyl]-(3-chloro-benzyl)-amino]-propionic acid methyl ester | I4 | Int 59 and int 121 | 498.1 | 499.4 (M + 1, $^{35}$Cl) |
| 174 | 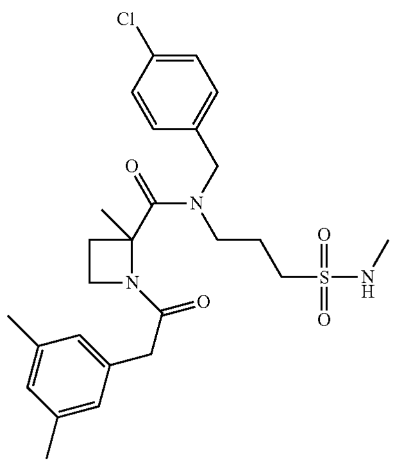 | 1-[2-(3,5-Dimethyl-phenyl)-acetyl]-2-methyl-azetidine-2-carboxylic acid (4-chloro-benzyl)-(3-methylsulfamoyl-propyl)-amide | R | Int 166 | 519.2 | 520.5 (M + 1, $^{35}$Cl) |
| 175 | 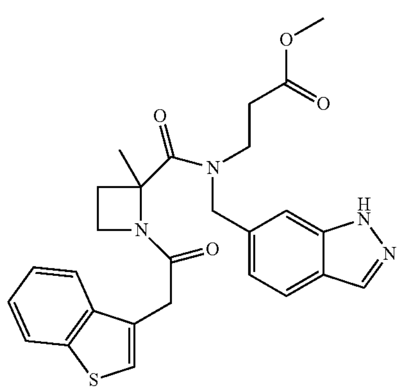 [SMILES: COC(=O)CCN(Cc1ccc2cn[nH]c2c1)C(=O)C1(C)CCN1C(=O)Cc1csc2ccccc12] | 3-[[1-(2-Benzo[b]thiophen-3-yl-acetyl)-2-methyl-azetidine-2-carbonyl]-(1H-indazol-6-ylmethyl)-amino]-propionic acid methyl ester | I4 | Int 79 and int 121 | 504.2 | 505.5 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 176 | 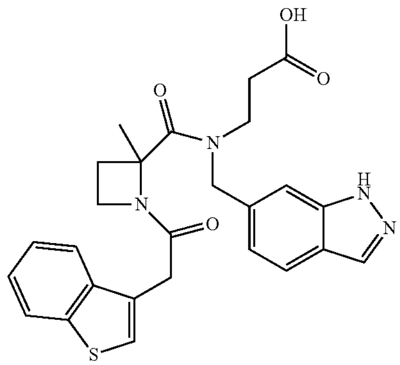 [SMILES: CC1(C(=O)N(CCC(=O)O)Cc2ccc3cn[nH]c3c2)CCN1C(=O)Cc1csc2ccccc12] | 3-[[1-(2-Benzo[b]thiophen-3-yl-acetyl)-2-methyl-azetidine-2-carbonyl]-(1H-indazol-6-ylmethyl)-amino]-propionic acid | J | Cpd 175 | 490.2 | 491.4 (M + 1) |
| 177 | 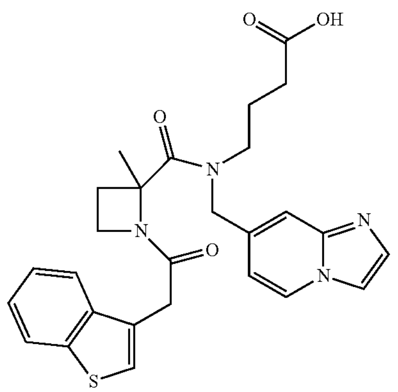 [SMILES: CC1(C(=O)N(CCCC(=O)O)Cc2ccn3ccnc3c2)CCN1C(=O)Cc1csc2ccccc12] | 4-{[1-(2-Benzo[b]thiophen-3-yl-acetyl)-2-methyl-azetidine-2-carbonyl]-imidazo[1,2-a]pyridin-7-ylmethyl-amino}-butyric acid | J | Int 167 | 504.2 | 505.5 (M + 1) |
| 178 | 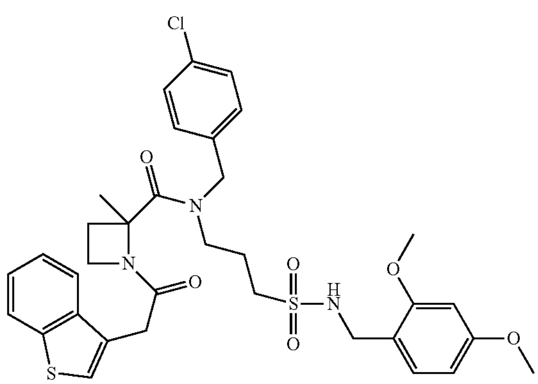 [SMILES: COc1ccc(CNS(=O)(=O)CCCN(Cc2ccc(Cl)cc2)C(=O)C2(C)CCN2C(=O)Cc2csc3ccccc23)c(OC)c1] | 1-(2-Benzo[b]thiophen-3-yl-acetyl)-2-methyl-azetidine-2-carboxylic acid (4-chloro-benzyl)-[3-(2,4-dimethoxy-benzylsulfamoyl)-propyl]-amide | I4 | Int 86 and int 121 | 683.2 | 684.6 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 179 | 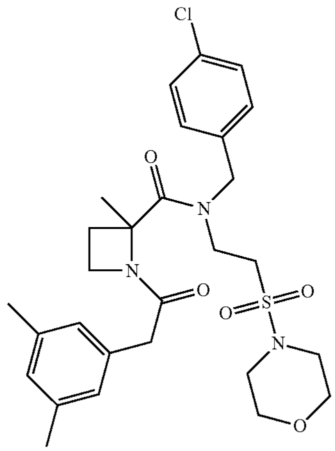 [SMILES: Cc1cc(C)cc(CC(=O)N2CCC2(C)C(=O)N(CCS(=O)(=O)N2CCOCC2)Cc2ccc(Cl)cc2)c1] | 1-[2-(3,5-Dimethyl-phenyl)-acetyl]-2-methyl-azetidine-2-carboxylic acid (4-chloro-benzyl)-[2-(morpholine-4-sulfonyl)-ethyl]-amide | I4 | Int 88 and int 119 | 561.2 | 562.6 (M + 1, $^{35}$Cl) |
| 180 | 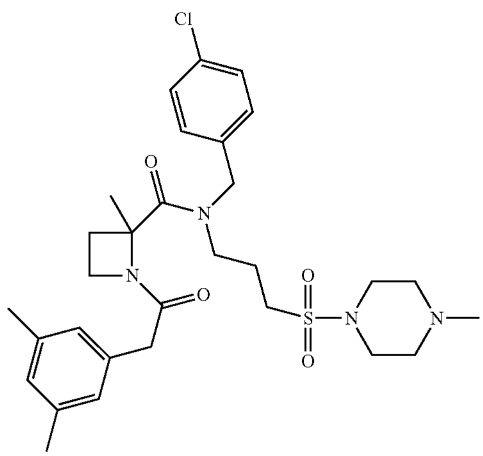 | 1-[2-(3,5-Dimethyl-phenyl)-acetyl]-2-methyl-azetidine-2-carboxylic acid (4-chloro-benzyl)-[3-(4-methyl-piperazine-1-sulfonyl)-propyl]-amide | I4 | Int 89 and int 119 | 588.3 | 589.6 (M + 1, $^{35}$Cl) |
| 181 | 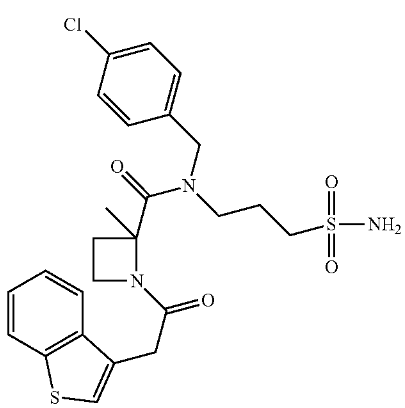 [SMILES: CC1(C(=O)N(CCCS(N)(=O)=O)Cc2ccc(Cl)cc2)CCN1C(=O)Cc1csc2ccccc12] | 1-(2-Benzo[b]thiophen-3-yl-acetyl)-2-methyl-azetidine-2-carboxylic acid (4-chloro-benzyl)-(3-sulfamoyl-propyl)-amide | R | Cpd 178 | 533.1 | 534.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 182 | 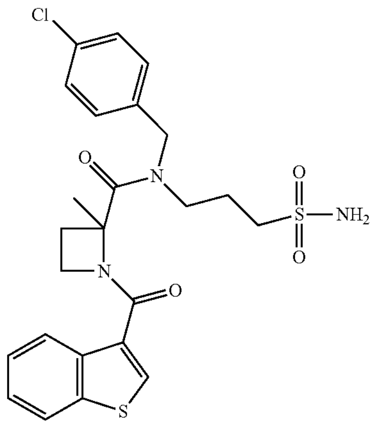 [SMILES: CC1(C(=O)N(CCCS(N)(=O)=O)Cc2ccc(Cl)cc2)CCN1C(=O)c1csc2ccccc12] | 1-(Benzo[b]thiophene-3-carbonyl)-2-methyl-azetidine-2-carboxylic acid (4-chloro-benzyl)-(3-sulfamoyl-propyl)-amide | R | Int 168 | 519.1 | 520.4 (M + 1, $^{35}$Cl) |
| 183 | 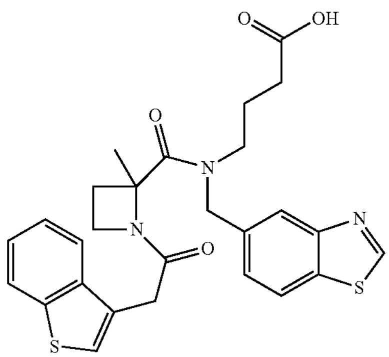 [SMILES: CC1(C(=O)N(CCCC(=O)O)Cc2ccc3scnc3c2)CCN1C(=O)Cc1csc2ccccc12] | 4-{[1-(2-Benzo[b]thiophen-3-yl-acetyl)-2-methyl-azetidine-2-carbonyl]-benzothiazol-5-ylmethyl-amino}-butyric acid | J | Int 109 | 521.1 | 522.4 (M + 1) |
| 184 | 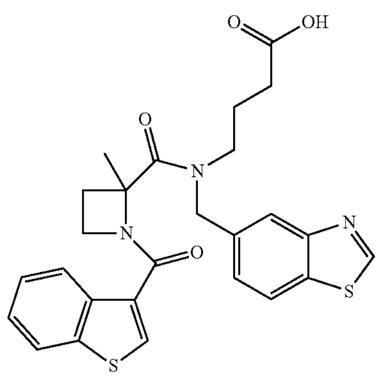 [SMILES: CC1(C(=O)N(CCCC(=O)O)Cc2ccc3scnc3c2)CCN1C(=O)c1csc2ccccc12] | 4-{[1-(Benzo[b]thiophene-3-carbonyl)-2-methyl-azetidine-2-carbonyl]-benzothiazol-5-ylmethyl-amino}-butyric acid | J | Int 110 | 507.1 | 508.4 (M + 1) |
| 185 | 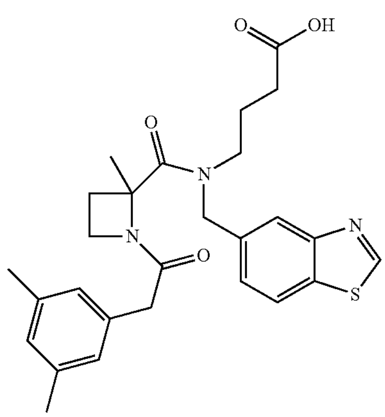 [SMILES: Cc1cc(C)cc(CC(=O)N2CCC2(C)C(=O)N(CCCC(=O)O)Cc2ccc3scnc3c2)c1] | 4-(Benzothiazol-5-ylmethyl-{1-[2-(3,5-dimethyl-phenyl)-acetyl]-2-methyl-azetidine-2-carbonyl}-amino)-butyric acid | J | Int 111 | 493.2 | 494.4 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 186 | 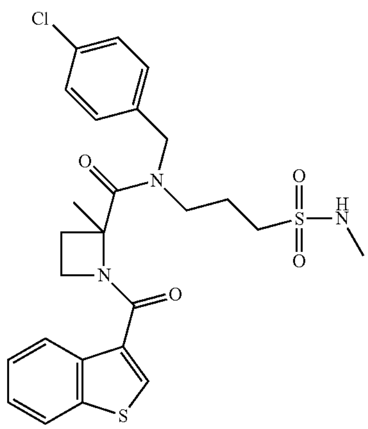 [SMILES: CNS(=O)(=O)CCCN(Cc1ccc(Cl)cc1)C(=O)C1(C)CCN1C(=O)c1csc2ccccc12] | 1-(Benzo[b]thiophene-3-carbonyl)-2-methyl-azetidine-2-carboxlic acid (4-chloro-benzyl)-(3-methylsulfamoyl-propyl)-amide | R | Int 170 | 533.1 | 534.4 (M + 1, $^{35}$Cl) |
| 187 | 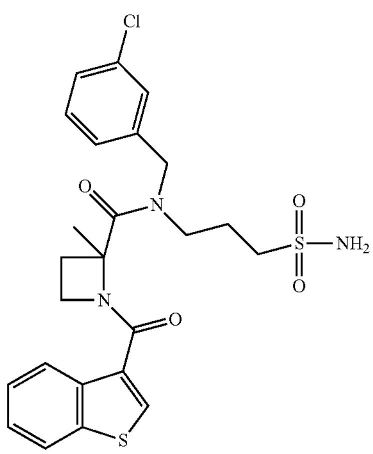 [SMILES: CC1(C(=O)N(CCCS(N)(=O)=O)Cc2cccc(Cl)c2)CCN1C(=O)c1csc2ccccc12] | 1-(Benzo[b]thiophene-3-carbonyl)-2-methyl-azetidine-2-carboxylic acid (3-chloro-benzyl)-(3-sulfamoyl-propyl)-amide | R | Int 171 | 519.1 | 520.3 (M + 1, $^{35}$Cl) |
| 188 | 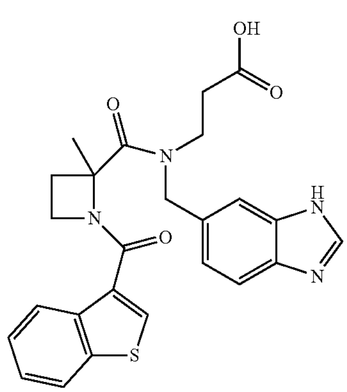 [SMILES: CC1(C(=O)N(CCC(=O)O)Cc2ccc3nc[nH]c3c2)CCN1C(=O)c1csc2ccccc12] | 3-[[1-(Benzo[b]thiophene-3-carbonyl)-2-methyl-azetidine-2-carbonyl]-(1H-indazol-6-ylmethyl)-amino]-propionic acid | J | Int 172 | 476.2 | 477.4 (M + 1) |

TABLE IIa-continued

Mass spectral data of the Compounds of the Invention

| Cpd # | Structures | Name | Mtd | SM | Exact mass | MS Ms'd |
|---|---|---|---|---|---|---|
| 189 | 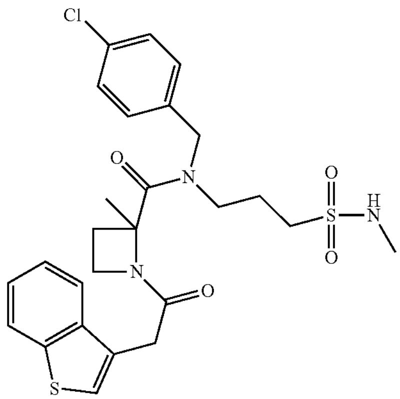 [SMILES: CNS(=O)(=O)CCCN(Cc1ccc(Cl)cc1)C(=O)C1(C)CCN1C(=O)Cc1csc2ccccc12] | 1-(2-Benzo[b]thiophen-3-yl-acetyl)-2-methyl-azetidine-2-carboxylic acid (4-chloro-benzyl)-(3-methylsulfamoyl-propyl)-amide | R | Int 173 | 547.1 | 548.5 (M + 1, $^{35}$Cl) |
| 190 | 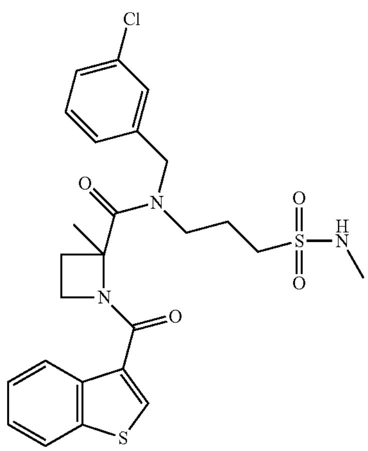 [SMILES: CNS(=O)(=O)CCCN(Cc1cccc(Cl)c1)C(=O)C1(C)CCN1C(=O)c1csc2ccccc12] | 1-(Benzo[b]thiophene-3-carbonyl)-2-methyl-azetidine-2-carboxylic acid (3-chloro-benzyl)-(3-methylsulfamoyl-propyl)-amide | R | Int 174 | 533.1 | 534.4 (M + 1, $^{35}$Cl) |
| 191 | Chiral | 4-[[(R)-1-(Benzo[b]thiophene-3-carbonyl)-2-methyl-azetidine-2-carbonyl]-(3-chloro-benzyl)-amino]-butyric acid | J | Int 112 | 484.1 | 485.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 192 | 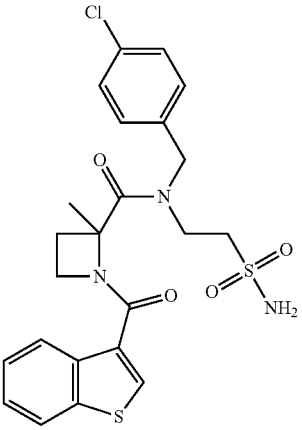 [SMILES: CC1(C(=O)N(CCS(N)(=O)=O)Cc2ccc(Cl)cc2)CCN1C(=O)c1csc2ccccc12] | 1-(Benzo[b]thiophene-3-carbonyl)-2-methyl-azetidine-2-carboxylic acid (4-chloro-benzyl)-(2-sulfamoyl-ethyl)-amide | R | Int 177 | 505.1 | 506.3 (M + 1, $^{35}$Cl) |
| 193 | 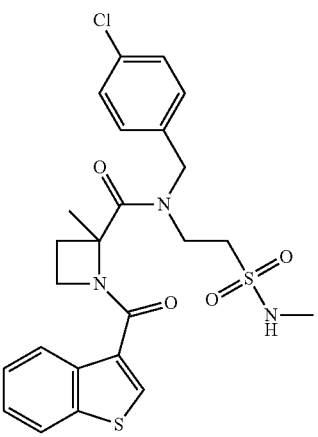 [SMILES: CNS(=O)(=O)CCN(Cc1ccc(Cl)cc1)C(=O)C1(C)CCN1C(=O)c1csc2ccccc12] | 1-(Benzo[b]thiophene-3-carbonyl)-2-methyl-azetidine-2-carboxylic acid (4-chloro-benzyl)-(2-methylsulfamoyl-ethyl)-amide | R | Int 178 | 519.1 | 520.4 (M + 1, $^{35}$Cl) |
| 194 | 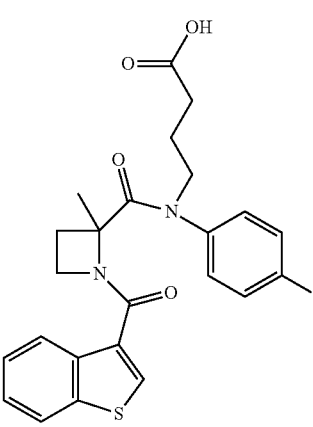 | 4-[[1-(Benzo[b]thiophene-3-carbonyl)-2-methyl-azetidine-2-carbonyl]-(4-chloro-phenyl)-amino]-butyric acid | J | Int 179 | 470.1 | 471.4 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 195 | 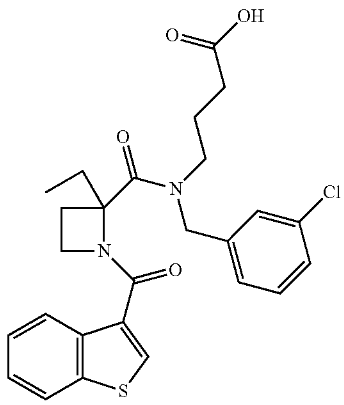 [SMILES: CCC1(C(=O)N(CCCC(=O)O)Cc2cccc(Cl)c2)CCN1C(=O)c1csc2ccccc12] | 4-[[1-(Benzo[b]thiophene-3-carbonyl)-2-ethyl-azetidine-2-carbonyl]-(3-chloro-benzyl)-amino]-butyric acid | J | Int 180 | 498.1 | 499.4 (M + 1, $^{35}$Cl) |
| 196 | 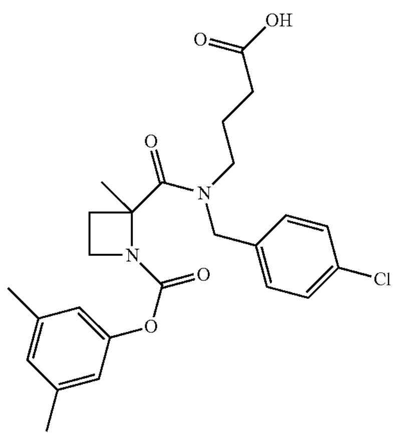 [SMILES: Cc1cc(C)cc(OC(=O)N2CCC2(C)C(=O)N(CCCC(=O)O)Cc2ccc(Cl)cc2)c1] | 2-[(3-Carboxy-propyl)-(4-chloro-benzyl)-carbamoyl]-2-methyl-azetidine-1-carboxylic acid 3,5-dimethyl-phenyl ester | J | Int 135 | 472.2 | 473.5 (M + 1, $^{35}$Cl) |
| 197 | Chiral | 4-{[(R)-1-(Benzo[b]thiophene-3-carbonyl)-2-methyl-azetidine-2-carbonyl]-[(R)-1-(4-chloro-phenyl)-ethyl]-amino}-butyric acid | J | Int 114 | 498.1 | 499.3 (M + 1, $^{35}$Cl) |
| 198 | Chiral | 4-{[(R)-1-(Benzo[b]thiophene-3-carbonyl)-2-methyl-azetidine-2-carbonyl]-[(S)-1-(4-chloro-phenyl)-ethyl]-amino}-butyric acid | J | Int 115 | 498.1 | 499.3 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 199 | 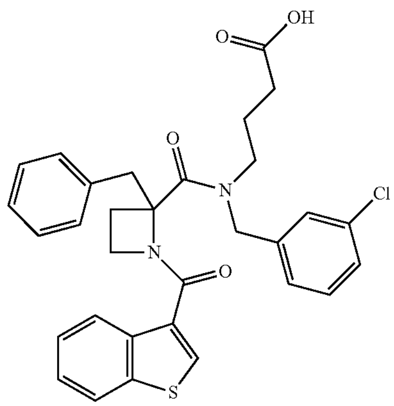 [SMILES: O=C(O)CCCN(Cc1cccc(Cl)c1)C(=O)C1(Cc2ccccc2)CCN1C(=O)c1csc2ccccc12] | 4-[[1-(Benzo[b]thiophene-3-carbonyl)-2-benzyl-azetidine-2-carbonyl]-(3-chloro-benzyl)-amino]-butyric acid | J | Int 184 | 560.2 | 561.4 (M + 1, $^{35}$Cl) |
| 200 | 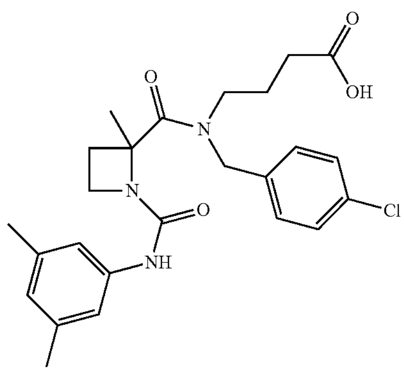 | 4-{(4-Chloro-benzyl)-[1-(3,5-dimethyl-phenylcarbamoyl)-2-methyl-azetidine-2-carbonyl]-amino}-butyric acid | W | Int 23 | 472.0 | 472.4 (M + 1, $^{35}$Cl) |
| 201 | 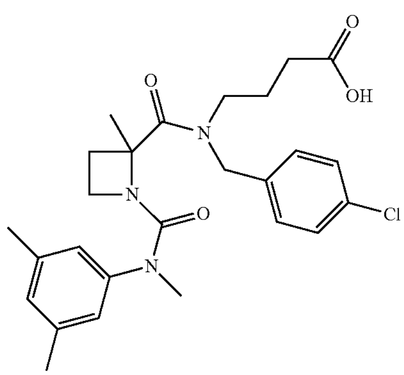 [SMILES: Cc1cc(C)cc(N(C)C(=O)N2CCC2(C)C(=O)N(CCCC(=O)O)Cc2ccc(Cl)cc2)c1] | 4-((4-Chloro-benzyl)-{1-[(3,5-dimethyl-phenyl)-methyl-carbamoyl]-2-methyl-azetidine-2-carbonyl}-amino)-butyric acid | W | Cpd 200 | 486.0 | 486.4 (M + 1, $^{35}$Cl) |
| 202 | 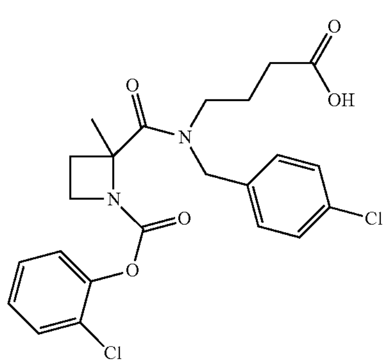 [SMILES: CC1(C(=O)N(CCCC(=O)O)Cc2ccc(Cl)cc2)CCN1C(=O)Oc1ccccc1Cl] | 2-[(3-Carboxy-propyl)-(4-chloro-benzyl)-carbamoyl]-2-methyl-azetidine-1-carboxylic acid 2-chloro-phenyl ester | J | Int 136 | 479.4 | 479.3 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 203 | 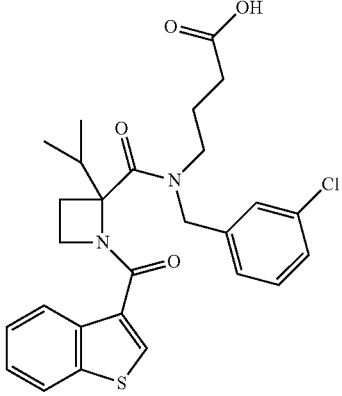 [SMILES: CC(C)C1(C(=O)N(CCCC(=O)O)Cc2cccc(Cl)c2)CCN1C(=O)c1csc2ccccc12] | 4-[[1-(Benzo[b]thiophene-3-carbonyl)-2-isopropyl-azetidine-2-carbonyl]-(3-chloro-benzyl)-amino]-butyric acid | J | Int 185 | 513.1 | 513.2 (M + 1, $^{35}$Cl) |
| 204 | 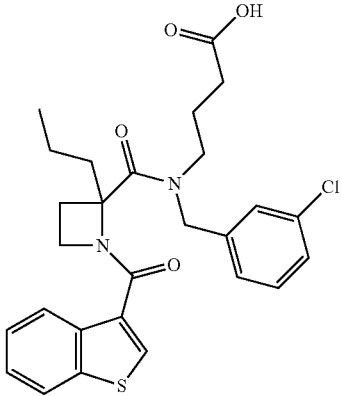 [SMILES: CCCC1(C(=O)N(CCCC(=O)O)Cc2cccc(Cl)c2)CCN1C(=O)c1csc2ccccc12] | 4-[[1-(Benzo[b]thiophene-3-carbonyl)-2-propyl-azetidine-2-carbonyl]-(3-chloro-benzyl)-amino]-butyric acid | J | Int 186 | 513.1 | 513.1 (M + 1, $^{35}$Cl) |
| 205 | 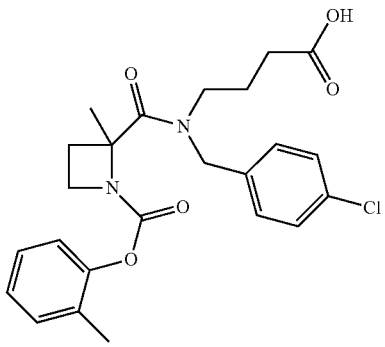 [SMILES: Cc1ccccc1OC(=O)N1CCC1(C)C(=O)N(CCCC(=O)O)Cc1ccc(Cl)cc1] | 2-[(3-Carboxy-propyl)-(4-chloro-benzyl)-carbamoyl]-2-methyl-azetidine-1-carboxylic acid o-tolyl ester | J | Int 137 | 458.9 | 459.1 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 206 | 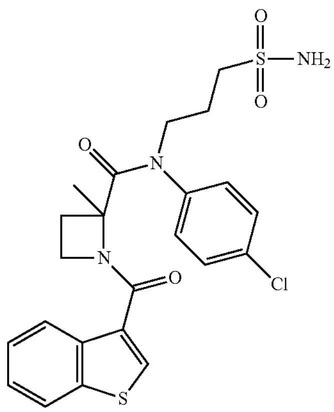 [SMILES: CC1(C(=O)N(CCCS(N)(=O)=O)c2ccc(Cl)cc2)CCN1C(=O)c1csc2ccccc12] | 1-(Benzo[b]thiophene-3-carbonyl)-2-methyl-azetidine-2-carboxylic acid (4-chloro-phenyl)-(3-sulfamoyl-propyl)-amide | R | Int 187 | 506.0 | 506.0 (M + 1, $^{35}$Cl) |
| 207 | 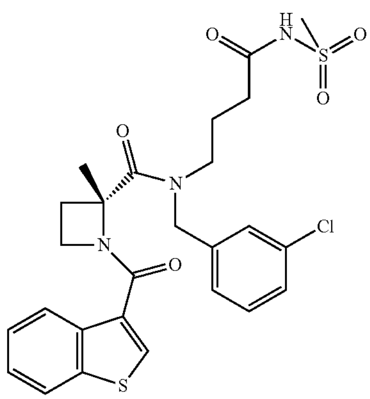 [SMILES: C[C@]1(C(=O)N(CCCC(=O)NS(C)(=O)=O)Cc2cccc(Cl)c2)CCN1C(=O)c1csc2ccccc12] | (R)-1-(benzo[b]thiophene-3-carbonyl)-N-(3-chlorobenzyl)-2-methyl-N-(4-(methylsulfonamido)-4-oxobutyl)azetidine-2-carboxamide | I4 | Cpd 191 and methane-sulfonamide | 561.1 | 562.1 (M + 1, $^{35}$Cl) |
| 208 | 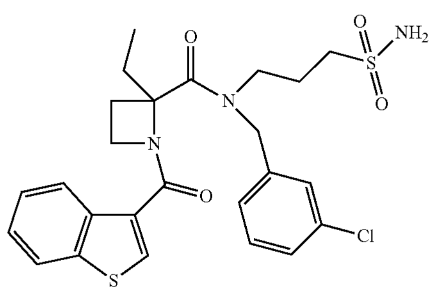 [SMILES: CCC1(C(=O)N(CCCS(N)(=O)=O)Cc2cccc(Cl)c2)CCN1C(=O)c1csc2ccccc12] | 1-(benzo[b]thiophene-3-carbonyl)-N-(3-chlorobenzyl)-2-ethyl-N-(3-sulfamoylpropyl)azetidine-2-carboxamide | R | Int 274 | 533.1 | 534.1 (M + 1, $^{35}$Cl) |
| 209 | 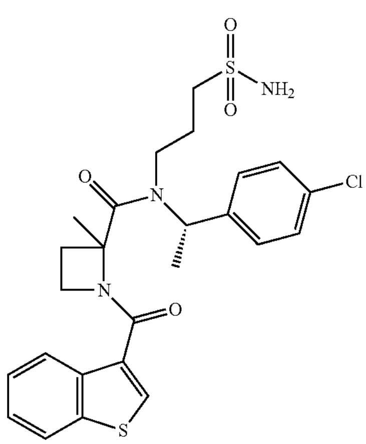 [SMILES: C[C@@H](c1ccc(Cl)cc1)N(CCCS(N)(=O)=O)C(=O)C1(C)CCN1C(=O)c1csc2ccccc12] | 1-(benzo[b]thiophene-3-carbonyl)-N-((S)-1-(4-chlorophenyl)ethyl)-2-methyl-N-(3-sulfamoylpropyl)azetidine-2-carboxamide | R | Int 256 | 533.1 | 534.1 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 210 | 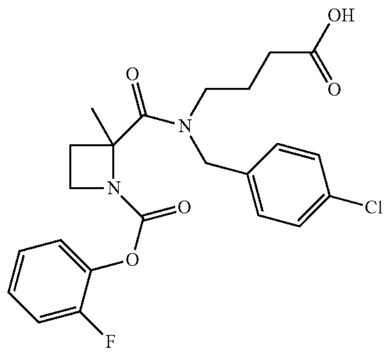 [SMILES: CC1(C(=O)N(CCCC(=O)O)Cc2ccc(Cl)cc2)CCN1C(=O)Oc1ccccc1F] | 4-(N-(4-chlorobenzyl)-1-((2-fluorophenoxy)carbonyl)-2-methylazetidine-2-carboxamido)butanoic acid | J | Int 269 | 462.1 | 463.1 (M + 1, $^{35}$Cl) |
| 211 | 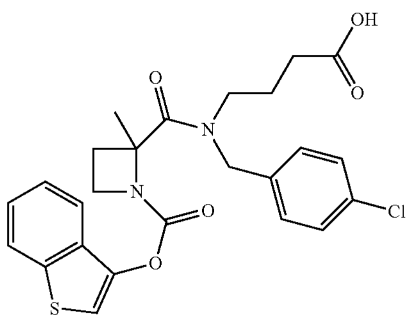 [SMILES: CC1(C(=O)N(CCCC(=O)O)Cc2ccc(Cl)cc2)CCN1C(=O)Oc1csc2ccccc12] | 4-(1-((benzo[b]thiophen-3-yloxy)carbonyl)-N-(4-chlorobenzyl)-2-methylazetidine-2-carboxamido)butanoic acid | J | Int 265 | 500.1 | 501.1 (M + 1 $^{35}$Cl) |
| 212 | 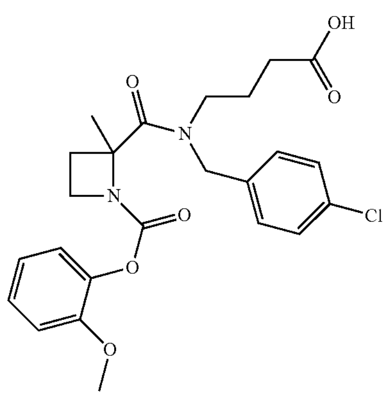 [SMILES: COc1ccccc1OC(=O)N1CCC1(C)C(=O)N(CCCC(=O)O)Cc1ccc(Cl)cc1] | 4-(N-(4-chlorobenzyl)-1-((2-methoxyphenoxy)carbonyl)-2-methylazetidine-2-carboxamido)butanoic acid | J | Int 266 | 474.2 | 475.1 (M + 1, $^{35}$Cl) |
| 213 | 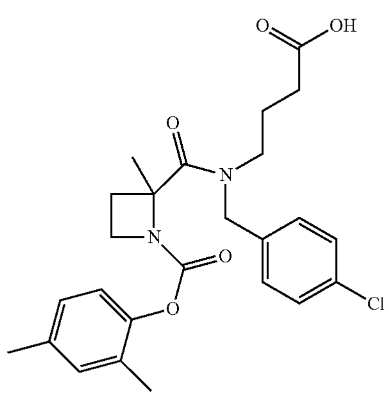 [SMILES: Cc1ccc(OC(=O)N2CCC2(C)C(=O)N(CCCC(=O)O)Cc2ccc(Cl)cc2)c(C)c1] | 4-(N-(4-chlorobenzyl)-1-((2,4-dimethylphenoxy)carbonyl)-2-methylazetidine-2-carboxamido)butanoic acid | J | Int 254 | 472.2 | 473.2 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 214 | 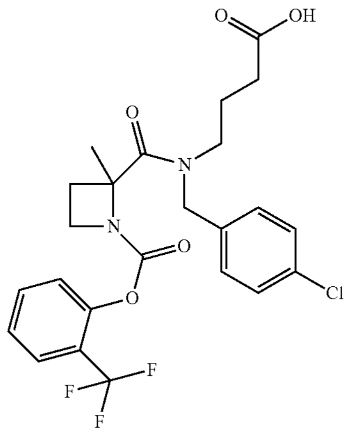 [SMILES: CC1(C(=O)N(CCCC(=O)O)Cc2ccc(Cl)cc2)CCN1C(=O)Oc1ccccc1C(F)(F)F] | 4-(N-(4-chlorobenzyl)-2-methyl-1-((2-(trifluoromethyl)phenoxy)carbonyl)azetidine-2-carboxamido)butanoic acid | J | Int 253 | 512.1 | 513.1 (M + 1, $^{35}$Cl) |
| 215 | 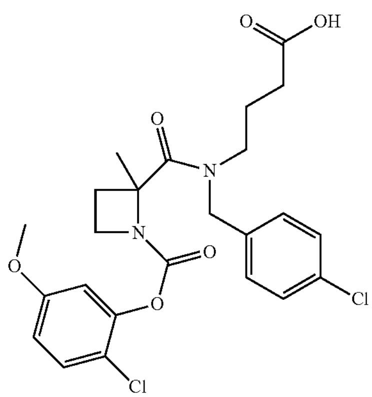 [SMILES: COc1ccc(Cl)c(OC(=O)N2CCC2(C)C(=O)N(CCCC(=O)O)Cc2ccc(Cl)cc2)c1] | 4-(1-((2-chloro-5-methoxyphenoxy)carbonyl)-N-(4-chlorobenzyl)-2-methylazetidine-2-carboxamido)butanoic acid | J (dioxane instead of MeOH) | Int 270 | 508.1 | 509.1 (M + 1, $^{35}$Cl) |
| 216 | 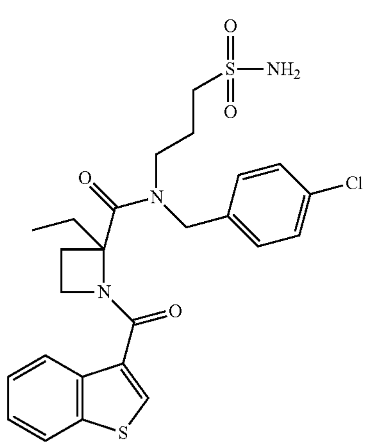 [SMILES: CCC1(C(=O)N(CCCS(N)(=O)=O)Cc2ccc(Cl)cc2)CCN1C(=O)c1csc2ccccc12] | 1-(benzo[b]thiophene-3-carbonyl)-N-(4-chlorobenzyl)-2-ethyl-N-(3-sulfamoylpropyl)azetidine-2-carboxamide | R | Int 257 | 533.1 | 534.1 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 217 | 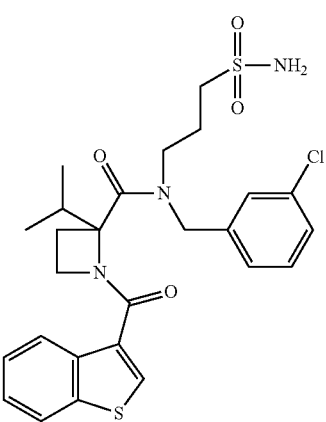 [SMILES: CC(C)C1(C(=O)N(CCCS(N)(=O)=O)Cc2cccc(Cl)c2)CCN1C(=O)c1csc2ccccc12] | 1-(benzo[b]thiophene-3-carbonyl)-N-(3-chlorobenzyl)-2-isopropyl-N-(3-sulfamoylpropyl)azetidine-2-carboxamide | R | Int 258 | 547.1 | 548.1 (M + 1, $^{35}$Cl) |
| 218 | 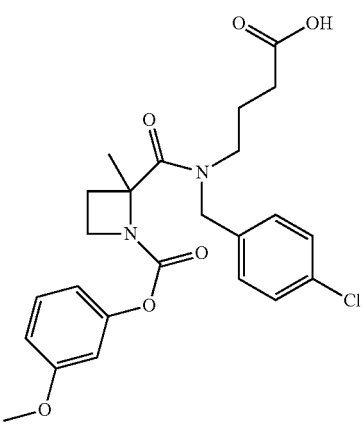 [SMILES: COc1cccc(OC(=O)N2CCC2(C)C(=O)N(CCCC(=O)O)Cc2ccc(Cl)cc2)c1] | 4-(N-(4-chlorobenzyl)-1-((3-methoxyphenoxy)carbonyl)-2-methylazetidine-2-carboxamido)butanoic acid | J | Int 252 | 474.2 | 475.1 (M + 1, $^{35}$Cl) |
| 219 | 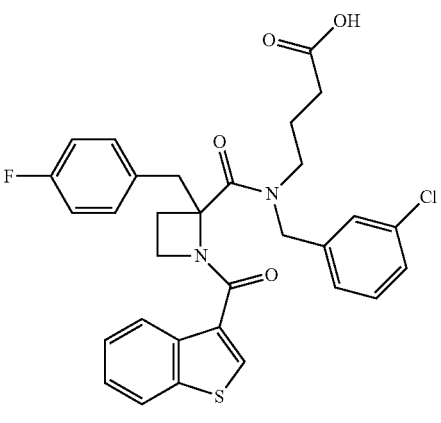 [SMILES: O=C(O)CCCN(Cc1cccc(Cl)c1)C(=O)C1(Cc2ccc(F)cc2)CCN1C(=O)c1csc2ccccc12] | 4-(1-(benzo[b]thiophene-3-carbonyl)-N-(3-chlorobenzyl)-2-(4-fluorobenzyl)azetidine-2-carboxamido)butanoic acid | J | Int 220 | 578.1 | 579.1 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 220 | 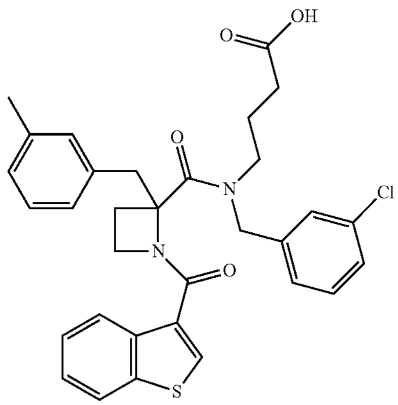 [SMILES: Cc1cccc(CC2(C(=O)N(CCCC(=O)O)Cc3cccc(Cl)c3)CCN2C(=O)c2csc3ccccc23)c1] | 4-(1-(benzo[b]thiophene-3-carbonyl)-N-(3-chlorobenzyl)-2-(3-methylbenzyl)azetidine-2-carboxamido)butanoic acid | J | Int 225 | 574.2 | 575.1 (M + 1, $^{35}$Cl) |
| 221 | 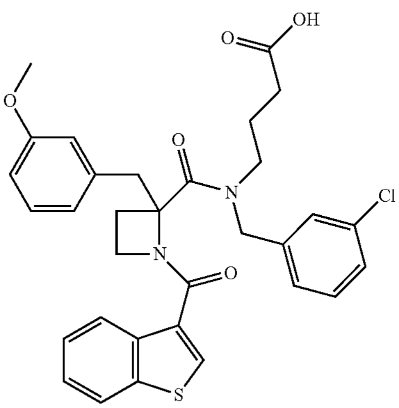 [SMILES: COc1cccc(CC2(C(=O)N(CCCC(=O)O)Cc3cccc(Cl)c3)CCN2C(=O)c2csc3ccccc23)c1] | 4-(1-(benzo[b]thiophene-3-carbonyl)-N-(3-chlorobenzyl)-2-(3-methoxybenzyl) azetidine-2-carboxamido)butanoic acid | J | Int 205 | 590.2 | 591.1 (M + 1, $^{35}$Cl) |
| 222 | 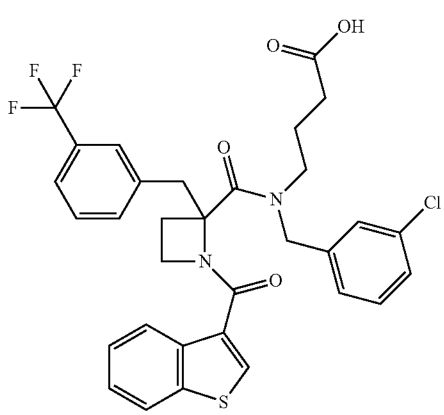 [SMILES: O=C(O)CCCN(Cc1cccc(Cl)c1)C(=O)C1(Cc2cccc(C(F)(F)F)c2)CCN1C(=O)c1csc2ccccc12] | 4-(1-(benzo[b]thiophene-3-carbonyl)-N-(3-chlorobenzyl)-2-(3-(trifluoromethyl)benzyl) azetidine-2-carboxamido)butanoic acid | J | Int 210 | 628.1 | 629.1 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 223 | 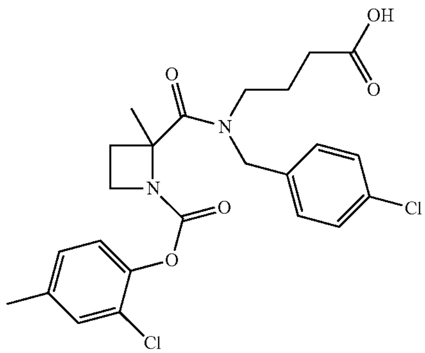 [SMILES: Cc1ccc(OC(=O)N2CCC2(C)C(=O)N(CCCC(=O)O)Cc2ccc(Cl)cc2)c(Cl)c1] | 4-(1-((2-chloro-4-methylphenoxy)carbonyl)-N-(4-chlorobenzyl)-2-methylazetidine-2-carboxamido)butanoic acid | J (dioxane instead of MeOH) | Int 267 | 492.1 | 493.1 (M + 1, $^{35}$Cl) |
| 224 | 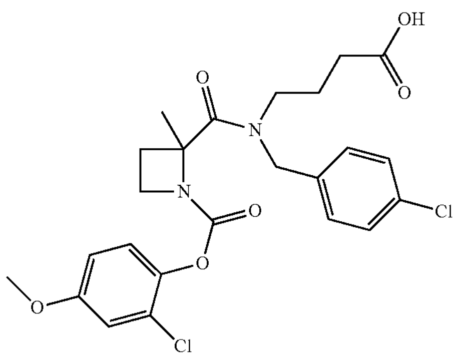 [SMILES: COc1ccc(OC(=O)N2CCC2(C)C(=O)N(CCCC(=O)O)Cc2ccc(Cl)cc2)c(Cl)c1] | 4-(1-((2-chloro-4-methoxyphenoxy)carbonyl)-N-(4-chlorobenzyl)-2-methylazetidine-2-carboxamido)butanoic acid | J (dioxane instead of MeOH) | Int 268 | 508.1 | 509.1 (M + 1, $^{35}$Cl) |
| 225 | 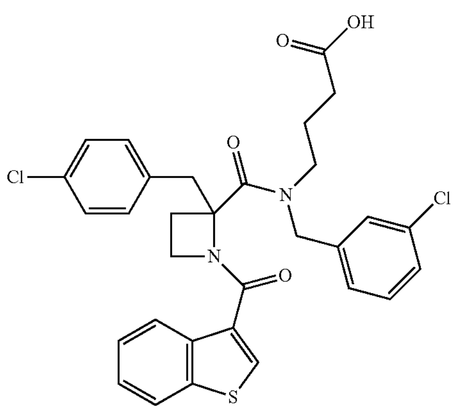 [SMILES: O=C(O)CCCN(Cc1cccc(Cl)c1)C(=O)C1(Cc2ccc(Cl)cc2)CCN1C(=O)c1csc2ccccc12] | 4-(1-(benzo[b]thiophene-3-carbonyl)-N-(3-chlorobenzyl)-2-(4-chlorobenzyl)azetidine-2-carboxamido)butanoic acid | J | Int 215 | 594.1 | 595.1 (M + 1, $^{35}$Cl) |
| 226 | 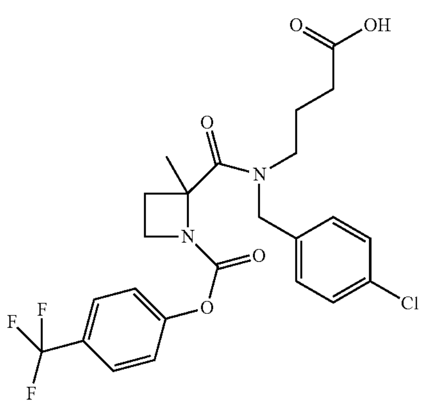 [SMILES: CC1(C(=O)N(CCCC(=O)O)Cc2ccc(Cl)cc2)CCN1C(=O)Oc1ccc(C(F)(F)F)cc1] | 4-(N-(4-chlorobenzyl)-2-methyl-1-((4-(trifluoromethyl)phenoxy)carbonyl)azetidine-2-carboxamido)butanoic acid | J | Int 251 | 512.1 | 513.1 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 227 | 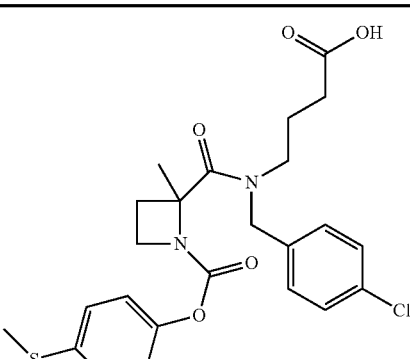 | 4-(N-(4-chlorobenzyl)-2-methyl-1-((4-(methylthio)phenoxy)carbonyl)azetidine-2-carboxamido)butanoic acid | J | Int 261 | 490.1 | 491.1 (M + 1, $^{35}$Cl) |
| 228 | 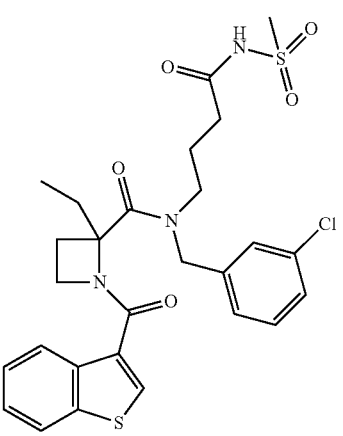 [SMILES: CCC1(C(=O)N(CCCC(=O)NS(C)(=O)=O)Cc2cccc(Cl)c2)CCN1C(=O)c1csc2ccccc12] | 1-(benzo[b]thiophene-3-carbonyl)-N-(3-chlorobenzyl)-2-ethyl-N-(4-(methylsulfonamido)-4-oxobutyl)azetidine-2-carboxamide | X | Cpd 195 | 575.1 | 576.1 (M + 1, $^{35}$Cl) |
| 229 | 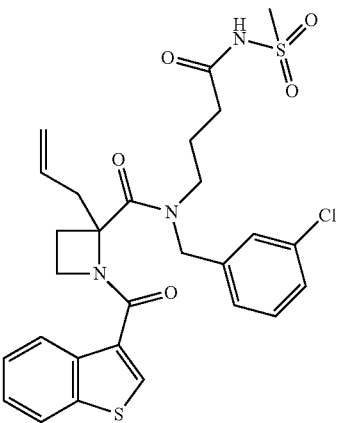 [SMILES: C=CCC1(C(=O)N(CCCC(=O)NS(C)(=O)=O)Cc2cccc(Cl)c2)CCN1C(=O)c1csc2ccccc12] | 2-allyl-1-(benzo[b]thiophene-3-carbonyl)-N-(3-chlorobenzyl)-N-(4-(methylsulfonamido)-4-oxobutyl)azetidine-2-carboxamide | X | Int 264 | 587.1 | 588.1 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 230 | 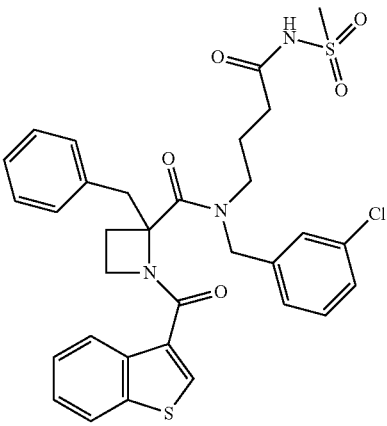 [SMILES: CS(=O)(=O)NC(=O)CCCN(Cc1cccc(Cl)c1)C(=O)C1(Cc2ccccc2)CCN1C(=O)c1csc2ccccc12] | 1-(benzo[b]thiophene-3-carbonyl)-2-benzyl-N-(3-chlorobenzyl)-N-(4-(methylsulfonamido)-4-oxobutyl)azetidine-2-carboxamide | X | Cpd 199 | 637.1 | 638.1 (M + 1, $^{35}$Cl) |
| 231 | 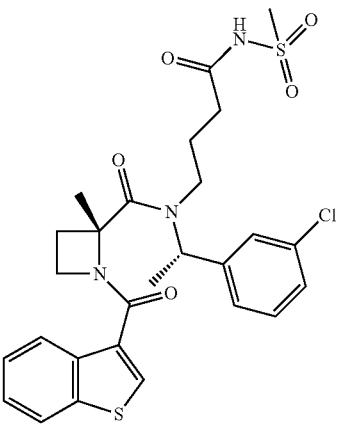 [SMILES: C[C@@H](c1cccc(Cl)c1)N(CCCC(=O)NS(C)(=O)=O)C(=O)[C@@]1(C)CCN1C(=O)c1csc2ccccc12] | (R)-1-(benzo[b]thiophene-3-carbonyl)-N-((S)-1-(3-chlorophenyl)ethyl)-2-methyl-N-(4-(methylsulfonamido)-4-oxobutyl)azetidine-2-carboxamide | X | Cpd 198 | 575.1 | 576.0 (M + 1, $^{35}$Cl) |
| 232 | 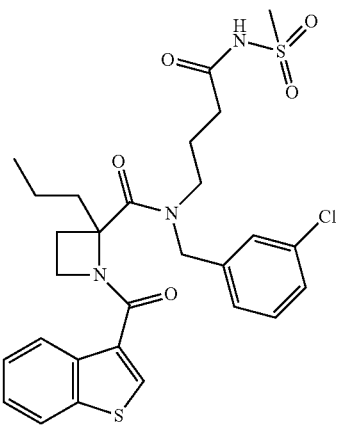 [SMILES: CCCC1(C(=O)N(CCCC(=O)NS(C)(=O)=O)Cc2cccc(Cl)c2)CCN1C(=O)c1csc2ccccc12] | 1-(benzo[b]thiophene-3-carbonyl)-N-(3-chlorobenzyl)-N-(4-(methylsulfonamido)-4-oxobutyl)-2-propylazetidine-2-carboxamide | X | Cpd 204 | 589.1 | 590.1 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 233 | 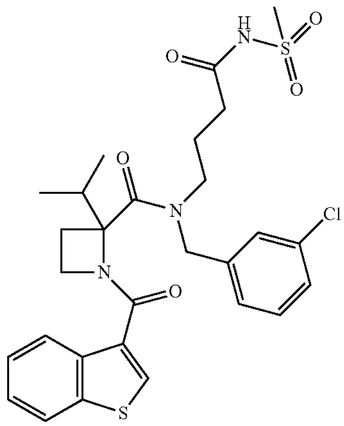 [SMILES: CC(C)C1(C(=O)N(CCCC(=O)NS(C)(=O)=O)Cc2cccc(Cl)c2)CCN1C(=O)c1csc2ccccc12] | 1-(benzo[b]thiophene-3-carbonyl)-N-(3-chlorobenzyl)-2-isopropyl-N-(4-(methylsulfonamido)-4-oxobutyl)azetidine-2-carboxamide | X | Cpd 203 | 589.1 | 590.1 (M + 1, $^{35}$Cl) |
| 234 | 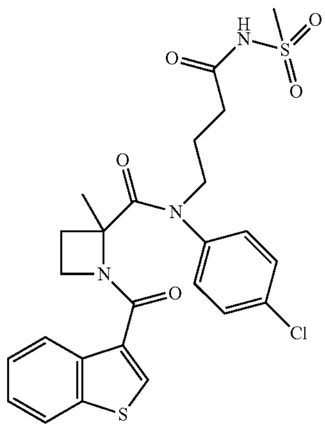 [SMILES: CC1(C(=O)N(CCCC(=O)NS(C)(=O)=O)c2ccc(Cl)cc2)CCN1C(=O)c1csc2ccccc12] | 1-(benzo[b]thiophene-3-carbonyl)-N-(4-chlorophenyl)-2-methyl-N-(4-(methylsulfonamido)-4-oxobutyl)azetidine-2-carboxamide | X | Cpd 194 | 547.1 | 548.0 (M + 1, $^{35}$Cl) |
| 235 | 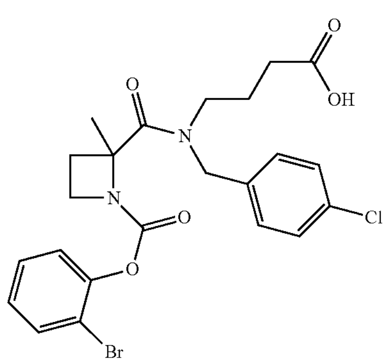 [SMILES: CC1(C(=O)N(CCCC(=O)O)Cc2ccc(Cl)cc2)CCN1C(=O)Oc1ccccc1Br] | 4-(1-((2-bromophenoxy)carbonyl)-N-(4-chlorobenzyl)-2-methylazetidine-2-carboxamido)butanoic acid | J (dioxane instead of MeOH) | Int 271 | 522.1 | 523.0 (M + 1) |
| 236 | 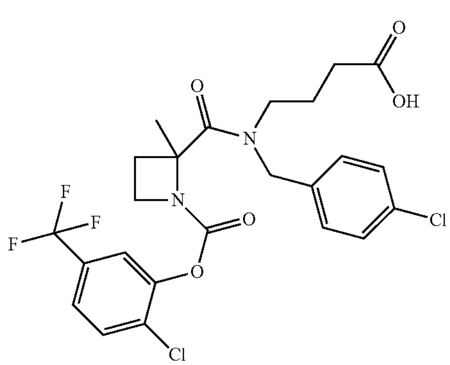 [SMILES: CC1(C(=O)N(CCCC(=O)O)Cc2ccc(Cl)cc2)CCN1C(=O)Oc1cc(C(F)(F)F)ccc1Cl] | 4-(1-((2-chloro-5-(trifluoromethyl)phenoxy)carbonyl)-N-(4-chlorobenzyl)-2-methylazetidine-2-carboxamido)butanoic acid | J (dioxane instead of MeOH) | Int 272 | 546.1 | 547.0 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 237 | 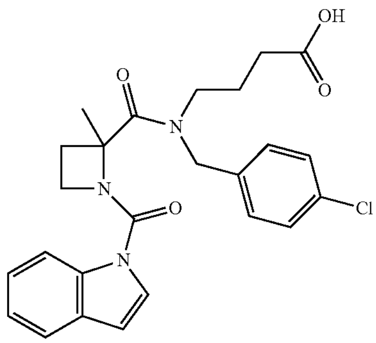 [SMILES: CC1(C(=O)N(CCCC(=O)O)Cc2ccc(Cl)cc2)CCN1C(=O)n1ccc2ccccc21] | 4-(N-(4-chlorobenzyl)-1-(1H-indole-1-carbonyl)-2-methylazetidine-2-carboxamido)butanoic acid | J (dioxane instead of MeOH) | Int 275 | 467.2 | 468.1 (M + 1, $^{35}$Cl) |
| 238 | 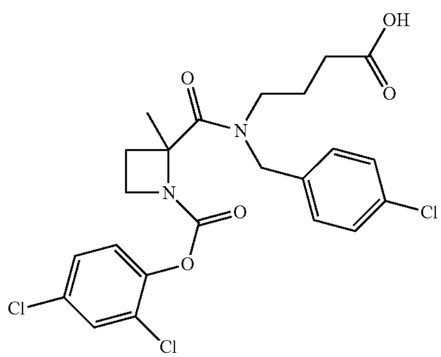 [SMILES: CC1(C(=O)N(CCCC(=O)O)Cc2ccc(Cl)cc2)CCN1C(=O)Oc1ccc(Cl)cc1Cl] | 4-(N-(4-chlorobenzyl)-1-((2,4-dichlorophenoxy)carbonyl)-2-methylazetidine-2-carboxamido)butanoic acid | J (dioxane instead of MeOH) | Int 273 | 512.1 | 513.0 (M + 1, $^{35}$Cl) |
| 239 | 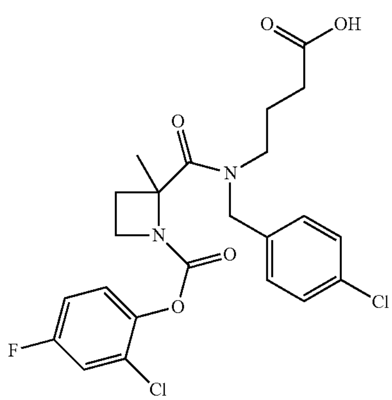 [SMILES: CC1(C(=O)N(CCCC(=O)O)Cc2ccc(Cl)cc2)CCN1C(=O)Oc1ccc(F)cc1Cl] | 4-(1-((2-chloro-4-fluorophenoxy)carbonyl)-N-(4-chlorobenzyl)-2-methylazetidine-2-carboxamido)butanoic acid | J (dioxane instead of MeOH) | Int 250 | 496.1 | 497.0 (M + 1, $^{35}$Cl) |
| 240 | 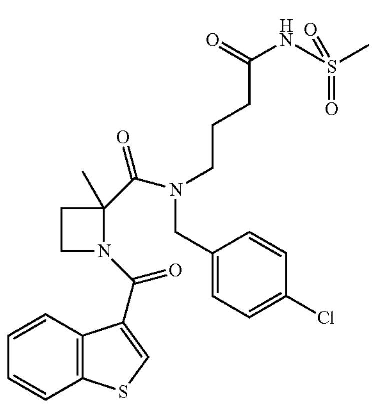 [SMILES: CC1(C(=O)N(CCCC(=O)NS(C)(=O)=O)Cc2ccc(Cl)cc2)CCN1C(=O)c1csc2ccccc12] | 1-(benzo[b]thiophene-3-carbonyl)-N-(4-chlorobenzyl)-2-methyl-N-(4-(methylsulfonamido)-4-oxobutyl)azetidine-2-carboxamide | X | Cpd 115 | 561.1 | 562.0 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 241 | 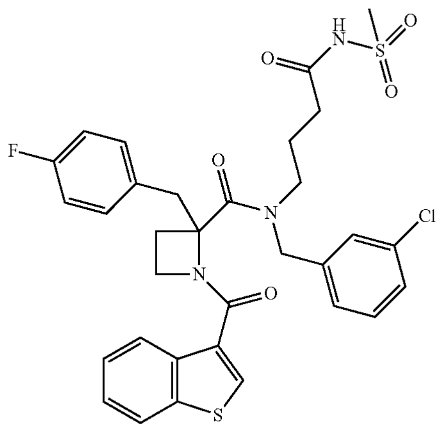 [SMILES: CS(=O)(=O)NC(=O)CCCN(Cc1cccc(Cl)c1)C(=O)C1(Cc2ccc(F)cc2)CCN1C(=O)c1csc2ccccc12] | 1-(benzo[b]thiophene-3-carbonyl)-N-(3-chlorobenzyl)-2-(4-fluorobenzyl)-N-(4-(methylsulfonamido)-4-oxobutyl)azetidine-2-carboxamide | X | Cpd 219 | 655.1 | 656.1 (M + 1, $^{35}$Cl) |
| 242 | 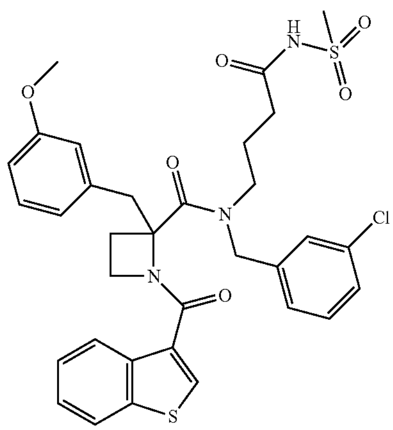 [SMILES: COc1cccc(CC2(C(=O)N(CCCC(=O)NS(C)(=O)=O)Cc3cccc(Cl)c3)CCN2C(=O)c2csc3ccccc23)c1] | 1-(benzo[b]thiophene-3-carbonyl)-N-(3-chlorobenzyl)-2-(3-methoxybenzyl)-N-(4-(methylsulfonamido)-4-oxobutyl)azetidine-2-carboxamide | X | Cpd 221 | 667.2 | 668.2 (M + 1, $^{35}$Cl) |
| 243 | 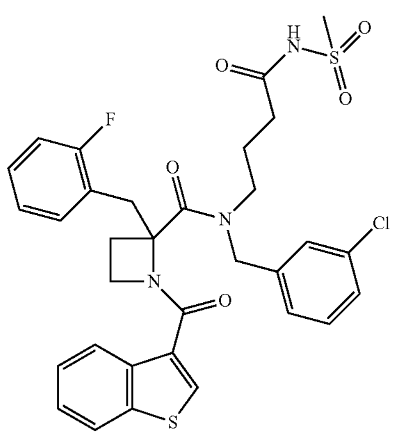 [SMILES: CS(=O)(=O)NC(=O)CCCN(Cc1cccc(Cl)c1)C(=O)C1(Cc2ccccc2F)CCN1C(=O)c1csc2ccccc12] | 1-(benzo[b]thiophene-3-carbonyl)-N-(3-chlorobenzyl)-2-(2-fluorobenzyl)-N-(4-(methylsulfonamido)-4-oxobutyl)azetidine-2-carboxamide | X | Int 236 | 655.1 | 656.2 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 244 | 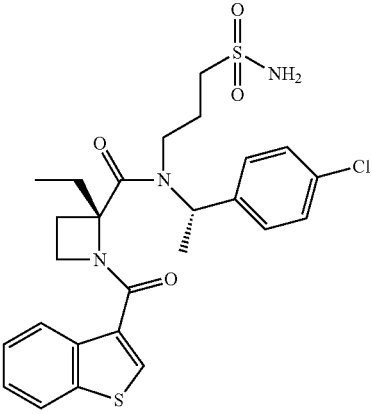 [SMILES: CC[C@]1(C(=O)N(CCCS(N)(=O)=O)[C@@H](C)c2ccc(Cl)cc2)CCN1C(=O)c1csc2ccccc12] | (R)-1-(benzo[b]thiophene-3-carbonyl)-N-((S)-1-(4-chlorophenyl)ethyl)-2-ethyl-N-(3-sulfamoylpropyl)azetidine-2-carboxamide | R | Int 259 | 547.1 | 548.1 (M + 1, $^{35}$Cl) |
| 245 | 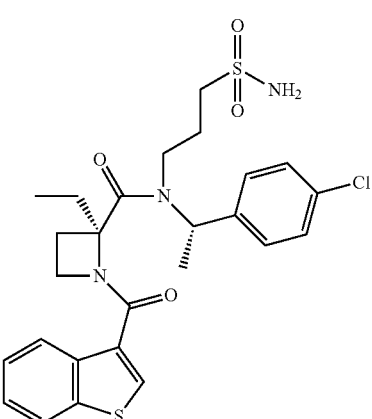 | (S)-1-(benzo[b]thiophene-3-carbonyl)-N-((S)-1-(4-chlorophenyl)ethyl)-2-ethyl-N-(3-sulfamoylpropyl)azetidine-2-carboxamide | R | Int 259 | 547.1 | 548.1 (M + 1, $^{35}$Cl) |
| 246 | 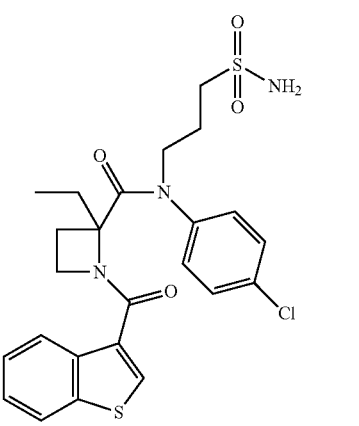 [SMILES: CCC1(C(=O)N(CCCS(N)(=O)=O)c2ccc(Cl)cc2)CCN1C(=O)c1csc2ccccc12] | 1-(benzo[b]thiophene-3-carbonyl)-N-(4-chlorophenyl)-2-ethyl-N-(3-sulfamoylpropyl)azetidine-2-carboxamide | R | Int 260 | 519.1 | 520.0 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 247 | 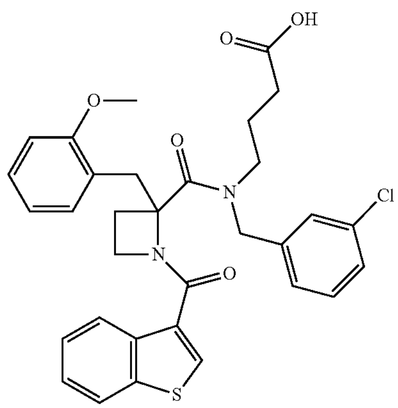 [SMILES: COc1ccccc1CC1(C(=O)N(CCCC(=O)O)Cc2cccc(Cl)c2)CCN1C(=O)c1csc2ccccc12] | 4-(1-(benzo[b]thiophene-3-carbonyl)-N-(3-chlorobenzyl)-2-(2-methoxybenzyl)azetidine-2-carboxamido)butanoic acid | J | Int 231 | 590.2 | 591.1 (M + 1, $^{35}$Cl) |
| 248 | 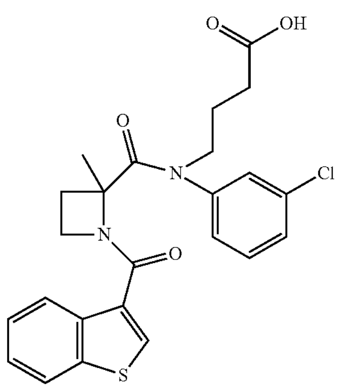 [SMILES: CC1(C(=O)N(CCCC(=O)O)c2cccc(Cl)c2)CCN1C(=O)c1csc2ccccc12] | 4-(1-(benzo[b]thiophene-3-carbonyl)-N-(3-chlorophenyl)-2-methylazetidine-2-carboxamido)butanoic acid | J | Int 243 | 470.1 | 471.0 (M + 1, $^{35}$Cl) |
| 249 | 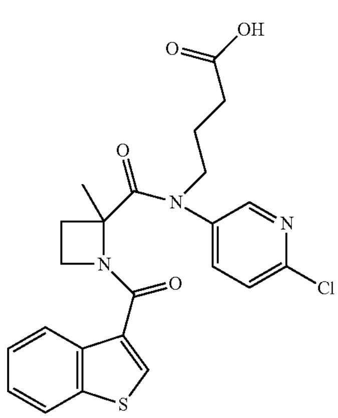 [SMILES: CC1(C(=O)N(CCCC(=O)O)c2ccc(Cl)nc2)CCN1C(=O)c1csc2ccccc12] | 4-(1-(benzo[b]thiophene-3-carbonyl)-N-(6-chloropyridin-3-yl)-2-methylazetidine-2-carboxamido)butanoic acid | Y | Int 239 | 471.1 | 472.0 (M + 1, $^{35}$Cl) |

TABLE IIa-continued

Mass spectral data of the Compounds of the Invention

| Cpd # | Structures | Name | Mtd | SM | Exact mass | MS Ms'd |
|---|---|---|---|---|---|---|
| 250 | 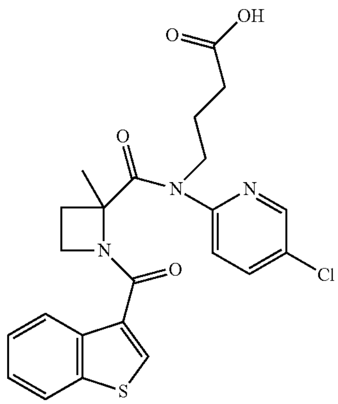 [SMILES: CC1(C(=O)N(CCCC(=O)O)c2ccc(Cl)cn2)CCN1C(=O)c1csc2ccccc12] | 4-(1-(benzo[b]thiophene-3-carbonyl)-N-(5-chloropyridin-2-yl)-2-methylazetidine-2-carboxamido)butanoic acid | Y | Int 241 | 471.1 | 472.0 (M + 1, $^{35}$Cl) |
| 251 | 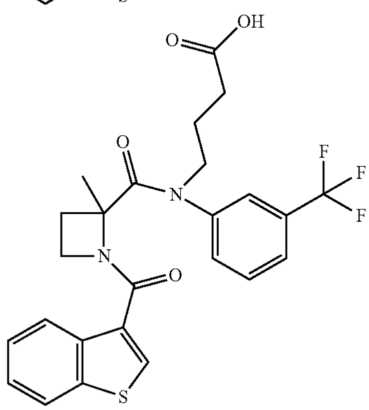 | 4-(1-(benzo[b]thiophene-3-carbonyl)-2-methyl-N-(3-(trifluoromethyl)phenyl)azetidine-2-carboxamido)butanoic acid | Y | Int 245 | 504.1 | 505.1 (M + 1, $^{35}$Cl) |
| 252 | 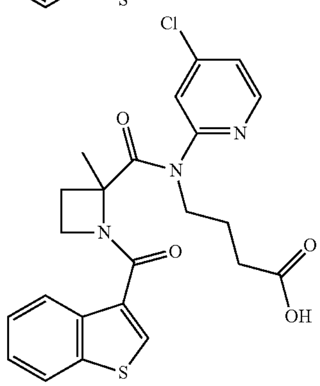 | 4-(1-(benzo[b]thiophene-3-carbonyl)-N-(4-chloropyridin-2-yl)-2-methylazetidine-2-carboxamido)butanoic acid | Y | Int 247 | 471.1 | 472.0 (M + 1, $^{35}$Cl) |
| 253 | 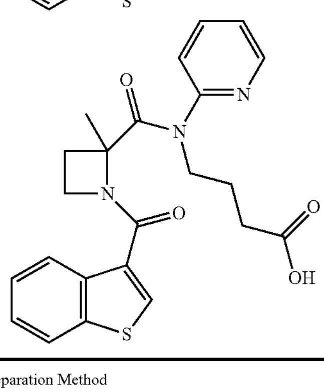 | 4-(1-(benzo[b]thiophene-3-carbonyl)-2-methyl-N-(pyridin-2-yl)azetidine-2-carboxamido)butanoic acid | Y | Int 249 | 437.1 | 438.1 (M + 1) |

Mtd = Preparation Method
SM = Starting Material
Ms'd = Measured mass

TABLE IIb

NMR Data of the Compounds of the Invention

| Cpd | NMR data (δ) |
|---|---|
| 1 | $^1$H NMR δ (ppm) (CDCl$_3$): 8.66 (1H, br s), 7.44 (1H, s), 7.30-7.15 (6H, m), 4.41 (2H, d), 4.20-4.02 (2H, m), 3.59-3.48 (2H, m), 3.01-2.90 (1H, m), 2.19-2.10 (1H, m), 1.81 (3H, s) |
| 2 | $^1$H NMR δ (ppm) (MeOD, d$_4$): 7.44-7.15 (7H, m), 7.02-6.94 (1H, m), 4.37-4.33 (2H, m), 4.29-3.94 (2H, m), 2.61-2.23 (2H, m), 1.88-1.75 (3H, m) |
| 3 | $^1$H NMR δ (ppm) (MeOD, d$_4$): 7.49-7.25 (4H, m), 7.02-6.89 (3H, m), 4.75-4.49 (2H, m), 4.22-4.05 (1H, m), 3.95-3.81 (1H, m), 3.51-3.35 (2H, m), 3.00-2.88 (3H, m), 2.70-2.36 (2H, m), 2.35-2.30 (6H, m), 2.00-1.87 (3H, m) |
| 4 | $^1$H NMR δ (ppm) (CDCl$_3$): 10.57 (1H, br s), 7.54 (2H, d), 7.47 (1H, s), 7.35-7.25 (4H, m), 4.25-4.05 (2H, m), 3.59 (2H, dd), 3.09-2.98 (1H, m), 2.25-2.13 (1H, m), 1.87 (3H, s) |
| 5 | $^1$H NMR δ (ppm) (CDCl$_3$): 7.38-7.07 (4H, m), 7.05-6.81 (3H, m), 4.68-4.52 (1H, m), 4.10-3.85 (2H, m), 3.86-3.47 (1H, m), 3.04-2.96 (2H, m), 2.96-2.84 (4H, m), 2.64-2.50 (1H, m), 2.31 (6H, s), 1.98-1.72 (3H, m) |
| 6 | $^1$H NMR δ (ppm) (CDCl$_3$): 7.23-7.04 (4H, m), 6.99-6.82 (3H, m), 4.81-4.21 (2H, m), 4.08-3.82 (2H, m), 3.81-3.15 (2H, m), 2.98-2.74 (3H, m), 2.64-2.44 (1H, m), 2.42-2.15 (10H, m), 1.96-1.74 (3H, m) |
| 7 | $^1$H NMR δ (ppm) (CDCl$_3$): 7.70-7.58 (2H, m), 7.45-7.32 (2H, m), 6.98 (1H, s), 6.95-6.81 (2H, m), 4.74-4.60 (1H, m), 4.09-3.85 (2H, m), 3.84-3.47 (1H, m), 3.02-2.87 (4H, m), 2.63-2.50 (1H, m), 2.38-2.26 (8H, m), 1.98-1.86 (3H) |
| 8 | $^1$H NMR δ (ppm) (MeOD, d$_4$): 7.85-7.60 (2H, m), 7.52-7.25 (5H, m), 7.18-7.06 (1H, m), 4.74-4.50 (2H, m), 4.26-4.07 (1H, m), 3.97-3.80 (2H, m), 3.62-3.45 (1H, m), 2.94 (3H, d), 2.72-2.38 (2H, m), 1.95 (3H, d) |
| 9 | $^1$H NMR δ (ppm) (MeOD, d$_4$): 7.53-7.37 (4H, m), 7.37-7.25 (4H, m), 4.72-4.54 (2H, m), 4.34-4.11 (1H, m), 4.06-3.83 (2H, m), 3.79-3.55 (1H, m), 2.97 (3H, s), 2.73-2.43 (2H, m), 1.97 (3H, d) |
| 10 | $^1$H NMR δ (ppm) (MeOD, d$_4$): 7.52-7.23 (8H, m), 4.74-4.51 (2H, m), 4.26-4.08 (1H, m), 3.98-3.48 (3H, m), 2.95 (3H, d), 2.72-2.40 (2H, m), 1.97 (3H, d) |
| 11 | $^1$H NMR δ (ppm) (MeOD, d$_4$): 7.51-7.25 (8H, m), 4.74-4.53 (2H, m), 4.26-4.07 (1H, m), 3.96-3.46 (3H, m), 2.95 (3H, d), 2.72-2.40 (2H, m), 1.96 (3H, d) |
| 12 | $^1$H NMR δ (ppm) (MeOD, d$_4$): 7.51-7.08 (7H, m), 4.75-4.53 (2H, m), 4.28-4.08 (1H, m), 3.98-3.47 (3H, m), 2.96 (3H, d), 2.73-2.42 (2H, m), 1.97 (3H, d) |
| 13 | $^1$H NMR δ (ppm) (MeOD, d$_4$): 8.05-7.85 (2H, m), 7.63-7.22 (7H, m), 4.73-4.53 (2H, m), 4.27-3.84 (3H, m), 3.84-3.69 (1H, m), 2.93 (3H, d), 2.75-2.39 (2H, m), 1.95 (3H, d) |
| 14 | $^1$H NMR δ (ppm) (MeOD, d$_4$): 7.94-7.79 (4H, m), 7.60-7.23 (7H, m), 4.76-4.49 (2H, m), 4.30-3.65 (4H, m), 2.94 (3H, d), 2.75-2.37 (2H, m), 1.98 (3H, d) |
| 15 | $^1$H NMR δ (ppm) (MeOD, d$_4$): 7.71-7.64 (2H, m), 7.62-7.56 (2H, m), 7.50-7.27 (6H, m), 7.25-7.17 (2H, m), 4.73-4.53 (2H, m), 4.29-4.09 (1H, m), 3.99-3.52 (3H, m), 2.96 (3H, d), 2.74-2.39 (2H, m), 1.98 (3H, d) |
| 16 | $^1$H NMR δ (ppm) (MeOD, d$_4$): 7.58-7.18 (11H, m), 7.10-6.91 (2H, m), 5.11 (2H, d), 4.68-4.47 (2H, m), 4.10-3.38 (4H, m), 2.88 (3H, d), 2.63-2.04 (2H, m), 1.69 (3H, d) |
| 17 | $^1$H NMR δ (ppm) (MeOD, d$_4$): 7.90 (2H, d), 7.52-7.26 (6H, m), 7.08-6.98 (1H, m), 4.78-4.55 (2H, m), 4.39-4.03 (1H, m), 3.99-3.80 (1H, m), 3.76-3.60 (1H, m), 3.44-3.35 (1H, m), 2.97 (3H, s), 2.73-2.42 (2H, m), 1.97 (3H, s) |
| 18 | $^1$H NMR δ (ppm) (MeOD, d$_4$): 7.65-7.22 (7H, m), 4.74-4.51 (2H, m), 4.29-4.08 (1H, m), 4.00-3.47 (3H, m), 2.95 (3H, d), 2.73-2.42 (2H, m), 1.96 (3H, d) |
| 19 | $^1$H NMR δ (ppm) (MeOD, d$_4$): 7.58-7.32 (4H, m), 7.17-7.01 (2H, m), 6.99-6.88 (1H, m), 4.82-4.57 (2H, m), 4.35-4.15 (1H, m), 4.10-3.57 (3H, m), 3.02 (3H, d), 2.80-2.48 (2H, m), 2.03 (3H, d) |
| 20 | $^1$H NMR δ (ppm) (MeOD, d$_4$): 7.88-7.68 (4H, m), 7.68-7.36 (9H, m), 4.89-4.61 (2H, m), 4.42-4.19 (1H, m), 4.13-3.63 (3H, m), 3.06 (3H, d), 2.87-2.49 (2H, m), 2.08 (3H, d) |
| 21 | $^1$H NMR δ (ppm) (MeOD, d$_4$): 7.87-7.66 (4H, m), 7.66-7.35 (8H, m), 4.86-4.62 (2H, m), 4.40-4.19 (1H, m), 4.11-3.62 (3H, m), 3.06 (3H, d), 2.84-2.49 (2H, m), 2.08 (3H, d) |
| 22 | $^1$H NMR δ (ppm) (MeOD, d$_4$): 8.16-8.03 (2H, m), 7.88-7.66 (4H, m), 7.66-7.32 (6H, m), 4.84-4.60 (2H, m), 4.40-4.19 (1H, m), 4.10-3.61 (3H, m), 3.03 (3H, d), 2.83-2.47 (2H, m), 2.06 (3H, d) |
| 23 | $^1$H NMR δ (ppm) (MeOD, d$_4$): 7.76-7.63 (4H, m), 7.59-7.36 (6H, m), 7.15 (2H, d), 4.86-4.63 (2H, m), 4.37-4.19 (1H, m), 3.99 (3H, s), 4.08-3.60 (3H, m), 3.06 (3H, d), 2.83-2.48 (2H, m), 2.08 (3H, d) |
| 24 | $^1$H NMR δ (ppm) (MeOD, d$_4$): 8.06-7.85 (4H, m), 7.85-7.73 (2H, m), 7.73-7.34 (6H, m), 4.88-4.60 (2H, m), 4.41-4.20 (1H, m), 4.13-3.61 (3H, m), 3.05 (3H, d), 2.83-2.48 (2H, m), 2.07 (3H, d) |
| 25 | $^1$H NMR δ (ppm) (MeOD, d$_4$): 7.63-7.28 (12H, m), 4.87-4.64 (2H, m), 4.42-4.22 (1H, m), 4.11-3.63 (3H, m), 3.07 (3H, d), 2.85-2.50 (2H, m), 2.40 (3H, d), 2.09 (3H, d) |
| 26 | $^1$H NMR δ (ppm) (MeOD, d$_4$): 8.38 (1H, s), 8.16-8.09 (1H, m), 7.98 (1H, d), 7.77-7.65 (3H, m), 7.63-7.33 (6H, m), 4.84-4.60 (2H, m), 4.36-4.18 (1H, m), 4.07 (3H, s), 4.06-3.59 (3H, m), 3.03 (3H, d), 2.81-2.47 (2H, m), 2.05 (3H, d) |
| 27 | $^1$H NMR δ (ppm) (MeOD-d$_4$): 7.85-7.73 (3H, m), 7.72-7.36 (10H, m), 4.80-4.60 (2H, m), 4.40-4.20 (1H, m), 4.13-3.62 (3H, m), 3.14-2.99 (3H, m), 2.84-2.49 (2H, m), 2.17-2.00 (3H, m) |
| 28 | $^1$H NMR δ (ppm) (MeOD, d$_4$): 7.92 (1H, d), 7.78 (1H, dd), 7.69 (1H, dd), 7.61-7.31 (9H, m), 4.86-4.60 (2H, m), 4.35-4.16 (1H, m), 4.09-3.62 (3H, m), 3.05 (3H, d), 2.81-2.47 (2H, m), 2.05 (3H, d) |
| 29 | $^1$H NMR δ (ppm) (MeOD, d$_4$): 7.87-7.61 (4H, m), 7.61-7.35 (8H, m), 4.85-4.58 (2H, m), 4.39-4.16 (1H, m), 4.14-3.62 (3H, m), 3.05 (3H, d), 2.82-2.48 (2H, m), 2.08 (3H, d) |
| 30 | $^1$H NMR δ (ppm) (CDCl$_3$): 7.59-7.45 (2H, m), 7.24-7.05 (2H, m), 7.04-6.80 (3H, m), 4.85-4.34 (2H, m), 4.10-3.86 (2H, m), 3.85-3.18 (2H, m), 2.88 (3H, s), 2.62-2.47 (1H, m), 2.39-2.19 (7H, s), 1.90 (3H, s) |

TABLE IIb-continued

NMR Data of the Compounds of the Invention

| Cpd | NMR data (δ) |
|---|---|
| 31 | $^1$H NMR δ (ppm) (CDCl$_3$): 7.49-7.11 (4H, m), 7.11-6.85 (3H, m), 4.85-4.27 (2H, m), 4.15-3.22 (4H, m), 3.12-2.80 (4H, m), 2.66-2.50 (1H, m), 2.48-2.21 (7H, m), 1.92 (3H, s), 1.28 (6H, d) |
| 32 | $^1$H NMR δ (ppm) (CDCl$_3$): 7.48-7.35 (2H, m), 7.26-7.10 (2H, m), 7.06-6.86 (3H, m), 4.85-4.27 (2H, m), 4.15-3.22 (4H, m), 2.90 (3H, s), 2.66-2.52 (1H, m), 2.38-2.24 (7H, m), 1.91 (3H, d), 1.35 (9H, s) |
| 33 | $^1$H NMR δ (ppm) (CDCl$_3$): 7.13-6.74 (6H, m), 5.05-4.18 (2H, m), 4.15-3.76 (3H, m), 3.61-3.38 (1H, m), 3.08-2.75 (3H, m), 2.67-2.52 (1H, m), 2.43-2.17 (13H, m), 2.00-1.77 (3H, m) |
| 34 | $^1$H NMR δ (ppm) (CDCl$_3$): 7.25-7.06 (4H, m), 7.06-6.84 (3H, m), 4.82-4.28 (2H, m), 4.11-3.38 (4H, m), 3.00-2.79 (3H, m), 2.65-2.45 (3H, m), 2.39-2.23 (7H, m), 1.99-1.82 (4H, m), 0.93 (6H, d) |
| 35 | $^1$H NMR δ (ppm) (CDCl$_3$): 7.46-7.28 (2H, m), 7.28-7.06 (2H, m), 7.06-6.70 (3H, m), 5.04-4.23 (2H, m), 4.13-3.00 (6H, m), 2.70-2.44 (1H, m), 2.41-2.21 (7H, m), 2.01-1.79 (3H, m), 1.32-1.08 (3H, m) |
| 36 | $^1$H NMR δ (ppm) (MeOD-d$_4$): 7.62-7.51 (1H, m), 7.46-7.25 (2H, m), 7.02-6.88 (3H, m), 4.90-4.60 (2H, m), 4.27-3.41 (4H, m), 2.99 (3H, d), 2.79-2.36 (2H, m), 2.32 (6H, s), 2.04-1.80 (3H, m) |
| 37 | $^1$H NMR δ (ppm) (MeOD-d$_4$): 7.51-7.28 (4H, m), 7.02-6.89 (3H, m), 4.80-4.55 (2H, m), 4.24-3.83 (2H, m), 3.83-3.43 (2H, m), 2.98 (3H, d), 2.72-2.36 (2H, m), 2.33 (3H, s), 2.32 (3H, s), 1.96 (3H, d) |
| 38 | $^1$H NMR δ (ppm) (MeOD-d$_4$): 7.69-7.57 (2H, m), 7.52-7.16 (9H, m), 7.01-6.93 (1H, m), 4.75-4.51 (2H, m), 4.28-3.50 (4H, m), 3.90 (3H, s), 2.95 (3H, d), 2.73-2.37 (2H, m), 1.97 (3H, d) |
| 39 | $^1$H NMR δ (ppm) (CDCl$_3$): 7.52-7.33 (2H, m), 7.30-7.09 (2H, m), 7.04-6.79 (3H, m), 4.80-4.23 (2H, m), 4.07-3.16 (4H, m), 2.86 (3H, s), 2.60-2.45 (1H, m), 2.37-2.21 (7H, m), 1.87 (3H, d) |
| 41 | $^1$H NMR δ (ppm) (MeOD-d$_4$): 7.40 (2H, d), 7.37-7.27 (2H, m), 7.08 (2H, d), 7.00 (1H, dd), 4.72-4.53 (2H, m), 4.21-3.82 (2H, m), 3.67-3.43 (2H, m), 2.95 (3H, d), 2.72-2.37 (2H, m), 2.31 (6H, d), 1.95 (3H, d) |
| 42 | $^1$H NMR δ (ppm) (MeOD-d$_4$): 7.59-7.45 (1H, m), 7.29-7.08 (2H, m), 7.02-6.88 (3H), 4.76-4.51 (2H, m), 4.25-3.82 (2H, m), 3.80-3.40 (2H, m), 2.96 (3H, d), 2.71-2.35 (2H, m), 2.32 (6H, m), 1.94 (3H, d) |
| 43 | $^1$H NMR δ (ppm) (CDCl$_3$): 8.59-8.50 (1H, m), 7.42 (1H, s), 7.22 (2H, s), 7.18-7.09 (4H, m), 4.44-4.39 (2H, m), 4.18-4.00 (2H, m), 3.56-3.50 (2H, m), 3.01-2.91 (1H, m), 2.36 (3H, s), 2.19-2.10 (1H, m), 1.81 (3H, s) |
| 44 | $^1$H NMR δ (ppm) (CDCl$_3$): 8.77 (1H, br s), 7.58 (2H, d), 7.43 (1H, s), 7.37 (2H, d), 7.25 (2H, d), 4.50 (2H, d), 4.21-4.06 (2H, m), 3.55 (2H, d), 3.02-2.93 (1H, m), 2.20-2.12 (1H, m), 1.82 (3H, s) |
| 45 | $^1$H NMR δ (ppm) (CDCl$_3$): 7.70-7.58 (2H, m), 7.49-7.33 (4H, m), 7.24 (1H, d), 4.89-4.44 (2H, m), 4.22-4.06 (1H, m), 4.04-3.73 (2H, m), 3.70-3.46 (1H, m), 2.93 (3H, s), 2.68-2.32 (2H, m), 1.95 (3H, s) |
| 46 | $^1$H NMR δ (ppm) (CDCl$_3$): 7.40-7.30 (2H, m), 7.24-7.14 (2H, m), 6.98-6.87 (3H, m), 4.74-4.42 (2H, m), 4.10-3.86 (2H, m), 3.79-3.30 (2H, m), 2.79-2.48 (2H, m), 2.37-2.20 (7H, m), 1.98 (3H, s), 0.93-0.58 (4H, m) |
| 47 | $^1$H NMR δ (ppm) (CDCl$_3$): 7.45-7.31 (2H, m), 7.28-7.03 (2H, m), 7.02-6.78 (3H, m), 5.04-4.24 (2H, m), 4.07-3.58 (5H, m), 3.54-3.06 (3H, m), 2.68-2.55 (1H, m), 2.38-2.23 (7H, m), 1.90 (3H, s) |
| 48 | $^1$H NMR δ (ppm) (CDCl$_3$): 7.42-7.23 (2H, m), 7.21-7.09 (2H, m), 6.99-6.72 (3H, m), 5.09-4.33 (2H, m), 4.26-3.81 (3H, m), 3.79-3.60 (4H, m), 3.48-3.15 (m, 2H), 2.75-2.60 (1H, m), 2.35-2.18 (7H, m), 1.91-1.76 (3H, m). |
| 49 | $^1$H NMR δ (ppm) (CDCl$_3$): 7.41-7.25 (2H, m), 7.21-7.10 (2H, m), 6.94-6.75 (3H, m), 5.16-4.60 (1H, m), 4.59-4.26 (1H, m), 4.25-3.64 (4H, m), 3.49-3.21 (2H, m), 2.70-2.59 (1H, m), 2.36-2.16 (7H, m), 1.91-1.76 (3H, m) |
| 50 | $^1$H NMR δ (ppm) (CDCl$_3$): 7.64 (1H, d), 7.50-7.38 (2H, m), 7.38-7.05 (5H, m), 4.90-4.00 (4H, m), 3.22-3.05 (1H, m), 2.98 (2H, s), 2.75-2.59 (4H, m), 2.47-2.29 (1H, m), 2.15-1.93 (3H, m) |
| 51 | $^1$H NMR δ (ppm) (CDCl$_3$): 8.56 (1H, br s), 7.42 (1H, s), 7.24-7.18 (3H, m), 7.10-7.04 (3H, m), 4.42 (2H, d), 4.18-4.02 (2H, m), 3.54 (2H, d), 3.01-2.92 (1H, m), 2.34 (3H, s), 2.19-2.11 (1H, m), 1.82 (3H, s) |
| 52 | $^1$H NMR δ (ppm) (CDCl$_3$): 8.66 (1H, br s), 7.44 (1H, s), 7.35-7.31 (2H, m), 7.28 (1H, s), 7.27-7.22 (3H, m), 4.51-4.35 (2H, m), 3.42-3.32 (1H, m), 3.19-3.09 (1H, m), 2.72-2.62 (1H, m), 1.94-1.84 (1H, m), 1.77 (3H, s), 1.77-1.70 (1H, m), 1.70-1.62 (1H, m), 1.22-1.14 (1H, m), 1.04-0.96 (1H, m) |
| 53 | $^1$H NMR δ (ppm) (MeOD-d$_4$): 7.50-7.21 (4H, m), 7.01-6.85 (3H, m), 4.84-4.74 (1H, m), 4.68-4.44 (1H, m), 4.24-4.00 (2H, m), 3.95-3.71 (2H, m), 3.65-3.50 (1H, m), 3.42-3.34 (3H, m), 2.85-2.74 (3H, m), 2.32 (6H, s), 2.01-1.86 (3H, m) |
| 54 | $^1$H NMR δ (ppm) (MeOD, d$_4$): 7.50-7.28 (4H, m), 7.00-6.85 (3H, m), 4.82-4.52 (2H, m), 4.43-4.08 (2H, m), 4.05-3.79 (2H, m), 3.78-3.52 (1H, m), 3.47-3.40 (1H, m), 3.07-2.96 (6H, m), 2.88-2.40 (2H, m), 2.35-2.29 (6H, m), 2.00-1.84 (3H, m) |
| 55 | $^1$H NMR δ (ppm) (MeOD, d$_4$): 7.60-7.24 (4H, m), 7.01-6.75 (3H, m), 4.90-4.50 (2H, m), 4.18-3.40 (7H, m), 3.35-3.15 (1H, m), 2.76-2.37 (2H, m), 2.33 (3H, s), 2.31 (3H, s), 2.04-1.80 (3H, m), 1.58-1.31 (3H, m) |
| 56 | $^1$H NMR δ (ppm) (CDCl$_3$): 7.45-7.28 (2H, m), 7.27-7.06 (2H, m), 7.04-6.76 (3H, m), 4.99-4.47 (2H, m), 4.16-3.09 (11H, m), 2.73-2.50 (1H, m), 2.38-2.21 (7H, m), 1.98-1.82 (3H, m) |

TABLE IIb-continued

NMR Data of the Compounds of the Invention

| Cpd | NMR data (δ) |
|---|---|
| 57 | $^1$H NMR δ (ppm) (CDCl$_3$): 8.74 (1H, br s), 7.91 (1H, d), 7.74 (1H, d), 7.45-7.35 (2H, m), 7.27-7.21 (3H, m), 7.15 (2H, d), 4.39 (2H, ddd), 4.10-3.94 (2H, m), 3.71 (2H, s), 2.96-2.86 (1H, m), 2.15-2.06 (1H, m), 1.81 (3H, s) |
| 58 | $^1$H NMR δ (ppm) (CDCl$_3$): 7.95-7.71 (2H, m), 7.46-7.27 (5H, m), 7.25-7.10 (2H, m), 5.04-3.53 (10H, m), 2.79-2.62 (1H, m), 2.42-2.22 (1H, m), 1.91 (3H, d), 1.38-1.22 (3H, m) |
| 59 | $^1$H NMR δ (ppm) (MeOD, d$_4$): 7.39-7.25 (1H, m), 7.25-7.06 (3H, m), 7.00-6.86 (3H, m), 4.87-4.51 (2H, m), 4.41-3.67 (5H, m), 3.62-3.41 (1H, m), 2.85-2.43 (2H, m), 2.45-2.37 (3H, m), 2.33 (3H, s), 2.31 (3H, s), 2.00-1.86 (3H, m) |
| 60 | $^1$H NMR δ (ppm) (CDCl$_3$): 7.95-7.69 (2H, m), 7.47-7.27 (5H, m), 7.27-7.07 (2H, m), 5.11-4.28 (3H, m), 4.12-3.89 (3H, m), 3.89-3.49 (5H, m), 2.78-2.65 (1H, m), 2.42-2.26 (1H, m), 1.98-1.75 (3H, m) |
| 61 | $^1$H NMR δ (ppm) (CDCl$_3$): 7.91-7.69 (2H, m), 7.48-7.29 (5H, m), 7.17 (2H, d), 4.71-4.33 (3H, m), 4.22-3.92 (3H, m), 3.86-3.61 (2H, m), 2.79-2.17 (2H, m), 2.01-1.69 (3H, m) |
| 62 | $^1$H NMR δ (ppm) (CDCl$_3$): 7.62-7.31 (2H, m), 7.26-7.06 (2H, m), 7.04-6.72 (3H, m), 4.99-4.35 (2H, m), 4.17-3.73 (3H, m), 3.72-3.61 (3H, m), 3.59-2.96 (3H, m), 2.73-2.47 (3H, m), 2.44-2.20 (7H, m), 1.95-1.77 (3H, m) |
| 63 | $^1$H NMR δ (ppm) (CDCl$_3$): 7.70-7.30 (2H, m), 7.27-7.04 (2H, m), 7.03-6.72 (3H, m), 5.00-4.28 (2H, m), 4.19-3.83 (2H, m), 3.83-3.33 (5H, m), 3.32-2.95 (2H, m), 2.79-2.16 (10H, m), 2.09-1.78 (5H, m) |
| 64 | $^1$H NMR δ (ppm) (CDCl$_3$): 7.45-7.30 (2H, m), 7.27-7.03 (2H, m), 7.03-6.74 (3H, m), 4.98-4.27 (2H, m), 4.11-2.95 (8H, m), 2.64-2.50 (1H, m), 2.44-2.22 (7H, m), 2.00-1.78 (5H, m) |
| 65 | $^1$H NMR δ (ppm) (CDCl$_3$): 7.46-7.31 (2H, m), 7.25-7.06 (2H, m), 7.01-6.75 (3H, m), 4.91-4.36 (2H, m), 4.01-3.18 (6H, m), 2.77-2.49 (3H, m), 2.37-2.22 (7H, m), 1.93-1.77 (3H, m) |
| 66 | $^1$H NMR δ (ppm) (CDCl$_3$): 7.92-7.70 (2H, m), 7.46-7.19 (6H, m), 7.12 (1H, s), 4.80-3.54 (8H, m), 2.78-2.59 (1H, m), 2.42-2.24 (1H, m), 1.98-1.70 (3H, m) |
| 67 | $^1$H NMR δ (ppm) (CDCl$_3$): 7.95-7.73 (2H, m), 7.47-7.26 (5H, m), 7.26-6.98 (2H, m), 4.85-4.23 (2H, m), 4.17-3.51 (6H, m), 3.59-3.05 (2H, m), 2.80-2.52 (1H, m), 2.37-2.22 (1H, m), 1.87 (3H, d), 1.96 (1H, br s) |
| 68 | $^1$H NMR δ (ppm) (CDCl$_3$): 7.49-7.33 (2H, m), 7.27-7.15 (2H, m), 7.02-6.80 (3H, m), 5.03-4.42 (3H, m), 4.18-3.87 (3H, m), 3.83-3.32 (2H, m), 2.80-2.67 (1H, m), 2.44-2.25 (7H, m), 1.92 (3H, d) |
| 69 | $^1$H NMR δ (ppm) (CDCl$_3$): 7.92-7.72 (2H, m), 7.49-7.22 (4H, m), 7.21-7.09 (1H, m), 7.03 (2H, s), 4.73-4.32 (2H, m), 4.32-4.12 (1H, m), 4.12-3.84 (3H, m), 3.84-3.58 (2H, m), 2.81-2.60 (1H, m), 2.43-2.24 (4H, m), 2.02-1.69 (3H, m) |
| 70 | $^1$H NMR δ (ppm) (CDCl$_3$): 7.96-7.87 (2H, m), 7.48-7.26 (5H, m), 7.26-7.00 (2H, m), 4.94-3.77 (5H, m), 3.71-3.43 (4H, m), 3.36-3.01 (1H, m), 2.66-2.27 (2H, m), 2.01-1.66 (5H, m) |
| 71 | $^1$H NMR δ (ppm) (CDCl$_3$): 7.45-7.31 (2H, m), 7.27-7.04 (2H, m), 7.00-6.74 (3H, m), 4.86-4.35 (2H, m), 4.09-3.85 (2H, m), 3.84-3.66 (1H, m), 3.59-3.23 (3H, m), 2.72-2.49 (3H, m), 2.50-2.17 (9H, m), 1.86 (3H, s) |
| 72 | $^1$H NMR δ (ppm) (CDCl$_3$): 7.44-7.31 (2H, m), 7.28-7.04 (2H, m), 7.02-6.76 (3H, m), 5.04-4.27 (2H, m), 4.14-3.70 (4H, m), 3.62-3.10 (3H, m), 2.93-2.81 (1H, m), 2.69-2.53 (1H, m), 2.34-2.26 (7H, m), 1.92-1.84 (3H, m), 1.23-1.08 (3H, m) |
| 73 | $^1$H NMR δ (ppm) (CDCl$_3$): 7.47-7.31 (2H, m), 7.26-7.06 (2H, m), 7.04-6.72 (3H, m), 5.01-4.35 (2H, m), 4.05-3.60 (6H, m), 3.59-3.10 (3H, m), 2.77-2.48 (3H, m), 2.42-2.18 (7H, m), 1.98-1.80 (3H, m) |
| 74 | $^1$H NMR δ (ppm) (CDCl$_3$): 7.45-7.31 (2H, m), 7.26-7.06 (2H, m), 7.01-6.75 (3H, m), 4.90-4.75 (1H, m), 4.56-4.36 (1H, m), 4.04-3.85 (2H, m), 3.85-3.37 (3H, m), 3.36-3.17 (1H, m), 2.78-2.48 (3H, m), 2.38-2.19 (7H, m), 1.95-1.78 (3H, m) |
| 75 | $^1$H NMR δ (ppm) (CDCl$_3$): 7.46-7.31 (2H, m), 7.26-6.93 (3H, m), 6.89 (2H, s), 4.94-4.44 (2H, m), 4.32-3.86 (3H, m), 3.86-3.28 (3H, m), 2.73-2.52 (1H, m), 2.33 (6H, s), 2.25-2.12 (1H, m), 1.87 (3H, s) |
| 76 | $^1$H NMR δ (ppm) (CDCl$_3$): 7.35 (2H, d), 7.04 (2H, d), 6.78 (3H, d), 5.08 (1H, d), 4.61 (1H, d), 4.28 (1H, d), 4.21-3.91 (3H, m), 3.40-3.26 (2H, m), 2.74-2.55 (1H, m), 2.31-2.19 (1H, m), 2.15 (6H, s), 1.88 (3H, s) |
| 77 | $^1$H NMR δ (ppm) (CDCl$_3$): 7.47-7.32 (2H, m), 7.21-7.10 (2H, m), 7.02-6.78 (3H, m), 4.95-4.47 (2H, m), 4.09-3.88 (2H, m), 3.87-3.40 (2H, m), 3.39-3.22 (2H, m), 2.89-2.55 (1H, m), 2.41-2.25 (7H, m), 1.94-1.82 (5H, m) |
| 78 | $^1$H NMR δ (ppm) (MeOD, d$_4$): 7.83-7.62 (2H, m), 7.54-7.45 (2H, m), 7.44-7.24 (5H, m), 4.84-4.49 (2H, m), 4.31-4.01 (2H, m), 4.00-3.84 (2H, m), 3.77-3.46 (2H, m), 2.85-2.38 (2H, m), 2.07-1.87 (3H, m) |
| 79 | $^1$H NMR δ (ppm) (MeOD, d$_4$): 8.12-7.87 (1H, m), 7.70-7.62 (2H, m), 7.48 (1H, d), 7.45-7.34 (3H, m), 7.34-7.27 (1H, m), 4.84-4.46 (2H, m), 4.41-4.30 (1H, m), 4.30-3.87 (5H, m), 2.89-2.49 (2H, m), 2.11-1.88 (3H, m) |
| 80 | $^1$H NMR δ (ppm) (CDCl$_3$): 7.45-7.30 (2H, m), 7.25-6.84 (5H, m), 4.85 (1H, d), 4.68-4.18 (2H, m), 4.18-4.03 (2H, m), 4.03-3.67 (2H, m), 3.42-3.24 (2H, m), 2.73-2.49 (1H, m), 2.32 (6H, s), 2.25-2.10 (1H, m), 1.87 (3H, s), 1.18 (6H, d) |
| 81 | $^1$H NMR δ (ppm) (CDCl$_3$): 7.47-7.30 (2H, m), 7.27-6.82 (5H, m), 4.86-4.37 (2H, m), 4.21-3.85 (3H, m), 3.83-3.27 (3H, m), 2.84-2.69 (1H, m), 2.62-2.46 (1H, m), 2.22-2.08 (1H, m), 2.33 (6H, s), 1.85 (3H, s), 0.78 (2H, d), 0.70-0.47 (2H, m) |
| 81a | $^1$H NMR δ (ppm) (CDCl$_3$): 7.46-7.31 (2H, m), 7.19 (2H, d), 6.99-6.80 (3H, m), 4.82-4.37 (2H, m), 4.25-3.88 (3H, m), 3.87-3.26 (3H, m), 2.79-2.61 (1H, m), 2.42-2.21 (7H, m), 1.96-1.78 (3H, m) |
| 82 | $^1$H NMR δ (ppm) (CDCl$_3$): 7.46-7.32 (2H, m), 7.25-7.16 (2H, m), 6.97-6.81 (3H, m), 4.91-4.30 (2H, m), 4.10-3.71 (4H, m), 3.52-3.27 (2H, m), 2.76-2.64 (1H, m), 2.37-2.23 (7H, m), 1.94-1.83 (3H, m) |

TABLE IIb-continued

NMR Data of the Compounds of the Invention

| Cpd | NMR data (δ) |
|---|---|
| 83 | $^1$H NMR δ (ppm) (CDCl$_3$): 7.45-7.31 (2H, m), 7.20 (2H, d), 7.03-6.82 (3H, m), 5.36-4.72 (1H, m), 4.64-3.84 (5H, m), 3.77-3.48 (7H, m), 3.45-3.28 (3H, m), 2.88-2.74 (1H, m), 2.40-2.23 (7H, m), 1.97-1.82 (3H, m) |
| 84 | $^1$H NMR δ (ppm) (CDCl$_3$): 7.94-7.73 (2H, m), 7.48-7.32 (5H, m), 7.26-7.11 (2H, m), 4.94-4.41 (3H, m), 4.30-3.87 (3H, m), 3.85-3.64 (2H, m), 2.75-2.60 (1H, m), 2.45-2.33 (1H, m), 1.92 (3H, d) |
| 85 | $^1$H NMR δ (ppm) (CDCl$_3$): 7.99-7.59 (2H, m), 7.53-7.31 (5H, m), 7.28-7.11 (2H, m), 4.72-4.35 (2H, m), 4.35-3.76 (6H, m), 3.76-3.56 (2H, m), 2.58-2.35 (2H, m) |
| 86 | $^1$H NMR δ (ppm) (CDCl$_3$): 7.95-7.71 (2H, m), 7.46-7.30 (5H, m), 7.22-7.04 (2H, m), 4.82-4.34 (2H, m), 4.15-3.81 (3H, m), 3.75-3.30 (6H, m), 2.71-2.50 (3H, m), 2.35-2.23 (1H, m), 1.96-1.76 (3H, m) |
| 87 | $^1$H NMR δ (ppm) (CDCl$_3$): 7.95-7.70 (2H, m), 7.46-7.29 (5H, m), 7.27-7.00 (2H, m), 4.85-4.23 (2H, m), 4.12 (2H, q), 4.09-3.80 (3H, m), 3.79-2.96 (3H, m), 2.63-2.47 (1H, m), 2.42-2.13 (3H, m), 2.03-1.75 (5H, m), 1.25 (3H, t) |
| 88 | $^1$H NMR δ (ppm) (CDCl$_3$): 8.25-7.80 (2H, m), 7.80-7.00 (7H, m), 6.40-5.60 (1H, m), 5.09-4.32 (2H, m), 4.30-3.31 (5H, m), 3.05-2.41 (3H, m), 2.39-2.11 (1H, m), 2.11-1.50 (3H, m) |
| 89 | $^1$H NMR δ (ppm) (MeOD, d$_4$): 7.89-7.63 (2H, m), 7.48-7.03 (7H, m), 4.67-3.86 (3H, m), 3.86-3.25 (3H, m), 3.20-2.92 (3H, m), 2.57-2.23 (2H, m), 2.12-1.93 (2H, m), 1.90-1.65 (5H, m) |
| 90 | $^1$H NMR δ (ppm) (CDCl$_3$): 7.47-7.27 (2H, m), 7.24-6.98 (2H, m), 6.97-6.56 (3H, m), 5.61-5.20 (1H, m), 4.97-4.52 (1H, m), 4.49-4.06 (1H, m), 4.04-3.52 (3H, m), 3.43-2.97 (2H, m), 2.62-2.43 (1H, m), 2.40-2.10 (7H, m), 2.09-1.73 (5H, m), 1.72-1.51 (2H, m) |
| 91 | $^1$H NMR δ (ppm) (CDCl$_3$): 7.71-7.54 (1H, m), 7.40-7.09 (8H, m), 4.83-4.28 (2H, m), 4.12-3.84 (2H, m), 3.78 (3H, s), 3.67-3.50 (2H, m), 2.88 (3H, s), 2.61-2.22 (2H, m), 1.90 (3H, d) |
| 92 | $^1$H NMR δ (ppm) (CDCl$_3$): 7.97-7.73 (2H, m), 7.66-7.47 (1H, m), 7.44-7.12 (5H, m), 4.77-4.37 (2H, m), 4.18-3.54 (4H, m), 2.89 (3H, d), 2.67-2.28 (2H, m), 1.92 (3H, d) |
| 93 | $^1$H NMR δ (ppm) (CDCl$_3$): 7.81-7.56 (2H, m), 7.51-7.12 (6H, m), 4.80-4.32 (2H, m), 4.10-3.55 (4H, m), 2.88 (3H, d), 2.68-2.22 (5H, m), 1.90 (3H, d) |
| 94 | $^1$H NMR δ (ppm) (CDCl$_3$): 7.32 (2H, d), 7.24-7.10 (3H, m), 6.91-6.89 (1H, m), 6.87-6.85 (2H, m), 4.50-4.22 (1H, m), 4.19-4.02 (2H, m), 3.47-3.25 (3H, m), 2.59-2.47 (1H, m), 2.37-2.21 (7H, m), 1.99 (3H, s) |
| 95 | $^1$H NMR δ (ppm) (CDCl$_3$): 7.35 (2H, d), 7.16 (2H, d), 6.96-6.87 (3H, m), 4.60-4.36 (2H, m), 4.19-3.95 (3H, m), 3.78-3.57 (1H, m), 3.46-3.32 (2H, m), 3.10 (3H, s), 2.64-2.52 (1H, m), 2.36-2.26 (7H, m), 1.99 (3H, s) |
| 96 | $^1$H NMR δ (ppm) (MeOD, d$_4$): 7.50-7.35 (2H, m), 7.22-7.08 (2H, m), 6.85-6.67 (4H, m), 6.37-6.28 (1H, m), 4.71-4.41 (2H, m), 4.03-3.54 (4H, m), 3.50-3.27 (2H, m), 2.79-2.23 (2H, m), 2.16 (3H, s), 2.12 (3H, s), 1.91-1.71 (3H, m) |
| 97 | $^1$H NMR δ (ppm) (CDCl$_3$): 7.49-7.31 (2H, m), 7.26-7.03 (3H, m), 7.02-6.74 (3H, m), 5.01-4.25 (2H, m), 4.21-3.64 (3H, m), 3.63-3.05 (3H, m), 2.71-2.56 (1H, m), 2.50-2.13 (9H, m), 2.01-2.69 (5H, m) |
| 98 | $^1$H NMR δ (ppm) (CDCl$_3$): 8.23 (1H, br s), 7.87 (1H, d), 7.50-7.38 (2H, m), 7.34 (2H, d), 7.32-7.09 (3H, m), 5.39-3.95 (4H, m), 3.01 (3H, s), 2.87-2.58 (1H, m), 2.48-2.35 (1H, m), 2.21-1.58 (3H, m) |
| 99 | $^1$H NMR δ (ppm) (CDCl$_3$): 7.95-7.74 (2H, m), 7.47-7.27 (5H, m), 7.22-6.95 (2H, m), 4.76 (1H, d), 4.53-3.80 (4H, m), 3.74-3.01 (3H, m), 2.68-2.52 (1H, m), 2.46-2.21 (3H, m), 2.00-1.80 (5H, m) |
| 100 | $^1$H NMR δ (ppm) (CDCl$_3$): 7.95-7.74 (2H, m), 7.47-4.31 (5H, m), 7.21-6.94 (2H, m), 4.73-4.58 (1H, m), 4.32-3.99 (3H, m), 3.69 (2H, s), 3.48-3.10 (2H, m), 2.99-2.79 (2H, m), 2.61-2.22 (2H, m), 2.04-1.79 (5H, m) |
| 101 | $^1$H NMR δ (ppm) (CDCl$_3$): 7.45-7.31 (2H, m), 7.28-7.01 (2H, m), 7.01-6.81 (3H, m), 4.90-4.18 (2H, m), 4.13-3.70 (3H, m), 3.69-3.03 (5H, m), 2.62-2.46 (1H, m), 2.37-2.17 (7H, m), 2.03-1.72 (7H, m) |
| 102 | $^1$H NMR δ (ppm) (CDCl$_3$): 7.45-7.31 (2H, m), 7.27-7.11 (1H, m), 7.10-6.85 (4H, m), 5.25-4.70 (1H, m), 4.64-4.21 (2H, m), 4.16-3.63 (3H, m), 3.50-3.21 (4H, m), 3.03-2.89 (4H, m), 2.77-2.49 (1H, m), 2.33 (6H, s), 1.86 (3H, s) |
| 103 | $^1$H NMR δ (ppm) (CDCl$_3$): 7.78-7.62 (2H, m), 7.48 (1H, t), 7.43-7.01 (6H, m), 4.84-4.50 (1H, m), 4.49-4.24 (1H, m), 4.08-3.87 (2H, m), 3.79-2.97 (4H, m), 2.64-2.16 (4H, m), 1.98-1.80 (5H, m) |
| 104 | $^1$H NMR δ (ppm) (CDCl$_3$): 8.06 (2H, d), 7.68-7.39 (3H, m), 7.36-7.17 (2H, m), 7.15-7.75 (5H, m), 4.72-7.16 (2H, m), 4.12-3.23 (5H, m), 2.71-2.51 (1H, m), 2.38-2.09 (7H, m), 1.94-1.66 (4H, m) |
| 105 | $^1$H NMR δ (ppm) (CDCl$_3$): 7.85-7.77 (1H, m), 7.70-7.45 (2H, m), 7.41-7.28 (4H, m), 7.28-7.06 (2H, m), 4.75-3.69 (6H, m), 2.86 (3H, d), 2.67-2.20 (2H, m), 1.91 (3H, d) |
| 106 | $^1$H NMR δ (ppm) (CDCl$_3$): 8.27-7.96 (2H, m), 7.66-7.52 (2H, m), 7.47-7.28 (3H, m), 7.28-7.05 (3H, m), 4.75-3.76 (6H, m), 2.87 (3H, d), 2.69-2.25 (2H, m), 1.92 (3H, d) |
| 107 | $^1$H NMR δ (ppm) (CDCl$_3$): 7.35 (2H, d), 7.21-6.98-(2H, m), 6.97-6.80 (3H, m), 4.72-4.51 (1H, m), 4.37-3.90 (4H, m), 3.36 (2H, bs), 3.07-2.86 (1H, m), 2.74-2.40 (3H, m), 2.35-2.10 (7H, m), 1.82 (3H, br s) |
| 108 | $^1$H NMR δ (ppm) (CDCl$_3$): 7.80 (1H, d), 7.72 (1H, d), 7.44-7.09 (7H, m), 4.77-3.56 (6H, m), 2.89 (3H, s), 2.65-2.26 (2H, m), 1.93 (3H, d) |
| 109 | $^1$H NMR δ (ppm) (CDCl$_3$): 7.33 (2H, d), 7.18-6.83 (5H, m), 4.53-4.35 (1H, m), 4.03-3.74 (3H, m), 3.50-3.37 (4H, m), 3.33-3.20 (2H, m), 2.51-2.38 (1H, m), 2.35-2.28 (6H, m), 2.18-2.06 (1H, m), 1.80-1.66 (3H, m) |
| 110 | $^1$H NMR δ (ppm) (CDCl$_3$): 8.11-7.95 (1H, m), 7.80-7.43 (2H, m), 7.12-6.67 (4H, m), 4.94-4.54 (2H, m), 4.24-3.69 (4H, m), 3.56-3.13 (2H, m), 2.82-2.68 (1H, m), 2.39-2.14 (7H, m), 2.00-1.83 (3H, m) |

TABLE IIb-continued

NMR Data of the Compounds of the Invention

| Cpd | NMR data (δ) |
|---|---|
| 111 | $^1$H NMR δ (ppm) (CDCl$_3$): 9.51-9.32 (1H, m), 7.44-7.29 (2H, m), 7.23-7.11 (2H, m), 6.97-6.75 (3H, m), 4.87 (1H, d), 4.65-4.32 (2H, m), 4.21-3.69 (3H, m), 3.45-3.21 (2H, m), 2.75-2.56 (1H, m), 2.36-2.21 (7H, m), 1.89 (3H, br s) |
| 112 | $^1$H NMR δ (ppm) (CDCl$_3$): 8.26-7.76 (2H, m), 7.53 (1H, d), 7.40-7.02 (6H, m), 4.86-3.61 (4H, m), 3.06 (3H, s), 2.91-2.57 (1H, m), 2.47-2.33 (1H, m), 2.05 (3H, s) |
| 113 | $^1$H NMR δ (ppm) (MeOD, d$_4$): 7.67-7.53 (1H, m), 7.43-7.24 (2H, m), 7.05-6.83 (4H, m), 6.49 (1H, br s), 5.03-4.55 (2H, m), 4.24-4.00 (1H, m), 3.95-3.05 (6H, m), 2.80-4.47 (1H, m), 2.44-2.21 (8H, m), 2.03-1.86 (5H, m) |
| 114 | $^1$H NMR δ (ppm) (CDCl$_3$): 7.40 (2H, d), 7.10 (2H, d), 6.91-6.78 (3H, m), 4.82-4.53 (2H, m), 4.37-3.70 (4H, m), 3.35 (2H, s), 2.68-2.55 (1H, m), 2.37-2.17 (7H, m), 1.90 (3H, s) |
| 115 | $^1$H NMR δ (ppm) (CDCl$_3$): 8.33-8.03 (1H, m), 7.90-7.81 (1H, m), 7.49-7.37 (2H, m), 7.33 (2H, d), 7.27-7.07 (2H, m), 6.83 (1H, br s), 5.33-4.73 (1H, m), 4.55-4.34 (1H, m), 4.30-3.72 (3H, m), 3.25-3.01 (1H, m), 2.89-2.67 (1H, m), 2.54-2.23 (3H, m), 2.18-1.83 (5H, m) |
| 116 | $^1$H NMR δ (ppm) (CDCl$_3$): 7.40-7.07 (2H, m), 7.03-6.91 (2H, m), 6.92-6.80 (3H, m), 5.49-5.33 (1H, m), 4.72-4.56 (1H, m), 4.11-3.72 (4H, m), 3.41-3.09 (3H, m), 3.02-2.74 (2H, m), 2.47-2.35 (1H, m), 2.28 (6H, s), 2.17-2.05 (1H, m), 1.83 (3H, s) |
| 117 | $^1$H NMR δ (ppm) (CDCl$_3$): 7.46-7.26 (2H, m), 7.24-7.04 (2H, m), 7.00-6.72 (3H, m), 5.02-4.89 (1H, m), 4.57-4.29 (1H, m), 4.01-3.81 (2H, m), 3.80-3.33 (3H, m), 3.33-3.08 (5H, m), 2.97-2.48 (3H, m), 2.35-2.25 (7H, m), 1.95-177 (3H, m) |
| 118 | $^1$H NMR δ (ppm) (CDCl$_3$): 7.42-7.28 (2H, m), 7.28-7.03 (2H, m), 7.01-6.74 (3H, m), 5.34 (1H, d), 4.89-4.23 (2H, m), 4.12-3.66 (5H, m), 3.59 (3H, d), 3.53-3.11 (3H, m), 2.89-2.72 (2H, m), 2.64-2.42 (1H, m), 2.34-2.20 (7H, m), 1.96-1.73 (3H, m), 1.42 (3H, t) |
| 119 | $^1$H NMR δ (ppm) (CDCl$_3$): 9.91 (1H, d), 7.45-7.32 (2H, m), 7.21-7.08 (2H, m), 6.98-6.75 (3H, m), 4.87-4.27 (2H, m), 4.06-3.73 (3H, m), 3.56-3.18 (3H, m), 2.87-2.77 (2H, m), 2.66-2.55 (1H, m), 2.35-2.46 (7H, m), 1.93-1.80 (3H, m) |
| 120 | $^1$H NMR δ (ppm) (CDCl$_3$): 7.44-7.11 (3H, m), 7.03-6.85 (4H, m), 5.60-5.40 (1H, m), 4.74 (1H, m), 4.28-3.75 (6H, m), 3.58-2.77 (6H, m), 2.35-2.09 (7H, m), 1.91-1.74 (3H, m), 1.41 (3H, t) |
| 121 | $^1$H NMR δ (ppm) (CDCl$_3$): 8.06-7.40 (3H, m), 7.38-7.30 (2H, m), 7.28-6.93 (3H, m), 6.80 (1H, s), 5.52-3.58 (4H, m), 3.07 (3H, s), 2.92-2.30 (2H, m), 2.04 (3H, s) |
| 122 | $^1$H NMR δ (ppm) (MeOD, d$_4$): 7.52-7.20 (4H, m), 7.02-6.83 (3H), 4.86-4.49 (2H, m), 4.22-3.73 (2H, m), 3.73-3.43 (10H, m), 3.35-3.12 (2H, m), 2.69-2.27 (10H, m), 2.06-1.81 (5H, m) |
| 123 | $^1$H NMR δ (ppm) (CDCl$_3$): 8.14-7.96 (1H, m), 7.84-7.39 (2H, m), 7.22-6.67 (4H, m), 5.11-4.49 (2H, m), 4.21-3.79 (2H, m), 3.79-3.27 (3H, m), 3.27-3.05 (2H, m), 2.74-2.46 (1H, m), 2.44-2.14 (8H, m), 2.04-1.79 (5H, m) |
| 124 | $^1$H NMR δ (ppm) (MeOD, d$_4$): 7.52-7.19 (4H, m), 7.03-6.83 (3H, m), 4.85-4.49 (2H, m), 4.23-3.69 (2H, m), 3.69-3.12 (7H, m), 2.69-2.26 (18H, m), 2.05-1.80 (5H, m) |
| 125 | $^1$H NMR δ (ppm) (CDCl$_3$): 7.44-7.04 (4H, m), 7.02-6.74 (3H, m), 4.92-4.32 (2H, m), 4.16-3.73 (2H, m), 3.73-3.04 (4H, m), 3.03-2.88 (6H, m), 2.62-2.45 (1H, m), 2.44-2.20 (9H, m), 2.04-1.76 (5H, m) |
| 126 | $^1$H NMR δ (ppm) (CDCl$_3$): 8.31-7.65 (4H, m), 7.63-7.50 (2H, m), 7.44-7.08 (5H, m), 5.56-3.63 (4H, m), 3.07 (3H, s), 2.93-2.34 (2H, m), 2.08 (3H, s) |
| 127 | $^1$H NMR δ (ppm) (CDCl$_3$): 7.93-7.75 (2H, m), 7.47-7.27 (5H, m), 7.27-6.97 (2H, m), 6.29 (1H, d), 5.48 (1H, d), 4.80-4.16 (2H, m), 4.16-3.79 (3H, m), 3.79-3.50 (2H, m), 3.28-3.04 (1H, m), 2.66-2.45 (1H, m), 2.42-2.12 (3H, m), 2.12-1.74 (5H, m) |
| 128 | $^1$H NMR δ (ppm) (MeOD, d$_4$): 8.07-7.77 (2H, m), 7.67-7.22 (6H, m), 7.08-6.87 (1H, m), 6.49 (1H, s), 5.02-4.53 (2H, m), 4.27-3.43 (5H, m), 3.33-3.10 (1H, m), 2.85-2.23 (4H, m), 2.03-1.85 (5H, m) |
| 129 | $^1$H NMR δ (ppm) (CDCl$_3$): 7.96-7.72 (2H, m), 7.52-7.31 (5H, m), 7.27-6.99 (2H, m), 4.87-4.22 (2H, m), 4.19-3.81 (3H, m), 3.80-3.01 (12H, m), 2.66-2.18 (3H, m), 2.03-1.75 (5H, m) |
| 130 | $^1$H NMR δ (ppm) (MeOD, d$_4$): 8.14-7.75 (4H, m), 7.65-7.34 (4H, m), 7.23-7.00 (1H, m), 5.03-4.59 (2H, m), 4.30-3.41 (5H, m), 3.31-3.11 (1H, m), 2.81-2.15 (4H, m), 2.04-1.84 (5H, m) |
| 131 | $^1$H NMR δ (ppm) (MeOD, d$_4$): 8.07-7.35 (8H, m), 7.32-7.08 (1H, m), 6.95-6.84 (1H, m), 4.90-4.54 (1H, m), 4.27-3.59 (5H, m), 3.48-3.10 (2H, m), 2.81-2.22 (4H, m), 2.03-1.85 (5H, m) |
| 132 | $^1$H NMR δ (ppm) (CDCl$_3$): 7.49-7.32 (2H, m), 7.24-7.09 (2H, m), 7.01-6.78 (3H, m), 5.92 (1H, br s), 5.05-4.23 (3H, m), 4.22-3.86 (3H, m), 3.86-3.21 (2H, m), 2.74-2.50 (1H, m), 2.40-2.24 (7H, m), 1.91 (3H, s) |
| 133 | $^1$H NMR δ (ppm) (CDCl$_3$): 7.43-7.29 (2H, m), 7.19-7.02 (2H, m), 6.97-6.90 (1H, m), 6.89-6.77 (3H, m), 5.57-5.35 (1H, m), 4.67 (2H, d), 4.49-4.13 (1H, m), 4.08-3.68 (3H, m), 3.52-3.14 (2H, m), 2.58-2.45 (1H, m), 2.34-2.14 (7H, m), 1.85 (3H, br s) |
| 134 | $^1$H NMR δ (ppm) (MeOD, d$_4$): 8.17-7.88 (2H, m), 7.66-7.23 (6H, m), 7.12-6.89 (1H, m), 6.50 (1H, s), 5.11-4.60 (2H, m), 4.39-3.70 (3H, m), 3.33-3.18 (1H, m), 2.86-2.27 (4H, m), 2.22-1.82 (5H, m) |
| 135 | $^1$H NMR δ (ppm) (MeOD, d$_4$): 8.26-7.59 (3H, m), 7.59-7.19 (6H, m), 5.20-4.55 (2H, m), 4.48-4.16 (1H, m), 3.99-3.71 (3H, m), 3.62-3.09 (2H, m), 2.87-2.65 (1H, m), 2.59-2.27 (3H, m), 2.06-1.92 (5H, m) |
| 136 | $^1$H NMR δ (ppm) (MeOD, d$_4$): 7.91-7.81 (1H, m), 7.78-7.50 (2H, m), 7.50-7.15 (6H, m), 4.81-3.72 (6H, m), 3.62-3.07 (2H, m), 2.74-2.19 (4H, m), 2.05-1.79 (5H, m) |
| 137 | $^1$H NMR δ (ppm) (MeOD, d$_4$): 7.85-7.54 (3H, m), 7.50 (1H, d), 7.44-7.21 (4H, m), 7.07-6.87 (1H, m), 6.49 (1H, br s), 5.04-4.55 (2H, m), 4.32-3.87 (2H, m), 3.80-3.41 (3H, m), 3.34-3.11 (1H, m), 2.84-2.19 (4H, m), 2.07-1.85 (5H, m) |
| 138 | $^1$H NMR δ (ppm) (CDCl$_3$): 8.17-6.97 (9H, m), 5.44-4.29 (2H, m), 4.08-2.72 (13H, m), 2.51-2.29 (2H, m), 2.18-1.91 (6H, m) |

TABLE IIb-continued

NMR Data of the Compounds of the Invention

| Cpd | NMR data (δ) |
|---|---|
| 139 | $^1$H NMR δ (ppm) (CDCl$_3$): 8.41-7.68 (2H, m), 7.53-6.72 (7H, m), 5.10 (1H, d), 4.46 (1H, d), 4.36-3.78 (3H, m), 3.77-3.34 (7H, m), 3.31-2.66 (3H, m), 2.51-1.85 (8H, m) |
| 140 | $^1$H NMR δ (ppm) (CDCl$_3$): 7.80-7.53 (2H, m), 7.53-7.45 (1H, m), 7.44-7.02 (6H, m), 4.90-3.84 (4H, m), 3.75-3.20 (11H, m), 3.18-3.01 (1H, m), 2.66-2.20 (4H, m), 2.04-1.79 (5H, m) |
| 141 | $^1$H NMR δ (ppm) (CDCl$_3$): 8.26-7.62 (2H, m), 7.50 (2H, d), 7.41-7.14 (4H, m), 6.50 (1H, br s), 5.47-4.31 (2H, m), 4.14-3.57 (4H, m), 3.21-2.55 (2H, m), 2.44-2.08 (3H, m), 2.07-1.43 (6H, m), 1.25-1.02 (3H, m) |
| 142 | $^1$H NMR δ (ppm) (CDCl$_3$): 8.30-7.95 (1H, m), 7.86-7.64 (1H, m), 7.50 (2H, d), 7.40-7.12 (4H, m), 6.43 (1H, br s), 5.49-4.30 (2H, m), 4.22-3.41 (5H, m), 3.20-2.52 (2H, m), 2.40-2.08 (3H, m), 2.05-1.65 (5H, m), 1.50 (2H, s), 1.24-1.02 (3H, m) |
| 143 | $^1$H NMR δ (ppm) (CDCl$_3$): 8.36-7.78 (2H, m), 7.50-7.35 (2H, m), 7.33-6.63 (5H, m), 5.48-4.75 (1H, m), 4.58-4.34 (1H, m), 4.31-3.72 (5H, m), 3.28-2.64 (2H, m), 2.49-2.19 (3H, m), 2.19-1.81 (4H, m), 1.65 (1H, s), 1.34-1.17 (3H, m) |
| 144 | $^1$H NMR δ (ppm) (CDCl$_3$): 7.97-7.55 (4H, m), 7.52-7.14 (5H, m), 4.95-4.28 (2H, m), 4.12-2.99 (6H, m), 2.64-2.48 (1H, m), 2.45-2.16 (3H, m), 2.02-1.73 (5H, m) |
| 145 | $^1$H NMR δ (ppm) (CDCl$_3$): 8.35-8.06 (1H, m), 7.95-7.75 (1H, m), 7.62 (2H, d), 7.49-7.30 (4H, m), 6.58 (1H, br s), 5.46 (1H, br s), 4.65-4.43 (1H, m), 4.12-3.69 (3H, m), 3.30-2.67 (2H, m), 2.55-2.25 (3H, m), 2.16-1.89 (5H, m) |
| 146 | $^1$H NMR δ (ppm) (CDCl$_3$): 8.34-8.08 (1H, m), 7.84 (1H, d), 7.50-7.36 (2H, m), 7.34-7.16 (3H, m), 7.08 (1H, br s), 6.83 (1H, br s), 5.34 (1H, br s), 4.60-4.34 (1H, m), 4.30-3.77 (3H, m), 3.31-2.69 (2H, m), 2.53-2.25 (3H, m), 2.17-1.87 (5H, m) |
| 147 | $^1$H NMR δ (ppm) (CDCl$_3$): 7.97-7.67 (2H, m), 7.56-7.33 (3H, m), 7.33-6.98 (4H, m), 4.91-4.27 (2H, m), 4.13 (2H, q), 4.06-3.83 (3H, m), 3.81-2.97 (3H, m), 2.64-2.49 (1H, m), 2.43-2.23 (3H, m), 2.04-1.61 (5H, m), 1.26 (3H, t) |
| 148 | $^1$H NMR δ (ppm) (CDCl$_3$): 7.94-7.68 (2H, m), 7.45-7.32 (3H, m), 7.32-6.96 (4H, m), 4.87-4.23 (2H, m), 4.19-3.82 (3H, m), 3.80-3.43 (2H, m), 3.37-3.01 (1H, m), 2.63-2.48 (1H, m), 2.45-2.17 (3H, m), 2.00-1.74 (5H, m) |
| 149 | $^1$H NMR δ (ppm) (CDCl$_3$): 7.43-7.31 (2H, m), 7.24-7.05 (2H, m), 7.02-6.94 (1H, m), 6.89 (1H, s), 6.80 (1H, br s), 4.94-4.28 (2H, m), 4.00-3.72 (2H, m), 3.62-2.94 (8H, m), 2.66-2.43 (1H, m), 2.42-2.20 (9H, m), 2.07-1.96 (2H, m), 1.93-1.68 (5H, m) |
| 150 | $^1$H NMR δ (ppm) (CDCl$_3$): 7.80-7.46 (3H, m), 7.45-7.04 (6H, m), 4.88-4.34 (2H, m), 4.25-3.75 (3H, m), 3.74-3.26 (6H, m), 2.75-2.25 (4H, m), 1.98-1.81 (3H, m) |
| 151 | $^1$H NMR δ (ppm) (CDCl$_3$): 8.40-8.07 (1H, m), 7.86 (1H, d), 7.49-7.37 (2H, m), 7.33 (2H, d), 7.27-6.75 (3H, m), 5.36-4.66 (1H, m), 4.62-4.42 (1H, m), 4.33-3.29 (7H, m), 2.85-2.33 (4H, m), 2.10-1.90 (3H, m) |
| 152 | $^1$H NMR δ (ppm) (CDCl$_3$): 8.16-8.03 (1H, m), 7.84-7.41 (4H, m), 7.40-6.89 (4H m), 5.11-4.47 (2H, m), 4.19-3.88 (4H, m), 3.75-3.05 (4H, m), 2.69-2.52 (1H, m), 2.43-2.13 (3H, m), 2.11-1.82 (5H, m), 1.32-1.17 (3H, m) |
| 153 | $^1$H NMR δ (ppm) (CDCl$_3$): 8.39-8.03 (2H, m), 7.94-7.66 (2H, m), 7.62-7.31 (3H, m), 7.19-6.93 (1H, m), 6.60 (1H, br s), 5.48-4.91 (1H, m), 4.73-4.51 (1H, m), 4.43-3.56 (5H, m), 3.34-3.04 (1H, m), 2.89-2.71 (1H, m), 2.50-2.20 (3H, m), 2.20-1.77 (5H, m), 1.32-1.13 (3H, m) |
| 154 | $^1$H NMR δ (ppm) (CDCl$_3$): 7.79-7.52 (2H, m), 7.48 (1H, dd), 7.44-7.23 (4H, m), 7.23-7.04 (2H, m), 4.81-4.34 (2H, m), 4.20-3.30 (6H, m), 2.76-2.48 (3H, m), 2.42-2.23 (1H, m), 1.96-1.78 (3H, d) |
| 155 | $^1$H NMR δ (ppm) (CDCl$_3$): 8.38-8.06 (1H, m), 7.86 (1H, d), 7.50-7.37 (2H, m), 7.33 (2H, d), 7.25-7.08 (2H, m), 6.99 (1H, br s), 5.28-4.68 (1H, m), 4.57-4.42 (1H, m), 4.09-3.79 (2H, m), 3.47-3.31 (1H, m), 3.10-2.56 (4H, m), 2.47-2.32 (1H, m), 2.14-1.89 (3H, m) |
| 156 | $^1$H NMR δ (ppm) (CDCl$_3$): 8.10-7.96 (1H, m), 7.80-7.34 (5H, m), 7.29-6.89 (3H, m), 5.06-4.44 (2H, m), 4.13-3.85 (2H, m), 3.80-2.96 (4H, m), 2.75-2.16 (4H, m), 2.05-1.79 (5H, m) |
| 157 | $^1$H NMR δ (ppm) (CDCl$_3$): 8.34-8.01 (2H, m), 7.90-7.62 (2H, m), 7.58-7.31 (3H, m), 7.18-6.74 (2H, m), 5.23-4.84 (1H, m), 4.70-4.48 (1H, m), 4.33-3.69 (3H, m), 3.27-3.10 (1H, m), 2.89-2.61 (1H, m), 2.53-2.23 (3H, m), 2.15-1.78 (5H, m) |
| 158 | $^1$H NMR δ (ppm) (CDCl$_3$): 8.34-8.09 (2H, m), 7.86 (1H, d), 7.50-7.37 (2H, m), 7.34 (2H, d), 7.27-7.09 (2H, m), 7.01-6.48 (1H, m), 5.44 (1H, br s), 5.21 (1H, br s), 4.43 (1H, d), 4.34-3.71 (3H, m), 3.30-3.09 (1H, m), 2.86-2.68 (1H, m), 2.48-2.24 (2H, m), 2.18-1.87 (5H, m) |
| 159 | $^1$H NMR δ (ppm) (CDCl$_3$): 7.74-7.55 (2H, m), 7.45-7.22 (2H, m), 7.02-6.70 (3H, m), 5.11-4.34 (2H, m), 4.19-3.66 (3H, m), 3.63-2.95 (3H, m), 2.65-2.48 (1H, m), 2.48-2.17 (9H, m), 2.01-1.75 (5H, m) |
| 160 | $^1$H NMR δ (ppm) (CDCl$_3$): 7.77-7.52 (4H, m), 7.48 (1H, dd), 7.43-7.19 (4H, m), 4.97-4.35 (2H, m), 4.04-3.87 (2H, m), 3.80-3.01 (4H, m), 2.66-2.49 (1H, m), 2.46-2.16 (3H, m), 2.02-1.79 (5H, m) |
| 161 | $^1$H NMR δ (ppm) (CDCl$_3$): 7.40-7.01 (4H, m), 7.01-6.85 (2H, m), 6.80 (1H, s), 5.02-4.23 (2H, m), 4.16-3.67 (3H, m), 3.61-2.99 (3H, m), 2.64-2.49 (1H, m), 2.45-2.18 (9H, m), 2.00-1.77 (5H, m) |
| 162 | $^1$H NMR δ (ppm) (MeOD, d$_4$): 7.85-7.76 (1H, m), 7.74-7.59 (1H, m), 7.57-7.36 (1H, m), 7.30-7.10 (1H, m), 7.03-6.83 (4H, m), 4.91-4.60 (2H, m), 4.16-4.01 (1H, m), 3.95-3.40 (3H, m), 3.40-3.11 (2H, m), 2.69-2.50 (1H, m), 2.47-2.20 (9H, m), 2.04-1.85 (5H, m) |
| 163 | $^1$H NMR δ (ppm) (MeOD, d$_4$): 8.33-8.04 (1H, m), 8.02-7.90 (1H, m), 7.81 (1H, d), 7.72-7.62 (1H, m), 7.61-7.40 (4H, m), 7.35-7.14 (1H, m), 6.89 (1H, m), 5.12-4.69 (2H, m), 4.39-3.95 (2H, m), 3.82-3.18 (2H, m), 2.85-2.46 (2H, m), 2.45-2.28 (3H, m), 2.23-1.86 (5H, m) |
| 164 | $^1$H NMR δ (ppm) (DMSO, d$_6$): 7.98 (1H, d), 7.78 (1H, dd), 7.72-7.57 (2H, m), 7.56-7.46 (2H, m), 7.33-7.15 (3H, m), 6.95 (1H, d), 4.82-4.51 (2H, m), 3.90-3.49 (4H, m), 3.20-3.01 (2H, m), 2.48-2.27 (2H, m), 2.26-2.09 (2H, m), 1.96-1.64 (5H, m) |

TABLE IIb-continued

NMR Data of the Compounds of the Invention

| Cpd | NMR data (δ) |
|---|---|
| 165 | $^1$H NMR δ (ppm) (CDCl$_3$): 7.74-7.56 (2H, m), 7.44-7.23 (2H, m), 7.03-6.69 (3H, m), 5.17-4.37 (2H, m), 4.12 (2H, q), 3.99-2.96 (6H, m), 2.68-2.48 (1H, m), 2.39-2.12 (9H, m), 2.02-1.76 (5H, m), 1.25 (3H, t) |
| 166 | $^1$H NMR δ (ppm) (CDCl$_3$): 7.76-7.57 (2H, m), 7.54-7.46 (1H, m), 7.44-7.00 (6H, m), 6.71-6.01 (1H, m), 5.58-5.26 (1H, m), 4.86-3.86 (4H, m), 3.73-3.08 (4H, m), 2.69-2.52 (1H, m), 2.43-2.17 (3H, m), 2.01-1.81 (5H, m) |
| 167 | $^1$H NMR δ (ppm) (CDCl$_3$): 7.81-7.57 (4H, m), 7.49 (1H, d), 7.44-7.20 (4H, m), 5.01-4.37 (2H, m), 4.12 (2H, q), 4.08-3.87 (2H, m), 3.80-2.83 (4H, m), 2.67-2.52 (1H, m), 2.46-2.15 (3H, m), 2.03-.1.80 (5H, m), 1.25 (3H, t) |
| 168 | $^1$H NMR δ (ppm) (CDCl$_3$): 7.45-7.31 (2H, m), 7.22-7.00 (3H, m), 7.00-6.72 (3H, m), 6.53-6.41 (2H, m), 5.00-4.48 (2H, m), 4.47-4.16 (3H, m), 4.01-3.38 (10H, m), 3.31-2.91 (2H, m), 2.91-2.63 (2H, m), 2.61-2.45 (1H, m), 2.38-2.19 (7H, m), 2.01-1.76 (5H, m) |
| 169 | $^1$H NMR δ (ppm) (CDCl$_3$): 8.11-7.99 (1H, m), 7.74 (1H, d), 7.39-7.24 (2H, m), 7.21-6.78 (5H, m), 5.13 (1H, br s), 4.39 (1H, br s), 4.00-3.23 (4H, m), 2.77-2.54 (3H, m), 2.38-2.22 (1H, m), 2.05-1.81 (3H, br s) |
| 170 | $^1$H NMR δ (ppm) (CDCl$_3$): 7.85-7.57 (2H, m), 7.38-7.15 (5H, m), 7.14-6.89 (2H, m), 4.71-3.24 (8H, m), 2.66-2.34 (3H, m), 2.29-2.08 (1H, m), 1.74 (3H, d) |
| 171 | $^1$H NMR δ (ppm) (CDCl$_3$): 7.43-7.29 (2H, m), 7.22-6.99 (2H, m), 6.96-6.79 (3H, m), 5.30-5.01 (2H, m), 4.75 (1H, d), 4.59-4.14 (1H, m), 4.06-3.80 (2H, m), 3.79-3.58 (1H, m), 3.34-3.01 (5H, m), 2.61-2.43 (1H, m), 2.33-2.24 (6H, m), 2.24-2.12 (1H, m), 2.13-2.03 (2H, m), 1.84 (3H, br s) |
| 172 | $^1$H NMR δ (ppm) (CDCl$_3$): 8.40-8.11 (1H, m), 7.85 (1H, d), 7.51-7.36 (2H, m), 7.33-6.77 (5H, m), 5.34 (1H, br s), 4.62-4.41 (1H, m), 4.35-3.78 (3H, m), 3.71 (3H, s), 3.62-3.30 (1H, m), 2.91-2.62 (3H, m), 2.48-2.35 (1H, m), 2.19-1.90 (3H, m) |
| 173 | $^1$H NMR δ (ppm) (CDCl$_3$): 7.97-7.69 (2H, m), 7.47-7.27 (5H, m), 7.26-7.01 (2H, m), 4.90-4.35 (2H, m), 4.14-3.80 (3H, m), 3.77-3.29 (6H, m), 2.75-2.52 (3H, m), 2.35-2.25 (1H, m), 1.85 (3H, d) |
| 174 | $^1$H NMR δ (ppm) (CDCl$_3$): 7.48-7.31 (2H, m), 7.27-7.02 (2H, m), 7.02-6.76 (3H, m), 4.97-4.23 (3H, m), 4.09-3.85 (2H, m), 3.85-2.88 (6H, m), 2.88-2.65 (3H, m), 2.65-2.49 (1H, m), 2.42-2.18 (7H, m), 2.14-1.80 (5H, m) |
| 175 | $^1$H NMR δ (ppm) (CDCl$_3$): 8.11 (1H, d), 7.98-7.63 (3H, m), 7.47-4.31 (4H, m), 7.13-6.93 (1H, m), 4.93-4.55 (2H, m), 4.18-3.70 (4H, m), 3.67 (3H, d), 3.63-3.40 (2H, m), 2.74-2.55 (3H, m), 2.37-2.24 (1H, m), 2.05-1.80 (3H, m) |
| 176 | $^1$H NMR δ (ppm) (MeOD, d$_4$): 8.09 (1H, d), 8.06-7.75 (3H, m), 7.63-7.35 (4H, m), 7.23-7.02 (1H, m), 4.92-3.87 (4H, m), 3.86-3.44 (4H, m), 2.84-2.62 (3H, m), 2.61-2.40 (1H, m), 2.07-1.87 (3H, m) |
| 177 | $^1$H NMR δ (ppm) (MeOD, d$_4$): 8.42-8.17 (1H, m), 7.88-7.59 (3H, m), 7.58-7.45 (1H, m), 7.45-7.15 (4H, m), 6.93-6.57 (1H, m), 4.73-4.43 (1H, m), 4.17-3.89 (1H, m), 3.86-3.52 (3H, m), 3.46-3.23 (2H, m), 2.64-2.26 (2H, m), 2.26-2.07 (2H, m), 1.91-1.68 (5H, m) |
| 178 | $^1$H NMR δ (ppm) (CDCl$_3$): 7.92-7.67 (2H, m), 7.44-7.31 (4H, m), 7.30-7.26 (1H, m), 7.18-6.90 (3H, m), 6.51-6.34 (2H, m), 4.97-4.80 (1H, m), 4.75-4.30 (1H, m), 4.26-4.14 (2H, m), 4.02-3.84 (2H, m), 3.85-3.71 (7H, m), 3.63-3.30 (2H, m), 3.25-2.90 (1H, m), 2.88-2.62 (2H, m), 2.56-2.37 (2H, m), 2.55-2.35 (1H, m), 2.36-2.13 (1H, m), 1.97-1.78 (4H, m) |
| 179 | $^1$H NMR δ (ppm) (CDCl$_3$): 7.45-7.31 (2H, m), 7.22-6.80 (5H, m), 4.85-4.51 (2H, m), 4.03-3.81 (3H, m), 3.81-3.73 (5H, m), 3.52-3.10 (8H, m), 2.74-2.59 (1H, m), 2.34-2.19 (7H, m), 1.87 (3H, s) |
| 180 | $^1$H NMR δ (ppm) (CDCl$_3$): 7.42-7.28 (2H, m), 7.21-7.04 (2H, m), 6.96 (1H, br s), 6.87 (1H, br s), 6.81 (1H, br s), 4.98-4.45 (2H, m), 4.06-3.75 (3H, m), 3.80-3.64 (5H, m), 3.61-3.39 (1H, m), 3.40-3.07 (8H, m), 2.74-2.53 (1H, m), 2.33-2.15 (7H, m), 1.82 (3H, br s), 1.62-1.57 (4H, m) |
| 181 | $^1$H NMR δ (ppm) (CDCl$_3$): 7.90-7.71 (2H, m), 7.46-7.26 (5H, m), 7.19-6.89 (2H, m), 5.20-4.88 (2H, m), 4.70-4.34 (1H, m), 4.08-3.85 (2H, m), 3.80-3.44 (3H, m), 3.29-2.88 (3H, m), 2.59-2.37 (1H, m), 2.36-2.13 (1H, m), 2.09-1.98 (1H, m), 1.86 (3H, br s) |
| 182 | $^1$H NMR δ (ppm) (CDCl$_3$): 8.18-8.06 (1H, m), 7.82 (1H, d), 7.45-7.35 (2H, m), 7.33-7.29 (2H, m), 7.19-7.03 (2H, m), 5.16-4.99 (2H, m), 4.47-4.34 (1H, m), 4.08-3.80 (3H, m), 3.23-3.09 (2H, m), 2.79-2.65 (1H, m), 2.43-2.27 (1H, m), 2.23-2.08 (2H, m), 1.99 (3H, br s) |
| 183 | $^1$H NMR δ (ppm) (CDCl$_3$): 9.08 (1H, br s), 8.11-7.57 (4H, m), 7.50-7.27 (4H, m), 5.30 (2H, s), 5.03-4.40 (2H, m), 4.14-3.96 (1H, m), 3.78-3.42 (3H, m), 3.41-3.02 (2H, m), 2.74-2.45 (1H, m), 2.42-2.16 (3H, m), 1.92 (3H, br s) |
| 184 | $^1$H NMR δ (ppm) (CDCl$_3$): 9.01 (1H, br s), 8.11-7.95 (2H, m), 7.92-7.69 (2H, m), 7.45-7.25 (2H, m), 7.25-7.15 (1H, m), 7.10-6.46 (1H, m), 5.39-5.21 (1H, m), 4.69-4.35 (3H, m), 4.10-3.92 (1H, m), 3.90-3.72 (1H, m), 3.27-3.06 (1H, m), 2.90-2.70 (1H, m), 2.44-2.18 (3H, m), 2.11-1.84 (3H, m) |
| 185 | $^1$H NMR δ (ppm) (CDCl$_3$): 9.05 (1H, br s), 8.08-7.83 (2H, m), 7.45-7.27 (1H, m), 6.93 (1H, br s), 6.82 (1H, br s), 6.73 (1H, br s), 5.11-4.89 (1H, m), 4.84-4.37 (2H, m), 4.00-3.64 (3H, m), 3.62-3.33 (1H, m), 3.31-3.01 (2H, m), 2.71-2.43 (2H, m), 2.40-2.13 (9H, m), 1.99-1.80 (3H, m) |
| 186 | $^1$H NMR δ (ppm) (CDCl$_3$): 8.27-8.05 (1H, m), 7.89-7.76 (1H, m), 7.47-7.35 (2H, m), 7.34-7.27 (2H, m), 7.21-6.90 (3H, m), 5.31-4.90 (1H, m), 4.60-4.32 (1H, m), 4.05-3.75 (3H, m), 3.26-2.95 (1H, m), 2.89-2.66 (3H, m), 2.47-2.28 (1H, m), 2.18-2.05 (2H, m), 2.05-1.90 (3H, m), 1.77 (3H, br s) |
| 187 | $^1$H NMR δ (ppm) (CDCl$_3$): 8.19-8.08 (1H, m), 7.81 (1H, d), 7.46-7.32 (2H, m), 7.30-7.22 (3H, m), 7.21-7.14 (1H, m), 7.11-6.99 (1H, m), 5.24-5.02 (2H, m), 4.45-4.29 (1H, m), 4.08-3.96 (1H, m), 3.96-3.78 (2H, m), 3.25-3.02 (2H, m), 2.81-2.63 (1H, m), 2.44-2.26 (1H, m), 2.22-2.08 (2H, m), 2.05-1.90 (3H, m) |

TABLE IIb-continued

NMR Data of the Compounds of the Invention

| Cpd | NMR data (δ) |
|---|---|
| 188 | $^1$H NMR δ (ppm) (CDCl$_3$): 8.30-7.87 (2H, m), 7.81-7.67 (1H, m), 7.66-7.51 (1H, m), 7.49-7.38 (1H, m), 7.37-7.23 (3H, m), 7.06-6.80 (1H, m), 5.87-5.32 (2H, m), 5.16-4.91 (1H, m), 4.68-4.40 (1H, m), 4.12-3.92 (1H, m), 3.97-3.67 (1H, m), 3.61-3.37 (1H, m), 2.87-2.48 (2H, m), 2.41-2.15 (1H, m), 2.14-1.87 (3H, m) |
| 189 | $^1$H NMR δ (ppm) (CDCl$_3$): 7.91-7.70 (2H, m), 7.44-7.27 (6H, m), 7.21-6.92 (2H, m), 4.77-4.62 (1H, m), 4.59-4.15 (1H, m), 4.03-3.83 (2H, m), 3.83-3.48 (3H, m), 3.34-3.06 (1H, m), 3.06-2.84 (1H, m), 2.79-2.63 (1H, m), 2.58-2.40 (1H, m), 2.32-2.15 (1H, m), 2.06-1.92 (3H, m), 1.93-1.77 (3H, m) |
| 190 | $^1$H NMR δ (ppm) (CDCl$_3$): 8.22-8.07 (1H, m), 7.89-7.74 (2H, m), 7.49-7.31 (3H, m), 7.23-7.13 (2H, m), 7.13-6.82 (2H, m), 5.38-5.14 (1H, m), 4.62-4.31 (3H, m), 4.06-3.77 (4H, m), 3.27-3.09 (1H, m), 2.83-2.72 (1H, m), 2.47-2.31 (2H, m), 2.19-2.06 (3H, m), 2.06-1.90 (3H, m) |
| 191 | $^1$H NMR δ (ppm) (DMSO, d$_6$) at 80° C.: 8.14-8.08 (1H, m), 7.99-7.93 (1H, m), 7.90 (1H, s), 7.44-7.31 (3H, m), 7.30-7.25 (2H, m), 7.22-7.16 (1H, m), 4.73-4.54 (2H, m), 4.11-3.98 (2H, m), 3.44-3.34 (1H, m), 3.26-3.15 (1H, m), 2.58-2.51 (1H, m), 2.41-2.32 (1H, m), 2.18 (2H, t), 1.85-1.76 (5H, m) |
| 192 | $^1$H NMR δ (ppm) (CDCl$_3$): 8.20 (1H, d), 7.83 (1H, d), 7.48-7.28 (5H, m), 7.20-7.07 (2H, m), 5.61-5.40 (1H, m), 4.96-4.78 (1H, m), 4.53-4.40 (1H, m), 4.38-4.20 (1H, m), 4.03-3.83 (1H, m), 3.47-3.12 (3H, m), 2.92-2.69 (1H, m), 2.42-2.23 (1H, m), 2.07-1.89 (3H, m) |
| 193 | $^1$H NMR δ (ppm) (CDCl$_3$): 8.20 (1H, d), 7.83 (1H, d), 7.47-7.29 (5H, m), 7.19-7.09 (2H, m), 5.31-5.11 (1H, m), 5.09-4.88 (1H, m), 4.61-4.41 (1H, m), 4.27-3.80 (3H, m), 3.48-3.35 (1H, m), 3.35-3.17 (2H, m), 2.42-2.24 (1H, m), 2.14-1.88 (3H, m), 1.68-1.47 (3H, m) |
| 194 | $^1$H NMR δ (ppm) (CDCl$_3$): 8.29 (1H, d), 7.82 (1H, d), 7.48-7.26 (6H, m), 7.10-6.95 (1H, m), 4.03-3.86 (1H, m), 3.86-3.59 (3H, m), 2.65-2.51 (1H, m), 2.46 (2H, t), 2.18-2.02 (1H, m), 1.99-1.84 (2H, m), 1.84-1.67 (3H, m) |
| 195 | $^1$H NMR δ (ppm) (CDCl$_3$): 8.13-8.03 (1H, m), 7.85-7.75 (1H, m), 7.46-7.31 (6H, m), 7.27-7.13 (4H, m), 7.10-6.98 (1H, m), 6.77-6.66 (1H, m), 5.56-5.31 (1H, m), 4.43-4.21 (1H, m), 4.09-3.80 (2H, m), 3.76-3.56 (1H, m), 3.08-2.90 (1H, m), 2.77-2.58 (2H, m), 2.59-2.10 (5H, m), 2.03-1.84 (2H, m), 1.15-1.01 (3H, m) |
| 196 | $^1$H NMR δ (ppm) (CDCl$_3$): 7.41-7.30 (2H, m), 7.23-7.09 (2H, m), 6.84-6.72 (2H, m), 6.59-6.43 (1H, m), 5.10-4.73 (1H, m), 4.55-4.36 (1H, m), 4.10-3.81 (3H, m), 3.72-3.58 (1H, m), 3.20-3.04 (1H, m), 2.72-2.62 (1H, m), 2.44-2.30 (4H, m), 2.30-2.25 (6H, m), 1.90-1.80 (3H, m) |
| 197 | $^1$H NMR δ (ppm) (CDCl$_3$): 8.07-7.99 (1H, m), 7.86 (1H, d), 7.52-7.14 (7H, m), 4.24-3.83 (2H, m), 3.64-3.44 (1H, m), 2.99-2.82 (1H, m), 2.82-2.68 (1H, m), 2.54-2.20 (3H, m), 2.15-1.78 (5H, m), 1.73 (3H, d) |
| 198 | $^1$H NMR δ (ppm) (CDCl$_3$): 8.27-8.16 (1H, m), 7.85 (1H, d), 7.75-7.61 (1H, m), 7.48-7.35 (2H, m), 7.36-7.29 (2H, m), 7.25-7.15 (2H, m), 5.53-5.31 (1H, m), 4.29-4.09 (1H, m), 4.09-3.90 (1H, m), 3.62-3.44 (1H, m), 2.90-2.61 (2H, m), 2.48-2.21 (3H, m), 2.17-1.99 (2H, m), 1.96-1.73 (3H, m), 1.67 (3H, d) |
| 199 | $^1$H NMR δ (ppm) (DMSO, d$_6$): 8.31-8.16 (1H, m), 8.08-7.90 (2H, m), 7.85-7.68 (1H, m), 7.52-7.20 (10H, m), 4.80-4.56 (2H, m), 4.09-3.83 (2H, m), 3.44-3.22 (2H, m), 3.22-3.06 (1H, m), 3.04-2.87 (2H, m), 2.45-2.33 (2H, m), 2.23 (2H, t), 1.91-1.71 (2H, m) |
| 200 | $^1$H NMR δ (ppm) (CDCl$_3$): 9.82-9.74 (1H, m), 7.44-7.40 (1H, m), 7.39-7.34 (1H, m), 7.26-7.21 (1H, m), 7.20-7.15 (2H, m), 7.13-7.11 (1H, m), 6.68 (1H, s), 4.79-4.62 (1H, m), 4.51-4.36 (1H, m), 4.19-3.97 (1H, m), 3.72-3.47 (2H, m), 3.36-3.10 (2H, m), 2.80-2.65 (1H, m), 2.48-2.35 (2H, m), 2.32 (3H, s), −2.30 (3H, s), 1.99-1.91 (2H, m), 1.82-1.71 (3H, m) |
| 201 | $^1$H NMR δ (ppm) (MeOD, d$_4$): 7.49-7.26 (4H, m), 7.03-6.85 (2H, m), 6.70-6.58 (1H, br s), 4.84-4.54 (2H, m), 3.50-3.35 (1H, m), 3.36-3.20 (1H, m), 3.20-3.05 (3H, m), 2.94-2.65 (1H, m), 2.43-2.18 (9H, m), 2.16-1.96 (1H, m), 1.96-1.78 (5H, m) |
| 202 | $^1$H NMR δ (ppm) (MeOD, d$_4$): 7.54-7.14 (8H, m), 4.76-4.45 (2H, m), 4.30-3.98 (1H, m), 3.97-3.78 (1H, m), 3.58-3.09 (1H, m), 2.75-2.43 (2H, m), 2.36-2.22 (2H, m), 2.07-1.75 (5H, m) |
| 203 | $^1$H NMR δ (ppm) (CDCl$_3$): 8.10-7.97 (1H, m), 7.86-7.73 (1H, m), 7.48-7.31 (2H, m), 7.24-7.11 (3H, m), 7.09-6.95 (1H, m), 6.73-6.61 (1H, m), 4.42 (1H, d), 4.18-3.89 (2H, m), 3.68-3.52 (1H, m), 3.05-2.75 (3H, m), 2.62-2.22 (4H, m), 2.09-1.84 (2H, m), 1.34-1.23 (3H, m), 1.06-0.95 (3H, m) |
| 204 | $^1$H NMR δ (ppm) (CDCl$_3$): 8.13-7.97 (1H, m), 7.81 (1H, d), 7.48-7.31 (2H, m), 7.28-7.14 (3H, m), 7.10-6.95 (1H, m), 6.78-6.62 (1H, m), 5.60-5.28 (1H, m), 4.46-4.27 (1H, m), 4.09-3.83 (2H, m), 3.75-3.53 (1H, m), 3.10-2.88 (1H, m), 2.83-2.64 (1H, m), 2.61-2.28 (4H, m), 2.25-2.07 (1H, m), 2.02-1.84 (2H, m), 1.60-1.35 (2H, m), 1.12-0.89 (3H, m) |
| 205 | $^1$H NMR δ (ppm) (MeOD, d$_4$): 7.50-6.98 (8H, m), 4.77-4.49 (2H, m), 4.24-3.94 (2H, m), 3.94-3.80 (1H, m), 3.57-3.38 (1H, m), 3.33-3.06 (2H, m), 2.71-2.42 (2H, m), 2.35-2.07 (5H, m), 1.95-1.77 (3H, m) |
| 206 | $^1$H NMR δ (ppm) (MeOD, d$_4$): 7.52-7.31 (4H, m), 7.07-6.91 (2H, m), 6.72-6.63 (1H, m), 4.87-4.61 (2H, m), 3.50-3.41 (1H, m), 3.23-3.10 (3H, m), 3.01-2.74 (2H, m), 2.44-2.23 (9H, m), 1.99-1.82 (5H, m), 1.39-1.10 (2H, m) |
| 207 | $^1$H NMR δ (ppm) (CDCl$_3$): 8.17 (1H, d), 7.83 (1H, d), 7.50-7.34 (2H, m), 7.33-7.22 (3H, m), 7.21-7.14 (1H, m), 7.13-7.01 (1H, m), 5.19-4.87 (1H, m), 4.43-4.28 (1H, m), 4.22-4.04 (1H, m), 4.03-3.87 (1H, m), 3.86-3.61 (1H, m), 3.30-3.07 (4H, m), 2.84-2.64 (1H, m), 2.42-2.22 (3H, m), 2.13-1.77 (5H, m) |
| 208 | $^1$H NMR δ (ppm) (CDCl$_3$): 8.16-7.93 (1H, m), 7.80-7.64 (1H, m), 7.37-7.21 (2H, m), 7.20-6.89 (4H, m), 6.87-6.69 (1H, m), 6.12-5.67 (2H, m), 4.38-4.18 (1H, m), 3.94-3.74 (2H, m), 3.68-3.50 (1H, m), 3.11-2.35 (6H, m), 2.14-1.91 (4H, m), 1.02-0.90 (3H, br s) |
| 209 | $^1$H NMR δ (ppm) (CDCl$_3$): 8.26-8.05 (1H, m), 7.85 (1H, t), 7.70 (1H, br s), 7.47-7.37 (2H, m), 7.34 (1H, d), 7.30 (1H, d), 7.25-7.11 (2H, m), 5.68-5.00 (2H, m), 4.28-3.85 (2H, m), |

TABLE IIb-continued

NMR Data of the Compounds of the Invention

| Cpd | NMR data (δ) |
|---|---|
| | 3.82-3.53 (1H, m), 3.20-2.64 (4H, m), 2.42-2.29 (1H, m), 2.27-1.91 (3H, m), 1.66 (3H, d), 1.61 (3H, br s) |
| 211 | $^1$H NMR δ (ppm) (MeOD, d$_4$): 7.87-7.80 (1H, m), 7.59-7.56 (1H, m), 7.47-7.22 (7H, m), 4.78-4.54 (1H, m), 4.34-4.08 (1H, m), 3.93 (1H, br s), 3.88-3.60 (1H, m), 3.28-3.12 (1H, m), 2.74-2.51 (2H, m), 2.38-2.24 (2H, m), 2.11-1.82 (6H, m) |
| 216 | $^1$H NMR δ (ppm) (CDCl$_3$): 8.25-8.02 (1H, m), 7.83 (1H, d), 7.46-7.34 (2H, m), 7.31 (2H, d), 7.10 (2H, d), 6.92 (1H, br s), 5.27-4.61 (3H, m), 4.36 (1H, d), 4.09-3.60 (3H, m), 3.27-2.92 (3H, m), 2.79-2.43 (3H, m), 2.28-1.99 (3H, m), 1.09 (3H, br s) |
| 217 | $^1$H NMR δ (ppm) (CDCl$_3$): 8.16-7.98 (1H, m), 7.90-7.77 (1H, m), 7.49-7.31 (2H, m), 7.30-7.11 (4H, m), 7.10-6.70 (1H, m), 5.75 (1H, d), 5.04-4.83 (2H, m), 4.42 (1H, d), 4.29-3.92 (2H, m), 3.76-3.58 (1H, m), 3.24-2.73 (5H, m), 2.58-2.48 (1H, m), 2.27-1.97 (2H, m), 1.30-1.24 (4H, m), 1.05-0.95 (2H, m) |
| 218 | $^1$H NMR δ (ppm) (CDCl$_3$): 7.39-7.08 (5H, m), 6.84-6.46 (3H, m), 5.00-4.70 (1H, m), 4.58-4.30 (1H, m), 4.18-3.85 (2H, m), 3.78 (3H, s), 3.70-3.46 (1H, m), 3.23-3.01 (1H, m), 2.79-2.21 (4H, m), 2.02-1.75 (5H, m) |
| 219 | $^1$H NMR δ (ppm) (CDCl$_3$): 8.35-8.20 (1H, m), 7.82 (1H, d), 7.45 (1H, t), 7.42-7.30 (3H, m), 7.29-7.04 (4H, m), 6.96 (3H, t), 5.34-4.73 (1H, m), 4.68-4.34 (1H, m), 4.18 (1H, d), 4.00-3.48 (2H, m), 3.34-2.98 (3H, m), 2.60-2.20 (4H, m), 2.07-1.84 (2H, m) |
| 221 | $^1$H NMR δ (ppm) (CDCl$_3$): 8.37-8.21 (1H, m), 7.81 (1H, d), 7.43 (1H, t), 7.37 (1H, t), 7.33-6.90 (8H, m), 6.79 (1H, d), 5.29-4.73 (1H, m), 4.70-4.35 (1H, m), 4.33-4.11 (1H, m), 3.99-3.69 (2H, m), 3.66 (3H, s), 3.38-3.00 (3H, m), 2.58-2.21 (4H, m), 2.07-1.88 (2H, m) |
| 227 | $^1$H NMR δ (ppm) (CDCl$_3$): 7.41-7.04 (7H, m), 6.89 (1H, br s), 4.93-4.30 (2H, m), 4.17-3.82 (2H, m), 3.71-2.99 (2H, m), 2.73-2.26 (7H, m), 2.00-1.75 (5H, m) |
| 228 | $^1$H NMR δ (ppm) (CDCl$_3$): 8.12 (1H, d), 7.83 (1H, d), 7.46-7.35 (2H, m), 7.29-7.23 (2H, m), 7.21-7.14 (1H, m), 7.09-7.00 (1H, m), 6.97-6.89 (1H, m), 5.31 (1H, d), 4.32 (1H, d), 4.05-3.88 (2H, m), 3.82-3.70 (1H, m), 3.35-3.22 (3H, m), 3.18-3.03 (1H, m), 2.80-2.59 (2H, m), 2.58-2.46 (1H, m), 2.45-2.27 (2H, m), 2.21-2.06 (1H, m), 2.05-1.81 (3H, m), 1.18-1.02 (3H, m) |
| 229 | $^1$H NMR δ (ppm) (CDCl$_3$): 8.15 (1H, d), 7.83 (1H, d), 7.48-7.35 (2H, m), 7.30-7.27 (2H, m), 7.20-7.15 (1H, m), 7.09-7.03 (1H, m), 6.96-6.89 (1H, m), 6.02-5.88 (1H, m), 5.44-5.30 (2H, m), 5.27 (1H, d), 4.31 (1H, d), 4.13-4.01 (1H, m), 3.99-3.87 (1H, m), 3.83-3.72 (1H, m), 3.55-3.45 (1H, m), 3.37-3.27 (3H, br s), 3.11-3.02 (1H, m), 2.87-2.77 (1H, m), 2.68-2.50 (2H, m), 2.47-2.29 (2H, m), 2.02-1.87 (2H, m), 1.57-1.53 (1H, m) |
| 230 | $^1$H NMR δ (ppm) (CDCl$_3$): 8.28 (1H, d), 7.85 (1H, d), 7.49 (1H, t), 7.46-7.34 (3H, m), 7.34-7.16 (7H, m), 7.15-7.05 (1H, m), 5.17 (1H, d), 4.40 (1H, d), 4.16 (1H, m), 4.10-3.98 (1H, m), 3.86-3.73 (1H, m), 3.39-3.18 (4H, m), 3.19-3.04 (2H, m), 2.55-2.37 (4H, m), 1.99-1.86 (2H, m) |
| 231 | $^1$H NMR δ (ppm) (CDCl$_3$): 8.20 (1H, d), 7.87 (1H, d), 7.78 (1H, br s), 7.46-7.36 (2H, m), 7.34 (2H, d), 7.18 (2H, d), 5.08 (1H, br s), 4.26-4.17 (1H, m), 4.07-3.98 (1H, m), 3.79-3.67 (1H, m), 3.21 (3H, br s), 2.82-2.72 (1H, m), 2.62-2.53 (1H, m), 2.45-2.22 (3H, m), 2.22-2.06 (3H, m), 2.06-1.82 (2H, m), 1.79-1.60 (4H, m) |
| 232 | $^1$H NMR δ (ppm) (CDCl$_3$): 8.09 (1H, d), 7.82 (1H, d), 7.47-7.34 (2H, m), 7.31-7.21 (2H, m), 7.17 (1H, br s), 7.10-7.00 (1H, m), 6.85 (1H, br s), 5.42 (1H, d), 4.32 (1H, d), 4.03-3.89 (2H, m), 3.80-3.68 (1H, m), 3.31 (3H, s), 3.18-3.05 (1H, m), 2.76-2.47 (3H, m), 2.46-2.27 (2H, m), 2.21-2.06 (1H, m), 2.05-1.87 (2H, m), 1.61-1.42 (2H, m), 1.05 (3H, t) |
| 233 | $^1$H NMR δ (ppm) (CDCl$_3$): 8.06 (1H, d), 7.81 (1H, d), 7.65-7.47 (2H, m), 7.46-7.11 (3H, m), 7.03 (1H, br s), 6.72 (1H, br s), 5.74 (1H, d), 4.37 (1H, d), 4.26-3.91 (2H, m), 3.70-3.58 (1H, m), 3.31 (3H, s), 3.09-2.96 (1H, m), 2.95-2.73 (2H, m), 2.58-2.48 (1H, m), 2.47-2.28 (2H, m), 2.07-1.89 (2H, m), 1.29 (4H, d), 1.05 (2H, br s) |
| 234 | $^1$H NMR δ (ppm) (CDCl$_3$): 8.40 (1H, d), 7.87 (1H, d), 7.48 (1H, t), 7.42 (1H, t), 7.30-7.20 (5H, m), 4.30-4.21 (1H, m), 4.07-3.99 (1H, m), 3.77-3.71 (1H, m), 3.46-3.31 (4H, m), 2.66-2.45 (3H, m), 2.09-1.94 (2H, m), 1.88-1.74 (5H, m) |
| 237 | $^1$H NMR δ (ppm) (MeOD, d$_4$): 8.00-7.87 (1H, m), 7.54 (2H, br s), 7.40-6.97 (6H, m), 6.66-6.45 (1H, m), 4.72-4.49 (1H, m), 4.45-4.23 (1H, m), 4.19-3.95 (1H, m), 3.73-3.52 (1H, m), 3.45-3.05 (2H, m), 2.86-2.66 (1H, m), 2.53-2.40 (1H, m), 2.37-2.20 (2H, m), 2.11-1.79 (5H, m) |
| 240 | $^1$H NMR δ (ppm) (CDCl$_3$): 8.15 (1H, d), 7.83 (1H, d), 7.49 (1H, t), 7.42 (1H, t), 7.39-7.25 (5H, m), 7.21 (1H, br s), 7.16-7.06 (1H, m), 6.96 (2H, t), 5.09 (1H, d), 4.42 (1H, d), 4.16 (1H, d), 4.07-3.77 (2H, m), 3.30 (3H, s), 3.27-3.02 (3H, m), 2.57-2.32 (4H, m), 2.03-1.82 (2H, m) |
| 241 | $^1$H NMR δ (ppm) (CDCl$_3$): 8.29 (1H, d), 7.85 (1H, d), 7.46-7.36 (2H, m), 7.35-7.27 (2H, m), 7.27-7.07 (3H, m), 5.02 (1H, d), 4.36 (1H, d), 4.15-4.05 (1H, m), 4.02-3.80 (2H, m), 3.27 (3H, s), 3.20-3.02 (1H, m), 2.78-2.68 (1H, m), 2.52-2.26 (3H, m), 2.08-1.89 (5H, m) |
| 242 | $^1$H NMR δ (ppm) (CDCl$_3$): 8.29 (1H, d), 7.83 (1H, d), 7.56-7.14 (7H, m), 7.10 (1H, br s), 7.02-6.83 (2H, m), 6.79 (1H, d), 5.17-4.70 (1H, m), 4.56-4.34 (1H, m), 4.30-4.11 (1H, m), 4.00-3.73 (2H, m), 3.63 (3H, s), 3.34-3.02 (6H, m), 2.56-2.18 (4H, m), 2.05-1.76 (2H, m) |
| 243 | $^1$H NMR δ (ppm) (CDCl$_3$): 8.29 (1H, d), 7.84 (1H, d), 7.57 (1H, br s), 7.54-7.44 (2H, m), 7.40 (1H, t), 7.36-7.20 (4H, m), 7.19-7.11 (1H, m), 7.05 (2H, t), 4.84 (1H, d), 4.53 (1H, d), 4.13 (1H, d), 3.96 (1H, q), 3.74-3.65 (1H, m), 3.42 (1H, d), 3.31-3.13 (5H, m), 2.60-2.23 (4H, m), 2.06-1.90 (1H, m), 1.84-1.74 (1H, m) |
| 245 | $^1$H NMR δ (ppm) (CDCl$_3$): 8.19 (1H, d), 7.87 (1H, d), 7.67 (1H, br s), 7.45 (1H, t), 7.40 (1H, t), 7.35 (2H, d), 7.25-7.15 (2H, m), 5.57-5.01 (3H, m), 4.26-4.13 (1H, m), 3.91-3.78 (1H, m), 3.69-3.55 (1H, m), 3.18-2.91 (3H, m), 2.84-2.56 (2H, m), 2.50-2.39 (1H, m), 2.26-2.12 (1H, m), 2.09-1.91 (2H, m), 1.69-1.58 (6H, m) |
| 246 | $^1$H NMR δ (ppm) (CDCl$_3$): 8.29 (1H, d), 7.84 (1H, d), 7.43 (1H, t), 7.39 (1H, t), 7.35-7.27 (4H, m), 7.00 (1H, s), 5.23 (2H, s), 3.93-3.84 (1H, m), 3.82-3.69 (2H, m), 3.56-3.49 (1H, |

TABLE IIb-continued

NMR Data of the Compounds of the Invention

| Cpd | NMR data ($\delta$) |
|---|---|
| | m), 3.34-3.19 (2H, m), 2.61-2.42 (2H, m), 2.24-2.09 (3H, m), 1.97-1.87 (1H, m), 0.92 (3H, t) |
| 248 | $^1$H NMR $\delta$ (ppm) (CDCl$_3$): 8.32 (1H, d), 7.82 (1H, d), 7.46-7.31 (3H, m), 7.30-7.20 (3H, m), 7.07 (1H, br s), 3.97 (1H, q), 3.76 (2H, t), 3.64 (1H, q), 2.67-2.57 (1H, m), 2.45 (2H, t), 2.16-2.09 (1H, m), 1.96-1.63 (5H, m) |
| 250 | $^1$H NMR $\delta$ (ppm) (CDCl$_3$): 8.43 (1H, d), 8.28 (1H, d), 7.81 (1H, d), 7.49 (1H, d), 7.41 (1H, t), 7.36 (1H, t), 7.28 (1H, s), 7.12 (1H, br s), 4.02-3.90 (2H, m), 3.81 (1H, q), 3.73-3.63 (1H, m), 2.99-2.90 (1H, m), 2.40 (2H, t), 2.13-2.05 (1H, m), 1.94-1.82 (2H, m), 1.76 (3H, br s) |
| 251 | $^1$H NMR $\delta$ (ppm) (CDCl$_3$): 8.28 (1H, d), 7.81 (1H, d), 7.42 (1H, t), 7.36 (1H, t), 7.34-7.24 (4H, m), 7.02 (1H, br s), 3.93 (1H, q), 3.81-3.61 (3H, m), 2.63-2.53 (1H, m), 2.42 (2H, t), 2.13-2.02 (1H, m), 1.96-1.66 (5H, m) |
| 252 | $^1$H NMR $\delta$ (ppm) (CDCl$_3$): 8.37 (1H, d), 8.33 (1H, d), 7.81 (1H, d), 7.42 (1H, t), 7.37 (1H, t), 7.32 (1H, s), 7.23-7.13 (2H, m), 4.05-3.91 (2H, m), 3.82-3.68 (2H, m), 3.00 (1H, q), 2.47 (2H, t), 2.15-2.06 (1H, m), 1.98-1.84 (2H, m), 1.77 (3H, br s) |

BIOLOGICAL EXAMPLES

Example 1

In Vitro Assays

Example 1.1

Cell Based Assay: Calcium Mobilization Assay without Probenecid

The following assay can be used for determination of GPR43 activation. The assay measures intracellular calcium release induced by activation of GPR43. On day 1, GPR43 stably expressing cells were detached with mild trypsinization (Trypsin, 0.25% with EDTA 4Na, 5× diluted in PBS) centrifuged at 1000 rpm for 5 min and resuspended at 6.000 cells/25 µL medium (DMEM supplemented with 10% FBS, 10 µg/mL puromycin and 1% Pen/Strep). The cells were distributed in poly-D-lysine coated 384 well plates (black with clear bottom, 25 µL/well) and incubated overnight at 37° C. 10% CO$_2$. On day 2, 25 µL of a fluorescent Ca$^{2+}$ indicator (Calcium 4 assay; Molecular Devices) was added on top of the cells and incubated for 2 h at 37° C. Subsequently, compounds at increasing concentration (10 µL/well) were added to the plate and incubated for 15 min at 37° C. Finally the cells were triggered with sodium acetate at EC$_{80}$ concentration (concentration which gives 80% of the activity of the GPR43) and the Ca-flux was measured simultaneously to the trigger injection on a fluorescence plate reader (FlexStation3), this measures the antagonist activity of the compounds. To measure agonist activity of the compounds, compound was added to the well and the Ca-flux was measured simultaneously to the injection of compound.

TABLE III

GPR43 assay without probenicid IC$_{50}$ (nM) of selected Compounds of the Invention.

| Cpd # | GPR43 |
|---|---|
| 1 | *** |
| 2 | * |
| 3 | * |
| 4 | * |
| 5 | * |
| 6 | ** |
| 7 | *** |
| 8 | ** |
| 9 | * |
| 10 | * |
| 11 | * |
| 12 | * |
| 13 | *** |
| 14 | ** |
| 15 | * |
| 16 | * |
| 17 | * |
| 18 | * |
| 20 | * |
| 21 | * |
| 22 | * |
| 23 | * |
| 24 | * |
| 25 | * |
| 26 | * |
| 27 | * |
| 28 | * |
| 29 | * |
| 30 | * |
| 31 | ** |
| 32 | * |
| 33 | ** |
| 34 | * |
| 35 | *** |
| 36 | * |
| 37 | ** |
| 38 | na |
| 42 | * |
| 43 | * |
| 44 | * |
| 45 | * |
| 46 | * |
| 47 | *** |
| 48 | ** |
| 49 | *** |
| 50 | * |
| 51 | * |
| 52 | * |
| 53 | *** |
| 54 | ** |
| 55 | * |
| 56 | * |
| 57 | * |
| 58 | *** |
| 59 | * |
| 60 | * |
| 61 | **** |

TABLE III-continued

GPR43 assay without probenicid $IC_{50}$ (nM) of selected Compounds of the Invention.

| Cpd # | GPR43 |
|---|---|
| 62 | ** |
| 63 | *** |
| 64 | *** |
| 65 | * |
| 66 | *** |
| 67 | **** |
| 68 | *** |
| 69 | * |
| 70 | *** |
| 71 | * |
| 72 | ** |
| 74 | * |
| 75 | *** |
| 77 | * |
| 78 | *** |
| 79 | * |
| 80 | * |
| 81a | na |
| 82 | *** |
| 83 | * |
| 84 | *** |
| 85 | * |
| 86 | *** |
| 87 | ** |
| 88 | *** |
| 89 | **** |
| 90 | **** |
| 91 | * |
| 92 | * |
| 93 | * |
| 94 | * |
| 95 | ** |
| 96 | *** |
| 97 | *** |
| 98 | *** |
| 100 | **** |
| 101 | *** |
| 102 | ** | na: not active
* >1001 nM
** 501-1000 nM
*** 101-500 nM
**** 0.01-100 nM

Example 1.2

Cell Based Assay

Calcium Mobilization Assay with Probenecid

The following assay can be used for determination of GPR43 activation. The assay measures intracellular calcium release induced by activation of GPR43. On day 1, GPR43 stably expressing cells were detached with mild trypsinization (Trypsin, 0.25% with EDTA 4Na, 5× diluted in PBS) centrifuged at 1000 rpm for 5 min and resuspended at 6.000 cells/25 μA medium (DMEM supplemented with 10% FBS, 10 μg/mL puromycin and 1% Pen/Strep). The cells were distributed in poly-D-lysine coated 384 well plates (black with clear bottom, 25 μL/well) and incubated overnight at 37° C. 10% $CO_2$.

On day 2, 25 μL of a fluorescent $Ca^{2+}$ indicator (Calcium 4 assay; Molecular Devices) supplemented with 2.5 mM probenecid was added on top of the cells and incubated for 2 h at 37° C. Subsequently, compounds at increasing concentration (10 μL/well) were added to the plate and incubated for 15 min at 37° C.

Finally the cells were triggered with sodium acetate at $EC_{80}$ concentration (concentration which gives 80% of the activity of the GPR43) and the $Ca^{2+}$-flux was measured simultaneously to the trigger injection on a fluorescence plate reader (FlexStation3), this measures the antagonist activity of the compounds. To measure agonist activity of the compounds, compound was added to the well and the $Ca^{2+}$-flux was measured simultaneously to the infection of compound.

TABLE IV

GPR43 assay with probenicid__IC50__(nM) of selected Compounds of the Invention.

| Cpd # | GPR43 |
|---|---|
| 2 | * |
| 4 | na |
| 5 | na |
| 6 | * |
| 7 | *** |
| 9 | na |
| 10 | na |
| 11 | na |
| 12 | na |
| 15 | na |
| 16 | na |
| 17 | na |
| 18 | na |
| 19 | * |
| 20 | na |
| 21 | na |
| 22 | * |
| 23 | na |
| 24 | na |
| 25 | na |
| 26 | na |
| 27 | * |
| 28 | na |
| 29 | na |
| 30 | na |
| 31 | * |
| 32 | * |
| 33 | * |
| 34 | na |
| 35 | *** |
| 36 | * |
| 37 | * |
| 38 | na |
| 39 | * |
| 41 | * |
| 42 | na |
| 43 | * |
| 44 | * |
| 45 | * |
| 46 | * |
| 48 | ** |
| 49 | *** |
| 50 | * |
| 51 | * |
| 52 | na |
| 53 | *** |
| 54 | * |
| 55 | * |
| 56 | * |
| 57 | * |
| 58 | *** |
| 59 | * |
| 60 | ** |
| 61 | **** |
| 63 | *** |
| 66 | ** |
| 67 | * |
| 68 | *** |
| 69 | ** |
| 71 | ** |
| 72 | *** |
| 73 | ** |
| 74 | * |
| 75 | *** |
| 76 | * |
| 77 | *** |

TABLE IV-continued

GPR43 assay with probenicid IC50 (nM) of selected Compounds of the Invention.

| Cpd # | GPR43 |
|---|---|
| 78 | *** |
| 79 | * |
| 80 | * |
| 81 | *** |
| 82 | *** |
| 83 | * |
| 84 | *** |
| 85 | *** |
| 86 | **** |
| 87 | ** |
| 88 | *** |
| 89 | **** |
| 90 | *** |
| 91 | * |
| 94 | * |
| 95 | * |
| 96 | *** |
| 97 | ** |
| 98 | *** |
| 99 | *** |
| 100 | **** |
| 101 | *** |
| 102 | *** |
| 103 | *** |
| 104 | ** |
| 105 | * |
| 106 | * |
| 107 | * |
| 108 | * |
| 109 | *** |
| 110 | *** |
| 111 | ** |
| 112 | ** |
| 113 | **** |
| 114 | ** |
| 115 | **** |
| 116 | * |
| 117 | * |
| 118 | * |
| 119 | * |
| 120 | * |
| 121 | * |
| 122 | *** |
| 123 | *** |
| 124 | ** |
| 125 | * |
| 126 | * |
| 127 | * |
| 128 | **** |
| 129 | **** |
| 130 | **** |
| 131 | **** |
| 132 | **** |
| 133 | **** |
| 134 | **** |
| 135 | ** |
| 136 | *** |
| 137 | **** |
| 138 | * |
| 139 | * |
| 140 | * |
| 141 | * |
| 142 | * |
| 143 | * |
| 144 | **** |
| 145 | *** |
| 146 | **** |
| 147 | ** |
| 148 | ** |
| 149 | * |
| 150 | *** |
| 151 | *** |
| 152 | *** |
| 153 | *** |
| 154 | * |
| 155 | **** |
| 156 | *** |
| 157 | *** |
| 158 | *** |
| 159 | ** |
| 160 | *** |
| 161 | * |
| 162 | ** |
| 163 | *** |
| 164 | *** |
| 165 | ** |
| 166 | *** |
| 167 | * |
| 168 | * |
| 169 | **** |
| 170 | *** |
| 171 | *** |
| 172 | *** |
| 173 | *** |
| 174 | *** |
| 175 | **** |
| 176 | *** |
| 177 | * |
| 178 | * |
| 179 | * |
| 180 | ** |
| 181 | **** |
| 182 | **** |
| 183 | **** |
| 184 | *** |
| 185 | ** |
| 186 | *** |
| 187 | **** |
| 188 | ** |
| 189 | **** |
| 190 | **** |
| 191 | **** |
| 192 | **** |
| 193 | *** |
| 194 | **** |
| 195 | **** |
| 196 | **** |
| 197 | ** |
| 198 | **** |
| 199 | *** |
| 200 | * |
| 201 | * |
| 202 | * |
| 203 | **** |
| 204 | **** |
| 205 | * |
| 206 | **** |
| 207 | **** |
| 208 | **** |
| 209 | *** |
| 210 | * |
| 211 | **** |
| 213 | * |
| 215 | * |
| 216 | *** |
| 217 | *** |
| 218 | *** |
| 219 | *** |
| 220 | ** |
| 221 | *** |
| 222 | * |
| 223 | * |
| 224 | * |
| 225 | ** |
| 226 | * |
| 227 | ** |
| 228 | **** |
| 229 | **** |
| 230 | *** |
| 231 | **** |

TABLE IV-continued

GPR43 assay with probenicid_IC50_(nM) of selected Compounds of the Invention.

| Cpd # | GPR43 |
|---|---|
| 232 | *** |
| 233 | *** |
| 234 | **** |
| 235 | * |
| 236 | * |
| 237 | * |
| 238 | * |
| 239 | * |
| 240 | *** |
| 241 | ** |
| 242 | ** |
| 243 | ** |
| 244 | * |
| 245 | *** |
| 246 | *** |
| 247 | * |
| 248 | *** |
| 249 | * |
| 250 | ** |
| 251 | *** |
| 252 | ** |
| 253 | * | na = not active
* >1001 nM
** 501-1000 nM
*** 101-500 nM
**** 0.01-100 nM

Example 1.3

Binding Assay: GTPγS Assay

The [35S]GTPγS binding assay measures the level of G protein activation following agonist occupation of a GPCR, by determining the binding of the non-hydrolysable analog [35S]GTPγS to Gα subunits.

The assay was performed in a 96 well plate where the following reagents were added. First 50 μL compound was added into the assay plate, followed by addition of 20 μL Sodium acetate at EC80 concentration (concentration which give 80% of the activity of the GPR43). In a last step, 30 μL of a mixture consisting of membranes-GTPγS-SpA beads was added (mixture consists of 10 μg/well membranes derived from stable cell line over expressing GPR43 (membranes were pre-incubated with 3 μM GDP for 15 minutes at 4° C.), 0.1 nM [35S]GTPγS (Perkin Elmer, NEG030) and 0.5 mg/well PVT-WGA SpA beads (perkin Elmer, RPNQ0001)). All components were diluted in assay buffer containing 20 mM Hepes pH 7.4; mM $MgCl_2$; 250 mM NaCl and 37.5 μg/mL saponin. Reactions were incubated for 240 minutes at room temperature followed by centrifugation at 2000 rpm for 15 minutes. Plates were read on a Topcount immediately after centrifugation (readout time, 1 minute/well).

TABLE V

GTPγS assay $IC_{50}$(nM) of selected Compounds of the invention.

| Cpd # | GTPγS $IC_{50}$ |
|---|---|
| 67 | ** |
| 115 | ** |
| 128 | ** |
| 134 | * |
| 144 | *** |
| 146 | ** |
| 155 | * |
| 169 | * |
| 182 | ** |
| 187 | ** |
| 191 | *** |
| 194 | * |
| 195 | ** |
| 198 | ** |

* >501 nM
** 101-500 nM
*** 51-100 nM

Example 2

Cellular Assays

Example 2.1

Neutrophil Migration Assay

G Protein-Coupled Receptor 43 (GPR43) was described as an essential player in the process of neutrophil recruitment during intestinal inflammation. It has been shown that sodium acetate and sodium propionate, two natural ligands of GPR43, act as chemoattractants for neutrophils and thus induce neutrophil migration (Brown, A. J., S. M. Goldsworthy, et al. (2003). "The Orphan G Protein-coupled Receptors GPR41 and GPR43 Are Activated by Propionate and Other Short Chain Carboxylic Acids" J. Biol. Chem. 278(13): 11312-11319.)

The effect of agonists or antagonists for GPR43 can therefore be assayed in a neutrophil migration test. In the neutrophil migration assay, neutrophils, isolated from buffy coats from human volunteers, are treated with a compound for 30 minutes. Subsequently, the neutrophils are transferred to the upper wells of a Corning HTS transwell 96 permeable support system, of which the lower wells are filled with a sodium acetate solution. After 1 h of incubation, migration of the neutrophils towards the sodium acetate can be quantified by measuring the ATP-content of the lower wells using the ATPlite luminescence ATP detection assay system (Perkin Elmer, Cat. N°.: 436110).

1.1.1 Neutrophil Migration Assay Protocol

The ACD buffer consists of 140 mM citric acid, 200 mM sodium citrate and 220 mM dextrose. The 6% dextran/0.9% NaCl solution consists of 15 g dextran T2000 and 2.25 g NaCl dissolved in 250 mL $H_2O$.

The chemotaxis buffer, freshly made for each experiment, consists of RPMI 1640 medium, supplemented with 10 mM HEPES.

Isolation of Neutrophils from Human Buffy Coat

A human buffy coat is diluted with an equal volume of ice cold DPBS. 20 mL of the diluted buffy coat is gently mixed with 4 mL of ACD buffer. Then, 12 mL of the 6% dextran/0.9% NaCl solution is added to the mixture and the samples are inverted gently up to 20 times. The total volume is transferred to a new recipient and incubated at room temperature for 1 h for complete separation of the two phases to occur. The yellowish supernatant is then transferred to a clean centrifugation tube and centrifuged for 12 minutes at 1300 rpm and 4° C. After centrifugation, the supernatant is discarded and the remaining cell pellet is rapidly resuspended in 12 mL of ice-cold $H_2O$ for red blood cell lysis to occur. After 20 seconds, 4 mL of ice-cold 0.6 M KCl is added. Samples are mixed carefully and centrifuged for 6 minutes at 1300 rpm, 4° C. The supernatant is discarded and the red blood cell lysis procedure is repeated one more time. Subsequently, the cell pellet is resuspended in 4 mL of DPBS and layered over 5 mL of Lymphoprep (Nycomed Pharma, Cat. N°.: 1114545) in a 15 mL centrifuge tube. After centrifugation for 12 min at 1300 rpm, 4° C., the supernatant is removed and the cell pellet, containing the neutrophils, is resuspended in 25 mL chemotaxis buffer.

Migration Assay

A cell suspension of $8.9 \times 10^6$ cells per milliliter is prepared. 20 μL of compound solution in chemotaxis buffer is added to 180 μl cell suspension. The mixture is incubated at 37° C. for 30 minutes with Intermediate resuspension of the cells after 15 minutes. Following this, 70 μL cell suspension is transferred to the upper compartment of a Corning HTS transwell 96 permeable support system with 5.0 μm pore size polycarbonate membrane (Corning, Cat. N°.: 3387). The receiver well of the transwell system is then filled with 200 μL chemotaxis buffer containing compound and chemotactic agent (sodium acetate). After incubation at 37° C. in 5% $CO_2$ for 1 h, the upper plate of the transwell system is removed and the cell suspension in the receiver plate is transferred to a 96-well V-bottom plate. 50 μL of DPBS is added to the receiver plate to prevent remaining cells from drying out. The V-bottom plate is centrifuged for 6 minutes at 1500 rpm. The supernatant is removed and the cells are resuspended in 50 μL DPBS. The cells are then transferred back to the receiver plate of the transwell system. After this, 100 μL ATPlite solution (Perkin Elmer, Cat. N°: 436110) is added to the cells. The plate is incubated for 10 minutes in the dark, while shaking. 170 μL of cell lysate is then transferred to a white 96-well plate and luminescence is measured. The detected luminescent signal is considered as linearly related to the number of migrated cells.

TABLE VI human neutrophil migration inhibition

| Cpd # | $EC_{50}$ (nM) |
|---|---|
| 61 | **** |
| 89 | **** |
| 90 | **** |
| 96 | **** |
| 103 | ** |
| 110 | *** |
| 113 | **** |
| 115 | **** |
| 122 | *** |
| 123 | **** |
| 128 | **** |
| 130 | *** |
| 131 | *** |
| 132 | *** |
| 134 | **** |
| 137 | **** |
| 144 | **** |
| 146 | **** |
| 155 | **** |
| 157 | **** |
| 169 | *** |
| 191 | **** |

\* >1001 nM
\*\* 501-1000 nM
\*\*\* 101-500 nM
\*\*\*\* 0.01-100 nM

Example 3

ADME, PK and Safety Models

Example 3.1

Aqueous Solubility

Starting from a 10 mM stock in DMSO, a serial dilution of the compound is prepared in DMSO. The dilution series is transferred to a 96 NUNC Maxisorb plate F-bottom and 0.1M phosphate buffer pH 7.4 or 0.1M citrate buffer pH3.0 at room temperature is added.

The final concentrations range from 18.75 to 300 μM in 5 equal dilution steps. The final DMSO concentration does not exceed 3%.

200 μM Pyrene is added to the corner points of each 96 well plate and serves as a reference point for calibration of Z-axis on the microscope.

The assay plates are sealed and incubated for 1 h at 37° C. while shaking at 230 rpm. The plates are then scanned under a white light microscope, yielding individual pictures of the precipitate per concentration. The precipitate is analyzed and converted into a number by a custom-developed software tool. The first concentration at which the compound appears completely dissolved is the concentration reported, however the true concentration lies somewhere between this concentration and one dilution step higher.

Solubility values are reported in μM and in mg/mL.

Example 3.2

Thermodynamic Solubility

Two individual solutions of 2 mg/mL of compound are prepared in a 0.1 M phosphate buffer pH 7.4 or a 0.1 M citrate buffer pH 3.0 at room temperature in a 2 mL glass vial.

After addition of a magnetic stir, the samples are stirred at room temperature for 24 h.

After 24 h, the vials are centrifuged 10 min at 1400 rpm. The supernatant of the sample is then transferred to a Multi-screenR Solubility Plate (Millipore, MSSLBPC50) and filtered (10-12" Hg) with the aid of a vacuum manifold into a clean Greiner polypropylene V-bottom 96 well plate. Per sample, two dilutions (factor 10 and 100) are made in DMSO. Other dilutions can be made if the acquired peak area is not within the standard curve.

A 10 mM DMSO stock, made from dry matter, is used to make a 200 μg/mL working stock. The standard curve for the compound is prepared in DMSO starting from the 200 μg/mL working stock. Eight concentrations and two quality control samples (QC) are made in 2 mL tubes. The first 3 concentrations (50, 35 and 15 μg/mL) and the first QC sample (20 μg/mL) are made starting with the 200 μg/mL working stock. The $4^{th}$ concentration (5 μg/mL) is made with the 50 μg/mL solution and the $5^{th}$ concentration (1 μg/mL) with the 15 μg/mL. The last three concentrations (0.2, 0.1 and 0.05 μg/mL) are made with the 1 μg/mL solution. The second QC sample (0.5 m/mL) is made with the first QC sample.

Of every step of the dilution series, quality control and sample dilutions, a volume is transferred to a 96-well Deep-well plate. The samples are injected on a LC-MS/MS system (API2000 from Applied Biosystems).

The samples are analyzed on LC-MS/MS with a flow rate of 0.5 mL/min. Solvent A is 0.1% Formic Acid in water and solvent B is 0.1% Formic Acid in methanol. The sample is run under positive ion spray on a Pursuit 5 C18 2.0 mm column (Varian). The solvent gradient has a total run time of 1.4 minutes and ranges from 10% B to 100% B.

The thermodynamic solubility samples are analyzed with the aid of QuanLynx software. For the standard curve a linear or quadratic curve can be used in the analysis. Samples of the standard curve that have more than 15% deviation are excluded; the lowest concentrations of the curve may vary up to 20%. Peak areas of the samples are plotted against the standard curve to obtain the solubility of the compound.

Solubility values are reported in µM or µg/mL.

Example 3.3

Microsomal Stability

A 10 mM stock solution of compound in DMSO is 1,668 fold diluted in a 105 mM phosphate buffer pH 7.4. Of this compound dilution, 50 µL is transferred in two 96 assay plates: one for time point 0 min (T0 plate) and one for time point 30 min (T30 plate) and pre-warmed at 37° C.

In the time zero reference sample (T0 plate), 100 µL MeOH (1:1) is added to the wells. In each assay plate (T0 and T30 min), 50 µL of microsomal mix is then added.

Final reaction concentrations are: 3 µM compound, 0.5 mg/mL microsomes, 0.4 U/mL GDPDH, 3.3 mM $MgCl_2$, 3.3 mM glucose-6-phosphate and 1.3 mM $NADP^+$ The T30 plate is incubated at 37° C., 300 rpm and after 30 minutes of incubation the reaction is stopped with MeOH (1:1). The samples are mixed, centrifuged and the supernatant is harvested for analysis on LC-MS/MS (API2000 from Applied Biosystems).

The samples are analyzed on LC-MS/MS with a flow rate of 0.5 mL/min. Solvent A is 0.1% Formic Acid in water and solvent B is 0.1% Formic Acid in methanol. The sample is run under positive ion spray on a Pursuit 5 C18 2.0 mm column (Varian). The solvent gradient has a total run time of 1.4 minutes and ranges from 10% B to 100% B. Peak area from the parent compound at time 0 is considered to be 100% remaining. The percentage remaining after 30 minutes incubation is calculated from time 0. The solubility of the compound in the final test concentration in buffer is inspected by microscope and results are also reported.

Example 3.4

Hepatocyte Stability

Test compounds (1 µM initial concentration, n=2) are incubated in Williams' Medium E, containing 4 mM L-glutamine and 2 mM magnesium sulphate, with pooled cryopreserved hepatocytes (Celsis International) in suspension at cell densities of 0.25-0.5 million viable cells/mL. The incubations are performed at 37° C. in a shaking water bath with 100 µL samples taken from the incubation at 0, 10, 20, 45 and 90 minutes, and reactions terminated by addition of 100 µL of acetonitrile containing carbamazepine as analytical internal standard. Samples are centrifuged and the supernatant fractions analysed by LC-MS/MS. The instrument responses (i.e. peak heights) are referenced to the zero time-point samples (as 100%) in order to determine the percentage of compound remaining. Ln plots of the % remaining for each compound are used to determine the half-life for the hepatocyte incubations. Half-life values are calculated from the relationship: $T_{1/2}$ (min)$=-0.693/\lambda$, where $\lambda$ is the slope of the Ln concentration vs time curve. Standard compounds testosterone, midazolam, and 4-methylumbelliferone are included in the assay design.

Example 3.5

Plasma Protein Binding (Equilibrium Dialysis)

A 10 mM stock solution of the compound in DMSO is diluted with a factor 10 in DMSO. This solution is further diluted in freshly thawed human, rat, mouse or dog plasma (BioReclamation INC) with a final concentration of 5 µM and final DMSO concentration of 0.5%.

A Pierce Red Device plate with inserts (ThermoScientific) is prepared and filled with 4504 PBS in the buffer chamber and 3004 of the spiked plasma in the plasma chamber. The plate is incubated for 4 h at 37° C. while shaking at 100 rpm. After incubation, 1204 of both chambers is transferred to 4804 methanol in a 96-well round bottom, PP deep-well plates (Nunc) and sealed with an aluminum foil lid. The samples are mixed and immediately centrifuged 30 min at 1400 rcf at 4° C. and the supernatant is transferred to a 96 v-bottom PP plate (Greiner, 651201) for analysis on LC-MS/MS (API2000 from Applied Biosystems).

The samples are analyzed on LC-MS/MS with a flow rate of 0.5 mL/min. Solvent A is 0.1% formic acid in water and solvent B is 0.1% formic acid in methanol. The sample is run under positive ion spray on a Pursuit 5 C18 2.0 mm column (Varian). The solvent gradient has a total run time of 1.4 minutes and ranges from 10% B to 100% B.

Peak area from the compound in the buffer chamber and the plasma chamber are considered to be 100% compound. The percentage bound to plasma is derived from these results and is reported as percentage bound to plasma.

The solubility of the compound in the final test concentration in PBS is inspected by microscope to indicate whether precipitation is observed or not.

Example 3.6

Caco2 Permeability

Bi-directional Caco-2 assays are performed as described below. Caco-2 cells are obtained from European Collection of Cell Cultures (ECACC, cat 86010202) and used after a 21 day cell culture in 24-well Transwell plates (Corning, cell growth area: 0.33 $cm^2$, Membrane pore size: 0.4 µM, membrane diameter: 6.5 mm).

$2\times10^5$ cells/well are seeded in plating medium consisting of DMEM+GlutaMAXT™-I+1% NEAA+10% FBS (Fetal-Clone II)+1% Pen/Strep. The medium is changed every 2-3 days.

Test and reference compounds (propranolol and rhodamine-123 or vinblastine, all purchased from Sigma) are prepared in Hanks' Balanced Salt Solution containing 25 mM HEPES (pH7.4) and added to either the apical (1254) or basolateral (600 µL) chambers of the Transwell plate assembly at a concentration of 10 µM with a final DMSO concentration of 0.25%.

50 µM Lucifer Yellow (Sigma) is added to the donor buffer in all wells to assess integrity of the cell layers by monitoring Lucifer Yellow permeation. As Lucifer Yellow (LY) cannot freely permeate lipophilic barriers, a high degree of LY transport indicates poor integrity of the cell layer.

After a 1 h incubation at 37° C. while shaking at an orbital shaker at 150 rpm, 70 µL aliquots are taken from both apical (A) and basal (B) chambers and added to 100 µL 50:50 acetonitrile:water solution containing analytical internal standard (0.5 µM carbamazepine) in a 96 well plate.

Lucifer yellow is measured with a Spectramax Gemini XS (Ex 426 nm and Em 538 nm) in a clean 96 well plate containing 150 μL of liquid from basolateral and apical side.

Concentrations of compound in the samples are measured by high performance liquid-chromatography/mass spectroscopy (LC-MS/MS).

Apparent permeability ($P_{app}$) values are calculated from the relationship:

$$P_{app} = [compound]_{acceptor\,final} \times V_{acceptor} / ([compound]_{donor\,initial} \times V_{donor}) / T_{inc} \times V_{donor} / \text{surface area} \times 60 \times 10^{-6} \text{ cm/s}$$

V=chamber volume
$T_{inc}$=incubation time.
Surface area=0.33 cm$^2$

The Efflux ratios, as an indication of active efflux from the apical cell surface, are calculated using the ratio of $P_{app}$B>A/$P_{app}$A>B.

The following assay acceptance criteria are used:
Propranolol: $P_{app}$ (A>B) value≥20(×10$^{-6}$ cm/s)
Rhodamine 123 or Vinblastine: $P_{app}$ (A>B) value<5 (×10$^{-6}$ cm/s) with Efflux ratio≥5.
Lucifer yellow permeability: ≤100 nm/s

Example 3.7

Liability for QT Prolongation

Potential for QT prolongation is assessed in the hERG manual patch clamp assay.

3.7.1 Conventional Whole-Cell Patch-Clamp

Whole-cell patch-clamp recordings are performed using an EPC10 amplifier controlled by Pulse v8.77 software (HEKA). Series resistance is typically less than 10 MΩ and compensated by greater than 60%, recordings are not leak subtracted. Electrodes are manufactured from GC150TF pipette glass (Harvard).

The external bathing solution contains: 135 mM NaCl, 5 mM KCl, 1.8 mM CaCl$_2$, 5 mM Glucose, 10 mM HEPES, pH 7.4.

The internal patch pipette solution contains: 100 mM Kgluconate, 20 mM KCl, 1 mM CaCl$_2$, 1 mM MgCl$_2$, 5 mM Na$_2$ATP, 2 mM Glutathione, 11 mM EGTA, 10 mM HEPES, pH 7.2.

Drugs are perfused using a Biologic MEV-9/EVH-9 rapid perfusion system.

All recordings are performed on HEK293 cells stably expressing hERG channels. Cells are cultured on 12 mm round coverslips (German glass, Bellco) anchored in the recording chamber using two platinum rods (Goodfellow). hERG currents are evoked using an activating pulse to +40 mV for 1000 ms followed by a tail current pulse to −50 mV for 2000 ms, holding potential is −80 mV. Pulses are applied every 20 s and all experiments are performed at room temperature.

3.7.2 Data Analysis

IC$_{50}$ values are calculated for each compound tested. The fold difference between the IC$_{50}$ in the manual hERG patch clamp and the unbound IC$_{50}$ in the whole blood assay is calculated.

For the concentration response curves, peak tail current amplitude is measured during the voltage step to −50 mV. Curve-fitting of concentration-response data is performed using the equation:

$$y = a + [(b-a)/(1+10^{((\log c - x)d)})]$$

where a is minimum response, b is maximum response and d is Hill slope, this equation can be used to calculate both IC$_{50}$ (where y=50 and c is the IC$_{50}$ value) and IC$_{20}$ (where y=20 and c is the IC$_{20}$ value). GraphPad® Prism® (Graphpad® Software Inc.) software is used for all curve fitting. A difference of 100 fold or greater indicates a low potential for QT prolongation.

Example 3.8

Pharmacokinetic Study 3.8.1 Single Dose Pharmacokinetic Study in Rats

Compounds are formulated in PEG200/physiological saline mixtures for the intravenous route and in PEG400/0.5% methylcellulose (10/90 v/v) for the oral route. Test compounds are orally dosed as a single esophageal gavage at 5-10 mg/kg and intravenously dosed as a bolus via the caudal vein at 1 mg/kg to male Sprague-Dawley rats. Each group consists of 3 rats. Blood samples are collected either via the jugular vein using cannulated rats or at the retro-orbital sinus with lithium heparin as anti-coagulant at the time points in the following range: 0.05 to 8 h (intravenous route), and 0.25 to 6 or 24 h (oral route). Whole blood samples are centrifuged at 5000 rpm for 10 min and the resulting plasma samples are stored at −20° C. pending analysis.

3.8.2 Multiple Dose Pharmacokinetic Study in Rats

Compounds are formulated in PEG400/0.5% methylcellulose (10/90 v/v) for the oral route. Test compounds are orally dosed as an esophageal daily gavage at 30 or 300 mg/kg to male Sprague-Dawley rats for 14 days. Each group consists of 3 rats. Blood samples are collected via the tail vein with lithium heparin as anti-coagulant at the following time points on day 1, 7 and 14: 0.25, 1, 4, 8 and 24 h. In addition, on day 2 blood samples are taken at 0.25, 1 and 4 h and at day 4 and 11 at 0.25 h. Whole blood samples are centrifuged at 5000 rpm for 10 min and the resulting plasma samples are stored at −20° C. pending analysis.

3.8.3 Quantification of Compound Levels in Plasma

Plasma concentrations of each test compound are determined by an LC-MS/MS method in which the mass spectrometer is operated in positive or negative electrospray mode.

3.8.4 Determination of Pharmacokinetic Parameters

Pharmacokinetic parameters are calculated using Winnonlin® (Pharsight®, US).

Example 3.9

7-Day Rat Toxicity Study

A 7-day oral toxicity study with test compounds is performed in Sprague-Dawley male rats to assess their toxic potential and toxicokinetics, at daily doses of 100, 300 and 1000 mg/kg/day, by gavage, at the constant dosage-volume of 10 mL/kg/day.

The test compounds are formulated in PEG400/0.5% methylcellulose (10/90, v/v). Each group includes 6 principal male rats as well as 3 satellite animals for toxicokinetics. A fourth group is given PEG400/0.5% methylcellulose (10/90, v/v) only, at the same frequency, dosage volume and by the same route of administration, and acts as the vehicle control group.

The goal of the study is to determine the lowest dose that results in no adverse events being identified (no observable adverse effect level—NOAEL).

Example 3.10

CD11b Whole Blood Assay

G Protein-Coupled Receptor 43 (GPR43) expression has been shown in polymorphonuclear leukocytes (PMN) and purified neutrophils ((Le Pouls et al., 2003, The Journal of Biological Chemistry, 278, 28, 25481-25489; Brown et al., 2003, The Journal of Biological Chemistry, 278, 13, 11312-11319; Stoddart et al., 2008, Pharmacological Reviews, 60, 405-417).

The effect of agonists or antagonists for GPR43 is therefore assayed for neutrophil activation measured by CD11b expression level at the surface of neutrophil.

Human blood is collected by venipuncture from human volunteers, who gave informed consent, in acid-citrate-dextrose (ACD) vacutubes, mixed well and processed as soon as possible, the latest within 90 nm after blood collection.

Blood is diluted 1/1 in RPMI1640. Diluted blood is treated simultaneously with a compound in DMSO solution or with DMSO (max. 0.3% of DMSO), and with 20 µg/mL cytochalasin B, TNFalpha 2 ng/mL. Blood is incubated at 37° C. for 15 nm without shaking. Then GPR43 agonist (sodium acetate) is added to blood. Blood is gently mixed and incubated at 37° C. for 30 nm without shaking.

Neutrophil surface expression of CD45, CD66b and CD11b markers is determined by flow cytometry. Unspecific binding of antibodies was blocked by addition of 2 µg/sample of normal mouse IgG (Invitrogen, Cat. No. 10400C) and incubation for 10 nm at +4° C. in the dark. Then 2 µL of CD45 V450 antibody (ref. 560367, BD Biosciences), 2.5 µL of CD11b APC Mouse Anti-Human CD11b/Mac-1 antibody (activation epitope; ref 17-0113-42, eBiosciences) and 10 µL of CD66b FITC antibody (ref 555724. BD Biosciences) are added to blood at the same time and samples incubated for 30 nm at +4° C. in the dark. Red blood cells are lysed and samples fixed by addition of RBC lysing Buffer (1× solution from BD FACS™ Lysing Solution 10×, cat. 349202, BD Pharmigen) and incubated for 10 nm at room temperature in the dark. The cells are centrifuged, 550 g for 10 nm at +4° C. and washed once with PBS (550 g for 5 nm at +4° C.). The cells are resuspended in cold 300 µL wash/staining buffer (PBS+2% FBS), transferred to polystyrene 5 mL tube and placed on ice protected from light until analysed with FACScan/CytekDev XDP8 and FlowJo Collector's, FlowJo V7.6 software. Neutrophils are gated and selected according to morphological characteristics using FSC and SSC parameters and immunophenotype as CD45high+CD66b high+CD11b(AE)+cells. Cellular expression of CD11b activation epitope is determined by determination of MFI units (Mean Fluorescence Intensity).

REFERENCES

Prentki et al., 2008, Endocrine Review, 29(6), 647-676
Sellin et al., 1999, News. Physiol. Sci, 14, 58-64
Le Pouls et al., 2003, The Journal of Biological Chemistry, 278, 28, 25481-25489
Brown et al., 2003, The Journal of Biological Chemistry, 278, 13, 11312-11319
Stoddart et al., 2008, Pharmacological Reviews, 60, 405-417
Dass et al., 2007, Neurogastroenterl. Motil., 19:66-74
Karaki et al., 2006, Cell Tissue Res., 324/353-360
Maslowski et al., 2009, Nature, 461, 1282-1287
Sina et al., 2009, The Journal of Immunology, 183:7514-7522
Bjursel et al., 2010, Am. J. Physiol. Endocrinol. Metab. in press
Hatanaka et al., 2010, Cancer Sci, 101: 54-59
Bjursel et al., 2010, Am. J. Physiol. Endocronl. Metab. in press
Bundgard, H., Design of Prodrugs, pp. 7-9, 21-24, Elsevier, Amsterdam 1985
Part 8 of Remington's Pharmaceutical Sciences, 17th edition, 1985, Mack Publishing Company, Easton, Pa.
T. W. Greene and P. G. M. Wuts, Protecting Groups in Organic Synthesis, Second Edition, Wiley, New York, 1991
EP101004
Lee et al., Tetrahedron, 1995, 4909-4922
Turner et al. A., J. Org. Chem. 1983, 3401-3408
WO2009/104155 A1
Rao et al., Tetrahedron Letters, 1983 5023-5024
McGinnity et al. Drug Metabolism and Disposition 2008, 32, 11, 1247

All publications, including but not limited to patents and patent applications, cited in this specification are herein incorporated by reference as if each individual publication were specifically and individually indicated to be incorporated by reference herein as though fully set forth.

From the foregoing description, various modifications and changes in the compositions and methods of this invention will occur to those skilled in the art. All such modifications coming within the scope of the appended claims are intended to be included therein.

It should be understood that factors such as the differential cell penetration capacity of the various compounds can contribute to discrepancies between the activity of the compounds in the in vitro biochemical and cellular assays.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using either ChemDraw® or ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

What is claimed is:
1. A compound according to Formula Ia:

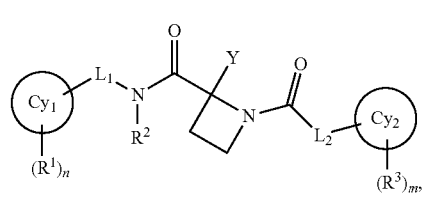

Ia wherein
$L_1$ is a single bond, or $CR^aR^b$;
$L_2$ is a single bond, O, $NR^e$ or $CR^cR^d$;
each of $R^a$, $R^b$, $R^c$, and $R^d$ is independently selected from H, and $C_{1-4}$ alkyl; or $R^a$ and $R^b$ together with the carbon to which they are attached may form a $C_{3-7}$ cycloalkyl; or $R^c$ and $R^d$ together with the carbon to which they are attached may form a $C_{3-7}$ cycloalkyl;

$R^e$ is $C_{1-4}$ alkyl;

Y is
  $C_{1-4}$ alkyl optionally substituted with one or more groups independently selected from fluoro, OH, and phenyl (optionally substituted with one or more groups independently selected from $C_{1-4}$ alkyl (optionally substituted with one or more halo), $C_{1-4}$ alkoxy, halo and cyano), or
  $C_{1-4}$ alkenyl comprising 1 double bond;

each of $Cy_1$ and $Cy_2$ is independently $C_{6-10}$ aryl, or 5-10 membered heteroaryl;

each $R^1$ is independently selected from halo, $C_{1-4}$ alkyl (optionally substituted with one or more halo), and $C_{1-4}$ alkoxy (optionally substituted with one or more halo);

$R^2$ is:
  H,
  $C_{1-4}$ alkyl optionally substituted with one or more independently selected $R^{2a}$ groups,
  $C_{3-7}$ cycloalkyl optionally substituted with one or more independently selected $R^{2a}$ groups, $R^{2a}$ is
  halo,
  $C_{1-6}$ alkoxy,
  OH,
  $C(=O)R^4$,
  $S(O)_2R^4$,
  CN,
  $NHC(=O)R^5$,
  $NHSO_2R^5$,
  5-7 membered heterocycloalkyl (optionally substituted with one or more groups independently selected from $C_{1-4}$ alkyl, and oxo), or
  5-6 membered heteroaryl (optionally substituted with one or more groups independently selected from halo, OH, $C_{1-4}$ alkoxy and $C_{1-4}$ alkyl);

$R^3$ is selected from halo, $C_{1-6}$ alkyl (optionally substituted with one or more halo), $C_{1-6}$ alkoxy (optionally substituted with one or more halo, or phenyl), $C_{1-6}$ thioalkoxy, phenyl (optionally substituted with one or more groups independently selected from halo, $C_{1-4}$ alkyl (optionally substituted with one or more halo), $C_{1-4}$ alkoxy, $C(=O)$—$C_{1-4}$ alkoxy and CN);

$R^4$ is
  —OH,
  —$C_{1-6}$ alkoxy,
  —N-linked 5-7 membered heterocycloalkyl (optionally substituted with one or more groups independently selected from $C_{1-6}$ alkyl, and oxo),
  —$NR^{4a}R^{4b}$, or
  —$NHSO_2R^{4c}$;

Each of $R^{4a}$ and $R^{4b}$ is independently H, $C_{1-4}$ alkyl (optionally substituted with phenyl (optionally substituted with one or more groups independently selected from halo, CN, $C_{1-6}$ alkyl, and $C_{1-6}$ alkoxy)), or $C_{3-7}$ cycloalkyl;

$R^{4c}$ is phenyl, 5-6 membered heteroaryl, 5-6 membered heterocycloalkyl (optionally substituted with one or more $C_{1-4}$ alkyl) or $C_{1-4}$ alkyl (optionally substituted with one or more halo);

$R^5$ is $C_{1-4}$ alkyl (optionally substituted with one or more halo) or phenyl; and the subscripts n and m are independently selected from 0, 1, and 2;

or a pharmaceutically acceptable salt, or a solvate, or a solvate of the pharmaceutically acceptable salts.

2. A compound or pharmaceutically acceptable salt thereof according to claim 1, wherein the compound is according to Formula Ib:

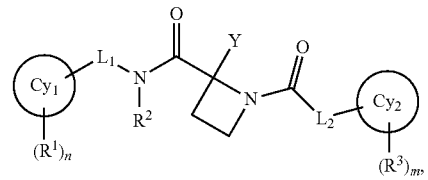

Ib wherein $L_1$, $L_2$, $R^1$, $R^2$, $R^3$, $Cy^1$, $Cy^2$, $R^a$, $R^b$, $R^c$, $R^d$, $R^e$, Y, n, and m are as described in claim 1.

3. A compound or pharmaceutically acceptable salt thereof according to claim 1, wherein Y is Me, Et, Pr, iPr, or —$CH_2$-Ph.

4. A compound or pharmaceutically acceptable salt thereof according to claim 1, wherein the compound is according to Formulae IIIa or IIIb:

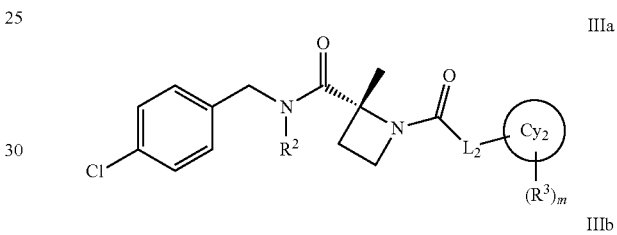

wherein $R^2$, $L_2$, $Cy_2$, $R^3$ and m are as described in claim 1.

5. A compound or pharmaceutically acceptable salt thereof according to claim 1, wherein $R^2$ is —$(CH_2)$—COOH, —$(CH_2)_3$—COOH, —$(CH_2)_3$—$SO_2NH_2$, or —$(CH_2)_3$—$SO_2NHMe$.

6. A compound or pharmaceutically acceptable salt thereof according to claim 1, wherein $Cy_2$ is phenyl, or naphthalene.

7. A compound or pharmaceutically acceptable salt thereof, according to claim 1, wherein $Cy_2$ is thiophenyl, benzothiophenyl, benzofuranyl, benzoisoxazolyl, benzoxazolyl or indolyl.

8. A compound or pharmaceutically acceptable salt thereof according to claim 1, wherein m is 1 or 2.

9. A compound or pharmaceutically acceptable salt thereof according to claim 8, wherein each $R^3$ group is independently selected from F, Cl, Br, Me, $CF_3$, and OMe.

10. A compound or pharmaceutically acceptable salt thereof according to claim 1, wherein m is 0.

11. A compound or pharmaceutically acceptable salt thereof according to claim 1, wherein $L_2$ is a single bond.

12. A compound or pharmaceutically acceptable salt thereof according to claim 1, wherein $L_2$ is —$CH_2$—.

13. A compound according to claim 1, wherein the compound is 4-[[(R)-1-(Benzo[b]thiophene-3-carbonyl)-2-methyl-azetidine-2-carbonyl]-(3-chloro-benzyl)-amino]-butyric acid; or a pharmaceutically acceptable salt, or a solvate, or a solvate of the pharmaceutically acceptable salt.

14. A pharmaceutical composition comprising a compound or pharmaceutically acceptable salt thereof, according to claim 1, and a pharmaceutically acceptable carrier.

15. The pharmaceutical composition according to claim 14 comprising a further therapeutic agent.

16. A method for the treatment of inflammatory conditions, infectious diseases, autoimmune diseases, diseases involving impairment of immune cell functions, cardiometabolic diseases, and/or proliferative diseases, said method comprising administering an effective amount of a compound, or pharmaceutically acceptable salt thereof, according to claim 1.

17. A method for the treatment of inflammatory conditions, infectious diseases, autoimmune diseases, diseases involving impairment of immune cell functions, cardiometabolic diseases, and/or proliferative diseases, said method comprising administering an effective amount of a pharmaceutical composition according to claim 14.

* * * * *